US009540424B2

(12) United States Patent
Gosselin et al.

(10) Patent No.: US 9,540,424 B2
(45) Date of Patent: Jan. 10, 2017

(54) SERUM ALBUMIN BINDING MOLECULES

(71) Applicant: BRISTOL-MYERS SQUIBB COMPANY, Princeton, NJ (US)

(72) Inventors: Michael L. Gosselin, Boston, MA (US); David Fabrizio, South Hamilton, MA (US); Joanna F. Swain, Concord, MA (US); Tracy Mitchell, Andover, MA (US); Ray Camphausen, Wayland, MA (US); Sharon T. Cload, Cambridge, MA (US); Eric Furfine, Concord, MA (US); Paul E. Morin, Pennington, NJ (US); Ranjan Mukerjee, Churchville, PA (US); Simeon I. Taylor, Princeton, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 59 days.

(21) Appl. No.: 14/552,823

(22) Filed: Nov. 25, 2014

(65) Prior Publication Data

US 2015/0152147 A1 Jun. 4, 2015

Related U.S. Application Data

(62) Division of application No. 13/098,851, filed on May 2, 2011, now Pat. No. 8,969,289.

(60) Provisional application No. 61/330,672, filed on May 3, 2010.

(51) Int. Cl.

| | |
|---|---|
| ***A61K 38/00*** | (2006.01) |
| ***C07K 14/435*** | (2006.01) |
| ***A61K 47/48*** | (2006.01) |
| ***C07K 14/78*** | (2006.01) |
| ***C12N 15/62*** | (2006.01) |
| ***C07K 14/50*** | (2006.01) |
| ***C07K 14/575*** | (2006.01) |

(52) U.S. Cl.

CPC ....... *C07K 14/435* (2013.01); *A61K 47/48238* (2013.01); *A61K 47/48284* (2013.01); *C07K 14/50* (2013.01); *C07K 14/575* (2013.01); *C07K 14/78* (2013.01); *C12N 15/62* (2013.01); *A61K 38/00* (2013.01); *C07K 2319/70* (2013.01)

(58) Field of Classification Search

None

See application file for complete search history.

(56) References Cited

U.S. PATENT DOCUMENTS

| | | | |
|---|---|---|---|
| 5,235,041 | A | 8/1993 | Cappello et al. |
| 5,514,581 | A | 5/1996 | Ferrari et al. |
| 5,545,620 | A | 8/1996 | Wahl et al. |
| 5,641,648 | A | 6/1997 | Ferrari et al. |
| 5,770,697 | A | 6/1998 | Ferrari et al. |
| 5,792,742 | A | 8/1998 | Gold et al. |
| 6,018,030 | A | 1/2000 | Ferrari et al. |
| 6,207,446 | B1 | 3/2001 | Szostak et al. |
| 6,214,553 | B1 | 4/2001 | Szostak et al. |
| 6,258,558 | B1 | 7/2001 | Szostak et al. |
| 6,261,804 | B1 | 7/2001 | Szostak et al. |
| 6,281,344 | B1 | 8/2001 | Szostak et al. |
| 6,316,412 | B1 | 11/2001 | Ginsberg et al. |
| 6,342,219 | B1 | 1/2002 | Thorpe et al. |
| 6,383,775 | B1 | 5/2002 | Duff et al. |
| 6,462,189 | B1 | 10/2002 | Koide |
| 6,518,018 | B1 | 2/2003 | Szostak et al. |
| 6,559,126 | B2 | 5/2003 | Tournaire et al. |
| 6,660,492 | B1 | 12/2003 | Bode et al. |
| 6,818,418 | B1 | 11/2004 | Lipovsek et al. |
| 7,115,396 | B2 | 10/2006 | Lipovsek et al. |
| 7,556,925 | B2 | 7/2009 | Koide et al. |
| 7,598,352 | B2 | 10/2009 | Koide |
| 7,847,062 | B2 | 12/2010 | Chen et al. |
| 7,858,739 | B2 | 12/2010 | Chen et al. |
| 8,067,201 | B2 | 11/2011 | Morin et al. |
| 8,221,765 | B2 | 7/2012 | Camphausen et al. |
| 8,258,265 | B2 | 9/2012 | Koide |
| 8,263,741 | B2 | 9/2012 | Koide |
| 8,278,419 | B2 | 10/2012 | Jacobs et al. |
| 8,293,482 | B2 | 10/2012 | Jacobs et al. |
| 8,728,483 | B2 | 5/2014 | Camphausen et al. |
| 8,969,289 | B2 | 3/2015 | Gosselin et al. |
| 2002/0019517 | A1 | 2/2002 | Koide |
| 2002/0061307 | A1 | 5/2002 | Whitlow et al. |
| 2003/0104520 | A1 | 6/2003 | Ellington et al. |

(Continued)

FOREIGN PATENT DOCUMENTS

| | | | |
|---|---|---|---|
| CA | 2293632 | A1 | 12/1998 |
| DE | 19646372 | C1 | 6/1997 |

(Continued)

OTHER PUBLICATIONS

Ackermann, Maximilian et al., "Anti-VEGFR2 and anti-IGF-1R-Adnectins inhibit Ewing's sarcoma A673-xenograft growth and normalize tumor vascular architecture," Angiogenesis, vol. 15:685-695 (2012).

(Continued)

*Primary Examiner* — Anand Desai

(74) *Attorney, Agent, or Firm* — Nelson Mullins Riley & Scarborough LLP; Jane E. Remillard, Esq.; Christopher L. Frank

(57) ABSTRACT

The present invention relates to an antibody-like protein based on the tenth fibronectin type III domain ($^{10}$Fn3) that binds to serum albumin. The invention further relates to fusion molecules comprising a serum albumin-binding $^{10}$Fn3 joined to a heterologous protein for use in diagnostic and therapeutic applications.

19 Claims, 22 Drawing Sheets

(56) References Cited

U.S. PATENT DOCUMENTS

Figure 1A:
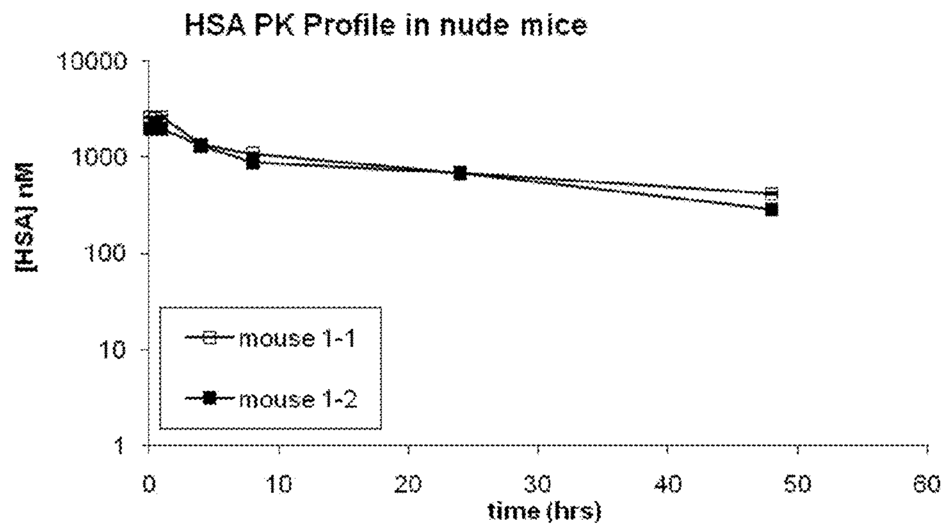

| | | | |
|---|---|---|---|
| 2003/0170753 | A1 | 9/2003 | Koide |
| 2003/0186385 | A1 | 10/2003 | Koide |
| 2005/0255548 | A1 | 11/2005 | Lipovsek et al. |
| 2006/0246059 | A1 | 11/2006 | Lipovsek et al. |
| 2007/0071675 | A1 | 3/2007 | Wu et al. |
| 2007/0082365 | A1 | 4/2007 | Lipovsek et al. |
| 2007/0160533 | A1 | 7/2007 | Chen et al. |
| 2008/0108798 | A1 | 5/2008 | Lipovsek et al. |
| 2008/0193445 | A1 | 8/2008 | Goetsch et al. |
| 2008/0220049 | A1 | 9/2008 | Chen et al. |
| 2009/0176654 | A1 | 7/2009 | Cappuccilli et al. |
| 2010/0144601 | A1 | 6/2010 | Jacobs et al. |
| 2010/0152063 | A1 | 6/2010 | Cappuccilli et al. |
| 2010/0273216 | A1 | 10/2010 | Morin et al. |
| 2010/0298541 | A1 | 11/2010 | Wu et al. |
| 2011/0021746 | A1 | 1/2011 | Cappuccilli et al. |
| 2011/0038866 | A1 | 2/2011 | Hastewell et al. |
| 2011/0123545 | A1 | 5/2011 | Marsh et al. |
| 2011/0124527 | A1 | 5/2011 | Cappuccilli et al. |
| 2011/0275535 | A1 | 11/2011 | Loew |
| 2012/0208704 | A1 | 8/2012 | Loew et al. |
| 2012/0270797 | A1 | 10/2012 | Wittrup et al. |
| 2013/0079243 | A1 | 3/2013 | Diem et al. |
| 2014/0094595 | A1 | 4/2014 | Lipovsek et al. |
| 2014/0349929 | A1 | 11/2014 | Camphausen et al. |

FOREIGN PATENT DOCUMENTS

| | | | |
|---|---|---|---|
| EP | 0962527 | A1 | 12/1999 |
| EP | 0985039 | B1 | 3/2000 |
| EP | 1477561 | B1 | 11/2004 |
| EP | 1266025 | B1 | 11/2006 |
| EP | 1137941 | B1 | 8/2009 |
| EP | 2141243 | A2 | 1/2010 |
| EP | 2385067 | A1 | 11/2011 |
| EP | 2439212 | A1 | 4/2012 |
| EP | 2379718 | B1 | 3/2013 |
| JP | 2001-500531 | | 1/2001 |
| JP | 2007-516707 | | 6/2007 |
| WO | 92/02536 | A1 | 2/1992 |
| WO | 93/03172 | A1 | 2/1993 |
| WO | 95/11922 | A1 | 5/1995 |
| WO | 96/22391 | A1 | 7/1996 |
| WO | 98/12226 | A1 | 3/1998 |
| WO | 98/31700 | A1 | 7/1998 |
| WO | 98/56915 | A2 | 12/1998 |
| WO | 99/51773 | A1 | 10/1999 |
| WO | 00/34784 | A1 | 6/2000 |
| WO | 00/34787 | A1 | 6/2000 |
| WO | 01/07657 | A1 | 2/2001 |
| WO | 01/64942 | A1 | 9/2001 |
| WO | 02/04523 | A2 | 1/2002 |
| WO | 02/32925 | A2 | 4/2002 |
| WO | 02/081497 | A2 | 10/2002 |
| WO | 02/088171 | A2 | 11/2002 |
| WO | 03/022858 | A2 | 3/2003 |
| WO | 03/104418 | A2 | 12/2003 |
| WO | 2005/056764 | A2 | 6/2005 |
| WO | 2006/020258 | A2 | 2/2006 |
| WO | 2007/012614 | A2 | 2/2007 |
| WO | 2007/044688 | A1 | 4/2007 |
| WO | 2007/062188 | A2 | 5/2007 |
| WO | 2007/092537 | A2 | 8/2007 |
| WO | 2007/096076 | A2 | 8/2007 |
| WO | 2007/121894 | A2 | 11/2007 |
| WO | 2008/031098 | A1 | 3/2008 |
| WO | 2008/048970 | A2 | 4/2008 |
| WO | 2008/066752 | A2 | 6/2008 |
| WO | 2008/097497 | A2 | 8/2008 |
| WO | 2008/108986 | A2 | 9/2008 |
| WO | 2009/023184 | A2 | 2/2009 |
| WO | 2009/025806 | A2 | 2/2009 |
| WO | 2009/058379 | A2 | 5/2009 |
| WO | 2009/073115 | A1 | 6/2009 |
| WO | 2009/083804 | A2 | 7/2009 |
| WO | 2009/086116 | A2 | 7/2009 |
| WO | 2009/102421 | A2 | 8/2009 |
| WO | 2009/133208 | A1 | 11/2009 |
| WO | 2009/142773 | A2 | 11/2009 |
| WO | 2010/051274 | A2 | 5/2010 |
| WO | 2010/051310 | A2 | 5/2010 |
| WO | 2010/060095 | A1 | 5/2010 |
| WO | 2010/069913 | A1 | 6/2010 |
| WO | 2010/093627 | A2 | 8/2010 |
| WO | 2010/093771 | A1 | 8/2010 |
| WO | 2011/020033 | A2 | 2/2011 |
| WO | 2011/035202 | A2 | 3/2011 |
| WO | 2011/051333 | A1 | 5/2011 |
| WO | 2011/051466 | A1 | 5/2011 |
| WO | 2011/092233 | A1 | 8/2011 |
| WO | 2011/100700 | A2 | 8/2011 |
| WO | 2011/103105 | A1 | 8/2011 |
| WO | 2011/130324 | A1 | 10/2011 |
| WO | 2011/130328 | A1 | 10/2011 |
| WO | 2011/130354 | A1 | 10/2011 |
| WO | 2011/137319 | A2 | 11/2011 |
| WO | 2011/140086 | A2 | 11/2011 |
| WO | 2011/150133 | A2 | 12/2011 |
| WO | 2012/016245 | A2 | 2/2012 |
| WO | 2012/088006 | A1 | 6/2012 |
| WO | 2012/142515 | A2 | 10/2012 |
| WO | 2012/158678 | A1 | 11/2012 |
| WO | 2012/158739 | A1 | 11/2012 |
| WO | 2013/049275 | A1 | 4/2013 |

OTHER PUBLICATIONS

Apte, Aaron N. et al., "Anchor-Ligated cDNA Libraries: A Technique for Generating a cDNA Library for the Immediate Cloning of the 5' Ends of mRNAs," BioTechniques, vol. 15(5):890-893 (1993).

Baggio, Rick et al., "Identification of epitope-like consensus motifs using mRNA display," Journal of Molecular Recognition, vol. 15:126-134 (2002).

Baron, Martin et al., "H NMR Assignment and Secondary Structure of the Cell Adhesion Type III Module of Fibronectin," Biochemistry, vol. 31:2068-2073 (1992).

Baron, Martin et al., "Protein modules," TIBS, vol. 16:13-17 (1991).

Batori, Vincent et al., "Exploring the potential of the monobody scaffold: effects of loop elongation on the stability of a fibronectin type III domain," Protein Engineering, vol. 15(12):1015-1020 (2002).

Bianchi, Elisabetta et al., "High Level Expression and Rational Mutagenesis of a Designed Protein, the Minibody," J. Mol. Biol., vol. 236:649-659 (1994).

Boder, Eric T. et al., "Directed evolution of antibody fragments with monovalent femtomolar antigen-binding affinity," PNAS, vol. 97(20):10701-10705 (2000).

Boder, Eric T. et al., "Yeast surface display for screening combinatorial polypeptide libraries," Nature Biotechnology, vol. 15:553-557 (1997).

Bork, P. et al. "The Immunoglobulin Fold, Structural Classification, Sequence Patterns and Common Core," J. Mol. Biol., vol. 242:309-320 (1994).

Bork, Peer et al., "Go hunting in sequence databases but watch out for the traps," TIG, vol. 12(10):425-427 (1996).

Bork, Peer et al., "Proposed acquisition of an animal protein domain by bacteria," Proc. Natl. Acad. Sci. USA, vol. 89:8990-8994 (1992).

Bork, Peer, "Powers and Pitfalls in Sequence Analysis: The 70% Hurdle," Genome Research, vol. 10:398-400 (2000).

Brenner, Steven E., "Errors in genome annotation," TIG, vol. 15(4):132-133 (1999).

Brock, Kenny V. et al., "Nucleotide sequencing of 5' and 3' termini of bovine viral diarrhea virus by RNA ligation and PCR," Journal of Virological Methods, vol. 38:39-46 (1992).

Bruzik, James P. et al., "Spliced leader RNAs from lower eukaryotes are trans-spliced in mammalian cells," Nature, vol. 360(6405):692-695 (1992).

(56) References Cited

OTHER PUBLICATIONS

Caliceti, Paolo et al., "Pharmacokinetic and biodistribution properties of poly(ethylene glycol)-protein conjugates," Advanced Drug Delivery Reviews, vol. 55:1261-1277 (2003).
Campbell, Iain D. et al., "Building proteins with fibronectin type III modules, Fibronectin type III modules are versatile components of many proteins. Recent structures of module pairs show how these modules are joined together," Structure, vol. 2:333-337 (1994).
Choy, E.H.S. et al., "Efficacy of a novel PEGylated humanized anti-TNF fragment (CDP870) in patients with rheumatoid arthritis: a phase II double-blinded, randomized, dose-escalating trial," Rheumatology, vol. 41:1133-1137 (2002).
Clackson, Tim et al., "In vitro selection from protein and peptide libraries," TibTech, vol. 12(5):173-184 (1994).
Clackson, Tim et al., "Making antibody fragments using phage display libraries," Nature, vol. 352:624-628 (1991).
Clarke, Jane et al., "Folding and Stability of a Fibronectin Type III Domain of Human Tenascin," J. Mol. Biol., vol. 270:771-778 (1997).
Connelly, Roberta et al., "Mitogenic properties of a bispecific single-chain Fv-lg fusion generated from CD2-specific mAb to distinct epitopes," International Immunology, vol. 10(12):1863-1872 (1998).
Copie, Valerie et al., "Solution Structure and Dynamics of Linked Cell Attachment Modules of Mouse Fibronectin Containing the RGD and Synergy Regions: Comparison wtih the Human Fibronectin Crystal Structure," J. Mol. Biol., vol. 277:663-682 (1998).
Cota, Ernesto et al., "Two Proteins with the Same Structure Respond very Differently to Mutation: The Role of Plasticity in Protein Stability," J. Mol. Biol., vol. 302:713-725 (2000).
Cujec, Thomas P. et al., "Selection of v-Abl Tyrosine Kinase Substrate Sequences from Randomized Peptide and Cellular Proteomic Libraries Using mRNA Display," Chemistry & Biology, vol. 9:253-264 (2002).
Devlin, James J. et al., "Random Peptide Libraries: A Source of Specific Protein Binding Molecules," Science, vol. 249:404-406 (1990).
DGENE Search Results, 33 pages (2005).
Dickinson, Craig D. et al., "Crystal Structure of the Tenth Type III Cell Adhesion Module of Human Fibronectin," J. Mol. Biol., vol. 236:1079-1092 (1994).
Dickinson, Craig D. et al., "Crystals of the Cell-binding Module of Fibronectin Obtained from a Series of Recombinant Fragments Differing in Length," J. Mol. Biol., vol. 238:123-127 (1994).
Doerks, Tobias et al., "Protein annotation: detective work for function prediction," TIG, vol. 14(6):248-250 (1998).
Duan, Jinzhu et al., "Fibronectin Type III Domain Based Monobody with High Avidity," Biochemistry, vol. 46:12656-12664 (2007).
Ely, Kathryn R. et al., "Common molecular scaffold for two unrelated RGD molecules," Protein Engineering, vol. 8(8):823-827 (1995).
Emanuel, Stuart L. et al., "A fibronectin scaffold approach to bispecific inhibitors of epidermal growth factor receptor and insulin-like growth factor-I receptor," MAbs, vol. 3(1):38-48 (2011).
Emanuel, Stuart L. et al., "Adnectins as a platform for multi-specific targeted biologics: A novel bispecific inhibitor of EGFR and IGF-IR growth factor receptors," Cancer Research, vol. 70(8 Suppl. 1), Abstract 2586, 1 page, AACR 101st Annual Meeting (2010).
European Office Action for Application No. 06013825.2, 9 pages, dated Sep. 17, 2008.
European Office Action for Application No. 09167669.2, 7 pages, dated Dec. 28, 2009.
Fenton, Bruce et al., "Pathophysiological effects of antibodies to IGF-1R and VEGFR-2 plus fractionated radiation in DU145 prostate carcinoma xenografts," Radiation Research Society 2005 Annual Meeting, Abstract No. PP109, 1 page (2005).
Ferguson, Kimberly C. et al., "The SL1 trans-spliced leader RNA performs an essential embryonic function in Caenorhabditis elegans that can also be supplied by SL2 RNA," Genes & Development, vol. 10:1543-1556 (1996).
GenBank Accession No. AAC48614, MacLeod, J.N. et al., "Fibronectin mRNA splice variant in articular cartilage lacks bases encoding the V, III-15, and I-10 protein segments," J. Biol. Chem., vol. 271(31):18954-18960 (1996), 2 pages, (1996).
GenBank Accession No. CAA26536, Kornblihtt, A.R. et al., "Primary structure of human fibronectin: differential splicing may generate at least 10 polypeptides froma single gene," EMBO J., vol. 4(7):1755-1759 (1985), 7 pages, (1996).
GenBank Accession No. P07589, Skorstengaard, K. et al., "Complete primary structure of bovine plasma fibronectin," Eur. J. Biochem., vol. 161(2):441-453 (1986), 9 pages, (1997).
GenBank Accession No. X02761, Kornblihtt, A.R. et al., "Primary structure of human fibronectin: differential splicing may generate at least 10 polypeptides from a single gene," EMBO J., vol. 4(7):1755-1759 (1985), 4 pages, (1996).
Ghosh, Gourisankar et al., "Structure of NF-kappaB p50 homodimer bound to a kappaB site," Nature, vol. 373:303-310 (1995).
Goedert, M. et al., "Cloning and sequencing of the cDNA encoding an isoform of microtubule-associated protein tau containing four tandem repeats: differential expression of tau protein mRNAs in human brain," The EMBO Journal, vol. 8(2):393-399 (1989).
Grant, Richard P. et al., "Structural Requirements for Biological Activity of the Ninth and Tenth FIII Domains of Human Fibronectin," The Journal of Biological Chemistry, vol. 272(10):6159-6166 (1997).
Hamers-Casterman, C. et al., "Naturally occurring antibodies devoid of light chains," Nature, vol. 363:446-448 (1993).
Hammond, Philip W. et al., "In Vitro Selection and Characterization of Bcl-XL-binding Proteins from a Mix of Tissue-specific mRNA Display Libraries," The Journal of Biological Chemistry, vol. 276(24):20898-20906 (2001).
Harpaz, Yahouda et al., "Many of the IMmunoglobulin Superfamily Domains in Cell Adhesion Molecules and Surface Receptors Belong to a New Structural Set Which is Close to That Containing Variable Domains," J. Mol. Biol., vol. 238:528-539 (1994).
Hocking, Denise C. et al., "A Novel Role for the Integrin-binding III-10 Module in Fibronectin Matrix Assembly," The Journal of Cell Biology, vol. 133(2):431-444 (1996).
Hocking, Denise C. et al., "Activation of Distinct alpha5beta1-mediated Signaling Pathways by Fibronectin's Cell Adhesion and Matrix Assembly Domains," The Journal of Cell Biology, vol. 141(1):241-253 (1998).
Husimi, Y. et al., "Role of the Virus-type Strategy in Encoded Molecular Evolution," Progress in Biophysics and Molecular Biology, vol. 65(Suppl. 1):64 (1996).
Hynes, Richard O. et al., "Integrins: Versability, Modulation, and Signaling in Cell Adhesion," Cell, vol. 69:11-25 (1992).
International Preliminary Examination Report for Application No. PCT/US01/06414, 6 pages, dated Aug. 27, 2002.
International Preliminary Examination Report for Application No. PCT/US01/32233, 5 pages, dated Dec. 10, 2003.
International Preliminary Examination Report for Application No. PCT/US99/29317, 4 pages, dated Aug. 14, 2000.
International Preliminary Report on Patentability and Written Opinion for Application No. PCT/US2009/003192, 12 pages, dated Nov. 23, 2010.
International Preliminary Report on Patentability and Written Opinion for Application No. PCT/US2011/034998, 10 pages, dated Nov. 6, 2012.
International Search Report for Application No. PCT/US01/06414, 5 pages, dated Aug. 7, 2001.
International Search Report for Application No. PCT/US01/32233, 3 pages, dated Jun. 12, 2003.
International Search Report for Application No. PCT/US2009/003192, 8 pages, dated Jun. 1, 2010.
International Search Report for Application No. PCT/US2011/034998, 5 pages, dated Jul. 17, 2012.

(56) References Cited

OTHER PUBLICATIONS

International Search Report for Application No. PCT/US99/29317, 2 pages, dated Apr. 6, 2000.
Jung, Gyoo Yeol et al., "A Functional Protein Chip for Pathway Optimization and in Vitro Metabolic Engineering," Science, vol. 304:428-431 (2004).
Keefe, Anthony D. et al., "Functional proteins from a random-sequence library," Nature, vol. 410:715-718 (2001).
King, Catherine A. et al., "DNA vaccines with single-chain Fv fused to fragment C of tetanus toxin induce protective immunity against lymphoma and myeloma," Nature Medicine, vol. 4(11):1281-1286 (1998).
Kohler, G. et al., "Continuous cultures of fused cells secreting antibody of predefined specificity," Nature, vol. 256:495-497 (1975).
Koide, Akiko et al., "Monobodies. Antibody Mimics Based on the Scaffold of the Fibronectin Type III Domain," Methods in Molecular Biology, vol. 352: Protein Engineering Protocols, K.M. ARndt (Ed.), Humana Press, Totowa, NJ, Chapter 6, pp. 95-109 (2007).
Koide, Akiko et al., "Stabilization of a Fibronectin Type III Domain by the Removal of Unfavorable Electrostatic Interactions on the Protein Surface," Biochemistry, vol. 40:10326-10333 (2001).
Koide, Akiko et al., "The Fibronectin Type III Domain as a Scaffold for Novel Binding Proteins," J. Mol. Biol., vol. 284:1141-1151 (1998).
Koide, Shohei et al., "Directed Evolution of Fibronectin Type III Domain to Novel Ligand Binding Proteins," FASEB J., vol. 11(9 Suppl.), Poster No. M40, p. A837, (1997).
Koide, Shohei et al., "Directed Evolution of Fibronectin Type III Domain to Novel Ligand Binding Proteins," The Faseb Journal, vol. 11(9):A1155, Poster No. 1739 (1997).
Ku, Jung et al., "Alternate protein frameworks for molecular recognition," Proc. Natl. Acad. Sci. USA, vol. 92:6552-6556 (1995).
Kurz, Markus et al., "Psoralen photo-crosslinked mRNA-puromycin conjugates: a novel template for the rapid and facile preparation of mRNA-protein fusions," Nucleic Acids Research, vol. 28(18):e83, 5 pages. (2000).
Leahy, Daniel J. et al., "2.0 A Crystal Structure of a Four-Domain Segment of Human Fibronectin Encompassing the RGD Loop and Synergy Region," Cell, vol. 84:155-164 (1996).
Leahy, Daniel J. et al., "Structure of a Fibronectin Type III Domain from Tenascin Phased by MAD Analysis of the Selenomethionyl Protein," Science, vol. 258:987-991 (1992).
Lee, Grace et al., "Strong Inhibition of Fibrogen Binding to Platelet Receptor Alpha2b beta 3 by RGD Sequences installed into the Presentation Scaffold," Prot. Eng., vol. 6:745-754 (1993).
Lipovsek, Dasa et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," J. Mol. Biol., vol. 368:1024-1041 (2007).
Lipovsek, Dasa et al., "In-vitro protein evolution by ribosome display and mRNA display," Journal of Immunological Methods, vol. 290:51-67 (2004).
Litvinovich, Sergei V. et al., "Interactions Between Type III Domains in the 110 kDa Cell-binding Fragments of Fibronectin," J. Mol. Biol., vol. 248:611-626 (1995).
Lombardo, A. et al., "Conformational flexibility and crystallization of tandemly linked type III modules of human fibronectin," Protein Science, vol. 5:1934-1938 (1996).
Lu, Dan et al., "Simultaneous Blockade of Both the Epidermal Growth Factor Receptor and the Insulin-like Growth Factor Receptor Signaling Pathways in Cancer Cells with a Fully Human Recombinant Bispecific Antibody," The Journal of Biological Chemistry, vol. 279(4):2856-2865 (2004).
Main, Alison L. et al., "The Three-Dimensional Structure of the Tenth Type III Module of Fibronectin: An Insight into RGD-Mediated Interactions," Cell, vol. 71:671-678 (1992).
Mao, Yong et al., "Fibronectin fibrillogenesis, a cell-mediated matrix assembly process," Matrix Biology, vol. 24:389-399 (2005).
Markland, William et al., "Iterative Optimization of High-Affinity Protease Inhibitors Using Phage Display. 1. Plasmin," Biochemistry, vol. 35:8045-8057 (1996).
Markland, William et al., "Iterative Optimization of High-Affinity Protease Inhibitors Using Phage Display. 2. Plasma Kallikrein and Thrombin," Biochemistry, vol. 35:8058-8067 (1996).
Maruyama, Kazuo et al., "Oligo-capping: a simple method to replace the cap structure of eukaryotic mRNAs with oligoribonucleotides," Gene, vol. 138:171-174 (1994).
Mattheakis, Larry C. et al., "An in vitro polysome display system for identifying ligands from very large peptide libraries," Proc. Natl. Acad. Sci. USA, vol. 91:9022-9026 (1994).
McConnell, Stephen J. et al., "Tendamistat as a Scaffold for Conformationally Constrained Phage Peptide Libraries," J. Mol. Biol., vol. 250:460-470 (1995).
Meinke, A. et al., "Cellulose-Binding Polypeptides from Cellulomonas fimi: Endoglucanase D (CenD), a Family A beta-1,4-Glucanase," Journal of Bacteriology, vol. 175(7):1910-1918 (1993).
Muller, Christoph W. et al., "Structure of the NF-kappaB p50 homodimer bound to DNA," Nature, vol. 373:311-317 (1995).
Muyldermans, Serge, "Single domain camel antibodies: current status," Reviews in Molecular Biotechnology, vol. 74:277-302 (2001).
Nemoto, Naoto et al., "In vitro virus: Bonding of mRNA bearing puromycin at the 3'-terminal end to the C-terminal end of its encoded protein on the ribosome in vitro," FEBS Letters, vol. 414:405-408 (1997).
Ngo, J. Thomas et al., "Computational Complexity Protein Structure Prediction, and the Levinthal Paradox," The Protein Folding Problem and Tertiary Structure Prediction, Birkhauser, Boston, MA, K. Merz (Ed.), Chapter 14, pp. 491-495 (1994).
Niemeyer, Christof M. et al., "Oligonucleotide-directed self-assembly of proteins: semisynthetic DNA—streptavidin hybrid molecules as connectors for the generation of macroscopic arrays and the construction of supramolecular bioconjugates," Nucleic Acids Research, vol. 22(25):5530-5539 (1994).
Nilsen, Timothy W., "Trans-Splicing in Protozoa and Helminths," Infections Agents and Disease, vol. 1:212-218 (1992).
Nord, Karin et al., "A combinatorial library of an alpha-helical bacterial receptor domain," Prot. Eng., vol. 8:601-608 (1995).
Nord, Karin et al., "Binding proteins selected from combinatorial libraries of an alpha-helical bacterial receptor domain," Nature Biotechnology, vol. 15:772-777 (1997).
Notice of Opposition to European Patent No. 1137941 (Application No. 99 967 261.1), 29 pages, dated May 11, 2010.
Nygren, Per-Ake et al., "Scaffolds for engineering novel binding sites in proteins," Current Opinion in Structural Biology, vol. 7:463-469 (1997).
Parker, M.H. et al., "Antibody mimics based on human fibronectin type three domain engineered for thermostability and high-affinity binding to vascular endothelial growth factor receptor two," Protein Engineering, Design & Selection, vol. 18(9):435-444 (2005).
Partial European Search Report for Application No. 01981621.4, 5 pages, dated Feb. 25, 2005.
Plaxco, Kevin W. et al., "A Comparison of the Folding Kinetics and Thermodynamics of Two Homologous Fibronectin Type III Modules," J. Mol. Biol., vol. 270:763-770 (1997).
Plaxco, Kevin W. et al., "Rapid refolding of a proline-rich all-beta-sheet fibronectin type III module," Proc. Natl. Acad. Sci. USA, vol. 93:10703-10706 (1996).
Potts, Jennifer R. et al., "Fibronectin structure and assembly," Current Biology, vol. 6:648-655 (1994).
Potts, Jennifer R. et al., "Structure and Function of Fibronectin Modules," Matrix Biology, vol. 15:313-320 (1996).
Roberts, Richard W. et al., "RNA-peptide fusions for the in vitro selection of peptides and proteins," Proc. Natl. Acad. Sci. USA, vol. 94:12297-12302 (1997).
Roberts, Richard W., "Totally in vitro protein selection using mRNA-protein fusions and ribosome display," Current Opinion in Chemical Biology, vol. 3:268-273 (1999).

(56) References Cited

OTHER PUBLICATIONS

Rottgen, Peter et al., "A human pancreatic secretory trypsin inhibitor presenting a hyperveriable highly constrained epitope via monovalent phagemid display," Gene, vol. 164:243-250 (1995).
Scott, Jamie K. et al., "Searching for Peptide Ligands with an Epitope Library," Science, vol. 249:386-390 (1990).
Shibata, K. et al., "An attempt to substitute the cell binding domain of human fibronectin in lambda phage J protein: Computer design and expression," Biochimie, vol. 75:459-465 (1993).
Skolnick, Jeffrey et al., "From genes to protein structure and function: novel applications of computational approaches in the genomic era," TibTech, vol. 18:34-39 (2000).
Smith, George P. et al., "Phage Display," Chem. Rev., vol. 97:391-410 (1997).
Smith, Temple F. et al., "The challenges of genome sequence annotation of 'The devil is in the details,'" Nature Biotechnology, vol. 15:1222-1223 (1997).
Supplementary European Search Report for Application No. 01913159.8, 3 pages, dated Dec. 21, 2004.
Supplementary European Search Report for Application No. 99967261.1, 3 pages, dated Mar. 6, 2002.
Tang, Lisa et al., "Pharmacokinetic Aspects of Biotechnology Products," Journal of Pharmaceutical Sciences, vol. 93 (9):2184-2204 (2004).
Tokuriki, Nobuhiko et al., "Stability effects of mutations and protein evolvability," Current Opinion in Structural Biology, vol. 19:596-604 (2009).
Tramontano, Anna et al., "The Making of the Minibody: an Engineered beta-Protein for the Display of Conformationally Constrained Peptides," Journal of Molecular Recognition, vol. 7:9-24 (1994).
Trinh, Ryan et al., "Optimization of codon pair use within the (GGGGS)3 linker sequence results in enhanced protein expression," Molecular Immunology, vol. 40:717-722 (2004).
Vuento, Matti et al., "Purification of Fibronectin from Human Plasma by Affinity Chromatography under Non-Denaturing Conditions," Biochem. J., vol. 183:331-337 (1979).
Wang, Cheng-I et al., "Isolation of a High Affinity Inhibitor of Urokinase-type Plasminogen Activator by Phage Display of Ecotin," The Journal of Biological Chemistry, vol. 270(20):12250-12256 (1995).
Watanabe, Takeshi et al., "Gene Cloning of Chitinase A1 from Bacillus circulans WL-12 Revealed Its Evolutionary Relationship to Serratia Chitinase and to the Type III Homology Units of Fibronectin," The Journal of Biological Chemistry, vol. 265:15659-15665 (1990).
Wells, James A., "Additivity of Mutational Effects in Proteins," Biochemistry, vol. 29(37):8509-8517 (1990).
Williams, Alan F. et al., "The Immunoglobulin Superfamily—Domains for Cell Surface Recognition," Ann. Rev. Immunol, vol. 6:381-405 (1988).
Williams, Michael J. et al., "Solution Structures of Modular Proteins by Nuclear Magnetic Resonance," Methods in Enzymology, vol. 245:451-469 (1994).
Wilson, David S. et al., "The use of mRNA display to select high-affinity protein-binding peptides," PNAS, vol. 98(7):3750-3755 (2001).
Written Opinion for Application No. PCT/US01/06414, 5 pages, dated Feb. 7, 2002.
Xu, Lihui et al., "Directed Evolution of High-Affinity Antibody Mimics Using mRNA Display," Chemistry & Biology, vol. 9:933-942 (2002).
Zdanov, Alexander et al., Structure of a single-chain antibody variable domain (Fv) fragment complexed with a carbohydrate antigen at 1.7—A resolution, Proc. Natl. Acad. Sci. USA, vol. 91:6423-6427 (1994).

Orthogonally Protected Amino Acids used in Solid Phase Synthesis

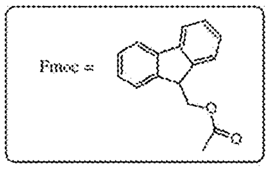

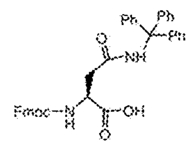

Fmoc-Asn(Trt)

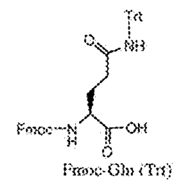

Fmoc-Gln (Trt)

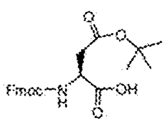

Fmoc-Asp(Bu$^t$)

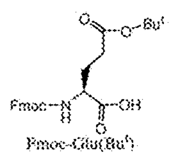

Fmoc-Glu(Bu$^t$)

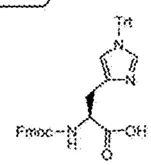

Fmoc-His (Trt)

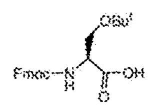

Fmoc-Ser(Bu$^t$)

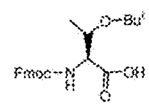

Fmoc-Thr-(Bu$^t$)

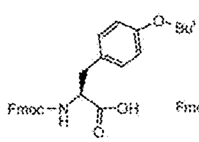

Fmoc-Tyr(Bu$^t$)

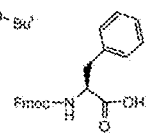

Fmoc-L-Phe

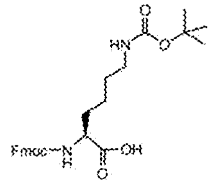

Fmoc-Lys (Boc)

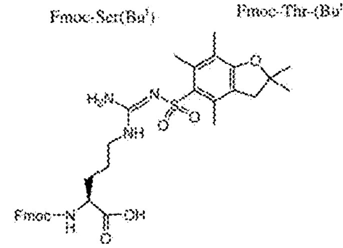

Fmoc-Arg (Pbf)

Fmoc-Gly

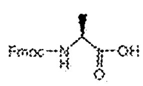

Fmoc-Ala

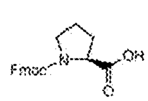

Fmoc-L-Pro

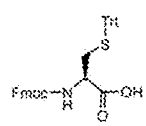

Fmoc-Cys(Trt)

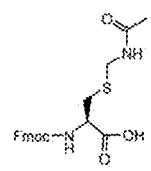

Fmoc-Cys(Acm)

Other Building Blocks Used for Solid Phase Synthesis

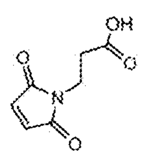

3-Maleimidopropionic acid (Mal)

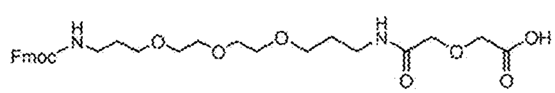

O-(N-Fmoc-3-aminopropyl)-O'-(N-diglycolyl-3-aminopropyl)-diethyleneglycol (Fmoc-$PEG_{20}$) - 20 atom PEG spacer

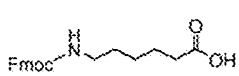

N-Fmoc-6-aminohexanoic acid (Fmoc-Ahx)

FIGURE 21

SERUM ALBUMIN BINDING MOLECULES

RELATED APPLICATIONS

This application is a divisional of U.S. patent application Ser. No. 13/098,851, filed May 2, 2011, which claims the benefit of U.S. Provisional Application No. 61/330,672, filed May 3, 2010, both of which are hereby incorporated by reference in their entireties.

INTRODUCTION

The utility of many therapeutics, particularly biologicals such as peptides, polypeptides and polynucleotides, suffer from inadequate serum half-lives. This necessitates the administration of such therapeutics at high frequencies and/or higher doses, or the use of sustained release formulations, in order to maintain the serum levels necessary for therapeutic effects. Frequent systemic administration of drugs is associated with considerable negative side effects. For example, frequent systemic injections represent a considerable discomfort to the subject, and pose a high risk of administration related infections, and may require hospitalization or frequent visits to the hospital, in particular when the therapeutic is to be administered intravenously. Moreover, in long term treatments daily intravenous injections can also lead to considerable side effects of tissue scarring and vascular pathologies caused by the repeated puncturing of vessels. Similar problems are known for all frequent systemic administrations of therapeutics, such as, for example, the administration of insulin to diabetics, or interferon drugs in patients suffering from multiple sclerosis. All these factors lead to a decrease in patient compliance and increased costs for the health system.

This application provides compounds that increase the serum half-life of various therapeutics, compounds having increased serum half-life, and methods for increasing the serum half-life of therapeutics. Such compounds and methods for increasing the serum half-life of therapeutics can be manufactured in a cost effective manner, possess desirable biophysical properties (e.g., Tm, substantially monomeric, or well-folded), and are of a size small enough to permit tissue penetration.

SUMMARY OF THE INVENTION

The present invention relates to serum albumin binding fibronectin type III tenth ($^{10}$Fn3) domains, and their use. Also disclosed herein are fusion molecules comprising serum albumin binding $^{10}$Fn3, and their use.

In one aspect, the present invention provides a polypeptide comprising a fibronectin type III tenth ($^{10}$Fn3) domain, wherein the $^{10}$Fn3 domain binds to domain I or II of human serum albumin (HSA) with a $K_D$ of 1 uM or less, and wherein the serum half-life of the polypeptide in the presence of albumin is at least 5-fold greater than the serum half-life of the polypeptide in the absence of serum albumin. In one embodiment, the $^{10}$Fn3 domain comprises a modified amino acid sequence in one or more of the BC, DE and FG loops relative to the wild-type $^{10}$Fn3 domain.

In certain embodiments, the $^{10}$Fn3 domain binds to HSA at a pH range of 5.5 to 7.4. In one embodiment, the $^{10}$Fn3 domain binds to HSA with a $K_D$ of 200 nM or less at pH range of 5.5 to 7.4. In another embodiment, the $^{10}$Fn3 domain binds to HSA with a $K_D$ of 200 nM or less at pH 5.5.

In some aspects, provided herein is a polypeptide comprising a $^{10}$Fn3 domain, wherein the $^{10}$Fn3 domain binds to HSA and comprises an amino acid sequence at least 70% identical to SEQ ID NO: 2. In one embodiment, the $^{10}$Fn3 domain comprises one or more of a BC loop comprising the amino acid sequence set forth in SEQ ID NO: 5, a DE loop comprising the amino acid sequence set forth in SEQ ID NO: 6, and an FG loop comprising the amino acid sequence set forth in SEQ ID NO: 7.

In any of the foregoing aspects and embodiments, the $^{10}$Fn3 domain also binds to one or more of rhesus serum albumin (RhSA), cynomolgous monkey serum albumin (CySA), or murine serum albumin (MuSA). In certain embodiments, the $^{10}$Fn3 domain does not cross-react with one or more of RhSA, CySA or MuSA.

In any of the foregoing aspects and embodiments, the $^{10}$Fn3 domain binds to HSA with a $K_D$ of 1 uM or less. In some embodiments, the $^{10}$Fn3 domain binds to HSA with a $K_D$ of 500 nM or less. In other embodiments, the $^{10}$Fn3 domain binds to HSA with a $K_D$ of at least 200 nM, 100 nM, 50 nM, 20 nM, 10 nM, or 5 nM.

In any of the foregoing aspects and embodiments, the $^{10}$Fn3 domain binds to domain I or II of HSA. In one embodiment, the $^{10}$Fn3 domain binds to both domains I and II of HSA. In some embodiments, the $^{10}$Fn3 domain binds to HSA at a pH range of 5.5 to 7.4. In other embodiments, the $^{10}$Fn3 domain binds to HSA with a $K_D$ of 200 nM or less at pH 5.5. In another embodiment, the $^{10}$Fn3 domain binds to HSA with a $K_D$ of at least 500 nM, 200 nM, 100 nM, 50 nM, 20 nM, 10 nM, or 5 nM at a pH range of 5.5 to 7.4. In one embodiment, the $^{10}$Fn3 domain binds to HSA with a $K_D$ of at least 500 nM, 200 nM, 100 nM, 50 nM, 20 nM, 10 nM, or 5 nM at pH 5.5.

In any of the foregoing aspects and embodiments, the serum half-life of the polypeptide in the presence of serum albumin is at least 2-fold greater than the serum half-life of the polypeptide in the absence of serum albumin. In certain embodiments, the serum half-life of the polypeptide in the presence of serum albumin is at least 5-fold, 7-fold, 10-fold, 12-fold, 15-fold, 20-fold, 22-fold, 25-fold, 27-fold, or 30-fold greater than the serum half-life of the polypeptide in the absence of serum albumin. In some embodiments, the serum albumin is any one of HSA, RhSA, CySA, or MuSA.

In any of the foregoing aspects and embodiments, the serum half-life of the polypeptide in the presence of serum albumin is at least 20 hours. In certain embodiments, the serum half-life of the polypeptide in the presence of serum albumin is at least 2 hours, 2.5 hours, 3 hours, 4 hours, 5 hours, 6 hours, 7 hours, 8 hours, 9 hours, 10 hours, 12 hours, 15 hours, 20 hours, 25 hours, 30 hours, 40 hours, 50 hours, 75 hours, 90 hours, 100 hours, 110 hours, 120 hours, 130 hours, 150 hours, 170 hours, or 200 hours. In some embodiments, the half-life of the polypeptide is observed in a primate (e.g., human or monkey) or a murine.

In one aspect, the present invention provides a polypeptide comprising a $^{10}$Fn3 domain, wherein the $^{10}$Fn3 domain binds to HSA and comprises a BC loop comprising the amino acid sequence set forth in SEQ ID NO: 5, a DE loop comprising the amino acid sequence set forth in SEQ ID NO: 6, and an FG loop comprising the amino acid sequence set forth in SEQ ID NO: 7. In another aspect, the $^{10}$Fn3 domain comprises one or more of a BC loop comprising the amino acid sequence set forth in SEQ ID NO: 5, a DE loop comprising the amino acid sequence set forth in SEQ ID NO: 6, and an FG loop comprising the amino acid sequence set forth in SEQ ID NO: 7.

In one aspect, the present invention provides a polypeptide comprising a $^{10}$Fn3 domain, wherein the $^{10}$Fn3 domain binds to HSA and comprises a BC loop comprising the amino acid sequence set forth in SEQ ID NO: 9, a DE loop comprising the amino acid sequence set forth in SEQ ID NO: 10, and an FG loop comprising the amino acid sequence set forth in SEQ ID NO: 11. In another aspect, the $^{10}$Fn3 domain comprises one or more of a BC loop comprising the amino acid sequence set forth in SEQ ID NO: 9, a DE loop comprising the amino acid sequence set forth in SEQ ID NO: 10, and an FG loop comprising the amino acid sequence set forth in SEQ ID NO: 11.

In one aspect, the present invention provides a polypeptide comprising a $^{10}$Fn3 domain, wherein the $^{10}$Fn3 domain binds to HSA and comprises a BC loop comprising the amino acid sequence set forth in SEQ ID NO: 13, a DE loop comprising the amino acid sequence set forth in SEQ ID NO: 14, and an FG loop comprising the amino acid sequence set forth in SEQ ID NO: 15. In another aspect, the $^{10}$Fn3 domain comprises one or more of a BC loop comprising the amino acid sequence set forth in SEQ ID NO: 13, a DE loop comprising the amino acid sequence set forth in SEQ ID NO: 14, and an FG loop comprising the amino acid sequence set forth in SEQ ID NO: 15.

In one aspect, the present invention provides a polypeptide comprising a $^{10}$Fn3 domain, wherein the $^{10}$Fn3 domain binds to HSA and comprises a BC loop comprising the amino acid sequence set forth in SEQ ID NO: 17, a DE loop comprising the amino acid sequence set forth in SEQ ID NO: 18, and an FG loop comprising the amino acid sequence set forth in SEQ ID NO: 19. In another aspect, the $^{10}$Fn3 domain comprises one or more of a BC loop comprising the amino acid sequence set forth in SEQ ID NO: 17, a DE loop comprising the amino acid sequence set forth in SEQ ID NO: 18, and an FG loop comprising the amino acid sequence set forth in SEQ ID NO: 19.

In any of the foregoing aspects and embodiments, the $^{10}$Fn3 domain also binds to one or more of rhesus serum albumin (RhSA), cynomolgous monkey serum albumin (CySA), or murine serum albumin (MuSA). In some embodiments, the $^{10}$Fn3 domain does not cross-react with one or more of RhSA, CySA or MuSA. In certain embodiments, the $^{10}$Fn3 domain binds to HSA with a $K_D$ of 1 uM or less. In other embodiments, the $^{10}$Fn3 domain binds to HSA with a $K_D$ of at least 1.5 uM, 1.2 uM, 1 uM, 700 nM, 500 nM, 300 nM, 200 nM, 100 nM, 75 nM, 50 nM, 25 nM, 10 nM, or 5 nM.

In any of the foregoing aspects and embodiments, the $^{10}$Fn3 domain binds to domain I or II of HSA. In certain embodiments, the $^{10}$Fn3 domain binds to both domains I and II of HSA. In certain embodiments, the $^{10}$Fn3 domain binds to HSA at a pH range of 5.5 to 7.4. In one embodiment, the $^{10}$Fn3 domain binds to HSA with a $K_D$ of 200 nM or less at pH 5.5. In another embodiment, the $^{10}$Fn3 domain binds to HSA with a $K_D$ of at least 500 nM, 200 nM, 100 nM, 50 nM, 20 nM, 10 nM, or 5 nM at a pH range of 5.5 to 7.4. In one embodiment, the $^{10}$Fn3 domain binds to HSA with a $K_D$ of at least 500 nM, 200 nM, 100 nM, 50 nM, 20 nM, 10 nM, or 5 nM at pH 5.5.

In any of the foregoing aspects and embodiments, the serum half-life of the polypeptide in the presence of serum albumin is at least 2-fold greater than the serum half-life of the polypeptide in the absence of serum albumin. In certain embodiments, the serum half-life of the polypeptide in the presence of serum albumin is at least 5-fold, 7-fold, 10-fold, 12-fold, 15-fold, 20-fold, 22-fold, 25-fold, 27-fold, or 30-fold greater than the serum half-life of the polypeptide in the absence of serum albumin. In some embodiments, the serum albumin is any one of HSA, RhSA, CySA, or MuSA.

In any of the foregoing aspects and embodiments, the serum half-life of the polypeptide in the presence of serum albumin is at least 20 hours. In certain embodiments, the serum half-life of the polypeptide in the presence of serum albumin is at least 2 hours, 2.5 hours, 3 hours, 4 hours, 5 hours, 6 hours, 7 hours, 8 hours, 9 hours, 10 hours, 12 hours, 15 hours, 20 hours, 25 hours, 30 hours, 40 hours, 50 hours, 75 hours, 90 hours, 100 hours, 110 hours, 120 hours, 130 hours, 150 hours, 170 hours, or 200 hours. In some embodiments, the half-life of the polypeptide is observed in a primate (e.g., human or monkey) or a murine.

In one aspect, the present invention provides a fusion polypeptide comprising a fibronectin type III tenth ($^{10}$Fn3) domain and a heterologous protein, wherein the $^{10}$Fn3 domain binds to HSA with a $K_D$ of 1 uM or less. In certain embodiments, the $^{10}$Fn3 domain comprises an amino acid sequence at least 70% identical to SEQ ID NO: 4. In one embodiment, the $^{10}$Fn3 domain comprises a BC loop having the amino acid sequence set forth in SEQ ID NO: 5, a DE loop having the amino acid sequence set forth in SEQ ID NO: 6, and an FG loop having the amino acid sequence set forth in SEQ ID NO:7. In another embodiment, the $^{10}$Fn3 domain comprises one or more of a BC loop having the amino acid sequence set forth in SEQ ID NO: 5, a DE loop having the amino acid sequence set forth in SEQ ID NO: 6, and an FG loop having the amino acid sequence set forth in SEQ ID NO: 7.

In one embodiment, the heterologous protein is selected from fibroblast growth factor 21 (FGF21), insulin, insulin receptor peptide, GIP (glucose-dependent insulinotropic polypeptide), bone morphogenetic protein 9 (BMP-9), amylin, peptide YY ($PYY_{3-36}$), pancreatic polypeptide (PP), interleukin 21 (IL-21), glucagon-like peptide 1 (GLP-1), Plectasin, Progranulin, Osteocalcin (OCN), Apelin, or a polypeptide comprising a $^{10}$Fn3 domain. In other embodiments, the heterologous protein is selected from GLP-1, Exendin 4, adiponectin, IL-1Ra (Interleukin 1 Receptor Antagonist), VIP (vasoactive intestinal peptide), PACAP (Pituitary adenylate cyclase-activating polypeptide), leptin, INGAP (islet neogenesis associated protein), BMP (bone morphogenetic protein), and osteocalcin (OCN). In one embodiment, the heterologous protein comprises the sequence set forth in SEQ ID NO: 118.

In certain embodiments, the heterologous protein comprises a second $^{10}$Fn3 domain that binds to a target protein other than serum albumin. In other embodiments, the fusion polypeptide further comprises a third $^{10}$Fn3 domain that binds to a target protein. In one embodiment, the third $^{10}$Fn3 domain binds to the same target as the second $^{10}$Fn3 domain. In other embodiments, the third $^{10}$Fn3 domain binds to a different target than the second $^{10}$Fn3 domain.

In one embodiment, the $^{10}$Fn3 domain of the fusion polypeptide also binds to one or more of rhesus serum albumin (RhSA), cynomolgous monkey serum albumin (CySA), or murine serum albumin (MuSA). In other embodiments, the $^{10}$Fn3 domain does not cross-react with one or more of RhSA, CySA or MuSA.

In certain embodiments, the $^{10}$Fn3 domain of the fusion polypeptide binds to HSA with a $K_D$ of 1 uM or less. In some embodiments, the $^{10}$Fn3 domain binds to HSA with a $K_D$ of 500 nM or less. In other embodiments, the $^{10}$Fn3 domain binds to HSA with a $K_D$ of at least 200 nM, 100 nM, 50 nM, 20 nM, 10 nM, or 5 nM.

In other embodiments, the $^{10}$Fn3 domain of the fusion polypeptide binds to domain I or II of HSA. In one embodiment, the $^{10}$Fn3 domain binds to both domains I and II of HSA. In some embodiments, the $^{10}$Fn3 domain binds to HSA at a pH range of 5.5 to 7.4. In other embodiments, the $^{10}$Fn3 domain binds to HSA with a $K_D$ of 200 nM or less at pH 5.5. In another embodiment, the $^{10}$Fn3 domain binds to HSA with a $K_D$ of at least 500 nM, 200 nM, 100 nM, 50 nM, 20 nM, 10 nM, or 5 nM at a pH range of 5.5 to 7.4. In one embodiment, the $^{10}$Fn3 domain binds to HSA with a $K_D$ of at least 500 nM, 200 nM, 100 nM, 50 nM, 20 nM, 10 nM, or 5 nM at pH 5.5.

In some embodiments, the serum half-life of the fusion polypeptide in the presence of serum albumin is at least 5-fold greater than the serum half-life of the polypeptide in the absence of serum albumin. In certain embodiments, the serum half-life of the fusion polypeptide in the presence of serum albumin is at least 2-fold, 5-fold, 7-fold, 10-fold, 12-fold, 15-fold, 20-fold, 22-fold, 25-fold, 27-fold, or 30-fold greater than the serum half-life of the polypeptide in the absence of serum albumin. In some embodiments, the serum albumin is any one of HSA, RhSA, CySA, or MuSA.

In certain embodiments, the serum half-life of the fusion polypeptide in the presence of serum albumin is at least 20 hours. In certain embodiments, the serum half-life of the fusion polypeptide in the presence of serum albumin is at least 2 hours, 2.5 hours, 3 hours, 4 hours, 5 hours, 6 hours, 7 hours, 8 hours, 9 hours, 10 hours, 12 hours, 15 hours, 20 hours, 25 hours, 30 hours, 40 hours, 50 hours, 75 hours, 90 hours, 100 hours, 110 hours, 120 hours, 130 hours, 150 hours, 170 hours, or 200 hours. In some embodiments, the half-life of the fusion polypeptide is observed in a primate (e.g., human or monkey) or a murine.

In any of the foregoing aspects and embodiments, the $^{10}$Fn3 domain comprises a sequence selected from SEQ ID NO: 8, 12, 16, 20, and 24-44.

In one aspect, the present invention provides a polypeptide comprising a fibronectin type III tenth ($^{10}$Fn3) domain, wherein the $^{10}$Fn3 domain (i) comprises a modified amino acid sequence in one or more of the AB, BC, CD, DE, EF and FG loops relative to the wild-type $^{10}$Fn3 domain, (ii) binds to a target molecule not bound by the wild-type $^{10}$Fn3 domain, and (iii) comprises a C-terminal tail having a sequence $(ED)_n$, wherein n is an integer from 3 to 7. In certain embodiments, the $^{10}$Fn3 domain comprises an amino acid sequence having at least 60% identity with the amino acid sequence set forth in residues 9-94 of SEQ ID NO: 1. In one embodiment, the C-terminal tail further comprises an E, I or EI at the N-terminus. In some embodiments, the C-terminal tail enhances the solubility and/or reduces aggregation of the polypeptide.

In certain embodiments, the $^{10}$Fn3 domain comprises a modified amino acid sequence in each of the BC, DE and FG loops relative to the wild-type $^{10}$Fn3 domain. In other embodiments, the polypeptide binds to the target with a $K_D$ of 1 uM or less.

In some aspects, the present invention provides a pharmaceutical composition comprising the polypeptide of any of the foregoing aspects and embodiments. In certain embodiments, the pharmaceutical composition comprises succinic acid, glycine, and sorbitol. In exemplary embodiments, the composition comprises 5 nM to 30 mM succinic acid, 5% to 15% sorbitol, and 2.5% to 10% glycine at pH 6.0. In certain embodiments, the composition comprises 10 mM succinic acid, 8% sorbitol, and 5% glycine at pH 6.0. In other embodiments, the pharmaceutical composition further comprises a physiologically acceptable carrier.

BRIEF DESCRIPTION OF THE DRAWINGS AND TABLES

Figure 1B:
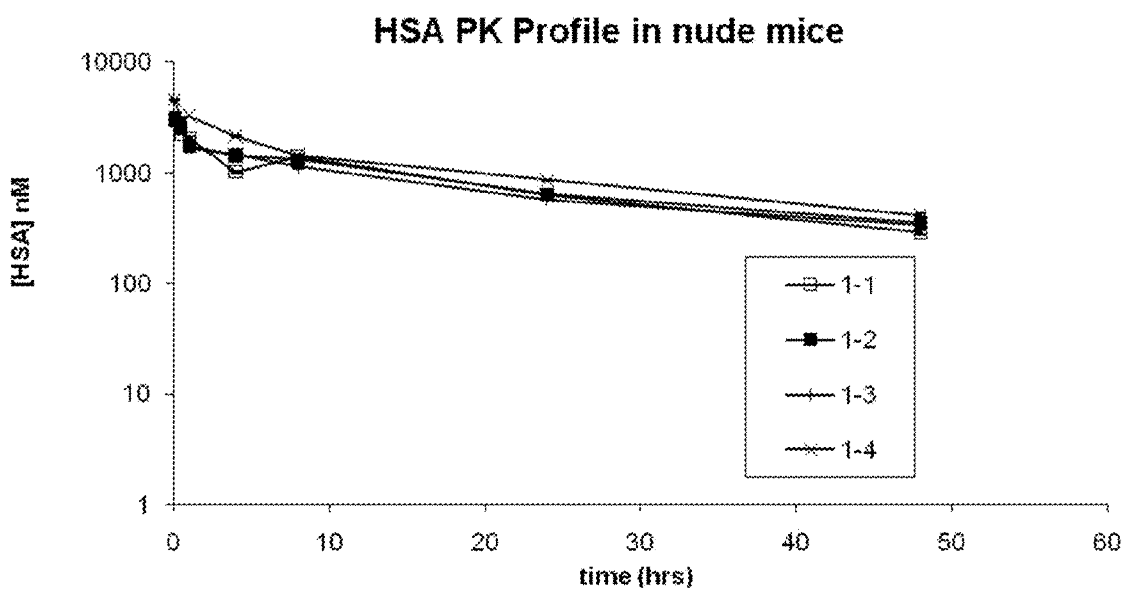

FIGS. 1A and 1B. In vivo HSA half-life in mice. HSA was injected into mice at 20 mg/kg (FIG. 1A) or 50 mg/kg (FIG. 1B).

Figure 2A:
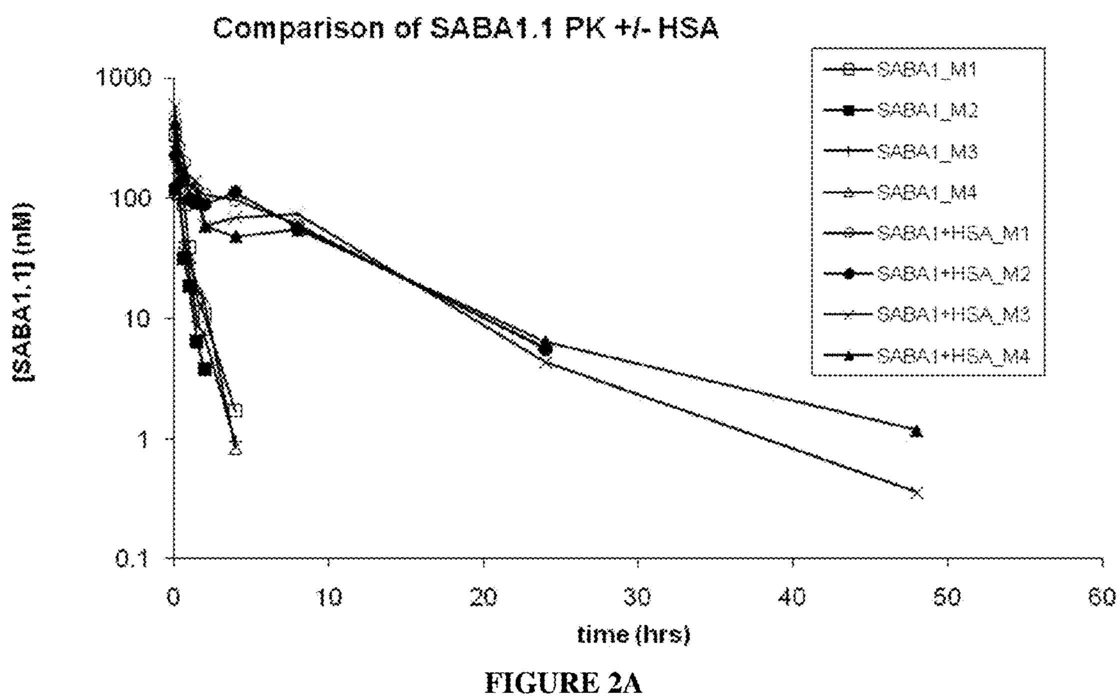
Figure 2B:
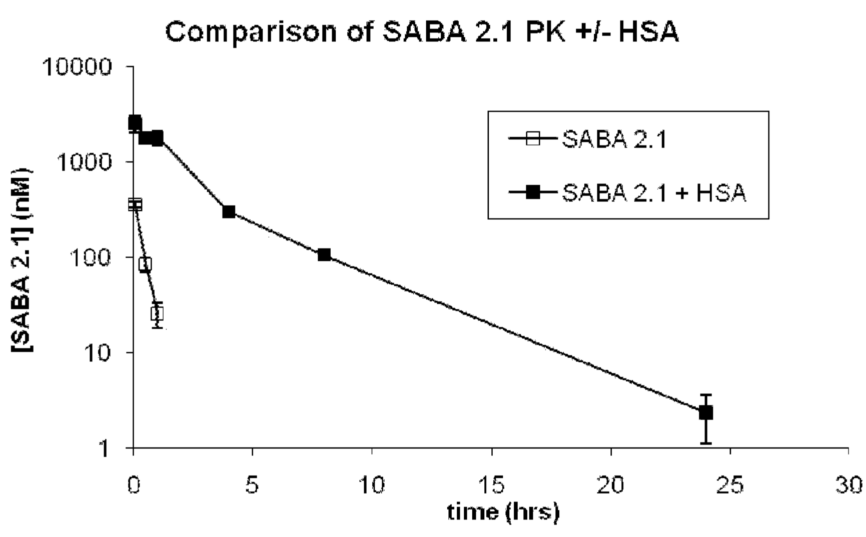
Figure 2C:
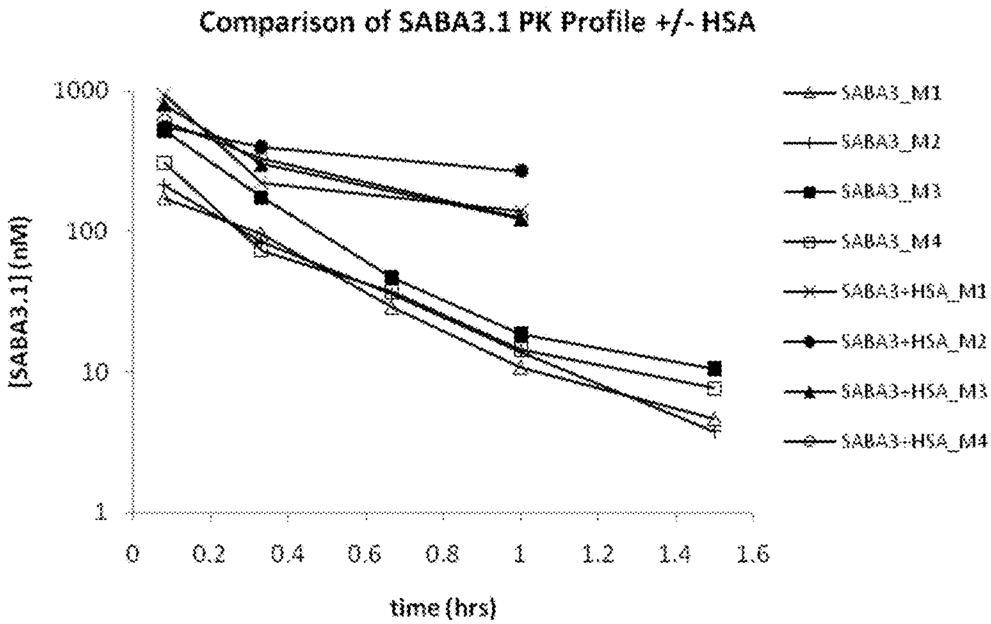

FIGS. 2A-2D. Half-life determination of SABA1-4 in mice. FIG. 2A: SABA1.1; FIG. 2B: SABA2.1; FIG. 2C: SABA3.1; and FIG. 2D: SABA4.1.

Figure 3:
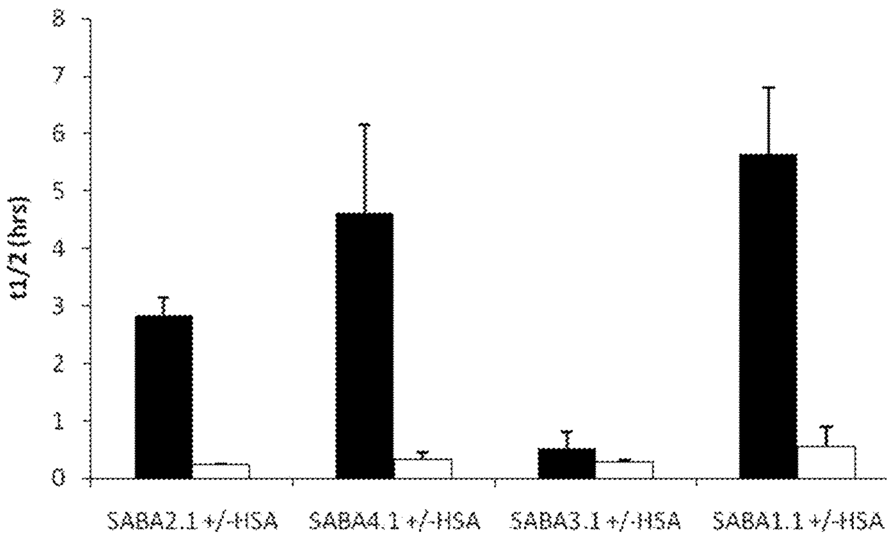

FIG. 3. Graph showing summary of half-life enhancement in mice of SABA1-4 when co-injected with HSA.

Figure 4A:
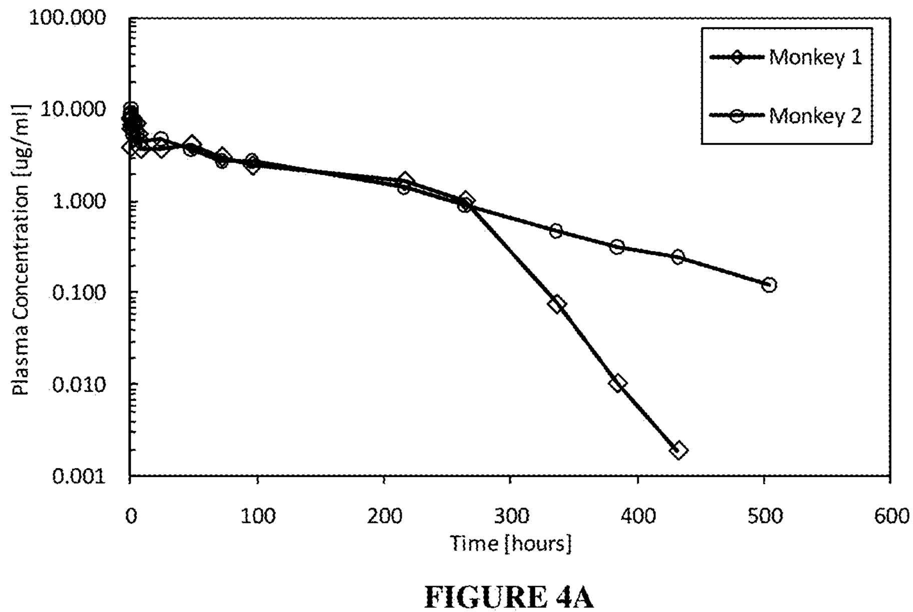
Figure 4B:
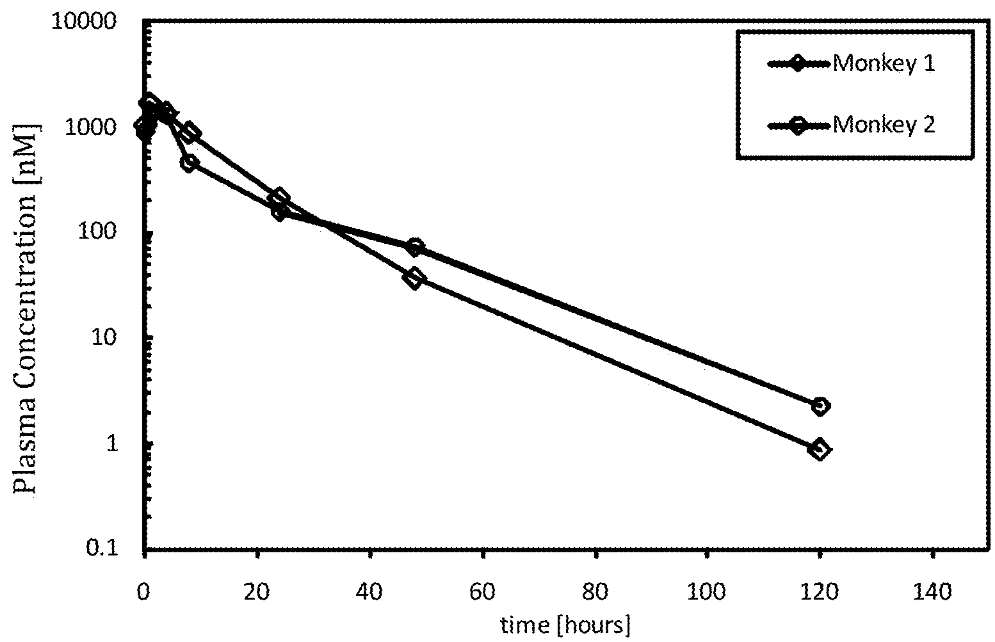

FIGS. 4A and 4B. Half-life determination for SABA1.1 (FIG. 4A) and SABA5.1 (FIG. 4B) in cynomolgous monkey.

Figure 5:
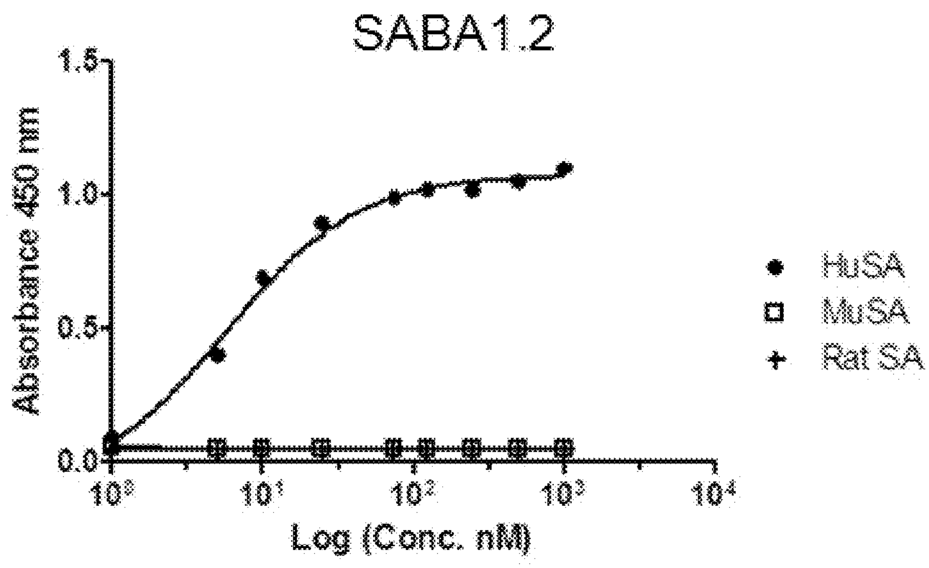

FIG. 5. SABA1.2 binding to albumins from human, mouse and rat by direct binding ELISA assay.

Figure 6:
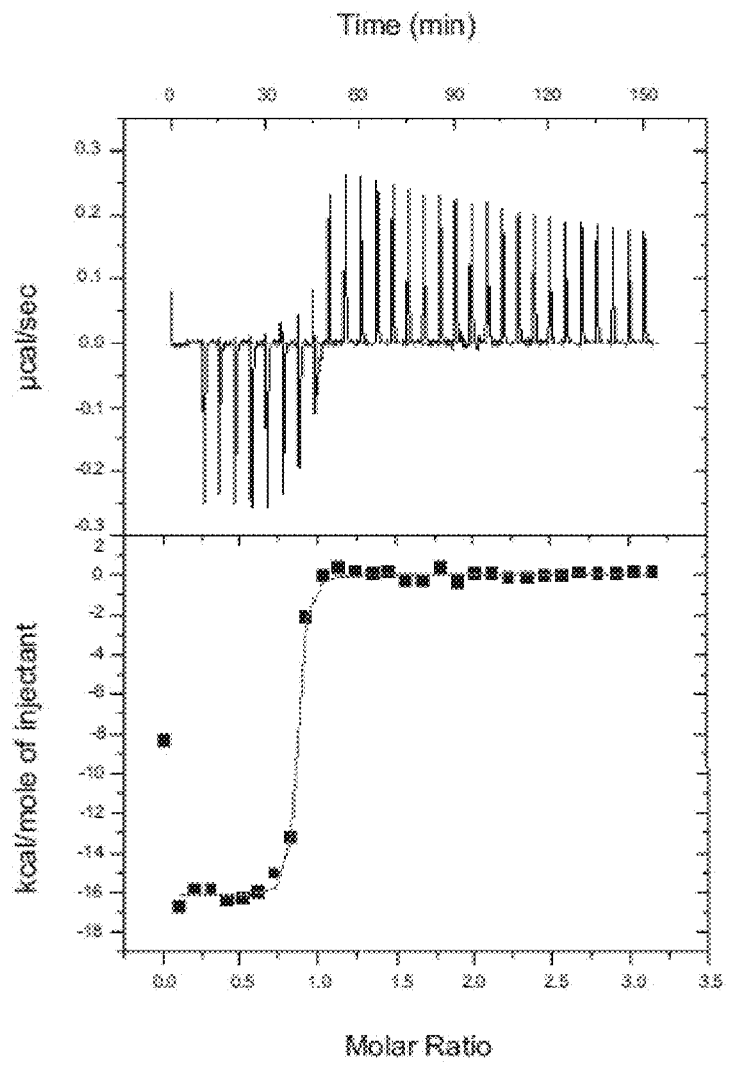

FIG. 6. Determination of SABA1.1 and HSA stoichiometry. SABA1.1 and HSA bind with a stoichiometry of 1:1.

Figure 7:
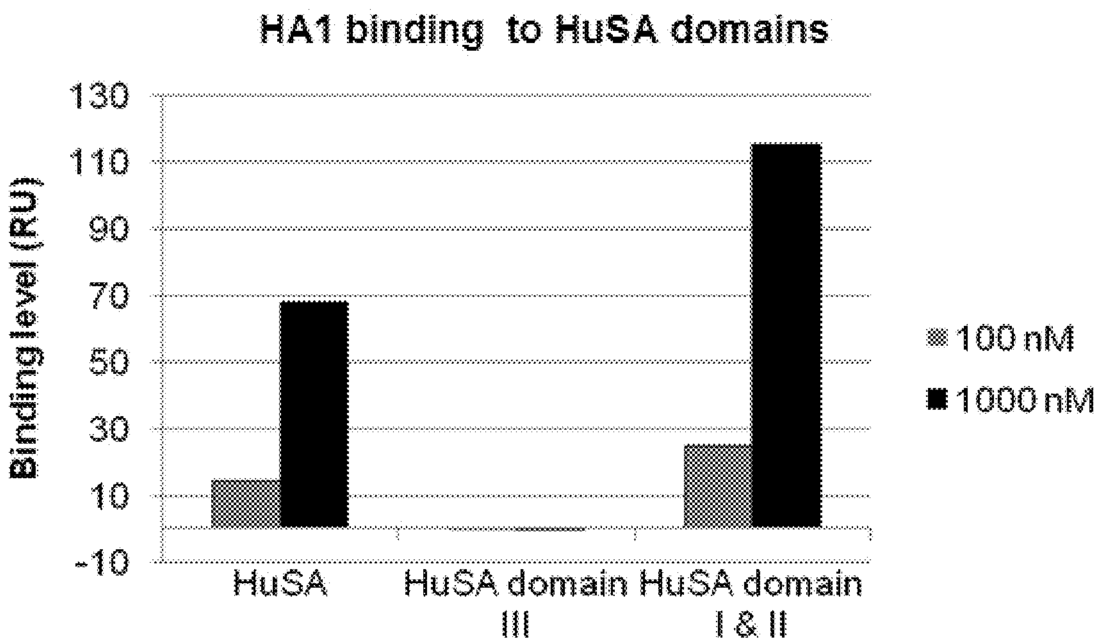

FIG. 7. Biacore analysis of SABA1.2 binding to recombinant domain fragments of HSA.

Figure 8:
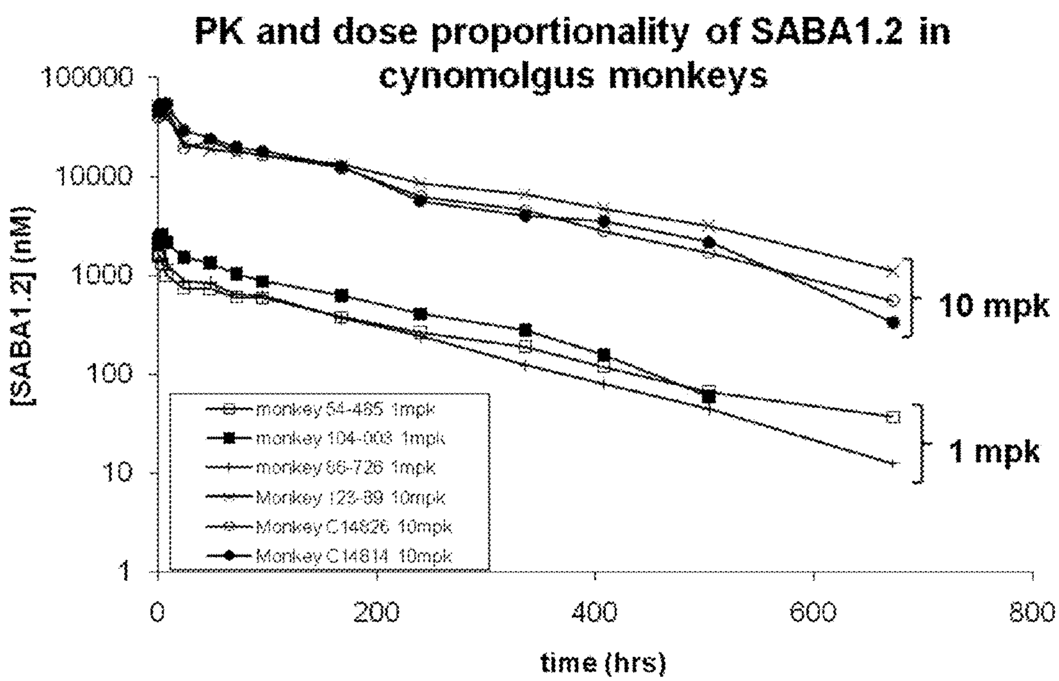

FIG. 8. Pharmacokinetic profile for SABA1.2 in monkeys dosed at 1 mpk and 10 mpk.

Figure 9:
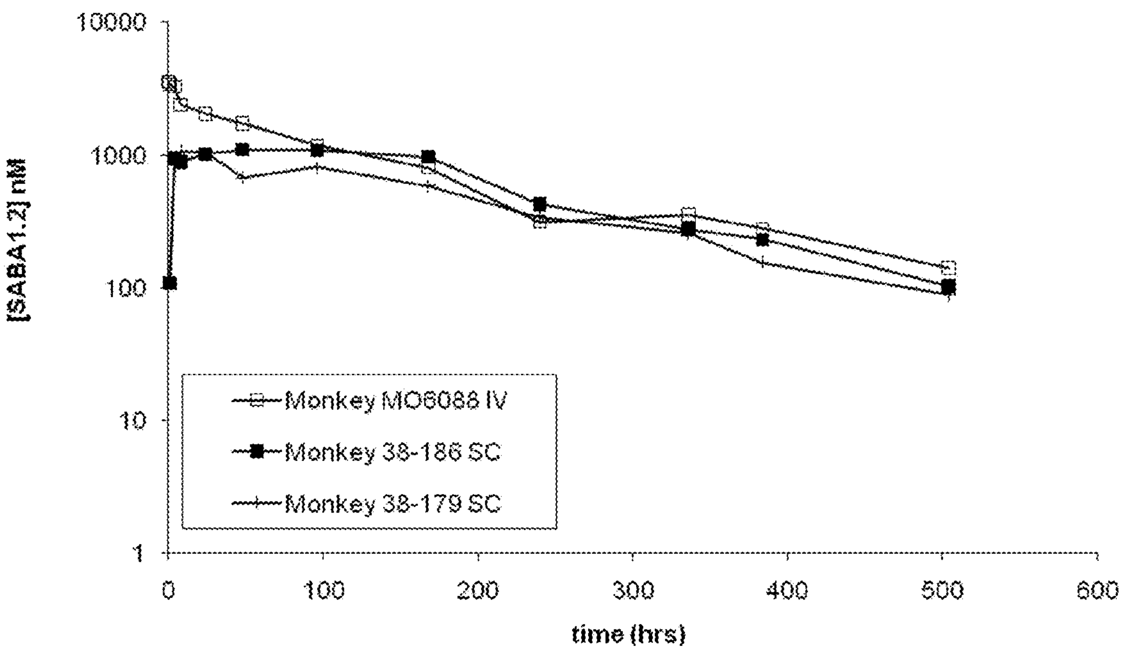

FIG. 9. Pharmacokinetic profile for SABA1.2 in monkeys dosed intravenously or subcutaneously at 1 mpk.

Figure 10:
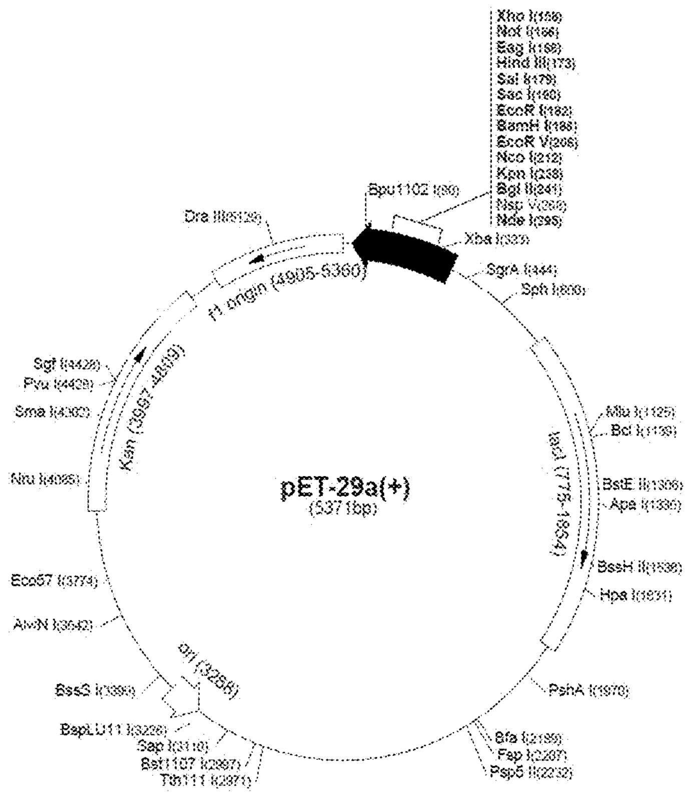

FIG. 10. Plamsid map of the pET29b vector used in the productive expression of FGF21 and SABA fusions.

Figure 11:
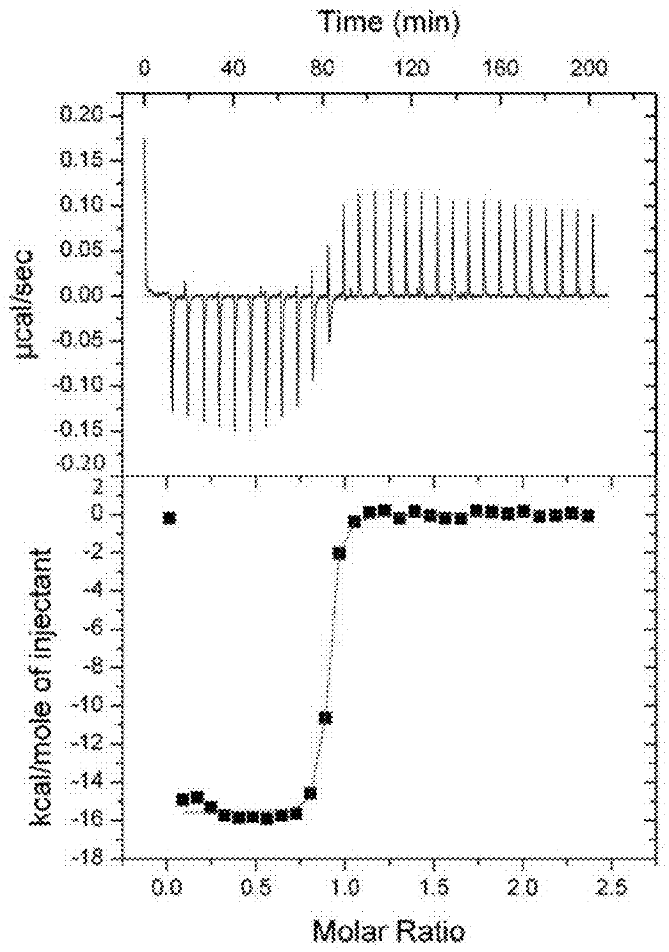
Figure 12A:
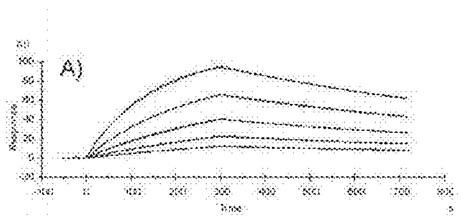
Figure 12D:
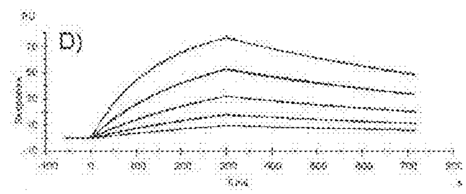
Figure 12B:
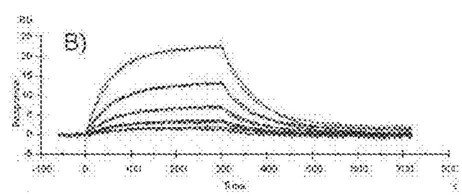
Figure 12E:
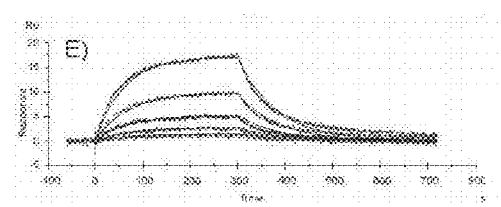
Figure 12C:
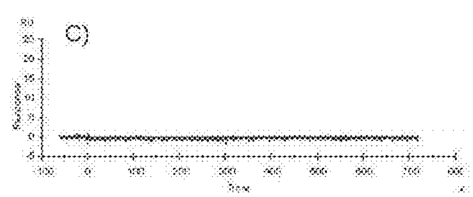
Figure 12F:
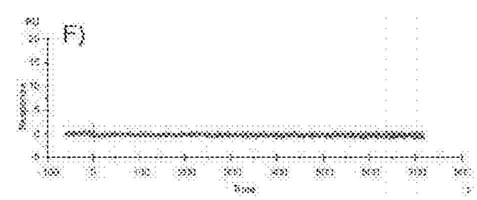

FIG. 11. Representative isothermal titration calorimetry of a SABA-FGF21v1 fusion with HSA at 37° C. in PBS buffer. Values determined in this assay: N=0.87; $K_D=3.8\times10^{-9}$ M; ΔH=−15360 cal/mole.

FIGS. 12A-12F. SPR sensogram data for the binding of SABA1-FGF21v1 to HSA (FIG. 12A), CySA (FIG. 12B), and MuSA (FIG. 12C), or SABA1-FGF21v3 to HSA (FIG. 12D), CySA (FIG. 12E), and MuSA (FIG. 12F) at 37° C.

Figure 13:
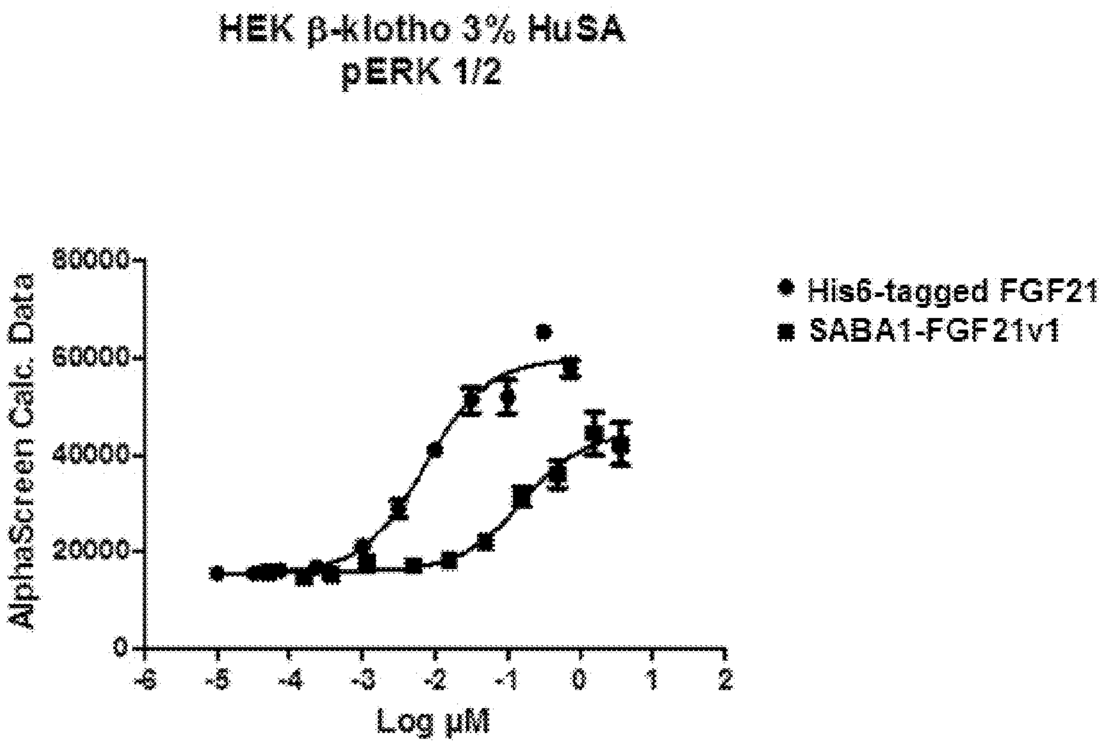

FIG. 13. Comparison of His-tagged FGF21 vs. SABA1-FGF21v1 activity in stimulating pERK 1/2 levels in HEK β-Klotho cells in the presence of human serum albumin.

Figure 14A:
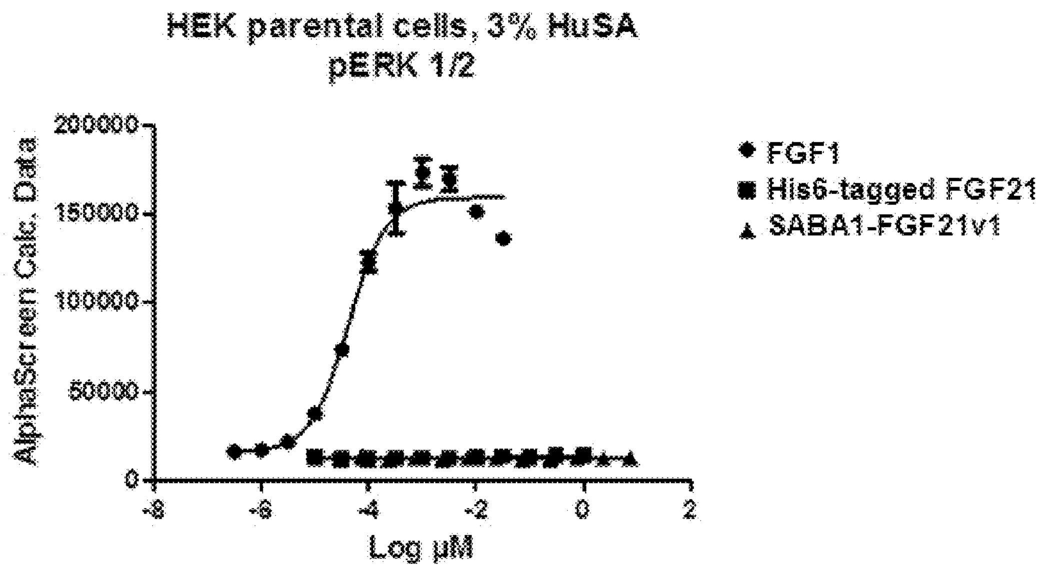
Figure 14B:
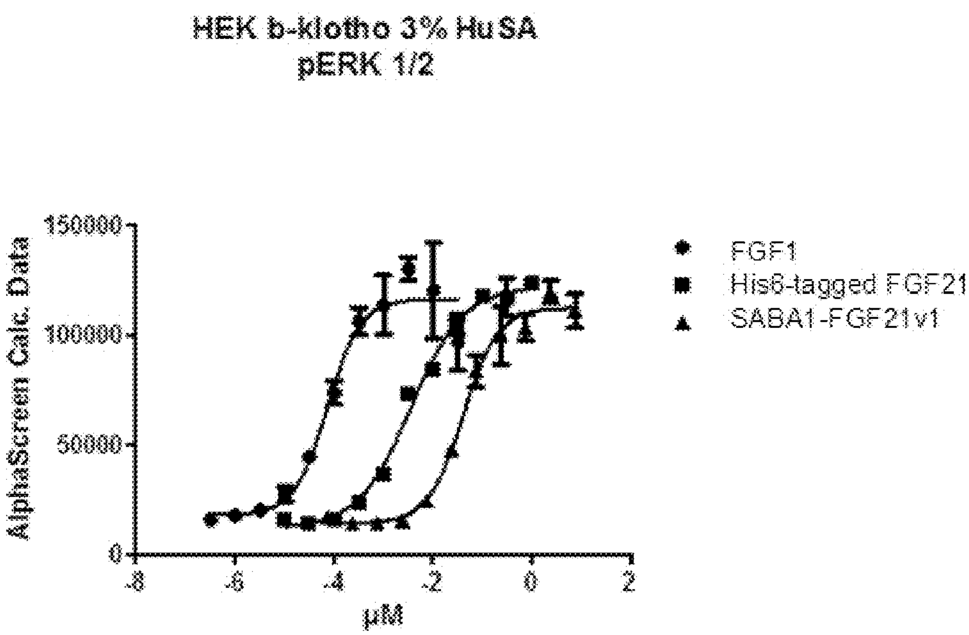

FIGS. 14A and 14B. Comparison of FGF1, His6-tagged FGF21 and SABA1-FGF21v1 activity in stimulating pERK 1/2 levels in HEK parental cells vs. HEK β-Klotho cells. Representative graphs of dose response stimulation of pERK 1/2 levels in HEK parental cells (FIG. 14A) and HEK β-Klotho expressing cells (FIG. 14B). Data is plotted as mean±sem of triplicate samples.

Figure 15A:
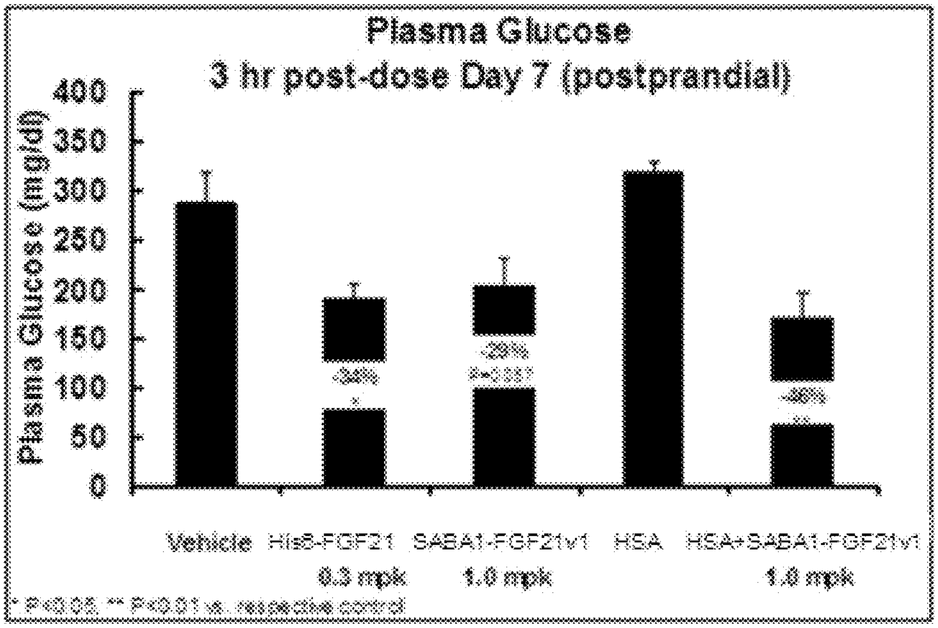
Figure 15B:
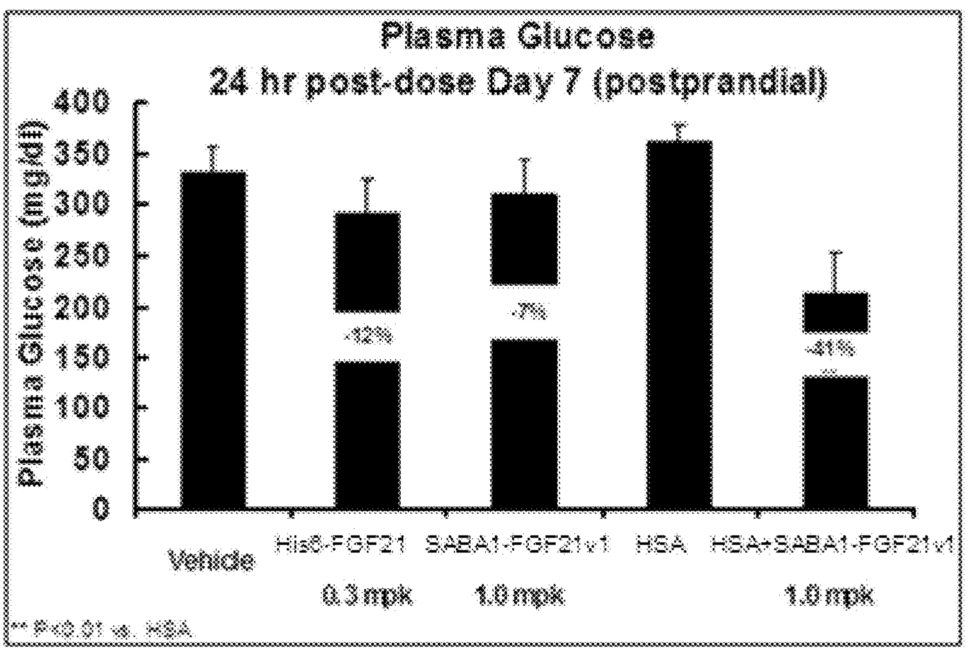

FIGS. 15A and 15B. Examination of in vivo efficacy of SABA1-FGF21v1 in diabetic ob/ob mice. Postprandial plasma glucose levels.

Figure 16:
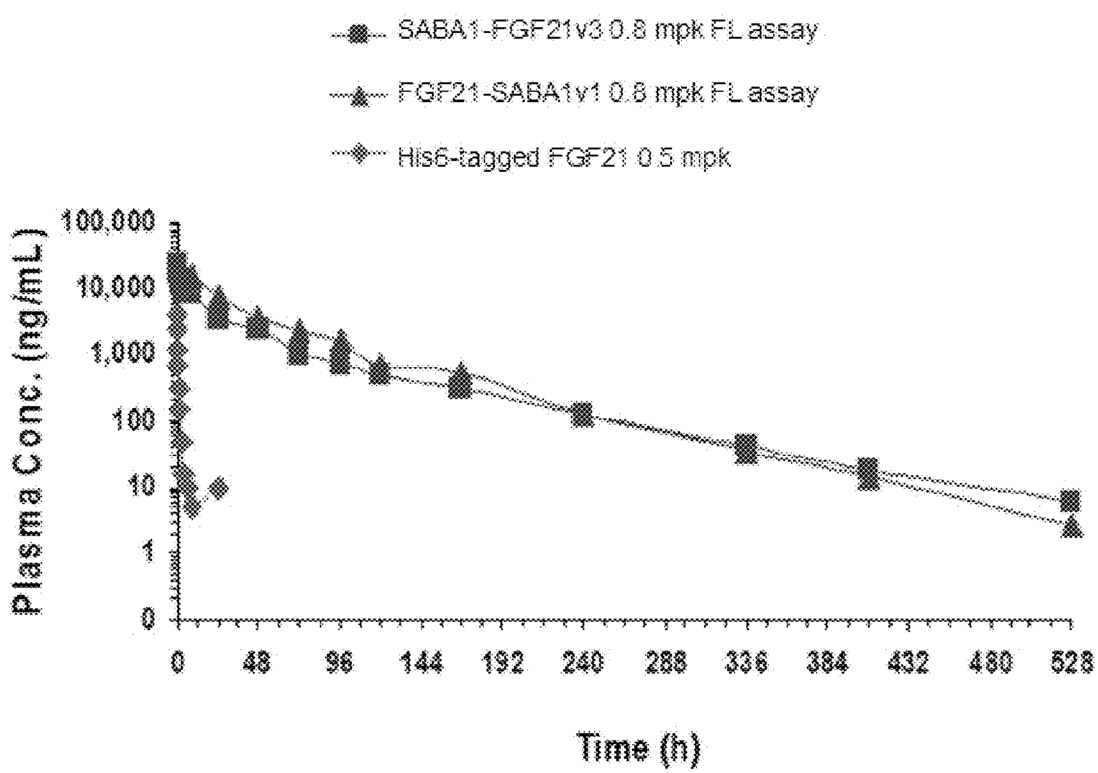

FIG. 16. SABA and FGF21 fusions increased $t_{1/2}$~27-fold compared to His-tagged FGF21 in monkeys.

Figure 17A:
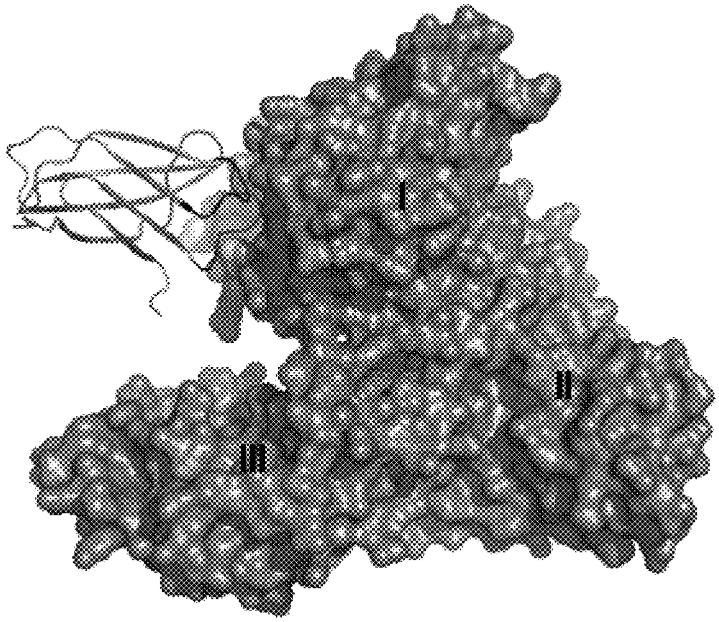
Figure 17B:
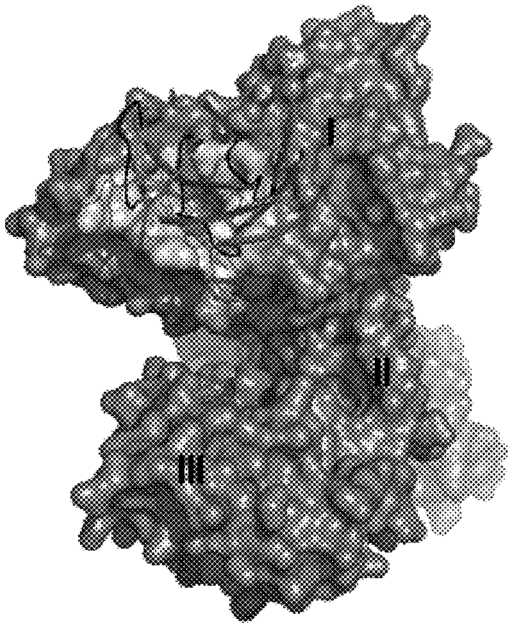

FIGS. 17A and 17B. Shows two views of the HuSA/SABA1.2 complex with the second view (FIG. 17B) rotated 70° about the vertical axis from first view (FIG. 17A). The HuSA is shown in a surface representation with SABA1.2 shown as a cartoon, i.e., with the β-strands as arrows and the loops as strings. The diversified loops on SABA1.2 are shown in black, while the contacting residues on the HuSA are shown in a lighter shade of gray. The three structural domains of HuSA are marked (i.e., I, II and III).

Figure 18:
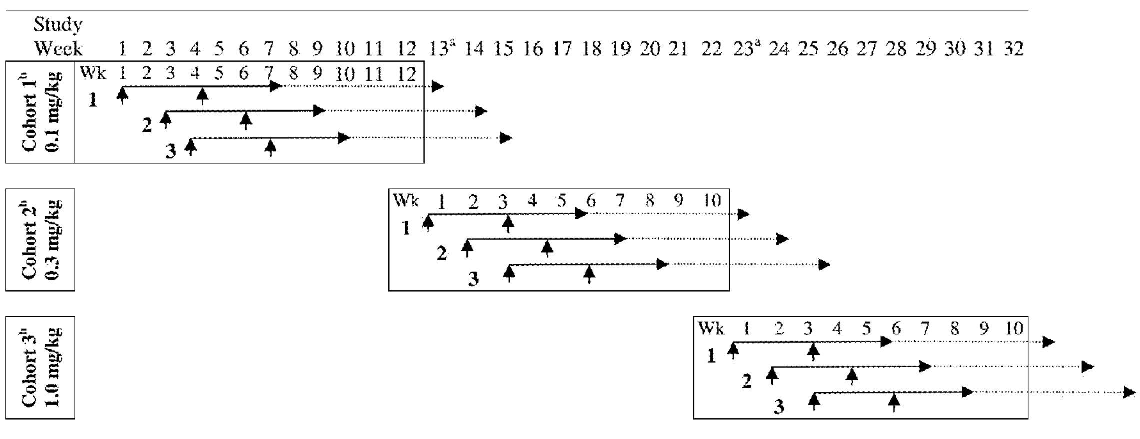

FIG. 18. Schematic of Dose Escalation and Treatment Cohorts (see Example A9). Study week indicates overall duration of the study. Weeks (Wk) within each cohort indicate duration from the start of treatment in that cohort. (a) Treatment in a given cohort will not begin until approximately 4 weeks after the last subject in the previous cohort completes the Day 29 visit to allow for PK analyses. (b) Rows 1, 2, or 3 in each cohort indicate subgroups that begin at 1-week staggered intervals (15-day interval between subgroups 1 and 2 in Cohort 1). Group 1 will comprise 1 SABA1.2 treated subject and 1 placebo subject; Group 2 will comprise 4 SABA1.2 treated subjects and 1 placebo subject; Group 3 will comprise 5 (for Cohort 1) or 4 (for Cohorts 2 and 3) SABA1.2 treated subjects and 1 (for all cohorts) placebo subjects. Arrows (I) indicate treatment (Days 1 and 15 for each group); solid lines (-) indicate active observation period; and dotted lines ( . . . ) indicate safety follow-up.

Figure 19:
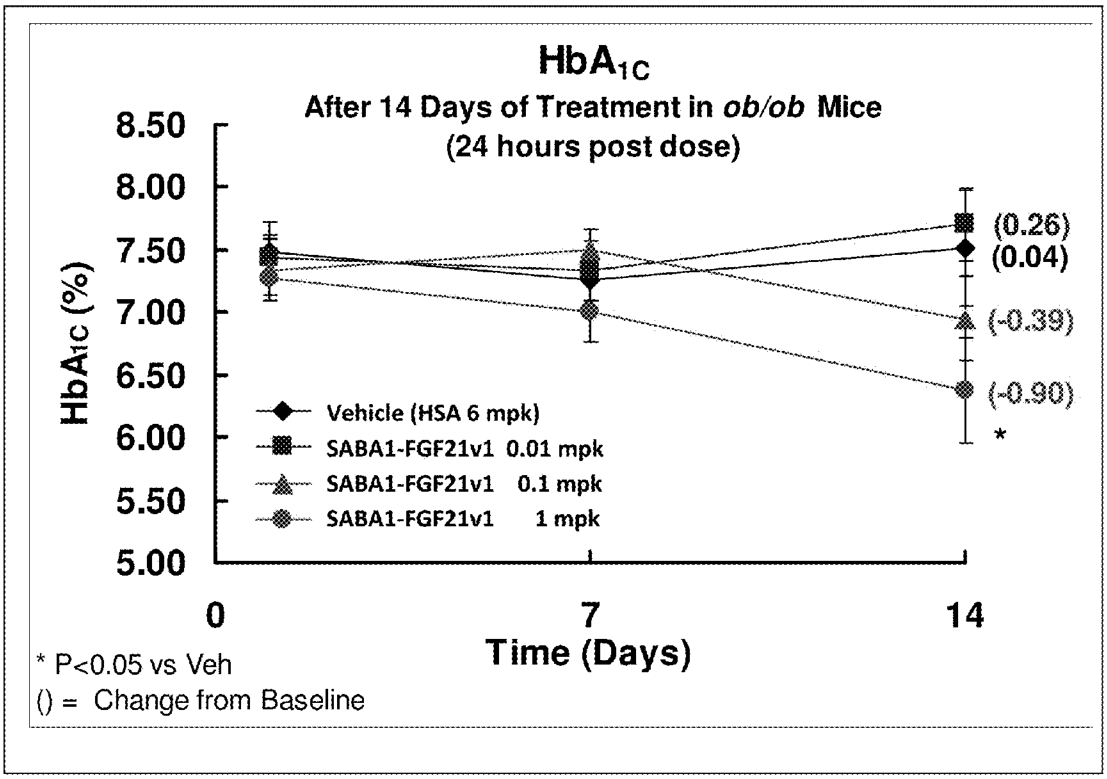

FIG. 19. Levels of HbA1c in ob/ob mice after 14 days of treatment with SABA1-FGF21v1.

Figure 20:
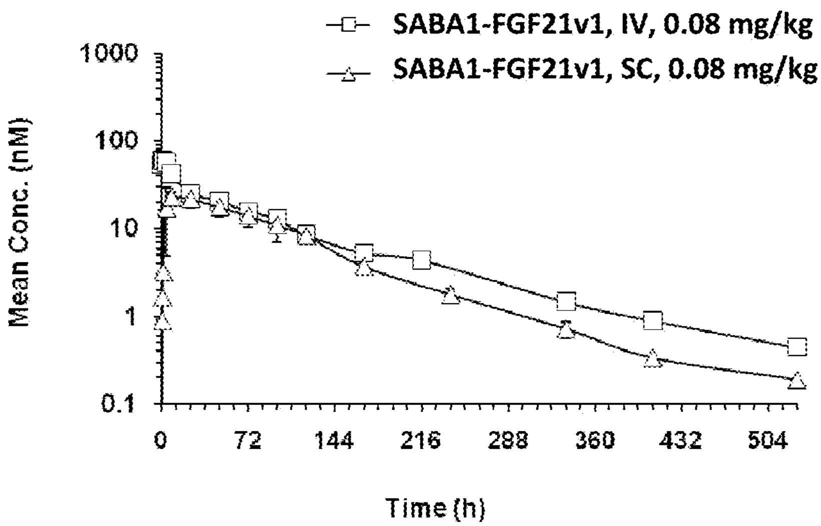

FIG. 20. Mean plasma concentration vs. time profile (mean±SD) of SABA1-FGF21v1 in Monkeys.

FIG. 21. Examples of orthogonally protected amino acids for use in solid phase peptide synthesis (top). Other building blocks useful for solid phase synthesis are also illustrated (bottom).

DETAILED DESCRIPTION OF THE INVENTION

Definitions

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The terms "comprise" and "comprising" are used in the inclusive, open sense, meaning that additional elements may be included.

The term "including" is used to mean "including but not limited to". "Including" and "including but not limited to" are used interchangeably.

The term "antibody-like protein" refers to a non-immunoglobulin protein having an "immunoglobulin-like fold", i.e., comprising about 80-150 amino acid residues that are structurally organized into a set of beta or beta-like strands, forming beta sheets, where the beta or beta-like strands are connected by intervening loop portions. The beta sheets form the stable core of the antibody-like protein, while creating two "faces" composed of the loops that connect the beta or beta-like strands. As described herein, these loops can be varied to create customized ligand binding sites, and such variations can be generated without disrupting the overall stability of the protein. An example of such an antibody-like protein is a "fibronectin-based scaffold protein", by which is meant a polypeptide based on a fibronectin type III domain (Fn3). In one aspect, an antibody-like protein is based on a tenth fibronectin type III domain ($^{10}$Fn3).

By a "polypeptide" is meant any sequence of two or more amino acids, regardless of length, post-translation modification, or function. "Polypeptide," "peptide," and "protein" are used interchangeably herein.

"Percent (%) amino acid sequence identity" herein is defined as the percentage of amino acid residues in a first sequence that are identical with the amino acid residues in a second sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The term "therapeutically effective amount" refers to an amount of a drug effective to treat a disease or disorder in a mammal and/or relieve to some extent one or more of the symptoms associated with the disorder.

The term "SABA" refers to a Serum Albumin Binding Adnectins™. Adnectins™ (Adnexus, a Bristol-Myers Squibb R&D Company) are ligand binding scaffold proteins based on the tenth fibronectin type III domain, i.e., the tenth module of Fn3, ($^{10}$Fn3).

The half-life ($t_{1/2}$) of an amino acid sequence or compound can generally be defined as the time taken for the serum concentration of the polypeptide to be reduced by 50% in vivo due to, e.g., degradation of the sequence or compound and/or clearance or sequestration of the sequence or compound by natural mechanisms. The half-life can be determined in any manner known in the art, such as by pharmacokinetic analysis. See e.g., M Gibaldi & D Perron "Pharmacokinetics", published by Marcel Dekker, 2nd Rev. edition (1982). Half-life can be expressed using parameters such as the $t_{1/2}$-alpha, $t_{1/2}$-beta and the area under the curve (AUC). An "increase in half-life" refers to an increase in any one of these parameters, any two of these parameters, or all three these parameters. In certain embodiments, an increase in half-life refers to an increase in the $t_{1/2}$-beta, either with or without an increase in the $t_{1/2}$-alpha or the AUC or both.

The term "PK" is an acronym for "pharmokinetic" and encompasses properties of a compound including, by way of example, absorption, distribution, metabolism, and elimination by a subject. A "PK modulation protein" or "PK moiety" refers to any protein, peptide, or moiety that affects the pharmokinetic properties of a biologically active molecule when fused to or administered together with the biologically active molecule.

Overview

Fn3 refers to a type III domain from fibronectin. An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face and loops BC, DE, and FG are located on the opposing face. Any or all of loops AB, BC, CD, DE, EF and FG may participate in ligand binding. There are at least 15 different modules of Fn3, and while the sequence homology between the modules is low, they all share a high similarity in tertiary structure.

Adnectins™ (Adnexus, a Bristol-Myers Squibb R&D Company) are ligand binding scaffold proteins based on the tenth fibronectin type III domain, i.e., the tenth module of Fn3, ($^{10}$Fn3). The amino acid sequence of a naturally occurring human $^{10}$Fn3 is set forth in SEQ ID NO: 1: VSDVPRDLEVVAATPTSLLISWDAPAVTVRYYRITY-GETGGNSPVQEFTVPGSKST ATISGLKPGVDYTITVY-AVTGRGDSPASSKPISINYRT (SEQ ID NO:1) (the AB, CD and EF loops are underlined, and the BC, FG, and DE loops are emphasized in bold).

In SEQ ID NO:1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87. (Xu et al., Chemistry & Biology 2002 9:933-942). The BC, DE and FG loops align along one face of the molecule and the AB, CD and EF loops align along the opposite face of the molecule. In SEQ ID NO: 1, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the formation strand A, loop AB, strand B, etc. The first 8 amino acids of SEQ ID NO:1 (italicized above) may be deleted while still retaining binding activity of the molecule. Residues involved in forming the hydrophobic core (the "core amino acid residues") include the amino acids corresponding to the following amino acids of SEQ ID NO: 1: L8, V10, A13, L18, 120, W22, Y32, I34, Y36, F48, V50, A57, I59, L62, Y68, I70, V72, A74, I188, I190 and Y92, wherein the core amino acid residues are represented by the single letter amino acid code followed by the position at which they are located within SEQ ID NO: 1. See e.g., Dickinson et al., J. Mol. Biol. 236: 1079-1092 (1994).

$^{10}$Fn3 are structurally and functionally analogous to antibodies, specifically the variable region of an antibody. While $^{10}$Fn3 domains may be described as "antibody mimics" or "antibody-like proteins", they do offer a number of advantages over conventional antibodies. In particular, they exhibit better folding and thermo stability properties as compared to antibodies, and they lack disulphide bonds, which are known to impede or prevent proper folding under certain conditions. Exemplary serum albumin $^{10}$Fn3 based binders are predominantly monomeric with Tm's averaging ~65° C.

The BC, DE, and FG loops of $^{10}$Fn3 are analogous to the complementary determining regions (CDRs) from immunoglobulins. Alteration of the amino acid sequence in these loop regions changes the binding specificity of $^{10}$Fn3. $^{10}$Fn3 domains with modifications in the AB, CD and EF loops may also be made in order to produce a molecule that binds to a desired target. The protein sequences outside of the loops are analogous to the framework regions from immunoglobulins and play a role in the structural conformation of the $^{10}$Fn3. Alterations in the framework-like regions of $^{10}$Fn3 are permissible to the extent that the structural conformation is not so altered as to disrupt ligand binding. Methods for generating $^{10}$Fn3 ligand specific binders have been described in PCT Publication Nos. WO 00/034787, WO 01/64942, and WO 02/032925, disclosing high affinity TNFα binders, PCT Publication No. WO 2008/097497, disclosing high affinity VEGFR2 binders, and PCT Publication No. WO 2008/066752, disclosing high affinity IGFIR binders. Additional references discussing $^{10}$Fn3 binders and methods of selecting binders include PCT Publication Nos. WO 98/056915, WO 02/081497, and WO 2008/031098 and U.S. Publication No. 2003186385.

As described above, amino acid residues corresponding to residues 21-30, 51-56, and 76-87 of SEQ ID NO: 1 define the BC, DE and FG loops, respectively. However, it should be understood that not every residue within the loop region needs to be modified in order to achieve a $^{10}$Fn3 binder having strong affinity for a desired target, such as human serum albumin. For example, in many of the examples described herein, only residues corresponding to amino acids 23-30 of the BC loop and 52-55 of the DE loop were modified to produce high affinity $^{10}$Fn3 binders. Accordingly, in certain embodiments, the BC loop may be defined by amino acids corresponding to residues 23-30 of SEQ ID NO: 1, and the DE loop may be defined by amino acids corresponding to residues 52-55 of SEQ ID NO: 1. Additionally, insertions and deletions in the loop regions may also be made while still producing high affinity $^{10}$Fn3 binders. For example, SEQ ID NO: 4 (SABA1) is an example of an HSA binder in which the FG loop contains a four amino acid deletion, i.e., the 11 residues corresponding to amino acids 21-29 of SEQ ID NO:1 were replaced with seven amino acids. SEQ ID NO: 113 is an example of an HSA binder in which the FG loop contains an amino acid insertion, i.e., the 11 residues corresponding to amino acids 21-29 of SEQ ID NO:1 were replaced with twelve amino acids.

Accordingly, in some embodiments, one or more loops selected from BC, DE, and FG may be extended or shortened in length relative to the corresponding loop in wild-type human $^{10}$Fn3. In some embodiments, the length of the loop may be extended by from 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to cover the CDR3 range of 4-28 residues to obtain the greatest possible flexibility and affinity in antigen binding. In some embodiments, the integrin-binding motif "arginine-glycine-aspartic acid" (RGD) may be replaced by a polar amino acid-neutral amino acid-acidic amino acid sequence (in the N-terminal to C-terminal direction).

$^{10}$Fn3 generally begin with the amino acid residue corresponding to number 1 of SEQ ID NO: 1. However, domains with amino acid deletions are also encompassed by the invention. In some embodiments, amino acid residues corresponding to the first eight amino acids of SEQ ID NO: 1 are deleted. Additional sequences may also be added to the N- or C-terminus. For example, an additional MG sequence may be placed at the N-terminus of $^{10}$Fn3. The M will usually be cleaved off, leaving a G at the N-terminus. In some embodiments, extension sequences may be placed at the C-terminus of the $^{10}$Fn3 domain, e.g., EIDKPSQ (SEQ ID NO: 54), EIEKPSQ (SEQ ID NO: 60), or EIDKPSQLE (SEQ ID NO: 61). Such C-terminal sequences are referred to herein as tails or extensions and are further described herein. In some embodiments, a His6-tag may be placed at the N-terminus or the C-terminus.

The non-ligand binding sequences of $^{10}$Fn3, i.e., the "$^{10}$Fn3 scaffold", may be altered provided that the $^{10}$Fn3 retains ligand binding function and/or structural stability. In some embodiments, one or more of Asp 7, Glu 9, and Asp 23 are replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Batori et al., Protein Eng. 2002 15(12):1015-20; Koide et al., Biochemistry 2001 40(34): 10326-33.

The $^{10}$Fn3 scaffold may be modified by one or more conservative substitutions. As many as 5%, 10%, 20% or even 30% or more of the amino acids in the $^{10}$Fn3 scaffold may be altered by a conservative substitution without substantially altering the affinity of the $^{10}$Fn3 for a ligand. For example, the scaffold modification preferably reduces the binding affinity of the $^{10}$Fn3 binder for a ligand by less than 100-fold, 50-fold, 25-fold, 10-fold, 5-fold, or 2-fold. It may be that such changes will alter the immunogenicity of the $^{10}$Fn3 in vivo, and where the immunogenicity is decreased, such changes will be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., Atlas of Protein Sequence and Structure 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In certain embodiments, antibody-like proteins based on the $^{10}$Fn3 scaffold can be defined generally by following the sequence:

(SEQ ID NO: 2)
EVVAAT(X)$_a$SLLI(X)$_x$YYRITYGE(X)$_b$QEFTV(X)$_y$ATI(X)$_c$

DYTITVYAV(X)$_z$ISINYRT.

In SEQ ID NO:2, the AB loop is represented by $X_a$, the CD loop is represented by $X_b$, the EF loop is represented by $X_c$, the BC loop is represented by $X_x$, the DE loop is represented by $X_y$, and the FG loop is represented by $X_z$. X represents any amino acid and the subscript following the X represents an integer of the number of amino acids. In particular, a may be anywhere from 1-15, 2-15, 1-10, 2-10, 1-8, 2-8, 1-5, 2-5, 1-4, 2-4, 1-3, 2-3, or 1-2 amino acids; and b, c, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, a is 2 amino acids, b is 7 amino acids, c is 7 amino acids, x is 9 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In exemplary embodiments, the BC, DE, and FG loops as represented by $(X)_x$, $(X)_y$, and $(X)_z$, respectively, are replaced with polypeptides comprising the BC, DE and FG loop sequences from any of the HSA binders shown in Table 2 below (i.e., SEQ ID NOs: 4, 8, 12, 16, 20, and 24-44 in Table 2).

In certain embodiments, Antibody-like proteins based on the $^{10}$Fn3 scaffold can be defined generally by the sequence:

(SEQ ID NO: 3)
EVVAATPTSLLI(X)$_x$YYRITYGETGGNSPVQEFTV(X)$_y$

ATISGLKPGVDYTITVYAV(X)$_z$ISINYRT

In SEQ ID NO:3, the BC loop is represented by $X_x$, the DE loop is represented by $X_y$, and the FG loop is represented by $X_z$. X represents any amino acid and the subscript following the X represents an integer of the number of amino acids. In particular, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, x is 9 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In exemplary embodiments, the BC, DE, and FG loops as represented by $(X)_x$, $(X)_y$, and $(X)_z$, respectively, are replaced with polypeptides comprising the BC, DE and FG loop sequences from any of the HSA binders shown in Table 2 below (i.e., SEQ ID NOs: 4, 8, 12, 16, 20, and 24-44 in Table 2).

$^{10}$Fn3 Domains with ED Tails

In one aspect, the present invention provides a polypeptide comprising a fibronectin type III tenth ($^{10}$Fn3) domain, wherein the $^{10}$Fn3 domain (i) comprises a modified amino acid sequence in one or more of the AB, BC, CD, DE, EF and FG loops relative to the wild-type $^{10}$Fn3 domain, (ii)

binds to a target molecule not bound by the wild-type $^{10}$Fn3 domain, and (iii) comprises a C-terminal tail having a sequence $(ED)_n$, wherein n is an integer from 2-10, 2-8, 2-5, 3-10, 3-8, 3-7, 3-5, or 4-7, or wherein n is 2, 3, 4, 5, 6, 7, 8, 9, or 10.

In certain embodiments, the $^{10}$Fn3 domain comprises an amino acid sequence having at least 60%, 65%, 70%, 75%, 80%, 85%, 90%, 95%, 97%, 98%, or 99% identity with the amino acid sequence set forth in residues 9-94 of SEQ ID NO: 1. In certain embodiments, the $^{10}$Fn3 domain comprises SEQ ID NO: 1, 2 or 3. In certain embodiments, the $^{10}$Fn3 domain comprises the amino acids 9-94 of SEQ ID NO: 1.

In certain embodiments, the $^{10}$Fn3 domain with an ED tail comprises an E, I or EI at the C-terminus just before the ED repeats. In some embodiments, the ED repeats enhance the solubility and/or reduces aggregation of the $^{10}$Fn3 domain.

In certain embodiments, a $^{10}$Fn3 domain with an ED tail comprises a modified amino acid sequence in each of the BC, DE and FG loops relative to the wild-type $^{10}$Fn3 domain. In other embodiments, a $^{10}$Fn3 domain with an ED tail binds to a desired target with a $K_D$ of 1 uM or less.

Serum Albumin Binders $^{10}$Fn3 domains are cleared rapidly from circulation via renal filtration and degradation due to their small size of ~10 kDa ($t_{1/2}$=15-45 minutes in mice; 3 hours in monkeys). In certain aspects, the application provides $^{10}$Fn3 domains that bind specifically to serum albumin, e.g., human serum albumin (HSA) to prolong the $t_{1/2}$ of the $^{10}$Fn3 domain.

HSA has a serum concentration of 600 μM and a $t_{1/2}$ of 19 days in humans. The extended $t_{1/2}$ of HSA has been attributed, in part, to its recycling via the neonatal Fc receptor (FcRn). HSA binds FcRn in a pH-dependent manner after endosomal uptake into endothelial cells; this interaction recycles HSA back into the bloodstream, thereby shunting it away from lysosomal degradation. FcRn is widely expressed and the recycling pathway is thought to be constitutive. In the majority of cell types, most FcRn resides in the intracellular sorting endosome. HSA is readily internalized by a nonspecific mechanism of fluid-phase pinocytosis and rescued from degradation in the lysosome by FcRn. At the acidic pH found in the endosome, HSA's affinity for FcRn increases (5 μM at pH 6.0). Once bound to FcRn, HSA is shunted away from the lysosomal degradation pathway, transcytosed to and released at the cell surface.

In one aspect, the disclosure provides antibody-like proteins comprising a serum albumin binding $^{10}$Fn3 domain. In exemplary embodiments, the serum albumin binding $^{10}$Fn3 proteins described herein bind to HSA with a $K_D$ of less than 3 uM, 2.5 uM, 2 uM, 1.5 uM, 1 uM, 500 nM, 100 nM, 50 nM, 10 nM, 1 nM, 500 pM, 100 pM. 100 pM, 50 pM or 10 pM. In certain embodiments, the serum albumin binding $^{10}$Fn3 proteins described herein bind to HSA with a $K_D$ of less than 3 uM, 2.5 uM, 2 uM, 1.5 uM, 1 uM, 500 nM, 100 nM, 50 nM, 10 nM, 1 nM, 500 pM, 100 pM. 100 pM, 50 pM or 10 pM at a pH range of 5.5 to 7.4 at 25° C. or 37° C. In some embodiments, the serum albumin binding $^{10}$Fn3 proteins described herein bind more tightly to HSA at a pH less than 7.4 as compared to the binding affinity for HSA at a pH of 7.4 or greater.

In certain embodiments, the HSA binding $^{10}$Fn3 proteins described herein may also bind serum albumin from one or more of monkey, rat, or mouse. In certain embodiments, the serum albumin binding $^{10}$Fn3 described herein bind to rhesus serum albumin (RhSA) or cynomolgous monkey serum albumin (CySA) with a $K_D$ of less than 3 uM, 2.5 uM, 2 uM, 1.5 uM, 1 uM, 500 nM, 100 nM, 50 nM, 10 nM, 1 nM, 500 pM or 100 pM.

In certain embodiments, the serum albumin binding $^{10}$Fn3 proteins described herein bind to domain I and/or domain II of HSA. In one embodiment, the serum albumin binding $^{10}$Fn3 proteins described herein do not bind to domain III of HSA.

In certain embodiments, the serum albumin binding $^{10}$Fn3 (SABA) comprises a sequence having at least 40%, 50%, 60%, 70%, 75%, 80% or 85% identity to the wild-type $^{10}$Fn3 domain (SEQ ID NO: 1). In one embodiment, at least one of the BC, DE, or FG loops is modified relative to the wild-type $^{10}$Fn3 domain. In another embodiment, at least two of the BC, DE, or FG loops are modified relative to the wild-type $^{10}$Fn3 domain. In another embodiment, all three of the BC, DE, and FG loops are modified relative to the wild-type $^{10}$Fn3 domain. In other embodiments, a SABA comprises a sequence having at least 40%, 50%, 60%, 70%, 75%, 80%, 85%, 90%, or 95% identity to any one of the 26 core SABA sequences shown in Table 2 (i.e., SEQ ID NO: 4, 8, 12, 16, 20, and 24-44) or any one of the extended SABA sequences shown in Table 2 (i.e., SEQ ID NO: 89-116, minus the 6×HIS tag).

In certain embodiments, a SABA as described herein may comprise the sequence as set forth in SEQ ID NO: 2 or 3, wherein the BC, DE, and FG loops as represented by $(X)_x$, $(X)_y$, and $(X)_z$, respectively, are replaced with a respective set of specified BC, DE, and FG loops from any of the 26 core SABA sequences (i.e., SEQ ID NOs: 4, 8, 12, 16, 20, and 24-44 in Table 2), or sequences at least 75%, 80%, 85%, 90%, 95%, 97%, 98%, or 99% identical to the BC, DE and FG loop sequences of the 26 core SABA sequences. In exemplary embodiments, a SABA as described herein is defined by SEQ ID NO: 3 and has a set of BC, DE and FG loop sequences from any of the 26 core SABA sequences (i.e., SEQ ID NOs: 4, 8, 12, 16, 20, and 24-44 in Table 2). The scaffold regions of such SABA may have anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 1. For example, SABA1 has the core sequence set forth in SEQ ID NO: 4 and comprises BC, DE, and FG loops as set forth in SEQ ID NO: 5-7, respectively. Therefore, a SABA based on the SABA1 core may comprise SEQ ID NO: 2 or 3, wherein $(X)_x$ comprises SEQ ID NO: 5, $(X)_y$ comprises SEQ ID NO: 6, and $(X)_z$ comprises SEQ ID NO: 7. Similar constructs are contemplated utilizing the set of BC, DE and FG loops from the other SABA core sequences. The scaffold regions of such SABA may comprise anywhere from 0 to 20, from 0 to 15, from 0 to 10, from 0 to 8, from 0 to 6, from 0 to 5, from 0 to 4, from 0 to 3, from 0 to 2, or from 0 to 1 substitutions, conservative substitutions, deletions or additions relative to the scaffold amino acids residues of SEQ ID NO: 1. Such scaffold modifications may be made, so long as the SABA is capable of binding serum albumin, e.g., HSA, with a desired $K_D$.

In certain embodiments, a SABA (e.g., a SABA core sequence or a sequence based thereon as described above) may be modified to comprise an N-terminal extension sequence and/or a C-terminal extension sequence. Exemplary extension sequences are shown in Table 2. For example, SEQ ID NO: 89 designated as SABA1.1 comprises the core SABA1 sequence (SEQ ID NO: 4) with an N-terminal sequence MGVSDVPRDLE (SEQ ID NO: 45, designated as AdNT1), and a C-terminal sequence EIDKPSQ (SEQ ID NO: 54, designated as AdCT1). SABA1.1 further comprises a His6 tag at the C-terminus, however, it should be understood that the His6 tag is completely optional and may be placed anywhere within the N- or C-terminal extension sequences. Further, any of the exemplary N- or C-terminal extension sequences provided in Table 2 (SEQ ID NO: 45-64 and 215), and any variants thereof, can be used to modify any given SABA core sequence provided in Table 2. In certain embodiments, a linker sequence provided in Table 2 (SEQ ID NOs: 65-88, 216-221 and 397) may be used as a C-terminal tail sequence, either alone or in combination with one of SEQ ID NOs: 54-64 or 215.

In certain embodiments, the C-terminal extension sequences (also called "tails"), comprise E and D residues, and may be between 8 and 50, 10 and 30, 10 and 20, 5 and 10, and 2 and 4 amino acids in length. In some embodiments, tail sequences include ED-based linkers in which the sequence comprises tandem repeats of ED. In exemplary embodiments, the tail sequence comprises 2-10, 2-7, 2-5, 3-10, 3-7, 3-5, 3, 4 or 5 ED repeats. In certain embodiments, the ED-based tail sequences may also include additional amino acid residues, such as, for example: EI, EID, ES, EC, EGS, and EGC. Such sequences are based, in part, on known Adnectin™ tail sequences, such as EIDKPSQ (SEQ ID NO: 54), in which residues D and K have been removed. In exemplary embodiments, the ED-based tail comprises an E, I or EI residues before the ED repeats.

In other embodiments, the tail sequences may be combined with other known linker sequences (e.g., SEQ ID NO: 65-88, 216-221 and 397 in Table 2) as necessary when designing a SABA fusion molecule, e.g., SEQ ID NO: 147 (SABA1-FGF21v16), in which EIEDEDEDEDED is joined with GSGSGSGS.

Fusions of Serum Albumin Binding Adnectin™ (SABA)

One aspect of the present invention provides for conjugates comprising a serum albumin binding $^{10}$Fn3 (SABA) and at least one additional moiety. The additional moiety may be useful for any diagnostic, imaging, or therapeutic purpose.

In certain embodiments, the serum half-life of the moiety fused to the SABA is increased relative to the serum half-life of the moiety when not conjugated to the SABA. In certain embodiments, the serum half-life of the SABA fusion is at least 20, 40, 60, 80, 100, 120, 150, 180, 200, 400, 600, 800, 1000, 1200, 1500, 1800, 1900, 2000, 2500, or 3000% longer relative to the serum half-life of the moiety when not fused to the SABA. In other embodiments, the serum half-life of the SABA fusion is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the moiety when not fused to the SABA. In some embodiments, the serum half-life of the SABA fusion is at least 2 hours, 2.5 hours, 3 hours, 4 hours, 5 hours, 6 hours, 7 hours, 8 hours, 9 hours, 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

In certain embodiments, the SABA fusion proteins bind to HSA with a $K_D$ of less than 3 uM, 2.5 uM, 2 uM, 1.5 uM, 1 uM, 500 nM, 100 nM, 50 nM, 10 nM, 1 nM, 500 pM, 100 pM. 100 pM, 50 pM or 10 pM. In certain embodiments, the SABA fusion proteins bind to HSA with a $K_D$ of less than 3 uM, 2.5 uM, 2 uM, 1.5 uM, 1 uM, 500 nM, 100 nM, 50 nM, 10 nM, 1 nM, 500 pM, 100 pM. 100 pM, 50 pM or 10 pM at a pH range of 5.5 to 7.4 at 25° C. or 37° C. In some embodiments, the SABA fusion proteins bind more tightly to HSA at a pH less than 7.4 as compared to binding at pH 7.4.

Accordingly, the SABA fusion molecules described herein are useful for increasing the half-life of a therapeutic moiety (e.g., FGF21) by creating a fusion between the therapeutic moiety and the SABA. Such fusion molecules may be used to treat conditions which respond to the biological activity of the therapeutic moiety contained in the fusion. The present invention contemplates the use of the SABA fusion molecules in diseases caused by the disregulation of any of the following proteins or molecules.

Heterologous Moiety

In some embodiments, the SABA is fused to a second moiety that is a small organic molecule, a nucleic acid, or a protein. In some embodiments, the SABA is fused to a therapeutic moiety that targets receptors, receptor ligands, viral coat proteins, immune system proteins, hormones, enzymes, antigens, or cell signaling proteins. The fusion may be formed by attaching the second moiety to either end of the SABA molecule, i.e., SABA-therapeutic molecule or therapeutic molecule-SABA arrangements.

In exemplary embodiments, the therapeutic moiety is VEGF, VEGF-R1, VEGF-R2, VEGF-R3, Her-1, Her-2, Her-3, EGF-I, EGF-2, EGF-3, Alpha3, cMet, ICOS, CD40L, LFA-I, c-Met, ICOS, LFA-I, IL-6, B7.1, W1.2, OX40, IL-Ib, TACI, IgE, BAFF or BLys, TPO-R, CD19, CD20, CD22, CD33, CD28, IL-I-R1, TNF-alpha, TRAIL-R1, Complement Receptor 1, FGFa, Osteopontin, Vitronectin, Ephrin A1-A5, Ephrin B1-B3, alpha-2-macroglobulin, CCL1, CCL2, CCL3, CCL4, CCL5, CCL6, CCL7, CXCL8, CXCL9, CXCL1O, CXCLI 1, CXCL12, CCL13, CCL14, CCL15, CXCL16, CCL16, CCL17, CCL18, CCL19, CCL20, CCL21, CCL22, PDGF, TGFb, GMCSF, SCF, p40 (IL12/IL23), ILIb, ILIa, ILlra, IL2, IL3, IL4, IL5, IL6, IL8, IL1O, IL12, IL15, IL23, Fas, FasL, Flt3 ligand, 41BB, ACE, ACE-2, KGF, FGF-7, SCF, Netrin1,2, IFNa,b,g, Caspase2, 3,7,8,10, ADAM S1,S5,8,9,15,TS1,TS5; Adiponectin, ALCAM, ALK-I, APRIL, Annexin V, Angiogenin, Amphiregulin, Angiopoietin1,2,4, B7-1/CD80, B7-2/CD86, B7-H1, B7-H2, B7-H3, Bcl-2, BACE-I, BAK, BCAM, BDNF, bNGF, bECGF, BMP2,3,4,5,6,7,8; CRP, Cadherin 6, 8, 11; Cathepsin A,B,C,D,E,L,S,V,X; CD1 la/LFA-1, LFA-3, GP2b3a, GH receptor, RSV F protein, IL-23 (p40, p19), IL-12, CD80, CD86, CD28, CTLA-4, alpha4-beta1, alpha4-beta7, TNF/Lymphotoxin, IgE, CD3, CD20, IL-6, IL-6R, BLYS/BAFF, IL-2R, HER2, EGFR, CD33, CD52, Digoxin, Rho (D), Varicella, Hepatitis, CMV, Tetanus, Vaccinia, Antivenom, Botulinum, Trail-R1, Trail-R2, cMet, TNF-R family, such as LA NGF-R, CD27, CD30, CD40, CD95, Lymphotoxin a/b receptor, WsI-I, TL1A/TNFSF15, BAFF, BAFF-R/TNFRSF13C, TRAIL R2/TNFRSF10B, TRAIL R2/TNFRSF10B, Fas/TNFRSF6 CD27/TNFRSF7, DR3/TNFRSF25, HVEM/TNFRSF14, TROY/TNFRSF19, CD40 Ligand/TNFSF5, BCMA/TNFRSF17, CD30/TNFRSF8, LIGHT/TNFSF14, 4-1BB/TNFRSF9, CD40/TNFRSF5, GITR/[Gamma]NFRSF 18, Osteoprotegerin/TNFRSF1 IB, RANK/TNFRSF1 IA, TRAIL R3/TNFRSF10C, TRAIL/TNFSFIO, TRANCE/RANK L/TNFSF11, 4-1BB Ligand/TNFSF9, TWEAK/TNFSF12, CD40 Ligand/TNFSF5, Fas Ligand/TNFSF6, RELT/TNFRSF19L, APRIL/TNFSF13, DcR3/TNFRSF6B, TNF RI/TNFRSFIA, TRAIL R1/TNFRSFIOA, TRAIL R4/TNFRSF10D, CD30 Ligand/TNFSF8, GITR Ligand/TNFSF18, TNFSF18, TACI/TNFRSF13B, NGF R/TNFRSF16, OX40 Ligand/TNFSF4, TRAIL R2/TNFRSF1OB, TRAIL R3/TNFRSF10C, TWEAK R/TNFRSF12, BAFF/BLyS/TNFSF13, DR6/TNFRSF21, TNF-alpha/TNFSFl A, Pro-TNF-alpha/TNFSFlA, Lymphotoxin beta R/TNFRSF3, Lymphotoxin beta R (LTbR)/Fc Chimera, TNF RI/TNFRSFIA, TNF-beta/

TNFSFIB, PGRP-S, TNF RI/TNFRSFIA, TNF RII/TNFRSFIB, EDA-A2, TNF-alpha/TNFSFIA, EDAR, XEDAR, TNF RI/TNFRSFIA.

Of particular interest are human target proteins that are commercially available in purified form as well as proteins that bind to these target proteins. Examples are: 4EBP1, 14-3-3 zeta, 53BP1, 2B4/SLAMF4, CCL21/6Ckine, 4-1BB/TNFRSF9, 8D6A, 4-1BB Ligand/TNFSF9, 8-oxo-dG, 4-Amino-1,8-naphthalimide, A2B5, Aminopeptidase LRAP/ERAP2, A33, Aminopeptidase N/ANPEP, Aag, Aminopeptidase P2/XPNPEP2, ABCG2, Aminopeptidase P1/XPNPEP1, ACE, Aminopeptidase PILS/ARTS1, ACE-2, Amnionless, Actin, Amphiregulin, beta-Actin, AMPK alpha 1/2, Activin A, AMPK alpha 1, Activin AB, AMPK alpha 2, Activin B, AMPK beta 1, Activin C, AMPK beta 2, Activin RIA/ALK-2, Androgen R/NR3C4, Activin RIB/ALK-4, Angiogenin, Activin RIIA, Angiopoietin-1, Activin RIIB, Angiopoietin-2, ADAMS, Angiopoietin-3, ADAM9, Angiopoietin-4, ADAM1O, Angiopoietin-like 1, ADAM12, Angiopoietin-like 2, ADAM15, Angiopoietin-like 3, TACE/ADAM17, Angiopoietin-like 4, ADAM19, Angiopoietin-like 7/CDT6, ADAM33, Angiostatin, ADAMTS4, Annexin A1/Annexin I, ADAMTS5, Annexin A7, ADAMTSl, Annexin AlO, ADAMTSL-1/Punctin, Annexin V, Adiponectin/Acrp30, ANP, AEBSF, AP Site, Aggrecan, APAF-I, Agrin, APC, AgRP, APE, AGTR-2, APJ, AIF, APLP-I, Akt, APLP-2, Akt1, Apolipoprotein AI, Akt2, Apolipoprotein B, Akt3, APP, Serum Albumin, APRIL/TNFSF13, ALCAM, ARC, ALK-I, Artemin, ALK-7, Arylsulfatase AJARSA, Alkaline Phosphatase, ASAH2/N-acylsphingosine Amidohydrolase-2, alpha 2u-Globulin, ASC, alpha-1-Acid Glycoprotein, ASGRl, alpha-Fetoprotein, ASKl, ALS, ATM, Ameloblastic ATRIP, AMICA/JAML, Aurora A, AMIGO, Aurora B, AMIG02, Axin-1, AMIG03, AxI, Aminoacylase/ACY1, Azurocidin/CAP37/HBP, Aminopeptidase A/ENPEP, B4GALT1, BIM, B7-1/CD80, 6-Biotin-17-NAD, B7-2/CD86, BLAME/SLAMF8, B7-H1/PD-L1, CXCL13/BLC/BCA-1, B7-H2, BLIMP1, B7-H3, Mk, B7-H4, BMI-I, BACE-I, BMP-1/PCP, BACE-2, BMP-2, Bad, BMP-3, BAFF/TNFSF13B, BMP-3b/GDF-10, BAFF R/TNFRSF 13C, BMP-4, Bag-1, BMP-5, BAK, BMP-6, BAMBI/NMA, BMP-7, BARD 1, BMP-8, Bax, BMP-9, BCAM, BMP-10, Bcl-10, BMP-15/GDF-9B, Bcl-2, BMPR-IA/ALK-3, Bcl-2 related protein Al, BMPR-IB/ALK-6, Bcl-w, BMPR-II, Bcl-x, BNIP3L, Bcl-xL, BOC, BCMA/TNFRSF17, BOK, BDNF, BPDE, Benzamide, Brachyury, Common beta Chain, B-Raf, beta IG-H3, CXCL14/BRAK, Betacellulin, BRCA1, beta-Defensin 2, BRCA2, BID, BTLA, Biglycan, Bub-1, Bik-like Killer Protein, c-jun, CD90/Thyl, c-Rel, CD94, CCL6/C10, CD97, CIq R1/CD93, CD151, CIqTNF1, CD160, ClqTNF4, CD163, ClqTNF5, CD164, Complement Component CIr, CD200, Complement Component CIs, CD200 R1, Complement Component C2, CD229/SLAMF3, Complement Component C3a, CD23/Fc epsilon RII, Complement Component C3d, CD2F-10/SLAMF9, Complement Component C5a, CD5L, Cadherin-4/R-Cadherin, CD69, Cadherin-6, CDC2, Cadherin-8, CDC25A, Cadherin-11, CDC25B, Cadherin-12, CDCP1, Cadherin-13, CDO, Cadherin-17, CDX4, E-Cadherin, CEACAM-1/CD66a, N-Cadherin, CEACAM-6, P-Cadherin, Cerberus 1, VE-Cadherin, CFTR, Calbindin D, cGMP, Calcineurin A, Chem R23, Calcineurin B, Chemerin, Calreticulin-2, Chemokine Sampler Packs, CaM Kinase II, Chitinase 3-like 1, cAMP, Chitotriosidase/CHIT1, Cannabinoid R1, Chk1, Cannabinoid R2/CB2/CNR2, Chk2, CAR/NR1I3, CHL-1/L1CAM-2, Carbonic Anhydrase I, Choline Acetyltransferase/CbAT, Carbonic Anhydrase II, Chondrolectin, Carbonic Anhydrase III, Chordin, Carbonic Anhydrase IV, Chordin-Like 1, Carbonic Anhydrase VA, Chordin-Like 2, Carbonic Anhydrase VB, CINC-I, Carbonic Anhydrase VI, CINC-2, Carbonic Anhydrase VII, CINC-3, Carbonic Anhydrase VIII, Claspin, Carbonic Anhydrase IX, Claudin-6, Carbonic Anhydrase X, CLC, Carbonic Anhydrase XII, CLEC-I, Carbonic Anhydrase XIII, CLEC-2, Carbonic Anhydrase XIV, CLECSF 13/CLEC4F, Carboxymethyl Lysine, CLECSF8, Carboxypeptidase A1/CPA1, CLF-I, Carboxypeptidase A2, CL-P1/COLEC12, Carboxypeptidase A4, Clusterin, Carboxypeptidase B1, Clusterin-like 1, Carboxypeptidase E/CPE, CMG-2, Carboxypeptidase X1, CMV UL146, Cardiotrophin-1, CMV UL147, Carnosine Dipeptidase 1, CNP, Caronte, CNTF, CART, CNTF R alpha, Caspase, Coagulation Factor II/Thrombin, Caspase-1, Coagulation Factor Ill/Tissue Factor, Caspase-2, Coagulation Factor VII, Caspase-3, Coagulation Factor X, Caspase-4, Coagulation Factor XI, Caspase-6, Coagulation Factor XIV/Protein C, Caspase-7, COCO, Caspase-8, Cohesin, Caspase-9, Collagen I, Caspase-10, Collagen II, Caspase-12, Collagen IV, Caspase-13, Common gamma Chain/IL-2 R gamma, Caspase Peptide Inhibitors, COMP/Thrombospondin-5, Catalase, Complement Component CIrLP, beta-Catenin, Complement Component CIqA, Cathepsin 1, Complement Component CIqC, Cathepsin 3, Complement Factor D, Cathepsin 6, Complement Factor I, Cathepsin A, Complement MASP3, Cathepsin B, Connexin 43, Cathepsin C/DPPI, Contactin-1, Cathepsin D, Contactin-2/TAG1, Cathepsin E, Contactin-4, Cathepsin F, Contactin-5, Cathepsin H, Corin, Cathepsin L, Cornulin, Cathepsin 0, CORS26/C1qTNF,3, Cathepsin S, Rat Cortical Stem Cells, Cathepsin V, Cortisol, Cathepsin XITJ?, COUP-TF I/NR2F1, CBP, COUP-TF II/NR2F2, CCI, COX-I, CCK-A R, COX-2, CCL28, CRACC/SLAMF7, CCR1, C-Reactive Protein, CCR2, Creatine Kinase, Muscle/CKMM, CCR3, Creatinine, CCR4, CREB, CCR5, CREG, CCR6, CRELD1, CCR7, CRELD2, CCR8, CRHBP, CCR9, CRHR-I, CCR1O, CRIM1, CD155/PVR, Cripto, CD2, CRISP-2, CD3, CRISP-3, CD4, Crossveinless-2, CD4+/45RA−, CRTAM, CD4+/45RO−, CRTH-2, CD4+/CD62L−/CD44, CRY1, CD4+/CD62L+/CD44, Cryptic, CD5, CSB/ERCC6, CD6, CCL27/CTACK, CD8, CTGF/CCN2, CD8+/45RA−, CTLA-4, CD8+/45RO−, Cubilin, CD9, CX3CR1, CD14, CXADR, CD27/TNFRSF7, CXCL16, CD27 Ligand/TNFSF7, CXCR3, CD28, CXCR4, CD30/TNFRSF8, CXCR5, CD30 Ligand/TNFSF8, CXCR6, CD31/PECAM-1, Cyclophilin A, CD34, Cyr61/CCN1, CD36/SR-B3, Cystatin A, CD38, Cystatin B, CD40/TNFRSF5, Cystatin C, CD40 Ligand/TNFSF5, Cystatin D, CD43, Cystatin E/M, CD44, Cystatin F, CD45, Cystatin H, CD46, Cystatin H2, CD47, Cystatin S, CD48/SLAMF2, Cystatin SA, CD55/DAF, Cystatin SN, CD58/LFA-3, Cytochrome c, CD59, Apocytochrome c, CD68, Holocytochrome c, CD72, Cytokeratin 8, CD74, Cytokeratin 14, CD83, Cytokeratin 19, CD84/SLAMF5, Cytonin, D6, DISP1, DAN, Dkk-1, DANCE, Dkk-2, DARPP-32, Dkk-3, DAX1/NROB1, Dkk-4, DCC, DLEC, DCIR/CLEC4A, DLL1, DCAR, DLL4, DcR3/TNFRSF6B, d-Luciferin, DC-SIGN, DNA Ligase IV, DC-SIGNR/CD299, DNA Polymerase beta, DcTRAIL R1/TNFRSF23, DNAM-I, DcTRAIL R2/TNFRSF22, DNA-PKcs, DDR1, DNER, DDR2, Dopa Decarboxylase/DDC, DEC-205, DPCR-I, Decapentaplegic, DPP6, Decorin, DPP A4, Dectin-1/CLEC7A, DPPA5/ESG1, Dectin-2/CLEC6A, DPPII/QPP/DPP7, DEP-1/CD148, DPPIV/CD26, Desert Hedgehog, DR3/TNFRSF25, Desmin, DR6/TNFRSF21, Desmoglein-1, DSCAM, Desmoglein-2, DSCAM-L1, Desmoglein-3, DSPG3, Dishevelled-1, Dtk, Dishevelled-3, Dynamin, EAR2/NR2F6, EphA5, ECE-I, EphA6, ECE-2, EphA7, ECF-L/CHI3L3, EphA8, ECM-I, EphB1, Ecotin, EphB2, EDA, EphB3, EDA-A2, EphB4, EDAR, EphB6, EDG-I, Ephrin, EDG-5, Ephrin-A1, EDG-8, Ephrin-A2, eEF-2, Ephrin-A3, EGF, Ephrin-A4, EGF R, Ephrin-A5, EGR1, Ephrin-B, EG-VEGF/PK1, Ephrin-B1, eIF2 alpha, Ephrin-B2, eIF4E, Ephrin-B3, EIk-I, Epigen, EMAP-II, Epimorphin/Syntaxin 2, EMMPRIN/CD147, Epiregulin, CXCL5/ENA, EPR-1/Xa Receptor, Endocan, ErbB2, Endoglin/CD105, ErbB3, Endoglycan, ErbB4, Endonuclease III, ERCC1, Endonuclease IV, ERCC3, Endonuclease V, ERK1/ERK2, Endonuclease VIII, ERK1, Endorepellin/Perlecan, ERK2, Endostatin, ERK3, Endothelin-1, ERK5/BMK1, Engrailed-2, ERR alpha/NR3B1, EN-RAGE, ERR beta/NR3B2, Enteropeptidase/Enterokinase, ERR gamma/NR3B3, CCL 1/Eotaxin, Erythropoietin, CCL24/Eotaxin-2, Erythropoietin R, CCL26/Eotaxin-3, ESAM, EpCAM/TROP-1, ER alpha/NR3A1, EPCR, ER beta/NR3A2, Eph, Exonuclease III, EphA1, Exostosin-like 2/EXTL2, EphA2, Exostosin-like 3/EXTL3, EphA3, FABP1, FGF-BP, FABP2, FGF R1-4, FABP3, FGF R1, FABP4, FGF R2, FABP5, FGF R3, FABP7, FGF R4, FABP9, FGF R5, Complement Factor B, Fgr, FADD, FHR5, FAM3A, Fibronectin, FAM3B, Ficolin-2, FAM3C, Ficolin-3, FAM3D, FITC, Fibroblast Activation Protein alpha/FAP, FKBP38, Fas/TNFRSF6, Flap, Fas Ligand/TNFSF6, FLIP, FATP1, FLRG, FATP4, FLRT1, FATP5, FLRT2, Fc gamma RI/CD64, FLRT3, Fc gamma RIIB/CD32b, Flt-3, Fc gamma RIIC/CD32c, Flt-3 Ligand, Fc gamma RIIA/CD32a, Follistatin, Fc gamma RIII/CD16, Follistatin-like 1, FcRH1/IRTA5, FosB/GOS3, FcRH2/IRTA4, FoxD3, FcRH4/IRTA1, FoxJ1, FcRH5/IRTA2, FoxP3, Fc Receptor-like 3/CD16-2, Fpg, FEN-I, FPR1, Fetuin A, FPRL1, Fetuin B, FPRL2, FGF acidic, CX3CL1/Fractalkine, FGF basic, Frizzled-1, FGF-3, Frizzled-2, FGF-4, Frizzled-3, FGF-5, Frizzled-4, FGF-6, Frizzled-5, FGF-8, Frizzled-6, FGF-9, Frizzled-7, FGF-IO, Frizzled-8, FGF-11, Frizzled-9, FGF-12, Frk, FGF-13, sFRP-1, FGF-16, sFRP-2, FGF-17, sFRP-3, FGF-19, sFRP-4, FGF-20, Furin, FGF-21, FXR/NR1H4, FGF-22, Fyn, FGF-23, G9a/EHMT2, GFR alpha-3/GDNF R alpha-3, GABA-A-R alpha 1, GFR alpha-4/GDNF R alpha-4, GABA-A-R alpha 2, GITR/TNFRSF18, GABA-A-R alpha 4, GITR Ligand/TNFSF18, GABA-A-R alpha 5, GLI-I, GABA-A-R alpha 6, GLI-2, GABA-A-R beta 1, GLP/EHMT1, GABA-A-R beta 2, GLP-I R, GABA-A-R beta 3, Glucagon, GABA-A-R gamma 2, Glucosamine (N-acetyl)-6-Sulfatase/GNS, GABA-B-R2, GIuR1, GAD1/GAD67, GluR2/3, GAD2/GAD65, GluR2, GADD45 alpha, GluR3, GADD45 beta, Glut1, GADD45 gamma, Glut2, Galectin-1, Glut3, Galectin-2, Glut4, Galectin-3, Glut5, Galectin-3 BP, Glutaredoxin 1, Galectin-4, Glycine R, Galectin-7, Glycophorin A, Galectin-8, Glypican 2, Galectin-9, Glypican 3, Ga1NAc4S-6ST, Glypican 5, GAP-43, Glypican 6, GAPDH, GM-CSF, Gasl, GM-CSF R alpha, Gash, GMF-beta, GASP-1/WFIKKNRP, gp130, GASP-2/WFIKKN, Glycogen Phosphorylase BB/GPBB, GATA-I, GPR15, GATA-2, GPR39, GATA-3, GPVI, GATA-4, GR/NR3C1, GATA-5, Gr-1/Ly-6G, GATA-6, Granulysin, GBL, Granzyme A, GCNF/NR6A1, Granzyme B, CXCL6/GCP-2, Granzyme D, G-CSF, Granzyme G, G-CSF R, Granzyme H, GDF-I, GRASP, GDF-3 GRB2, GDF-5, Gremlin, GDF-6, GRO, GDF-7, CXCL1/GRO alpha, GDF-8, CXCL2/GRO beta, GDF-9, CXCL3/GRO gamma, GDF-11, Growth Hormone, GDF-15, Growth Hormone R, GDNF, GRP75/HSPA9B, GFAP, GSK-3 alpha/beta, GFI-I, GSK-3 alpha, GFR alpha-1/GDNF R alpha-1, GSK-3 beta, GFR alpha-2/GDNF R alpha-2, EZFIT, H2AX, Histidine, H60, HM74A, HAI-I, HMGA2, HAI-2, HMGB1, HAI-2A, TCF-2/HNF-1 beta, HAI-2B, HNF-3 beta/FoxA2, HAND1, HNF-4 alpha/NR2 A1, HAPLN1, HNF-4 gamma/NR2A2, Airway Trypsin-like Protease/HAT, HO-1/HMOX1/HSP32, HB-EGF, HO-2/HMOX2, CCL 14a/HCC-1, HPRG, CCL14b/HCC-3, Hrk, CCL16/HCC-4, HRP-I, alpha HCG, HS6ST2, Hck, HSD-I, HCR/CRAM-A/B, HSD-2, HDGF, HSP 10/EPF, Hemoglobin, HSP27, Hepassocin, HSP60, HES-1, HSP70, HES-4, HSP90, HGF, HTRA/Protease Do, HGF Activator, HTRA1/PRSS11, HGF R, HTRA2/0mi, HIF-I alpha, HVEM/TNFRSF14, HIF-2 alpha, Hyaluronan, HIN-1/Secretoglobulin 3A1,4-Hydroxynonenal, Hip, CCL1/I-309/TCA-3, IL-I0, cIAP (pan), IL-I0 R alpha, cIAP-1/HIAP-2, IL-I0 R beta, cIAP-2/HIAP-1, IL-11, IBSP/Sialoprotein II, EL-11 R alpha, ICAM-1/CD54, IL-12, ICAM-2/CD102, IL-12/IL-23 p40, ICAM-3/CD50, IL-12 R beta 1, ICAM-5, IL-12 R beta 2, ICAT, IL-13, ICOS, IL-13 R alpha 1, Iduronate 2-Sulfatase/EOS, IL-13 R alpha 2, EFN, IL-15, IFN-alpha, IL-15 R alpha, IFN-alpha 1, IL-16, IFN-alpha 2, IL-17, IFN-alpha 4b, IL-17 R, IFN-alpha A, IL-17 RC, IFN-alpha B2, IL-17 RD, IFN-alpha C, IL-17B, IFN-alpha D, IL-17B R, IFN-alpha F, IL-17C, IFN-alpha G, IL-17D, IFN-alpha H2, IL-17E, IFN-alpha I, IL-17F, IFN-alpha J1, IL-18/IL-1F4, IFN-alpha K, IL-18 BPa, IFN-alpha WA, IL-18 BPc, IFN-alpha/beta R1, IL-18 BPd, IFN-alpha/beta R2, IL-18 R alpha/IL-1 R5, IFN-beta, IL-18 R beta/IL-1 R7, IFN-gamma, IL-19, IFN-gamma R1, IL-20, IFN-gamma R2, IL-20 R alpha, IFN-omega, IL-20 R beta, IgE, IL-21, IGFBP-I, IL-21 R, IGFBP-2, IL-22, IGFBP-3, IL-22 R, IGFBP-4, IL-22BP, IGFBP-5, IL-23, IGFBP-6, IL-23 R, IGFBP-L1, IL-24, IGFBP-rp1/IGFBP-7, IL-26/AK155, IGFBP-rPIO, IL-27, IGF-I, EL-28A, IGF-I R, IL-28B, IGF-II, IL-29/EFN-lambda 1, IGF-II R, IL-31, IgG, EL-31 RA, IgM, IL-32 alpha, IGSF2, IL-33, IGSF4A/SynCAM, ILT2/CD85J, IGSF4B, ILT3/CD85k, IGSF8, ILT4/CD85d, IgY, ILT5/CD85a, IlcB-beta, ILT6/CD85e, IKK alpha, Indian Hedgehog, IKK epsilon, INSRR, EKK gamma, Insulin, IL-I alpha/IL-IF1, Insulin R/CD220, IL-I beta/IL-1F2, Proinsulin, IL-lra/IL-1F3, Insulysin/EDE, IL-1F5/FIL1 delta, Integrin alpha 2/CD49b, IL-1F6/FIL1 epsilon, Integrin alpha 3/CD49c, IL-1F7/FIL1 zeta, Integrin alpha 3 beta 1/VLA-3, IL-1F8/FIL1 eta, Integrin alpha 4/CD49d, IL-1F9/IL-1 H1, Integrin alpha 5/CD49e, IL-1F10/IL-1HY2, Integrin alpha 5 beta 1, IL-I RI, Integrin alpha 6/CD49f, IL-I RII, Integrin alpha 7, IL-I R3/IL-1 R AcP, Integrin alpha 9, IL-I R4/ST2, Integrin alpha E/CD103, IL-I R6/IL-1 R rp2, Integrin alpha L/CD1 Ia, IL-I R8, Integrin alpha L beta 2, IL-I R9, Integrin alpha M/CD1 lb, IL-2, Integrin alpha M beta 2, IL-2 R alpha, Integrin alpha V/CD51, IL-2 R beta, Integrin alpha V beta 5, IL-3, Integrin alpha V beta 3, IL-3 R alpha, Integrin alpha V beta 6, IL-3 R beta, Integrin alpha XJCD1 Ic, IL-4, Integrin beta 1/CD29, IL-4 R, Integrin beta 2/CD18, IL-5, Integrin beta 3/CD61, IL-5 R alpha, Integrin beta 5, IL-6, Integrin beta 6, IL-6 R, Integrin beta 7, IL-7, CXCL10/EP-10/CRG-2, IL-7 R alpha/CD127, IRAKI, CXCR1/IL-8 RA, IRAK4, CXCR2/IL-8 RB, ERS-I, CXCL8/IL-8, Islet-1, IL-9, CXCL1 1/I-TAC, IL-9 R, Jagged 1, JAM-4/IGSF5, Jagged 2, JNK, JAM-A, JNK1/JNK2, JAM-B/VE-JAM, JNK1, JAM-C, JNK2, Kininogen, Kallikrein 3/PSA, Kininostatin, Kallikrein 4, KER/CD158, Kallikrein 5, KER2DL1, Kallikrein 6/Neurosin, KIR2DL3, Kallikrein 7, KIR2DL4/CD158d, Kallikrein 8/Neuropsin, KIR2DS4, Kallikrein 9, KIR3DL1, Plasma Kallikrein/KLKB1, KER3DL2, Kallikrein 10, Kirrel2, Kallikrein 11, KLF4, Kallikrein 12, KLF5, Kallikrein 13, KLF6, Kallikrein 14, Klotho, Kallikrein 15, Klotho beta, KC, KOR, Keapl, Kremen-1, KeIl, Kremen-2, KGF/FGF-7, LAG-3, LINGO-2, LAIR1, Lipin 2, LAIR2, Lipocalin-1, Laminin alpha 4, Lipocalin-2/NGAL, Laminin gamma 1, 5-Lipoxygenase, Laminin I, LXR alpha/NR1H3, Laminin S, LXR beta/NR1H2, Laminin-1, Livin, Laminin-5, LEX, LAMP, LMIR1/CD300A, Langerin, LMIR2/CD300c, LAR, LMIR3/CD300LF, Latexin, LMIR5/CD300LB, Layilin, LMIR6/CD300LE, LBP, LMO2, LDL R, LOX-1/SR-E1, LECT2, LRH-1/NR5A2, LEDGF, LRIG1, Lefty, LRIG3, Lefty-1, LRP-I, Lefty-A, LRP-6, Legumain, LSECtin/CLEC4G, Leptin, Lumican, Leptin R, CXCL15/Lungkine, Leukotriene B4, XCL1/Lymphotactin, Leukotriene B4 R1, Lymphotoxin, LEF, Lymphotoxin beta/TNFSF3, LIF R alpha, Lymphotoxin beta R/TNFRSF3, LIGHT/TNFSF14, Lyn, Limitin, Lyp, LIMPII/SR-B2, Lysyl Oxidase Homolog 2, LIN-28, LYVE-I, LINGO-I, alpha 2-Macroglobulin, CXCL9/MIG, MAD2L1, Mimecan, MAdCAM-1, Mindin, MafB, Mineralocorticoid R/NR3C2, MafF, CCL3L1/MIP-1 alpha Isoform LD78 beta, MafG, CCL3/MIP-1 alpha, MafK, CCL4L1/LAG-1, MAG/Siglec-4a, CCL4/MIP-1 beta, MANF, CCL15/MEP-1 delta, MAP2, CCL9/10/MIP-1 gamma, MAPK, MIP-2, Marapsin/Pancreasin, CCL19/MIP-3 beta, MARCKS, CCL20/MIP-3 alpha, MARCO, MIP-I, Mashl, MIP-II, Matrilin-2, MIP-III, Matrilin-3, MIS/AMH, Matrilin-4, MIS RII, Matriptase/ST14, MIXL1, MBL, MKK3/MKK6, MBL-2, MKK3, Melanocortin 3R/MC3R, MKK4, MCAM/CD146, MKK6, MCK-2, MKK7, McI-I, MKP-3, MCP-6, MLH-I, CCL2/MCP-1, MLK4 alpha, MCP-11, MMP, CCL8/MCP-2, MMP-1, CCL7/MCP-3/MARC, MMP-2, CCL13/MCP-4, MMP-3, CCL12/MCP-5, MMP-7, M-CSF, MMP-8, M-CSF R, MMP-9, MCV-type II, MMP-IO, MD-I, MMP-I 1, MD-2, MMP-12, CCL22/MDC, MMP-13, MDL-1/CLEC5A, MMP-14, MDM2, MMP-15, MEA-I, MMP-16/MT3-MMP, MEK1/MEK2, MMP-24/MT5-MMP, MEK1, MMP-25/MT6-MMP, MEK2, MMP-26, Melusin, MMR, MEPE, MOG, Meprin alpha, CCL23/MPIF-1, Meprin beta, M-Ras/R-Ras3, Mer, Mrel 1, Mesothelin, MRP1 Meteorin, MSK1/MSK2, Methionine Aminopeptidase 1, MSK1, Methionine Aminopeptidase, MSK2, Methionine Aminopeptidase 2, MSP, MFG-E8, MSP R/Ron, MFRP, Mug, MgcRacGAP, MULT-I, MGL2, Musashi-1, MGMT, Musashi-2, MIA, MuSK, MICA, MutY DNA Glycosylase, MICB, MyD88, MICL/CLEC12A, Myeloperoxidase, beta 2 Microglobulin, Myocardin, Midkine, Myocilin, MIF, Myoglobin, NAIP NGFI-B gamma/NR4A3, Nanog, NgR2/NgRH1, CXCL7/NAP-2, NgR3/NgRH2, Nbsl, Nidogen-1/Entactin, NCAM-1/CD56, Nidogen-2, NCAM-L1, Nitric Oxide, Nectin-1, Nitrotyrosine, Nectin-2/CD1 12, NKG2A, Nectin-3, NKG2C, Nectin-4, NKG2D, Neogenin, NKp30, Neprilysin/CDIO, NKp44, Neprilysin-2/MMEL1/MMEL2, NKp46/NCR1, Nestin, NKp80/KLRF1, NETO2, NKX2.5, Netrin-1, NMDA R, NR1 Subunit, Netrin-2, NMDA R, NR2A Subunit, Netrin-4, NMDA R, NR2B Subunit, Netrin-Gla, NMDA R, NR2C Subunit, Netrin-G2a, N-Me-6,7-diOH-TIQ, Neuregulin-1/NRG1, Nodal, Neuregulin-3/NRG3, Noggin, Neuritin, Nogo Receptor, NeuroDl, Nogo-A, Neurofascin, NOMO, Neurogenin-1, Nope, Neurogenin-2, Norrin, Neurogenin-3, eNOS, Neurolysin, iNOS, Neurophysin II, nNOS, Neuropilin-1, Notch-1, Neuropilin-2, Notch-2, Neuropoietin, Notch-3, Neurotrimin, Notch-4, Neurturin, NOV/CCN3, NFAM1, NRAGE, NF-H, NrCAM, NFkB1, NRL, NFkB2, NT-3, NF-L, NT-4, NF-M, NTB-A/SLAMF6, NG2/MCSP, NTH1, NGF R/TNFRSF16, Nucleostemin, beta-NGF, Nurr-1/NR4A2, NGFI-B alpha/NR4A1, OAS2, Orexin B, OBCAM, OSCAR, OCAM, OSF-2/Periostin, OCIL/CLEC2d, Oncostatin M/OSM, OCILRP2/CLEC2i, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF1 IB, Oligodendrocyte Marker 01, Otx2, Oligodendrocyte Marker 04, OV-6, OMgp, OX40/TNFRSF4, Opticin, OX40 Ligand/TNFSF4, Orexin A, OAS2, Orexin B, OBCAM, OSCAR, OCAM, OSF-2/Periostin, OCIL/CLEC2d, Oncostatin M/OSM, OCILRP2/CLEC2i, OSM R beta, Oct-3/4, Osteoactivin/GPNMB, OGG1, Osteoadherin, Olig 1, 2, 3, Osteocalcin, Olig1, Osteocrin, Olig2, Osteopontin, Olig3, Osteoprotegerin/TNFRSF1 IB, Oligodendrocyte Marker 01, Otx2, Oligodendrocyte Marker 04, OV-6, OMgp, OX40/TNFRSF4, Opticin, OX40 Ligand/TNFSF4, Orexin A, RACK1, Ret, Radl, REV-ERB alpha/NR1D1, Rad17, REV-ERB beta/NR1D2, Rad51, Rex-1, Rae-1, RGM-A, Rae-1 alpha, RGM-B, Rae-1 beta, RGM-C, Rae-1 delta, Rheb, Rae-1 epsilon, Ribosomal Protein S6, Rae-1 gamma, RIP1, Raf-1, ROBOl, RAGE, R0B02, RalA/RalB, R0B03, RaIA, ROBO4, RaIB, R0R/NR1F1-3 (pan), RANK/TNFRSF1 1A, ROR alpha/NR1F1, CCL5/RANTES, ROR gamma/NR1F3, Rap1A/B, RTK-like Orphan Receptor 1/ROR1, RAR alpha/NR1B1, RTK-like Orphan Receptor 2/ROR2, RAR beta/NR1B2, RP105, RAR gamma/NR1B3, RP A2, Ras, RSK (pan), RBP4, RSK1/RSK2, RECK, RSK1, Reg 2/PAP, RSK2, Reg I, RSK3, Reg II, RSK4, Reg III, R-Spondin 1, Reg Ilia, R-Spondin 2, Reg IV, R-Spondin 3, Relaxin-1, RUNX1/CBFA2, Relaxin-2, RUNX2/CBFA1, Relaxin-3, RUNX3/CBFA3, RELM alpha, RXR alpha/NR2B1, RELM beta, RXR beta/NR2B2, RELT/TNFRSF19L, RXR gamma/NR2B3, Resistin, S100AlO, SLITRK5, S100A8, SLPI, S100A9, SMAC/Diablo, S100B, Smad1, SlOOP, Smad2, SALL1, Smad3, delta-Sarcoglycan, Smad4, Sca-1/Ly6, Smad5, SCD-I, Smad7, SCF, Smad8, SCF R/c-kit, SMC1, SCGF, alpha-Smooth Muscle Actin, SCL/Tall, SMUG1, SCP3/SYCP3, Snail, CXCL12/SDF-1, Sodium Calcium Exchanger 1, SDNSF/MCFD2, Soggy-1, alpha-Secretase, Sonic Hedgehog, gamma-Secretase, SorCS1, beta-Secretase, SorCS3, E-Selectin, Sortilin, L-Selectin, SOST, P-Selectin, SOX1, Semaphorin 3A, SOX2, Semaphorin 3C, SOX3, Semaphorin 3E, SOX7, Semaphorin 3F, SOX9, Semaphorin 6A, SOX1O, Semaphorin 6B, SOX 17, Semaphorin 6C, SOX21 Semaphorin 6D,SPARC, Semaphorin 7 A, SPARC-like 1, Separase, SP-D, Serine/Threonine Phosphatase Substrate I, Spinesin, Serpin A1, F-Spondin, Serpin A3, SR-AI/MSR, Serpin A4/Kallistatin, Src, Serpin A5/Protein C Inhibitor, SREC-I/SR-F1, Serpin A8/Angiotensinogen, SREC-II, Serpin B5, SSEA-I, Serpin C1/Antithrombin-III, SSEA-3, Serpin D1/Heparin Cofactor II, SSEA-4, Serpin E1/PAI-1, ST7/LRP12, Serpin E2, Stabilin-1, Serpin F1, Stabilin-2, Serpin F2, Stanniocalcin 1, Serpin G1/C1 Inhibitor, Stanniocalcin 2, Serpin 12, STAT1, Serum Amyloid A1, STAT2, SF-1/NR5A1, STAT3, SGK, STAT4, SHBG, STAT5a/b, SHIP, STAT5a, SHP/NROB2, STAT5b, SHP-I, STATE, SHP-2, VE-Statin, SIGIRR, Stella/Dppa3, Siglec-2/CD22, STRO-I, Siglec-3/CD33, Substance P, Siglec-5, Sulfamidase/SGSH, Siglec-6, Sulfatase Modifying Factor 1/SUMF1, Siglec-7, Sulfatase Modifying Factor 2/SUMF2, Siglec-9, SUMO1, Siglec-10, SUMO2/3/4, Siglec-11, SUMO3, Siglec-F, Superoxide Dismutase, SIGNR1/CD209, Superoxide Dismutase-1/Cu-Zn SOD, SIGNR4, Superoxide Dismutase-2/Mn-SOD, SIRP beta 1, Superoxide Dismutase-3/EC-SOD, SKI, Survivin, SLAM/CD150, Synapsin I, Sleeping Beauty Transposase, Syndecan-I/CD 138, Slit3, Syndecan-2, SLITRK1, Syndecan-3, SLITRK2, Syndecan-4, SLITRK4, TACI/TNFRSF13B, TMEFF 1/Tomoregulin-1, TAO2, TMEFF2, TAPP1, TNF-alpha/TNFSF IA, CCL17/TARC, TNF-beta/TNFSF1B, Tau, TNF RI/TNFRSFIA, TC21/R-Ras2, TNF RII/TNFRSF1B, TCAM-I, TOR, TCCR/WSX-1, TP-I, TC-PTP, TP63/TP73L, TDG, TR, CCL25/TECK, TR alpha/NR1A1, Tenascin C, TR beta 1/NR1A2, Tenascin R, TR2/NR2C1, TER-119, TR4/NR2C2, TERT, TRA-1-85, Testican 1/SPOCK1, TRADD, Testican 2/SPOCK2, TRAF-1, Testican 3/SPOCK3, TRAF-2, TFPI, TRAF-3, TFPI-2, TRAF-4, TGF-alpha, TRAF-6, TGF-beta, TRAIL/TNFSF10, TGF-beta 1, TRAIL R1/TNFRSFIOA, LAP (TGF-beta 1), TRAIL R2/TNFRSF10B, Latent TGF-beta 1, TRAIL R3/TNFRSF10C, TGF-beta 1.2, TRAIL R4/TNFRSF10D, TGF-beta 2, TRANCE/TNFSF1 1, TGF-beta 3, TfR (Transferrin R), TGF-beta 5, Apo-Transferrin, Latent TGF-beta by 1, Holo-Transferrin, Latent TGF-beta bp2, Trappin-2/Elafin, Latent TGF-beta bp4, TREM-1, TGF-beta RI/ALK-5, TREM-2, TGF-beta RII, TREM-3, TGF-beta RIIb, TREML1/TLT-1, TGF-beta RIII, TRF-I, Thermolysin, TRF-2, Thioredoxin-1, TRH-degrading Ectoenzyme/TRHDE, Thioredoxin-2, TRIMS, Thioredoxin-80, Tripeptidyl-Peptidase I, Thioredoxin-like 5/TRP14, TrkA, THOP1, TrkB, Thrombomodulin/CD141, TrkC, Thrombopoietin, TROP-2, Thrombopoietin R, Troponin I Peptide 3, Thrombospondin-1, Troponin T, Thrombospondin-2, TROY/TNFRSF 19, Thrombospondin-4, Trypsin 1, Thymopoietin, Trypsin 2/PRSS2, Thymus Chemokine-1, Trypsin 3/PRSS3, Tie-1, Tryptase-5/Prss32, Tie-2, Tryptase alpha/TPS1, TIM-I/KIM-I/HAVCR, Tryptase beta-1/MCPT-7, TIM-2, Tryptase beta-2/TPSB2, TIM-3, Tryptase epsilon/BSSP-4, TIM-4, Tryptase gamma-1/TPSG1, TIM-5, Tryptophan Hydroxylase, TIM-6, TSC22, TIMP-I, TSG, TIMP-2, TSG-6, TIMP-3, TSK, TIMP-4, TSLP, TL1A/TNFSF15, TSLP R, TLR1, TSP50, TLR2, beta-III Tubulin, TLR3, TWEAK/TNFSF12, TLR4, TWEAK R/TNFRSF 12, TLR5, Tyk2, TLR6, Phospho-Tyrosine, TLR9, Tyrosine Hydroxylase, TLX/NR2E1, Tyrosine Phosphatase Substrate I, Ubiquitin, UNC5H3, Ugi, UNC5H4, UGRP1, UNG, ULBP-I, uPA, ULBP-2, uPAR, ULBP-3, URB, UNC5H1, UVDE, UNC5H2, Vanilloid R1, VEGF R, VASA, VEGF R1/Flt-1, Vasohibin, VEGF R2/KDR/Flk-1, Vasorin, VEGF R3/FU-4, Vasostatin, Versican, Vav-1, VG5Q, VCAM-I, VHR, VDR/NR1I1, Vimentin, VEGF, Vitronectin, VEGF-B, VLDLR, VEGF-C, vWF-A2, VEGF-D, Synuclein-alpha, Ku70, WASP, Wnt-7b, WIF-I, Wnt-8a WISP-1/CCN4, Wnt-8b, WNKI, Wnt-9a, Wnt-1, Wnt-9b, Wnt-3a, Wnt-10a, Wnt-4, Wnt-10b, Wnt-5a, Wnt-11, Wnt-5b, wnvNS3, Wnt7a, XCR1, XPE/DDB1, XEDAR, XPE/DDB2, Xg, XPF, XIAP, XPG, XPA, XPV, XPD, XRCC1, Yes, YY1, EphA4.

Numerous human ion channels are targets of particular interest. Non-limiting examples include 5-hydroxytryptamine 3 receptor B subunit, 5-hydroxytryptamine 3 receptor precursor, 5-hydroxytryptamine receptor 3 subunit C, AAD 14 protein, Acetylcholine receptor protein, alpha subunit precursor, Acetylcholine receptor protein, beta subunit precursor, Acetylcholine receptor protein, delta subunit precursor, Acetylcholine receptor protein, epsilon subunit precursor, Acetylcholine receptor protein, gamma subunit precursor, Acid sensing ion channel 3 splice variant b, Acid sensing ion channel 3 splice variant c, Acid sensing ion channel 4, ADP-ribose pyrophosphatase, mitochondrial precursor, Alpha1 A-voltage-dependent calcium channel, Amiloride-sensitive cation channel 1, neuronal, Amiloride-sensitive cation channel 2, neuronal Amiloride-sensitive cation channel 4, isoform 2, Amiloride-sensitive sodium channel, Amiloride-sensitive sodium channel alpha-subunit, Amiloride-sensitive sodium channel beta-subunit, Amiloride-sensitive sodium channel delta-subunit, Amiloride-sensitive sodium channel gamma-subunit, Annexin A7, Apical-like protein, ATP-sensitive inward rectifier potassium channel 1, ATP-sensitive inward rectifier potassium channel 10, ATP-sensitive inward rectifier potassium channel 11, ATP-sensitive inward rectifier potassium channel 14, ATP-sensitive inward rectifier potassium channel 15, ATP-sensitive inward rectifier potassium channel 8, Calcium channel alpha12.2 subunit, Calcium channel alpha12.2 subunit, Calcium channel alphalE subunit, delta19 delta40 delta46 splice variant, Calcium-activated potassium channel alpha subunit 1, Calcium-activated potassium channel beta subunit 1, Calcium-activated potassium channel beta subunit 2, Calcium-activated potassium channel beta subunit 3, Calcium-dependent chloride channel-1, Cation channel TRPM4B, CDNA FLJ90453 fis, clone NT2RP3001542, highly similar to Potassium channel tetramerisation domain containing 6, CDNA FLJ90663 fis, clone PLACE 1005031, highly similar to Chloride intracellular channel protein 5, CGMP-gated cation channel beta subunit, Chloride channel protein, Chloride channel protein 2, Chloride channel protein 3, Chloride channel protein 4, Chloride channel protein 5, Chloride channel protein 6, Chloride channel protein C1C-Ka, Chloride channel protein C1C-Kb, Chloride channel protein, skeletal muscle, Chloride intracellular channel 6, Chloride intracellular channel protein 3, Chloride intracellular channel protein 4, Chloride intracellular channel protein 5, CHRNA3 protein, Clcn3e protein, CLCNKB protein, CNGA4 protein, Cullin-5, Cyclic GMP gated potassium channel, Cyclic-nucleotide-gated cation channel 4, Cyclic-nucleotide-gated cation channel alpha 3, Cyclic-nucleotide-gated cation channel beta 3, Cyclic-nucleotide-gated olfactory channel, Cystic fibrosis transmembrane conductance regulator, Cytochrome B-245 heavy chain, Dihydropyridine-sensitive L-type, calcium channel alpha-2/delta subunits precursor, FXYD domain-containing ion transport regulator 3 precursor, FXYD domain-containing ion transport regulator 5 precursor, FXYD domain-containing ion transport regulator 6 precursor, FXYD domain-containing ion transport regulator 7, FXYD domain-containing ion transport regulator 8 precursor, G protein-activated inward rectifier potassium channel 1, G protein-activated inward rectifier potassium channel 2, G protein-activated inward rectifier potassium channel 3, G protein-activated inward rectifier potassium channel 4, Gamma-aminobutyric-acid receptor alpha-1 subunit precursor, Gamma-aminobutyric-acid receptor alpha-2 subunit precursor, Gamma-aminobutyric-acid receptor alpha-3 subunit precursor, Gamma-aminobutyric-acid receptor alpha-4 subunit precursor, Gamma-aminobutyric-acid receptor alpha-5 subunit precursor, Gamma-aminobutyric-acid receptor alpha-6 subunit precursor, Gamma-aminobutyric-acid receptor beta-1 subunit precursor, Gamma-aminobutyric-acid receptor beta-2 subunit precursor, Gamma-aminobutyric-acid receptor beta-3 subunit precursor, Gamma-aminobutyric-acid receptor delta subunit precursor, Gamma-aminobutyric-acid receptor epsilon subunit precursor, Gamma-aminobutyric-acid receptor gamma-1 subunit precursor, Gamma-aminobutyric-acid receptor gamma-3 subunit precursor, Gamma-aminobutyric-acid receptor pi subunit precursor, Gamma-aminobutyric-acid receptor rho-1 subunit precursor, Gamma-aminobutyric-acid receptor rho-2 subunit precursor, Gamma-aminobutyric-acid receptor theta subunit precursor, GluR6 kainate receptor, Glutamate receptor 1 precursor, Glutamate receptor 2 precursor, Glutamate receptor 3 precursor, Glutamate receptor 4 precursor, Glutamate receptor 7, Glutamate receptor B, Glutamate receptor delta-1 subunit precursor, Glutamate receptor, ionotropic kainate 1 precursor, Glutamate receptor, ionotropic kainate 2 precursor, Glutamate receptor, ionotropic kainate 3 precursor, Glutamate receptor, ionotropic kainate 4 precursor, Glutamate receptor, ionotropic kainate 5 precursor, Glutamate [NMDA] receptor subunit 3A precursor, Glutamate [NMDA] receptor subunit 3B precursor, Glutamate [NMDA] receptor subunit epsilon 1 precursor, Glutamate [NMDA] receptor subunit epsilon 2 precursor, Glutamate [NMDA] receptor subunit epsilon 4 precursor, Glutamate [NMDA] receptor subunit zeta 1 precursor, Glycine receptor alpha-1 chain precursor, Glycine receptor alpha-2 chain precursor, Glycine receptor alpha-3 chain precursor, Glycine receptor beta chain precursor, H/ACA ribonucleoprotein complex subunit 1, High affinity immunoglobulin epsilon receptor beta-subunit, Hypothetical protein DKFZp31310334, Hypothetical protein DKFZp761M1724, Hypothetical protein FLJ12242, Hypothetical protein FLJ14389, Hypothetical protein FLJ14798, Hypothetical protein FLJ14995, Hypothetical protein FLJ16180, Hypothetical protein FLJ16802, Hypothetical protein FLJ32069, Hypothetical protein FLJ37401, Hypothetical protein FLJ38750, Hypothetical protein FLJ40162, Hypothetical protein FLJ41415, Hypothetical protein FLJ90576, Hypothetical protein FLJ90590, Hypothetical protein FLJ90622, Hypothetical protein KCTD15, Hypothetical protein MGC15619, Inositol 1,4,5-trisphosphate receptor type 1, Inositol 1,4,5-trisphosphate receptor type 2, Inositol 1,4,5-trisphosphate receptor type 3, Intermediate conductance calcium-activated potassium channel protein 4, Inward rectifier potassium channel 13, Inward rectifier potassium channel 16, Inward rectifier potassium channel 4, Inward rectifying K(+) channel negative regulator Kir2.2v, Kainate receptor subunit KA2a, KCNHS protein, KCTD 17 protein, KCTD2 protein, Keratinocytes associated transmembrane protein 1, Kv channel-interacting protein 4, Melastatin 1, Membrane protein MLC1, MGC 15619 protein, Mucolipin-1, Mucolipin-2, Mucolipin-3, Multidrug resistance-associated protein 4, N-methyl-D-aspartate receptor 2C subunit precursor, NADPH oxidase homolog 1, Nav1.5, Neuronal acetylcholine receptor protein, alpha-10 subunit precursor, Neuronal acetylcholine receptor protein, alpha-2 subunit precursor, Neuronal acetylcholine receptor protein, alpha-3 subunit precursor, Neuronal acetylcholine receptor protein, alpha-4 subunit precursor, Neuronal acetylcholine receptor protein, alpha-5 subunit precursor, Neuronal acetylcholine receptor protein, alpha-6 subunit precursor, Neuronal acetylcholine receptor protein, alpha-7 subunit precursor, Neuronal acetylcholine receptor protein, alpha-9 subunit precursor, Neuronal acetylcholine receptor protein, beta-2 subunit precursor, Neuronal acetylcholine receptor protein, beta-3 subunit precursor, Neuronal acetylcholine receptor protein, beta-4 subunit precursor, Neuronal voltage-dependent calcium channel alpha 2D subunit, P2X purinoceptor 1, P2X purinoceptor 2, P2X purinoceptor 3, P2X purinoceptor 4, P2X purinoceptor 5, P2X purinoceptor 6, P2X purinoceptor 7, Pancreatic potassium channel TALK-Ib, Pancreatic potassium channel TALK-Ic, Pancreatic potassium channel TALK-Id, Phospholemman precursor, Plasmolipin, Polycystic kidney disease 2 related protein, Polycystic kidney disease 2-like 1 protein, Polycystic kidney disease 2-like 2 protein, Polycystic kidney disease and receptor for egg jelly related protein precursor, Polycystin-2, Potassium channel regulator, Potassium channel subfamily K member 1, Potassium channel subfamily K member 10, Potassium channel subfamily K member 12, Potassium channel subfamily K member 13, Potassium channel subfamily K member 15, Potassium channel subfamily K member 16, Potassium channel subfamily K member 17, Potassium channel subfamily K member 2, Potassium channel subfamily K member 3, Potassium channel subfamily K member 4, Potassium channel subfamily K member 5, Potassium channel subfamily K member 6, Potassium channel subfamily K member 7, Potassium channel subfamily K member 9, Potassium channel tetramerisation domain containing 3, Potassium channel tetramerisation domain containing protein 12, Potassium channel tetramerisation domain containing protein 14, Potassium channel tetramerisation domain containing protein 2, Potassium channel tetramerisation domain containing protein 4, Potassium channel tetramerisation domain containing protein 5, Potassium channel tetramerization domain containing 10, Potassium channel tetramerization domain containing protein 13, Potassium channel tetramerization domain-containing 1, Potassium voltage-gated channel subfamily A member 1, Potassium voltage-gated channel subfamily A member 2, Potassium voltage-gated channel subfamily A member 4, Potassium voltage-gated channel subfamily A member 5, Potassium voltage-gated channel subfamily A member 6, Potassium voltage-gated channel subfamily B member 1, Potassium voltage-gated channel subfamily B member 2, Potassium voltage-gated channel subfamily C member 1, Potassium voltage-gated channel subfamily C member 3, Potassium voltage-gated channel subfamily C member 4, Potassium voltage-gated channel subfamily D member 1, Potassium voltage-gated channel subfamily D member 2, Potassium voltage-gated channel subfamily D member 3, Potassium voltage-gated channel subfamily E member 1, Potassium voltage-gated channel subfamily E member 2, Potassium voltage-gated channel subfamily E member 3, Potassium voltage-gated channel subfamily E member 4, Potassium voltage-gated channel subfamily F member 1, Potassium voltage-gated channel subfamily G member 1, Potassium voltage-gated channel subfamily G member 2, Potassium voltage-gated channel subfamily G member 3, Potassium voltage-gated channel subfamily G member 4, Potassium voltage-gated channel subfamily H member 1, Potassium voltage-gated channel subfamily H member 2, Potassium voltage-gated channel subfamily H member 3, Potassium voltage-gated channel subfamily H member 4, Potassium voltage-gated channel subfamily H member 5, Potassium voltage-gated channel subfamily H member 6, Potassium voltage-gated channel subfamily H member 7, Potassium voltage-gated channel subfamily H member 8, Potassium voltage-gated channel subfamily KQT member 1, Potassium voltage-gated channel subfamily KQT member 2, Potassium voltage-gated channel subfamily KQT member 3, Potassium voltage-gated channel subfamily KQT member 4, Potassium voltage-gated channel subfamily KQT member 5, Potassium voltage-gated channel subfamily S member 1, Potassium voltage-gated channel subfamily S member 2, Potassium voltage-gated channel subfamily S member 3, Potassium voltage-gated channel subfamily V member 2, Potassium voltage-gated channel, subfamily H, member 7, isoform 2, Potassium/sodium hyperpolarization-activated cyclic nucleotide-gated channel 1, Potassium/sodium hyperpolarization-activated cyclic nucleotide-gated channel 2, Potassium/sodium hyperpolarization-activated cyclic nucleotide-gated channel 3, Potassium/sodium hyperpolarization-activated cyclic nucleotide-gated channel 4, Probable mitochondrial import receptor subunit TOM40 homolog, Purinergic receptor P2X5, isoform A, Putative 4 repeat voltage-gated ion channel, Putative chloride channel protein 7, Putative GluR6 kainate receptor, Putative ion channel protein CATSPER2 variant 1, Putative ion channel protein CATSPER2 variant 2, Putative ion channel protein CATSPER2 variant 3, Putative regulator of potassium channels protein variant 1, Putative tyrosine-protein phosphatase TPTE, Ryanodine receptor 1, Ryanodine receptor 2, Ryanodine receptor 3, SH3KBP1 binding protein 1, Short transient receptor potential channel 1, Short transient receptor potential channel 4, Short transient receptor potential channel 5, Short transient receptor potential channel 6, Short transient receptor potential channel 7, Small conductance calcium-activated potassium channel protein 1, Small conductance calcium-activated potassium channel protein 2, isoform b, Small conductance calcium-activated potassium channel protein 3, isoform b, Small-conductance calcium-activated potassium channel SK2, Small-conductance calcium-activated potassium channel SK3, Sodium channel, Sodium channel beta-1 subunit precursor, Sodium channel protein type II alpha subunit, Sodium channel protein type III alpha subunit, Sodium channel protein type IV alpha subunit, Sodium channel protein type IX alpha subunit, Sodium channel protein type V alpha subunit, Sodium channel protein type VII alpha subunit, Sodium channel protein type VIII alpha subunit, Sodium channel protein type X alpha subunit, Sodium channel protein type XI alpha subunit, Sodium- and chloride-activated ATP-sensitive potassium channel, Sodium/potassium-transporting ATPase gamma chain, Sperm-associated cation channel 1, Sperm-associated cation channel 2, isoform 4, Syntaxin-1B1, Transient receptor potential cation channel subfamily A member 1, Transient receptor potential cation channel subfamily M member 2, Transient receptor potential cation channel subfamily M member 3, Transient receptor potential cation channel subfamily M member 6, Transient receptor potential cation channel subfamily M member 7, Transient receptor potential cation channel subfamily V member 1, Transient receptor potential cation channel subfamily V member 2, Transient receptor potential cation channel subfamily V member 3, Transient receptor potential cation channel subfamily V member 4, Transient receptor potential cation channel subfamily V member 5, Transient receptor potential cation channel subfamily V member 6, Transient receptor potential channel 4 epsilon splice variant, Transient receptor potential channel 4 zeta splice variant, Transient receptor potential channel 7 gamma splice variant, Tumor necrosis factor, alpha-induced protein 1, endothelial, Two-pore calcium channel protein 2, VDAC4 protein, Voltage gated potassium channel Kv3.2b, Voltage gated sodium channel betalB subunit, Voltage-dependent anion channel, Voltage-dependent anion channel 2, Voltage-dependent anion-selective channel protein 1, Voltage-dependent anion-selective channel protein 2, Voltage-dependent anion-selective channel protein 3, Voltage-dependent calcium channel gamma-1 subunit, Voltage-dependent calcium channel gamma-2 subunit, Voltage-dependent calcium channel gamma-3 subunit, Voltage-dependent calcium channel gamma-4 subunit, Voltage-dependent calcium channel gamma-5 subunit, Voltage-dependent calcium channel gamma-6 subunit, Voltage-dependent calcium channel gamma-7 subunit, Voltage-dependent calcium channel gamma-8 subunit, Voltage-dependent L-type calcium channel alpha-1C subunit, Voltage-dependent L-type calcium channel alpha-1D subunit, Voltage-dependent L-type calcium channel alpha-IS subunit, Voltage-dependent L-type calcium channel beta-1 subunit, Voltage-dependent L-type calcium channel beta-2 subunit, Voltage-dependent L-type calcium channel beta-3 subunit, Voltage-dependent L-type calcium channel beta-4 subunit, Voltage-dependent N-type calcium channel alpha-1B subunit, Voltage-dependent P/Q-type calcium channel alpha-1A subunit, Voltage-dependent R-type calcium channel alpha-1E subunit, Voltage-dependent T-type calcium channel alpha-1G subunit, Voltage-dependent T-type calcium channel alpha-1H subunit, Voltage-dependent T-type calcium channel alpha-1I subunit, Voltage-gated L-type calcium channel alpha-1 subunit, Voltage-gated potassium channel beta-1 subunit, Voltage-gated potassium channel beta-2 subunit, Voltage-gated potassium channel beta-3 subunit, Voltage-gated potassium channel KCNA7. The Nav1.x family of human voltage-gated sodium channels is also a particularly promising target. This family includes, for example, channels Nav1.6 and Nav1.8.

In other embodiments, the therapeutic protein may be a G-Protein Coupled Receptors (GPCRs). Exemplary GPCRs include but are not limited to Class A Rhodopsin like receptors such as Muscatinic (Muse.) acetylcholine Vertebrate type 1, Muse, acetylcholine Vertebrate type 2, Muse, acetylcholine Vertebrate type 3, Muse, acetylcholine Vertebrate type 4; Adrenoceptors (Alpha Adrenoceptors type 1, Alpha Adrenoceptors type 2, Beta Adrenoceptors type 1, Beta Adrenoceptors type 2, Beta Adrenoceptors type 3, Dopamine Vertebrate type 1, Dopamine Vertebrate type 2, Dopamine Vertebrate type 3, Dopamine Vertebrate type 4, Histamine type 1, Histamine type 2, Histamine type 3, Histamine type 4, Serotonin type 1, Serotonin type 2, Serotonin type 3, Serotonin type 4, Serotonin type 5, Serotonin type 6, Serotonin type 7, Serotonin type 8, other Serotonin types, Trace amine, Angiotensin type 1, Angiotensin type 2, Bombesin, Bradykinin, C5a anaphylatoxin, Fmet-leu-phe, APJ like, Interleukin-8 type A, Interleukin-8 type B, Interleukin-8 type others, C-C Chemokine type 1 through type 11 and other types, C-X-C Chemokine (types 2 through 6 and others), C-X3-C Chemokine, Cholecystokinin CCK, CCK type A, CCK type B, CCK others, Endothelin, Melanocortin (Melanocyte stimulating hormone, Adrenocorticotropic hormone, Melanocortin hormone), Duffy antigen, Prolactin-releasing peptide (GPR1O), Neuropeptide Y (type 1 through 7), Neuropeptide Y, Neuropeptide Y other, Neurotensin, Opioid (type D, K, M, X), Somatostatin (type 1 through 5), Tachykinin (Substance P (NK1), Substance K (NK2), Neuromedin K (NK3), Tachykinin like 1, Tachykinin like 2, Vasopressin/vasotocin (type 1 through 2), Vasotocin, Oxytocin/mesotocin, Conopressin, Galanin like, Proteinase-activated like, Orexin & neuropeptides FF.QRFP, Chemokine receptor-like, Neuromedin U like (Neuromedin U, PRXamide), hormone protein (Follicle stimulating hormone, Lutropin-choriogonadotropic hormone, Thyrotropin, Gonadotropin type I, Gonadotropin type II), (Rhod)opsin, Rhodopsin Vertebrate (types 1-5), Rhodopsin Vertebrate type 5, Rhodopsin Arthropod, Rhodopsin Arthropod type 1, Rhodopsin Arthropod type 2, Rhodopsin Arthropod type 3, Rhodopsin Mollusc, Rhodopsin, Olfactory (Olfactory II fam 1 through 13), Prostaglandin (prostaglandin E2 subtype EP1, Prostaglandin E2/D2 subtype EP2, prostaglandin E2 subtype EP3, Prostaglandin E2 subtype EP4, Prostaglandin F2-alpha, Prostacyclin, Thromboxane, Adenosine type 1 through 3, Purinoceptors, Purinoceptor P2RY1-4,6,1 1 GPR91, Purinoceptor P2RY5,8,9,10 GPR35,92,174, Purinoceptor P2RY12-14 GPR87 (UDP-Glucose), Cannabinoid, Platelet activating factor, Gonadotropin-releasing hormone, Gonadotropin-releasing hormone type I, Gonadotropin-releasing hormone type II, Adipokinetic hormone like, Corazonin, Thyrotropin-releasing hormone & Secretagogue, Thyrotropin-releasing hormone, Growth hormone secretagogue, Growth hormone secretagogue like, Ecdysis-triggering hormone (ETHR), Melatonin, Lysosphingolipid & LPA (EDG), Sphingosine 1-phosphate Edg-1, Lysophosphatidic acid Edg-2, Sphingosine 1-phosphate Edg-3, Lysophosphatidic acid Edg-4, Sphingosine 1-phosphate Edg-5, Sphingosine 1-phosphate Edg-6, Lysophosphatidic acid Edg-7, Sphingosine 1-phosphate Edg-8, Edg Other Leukotriene B4 receptor, Leukotriene B4 receptor BLT1, Leukotriene B4 receptor BLT2, Class A Orphan/other, Putative neurotransmitters, SREB, Mas proto-oncogene & Mas-related (MRGs), GPR45 like, Cysteinyl leukotriene, G-protein coupled bile acid receptor, Free fatty acid receptor (GP40,GP41,GP43), Class B Secretin like, Calcitonin, Corticotropin releasing factor, Gastric inhibitory peptide, Glucagon, Growth hormone-releasing hormone, Parathyroid hormone, PACAP, Secretin, Vasoactive intestinal polypeptide, Latrophilin, Latrophilin type 1, Latrophilin type 2, Latrophilin type 3, ETL receptors, Brain-specific angiogenesis inhibitor (BAI), Methuselah-like proteins (MTH), Cadherin EGF LAG (CELSR), Very large G-protein coupled receptor, Class C Metabotropic glutamate/pheromone, Metabotropic glutamate group I through III, Calcium-sensing like, Extracellular calcium-sensing, Pheromone, calcium-sensing like other, Putative pheromone receptors, GABA-B, GABA-B subtype 1, GABA-B subtype 2, GABA-B like, Orphan GPRC5, Orphan GPCR6, Bride of sevenless proteins (BOSS), Taste receptors (T1R), Class D Fungal pheromone, Fungal pheromone A-Factor like (STE2.STE3), Fungal pheromone B like (BAR,BBR,RCB, PRA), Class E cAMP receptors, Ocular albinism proteins, Frizzled/Smoothened family, frizzled Group A (Fz 1&2&4&5&7-9), frizzled Group B (Fz 3 & 6), frizzled Group C (other), Vomeronasal receptors, Nematode chemoreceptors, Insect odorant receptors, and Class Z Archaeal/bacterial/fiingal opsins.

In other embodiments, the SABA fusions described herein may comprise any of the following active polypeptides: BOTOX, Myobloc, Neurobloc, Dysport (or other serotypes of botulinum neurotoxins), alglucosidase alfa, daptomycin, YH-16, choriogonadotropin alfa, filgrastim, cetrorelix, interleukin-2, aldesleukin, teceleukin, denileukin diftitox, interferon alfa-n3 (injection), interferon alfa-nl, DL-8234, interferon, Suntory (gamma-Ia), interferon gamma, thymosin alpha 1, tasonermin, DigiFab, ViperaTAb, EchiTAb, CroFab, nesiritide, abatacept, alefacept, Rebif, eptotermin alfa, teriparatide (osteoporosis), calcitonin injectable (bone disease), calcitonin (nasal, osteoporosis), etanercept, hemoglobin glutamer 250 (bovine), drotrecogin alfa, collagenase, carperitide, recombinant human epidermal growth factor (topical gel, wound healing), DWP-401, darbepoetin alfa, epoetin omega, epoetin beta, epoetin alfa, desirudin, lepirudin, bivalirudin, nonacog alpha, Mononine, eptacog alfa (activated), recombinant Factor VIII+VWF, Recombinate, recombinant Factor VIII, Factor VIII (recombinant), Alphanate, octocog alfa, Factor VIII, palifermin, Indikinase, tenecteplase, alteplase, pamiteplase, reteplase, nateplase-.monteplase, follitropin alfa, rFSH, hpFSH, micafungin, pegfilgrastim, lenograstim, nartograstim, sermorelin, glucagon, exenatide, pramlintide, imiglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, somatropin, Eutropin, KP-102 program, somatropin, somatropin, mecasermin (growth failure), enfuvirtide, Org-33408, insulin glargine, insulin glulisine, insulin (inhaled), insulin lispro, insulin detemir, insulin (buccal, RapidMist), mecasermin rinfabate, anakinra, celmoleukin, 99mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasermin, Roferon-A, interferon-alpha 2, Alfaferone, interferon alfacon-1, interferon alpha, Avonex recombinant human luteinizing hormone, dornase alfa, trafermin, ziconotide, taltirelin, dibotermin alfa, atosiban, becaplermin, eptifibatide, Zemaira, CTC-111, Shanvac-B, HPV vaccine (quadrivalent), NOV-002, octreotide, lanreotide, ancestim, agalsidase beta, agalsidase alfa, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-2 IS, vapreotide, idursulfase, omapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-I, interferon (alpha), lucinactant, aviptadil (inhaled, pulmonary disease), icatibant, ecallantide, omiganan, Aurograb, pexiganan acetate, ADI-PEG-20, LDI-200, degarelix, cintredekin besudotox, FavId, MDX-1379, ISAtx-247, liraglutide, teriparatide (osteoporosis), tifacogin, AA-4500, T4N5 liposome lotion, catumaxomab, DWP-413, ART-123, Chrysalin, desmoteplase, amediplase, corifollitropin alpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alfa-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99mTc-Hynic-Annexin V, kahalalide F, CTCE-9908, teverelix (extended release), ozarelix, romidepsin, BAY-50-4798, interleukin-4, PRX-321, Pepscan, iboctadekin, rh lactoferrin, TRU-015, IL-21, ATN-161, cilengitide, Albuferon, Biphasix, IRX-2, omega interferon, PCK-3145, CAP-232, pasireotide, huN901-DM1, ovarian cancer immunotherapeutic vaccine, SB-249553, Oncovax-CL, OncoVax-P, BLP-25, CerVax-16, multi-epitope peptide melanoma vaccine (MART-I, gp100, tyrosinase), nemifitide, rAAT (inhaled), rAAT (dermatological), CGRP (inhaled, asthma), pegsunercept, thymosin beta-4, plitidepsin, GTP-200, ramoplanin, GRASPA, OBI-I, AC-100, salmon calcitonin (oral, eligen), calcitonin (oral, osteoporosis), examorelin, capromorelin, Cardeva, velafermin, 131I-TM-601, KK-220, TP-10, ularitide, depelestat, hematide, Chrysalin (topical), rNAPc2, recombinant Factor VIII (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, AOD-9604, linaclotide acetate, CETi-I, Hemospan, VAL (injectable), fast-acting insulin (injectable, Viadel), intranasal insulin, insulin (inhaled), insulin (oral, eligen), recombinant methionyl human leptin, pitrakinra subcutaneous injection, eczema), pitrakinra (inhaled dry powder, asthma), Multikine, RG-1068, MM-093, NBI-6024, AT-001, PI-0824, Org-39141, Cpn10 (autoimmune iseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alfa-n3 (topical), IRX-3, RDP-58, Tauferon, bile salt stimulated lipase, Merispase, alkaline phosphatase, EP-2104R, Melanotan-II, bremelanotide, ATL-104, recombinant human microplasmin, AX-200, SEMAX, ACV-I, Xen-2174, CJC-1008, dynorphin A, SI-6603, LAB GHRH, AER-002, BGC-728, malaria vaccine (virosomes, PeviPRO), ALTU-135, parvovirus B 19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85 A vaccine (tuberculosis), FAR-404, BA-210, recombinant plague F1V vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT388IL-3, TST-10088, PRO-1762, Combotox, cholecystokinin-B/gastrin-receptor binding peptides, 1 1 lln-hEGF, AE-37, trastuzumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/I540/KLH vaccine (cancer), VX-001, AVE-9633, AC-9301, NY-ESO-I vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A2 (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1001 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV-4710, ALG-889, Org-41259, rhCCIO, F-991, thymopentin (pulmonary diseases), r(m)CRP, hepatoselective insulin, subalin, L 19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S. pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumine, BIM-23190, tuberculosis vaccine, multi-epitope tyrosinase peptide, cancer vaccine, enkastim, APC-8024, GI-5005, ACC-OOl, TTS-CD3, vascular-targeted TNF (solid tumors), desmopressin (buccal controlled-release), onercept, TP-9201.

In other exemplary embodiments, the SABA is fused to a moiety selected from, but not limited to, the following: FGF21 (Fibroblast Growth Factor 21), GLP-1 (glucagon-like peptide 1), Exendin 4, insulin, insulin receptor peptide, GIP (glucose-dependent insulinotropic polypeptide), adiponectin, IL-1Ra (Interleukin 1 Receptor Antagonist), VIP (vasoactive intestinal peptide), PACAP (Pituitary adenylate cyclase-activating polypeptide), leptin, INGAP (islet neogenesis associated protein), BMP-9 (bone morphogenetic protein-9), amylin, PYY3-36 (Peptide $YY_{3-36}$), PP (Pancreatic polypeptide), IL-21 (interleukin 21), plectasin, PRGN (Progranulin), Atstrrin, IFN (interferon), Apelin and osteocalcin (OCN).

In other exemplary embodiments, the SABA is fused to one or more additional $^{10}$Fn3 domains. For example, the SABA may be fused to one, two, three, four or more additional $^{10}$Fn3 domains. The additional $^{10}$Fn3 domains may bind to the same or different targets other than serum albumin.

In certain embodiments, the application provides a SABA-Y fusion that may be represented by the formula: SABA-$X_1$-Y or Y-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and Y is a therapeutic moiety as described herein.

In certain embodiments, the application provides a SABA-Y fusion that may be represented by the formula: SABA-$X_1$-Cys-$X_2$-Y or Y-$X_1$-Cys-$X_2$-SABA, wherein SABA is a SABA polypeptide as described herein (including any N-terminal and/or C-terminal extensions), $X_1$ is an optional polypeptide linker (suitable linkers include, for example, any one of SEQ ID NOs: 65-88, 216-221 or 397), Cys is a cysteine residue, $X_2$ is a chemically derived spacer (examples of suitable spacers are shown in Table 1), and Y is a therapeutic moiety as described herein. In exemplary embodiments, the chemically derived spacer contains a maleimide moiety which may used to conjugate the therapeutic moiety to the C-terminal Cys of the SABA polypeptide, or to conjugate the SABA polypeptide to the C-terminal Cys of the therapeutic moiety, by Michael addition as described further herein.

In other aspects, a SABA may be bound to two or more therapeutic moieties. For example, two moieties can be bound to a SABA in various arrangements, such as for example, from N-terminus to C-terminus of a fusion sequence, as follows: X-Y-SABA, X-SABA-Y, or SABA-X-Y, wherein X and Y represent two different therapeutic moieties. The two different therapeutic moieties may be selected from any of the moieties disclosed herein.

1. FGF21

Fibroblast Growth Factor 21 (FGF21) is a member of the FGF family of signaling proteins. These proteins function by binding and activating FGF receptors, members of the cell surface tyrosin kinase family. FGF21 is an atypical member of the family since it does not bind heparin but requires β-klotho, a single pass transmembrane protein as a co-receptor for activity. These receptors have a wide tissue distribution but β-klotho expression is restricted to certain tissues (liver, adipose and pancreas) and it is the tissue selective expression of β-klotho that imparts the target specificity for FGF21. In vitro studies indicate that FGFR1c (an isoform of FGFR1) and FGFR4 are the preferred receptors in white adipose tissue and liver, respectively.

FGF21 functions as a metabolic regulator, and disregulation of FGF21 may lead to various metabolic disorders.

FGF21 increases glucose uptake in 3T3-L1 adipocytes and primary human adipocyte cultures by inducing ERK phosphorylation and GLUT1 expression. In INS-1E cells and isolated islets, FGF21 induces ERK and AKT phosphorylation. In liver cell lines, FGF21 stimulated typical FGF signaling (ERK phosphorylation) and decreased glucose production. As described further below, the SABA-FGF21 fusions described herein may be used for treating or preventing a variety of metabolic diseases and disorders.

In one aspect, the application provides FGF21 fused to a serum albumin binding $^{10}$Fn3 (i.e., SABA) and uses of such fusions, referred to herein generically as FGF21-SABA fusions. The FGF21-SABA fusions refer to fusions having various arrangements including, for example, SABA-FGF21, FGF21-SABA, FGF21-SABA-FGF21, etc. Certain exemplary constructs are shown in Table 2. It should be understood, however, that FGF21 as disclosed herein includes FGF21 variants, truncates, and any modified forms that retain FGF21 functional activity. That is, FGF-21 as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of FGF-21.

For example, wild-type full-length FGF21 is shown in SEQ ID NO: 117. All the FGF21 variants presented in Table 2 contain the core FGF21 sequence set forth in SEQ ID NO: 118. Various N-terminal sequences, such as those set forth in any one of SEQ ID NOs: 119-124, can be added to the N-terminus of the core FGF21 sequence (SEQ ID NO:118) and retain functional activity. Additionally, a His6-tag may be added to the N-terminus (e.g., SEQ ID NO: 128-131). The core FGF21 sequence lacks a C-terminal serine which may or may not be added to the C-terminus of the core sequence without affecting its activity. Furthermore, FGF21 and SABA fusion molecules can be joined in the order FGF21-SABA, or SABA-FGF21 (including any optional terminal extension and linker sequences as described herein and known in the art) without affecting the FGF21 functional activity (see, e.g., Example B6).

In exemplary embodiments, the application provides a SABA-FGF21 fusion, wherein the FGF21 portion comprises a sequence of SEQ ID NO: 117-118 or 125-131, or a sequence having at least 70%, 75%, 80%, 85%, 90%, 95%, 97%, 98%, or 99% identity with any one of SEQ ID NO: 117-118 or 125-131. In certain embodiments, the SABA-FGF21 fusion comprises a sequence of any one of SEQ ID NOs: 132-174, or a sequence having at least 70%, 75%, 80%, 85%, 90%, 95%, 97%, 98%, or 99% identity with any one of SEQ ID NOs: 132-174.

In certain embodiments, the application provides a SABA-FGF21 fusion that may be represented by the formula: SABA-$X_1$-FGF21 or FGF21-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and FGF21 is an FGF21 peptide as described herein.

2. Insulin

In another aspect, the present invention describes SABA and insulin fusion molecules. Insulin is a hormone that regulates the energy and glucose metabolism in the body. The polypeptide is secreted into the blood by pancreatic β-islet cells, where it stimulates glucose uptake from the blood by liver, muscle, and fat cells, and promotes glycogenesis and lipogenesis. Malfunctioning of any step(s) in insulin secretion and/or action can lead to many disorders, including the dysregulation of oxygen utilization, adipogenesis, glycogenesis, lipogenesis, glucose uptake, protein synthesis, thermogenesis, and maintenance of the basal metabolic rate. This malfunctioning results in diseases and/or disorders that include, but are not limited to, hyperinsulinemia, insulin resistance, insulin deficiency, hyperglycemia, hyperlipidemia, hyperketonemia, diabetes mellitus, and diabetic nephropathy. Accordingly, the SABA-insulin fusion polypeptides described herein may be useful in treating subjects with such diseases and/or disorders.

In exemplary embodiments, insulin moieties that can be applied to the present invention include naturally occurring insulin, biosynthethic insulin, insulin derivatives and analogs. Insulin analogs are analogs of naturally-occurring insulin proteins such as human insulin or animal forms of insulin, to which at least one amino acid residue has been substituted, added and/or removed. Such amino acids can be synthetic or modified amino acids. Insulin derivatives are derivatives of either naturally-occurring insulin or insulin analogs which have been chemically-modified, for example by the addition of one or more specific chemical groups to one or more amino acids. Exemplary insulin analogs are described in U.S. Pat. No. 7,476,652, incorporated herein by reference in its entirety.

3. Insulin Receptor Peptide

In one aspect, the present invention describes SABA and insulin receptor peptide fusion molecules. In certain embodiments, the insulin receptor peptide comprises amino acids 687 to 710 of the insulin receptor (KTDSQILKELEESSFRKTFEDYLH; SEQ ID NO: 175). The insulin receptor is a transmembrane receptor tyrosine kinase activated by the hormone insulin. Activation of the insulin receptor triggers a signaling cascade that eventually results in transport of a glucose transporter to the cell surface, so that cells can take up glucose from the blood. Uptake of glucose occurs primarily in adipocytes and myocytes. Dysfunction of the insulin receptor is associated with insulin insensitivity or resistance, which often leads to diabetes mellitus type 2 and other complications that result when cells are unable to take up glucose. Other disorders associated with mutations in the insulin receptor gene include Donohue Syndrome and Rabson-Mendenhall Syndrome. Therefore, exemplary uses for the SABA-insulin receptor peptide fusions described herein may include the treatment of subjects with disorders like diabetes mellitus type 2 or other disorders associated with insufficient cellular glucose uptake, Donohue Syndrome and Rabson-Mendenhall Syndrome.

4. BMP-9

In certain aspects, the present invention describes SABA and BMP-9 fusion molecules. Various BMP-9 compositions are described in U.S. Pat. Nos. 5,661,007 and 6,287,816, incorporated herein by reference in its entirety. The bone morphogenetic proteins (BMPs) belong to the TGF-β family of growth factors and cytokines. BMPs induce formation of bone and cartilage, and mediate morphogenetic changes in many other tissues. BMP signaling is essential for embryonic development as well as growth and maintenance of postnatal tissues. The signaling pathway has also been associated in diseases ranging from spinal disorders to cancer to reflux-induced esophagitis, and more.

Over twenty BMPs have been discovered. Of these molecules, BMP-9 is primarily expressed in nonparenchymal liver cells, and has been implicated in proliferation and function of hepatocytes, in particular, hepatic glucose production. BMP-9 also appears to play other roles in apoptosis of cancer cells, signaling in endothelial cells, osteogenesis, chondrogenesis, cognition, and more. Accordingly, the SABA-BMP-9 fusion polypeptides described herein may be useful for treating various diseases and disorders, such as, for example, the treatment of various types of wounds and diseases exhibiting degeneration of the liver, as well as in the treatment of other diseases and/or disorders that include bone and/or cartilage defects, periodontal disease and various cancers.

5. Amylin

In some aspects, the present invention describes SABA and amylin fusion molecules. Amylin (or islet amyloid polypeptide, IAPP) is a small peptide hormone of 37 amino acids secreted by pancreatic β-cells. Amylin is secreted concurrently with insulin, and is thought to play a role in controlling insulin secretion, glucose homeostasis, gastric emptying, and transmitting satiety signals to the brain. Amylin forms fibrils, which have been implicated in apoptotic cell death of pancreatic β-cells. Consistent with this finding, amylin is commonly found in pancreatic islets of patients suffering from diabetes mellitus type 2 or harboring insulinoma, a neuroendocrine tumor.

Amylin may be used as a therapeutic for patients with diabetes mellitus. Preparation of amylin peptides is described in U.S. Pat. No. 5,367,052, incorporated by reference herein in its entirety. Similarly, U.S. Pat. Nos. 6,610, 824 and 7,271,238 (incorporated by reference herein in its entirety) describes agonist analogs of amylin formed by glycosylation of Asn, Ser and/or Thr residues, which may be used to treat or prevent hypoglycemic conditions. Accordingly, the SABA-amylin fusion polypeptide described herein may for example be useful in the treatment of subjects with hypoglycemia, obesity, diabetes, eating disorders, insulin-resistance syndrome, and cardiovascular disease. Preparation of SABA-Amylin fusions is described in the Examples.

In one aspect, the application provides Amylin fused to a serum albumin binding $^{10}$Fn3 (i.e., SABA) and uses of such fusions, referred to herein generically as SABA-Amylin fusions. The SABA-Amylin fusions refer to fusions having various arrangements including, for example, SABA-Amylin and Amylin-SABA. In exemplary embodiments, the SABA-Amylin fusions are arranged such that the C-terminus of the Amylin peptide is free, which permits amidation of the carboxy terminus. Certain exemplary SABA-Amylin fusion constructs are shown in Table 2. It should be understood, however, that Amylin as disclosed herein includes Amylin variants, truncates, and any modified forms that retain Amylin functional activity. That is, Amylin as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of Amylin. Exemplary Amylin sequences are presented in Table 2 as SEQ ID NOs: 296-303.

In exemplary embodiments, the application provides a SABA-Amylin fusion, wherein the Amylin portion comprises a sequence of any one of SEQ ID NO: 296-303, or a sequence having at least 70%, 75%, 80%, 85%, 90%, 95%, 97%, 98%, or 99% identity with any one of SEQ ID NOs: 296-303. In certain embodiments, the SABA-Amylin fusion comprises a sequence of any one of SEQ ID NOs: 304-328, or a sequence having at least 70%, 75%, 80%, 85%, 90%, 95%, 97%, 98%, or 99% identity with any one of SEQ ID NOs: 304-328.

In certain embodiments, the application provides a SABA-Amylin fusion that may be represented by the formula: SABA-$X_1$-Amylin, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and Amylin is an Amylin peptide as described herein. Preferably, the Amylin peptide is amidated at the C-terminus. The Amylin peptide may additionally comprise a $Cys^{1,7}$ or $Cys^{2,7}$ disulfide bond.

In certain embodiments, the application provides a SABA-Amylin fusion that may be represented by the formula: SABA-$X_1$-Cys-$X_2$-Amylin, wherein SABA is a SABA polypeptide as described herein (including any N-terminal and/or C-terminal extensions), $X_1$ is an optional polypeptide linker (suitable linkers include, for example, any one of SEQ ID NOs: 65-88, 215-221 or 397), Cys is a cysteine residue, $X_2$ is a chemically derived spacer (examples of suitable spacers are shown in Table 1), and Amylin is an Amylin peptide as described herein. Preferably, the Amylin peptide is amidated at the C-terminus. The Amylin peptide may additionally comprise a $Cys^{1,7}$ or $Cys^{2,7}$ disulfide bond. In exemplary embodiments, the chemically derived spacer contains a maleimide moiety which may used to conjugate the Amylin peptide to the C-terminal Cys of the SABA polypeptide by Michael addition as described further herein.

6. $PYY_{3-36}$

In other aspects, the present invention describes SABA and PYY fusion molecules. Peptide YY (also known as PYY, Peptide Tyrosine Tyrosine, or Pancreatic Peptide YY) is a 36-amino acid protein released by cells in the ileum and colon in response to feeding. PYY is secreted in the pancreas and helps control energy homeostasis through inhibition of pancreatic secretions such as, for example, insulin thus leading to an increased blood glucose level and signaling a need for reduced feeding. There are two major forms of PYY, the full-length form (1-36) and the truncated form (3-36). The most common form of circulating PYY immunoreactivity is $PYY_{3-36}$. $PYY_{3-36}$ has higher affinity to Y2 receptor than $PYY_{1-36}$. In addition $PYY_{13-36}$ has similar high potency at the Y2 receptor, suggesting that residues 4-12 are not important with this receptor (K. McCrea, et al., 2-36[K4,RYYSA(19-23)]PP a novel Y5-receptor preferring ligand with strong stimulatory effect on food intake, *Regul. Pept* 87 1-3 (2000), pp. 47-58.). Furthermore, even shorter PYY fragment analogues based on the structure of PYY(22-36) and (25-36) have been described, showing Y2 selectivity over the other NPY receptors (Y1, Y4 and Y5). See e.g., U.S. Pat. Nos. 5,604,203, and 6,046,167, incorporated by reference herein. PYY peptides and functional derivatives coupled to reactive groups are described in U.S. Pat. No. 7,601,691, incorporated by reference herein.

PYY has been implicated in a number of physiological activities including nutrient uptake, cell proliferation, lipolysis, and vasoconstriction. In particular, $PYY_{3-36}$ has been shown to reduce appetite and food intake in humans (see e.g. Batterham et al., Nature 418:656-654, 2002). Accordingly, exemplary uses for the the SABA-PYY fusion polypeptides described herein may include the treatment of obesity, diabetes, eating disorders, insulin-resistance syndrome, and cardiovascular disease.

In one aspect, the application provides PYY fused to a serum albumin binding $^{10}$Fn3 (i.e., SABA) and uses of such fusions, referred to herein generically as SABA-PYY fusions. The SABA-PYY fusions refer to fusions having various arrangements including, for example, SABA-PYY and PYY-SABA. In exemplary embodiments, the SABA-PYY fusions are arranged such that the C-terminus of the PYY peptide is free, which permits amidation of the carboxy terminus. Certain exemplary SABA-PYY fusion constructs are shown in Table 2. It should be understood, however, that PYY as disclosed herein includes PYY variants, truncates, and any modified forms that retain PYY functional activity. That is, PYY as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of PYY. Exemplary PYY sequences are presented in Table 2 as SEQ ID NOs: 329-337 and 408-418.

In exemplary embodiments, the application provides a SABA-PYY fusion, wherein the PYY portion comprises a sequence of any one of SEQ ID NO: 329-337 or 408-418; a sequence having at least 70%, 75%, 80%, 85%, 90%, 95%, 97%, 98%, or 99% identity with any one of SEQ ID NOs: 329-337 or 408-418; a sequence having residues 3-36, 13-36, 21-36, 22-36, 24-36, or 25-36 of any one of SEQ ID NOs: 329-333 or 335-337; a sequence having at least 70%, 75%, 80%, 85%, 90%, 95%, 97%, 98%, or 99% identity with a sequence having residues 3-36, 13-36, 21-36, 22-36, 24-36, or 25-36 of any one of SEQ ID NOs: 329-333 or 335-337; or any one of the foregoing sequences having a V31L substitution. In certain embodiments, the SABA-PYY fusion comprises a sequence of any one of SEQ ID NOs: 338-344, or a sequence having at least 70%, 75%, 80%, 85%, 90%, 95%, 97%, 98%, or 99% identity with any one of SEQ ID NOs: 338-344.

In certain embodiments, the application provides a SABA-PYY fusion that may be represented by the formula: SABA-$X_1$-PYY, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and PYY is a PYY peptide as described herein. Preferably, the PYY peptide is amidated at the C-terminus.

In certain embodiments, the application provides a SABA-PYY fusion that may be represented by the formula: SABA-$X_1$-Cys-$X_2$-PYY, wherein SABA is a SABA polypeptide as described herein (including any N-terminal and/or C-terminal extensions), $X_1$ is an optional polypeptide linker (suitable linkers include, for example, any one of SEQ ID NOs: 65-88, 215-221 or 397), Cys is a cysteine residue, $X_2$ is a chemically derived spacer (examples of suitable spacers are shown in Table 1), and PYY is a PYY peptide as described herein. Preferably, the PYY peptide is amidated at the C-terminus. In exemplary embodiments, the chemically derived spacer contains a maleimide moiety which may used to conjugate the PYY peptide to the C-terminal Cys of the SABA polypeptide by Michael addition as described further herein.

7. Pancreatic Polypeptide

In some aspects, the present invention describes SABA and Pancreatic polypeptide fusion molecules. Pancreatic polypeptide (PP) is a member of the pancreatic polypeptide hormone family that also includes neuropeptide Y (NPY) and peptide YY (PYY). PP is a 36 amino acid protein released by pancreatic polypeptide cells in response to eating, exercising, and fasting. PP is found in the pancreas, gastrointestinal tract, and CNS, where it affects gallbladder contraction, pancreatic secretion, intestinal mobility, as well as metabolic functions such as glycogenolysis and reduction in fatty acid levels. PP has also been implicated in food intake, energy metabolism, and expression of hypothalamic peptides and gastric ghrelin. In addition, PP is reduced in conditions associated with increased food intake. PP may also be involved in tumorogenesis, such as rare malignant tumors of the pancreatic peptide cells. PP may be administered to patients, for example, to reduce hepatic glucose production (U.S. Pat. No. 5,830,434). Exemplary uses for the SABA-PP fusion polypeptides disclosed herein may include the treatment of obesity, diabetes, eating disorders, insulin-resistance syndrome, and cardiovascular disease.

In one aspect, the application provides PP fused to a serum albumin binding $^{10}$Fn3 (i.e., SABA) and uses of such fusions, referred to herein generically as SABA-PP fusions. The SABA-PP fusions refer to fusions having various arrangements including, for example, SABA-PP and PP-SABA. In exemplary embodiments, the SABA-PP fusions are arranged such that the C-terminus of the PP peptide is free, which permits amidation of the carboxy terminus. Certain exemplary SABA-PP fusion constructs are shown in Table 2. It should be understood, however, that PP as disclosed herein includes PP variants, truncates, and any modified forms that retain PP functional activity. That is, PP as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of PP. Exemplary PP sequences are presented in Table 2 as SEQ ID NOs: 345-357.

In exemplary embodiments, the application provides a SABA-PP fusion, wherein the PP portion comprises a sequence of any one of SEQ ID NO: 345-357, or a sequence having at least 70%, 75%, 80%, 85%, 90%, 95%, 97%, 98%, or 99% identity with any one of SEQ ID NOs: 345-357. In certain embodiments, the SABA-PP fusion comprises a sequence of any one of SEQ ID NOs: 358-364, or a sequence having at least 70%, 75%, 80%, 85%, 90%, 95%, 97%, 98%, or 99% identity with any one of SEQ ID NOs: 358-364.

In certain embodiments, the application provides a SABA-PP fusion that may be represented by the formula: SABA-$X_1$-PP, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and PP is a PP peptide as described herein. Preferably, the PP peptide is amidated at the C-terminus.

In certain embodiments, the application provides a SABA-PP fusion that may be represented by the formula: SABA-$X_1$-Cys-$X_2$-PP, wherein SABA is a SABA polypeptide as described herein (including any N-terminal and/or C-terminal extensions), $X_1$ is an optional polypeptide linker (suitable linkers include, for example, any one of SEQ ID NOs: 65-88, 215-221 or 397), Cys is a cysteine residue, $X_2$ is a chemically derived spacer (examples of suitable spacers are shown in Table 1), and PP is a PP peptide as described herein. Preferably, the PP peptide is amidated at the C-terminus. In exemplary embodiments, the chemically derived spacer contains a maleimide moiety which may used to conjugate the PP peptide to the C-terminal Cys of the SABA polypeptide by Michael addition as described further herein.

8. Interleukin 21 (IL-21)

In another aspect, the present invention describes SABA and IL-21 fusion molecules. IL-21 is a type I cytokine that shares the common receptor γ-chain with IL-2, IL-4, IL-7, IL-9, and IL-15. IL-21 is expressed in activated human CD4+ T cells, up-regulated in Th2 and Th17 subsets of T helper cells, T follicular cells and NK T cells. The cytokine has a role in regulating the function of all of these cell types. B cells are also regulated by IL-21. Depending on the interplay with costimulatory signals and on the developmental stage of a B cell, IL-21 can induce proliferation, differentiation into Ig-producing plasma cells, or apoptosis in both mice and humans. Alone and in combination with Th cell-derived cytokines, IL-21 can regulate class switch recombination to IgG, IgA, or IgE isotypes, indicating its important role in shaping the effector function of B cells. Thus, through its multiple effects on immune cells, IL-21 plays a role in many aspects of the normal immune response.

As a regulator of the immune system, the use of IL-21 as an immunostimulator for cancer therapy—either alone or in combination with other therapies, use as an adjunct to immunotherapy, and use as a viral therapy have been studied, among other uses where up-regulation of the immune system is desired. Particular cancers treated both clinically and pre-clinically have been metastatic melanoma, renal cell carcinoma, colon carcinoma, pancreatic carcinoma, mammary carcinoma, thyoma, head and neck squamous cell carcinoma, and gliomas (for a review, see Sondergaard and Skak, Tissue Antigens, 74(6): 467-479, 2009). Additionally, IL-21 up-regulation has been linked to various human T cell-mediated or T cell-linked inflammatory pathologies including Crohn's disease (CD), ulcerative colitis, the major forms of inflammatory bowel disease (IBD), *Helicobacter pylori*-related gastritis, celiac disease, atopic dermatitis (AD), systemic lupus erthyematosus, rheumatoid arthritis, and psoriasis (for a review, see Monteleone et al, Trends Pharmacol Sci, 30(8), 441-7, 2009). Exemplary IL-21 proteins are described in U.S. Pat. Nos. 6,307,024 and 7,473,765, which are herein incorporated by reference.

Exemplary uses for the SABA-IL21 fusion polypeptides described herein include the treatment of certain types of cancers, viral-related diseases, as well as various T cell-mediated or T cell-linked inflammatory disorders such as Crohn's disease (CD), ulcerative colitis, the major forms of inflammatory bowel disease (IBD), *Helicobacter pylori*-related gastritis, celiac disease, atopic dermatitis (AD), systemic lupus erthyematosus, rheumatoid arthritis, and psoriasis.

In one aspect, the application provides IL-21 fused to a serum albumin binding $^{10}$Fn3 (i.e., SABA) and uses of such fusions, referred to herein generically as SABA-IL21 fusions. The SABA-IL21 fusions refer to fusions having various arrangements including, for example, SABA-IL-21 and IL21-SABA. Certain exemplary SABA-IL21 fusion constructs are shown in Table 2. It should be understood, however, that IL-21 as disclosed herein includes IL-21 variants, truncates, and any modified forms that retain IL-21 functional activity. That is, IL-21 as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of IL-21. Exemplary IL-21 sequences are presented in Table 2 as SEQ ID NOs: 286-287.

In exemplary embodiments, the application provides a SABA-IL21 fusion, wherein the IL-21 portion comprises a sequence of any one of SEQ ID NO: 286-287, or a sequence having at least 70%, 75%, 80%, 85%, 90%, 95%, 97%, 98%, or 99% identity with any one of SEQ ID NOs: 286-287. In certain embodiments, the SABA-IL21 fusion comprises a sequence of any one of SEQ ID NOs: 290-295, or a sequence having at least 70%, 75%, 80%, 85%, 90%, 95%, 97%, 98%, or 99% identity with any one of SEQ ID NOs: 290-295.

In certain embodiments, the application provides a SABA-IL21 fusion that may be represented by the formula: SABA-$X_1$-IL21 or IL21-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and IL21 is an IL-21 peptide as described herein.

9. Glucagon-Like Peptide 1 (GLP-1)/Exendin-4

In another aspect, the present invention describes SABA and GLP-1 fusion molecules. Glucagon-like peptide 1 (GLP-1) is a 30 or 31 amino acid peptide (SEQ ID NOs: 226 and 227) released from enteroendocrine L cells in response to nutrient ingestion. This hormone can act by multiple mechanisms to modulate glucose homeostasis and exert antidiabetic effects. GLP-1 signaling enhances glucose-dependent insulin secretion, inhibits glucagon secretion in a glucose-dependent manner, delays gastric emptying, leads to reduced food intake and body weight, and causes an increase in beta cell mass in animal models.

The therapeutic utility of native GLP-1 is limited because it has a half-life of less than 2 minutes in vivo due to its rapid degradation by the ubiquitous protease, dipeptidyl peptidase IV (DPP-IV). Because DPP-IV preferentially cleaves amino terminal dipeptides with alanine or proline at the second position, one strategy to increase the half-life is to alter the second amino acid (position 8) in active GLP-1 such that the peptide is no longer a DPP-IV substrate. The alanine in position 8 can be replaced by a wide variety of natural (or unnatural) amino acids, including glycine, serine, threonine, or valine to produce DPP-IV resistant GLP-1 analogs. However, DPP-IV resistant GLP-1 analogs still have a relatively short pharmacokinetic half-life because they are eliminated via renal clearance. For example, the potent and DPP-IV resistant GLP-1 receptor agonist, synthetic exendin-4 (SEQ ID NO: 228; active pharmaceutical ingredient in Byetta), must still be administered twice daily in human diabetic patients because it is rapidly cleared by the kidney.

Another approach to produce long-acting GLP-1 receptor agonists has been to express a DPP-IV resistant GLP-1 analog in the same open reading frame as a long-lived protein such as albumin or transferrin. One such fusion protein, albiglutide, a DPP-IV resistant GLP-1 analog fused to human serum albumin, is currently being evaluated in phase III clinical trials. In all cases reported, the active fusion protein has had the DPP-IV resistant GLP-1 receptor agonist at the amino terminus of the fusion protein; c-terminal fusions are markedly less potent.

In exemplary embodiments, a SABA-GLP-1 fusion protein comprises from N-terminus to C-terminus: a DPP-IV resistant GLP-1 receptor agonist (potentially including sequences based on GLP-1 or exendin-4), a linker, and a SABA.

Exemplary uses for the SABA-GLP-1 and SABA-Exendin fusion polypeptides include the treatment of diabetes, obesity, initable bowel syndrome and other conditions that would be benefited by lowering plasma glucose, inhibiting gastric and/or intestinal motility and inhibiting gastric and/or intestinal emptying, or inhibiting food intake.

In one aspect, the application provides GLP-1 or Exendin fused to a serum albumin binding $^{10}$Fn3 (i.e., SABA) and uses of such fusions, referred to herein generically as SABA-GLP-1 or SABA-Exendin fusions. The SABA-GLP-1 or SABA-Exendin fusions refer to fusions having various arrangements including, for example, SABA-GLP-1, GLP-1-SABA, SABA-Exendin and Exendin-SABA. Certain exemplary SABA-GLP-1 and SABA-Exendin fusion constructs are shown in Table 2. It should be understood, however, that GLP-1 and Exendin as disclosed herein includes GLP-1 and Exendin variants, truncates, and any modified forms that retain GLP-1 or Exendin functional activity. That is, GLP-1 and Exendin as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of GLP-1 or Exendin. Exemplary GLP-1 sequences are presented in Table 2 as SEQ ID NOs: 226-227 and an exemplary Exendin sequence is presented in Table 2 as SEQ ID NO: 228.

In exemplary embodiments, the application provides a SABA-GLP-1 fusion, wherein the GLP-1 portion comprises a sequence of any one of SEQ ID NO: 226-227, or a sequence having at least 70%, 75%, 80%, 85%, 90%, 95%, 97%, 98%, or 99% identity with any one of SEQ ID NOs: 226-227. In certain embodiments, the SABA-GLP-1 fusion comprises a sequence of any one of SEQ ID NOs: 229-232, or a sequence having at least 70%, 75%, 80%, 85%, 90%, 95%, 97%, 98%, or 99% identity with any one of SEQ ID NOs: 229-232.

In certain embodiments, the application provides a SABA-GLP-1 fusion that may be represented by the formula: SABA-$X_1$-GLP-1 or GLP-1-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and GLP-1 is a GLP-1 peptide as described herein.

In exemplary embodiments, the application provides a SABA-Exendin fusion, wherein the Exendin portion comprises SEQ ID NO: 228, or a sequence having at least 70%, 75%, 80%, 85%, 90%, 95%, 97%, 98%, or 99% identity to SEQ ID NO: 228. In certain embodiments, the SABA-Exendin fusion comprises a sequence of any one of SEQ ID NOs: 233-236, or a sequence having at least 70%, 75%, 80%, 85%, 90%, 95%, 97%, 98%, or 99% identity with any one of SEQ ID NOs: 233-236.

In certain embodiments, the application provides a SABA-Exendin fusion that may be represented by the formula: SABA-$X_1$-Exendin or Exendin-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and Exendin is an Exendin peptide as described herein.

10. Plectasin

In another aspect, the present invention describes SABA and Plectasin fusion molecules. Plectasin is a novel bactericidal antimicrobial peptide isolated from a fungus, the saprophytic ascomycete *Pseudoplectania nigrella*. In vitro, plectasin can kill *Staphylococcus aureus* and *Streptococcus pneumonia*, including numerous strains resistant to conventional antibiotics, rapidly at rates comparable to both vancomycin and penicillin, but without cytotoxic effect on mammalian cells. In vivo, plectasin also shows extremely low toxicity in mice and can cure the peritonitis and pneumonia caused by *S. pneumoniae* as efficaciously as vancomycin and penicillin. See e.g., Mygind P H, et al., Plectasin is a peptide antibiotic with therapeutic potential from a saprophytic fungus, Nature 437:975-980 (2005); Brinch K S, et al., Plectasin shows intracellular activity against *Staphylococcus aureus* in human THP-1 monocytes and in the mouse peritonitis model, Antimicrob Agents Chemother 53:4801-4808 (2009); 3. Hara S, et al., Plectasin has antibacterial activity and no effect on cell viability or IL-8 production, Biochem Biophys Res Commun 374:709-713 (2008); and Ostergaard C, et al., High cerebrospinal fluid (CSF) penetration and potent bactericidal activity in CSF of NZ2114, a novel plectasin variant, during experimental pneumococcal meningitis, Antimicrob Agents Chemother 53:1581-1585 (2009). Given these characteristics, plectasin is an attractive candidate to serve as a prospective antibiotics product. See e.g., Xiao-Lan J, et al., High-Level Expression of the Antimicrobial Peptide Plectasin in *Escherichia coli*, Curr Microbiol 61:197-202 (2010). Accordingly, the SABA-plectasin fusion polypeptides described herein may be used as antibacterial agents.

In one aspect, the application provides Plectasin fused to a serum albumin binding $^{10}$Fn3 (i.e., SABA) and uses of such fusions, referred to herein generically as SABA-Plectasin fusions. The SABA-Plectasin fusions refer to fusions having various arrangements including, for example, SABA-Plectasin and Plectasin-SABA. Certain exemplary SABA-Plectasin fusion constructs are shown in Table 2. It should be understood, however, that Plectasin as disclosed herein includes Plectasin variants, truncates, and any modified forms that retain Plectasin functional activity. That is, Plectasin as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of Plectasin. An exemplary Plectasin sequence is presented in Table 2 as SEQ ID NO: 237.

In exemplary embodiments, the application provides a SABA-Plectasin fusion, wherein the Plectasin portion comprises SEQ ID NO: 237, or a sequence having at least 70%, 75%, 80%, 85%, 90%, 95%, 97%, 98%, or 99% identity with SEQ ID NO: 237. In certain embodiments, the SABA-Plectasin fusion comprises a sequence of any one of SEQ ID NOs: 238-239, or a sequence having at least 70%, 75%, 80%, 85%, 90%, 95%, 97%, 98%, or 99% identity with any one of SEQ ID NOs: 238-239.

In certain embodiments, the application provides a SABA-Plectasin fusion that may be represented by the formula: SABA-$X_1$-Plectasin or Plectasin-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and Plectasin is a Plectasin peptide as described herein.

11. Progranulin (PRGN) and Atstrrin

In another aspect, the present invention describes SABA and Progranulin or SABA and Atstrrin fusion molecules. Progranulin and Atstrrin, an engineered protein comprising 3 fragments from Progranulin, are tumor necrosis factor (TNF) receptor binders that antagonize TNF signaling. Progranulin and Atstrrin prevent inflammation in mouse models of arthritis. See e.g., Tang, W. et. al., The Growth Factor Progranulin Binds to TNF Receptors and Is Therapeutic Against Inflammatory Arthritis in Mice, Science, ScienceExpress, Mar. 10, 2011, Supplementary Material. SABA fusions of either protein may be potential therapeutics for TNFα-mediated diseases.

In one aspect, the application provides Progranulin or Atstrrin fused to a serum albumin binding $^{10}$Fn3 (i.e., SABA) and uses of such fusions, referred to herein generically as SABA-PRGN or SABA-Atstrrin fusions. The SABA-PRGN or SABA-Atstrrin fusions refer to fusions having various arrangements including, for example, SABA-PRGN, PRGN-SABA, SABA-Atstrrin and Atstrrin-SABA. Certain exemplary SABA-PRGN and SABA-Atstrrin fusion constructs are shown in Table 2. It should be understood, however, that Progranulin and Atstrrin as disclosed herein includes Progranulin and Atstrrin variants, truncates, and any modified forms that retain Progranulin or Atstrrin functional activity. That is, Progranulin and Atstrrin as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of Progranulin or Atstrrin. Exemplary Progranulin sequences are presented in Table 2 as SEQ ID NOs: 240-241 and an exemplary Atstrrin sequence is presented in Table 2 as SEQ ID NO: 242.

In exemplary embodiments, the application provides a SABA-PRGN fusion, wherein the PRGN portion comprises a sequence of any one of SEQ ID NO: 240-241, or a sequence having at least 70%, 75%, 80%, 85%, 90%, 95%, 97%, 98%, or 99% identity with any one of SEQ ID NOs: 240-241. In certain embodiments, the SABA-PRGN fusion comprises a sequence of any one of SEQ ID NOs: 243-246, or a sequence having at least 70%, 75%, 80%, 85%, 90%, 95%, 97%, 98%, or 99% identity with any one of SEQ ID NOs: 243-246.

In certain embodiments, the application provides a SABA-PRGN fusion that may be represented by the formula: SABA-$X_1$-PRGN or PRGN-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and PRGN is a Progranulin peptide as described herein.

In exemplary embodiments, the application provides a SABA-Atstrrin fusion, wherein the Atstrrin portion comprises SEQ ID NO: 242, or a sequence having at least 70%, 75%, 80%, 85%, 90%, 95%, 97%, 98%, or 99% identity to SEQ ID NO: 242. In certain embodiments, the SABA-Atstrrin fusion comprises a sequence of any one of SEQ ID NOs: 247-250, or a sequence having at least 70%, 75%, 80%, 85%, 90%, 95%, 97%, 98%, or 99% identity with any one of SEQ ID NOs: 247-250.

In certain embodiments, the application provides a SABA-Atstrrin fusion that may be represented by the formula: SABA-$X_1$-Atstrrin or Atstrrin-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and Atstrrin is an Atstrrin peptide as described herein.

12. Osteocalcin (OCN)

In certain aspects, the present invention describes SABA and Osteocalcin fusion molecules. Osteocalcin (OCN, also known as Bone Gla Protein, or BGP) is a 49 amino acid protein produced by osteoblasts, and secreted into the bloodstream and bone matrix. Plasma OCN levels are subjected to biological variations including diurnal cycle, season, gender, age and menstrual cycle. OCN exists as carboxylated, uncarboxylated and undercarboxylated forms, the uncarboxylated and undercarboxylated forms are involved in the regulation of energy metabolism through stimulating insulin secretion, pancreatic β-cell proliferation and enhancing insulin sensitivity which is partially mediated through adiponectin. Insulin promotes bone remodeling, and it's signaling in osteoblasts increases the release of uncarboxylated and/or undercarboxylated OCN into circulation, which in turn improves glucose handling. Accordingly, the SABA-OCN fusion polypeptides described herein may be used in the treatment of insulin related disorders, including the dysregulation of oxygen utilization, adipogenesis, glycogenesis, lipogenesis, glucose uptake, protein synthesis, thermogenesis, and maintenance of the basal metabolic rate. This malfunctioning results in diseases and/or disorders that include, but are not limited to, hyperinsulinemia, insulin resistance, insulin deficiency, hyperglycemia, hyperlipidemia, hyperketonemia, diabetes mellitus, and diabetic nephropathy.

In one aspect, the application provides OCN fused to a serum albumin binding $^{10}$Fn3 (i.e., SABA) and uses of such fusions, referred to herein generically as SABA-OCN fusions. The SABA-OCN fusions refer to fusions having various arrangements including, for example, SABA-OCN and OCN-SABA. Certain exemplary SABA-OCN fusion constructs are shown in Table 2. It should be understood, however, that OCN as disclosed herein includes OCN variants, truncates, and any modified forms that retain OCN functional activity. That is, OCN as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of OCN. Exemplary OCN sequences are presented in Table 2 as SEQ ID NOs: 365-378.

In exemplary embodiments, the application provides a SABA-OCN fusion, wherein the OCN portion comprises a sequence of any one of SEQ ID NO: 365-378, or a sequence having at least 70%, 75%, 80%, 85%, 90%, 95%, 97%, 98%, or 99% identity with any one of SEQ ID NOs: 365-378. In certain embodiments, the SABA-OCN fusion comprises a sequence of any one of SEQ ID NOs: 379-396, or a sequence having at least 70%, 75%, 80%, 85%, 90%, 95%, 97%, 98%, or 99% identity with any one of SEQ ID NOs: 379-396.

In certain embodiments, the application provides a SABA-OCN fusion that may be represented by the formula: SABA-$X_1$-OCN or OCN-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and OCN is an OCN peptide as described herein.

In certain embodiments, the application provides a SABA-OCN fusion that may be represented by the formula: SABA-$X_1$-Cys-$X_2$-OCN or OCN-$X_1$-Cys-$X_2$-SABA, wherein SABA is a SABA polypeptide as described herein (including any N-terminal and/or C-terminal extensions), $X_1$ is an optional polypeptide linker (suitable linkers include, for example, any one of SEQ ID NOs: 65-88, 216-221 or 397), Cys is a cysteine residue, $X_2$ is a chemically derived spacer (examples of suitable spacers are shown in Table 1), and OCN is an OCN peptide as described herein. In exemplary embodiments, the chemically derived spacer contains a maleimide moiety which may used to conjugate the OCN peptide to the C-terminal Cys of the SABA polypeptide, or to conjugate the SABA polypeptide to the C-terminal Cys of the OCN peptide, by Michael addition as described further herein.

13. Interferon Lambda (IFNλ)

In another aspect, the present invention describes SABA and interferon-lambda (IFN-λ) fusion molecules. Human interferons (IFNs) are classified into three major types: Type I, Type II and Type III. Type I IFNs are expressed as a first line of defense against viral infections. The primary role of type I IFN is to limit viral spread during the first days of a viral infection allowing sufficient time for generation of a strong adaptive immune response against the infection. Type II and Type III IFNs display some of the antiviral properties of type I IFNs.

IFN-λ is a Type III IFN. Humans encode three IFN-λ molecules: IFN-λ1 (IL-29), IFN-λ2 (IL-28A) and IFN-λ3 (IL-28B). As described in U.S. Pat. No. 7,135,170, IL-28 and IL-29 have been shown to be useful in the treatment of hepatitis virus infection. Importantly, IL-28 and IL-29 were shown to possess these antiviral activities without some of the toxicities associated with the use of other previously known IFN therapies. One of the toxicities related to type I IFN therapy is myelosuppression. This is due to type I IFN suppression of bone marrow progenitor cells. Because IL-29 does not significantly suppress bone marrow cell expansion or B cell proliferation as seen with Type I IFN treatment, IL-29 will have less toxicity associated with treatment. Similar results would be expected with IL-28A and IL-28B.

Accordingly, exemplary uses for the SABA-IFN-λ fusion polypeptides described herein include the treatment of a subject with a viral infection, including, for example, viral infections such as hepatitis A, hepatitis B, hepatitis C, and hepatitis D. The SABA-IFN-λ fusion polypeptides described herein may also be used as an antiviral agent to treat viral infections associated with respiratory syncytial virus, herpes virus, Epstein-Barr virus, influenza virus, adenovirus, parainfluenza virus, rhino virus, coxsackie virus, vaccinia virus, west nile virus, dengue virus, Venezuelan equine encephalitis virus, pichinde virus and polio virus. The SABA-IFN-λ fusion polypeptides described herein may be used to treat subjects having either a chronic or acute viral infection.

In certain embodiments, the SABA-IFNλ fusions described herein may provide benefits over IFNλ, polypeptides fused to other pharmacokinetic moieties, such as, for example, PEG. In particular, the SABA-IFNλ fusions provided herein may provide a significant improvement in serum half-life of the IFNλ, molecule as compared to PEG-IFNλ conjugates. Such increases in half-life may permit a dosing regimen with a decreased frequency, e.g., a SABA-IFNλ fusion may permit once monthly dosing as compared to more frequent dosing, such as once weekly dosing, with other IFNλ, therapeutics like PEG-IFNλ conjugates.

In one aspect, the application provides IFNλ, fused to a serum albumin binding $^{10}$Fn3 (i.e., SABA) and uses of such fusions, referred to herein generically as SABA-IFNλ fusions. The SABA-IFNλ fusions refer to fusions having various arrangements including, for example, SABA-IFNλ, and IFNλ-SABA. Certain exemplary SABA-IFNλ fusion constructs are shown in Table 2. It should be understood, however, that IFNλ, as disclosed herein includes IFNλ, variants, truncates, and any modified forms that retain IFNλ, functional activity. That is, IFNλ, as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of IFNλ. Exemplary IFNλ, sequences are presented in Table 2 as SEQ ID NOs: 251-257.

In exemplary embodiments, the application provides a SABA-IFNλ fusion, wherein the IFNλ portion comprises a sequence of any one of SEQ ID NO: 251-257, or a sequence having at least 70%, 75%, 80%, 85%, 90%, 95%, 97%, 98%, or 99% identity with any one of SEQ ID NOs: 251-257. In certain embodiments, the SABA-IFNλ fusion comprises a sequence of any one of SEQ ID NOs: 258-285, or a sequence having at least 70%, 75%, 80%, 85%, 90%, 95%, 97%, 98%, or 99% identity with any one of SEQ ID NOs: 258-285.

In certain embodiments, the application provides a SABA-IFNλ fusion that may be represented by the formula: SABA-$X_1$-IFNλ or IFNλ-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and IFNλ is an IFNλ peptide as described herein.

14. Apelin

In another aspect, the application provides SABA and Apelin fusion molecules. Apelin is the endogenous ligand for the G-protein coupled receptor, APJ. The apelin gene encodes a 77 amino acid preproprotein that is cleaved to shorter active fragments. The full-length mature peptide is apelin-36, but apelin-17 and apelin-13 are also active (M Kleinz, et al., Pharmacol. Ther. 107:198-211 (2005)). Apelin is widely expressed in the central nervous system and peripheral tissues, and cellular expression includes endothelial cells and adipocytes (Supra). Apelin has been shown to produce vasodilation and improve the hemodynamic and cardiac profile of patients with heart failure, as well as prevent atherosclerosis in preclinical models (AG Japp, et al., Circ. 121: 1818-1827 (2010); and HY Chun, et al., J. Clin. Invest. 118: 3343-3354 (2008)). In addition, apelin administration is associated with improvement in insulin sensitivity in preclinical models of diabetes (C Dray, et al., Cell Metabolism 8: 437-445 (2008)). Accordingly, exemplary uses for the SABA-Apelin fusion polypeptides described herein may include the treatment of diabetes, obesity, eating disorders, insulin-resistance syndrome and cardiovascular disease (e.g., heart failure, atherosclerosis, and hypertension).

In one aspect, the application provides Apelin fused to a serum albumin binding $^{10}$Fn3 (i.e., SABA) and uses of such fusions, referred to herein generically as SABA-APLN fusions. The SABA-APLN fusions refer to fusions having various arrangements including, for example, SABA-APLN and APLN-SABA. Certain exemplary SABA-APLN fusion constructs are shown in Table 2. It should be understood, however, that Apelin as disclosed herein includes Apelin variants, truncates, and any modified forms that retain Apelin functional activity. That is, Apelin as described herein also includes modified forms, including fragments as well as variants in which certain amino acids have been deleted or substituted, and modifications wherein one or more amino acids have been changed to a modified amino acid, or a non-naturally occurring amino acid, and modifications such as glycosylations so long as the modified form retains the biological activity of Apelin. Exemplary Apelin sequences are presented in Table 2 as SEQ ID NOs: 419-423.

In exemplary embodiments, the application provides a SABA-APLN fusion, wherein the Apelin portion comprises a sequence of any one of SEQ ID NO: 419-423, or a sequence having at least 70%, 75%, 80%, 85%, 90%, 95%, 97%, 98%, or 99% identity with any one of SEQ ID NOs: 419-423. In certain embodiments, the SABA-APLN fusion comprises a sequence of any one of SEQ ID NOs: 424-430, or a sequence having at least 70%, 75%, 80%, 85%, 90%, 95%, 97%, 98%, or 99% identity with any one of SEQ ID NOs: 424-430.

In certain embodiments, the application provides a SABA-APLN fusion that may be represented by the formula: SABA-$X_1$-APLN or APLN-$X_1$-SABA, wherein SABA is a SABA polypeptide as described herein (including any N-terminal and/or C-terminal extensions), $X_1$ is a polypeptide linker (suitable linkers include, for example, any one of SEQ ID NOs: 65-88, 216-221 or 397), and APLN is an APLN peptide as described herein.

15. Other Adnectins™

In certain aspects, the application provides SABA fused to a $^{10}$Fn3 domain that binds to a target molecule other than serum albumin (e.g., HSA), resulting in an Adnectin™ dimer fusion molecule of SABA-$^{10}$Fn3 or $^{10}$Fn3-SABA configuration. In other aspects, the application provides SABA fused to two or more $^{10}$Fn3 domains thus forming a multimer. For example, in one embodiment, the application provides SABA fused to two $^{10}$Fn3 domains, $^{10}Fn3_n$ and $^{10}Fn3_b$, wherein each $^{10}Fn3_a$ and $^{10}Fn3_b$ binds to a different target molecule, and neither binds to serum albumin (e.g., HSA). The configuration of the resulting Adnectm™ trimer may be: SABA-$^{10}Fn3_a$-$^{10}Fn3_b$, $^{10}Fn3_a$-SABA-$^{10}Fn3_b$, or $^{10}Fn3_a$-$^{10}Fn3_b$-SABA.

In exemplary embodiments, the SABA is fused to a $^{10}$Fn3 domain comprising any one of SEQ ID NOs: 1-3, or a sequence having at least 50%, 60%, 65%, 70%, 75%, 80%, 85%, 90%, 95%, 97%, 98%, or 99% identity with any one of SEQ ID NOs: 1-3, wherein the BC, DE and FG loops have been modified relative to the sequences of the wild-type BC, DE and FG loops, respectively, and wherein the $^{10}$Fn3 domain binds to a target (other than integrin) with a $K_D$ of less than 500 μM. The $^{10}$Fn3 domain may additional comprise an N-terminal and/or C-terminal extension as described herein. In certain embodiments, the $^{10}$Fn3 domain binds to a target that is a therapeutic moiety as described herein. In exemplary embodiments, in a fusion comprising one additional $^{10}$Fn3 domain, the $^{10}$Fn3 domain binds to VEGFR2, TNFα, IGF1R, or EGFR. In exemplary embodiments, in a fusion comprising two additional $^{10}$Fn3 domain, the $^{10}$Fn3 domains bind to VEGFR2 and IGF1R, or EGFR and IGF1R.

Conjugation/Linkers

SABA fusions may be covalently or non-covalently linked. In some embodiments, a serum albumin binding $^{10}$Fn3 may be directly or indirectly linked to a heterologous molecule via a polypeptide linker. Suitable linkers for joining a SABA to a protein of interest are those which allow the separate domains to fold independently of each other forming a three dimensional structure that does not disrupt the functionality of either member of the fusion protein. Exemplary linkers are provided in Table 2 as SEQ ID NOs: 65-88, 216-221 and 397.

The disclosure provides a number of suitable linkers, including glycine-serine based linkers, glycine-proline based linkers, as well as the linker having the amino acid sequence PSTSTST (SEQ ID NO: 85). In some embodiments, the linker is a glycine-serine based linker. These linkers comprise glycine and serine residues and may be between 8 and 50, 10 and 30, and 10 and 20 amino acids in length. Examples include linkers having an amino acid sequence $(GS)_7$ (SEQ ID NO: 72), $G(GS)_6$ (SEQ ID NO: 67), and $G(GS)_7G$ (SEQ ID NO: 69). Other linkers contain glutamic acid, and include, for example, $(GSE)_5$ (SEQ ID NO: 74) and GGSE GGSE (SEQ ID NO: 78). Other exemplary glycine-serine linkers include $(GS)_4$ (SEQ ID NO: 71), $(GGGGS)_7$ (SEQ ID NO: 80), $(GGGGS)_5$ (SEQ ID NO: 81), and $(GGGGS)_3G$ (SEQ ID NO: 82). In some embodiments, the linker is a glycine-proline based linker. These linkers comprise glycine and proline residues and may be between 3 and 30, 10 and 30, and 3 and 20 amino acids in length. Examples include linkers having an amino acid sequence $(GP)_3G$ (SEQ ID NO: 83), $(GP)_5G$ (SEQ ID NO: 84), and GPG. In other embodiments, the linker may be a proline-alanine based linker having between 3 and 30, 10 and 30, and 3 and 20 amino acids in length. Examples of proline alanine based linkers include, for example, $(PA)_3$ (SEQ ID NO: 86), $(PA)_6$ (SEQ ID NO: 87) and $(PA)_9$ (SEQ ID NO: 88). It is contemplated, that the optimal linker length and amino acid composition may be determined by routine experimentation by methods well known in the art.

In some embodiments, the fusions described herein are linked to the SABA via a polypeptide linker having a protease site that is cleavable by a protease in the blood or target tissue. Such embodiments can be used to release a therapeutic protein for better delivery or therapeutic properties or more efficient production.

Additional linkers or spacers, may be introduced at the C-terminus of an Fn3 domain between the Fn3 domain and the polypeptide linker. Additional linkers or spacers may be introduced at the N-terminus of an Fn3 domain between the Fn3 domain and the polypeptide linker.

In some embodiments, a therapeutic moiety may be directly or indirectly linked to a SABA via a polymeric linker. Polymeric linkers can be used to optimally vary the distance between each component of the fusion to create a protein fusion with one or more of the following characteristics: 1) reduced or increased steric hindrance of binding of one or more protein domains when binding to a protein of interest, 2) increased protein stability or solubility, 3) decreased protein aggregation, and 4) increased overall avidity or affinity of the protein.

In some embodiments, a therapeutic moiety is linked to a SABA via a biocompatible polymer such as a polymeric sugar. The polymeric sugar can include an enzymatic cleavage site that is cleavable by an enzyme in the blood or target tissue. Such embodiments can be used to release a therapeutic proteins for better delivery or therapeutic properties or more efficient production.

SABA-Neuropeptide Fusions

In certain embodiments, the application provides SABA-neuropeptide fusions. Exemplary neuropeptides include, for example, Amylin, PYY and PP. The SABA-neuropeptide fusions may be constructed as polypeptide fusions or as conjugates linked via a chemically derived spacer. In one embodiment, a SABA-neuropeptide fusion is a polypeptide fusion comprising a SABA, an amino acid linker, and a neuropeptide. Since many neuropeptides are amidated at the C-terminus, an exemplary arrangement of a fusion protein is from N-terminus to C-terminus, a SABA, an amino acid linker, and a neuropeptide. In another embodiment, a SABA-neuropeptide fusion contains a chemically derived spacer that links the SABA to the neuropeptide. Exemplary arrangements of SABA-neuropeptide conjugates are as follows: (1) SABA-Cys-chemically derived spacer-neuropeptide, or (2) SABA-amino acid linker-Cys-chemically derived spacer-neuropeptide. SABA-neuropeptide fusions may be produced in host cells, such as micro-organisms or mammalian cells as described further herein. The peptide components of a SABA-neuropeptide fusion linked by a chemically derived spacer may be produced either by host cells or by chemical synthesis, or a combination thereof. In an exemplary embodiment, a SABA-neuropeptide fusion linked by a chemically derived spacer is assembled from a SABA produced in host cells (such as *E. coli*) and a neuropeptide produced by chemical synthesis. Further details on producing SABA-neuropeptide fusions are described below and in the Examples.

Many neuropeptides contain a C-terminal α-amide group which is important for their biological activity. For example, Amylin, PYY and PP peptides all have C-terminal amidations. In mammalian cells, the α-amidation can be processed by peptidyl-glycine α-amidating monooxygenase (PAM), a binfunctional enzyme catalyzing the conversion of peptidyl-glycine substrates into α-amidated products.

There are various techniques for producing C-terminally amidated peptides. For example, peptide precursors (with a C-terminal-glycine or -glycine-lyisne-arginine or other extension) may be processed in vitro by a purified PAM enzyme. PAM and methods for using PAM to produce C-terminally amidated peptides are known to those of skill in the art. See, e.g., U.S. Pat. No. 4,708,934, U.S. Pat. No. 5,789,234 and U.S. Pat. No. 6,319,685. C-terminal amidation may also be accomplished in mammalian expression systems which express endogenous PAM. The fusion protein may be expressed as a precursor molecule extended by a -glycine or a -glycine-lysine-arginine sequence. When expressed as a secretory protein in eukaryotic cells (e.g., CHO, NIH 3T3 and BHK), the protein may be cleaved by the endogenous PAM enzyme and result in the C-terminal carboxyamides. See, e.g., Endocrinology (1991) V129:553-555 (1991); and Molecular and Cellular Endocrinology 91:135-141 (1993). C-terminal amidation may also be accomplished in mammalian expression systems in which human PAM is co-expressed. See, e.g., Chinese Journal of Biotechnology (2002) v18:20-24 (2002).

In addition to in vitro PAM enzymatic conversion of COOH to $CONH_2$, carboxamide termini on proteins of interest may be created using Merrifield synthesis. Merrifield synthesis permits a Maleimide moiety to be attached to the N-termini of the peptide during the Merrifield synthesis process. The maleimide moiety allows the creation of conjugates between two amino acid sequences (including, for example, a SABA and a carboxy amidated neuropeptide) using a variety of non-amino acid moieties placed between the two polypeptide domains that can serve as a spacer. Examples of suitable non-amino acid moieties that can be used as spacers are shown below in Table 1. Benefits of the maleimide conjugation reaction are that it can be readily performed on proteins, it offers high yields under gentle conditions that are favorable to protein molecules, and it is highly specific with few side products.

TABLE 1

Exemplary Linkers/Spacer for Conjugation of a SABA Molecule to Peptides Havinga Maleimide Moiety at the N-Terminus.

| | Linker/Spacer | Structure or Sequence |
|---|---|---|
| 1 | 6-aminohexanoic acid (Ahx) | 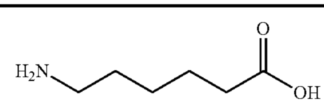 |
| 2 | $(GS)_5$ | Gly-Ser-Gly-Ser-Gly-Ser-Gly-Ser-Gly-Ser |
| 3 | PEG(9-atoms) | 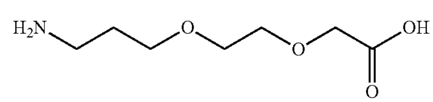 [SMILES: NCCCOCCOCC(=O)O] |
| 4 | PEG(13-atoms) | 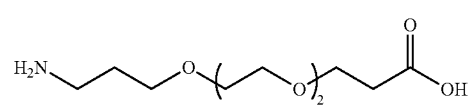 |
| 5 | PEG(16-atoms) | 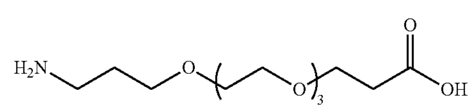 |
| 6 | PEG(20-atom) | 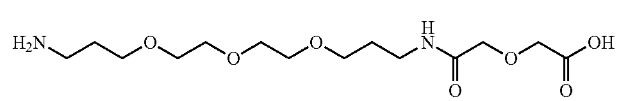 [SMILES: NCCCOCCOCCOCCCNC(=O)COCC(=O)O] |
| 7 | PEG(40-atom) | 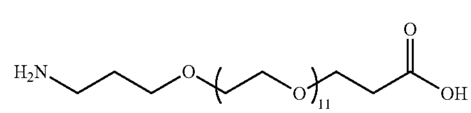 |

TABLE 1-continued

| Exemplary Linkers/Spacer for Conjugation of a SABA Molecule to Peptides Havinga Maleimide Moiety at the N-Terminus. | | |
|---|---|---|
| | Linker/Spacer | Structure or Sequence |
| 8 | 4-(N-maleimidomethyl)-cyclohexane-1-carboxylic acid (MCC) | 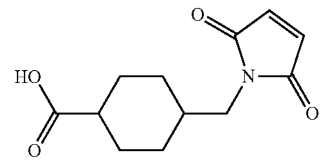 [SMILES: O=C(O)C1CCC(CN2C(=O)C=CC2=O)CC1] |
| 9 | 3-Maleimidobenzoic acid (MB) | 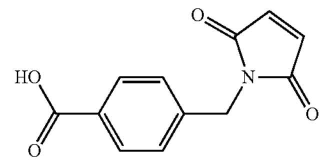 [SMILES: O=C(O)c1ccc(CN2C(=O)C=CC2=O)cc1] |
| 10 | 4-((Iodoacetyl)aminomethyl)cyclohexane-1-carboxylic acid (IAC) | 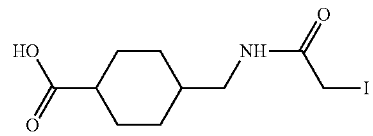 [SMILES: O=C(CI)NCC1CCC(C(=O)O)CC1] |
| 11 | 3-(iodoacetyl)-aminobenzoic acid (IAB) | 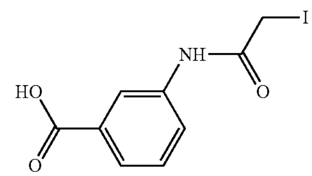 [SMILES: O=C(CI)Nc1cccc(C(=O)O)c1] |

In some embodiments, a C-terminally amidated synthetic peptide described herein can be conjugated with a SABA containing a C-terminal Cys residue in solution by Michael addition of a sulfhydryl group of the C-terminal Cys of the SABA onto a maleimido derivative of the peptide, with the maleimido group typically at the N-terminus of the peptide, to yield a stable thioether linkage. The same conjugation may be achieved by alkylation of the Cys sulfhydryl of the SABA with a haloalkyl derivative of the peptide, such as a bromo- or an iodo-methyl group introduced onto the peptide via acylation using bromo- or iodo-acetic acid. Those trained in the art will recognize that this type of peptide-protein conjugation may be achievable using several different methods such as, for example, bioconjugation procedures like those described in G. T. Hermanson, "Bioconjugate Techniques", Academic Press, San Diego, Calif., 1996.

In another embodiment, a neutral linker or spacer is placed between the thiol-reactive group on the peptide and the native or modified peptide sequence. The linker or spacer may provide reduced steric hindrance and facilitate the binding of the peptide to its cognate receptor or protein partner. Suitable linkers include, but are not limited to, those linkers described in Table 1. Linkers 8-11 are shown with the thiol-reactive Maleimido or Iodoacetyl groups and can be coupled to the peptide using the corresponding N-succinimidyl active esters described in the art.

The peptides and peptide analogs described herein may be produced by chemical synthesis using various solid-phase techniques such as those described in G. Barany and R. B. Merrifield, "The Peptides: Analysis, Synthesis, Biology"; Volume 2 "Special Methods in Peptide Synthesis, Part A", pp. 3-284, E. Gross and J. Meienhofer, Eds., Academic Press, New York, 1980; or in W. C. Chan and P. D. White, "Fmoc Solid Phase Peptide Synthesis—A Practical Approach", Oxford University Press., Oxford, UK, 2000. An exemplary strategy for peptide synthesis is based on the Fmoc (9-Fluorenylmethylmethyloxycarbonyl) group for temporary protection of the α-amino group, in combination with the tert-butyl group for temporary protection of the amino acid side chains (see for example E. Atherton and R. C. Sheppard, "The Fluorenylmethoxycarbonyl Amino Protecting Group", in "The Peptides: Analysis, Synthesis, Biology"; Volume 9 "Special Methods in Peptide Synthesis, Part C", pp. 1-38, S. Undenfriend and J. Meienhofer, Eds., Academic Press, San Diego, 1987.

Peptides can be synthesized in a stepwise manner on an insoluble polymer support (also referred to as a "resin") starting from the Carboxy-terminus of the peptide. A synthesis is begun by appending the C-terminal amino acid of the peptide to the resin through formation of an amide or ester linkage. This allows the eventual release of the resulting peptide as a C-terminal amide or carboxylic acid, respectively.

The C-terminal amino acid and all other amino acids used in the synthesis preferably have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The cycle of α-amino group deprotection and coupling is repeated until the entire peptide sequence is assembled. The peptide is then released from the resin with concomitant deprotection of the side chain functionalities, usually in the presence of appropriate scavengers to limit side reactions. The resulting peptide may be purified by reverse phase preparative HPLC.

The synthesis of the peptidyl-resins used as precursors to the final peptides may utilize commercially available cross-linked polystyrene polymer resins (Novabiochem, San Diego, Calif.) or ChemMatrix PEG polymer resins (PCAS BioMatrix, Quebec City, Canada). Preferred solid supports include, for example: 4-(2',4'-dimethoxyphenyl-Fmoc-aminomethyl)-phenoxyacetyl-p-methyl benzhydrylamine resin (Rink amide MBHA resin); 9-Fmoc-amino-xanthen-3-yloxy-Merrifield resin (Sieber amide resin); 4-(9-Fmoc) aminomethyl-3,5-dimethoxyphenoxy)valeryl-aminomethyl-Merrifield resin (PAL resin), for C-terminal carboxamides, and the corresponding ChemMatrix PEG-based resins. Coupling of first and subsequent amino acids can be accomplished using HOBt or 6-Cl-HOBt active esters produced from DIC/HOBt, HBTU/HOBt or from DIC/6-Cl-HOBt or HCTU/6-Cl-HOBt, respectively.

The syntheses of the peptides and peptide analogs described herein can be carried out using an automated peptide synthesizer, such as Liberty microwave peptide synthesizer (CEM Corp., Matthews, N.C.). The stepwise solid phase peptide synthesis may be performed using the Fmoc/t-butyl protection strategy described in the Examples. In some embodiments, the Fmoc amino acids derivatives shown in FIG. 21 may be used.

In the case of Amylin derivatives, the disulfide bond between the Acm-protected Cys residues (e.g., $Cys^{2,7}$ or $Cys^{1,7}$) may be formed via iodine-mediated oxidation on the resin (Chan and White, 2000). The peptidyl-resin precursors for their respective peptides may be cleaved and de-protected using any standard procedure (see, for example, D. S. King et al., Int. J. Peptide Protein Res. 36: 255-266 (1990)). In some embodiments, TFA is used in the presence of water, TIS and phenol as scavengers. Typically, the peptidyl-resin is stirred in TFA/water/TIS (94:3:3, v:v:v; 1 mL/100 mg of peptidyl resin) or TFA/water/phenol (90:5:5; v:v:w) for 2-3 hrs at room temperature. The spent resin is then filtered off and the TFA solution is concentrated or dried under reduced pressure. The resulting crude peptide may be either precipitated and washed with $Et_2O$ or re-dissolved directly into DMSO, DMF or 50% aqueous AcCN for purification by preparative HPLC.

Peptides with the desired purity can be obtained by purification using preparative HPLC, for example, on a Shimadzu Model LC-8A liquid chromatograph. For example, the solution of crude peptide may be injected onto a Phenomenex Luna C18 (5 μm, 21.2×250 mm) column and eluted with a linear gradient of MeCN in water, both buffered with 0.1% TFA, using a flow rate of 14-20 mL/min with effluent monitoring by UV absorbance at 220 nm. The structures of the purified peptides can be confirmed by electrospray LCMS analysis. For example, peptide samples may be analyzed by LC/MS on a Waters ZQ 2000 single quadrupole mass spectrometer (Milford, Mass.) interfaced to a Waters Acquity ultra performance liquid chromatograph (UPLC). Chromatographic separations may be achieved employing a 2.1×50 mm, 1.7 μm, 300 Å, Acquity BEH300 C18 column (Waters, Milford, Mass.) with gradient elution at 0.8 mL/min. The column temperature may be 50° C. Mobile phase A may be 98:2 water:acetonitrile with 0.05% TFA and mobile phase B may be acetonitrile with 0.04% TFA. A linear gradient may be formed from 2% to 80% mobile phase B over 1, 2, or 5 minutes. A 2 μL injection may be used and ESI MS data may be acquired from m/z 500 to m/z 1500 or from m/z 1000 to m/z 2000. The instrument may be operated at unit resolution.

Deimmunization of Binding Polypeptides

The amino acid sequences of serum albumin binders and their fusions may be altered to eliminate one or more B- or T-cell epitopes. A protein, including the SABA fusions described herein, may be deimmunized to render it non-immunogenic, or less immunogenic, to a given species. Deimmunization can be achieved through structural alterations to the protein. Any deimmunization technique known to those skilled in the art can be employed, see e.g., WO 00/34317, the disclosure of which is incorporated herein in its entirety.

In one embodiment, the sequences of the serum albumin binders and their fusions can be analyzed for the presence of MHC class II binding motifs. For example, a comparison may be made with databases of MHC-binding motifs such as, for example by searching the "motifs" database on the worldwide web at sitewehil.wehi.edu.au. Alternatively, MHC class II binding peptides may be identified using computational threading methods such as those devised by Altuvia et al. (J. Mol. Biol. 249 244-250 (1995)) whereby consecutive overlapping peptides from the polypeptide are testing for their binding energies to MHC class II proteins. Computational binding prediction algorithms include iTope™, Tepitope, SYFPEITHI, EpiMatrix (EpiVax), and MHCpred. In order to assist the identification of MHC class II-binding peptides, associated sequence features which relate to successfully presented peptides such as amphipathicity and Rothbard motifs, and cleavage sites for cathepsin B and other processing enzymes can be searched for.

Having identified potential (e.g. human) T-cell epitopes, these epitopes are then eliminated by alteration of one or more amino acids, as required to eliminate the T-cell epitope. Usually, this will involve alteration of one or more amino acids within the T-cell epitope itself. This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can be accomplished by recombinant DNA technology, so that the final molecule may be prepared by expression from a recombinant host, for example by well established methods, but the use of protein chemistry or any other means of molecular alteration may also be used.

Once identified T-cell epitopes are removed, the deimmunized sequence may be analyzed again to ensure that new T-cell epitopes have not been created and, if they have, the epitope(s) can be deleted.

Not all T-cell epitopes identified computationally need to be removed. A person skilled in the art will appreciate the significance of the "strength" or rather potential immunogenicity of particular epitopes. The various computational methods generate scores for potential epitopes. A person skilled in the art will recognize that only the high scoring epitopes may need to be removed. A skilled person will also recognize that there is a balance between removing potential epitopes and maintaining binding affinity or other biological activity of the protein. Therefore, one strategy is to sequentially introduce substitutions into the SABA or SABA fusion protein and then test for target binding or other biological activity and immunogenicity.

In one aspect, the deimmunized SABA or SABA fusion protein is less immunogenic (or rather, elicits a reduced HAMA response) than the original protein in a human subject. Assays to determine immunogenicity are well within the knowledge of the skilled person. Art-recognized methods of determining immune response can be performed to monitor a HAMA response in a particular subject or during clinical trials. Subjects administered deimmunized protein can be given an immunogenicity assessment at the beginning and throughout the administration of said therapy. The HAMA response is measured, for example, by detecting antibodies to the deimmunized protein in serum samples from the subject using a method known to one in the art, including surface plasmon resonance technology (BIAcore) and/or solid-phase ELISA analysis. Alternatively, in vitro assays designed to measure a T-cell activation event are also indicative of immunogenicity.

Additional Modifications

In certain embodiments, the serum albumin binders and their fusions may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified serum albumin binders and their fusions s may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See, e.g., Raju et al. Biochemistry. 2001 Jul. 31; 40(30):8868-76. Effects of such non-amino acid elements on the functionality of the serum albumin binders or their fusions may be tested for their ability to bind a particular serum albumin (e.g., HSA or RhSA) and/or the functional role conferred by a specific non-$^{10}$Fn3 moiety in the context of a fusion (e.g., the effect of FGF21 on glucose uptake).

Vectors & Polynucleotides Embodiments

Also included in the present disclosure are nucleic acid sequences encoding any of the proteins described herein. As appreciated by those skilled in the art, because of third base degeneracy, almost every amino acid can be represented by more than one triplet codon in a coding nucleotide sequence. In addition, minor base pair changes may result in a conservative substitution in the amino acid sequence encoded but are not expected to substantially alter the biological activity of the gene product. Therefore, a nucleic acid sequence encoding a protein described herein may be modified slightly in sequence and yet still encode its respective gene product. Certain exemplary nucleic acids encoding the serum albumin binders and their fusions described herein include nucleic acids having the sequences set forth in Table 3.

Nucleic acids encoding any of the various proteins or polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc Natl Acad Sci USA. 2003 100(2):438-42; Sinclair et al. Protein Expr Purif. 2002 (1):96-105; Connell N D. Curr Opin Biotechnol. 2001 (5):446-9; Makrides et al. Microbiol Rev. 1996 60(3):512-38; and Sharp et al. Yeast. 1991 7(7):657-78.

General techniques for nucleic acid manipulation are within the purview of one skilled in the art and are also described for example in Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates, herein incorporated by reference. The DNA encoding a protein is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated. Suitable regulatory elements are well-known in the art.

The proteins and fusion proteins described herein may be produced as a fusion protein with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, 1 pp, or heat-stable enterotoxin II leaders. For yeast secretion, the native signal sequence may be substituted by, e.g., the yeast invertase leader, a factor leader (including *Saccharomyces* and *Kluyveromyces* alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the multivalent antibody. One useful transcription termination component is the bovine growth hormone polyadenylation region. See PCT Publication No. WO 94/11026 and the expression vector disclosed therein.

The recombinant DNA can also include any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, New York, 1985), the relevant disclosure of which is hereby incorporated by reference.

The expression construct is introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). In some instance it will be desired to produce proteins in vertebrate cells, such as for glycosylation, and the propagation of vertebrate cells in culture (tissue culture) has become a routine procedure. Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. For many applications, the small size of the protein multimers described herein would make *E. coli* the preferred method for expression.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the proteins of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-translation systems. For such purposes, the nucleic acids encoding the proteins must be modified to allow in vitro transcription to produce mRNA and to allow cell-free translation of the mRNA in the particular cell-free system being utilized. Exemplary eukaryotic cell-free translation systems include, for example, mammalian or yeast cell-free translation systems, and exemplary prokaryotic cell-free translation systems include, for example, bacterial cell-free translation systems.

Proteins disclosed herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis.

The purified proteins are preferably at least 85% pure, more preferably at least 95% pure, and most preferably at least 98% pure. Regardless of the exact numerical value of the purity, the proteins are sufficiently pure for use as a pharmaceutical product.

Imaging, Diagnostic and Other Applications

The SABA fusions provided herein may be used to treat a variety of diseases and disorders, based on the identity of the heterogenous molecule fused to the SABA. The applications for the SABA fusions may be determined by the skilled artisan based on the knowledge in the art and the information provided herein. Uses for various SABA fusion proteins are described in detail herein. SABA fusions may be administered to any mammalian subject or patient, including both human and non-human organisms.

The serum albumin binders and fusion molecules described herein can be detectably labeled and used to contact cells expressing, e.g., a protein bound by the fusion molecule for imaging or diagnostic applications. Any method known in the art for conjugating a protein to the detectable moiety may be employed, including those methods described by Hunter, et al., Nature 144:945 (1962); David, et al., Biochemistry 13:1014 (1974); Pain, et al., J. Immunol. Meth. 40:219 (1981); and Nygren, J. Histochem. and Cytochem. 30:407 (1982).

In certain embodiments, the serum albumin binders and fusion molecules described herein are further attached to a label that is able to be detected (e.g., the label can be a radioisotope, fluorescent compound, enzyme or enzyme co-factor). The label may be a radioactive agent, such as: radioactive heavy metals such as iron chelates, radioactive chelates of gadolinium or manganese, positron emitters of oxygen, nitrogen, iron, carbon, or gallium, $^{43}K$, $^{52}Fe$, $^{57}Co$, $^{67}Cu$, $^{67}Ga$, $^{68}Ga$, $^{123}I$, $^{125}I$, $^{131}I$, $^{132}I$, or $^{99}Tc$. A serum albumin binder or fusion molecule affixed to such a moiety may be used as an imaging agent and is administered in an amount effective for diagnostic use in a mammal such as a human and the localization and accumulation of the imaging agent is then detected. The localization and accumulation of the imaging agent may be detected by radioscintigraphy, nuclear magnetic resonance imaging, computed tomography or positron emission tomography. As will be evident to the skilled artisan, the amount of radioisotope to be administered is dependent upon the radioisotope. Those having ordinary skill in the art can readily formulate the amount of the imaging agent to be administered based upon the specific activity and energy of a given radionuclide used as the active moiety.

Serum albumin binders and fusion molecules also are useful as affinity purification agents. In this process, the proteins are immobilized on a suitable support, such a Sephadex resin or filter paper, using methods well known in the art. The proteins can be employed in any known assay method, such as competitive binding assays, direct and indirect sandwich assays, and immunoprecipitation assays (Zola, Monoclonal Antibodies: A Manual of Techniques, pp. 147-158 (CRC Press, Inc., 1987)).

Exemplary Uses of SABA-FGF21 Fusions

The SABA-FGF21 fusions provided herein may be used in treating or preventing one or more of the following: diabetes, hyperglycemia, impaired glucose tolerance, gestational diabetes, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, glaucoma and inflammatory diseases, such as, psoriasis, rheumatoid arthritis and osteoarthritis, and treatment of side-effects related to diabetes, lipodystrophy and osteoporosis from corticosteroid treatment. In certain embodiments a SABA-FGF21 fusion provided herein may be used for treating or preventing obesity or reducing weight or preventing weight gain in a subject. In an exemplary embodiment, a SABA-FGF21 fusion may be used for reducing weight or preventing weight gain in a subject having a BMI of 25-29.9. In another exemplary embodiment, a SABA-FGF21 fusion may be used for reducing weight or preventing weight gain in a subject having a BMI of ≥30. In another embodiment, a SABA-FGF21 fusion may be used for treating a subject having a total cholesterol level ≥200 mg/dL and/or a triglyceride level ≥150 mg/dL. In other embodiments, a SABA-FGF21 fusion may be used for treating or lowering insulin resistance and/or increasing glucose uptake in adipose tissue. In other embodiments, a SABA-FGF21 fusion may be used for slowing the progression of diabetes in a prediabetic subject. In other embodiments, a SABA-FGF21 fusion may be used for lowering blood glucose levels, lower triglyceride levels, lowering cholesterol levels, increasing energy expenditure, increasing fat utilization and/or increasing lipid excretion in a subject.

As used herein, "preventing" a disease or disorder refers to reducing the probability of occurrence of a disease-state in a stastical sample relative to an untreated control sample, or delaying the onset or reducing the severity of one or more symptoms of the disease or disorder relative to the untreated control sample. Patients may be selected for preventative therapy based on factors that are known to increase risk of suffering a clinical disease state compared to the general population. The term "treating" as used herein includes (a) inhibiting the disease-state, i.e., arresting its development; and/or (b) relieving the disease-state, i.e., causing regression of the disease state once it has been established.

In certain embodiments, the application provides pharmaceutical compositions comprising, as an active ingredient, a therapeutically effective amount of a SABA-FGF21 fusion, alone or in combination with a pharmaceutical carrier. Optionally, a SABA-FGF21 fusion can be used alone, in combination with other fusions described herein, or in combination with one or more other therapeutic agent(s), e.g., an antidiabetic agent or other pharmaceutically active material.

In certain embodiments, a SABA-FGF21 fusion can be administered alone or in combination with one or more additional therapeutic agents. By "administered in combination" or "combination therapy" it is meant that the SABA-FGF21 fusion and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The SABA-FGF21 fusions provided herein may be employed in combination with antidiabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

The antidiabetic agents used in combination with the SABA-FGF21 fusion include, but are not limited to, insulin secretagogues or insulin sensitizers, GPR40 receptor modulators, or other antidiabetic agents. These agents include, but are not limited to, dipeptidyl peptidase IV (DP4) inhibitors (for example, sitagliptin, saxagliptin, alogliptin, vildagliptin and the like), biguanides (for example, metformin, phenformin and the like), sulfonyl ureas (for example, gliburide, glimepiride, glipizide and the like), glucosidase inhibitors (for example, acarbose, miglitol, and the like), PPARγ agonists such as thiazolidinediones (for example, rosiglitazone, pioglitazone, and the like), PPAR α/γ dual agonists (for example, muraglitazar, tesaglitazar, aleglitazar, and the like), glucokinase activators (as described in Fyfe, M. C. T. et al., *Drugs of the Future,* 34(8):641-653 (2009) and incorporated herein by reference), GPR119 receptor modulators (MBX-2952, PSN821, APD597 and the like), SGLT2 inhibitors (dapagliflozin, canagliflozin, remagliflozin and the like), amylin analogs such as pramlintide, and/or insulin. Reviews of current and emerging therapies for the treatment of diabetes can be found in: Mohler, M. L. et al., *Medicinal Research Reviews,* 29(1):125-195 (2009), and Mizuno, C. S. et al., *Current Medicinal Chemistry,* 15:61-74 (2008).

A SABA-FGF21 fusion may also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. A SABA-FGF21 fusion also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery,* 5:369-370 (2006); Jones, D., *Nature Reviews: Drug Discovery,* 8:833-834 (2009); Obici, S., *Endocrinology,* 150(6):2512-2517 (2009); and Elangbam, C. S., *Vet. Pathol.,* 46(1):10-24 (2009).

In certain embodiments, a SABA-FGF21 fusion is administered at a dose of about 10 ng to 20 mg, 10 ng to 5 mg, 10 ng to 2 mg, 10 ng to 1 mg, 100 ng to 20 mg, 100 ng to 5 mg, 100 ng to 2 mg, 100 ng to 1 mg, 1 μg to 20 mg, 1 μg to 5 mg, 1 μg to 2 mg, 1 μg to 1 mg, 10 μg to 20 mg, 10 μg to 5 mg, 10 μg to 2 mg, 10 μg to 1 mg, 0.01 to 20 mg, 0.01 to 10 mg, 0.1 to 20 mg, 0.1 to 10 mg, 0.01 to 5 mg, 0.1 to 5 mg, or 0.7 to 5 mg, or about 10 ng, 100 ng, 1 μg, 10 μg, 100 μg, or about 1, 2, 2.5, 3, 4, 5, 6, 7, 8, 9, 10 mg. In certain embodiments, a SABA-FGF21 fusion is administered at a dose of about 100 pg/kg to 200 μg/kg, 100 pg/kg to 50 μg/kg, 100 pg/kg to 20 μg/kg, 100 pg/kg to 10 μg/kg, 1 ng/kg to 200 μg/kg, 1 ng/kg to 50 μg/kg, 1 ng/kg to 20 μg/kg, 1 ng/kg to 10 μg/kg, 10 ng/kg to 200 μg/kg, 10 ng/kg to 50 μg/kg, 10 ng/kg to 20 μg/kg, 10 ng/kg to 10 μg/kg, 100 ng/kg to 200 μg/kg, 100 ng/kg to 50 μg/kg, 100 ng/kg to 20 μg/kg, 100 ng/kg to 10 μg/kg, 0.1 to 200 μg/kg, 0.1 to 100 μg/kg, 1 to 200 μg/kg, 1 to 100 μg/kg, 0.1 to 50 μg/kg, 1 to 50 μg/kg, or 7 to 50 μg/kg, or about 100 pg/kg, 1 ng/kg, 10 ng/kg, 100 ng/kg, or 1, 2, 5, 10, 20, 25, 30, 40, 50, 60, 75, 100, 125, 150, 200 or 250 μg/kg. The SABA-FGF21 fusion may be given daily (e.g., once, twice, three times, or four times daily) or less frequently (e.g., once every other day, once or twice weekly, or monthly). In exemplary embodiments, a SABA-FGF21 fusion is administered at a dose of about 0.01 to 20 mg, about 0.01 to 10 mg, about 0.1 to 20 mg, about 0.1 to 10 mg, about 0.01 to 5 mg, about 0.1 to 5 mg, or about 0.7 to 5 mg, or about 1, 2, 2.5, 3, 4, 5, 6, 7, 8, 9, 10 mg on a weekly basis. In exemplary embodiments, a SABA-FGF21 fusion is administered at a dose of about 0.1 to 200 μg/kg, about 0.1 to 100 μg/kg, about 1 to 200 μg/kg, about 1 to 100 μg/kg, about 0.1 to 50 μg/kg, about 1 to 50 μg/kg, or about 7 to 50 μg/kg, or about 1, 2, 5, 10, 20, 25, 30, 40, 50, 60, 75, 100, 125, 150, 200 or 250 μg/kg on a weekly basis. In exemplary embodiments, a SABA-FGF21 fusion is administered at a dose of about 10 ng to 20 mg, about 10 ng to 5 mg, about 10 ng to 2 mg, about 10 ng to 1 mg, about 10 ng to 500 μg, about 10 ng to 200 μg, about 100 ng to 20 mg, about 100 ng to 5 mg, about 100 ng to 2 mg, about 100 ng to 1 mg, about 100 ng to 500 μg, about 100 ng to 200 μg, about 1 μg to 20 mg, about 11.4 to 5 mg, about 1 μg to 2 mg, about 1 μg to 1 mg, about 1 μg to 500 μg, about 1 μg to 200 μg, about 10 μg to 20 mg, about 10 μg to 5 mg, about 10 μg to 2 mg, about 10 μg to 1 mg, about 10 μg to 500 μg, about 10 μg to 200 μg, or about 10 ng, 100 ng, 1 μg, 10 μg, 100 μg, 200 μg, 500 μg, 1 mg, 1.5 mg, 2 mg, 2.5 mg, 3 mg, or 5 mg on a daily basis. In exemplary embodiments, a SABA-FGF21 fusion is administered at a dose of about 100 pg/kg to 200 μg/kg, about 100 pg/kg to 50 μg/kg, about 100 pg/kg to 20 μg/kg, about 100 pg/kg to 5 μg/kg, about 100 pg/kg to 2 μg/kg, about 1 ng/kg to 200 μg/kg, about 1 ng/kg to 50 μg/kg, about 1 ng/kg to 20 μg/kg, about 1 ng/kg to 5 μg/kg, about 1 ng/kg to 2 μg/kg, about 10 ng/kg to 200 μg/kg, about 10 ng/kg to 50 μg/kg, about 10 ng/kg to 20 μg/kg, about 10 ng/kg to 5 μg/kg, about 10 ng/kg to 2 μg/kg, about 100 ng/kg to 200 μg/kg, about 100 ng/kg to 50 μg/kg, about 100 ng/kg to 20 μg/kg, about 100 ng/kg to 5 μg/kg, about 100 ng/kg to 2 μg/kg, about 1 μg/kg to 200 μg/kg, about 1 μg/kg to 50 μg/kg, about 1 μg/kg to 20 μg/kg, about 1 μg/kg to 5 μg/kg, about 1 μg/kg to 2 μg/kg, about 10 μg/kg to 200 μg/kg, about 10 μg/kg to 50 μg/kg, or about 10 μg/kg to 20 μg/kg, or about 100 pg/kg, 1 ng/kg, 10 ng/kg, 100 ng/kg, 500 ng/kg, 1 μg/kg, 5 μg/kg, 10 μg/kg, 20 μg/kg, 50 μg/kg, 100 μg/kg or 200 μg/kg on a daily basis. In addition, as is known in the art, adjustments for age as well as the body weight, general health, sex, diet, time of administration, drug interaction, and the severity of the disease may be necessary, and will be ascertainable with routine experimentation by those skilled in the art.

Therapeutic Formulations and Modes of Administration

The present application provides methods for administering a therapeutic moiety fused to a SABA, wherein the half-life of the therapeutic moiety is extended when fused to the SABA. Techniques and dosages for administration of the fusion constructs will vary depending on the type of therapeutic moiety fused to the SABA and the specific condition being treated but can be readily determined by the skilled artisan. In general, regulatory agencies require that a protein reagent to be used as a therapeutic is formulated so as to have acceptably low levels of pyrogens. Accordingly, therapeutic formulations will generally be distinguished from other formulations in that they are substantially pyrogen free, or at least contain no more than acceptable levels of pyrogen as determined by the appropriate regulatory agency (e.g., FDA). In certain embodiments, pharmaceutical formulations of SABA and their fusion molecules comprise, e.g., 1-20 mM succinic acid, 2-10% sorbitol, and 1-10% glycine at pH 4.0-7.0. In an exemplary embodiment, pharmaceutical formulations of SABA and their fusion molecules comprise, e.g., 10 mM succinic acid, 8% sorbitol, and 5% glycine at pH 6.0.

In some embodiments, the SABA and fusions thereof are pharmaceutically acceptable to a mammal, in particular a human. A "pharmaceutically acceptable" polypeptide refers to a polypeptide that is administered to an animal without significant adverse medical consequences. Examples of pharmaceutically acceptable SABA and fusions thereof include $^{10}$Fn3 domains that lack the integrin-binding domain (RGD) and compositions of SABAs or SABA fusions that are essentially endotoxin free or have very low endotoxin levels.

Therapeutic compositions may be administered with a pharmaceutically acceptable diluent, carrier, or excipient, in unit dosage form. Administration may be parenteral (e.g., intravenous, subcutaneous), oral, or topical, as non-limiting examples. The composition can be in the form of a pill, tablet, capsule, liquid, or sustained release tablet for oral administration; a liquid for intravenous, subcutaneous or parenteral administration; or a gel, lotion, ointment, cream, or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. The concentration of the compound in the formulation varies depending upon a number of factors, including the dosage of the drug to be administered, and the route of administration.

The polypeptide may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the polypeptide is formulated in the presence of sodium acetate to increase thermal stability.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

A therapeutically effective dose refers to a dose that produces the therapeutic effects for which it is administered. The exact dose will depend on the disorder to be treated, and may be ascertained by one skilled in the art using known techniques. In general, the SABA or SABA fusion is administered at about 0.01 μg/kg to about 50 mg/kg per day, preferably 0.01 mg/kg to about 30 mg/kg per day, most preferably 0.1 mg/kg to about 20 mg/kg per day. The polypeptide may be given daily (e.g., once, twice, three times, or four times daily) or less frequently (e.g., once every other day, once or twice weekly, or monthly). In addition, as is known in the art, adjustments for age as well as the body weight, general health, sex, diet, time of administration, drug interaction, and the severity of the disease may be necessary, and will be ascertainable with routine experimentation by those skilled in the art.

EXEMPLIFICATION

The invention now being generally described will be more readily understood by reference to the following examples which are included merely for purposes of illustration of certain aspects and embodiments of the present invention, and are not intended to limit the invention in any way.

Summary of Sequences

Many of the sequences referenced in this application are summarized in Table 2 below. Unless otherwise specified, all N-terminal extensions are indicated with a single underline, all C-terminal tails/extensions are indicated with a double underline, and linker sequences are boxed. Loop regions BC, DE and FG are shaded for each core SABA sequence.

TABLE 2

Summary of exemplary sequences

| SEQ ID NO: | Sequence Name | Description | Sequence |
|---|---|---|---|
| | | Exemplary Serum Albumin-Binding Adnectins ™ (SABA) | |
| 1 | $^{10}$Fn3WT | WT human $^{10}$Fn3 domain | VSDVPRDLEVVAATPTSLLISWDAPAVT<br>VRYYRITYGETGGNSPVQEFTVPGSKST<br>ATISGLKPGVDYTITVYAVTGRGDSPAS<br>SKPISINYRT |
| 2 | $^{10}$Fn3v6 | Generic $^{10}$Fn3 having 6 variable loops | EVVAAT $(X)_a$SLLI $(X)_x$YYRITYGE (X)<br>$_b$QEFTV $(X)_y$ATI $(X)_c$DYTITVYAV (X)<br>$_z$ISINYRT |
| 3 | $^{10}$Fn3v3 | Generic $^{10}$Fn3 having 3 variable loops | EVVAATPTSLLI $(X)_x$YYRITYGETGGN<br>SPVQEFTV $(X)_y$ATISGLKPGVDYTITV<br>YAV $(X)_z$ISINYRT |
| 4 | SABA1 | Core 1 Adnectin ™ | EVVAATPTSLLISWHSYYEQNSYYRITY<br>GETGGNSPVQEFTVPYSQTTATISGLKP<br>GVDYTITVYAVYGSKYYYPISINYRT |
| 5 | SABA1BC | Core 1 BC Loop | HSYYEQNS |
| 6 | SABA1DE | Core 1 DE Loop | YSQT |
| 7 | SABA1FG | Core 1 FG Loop | YGSKYYY |
| 8 | SABA2 | Core 2 Adnectin ™ | EVVAATPTSLLISWPKYDKTGHYYRITY<br>GETGGNSPVQEFTVPTRQTTATISGLKP<br>GVDYTITVYAVSKDDYYPHEHRPISINY<br>RT |
| 9 | SABA2BC | Core 2 BC Loop | PKYDKTGH |
| 10 | SABA2DE | Core 2 DE Loop | TRQT |
| 11 | SABA2FG | Core 2 FG Loop | SKDDYYPHEHR |

TABLE 2 -continued

Summary of exemplary sequences

| SEQ ID NO: | Sequence Name | Description | Sequence |
|---|---|---|---|
| 12 | SABA3 | Core 3 Adnectin ™ | EVVAATPTSLLISWSNDGPGLSYYRITYGETGGNSPVQEFTVPSSQTTATISGLKPGVDYTITVYAVSYYTKKAYSAGPISINYRT |
| 13 | SABA3BC | Core 3 BC Loop | SNDGPGLS |
| 14 | SABA3DE | Core 3 DE Loop | SSQT |
| 15 | SABA3FG | Core 3 FG Loop | SYYTKKAYSAG |
| 16 | SABA4 | Core 4 Adnectin ™; contains a scaffold mutation (bolded); scaffold-perfect version is SABA5 | E**M**VAATPTSLLISWEDDSYYSRYYRITYGETGGNSPVQEFTVPSDLYTATISGLKPGVDYTITVYAVTYDVTDLIMHEPISINYRT |
| 17 | SABA4BC | Core 4 BC Loop | EDDSYYSR |
| 18 | SABA4DE | Core 4 DE Loop | SDLY |
| 19 | SABA4FG | Core 4 FG Loop | YDVTDLIMHE |
| 20 | SABA5 | Core 5 Adnectin ™; see description for SABA4; corrected residue is bolded | E**V**VAATPTSLLISWEDDSYYSRYYRITYGETGGNSPVQEFTVPSDLYTATISGLKPGVDYTITVYAVTYDVTDLIMHEPISINYRT |
| 21 | SABA5BC | Core 5 BC Loop | EDDSYYSR |
| 22 | SABA5DE | Core 5 DE Loop | SDLY |
| 23 | SABA5FG | Core 5 FG Loop | YDVTDLIMHE |
| 24 | SABA6 | Core 6 Adnectin ™ | EVVAATPTSLLISWYMDEYDVRYYRITYGETGGNSPVQEFTVPNYYNTATISGLKPGVDYTITVYAVTRIKANNYMYGPISINYRT |
| 25 | SABA7 | Core 7 Adnectin ™ | EVVAATPTSLLISWNHLEHVARYYRITYGETGGNSPVQEFTVPEYPTTATISGLKPGVDYTITVYAVTITMLKYPTQSPISINYRT |
| 26 | SABA8 | Core 8 Adnectin ™ | EVVAATPTSLLISWGHYRRSGHYYRITYGETGGNSPVQEFTVDPSSYTATISGLKPGVDYTITVYAVSKDDYYPHEHRPISINYRT |
| 27 | SABA9 | Core 9 Adnectin ™ | EVVAATPTSLLISWDASHYERRYYRITYGETGGNSPVQEFTVPRYHHTATISGLKPGVDYTITVYAVTQAQEHYQPPISINYRT |
| 28 | SABA10 | Core 10 Adnectin ™ | EVVAATPTSLLISWNNSYYHSADYYRITYGETGGNSPVQEFTVPYPPTTATISGLKPGVDYTITVYAVYSAKSYYPISINYRT |
| 29 | SABA11 | Core 11 Adnectin ™ | EVVAATPTSLLISWSKYSKHGHYYRITYGETGGNSPVQEFTVPSGNATATISGLKPGVDYTITVYAVEDTNDYPHTHRPISINYRT |
| 30 | SABA12 | Core 12 Adnectin ™ | EVVAATPTSLLISWHGEPDQTRYYRITYGETGGNSPVQEFTVPPYRRTATISGLKPGVDYTITVYAVTSGYTGHYQPISINYRT |
| 31 | SABA13 | Core 13 Adnectin ™ | EVVAATPTSLLISWSKYSKHGHYYRITYGETGGNSPVQEFTVDPSSYTATISGLKPGVDYTITVYAVSKDDYYPHEHRPISINYRT |

TABLE 2 -continued

Summary of exemplary sequences

| SEQ ID NO: | Sequence Name | Description | Sequence |
|---|---|---|---|
| 32 | SABA14 | Core 14 Adnectin ™ | EVVAATPTSLLISWYEPYTPIHYYRITYGETGGNSPVQEFTVPGYYGTATISGLKPGVDYTITVYAVYGYYQYTPISINYRT |
| 33 | SABA15 | Core 15 Adnectin ™ | EVVAATPTSLLISWSKYSKHGHYYRITYGETGGNSPVQEFTVPSGNATATISGLKPGVDYTITVYAVSDDNKYYHQHRPISINYRT |
| 34 | SABA16 | Core 16 Adnectin ™ | EVVAATPTSLLISWGHYRRSGHYYRITYGETGGNSPVQEFTVDPSSYTATISGLKPGVDYTITVYAVSKDDYYPHEHRPISINYRT |
| 35 | SABA17 | Core 17 Adnectin ™ | EVVAATPTSLLISWSKYSKHGHYYRITYGETGGNSPVQEFTVPSGNATATISGLKPGVDYTITVYAVEDTNDYPHTHRPISINYRT |
| 36 | SABA18 | Core 18 Adnectin ™ | EVVAATPTSLLISWYEPGASVYYYRITYGETGGNSPVQEFTVPSYYHTATISGLKPGVDYTITVYAVYGYYEYEPISINYRT |
| 37 | SABA19 | Core 19 Adnectin ™ | EVVAATPTSLLISWQSYYAHSDYYRITYGETGGNSPVQEFTVPYPPQTATISGLKPGVDYTITVYAVYAGSSYYPISINYRT |
| 38 | SABA20 | Core 20 Adnectin ™ | EVVAATPTSLLISWGHYRRSGHYYRITYGETGGNSPVQEFTVDPSSYTATISGLKPGVDYTITVYAVSKDDYYPHEHRPISINYRT |
| 39 | SABA21 | Core 21 Adnectin ™ | EVVAATPTSLLISWPEPGTPVYYYRITYGETGGNSPVQEFTVPAYYGTATISGLKPGVDYTITVYAVYGYYDYSPISINYRT |
| 40 | SABA22 | Core 22 Adnectin ™ | EVVAATPTSLLISWYRYEKTQHYYRITYGETGGNSPVQEFTVPPESGTATISGLKPGVDYTITVYAVYAGYEYPHTHRPISINYRT |
| 41 | SABA23 | Core 23 Adnectin ™ | EVVAATPTSLLISWVKSEEYYRYYRITYGETGGNSPVQEFTVPYYVHTATISGLKPGVDYTITVYAVTEYYYAGAVVSVPISINYRT |
| 42 | SABA24 | Core 24 Adnectin ™ | EVVAATPTSLLISWYDPYTYGSYYRITYGETGGNSPVQEFTVGPYTTTATISGLKPGVDYTITVYAVSYYYSTQPISINYRT |
| 43 | SABA25 | Core 25 Adnectin ™ | EVVAATPTSLLISWSNDGPGLSYYRITYGETGGNSPVQEFTVPSSQTTATISGLKPGVDYTITVYAVSYYTKKAYSAGPISINYRT |
| 44 | SABA26 | Core 26 Adnectin ™ | EVVAATPTSLLISWPDPYYKPDYYRITYGETGGNSPVQEFTVPRDYTTATISGLKPGVDYTITVYAVYSYYGYYPISINYRT |
| | | Exemplary Adnectin ™ N-Terminal Extension Sequences | |
| 45 | AdNT1 | Exemplary leader | MGVSDVPRDL |
| 46 | AdNT2 | Exemplary leader | GVSDVPRDL |
| 47 | AdNT3 | Exemplary leader | VSDVPRDL |
| 48 | AdNT4 | Exemplary leader | SDVPRDL |
| 49 | AdNT5 | Exemplary leader | DVPRDL |
| 50 | AdNT6 | Exemplary leader | VPRDL |

TABLE 2 -continued

| SEQ ID NO: | Sequence Name | Description | Sequence |
|---|---|---|---|
| | | Summary of exemplary sequences | |
| 51 | AdNT7 | Exemplary leader | PRDL |
| 52 | AdNT8 | Exemplary leader | RDL |
| 53 | AdNT9 | Exemplary leader | DL |
| | | Exemplary Adnectin ™ C-Terminal Extension Sequences | |
| 54 | AdCT1 | Exemplary tail | EIDKPSQ |
| 55 | AdCT2 | Exemplary tail | EIDKPS |
| 56 | AdCT3 | Exemplary tail | EIDKPC |
| 57 | AdCT4 | Exemplary tail | EIDKP |
| 58 | AdCT5 | Exemplary tail | EIDK |
| 59 | AdCT6 | Exemplary tail | EI |
| 60 | AdCT7 | Exemplary tail | EIEKPSQ |
| 61 | AdCT8 | Exemplary tail | EIDKPSQLE |
| 62 | AdCT9 | Exemplary tail | EIEDEDEDED |
| 63 | AdCT10 | Exemplary tail | EIEKPSQEDEDEDED |
| 64 | AdCT11 | Exemplary tail | EGSGS |
| 215 | AdCT12 | Exemplary tail | E |
| 65 | L1 | $G(GS)_2$ | GGSGS |
| 66 | L2 | $G(GS)_4$ | GGSGSGSGS |
| 67 | L3 | $G(GS)_6$ | GGSGSGSGSGSGS |
| 68 | L4 | $G(GS)_7$ | GGSGSGSGSGSGSGS |
| 69 | L5 | $G(GS)_7G$ | GGSGSGSGSGSGSGSG |
| 70 | L6 | GSGS | GSGS |
| 71 | L7 | $(GS)_4$ | GSGSGSGS |
| 72 | L7 | $(GS)_7$ | GSGSGSGSGSGSGS |
| 73 | L9 | $GS(A)_9GS$ | GSAAAAAAAAAGS |
| 74 | L10 | $(GSE)_5$ | GSEGSEGSEGSEGSE |
| 75 | L11 | $(PAS)_5$ | PASPASPASPASPAS |
| 76 | L12 | $(GSP)_5$ | GSPGSPGSPGSPGSP |
| 77 | L13 | $GS(TVAAPS)_2$ | GSTVAAPSTVAAPS |
| 78 | L14 | $(GGSE)_2$ | GGSEGGSE |
| 79 | L15 | $(ST)_3G$ | STSTSTG |
| 80 | L16 | $(GGGGS)_7$ | GGGGSGGGGSGGGGSGGGGSGGGGSGGG GSGGGGS |
| 81 | L17 | $(GGGGS)_5$ | GGGGSGGGGSGGGGSGGGGSGGGGSGGG GS |
| 82 | L18 | $(GGGGS)_3G$ | GGGGSGGGGSGGGGSG |
| 83 | L19 | $(GP)_3G$ | GPGPGPG |
| 84 | L20 | $(GP)_5G$ | GPGPGPGPGPG |

TABLE 2 -continued

| SEQ ID NO: | Sequence Name | Description | Sequence |
|---|---|---|---|
| | | Summary of exemplary sequences | |
| 85 | L21 | $P(ST)_3$ | PSTSTST |
| 86 | L22 | $(PA)_3$ | PAPAPA |
| 87 | L23 | $(PA)_6$ | PAPAPAPAPAPA |
| 88 | L24 | $(PA)_9$ | PAPAPAPAPAPAPAPAPA |
| 216 | L25 | $(GGGGS)_3$ | GGGGSGGGGSGGGGS |
| 217 | L26 | $(ED)_5$ | EDEDEDEDED |
| 218 | L27 | $(ED)_3$ | EDEDED |
| 219 | L28 | $(ED)_4$ | EDEDEDED |
| 220 | L29 | $(ED)_6$ | EDEDEDEDEDED |
| 221 | L30 | $(GSP)_4GS$ | GSPGSPGSPGSPGS |
| 397 | L31 | $(ED)_5G$ | EDEDEDEDEDG |
| | | Exemplary Extensions to Adnectin ™ Core Sequences | |
| 89 | SABA1.1 | Adnectin ™ core 1 sequence having AdNT1 and AdCT1 terminal sequences with His6 tag | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSQHHHHHH |
| 90 | SABA1.2 | Adnectin ™ core 1 sequence having AdNT1 and AdCT8 terminal sequences | MGVSDVPRDLEVVAATPTSLLISWHSYY EQNSYYRITYGETGGNSPVQEFTVPYSQ TTATISGLKPGVDYTITVYAVYGSKYYY PISINYRTEIEDEDEDEDED |
| 91 | SABA1.3 | Adnectin ™ core 1 sequence having AdNT1 and AdCT9 terminal sequences with His6 tag | MGVSDVPRDLEVVAATPTSLLISWHSYY EQNSYYRITYGETGGNSPVQEFTVPYSQ TTATISGLKPGVDYTITVYAVYGSKYYY PISINYRTEIEDEDEDEDEDHHHHHH |
| 222 | SABA1.4 | Adnectin ™ core 1 sequence having AdNT2 and AdCT12 terminal sequences | GVSDVPRDLEVVAATPTSLLISWHSYYE QNSYYRITYGETGGNSPVQEFTVPYSQT TATISGLKPGVDYTITVYAVYGSKYYYP ISINYRTE |
| 223 | SABA1.5 | Adnectin ™ core 1 sequence having AdNT1 and AdCT7 terminal sequences | MGVSDVPRDLEVVAATPTSLLISWHSYY EQNSYYRITYGETGGNSPVQEFTVPYSQ TTATISGLKPGVDYTITVYAVYGSKYYY PISINYRTE |
| 224 | SABA1.6 | Adnectin ™ core 1 sequence having AdNT1 and AdCT12 terminal sequences | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQ |
| 225 | SABA1.7 | Adnectin ™ core 1 sequence having AdNT1 and AdCT6 terminal sequences | MGVSDVPRDLEVVAATPTSLLISWHSYY EQNSYYRITYGETGGNSPVQEFTVPYSQ TTATISGLKPGVDYTITVYAVYGSKYYY PISINYRTEI |
| 92 | SABA2.1 | Adnectin ™ core 2 sequence having AdNT1 and AdCT1 terminal sequences with His6 tag | MGVSDVPRDLEVVAATPTSLLISWPKYD KTGHYYRITYGETGGNSPVQEFTVPTRQ TTATISGLKPGVDYTITVYAVSKDDYYP HEHRPISINYRTEIDKPSQHHHHHH |
| 93 | SABA3.1 | Adnectin ™ core 3 sequence having AdNT1 and AdCT1 terminal sequences with His6 tag | MGVSDVPRDLEVVAATPTSLLISWSNDG PGLSYYRITYGETGGNSPVQEFTVPSSQ TTATISGLKPGVDYTITVYAVSYYTKKA YSAGPISINYRTEIDKPSQHHHHHH |

TABLE 2 -continued

Summary of exemplary sequences

| SEQ ID NO: | Sequence Name | Description | Sequence |
|---|---|---|---|
| 94 | SABA4.1 | Adnectin ™ core 4 sequence having AdNT1 and AdCT1 terminal sequences with His6 tag | MGVSDVPRDLEMVAATPTSLLISWEDDS YYSRYYRITYGETGGNSPVQEFTVPSDL YTATISGLKPGVDYTITVYAVTYDVTDL IMHEPISINYRTEIDKPSQHHHHHH |
| 95 | SABA5.1 | Adnectin ™ core 5 sequence having AdNT1 and AdCT1 terminal sequences with His6 tag | MGVSDVPRDLEVVAATPTSLLISWEDDS YYSRYYRITYGETGGNSPVQEFTVPSDL YTATISGLKPGVDYTITVYAVTYDVTDL IMHEPISINYRTEIDKPSQHHHHHH |
| 96 | SABA6.1 | Adnectin ™ core 6 sequence having AdNT1 and AdCT1 terminal sequences with His6 tag | MGVSDVPRDLEVVAATPTSLLISWYMDE YDVRYYRITYGETGGNSPVQEFTVPNYY NTATISGLKPGVDYTITVYAVTRIKANN YMYGPISINYRTEIDKPSQHHHHHH |
| 97 | SABA7.1 | Adnectin ™ core 7 sequence having AdNT1 and AdCT1 terminal sequences with His6 tag | MGVSDVPRDLEVVAATPTSLLISWNHLE HVARYYRITYGETGGNSPVQEFTVPEYP TTATISGLKPGVDYTITVYAVTITMLKY PTQSPISINYRTEIDKPSQHHHHHH |
| 98 | SABA8.1 | Adnectin ™ core 8 sequence having AdNT1 and AdCT1 terminal sequences with His6 tag | MGVSDVPRDLEVVAATPTSLLISWGHYR RSGHYYRITYGETGGNSPVQEFTVDPSS YTATISGLKPGVDYTITVYAVSKDDYYP HEHRPISINYRTEIDKPSQHHHHHH |
| 99 | SABA9.1 | Adnectin ™ core 9 sequence having AdNT1 and AdCT1 terminal sequences with His6 tag | MGVSDVPRDLEVVAATPTSLLISWDASH YERRYYRITYGETGGNSPVQEFTVPRYH HTATISGLKPGVDYTITVYAVTQAQEHY QPPISINYRTEIDKPSQHHHHHH |
| 100 | SABA10.1 | Adnectin ™ core 10 sequence having AdNT1 and AdCT1 terminal sequences with His6 tag | MGVSDVPRDLEVVAATPTSLLISWNSYY HSADYYRITYGETGGNSPVQEFTVPYPP TTATISGLKPGVDYTITVYAVYSAKSYY PISINYRTEIDKPSQHHHHHH |
| 101 | SABA11.1 | Adnectin ™ core 11 sequence having AdNT1 and AdCT1 terminal sequences with His6 tag | MGVSDVPRDLEVVAATPTSLLISWSKYS KHGHYYRITYGETGGNSPVQEFTVPSGN ATATISGLKPGVDYTITVYAVEDTNDYP HTHRPISINYRTEIDKPSQHHHHHH |
| 102 | SABA12.1 | Adnectin ™ core 12 sequence having AdNT1 and AdCT1 terminal sequences with His6 tag | MGVSDVPRDLEVVAATPTSLLISWHGEP DQTRYYRITYGETGGNSPVQEFTVPPYR RTATISGLKPGVDYTITVYAVTSGYTGH YQPISINYRTEIDKPSQHHHHHH |
| 103 | SABA13.1 | Adnectin ™ core 13 sequence having AdNT1 and AdCT1 terminal sequences with His6 tag | MGVSDVPRDLEVVAATPTSLLISWSKYS KHGHYYRITYGETGGNSPVQEFTVDPSS YTATISGLKPGVDYTITVYAVSKDDYYP HEHRPISINYRTEIDKPSQHHHHHH |
| 104 | SABA14.1 | Adnectin ™ core 14 sequence having AdNT1 and AdCT1 terminal sequences with His6 tag | MGVSDVPRDLEVVAATPTSLLISWYEPY TPIHYYRITYGETGGNSPVQEFTVPGYY GTATISGLKPGVDYTITVYAVYGYYQYT PISINYRTEIDKPSQHHHHHH |
| 105 | SABA15.1 | Adnectin ™ core 15 sequence having AdNT1 and AdCT1 terminal sequences with His6 tag | MGVSDVPRDLEVVAATPTSLLISWSKYS KHGHYYRITYGETGGNSPVQEFTVPSGN ATATISGLKPGVDYTITVYAVSDDNKYY HQHRPISINYRTEIDKPSQHHHHHH |
| 106 | SABA16.1 | Adnectin ™ core 16 sequence having | MGVSDVPRDLEVVAATPTSLLISWGHYR RSGHYYRITYGETGGNSPVQEFTVDPSS |

TABLE 2 -continued

Summary of exemplary sequences

| SEQ ID NO: | Sequence Name | Description | Sequence |
|---|---|---|---|
| | | AdNT1 and AdCT1 terminal sequences with His6 tag | YTATISGLKPGVDYTITVYAVSKDDYYP HEHRPISINYRTEIDKPSQHHHHHH |
| 107 | SABA17.1 | Adnectin ™ core 17 sequence having AdNT1 and AdCT1 terminal sequences with His6 tag | MGVSDVPRDLEVVAATPTSLLISWSKYS KHGHYYRITYGETGGNSPVQEFTVPSGN ATATISGLKPGVDYTITVYAVEDTNDYP HTHRPISINYRTEIDKPSQHHHHHH |
| 108 | SABA18.1 | Adnectin ™ core 18 sequence having AdNT1 and AdCT1 terminal sequences with His6 tag | MGVSDVPRDLEVVAATPTSLLISWYEPG ASVYYYRITYGETGGNSPVQEFTVPSYY HTATISGLKPGVDYTITVYAVYGYYEYE PISINYRTEIDKPSQHHHHHH |
| 109 | SABA19.1 | Adnectin ™ core 19 sequence having AdNT1 and AdCT1 terminal sequences with His6 tag | MGVSDVPRDLEVVAATPTSLLISWQSYY AHSDYYRITYGETGGNSPVQEFTVPYPP QTATISGLKPGVDYTITVYAVYAGSSYY PISINYRTEIDKPSQHHHHHH |
| 110 | SABA20.1 | Adnectin ™ core 20 sequence having AdNT1 and AdCT1 terminal sequences with His6 tag | MGVSDVPRDLEVVAATPTSLLISWGHYR RSGHYYRITYGETGGNSPVQEFTVDPSS YTATISGLKPGVDYTITVYAVSKDDYYP HEHRPISINYRTEIDKPSQHHHHHH |
| 111 | SABA21.1 | Adnectin ™ core 21 sequence having AdNT1 and AdCT1 terminal sequences with His6 tag | MGVSDVPRDLEVVAATPTSLLISWPEPG TPVYYYRITYGETGGNSPVQEFTVPAYY GTATISGLKPGVDYTITVYAVYGYYDYS PISINYRTEIDKPSQHHHHHH |
| 112 | SABA22.1 | Adnectin ™ core 22 sequence having AdNT1 and AdCT1 terminal sequences with His6 tag | MGVSDVPRDLEVVAATPTSLLISWYRYE KTQHYYRITYGETGGNSPVQEFTVPPES GTATISGLKPGVDYTITVYAVYAGYEYP HTHRPISINYRTEIDKPSQHHHHHH |
| 113 | SABA23.1 | Adnectin ™ core 23 sequence having AdNT1 and AdCT1 terminal sequences with His6 tag | MGVSDVPRDLEVVAATPTSLLISWVKSE EYYRYYRITYGETGGNSPVQEFTVPYYV HTATISGLKPGVDYTITVYAVTEYYYAG AVVSVPISINYRTEIDKPSQHHHHHH |
| 114 | SABA24.1 | Adnectin ™ core 24 sequence having AdNT1 and AdCT1 terminal sequences with His6 tag | MGVSDVPRDLEVVAATPTSLLISWYDPY TYGSYYRITYGETGGNSPVQEFTVGPYT TTATISGLKPGVDYTITVYAVSYYYSTQ PISINYRTEIDKPSQHHHHHH |
| 115 | SABA25.1 | Adnectin ™ core 25 sequence having AdNT1 and AdCT1 terminal sequences with His6 tag | MGVSDVPRDLEVVAATPTSLLISWSNDG PGLSYYRITYGETGGNSPVQEFTVPSSQ TTATISGLKPGVDYTITVYAVSYYTKKA YSAGPISINYRTEIDKPSQHHHHHH |
| 116 | SABA26.1 | Adnectin ™ core 26 sequence having AdNT1 and AdCT1 terminal sequences with His6 tag | MGVSDVPRDLEVVAATPTSLLISWPDPY YKPDYYRITYGETGGNSPVQEFTVPRDY TTATISGLKPGVDYTITVYAVYSYYGYY PISINYRTEIDKPSQHHHHHH |
| | | Exemplary FGF21 Sequences | |
| 117 | FGF21 | WT full-length FGF21 | MDSDETGFEHSGLWVSVLAGLLGACQAH PIPDSSPLLQFGGQVRQRYLYTDDAQQT EAHLEIREDGTVGGAADQSPESLLQLKA LKPGVIQILGVKTSRFLCQRPDGALYGS LHFDPEACSFRELLLEDGYNVYQSEAHG LPLHLPGNKSPHRDPAPRGPARFLPLPG LPPALPEPPGILAPQPPDVGSSDPLSMV GPSQGRSPSYAS |

TABLE 2 -continued

| SEQ ID NO: | Sequence Name | Description | Sequence |
|---|---|---|---|
| Summary of exemplary sequences | | | |
| 118 | FGF21core | FGF21 core sequence | PLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYA |
| Exemplary FGF21 N-terminal Sequences | | | |
| 119 | FNT1 | Exemplary leader | MDSDETGFEHSGLWVSVLAGLLGACQAHPIPDSS |
| 120 | FNT2 | Exemplary leader | HPIPDSS |
| 121 | FNT3 | Exemplary leader | PIPDSS |
| 122 | FNT4 | Exemplary leader | DSS |
| 123 | FNT5 | Exemplary leader | IPDSS |
| 124 | FNT6 | Exemplary leader | PDSS |
| Exemplary Extensions to FGF21 Core Sequence | | | |
| 125 | FGF21v1 | FGF21 variant 1: FGF21 core sequence having a His6-tag followed by an FNT3 leader sequence, and a C-terminal S | MHHHHHHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 126 | FGF21v2 | FGF21 variant 2 | MHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAHHHHHH |
| 127 | FGF21v3 | FGF21 variant 3 | MHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYASHHHHHH |
| 128 | FGF21v4 | FGF21 variant 4 | MHHHHHHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYA |
| 129 | FGF21v5 | FGF21 variant 5 | MHHHHHHDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 130 | FGF21v6 | FGF21 variant 6 | MHHHHHHIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |

TABLE 2 -continued

Summary of exemplary sequences

| SEQ ID NO: | Sequence Name | Description | Sequence |
|---|---|---|---|
| 131 | FGF21v7 | FGF21 variant 7 | MHHHHHHPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYAS |
| | | Exemplary Fusions: $X_{AdL}$—SABA—$X_{AdT}$—$X_{LK}$—$X_{FL}$—FGF21 | |
| 132 | SABA1-FGF21v1 | SABA1-FGF21 variant 1: SABA core 1 sequence having an AdNT1 leader sequence and AdCT7 tail sequence followed by a $(GS)_7$ linker which joins an FGF21 core sequence having an FGF21 leader sequence FNT3 and a C-terminal S | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQGSGSGSGSGSGSG SPIPDSSPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYAS |
| 133 | SABA1-FGF21v2 | SABA1-FGF21 variant 2; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSQHHHHHHGSGSGSG SGSGSGSHPIPDSSPLLQFGGQVRQRYL YTDDAQQTEAHLEIREDGTVGGAADQSP ESLLQLKALKPGVIQILGVKTSRFLCQR PDGALYGSLHFDPEACSFRELLLEDGYN VYQSEAHGLPLHLPGNKSPHRDPAPRGP ARFLPLPGLPPALPEPPGILAPQPPDVG SSDPLSMVGPSQGRSPSYA |
| 134 | SABA1-FGF21v3 | SABA1-FGF21 variant 3; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSQHHHHHHGSGSGSG SGSGSGSPIPDSSPLLQFGGQVRQRYLY TDDAQQTEAHLEIREDGTVGGAADQSPE SLLQLKALKPGVIQILGVKTSRFLCQRP DGALYGSLHFDPEACSFRELLLEDGYNV YQSEAHGLPLHLPGNKSPHRDPAPRGPA RFLPLPGLPPALPEPPGILAPQPPDVGS SDPLSMVGPSQGRSPSYAS |
| 135 | SABA1-FGF21v4 | SABA1-FGF21 variant 4; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSGGSGSGSGSGSGSG SPIPDSSPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYASHHHHHH |
| 136 | SABA1-FGF21v5 | SABA1-FGF21 variant 5; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSGGSGSGSGSGSGSG SHPIPDSSPLLQFGGQVRQRYLYTDDAQ QTEAHLEIREDGTVGGAADQSPESLLQL KALKPGVIQILGVKTSRFLCQRPDGALY GSLHFDPEACSFRELLLEDGYNVYQSEA HGLPLHLPGNKSPHRDPAPRGPARFLPL PGLPPALPEPPGILAPQPPDVGSSDPLS MVGPSQGRSPSYAHHHHHH |

TABLE 2 -continued

| Summary of exemplary sequences | | | |
|---|---|---|---|
| SEQ ID NO: | Sequence Name | Description | Sequence |
| 137 | SABA1-FGF21v6 | SABA1-FGF21 variant 6; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSGGSGSGSGSGSGSG SPIPDSSPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYAS |
| 138 | SABA1-FGF21v7 | SABA1-FGF21 variant 7; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIDKPSGGSGSGSGSGSGSG SHPIPDSSPLLQFGGQVRQRYLYTDDAQ QTEAHLEIREDGTVGGAADQSPESLLQL KALKPGVIQILGVKTSRFLCQRPDGALY GSLHFDPEACSFRELLLEDGYNVYQSEA HGLPLHLPGNKSPHRDPAPRGPARFLPL PGLPPALPEPPGILAPQPPDVGSSDPLS MVGPSQGRSPSYA |
| 139 | SABA1-FGF21v8 | SABA1-FGF21 variant 8; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQHHHHHHGSGSGSG SGSGSGSPIPDSSPLLQFGGQVRQRYLY TDDAQQTEAHLEIREDGTVGGAADQSPE SLLQLKALKPGVIQILGVKTSRFLCQRP DGALYGSLHFDPEACSFRELLLEDGYNV YQSEAHGLPLHLPGNKSPHRDPAPRGPA RFLPLPGLPPALPEPPGILAPQPPDVGS SDPLSMVGPSQGRSPSYAS |
| 140 | SABA1-FGF21v9 | SABA1-FGF21 variant 9; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIGGSGSGSGSPIPDSSPLL QFGGQVRQRYLYTDDAQQTEAHLEIRED GTVGGAADQSPESLLQLKALKPGVIQIL GVKTSRFLCQRPDGALYGSLHFDPEACS FRELLLEDGYNVYQSEAHGLPLHLPGNK SPHRDPAPRGPARFLPLPGLPPALPEPP GILAPQPPDVGSSDPLSMVGPSQGRSPS YAS |
| 141 | SABA1-FGF21v10 | SABA1-FGF21 variant 10; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIGGSGSPIPDSSPLLQFGG QVRQRYLYTDDAQQTEAHLEIREDGTVG GAADQSPESLLQLKALKPGVIQILGVKT SRFLCQRPDGALYGSLHFDPEACSFREL LLEDGYNVYQSEAHGLPLHLPGNKSPHR DPAPRGPARFLPLPGLPPALPEPPGILA PQPPDVGSSDPLSMVGPSQGRSPSYAS |
| 142 | SABA1-FGF21v11 | SABA1-FGF21 variant 11; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIPIPDSSPLLQFGGQVRQR YLYTDDAQQTEAHLEIREDGTVGGAADQ SPESLLQLKALKPGVIQILGVKTSRFLC QRPDGALYGSLHFDPEACSFRELLLEDG YNVYQSEAHGLPLHLPGNKSPHRDPAPR GPARFLPLPGLPPALPEPPGILAPQPPD VGSSDPLSMVGPSQGRSPSYAS |

TABLE 2 -continued

Summary of exemplary sequences

| SEQ ID NO: | Sequence Name | Description | Sequence |
|---|---|---|---|
| 143 | SABA1-FGF21v12 | SABA1-FGF21 variant 12; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIHHHHHHGSGSGSGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 144 | SABA1-FGF21v13 | SABA1-FGF21 variant 13; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIHHHHHHGSGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 145 | SABA1-FGF21v14 | SABA1-FGF21 variant 14; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIHHHHHHPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 146 | SABA1-FGF21v15 | SABA1-FGF21 variant 15; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 147 | SABA1-FGF21v16 | SABA1-FGF21 variant 16; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGSGSGSGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 148 | SABA1-FGF21v17 | SABA-FGF21 variant 17; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIGSAAAAAAAAAGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |

TABLE 2 -continued

Summary of exemplary sequences

| SEQ ID NO: | Sequence Name | Description | Sequence |
|---|---|---|---|
| 149 | SABA1-FGF21v18 | SABA1-FGF21 variant 18; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIGSEGSEGSEGSEGSEPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 150 | SABA1-FGF21v19 | SABA1-FGF21 variant 19; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIPASPASPASPASPASPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 151 | SABA1-FGF21v20 | SABA1-FGF21 variant 20; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIGSPGSPGSPGSPGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 152 | SABA1-FGF21v21 | SABA1-FGF21 variant 21; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIGSTVAAPSTVAAPSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 153 | SABA1-FGF21v22 | SABA1-FGF21 variant 22; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIGGSEGGSEPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 154 | SABA1-FGF21v23 | SABA1-FGF21 variant 23; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEISTSTSTGPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |

TABLE 2 -continued

Summary of exemplary sequences

| SEQ ID NO: | Sequence Name | Description | Sequence |
|---|---|---|---|
| 155 | SABA1-FGF21v24 | SABA1-FGF21 variant 24; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQGSGSGSGSGSPIPD SSPLLQFGGQVRQRYLYTDDAQQTEAHL EIREDGTVGGAADQSPESLLQLKALKPG VIQILGVKTSRFLCQRPDGALYGSLHFD PEACSFRELLLEDGYNVYQSEAHGLPLH LPGNKSPHRDPAPRGPARFLPLPGLPPA LPEPPGILAPQPPDVGSSDPLSMVGPSQ GRSPSYAS |
| 156 | SABA1-FGF21v25 | SABA1-FGF21 variant 25; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQGSGSPIPDSSPL LQFGGQVRQRYLYTDDAQQTEAHLEIRE DGTVGGAADQSPESLLQLKALKPGVIQI LGVKTSRFLCQRPDGALYGSLHFDPEAC SFRELLLEDGYNVYQSEAHGLPLHLPGN KSPHRDPAPRGPARFLPLPGLPPALPEP PGILAPQPPDVGSSDPLSMVGPSQGRSP SYAS |
| 157 | SABA1-FGF21v26 | SABA1-FGF21 variant 26; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQPIPDSSPLLQFGG QVRQRYLYTDDAQQTEAHLEIREDGTVG GAADQSPESLLQLKALKPGVIQILGVKT SRFLCQRPDGALYGSLHFDPEACSFREL LLEDGYNVYQSEAHGLPLHLPGNKSPHR DPAPRGPARFLPLPGLPPALPEPPGILA PQPPDVGSSDPLSMVGPSQGRSPSYAS |
| 158 | SABA1-FGF21v27 | SABA1-FGF21 variant 27; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQHHHHHHGSGSGSG SPIPDSSPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYAS |
| 159 | SABA1-FGF21v28 | SABA1-FGF21 variant 28; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQHHHHHHGSGSPIP DSSPLLQFGGQVRQRYLYTDDAQQTEAH LEIREDGTVGGAADQSPESLLQLKALKP GVIQILGVKTSRFLCQRPDGALYGSLHF DPEACSFRELLLEDGYNVYQSEAHGLPL HLPGNKSPHRDPAPRGPARFLPLPGLPP ALPEPPGILAPQPPDVGSSDPLSMVGPS QGRSPSYAS |
| 160 | SABA1-FGF21v29 | SABA1-FGF21 variant 29; see similar description for variant 1 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQHHHHHHPIPDSSP LLQFGGQVRQRYLYTDDAQQTEAHLEIR EDGTVGGAADQSPESLLQLKALKPGVIQ ILGVKTSRFLCQRPDGALYGSLHFDPEA CSFRELLLEDGYNVYQSEAHGLPLHLPG NKSPHRDPAPRGPARFLPLPGLPPALPE PPGILAPQPPDVGSSDPLSMVGPSQGRS PSYAS |
| 161 | SABA1-FGF21v30 | SABA1-FGF21 variant 30; see similar description for variant | MGVSDVPRDLEVVAATPTSLLISWHSYY EQNSYYRITYGETGGNSPVQEFTVPYSQ TTATISGLKPGVDYTITVYAVYGSKYYY |

TABLE 2 -continued

Summary of exemplary sequences

| SEQ ID NO: | Sequence Name | Description | Sequence |
|---|---|---|---|
| | | 1 | PISINYRTEIEKPSQEDEDEDEDEDPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 162 | SABA1-FGF21v31 | SABA1-FGF21 variant 31; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQEDEDEDEDEDGSGSGSGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 163 | SABA1-FGF21v32 | SABA1-FGF21 variant 32; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGSAAAAAAAAAGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGSPPALPEPPGILAPQPPDVGSSDPLSMVGPSQGRSPSYAS |
| 164 | SABA1-FGF21v33 | SABA1-FGF21 variant 33; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGSEGSEGSEGSEGSEPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 165 | SABA1-FGF21v34 | SABA1-FGF21 variant 34; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQPASPASPASPASPASPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 166 | SABA1-FGF21v35 | SABA1-FGF21 variant 35; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGSPGSPGSPGSPGSPPIPDSSPLLQFGGQVRQRYLYTDDAQQTEAHLEIREDGTVGGAADQSPESLLQLKALKPGVIQILGVKTSRFLCQRPDGALYSSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |

TABLE 2 -continued

Summary of exemplary sequences

| SEQ ID NO: | Sequence Name | Description | Sequence |
|---|---|---|---|
| 167 | SABA1-FGF21v36 | SABA1-FGF21 variant 36; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGSTVAAPSTVAAPSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 168 | SABA1-FGF21v37 | SABA1-FGF21 variant 37; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGGSEGGSEPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 169 | SABA1-FGF21v38 | SABA1-FGF21 variant 38; see similar description for variant 1 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQSTSTSTGPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYAS |
| 170 | SABA5-FGF21v39 | SABA1-FGF21 variant 39; see similar description for variant 1 | MGVSDVPRDLEVVAATPTSLLISWEDDSYYSRYYRITYGETGGNSPVQEFTVPSDLYTATISGLKPGVDYTITVYAVTYDVTDLIMHEPISINYRTEIEKPSGGSGSGSGSGSGSGSPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYASHHHHHH |
| | | **Exemplary Fusions: $X_{FL}$—FGF21-$X_{LK}$—$X_{AL}$—SABA—$X_{AT}$** | |
| 171 | FGF21-SABA1v1 | FGF21-SABA1 variant 1: FGF21 core sequence having an FNT3 leader sequence and a C-terminal S followed by a $G(GS)_7G$ linker which joins SABA core 1 sequence having AdNT3 leader sequence and a AdCT1 tail followed by a His6-tag | MPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYASGGSGSGSGSGSGSGSGVSDVPRDLEVVAATPTSLLISWHSYYEQNSYYRITYGETGGNSPVQEFTVPYSQTTATISGLKPGVDYTITVYAVYGSKYYYPISINYRTEIDKPSQHHHHHH |
| 172 | FGF21-SABA1v2 | FGF21-SABA1 variant 2; see similar description for variant 1 | MPIPDSSPLLQFGGQVRQRYLYTDDAQQTEAHLEIREDGTVGGAADQSPESLLQLKALKPGVIQILGVKTSRFLCQRPDGALYGSLHFDPEACSFRELLLEDGYNVYQSEAHGLPLHLPGNKSPHRDPAPRGPARFLPLPGLPPALPEPPGILAPQPPDVGSSDPLSMVGPSQGRSPSYASGGSGSGSGSGSGSGSGVSDVPRDLEVVAATPTSLLISWHSYYEQNSYYRITYGETGGNSPVQEFTVPYSQTTATISGLKPGVDYTITVYAVYGSKYYYPISINYRTEIEKPSQHHHHHH |

TABLE 2 -continued

Summary of exemplary sequences

| SEQ ID NO: | Sequence Name | Description | Sequence |
|---|---|---|---|
| 173 | FGF21-SABA1v3 | FGF21-SABA1 variant 3; see similar description for variant 1 | MPIPDSSPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYASGGSGSGSGSGSGSGS GVSDVPRDLEVVAATPTSLLISWHSYYE QNSYYRITYGETGGNSPVQEFTVPYSQT TATISGLKPGVDYTITVYAVYGSKYYYP ISINYRTEIEKPSQ |
| Exemplary Trimer Fusion: $X_{FL}$—FGF21-$X_{LK}$—$X_{AL}$—SABA—$X_{AT}$—$X_{LK}$—$X_{FL}$—FGF21 | | | |
| 174 | FGF21-SABA1-FGF21v1 | An exemplary trimer fusion in which a sequence comprising SABA core 1 is flanked by FGF21 core sequence, each comprising unique N— and C— extension sequences | MHHHHHHIPDSSPLLQFGGQVRQRYLYT DDAQQTEAHLEIREDGTVGGAADQSPES LLQLKALKPGVIQILGVKTSRFLCQRPD GALYGSLHFDPEACSFRELLLEDGYNVY QSEAHGLPLHLPGNKSPHRDPAPRGPAR FLPLPGLPPALPEPPGILAPQPPDVGSS DPLSMVGPSQGRSPSYASGSGSGSGSGS GSGSVSDVPRDLEVVAATPTSLLISWHS YYEQNSYYRITYGETGGNSPVQEFTVPY SQTTATISGLKPGVDYTITVYAVYGSKY YYPISINYRTEIDKPSGGSGSGSGSGSG SGSPDSSPLLQFGGQVRQRYLYTDDAQQ TEAHLEIREDGTVGGAADQSPESLLQLK ALKPGVIQILGVKTSRFLCQRPDGALYG SLHFDPEACSFRELLLEDGYNVYQSEAH GLPLHLPGNKSPHRDPAPRGPARFLPLP GLPPALPEPPGILAPQPPDVGSSDPLSM VGPSQGRSPSYAS |
| Exemplary GLP-1 and Exendin Sequences and Fusions | | | |
| 226 | GLP-1V1 | GLP-1 variant 1: GLP-1(7-36), optionally may contain a C-terminal α-amide group | HAEGTFTSDVSSYLEGQAAKEFIAWLVK GR |
| 227 | GLP-1v2 | GLP-1 variant 2: GLP-1(7-37) | HAEGTFTSDVSSYLEGQAAKEFIAWLVK GRG |
| 228 | Exendin-4 | Exendin-4, optionally may contain a C-terminal α-amide group | HGEGTFTSDLSKQMEEEAVRLFIEWLKN GGPSSGAPPPS |
| 229 | GLP-1-SABA1v1 | GLP-1-SABA1 variant 1: GLP-1(7-37) with an N— terminal Met fused to a $(GGGGS)_3$ linker, fused to SABA1.4 | MHAEGTFTSDVSSYLEGQAAKEFIAWLV KGRGGGGGSGGGGSGGGGSGVSDVPRDL EVVAATPTSLLISWHSYYEQNSYYRITY GETGGNSPVQEFTVPYSQTTATISGLKP GVDYTITVYAVYGSKYYYPISINYRTE |
| 230 | GLP-1-SABA1v2 | GLP-1-SABA1 variant 2: GLP-1(7-37 with an N— terminal Met, fused to an $(ED)_5$ linker, fused to SABA1.4 | MHAEGTFTSDVSSYLEGQAAKEFIAWLV KGRGEDEDEDEDEDGVSDVPRDLEVVAA TPTSLLISWHSYYEQNSYYRITYGETGG NSPVQEFTVPYSQTTATISGLKPGVDYT ITVYAVYGSKYYYPISINYRTE |
| 231 | SABA1-GLP-1v1 | SABA1-GLP-1 variant 1: SABA1.5 fused to a $(GGGGS)_3$ linker, fused to GLP-1(7-37) | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSHAEG TFTSDVSSYLEGQAAKEFIAWLVKGRG |
| 232 | SABA1-GLP-1v2 | SABA1-GLP-1 variant 2: SABA1.5 fused to an $(ED)_5$ linker, fused to GLP-1(7-37) | MGVSDVPRDLEVVAATPTSLLISWHSYY EQNSYYRITYGETGGNSPVQEFTVPYSQ TTATISGLKPGVDYTITVYAVYGSKYYY PISINYRTEEDEDEDEDEDHAEGTFTSD VSSYLEGQAAKEFIAWLVKGRG |

TABLE 2 -continued

| SEQ ID NO: | Sequence Name | Description | Sequence |
|---|---|---|---|
| | | Summary of exemplary sequences | |
| 233 | Exendin-4-SABA1v1 | Exendin-4-SABA1 variant 1: Exendin-4 with an N-terminl Met, fused to a $(GGGGS)_3$ linker, fused to SABA1.4 | MHGEGTFTSDLSKQMEEEAVRLFIEWLK<br>NGGPSSGAPPPSGGGGSGGGGSGGGGSG<br>VSDVPRDLEVVAATPTSLLISWHSYYEQ<br>NSYYRITYGETGGNSPVQEFTVPYSQTT<br>ATISGLKPGVDYTITVYAVYGSKYYYPI<br>SINYRTE |
| 234 | Exendin-4-SABA1v2 | Exendin-4-SABA1 variant 1: Exendin-4 with N-terminal Met, fused to an $(ED)_5$ linker, fused to SABA1.4 | MHAEGTFTSDVSSYLEGQAAKEFIAWLV<br>KGRGEDEDEDEDEDGVSDVPRDLEVVAA<br>TPTSLLISWHSYYEQNSYYRITYGETGG<br>NSPVQEFTVPYSQTTATISGLKPGVDYT<br>ITVYAVYGSKYYYPISINYRTE |
| 235 | SABA1-Exendin-4v1 | SABA1-Exendin-4 variant 1: SABA1.5 fused to a $(GGGGS)_3$ linker, fused to Exendin-4 | MGVSDVPRDLEVVAATPTSLLISWHSYY<br>EQNSYYRITYGETGGNSPVQEFTVPYSQ<br>TTATISGLKPGVDYTITVYAVYGSKYYY<br>PISINYRTEGGGGSGGGGSGGGGSHGEG<br>TFTSDLSKQMEEEAVRLFIEWLKNGGPS<br>SGAPPPS |
| 236 | SABA1-Exendin-4v2 | SABA1-Exendin-4 variant 2: SABA1.5 fused to an $(ED)_5$ linker, fused to Exendin-4 | MGVSDVPRDLEVVAATPTSLLISWHSYY<br>EQNSYYRITYGETGGNSPVQEFTVPYSQ<br>TTATISGLKPGVDYTITVYAVYGSKYYY<br>PISINYRTEEDEDEDEDEDHGEGTFTSD<br>LSKQMEEEAVRLFIEWLKNGGPSSGAPP<br>PS |
| | | Exemplary Plectasin Sequences and Fusions | |
| 237 | Plec | Plectasin (Plec) | MGFGCNGPWDEDDMQCHNHCKSIKGYKG<br>GYCAKGGFVCKCY |
| 238 | SABA1-Plec | SABA1 core with AdNT1 extension, fused to an $(ED)_5$ linker, fused to Plectasin | MGVSDVPRDLEVVAATPTSLLISWHSYY<br>EQNSYYRITYGETGGNSPVQEFTVPYSQ<br>TTATISGLKPGVDYTITVYAVYGSKYYY<br>PISINYRTEDEDEDEDEDMGFGCNGPWD<br>EDDMQCHNHCKSIKGYKGGYCAKGGFVC<br>KCY |
| 239 | Plec-SABA1 | Plectasin, fused to a SABA1 core with AdNT3 and L26 extensions | MGFGCNGPWDEDDMQCHNHCKSIKGYKG<br>GYCAKGGFVCKCYVSDVPRDLEVVAATP<br>TSLLISWHSYYEQNSYYRITYGETGGNS<br>PVQEFTVPYSQTTATISGLKPGVDYTIT<br>VYAVYGSKYYYPISINYRTEDEDEDEDE<br>D |
| | | Exemplary Pragranulin and Atstrrin Sequences and Fusions | |
| 240 | PRGNv1 | Progranulin (PRGN) variant 1, the signal sequence is underlined and the elements used in Atstrrin are in indicated in *lower case/italics/dotted underline* | MWTLVSWVALTAGLVAGTRCPDGQFCPV<br>ACCLDPGGASYSCCRPLLDKWPTTLSRH<br>LGGPCQVDAHCSAGHSCIFTVSGTSSCC<br>PFPEAVACGDGHHCCPRGFHCSADGRSC<br>FQRSGNNSVGAIQCPDSQFECPDFSTCC<br>VMVDGSWGCCPM*pqasccedrvhccphg*<br>*afcdlvhtrcitptgthplakklpaqrt*<br>*nravalsss*VMCPDARSRCPDGSTCCEL<br>PSGKYGCCPMPNATCCSDHLHCCPQDTV<br>CDLIQSKCL*skenattdlltklpahtvg*<br>*dvkcdmevscpdgytccrlqsgaw*GCCP<br>FTQAVCCEDHIHCCPAGFTCDTQKGT*ce*<br>*qgphqvpwmekapahlslpdpqalkrdv*<br>*pcdnvsscpssdtccqltsgewgccpip*<br>*eavccsdhqhccpqgytc*VAEGQCQRGS<br>EIVAGLEKMPARRASLSHPRDIGCDQHT<br>SCPVGQTCCPSLGGSWACCQLPHAVCCE<br>DRQHCCPAGYTCNVKARSCEKEVVSAQP<br>ATFLARSPHVGVKDVECGEGHFCHDNQT<br>CCRDNRQGWACCPYRQGVCCADRRHCCP<br>AGFRCAARGTKCLRREAPRWDAPLRDPA<br>LRQLL |

TABLE 2 -continued

Summary of exemplary sequences

| SEQ ID NO: | Sequence Name | Description | Sequence |
|---|---|---|---|
| 241 | PRGNv2 | PRGN variant 2: PRGN(21-588) | TRCPDGQFCPVACCLDPGGASYSCCRPL LDKWPTTLSRHLGGPCQVDAHCSAGHSC IFTVSGTSSCCPFPEAVACGDGHHCCPR GFHCSADGRSCFQRSGNNSVGAIQCPDS QFECPDFSTCCVMVDGSWGCCPMPQASC CEDRVHCCPHGAFCDLVHTRCITPTGTH PLAKKLPAQRTNRAVALSSSVMCPDARS RCPDGSTCCELPSGKYGCCPMPNATCCS DHLHCCPQDTVCDLIQSKCLSKENATTD LLTKLPAHTVGDVKCDMEVSCPDGYTCC RLQSGAWGCCPFTQAVCCEDHIHCCPAG FTCDTQKGTCEQGPHQVPWMEKAPAHLS LPDPQALKRDVPCDNVSSCPSSDTCCQL TSGEWGCCPIPEAVCCSDHQHCCPQGYT CVAEGQCQRGSEIVAGLEKMPARRASLS HPRDIGCDQHTSCPVGQTCCPSLGGSWA CCQLPHAVCCEDRQHCCPAGYTCNVKAR SCEKEVVSAQPATFLARSPHVGVKDVEC GEGHFCHDNQTCCRDNRQGWACCPYRQG VCCADRRHCCPAGFRCAARGTKCLRREA PRWDAPLRDPALRQLL |
| 242 | ATST | Atstrrin (ATST) | PQASCCEDRVHCCPHGAFCDLVHTRCIT PTGTHPLAKKLPAQRTNRAVALSSSSKE DATTDLLTKLPAHTVGDVKCDMEVSCPD GYTCCRLQSGAWCEQGPHQVPWMEKAPA HLSLPDPQALKRDVPCDNVSSCPSSDTC CQLTSGEWGCCPIP |
| 243 | PRGN-SABA1v1 | PRGN-SABA1 variant 1: PRGN(21-588) with an N-terminal Met, fused to a $(GGGGS)_3$ linker fused to SABA1.4 | MTRCPDGQFCPVACCLDPGGASYSCCRP LLDKWPTTLSRHLGGPCQVDAHCSAGHS CIFTVSGTSSCCPFPEAVACGDGHHCCP RGFHCSADGRSCFQRSGNNSVGAIQCPD SQFECPDFSTCCVMVDGSWGCCPMPQAS CCEDRVHCCPHGAFCDLVHTRCITPTGT HPLAKKLPAQRTNRAVALSSSVMCPDAR SRCPDGSTCCELPSGKYGCCPMPNATCC SDHLHCCPQDTVCDLIQSKCLSKENATT DLLTKLPAHTVGDVKCDMEVSCPDGYTC CRLQSGAWGCCPFTQAVCCEDHIHCCPA GFTCDTQKGTCEQGPHQVPWMEKAPAHL SLPDPQALKRDVPCDNVSSCPSSDTCCQ LTSGEWGCCPIPEAVCCSDHQHCCPQGY TCVAEGQCQRGSEIVAGLEKMPARRASL SHPRDIGCDQHTSCPVGQTCCPSLGGSW ACCQLPHAVCCEDRQHCCPAGYTCNVKA RSCEKEVVSAQPATFLARSPHVGVKDVE CGEGHFCHDNQTCCRDNRQGWACCPYRQ GVCCADRRHCCPAGFRCAARGTKCLRRE APRWDAPLRDPALRQLLGGGGSGGGGSG GGGSGVSDVPRDLEVVAATPTSLLISWH SYYEQNSYYRITYGETGGNSPVQEFTVP YSQTTATISGLKPGVDYTITVYAVYGSK YYYPISINYRTE |

TABLE 2 -continued

Summary of exemplary sequences

| SEQ ID NO: | Sequence Name | Description | Sequence |
|---|---|---|---|
| 244 | PRGN-SABA1v2 | PRGN-SABA1 variant 2: PRGN(21-588 with an N-terminal Met, fused to an $(ED)_5$ linker, fused to SABA1.4 | MTRCPDGQFCPVACCLDPGGASYSCCRPLLDKWPTTLSRHLGGPCQVDAHCSAGHSCIFTVSGTSSCCPFPEAVACGDGHHCCPRGFHCSADGRSCFQRSGNNSVGAIQCPDSQFECPDFSTCCVMVDGSWGCCPMPQASCCEDRVHCCPHGAFCDLVHTRCITPTGTHPLAKKLPAQRTNRAVALSSSVMCPDARSRCPDGSTCCELPSGKYGCCPMPNATCCSDHLHCCPQDTVCDLIQSKCLSKENATTDLLTKLPAHTVGDVKCDMEVSCPDGYTCCRLQSGAWGCCPFTQAVCCEDHIHCCPAGFTCDTQKGTCEQGPHQVPWMEKAPAHLSLPDPQALKRDVPCDNVSSCPSSDTCCQLTSGEWGCCPIPEAVCCSDHQHCCPQGYTCVAEGQCQRGSEIVAGLEKMPARRASLSHPRDIGCDQHTSCPVGQTCCPSLGGSWACCQLPHAVCCEDRQHCCPAGYTCNVKARSCEKEVVSAQPATFLARSPHVGVKDVECGEGHFCHDNQTCCRDNRQGWACCPYRQGVCCADRRHCCPAGFRCAARGTKCLRREAPRWDAPLRDPALRQLLEDEDEDEDEDGVSDVPRDLEVVAATPTSLLISWHSYYEQNSYYRITYGETGGNSPVQEFTVPYSQTTATISGLKPGVDYTITVYAVYGSKYYYPISINYRTE |
| 245 | SABA1-PRGNv1 | SABA1-PRGN variant 1: SABA1.5, fused to a $(GGGGS)_3$ linker, fused to PRGN(21-588) | MGVSDVPRDLEVVAATPTSLLISWHSYYEQNSYYRITYGETGGNSPVQEFTVPYSQTTATISGLKPGVDYTITVYAVYGSKYYYPISINYRTEGGGGSGGGGSGGGGSTRCPDGQFCPVACCLDPGGASYSCCRPLLDKWPTTLSRHLGGPCQVDAHCSAGHSCIFTVSGTSSCCPFPEAVACGDGHHCCPRGFHCSADGRSCFQRSGNNSVGAIQCPDSQFECPDFSTCCVMVDGSWGCCPMPQASCCEDRVHCCPHGAFCDLVHTRCITPTGTHPLAKKLPAQRTNRAVALSSSVMCPDARSRCPDGSTCCELPSGKYGCCPMPNATCCSDHLHCCPQDTVCDLIQSKCLSKENATTDLLTKLPAHTVGDVKCDMEVSCPDGYTCCRLQSGAWGCCPFTQAVCCEDHIHCCPAGFTCDTQKGTCEQGPHQVPWMEKAPAHLSLPDPQALKRDVPCDNVSSCPSSDTCCQLTSGEWGCCPIPEAVCCSDHQHCCPQGYTCVAEGQCQRGSEIVAGLEKMPARRASLSHPRDIGCDQHTSCPVGQTCCPSLGGSWACCQLPHAVCCEDRQHCCPAGYTCNVKARSCEKEVVSAQPATFLARSPHVGVKDVECGEGHFCHDNQTCCRDNRQGWACCPYRQGVCCADRRHCCPAGFRCAARGTKCLRREAPRWDAPLRDPALRQLL |
| 246 | SABA1-PRGNv2 | SABA1-PRGN variant 2: SABA1.5, fused to an $(ED)_5$ linker, fused to PRGN(21-588) | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDTRCPDGQFCPVACCLDPGGASYSCCRPLLDKWPTTLSRHLGGPCQVDAHCSAGHSCIFTVSGTSSCCPFPEAVACGDGHHCCPRGFHCSADGRSCFQRSGNNSVGAIQCPDSQFECPDFSTCCVMVDGSWGCCPMPQASCCEDRVHCCPHGAFCDLVHTRCITPTGTHPLAKKLPAQRTNRAVALSSSVMCPDARSRCPDGSTCCELPSGKYGCCPMPNATCCSDHLHCCPQDTVCDLIQSKCLSKENATTDLLTKLPAHTVGDVKCDMEVSCPDGYTCCRLQSGAWGCCPFTQAVCCEDHIHCCPAGFTCDTQKGTCEQGPHQVPWMEKAPAHLSLPDPQALKRDVPCDNVSSCPSSDTCCQLTSGEWGCCPIPEAVCCSDHQHCCPQGYTCVAEGQCQRGSEIVAGLEKMPARRASLSHPRDIGCDQHTSCPVGQTCCPSLGGSWACCQLPHAVCCEDRQHCCPAGYTCNVKARSCEKEVVSAQPATFLARSPHVGVKDVECGEGHFCHDNQTCCRDNRQGWACCPYRQGVCCADRRHCCPAGFRCAARGTKCLRREAPRWDAPLRDPALRQLL |

TABLE 2 -continued

| SEQ ID NO: | Sequence Name | Description | Sequence |
|---|---|---|---|
| | | Summary of exemplary sequences | |
| 247 | ATST-SABA1v1 | ATST-SABA1 variant 1: Atstrrin with an N-terminal Met, fused to a $(GGGGS)_3$ linker, fused to SABA1.4 | MPQASCCEDRVHCCPHGAFCDLVHTRCI<br>TPTGTHPLAKKLPAQRTNRAVALSSSSK<br>EDATTDLLTKLPAHTVGDVKCDMEVSCP<br>DGYTCCRLQSGAWCEQGPHQVPWMEKAP<br>AHLSLPDPQALKRDVPCDNVSSCPSSDT<br>CCQLTSGEWGCCPIPGGGGSGGGGSGGG<br>GSGVSDVPRDLEVVAATPTSLLISWHSY<br>YEQNSYYRITYGETGGNSPVQEFTVPYS<br>QTTATISGLKPGVDYTITVYAVYGSKYY<br>YPISINYRTE |
| 248 | ATST-SABA1v2 | ATST-SABA1 variant 2: Atstrrin with an N-terminal Met, fused to an $(ED)_5$ linker, fused to SABA1.4 | MPQASCCEDRVHCCPHGAFCDLVHTRCI<br>TPTGTHPLAKKLPAQRTNRAVALSSSSK<br>EDATTDLLTKLPAHTVGDVKCDMEVSCP<br>DGYTCCRLQSGAWCEQGPHQVPWMEKAP<br>AHLSLPDPQALKRDVPCDNVSSCPSSDT<br>CCQLTSGEWGCCPIPEDEDEDEDEDGVS<br>DVPRDLEVVAATPTSLLISWHSYYEQNS<br>YYRITYGETGGNSPVQEFTVPYSQTTAT<br>ISGLKPGVDYTITVYAVYGSKYYYPISI<br>NYRTE |
| 249 | SABA1-ATSTv1 | SABA1-ATST variant 1: SABA1.5, fused to a $(GGGGS)_3$ linker, fused to Atstrrin | MGVSDVPRDLEVVAATPTSLLISWHSYY<br>EQNSYYRITYGETGGNSPVQEFTVPYSQ<br>TTATISGLKPGVDYTITVYAVYGSKYYY<br>PISINYRTEGGGGSGGGGSGGGGSPQAS<br>CCEDRVHCCPHGAFCDLVHTRCITPTGT<br>HPLAKKLPAQRTNRAVALSSSSKEDATT<br>DLLTKLPAHTVGDVKCDMEVSCPDGYTC<br>CRLQSGAWCEQGPHQVPWMEKAPAHLSL<br>PDPQALKRDVPCDNVSSCPSSDTCCQLT<br>SGEWGCCPIP |
| 250 | SABA1-ATSTv2 | SABA1-ATST variant 2: SABA1.5, fused to an $(ED)_5$ linker, fused to Atstrrin | MGVSDVPRDLEVVAATPTSLLISWHSYY<br>EQNSYYRITYGETGGNSPVQEFTVPYSQ<br>TTATISGLKPGVDYTITVYAVYGSKYYY<br>PISINYRTEEDEDEDEDEDPQASCCEDR<br>VHCCPHGAFCDLVHTRCITPTGTHPLAK<br>KLPAQRTNRAVALSSSSKEDATTDLLTK<br>LPAHTVGDVKCDMEVSCPDGYTCCRLQS<br>GAWCEQGPHQVPWMEKAPAHLSLPDPQA<br>LKRDVPCDNVSSCPSSDTCCQLTSGEWG<br>CCPIP |
| | | Exemplary IFN Sequences and Fusions | |
| 251 | IFNλv1 | IFN lambda1 variant 1 | GPVPTSKPTTTGKGCHIGRFKSLSPQEL<br>ASFKKARDALEESLKLKNWSCSSPVFPG<br>NWDLRLLQVRERPVALEAELALTLKVLE<br>AAAGPALEDVLDQPLHTLHHILSQLQAC<br>IQPQPTAGPRPRGRLHHWLHRLQEAPKK<br>ESAGCLEASVTFNLFRLLTRDLKYVADG<br>NLCLRTSTHPEST |
| 252 | IFNλv2 | IFN lambda1 variant 2: IFN lambda1 with C171S substitution | GPVPTSKPTTTGKGCHIGRFKSLSPQEL<br>ASFKKARDALEESLKLKNWSCSSPVFPG<br>NWDLRLLQVRERPVALEAELALTLKVLE<br>AAAGPALEDVLDQPLHTLHHILSQLQAC<br>IQPQPTAGPRPRGRLHHWLHRLQEAPKK<br>ESAGCLEASVTFNLFRLLTRDLKYVADG<br>NLSLRTSTHPEST |
| 253 | IFNλv3 | IFN lambda1 variant 3: IFN lambda1, with 6 amino acid deleted from the N-terminus, and C165S substitution | KPTTTGKGCHIGRFKSLSPQELASFKKA<br>RDALEESLKLKNWSCSSPVFPGNWDLRL<br>LQVRERPVALEAELALTLKVLEAAAGPA<br>LEDVLDQPLHTLHHILSQLQACIQPQPT<br>AGPRPRGRLHHWLHRLQEAPKKESAGCL<br>EASVTFNLFRLLTRDLKYVADGNLSLRT<br>STHPEST |
| 254 | IFNλv4 | IFN lambda1 variant 4: IFN lambda1, with 6 amino acid deleted | KPTTTGKGCHIGRFKSLSPQELASFKKA<br>RDALEESLKLKNWSCSSPVFPGNWDLRL<br>LQVRERPVALEAELALTLKVLEAAAGPA |

TABLE 2 -continued

Summary of exemplary sequences

| SEQ ID NO: | Sequence Name | Description | Sequence |
|---|---|---|---|
| | | from the N-terminus, and D161E and C165S substitutions | LEDVLDQPLHTLHHILSQLQACIQPQPTAGPRPRGRLHHWLHRLQEAPKKESAGCLEASVTFNLFRLLTRDLKYVAEGNLSLRTSTHPEST |
| 255 | IFNλv5 | IFN lambda1 variant 5: IFN lambda1, with 6 amino acid deleted from the N-terminus, and G162A and C165S substitutions | KPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADANLSLRTSTHPEST |
| 256 | IFNλv6 | IFN lambda1 variant 6: IFN lambda1 with D167E and C171S substitutions | GPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVAEGNLSLRTSTHPEST |
| 257 | IFNλv7 | IFN lambda1 variant 7: IFN lambda1 with G168A and C171S substitutions | GPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADANLSLRTSTHPEST |
| 258 | IFNλ-SABA1v1 | IFNλ-SABA1 variant 1: IFNλv1 with an N-terminal Met, fused to a $(GGGGS)_3$ linker, fused to SABA1.4 | MGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLCLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 259 | IFNλ-SABA1v2 | IFNλ-SABA1 variant 2: IFNλv2 with an N-terminal Met, fused to a $(GGGGS)_3$ linker, fused to SABA1.4 | MGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLSLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 260 | IFNλ-SABA1v3 | IFNλ-SABA1 variant 3: IFNλv3 with an N-terminal Met, fused to a $(GGGGS)_3$ linker, fused to SABA1.4 | MKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLSLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |

TABLE 2 -continued

Summary of exemplary sequences

| SEQ ID NO: | Sequence Name | Description | Sequence |
|---|---|---|---|
| 261 | IFNλ-SABA1v4 | IFNλ-SABA1 variant 4: IFNλv4 with an N-terminal Met, fused to a $(GGGGS)_3$ linker, fused to SABA1.4 | MKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVAEGNLSLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 262 | IFNλ-SABA1v5 | IFNλ-SABA1 variant 5: IFNλv5 with an N-terminal Met, fused to a $(GGGGS)_3$ linker, fused to SABA1.4 | MKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADANLSLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 263 | IFNλ-SABA1v6 | IFNλ-SABA1 variant 6: IFNλv6 with an N-terminal Met, fused to a $(GGGGS)_3$ linker, fused to SABA1.4 | MGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVAEGNLSLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 264 | IFNλ-SABA1v7 | IFNλ-SABA1 variant 7: IFNλv7 with an N-terminal Met, fused to a $(GGGGS)_3$ linker, fused to SABA1.4 | MGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADANLSLRTSTHPESTGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 265 | IFNλ-SABA1v8 | IFNλ-SABA1 variant 8: IFNλv1 with an N-terminal Met, fused to a $(ED)_5$ linker, fused to SABA1.4 | MGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLCLRTSTHPESTEDEDEDEDEDGVSDVPRDLEVVAATPTSLLISWHSYYEQNSYYRITYGETGGNSPVQEFTVPYSQTTATISGLKPGVDYTITVYAVYGSKYYYPISINYRTE |
| 266 | IFNλ-SABA1v9 | IFNλ-SABA1 variant 9: IFNλv2 with an N-terminal Met, fused to a $(ED)_5$ linker, fused to SABA1.4 | MGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLSLRTSTHPESTEDEDEDEDEDGVSDVPRDLEVVAATPTSLLISWHSYYEQNSYYRITYGETGGNSPVQEFTVPYSQTTATISGLKPGVDYTITVYAVYGSKYYYPISINYRTE |

TABLE 2 -continued

Summary of exemplary sequences

| SEQ ID NO: | Sequence Name | Description | Sequence |
|---|---|---|---|
| 267 | IFNλ-SABA1 v10 | IFNλ-SABA1 variant 10: IFNλv3 with an N-terminal Met, fused to an $(ED)_5$ linker, fused to SABA1.4 | MKPTTTGKGCHIGRFKSLSPQELASFKK ARDALEESLKLKNWSCSSPVFPGNWDLR LLQVRERPVALEAELALTLKVLEAAAGP ALEDVLDQPLHTLHHILSQLQACIQPQP TAGPRPRGRLHHWLHRLQEAPKKESAGC LEASVTFNLFRLLTRDLKYVADGNLSLR TSTHPESTEDEDEDEDEDGVSDVPRDLE VVAATPTSLLISWHSYYEQNSYYRITYG ETGGNSPVQEFTVPYSQTTATISGLKPG VDYTITVYAVYGSKYYYPISINYRTE |
| 268 | IFNλ-SABA1 v11 | IFNλ-SABA1 variant 11: IFNλv4 with an N-terminal Met, fused to an $(ED)_5$ linker, fused to SABA1.4 | MKPTTTGKGCHIGRFKSLSPQELASFKK ARDALEESLKLKNWSCSSPVFPGNWDLR LLQVRERPVALEAELALTLKVLEAAAGP ALEDVLDQPLHTLHHILSQLQACIQPQP TAGPRPRGRLHHWLHRLQEAPKKESAGC LEASVTFNLFRLLTRDLKYVAEGNLSLR TSTHPESTEDEDEDEDEDGVSDVPRDLE VVAATPTSLLISWHSYYEQNSYYRITYG ETGGNSPVQEFTVPYSQTTATISGLKPG VDYTITVYAVYGSKYYYPISINYRTE |
| 269 | IFNλ-SABA1 v12 | IFNλ-SABA1 variant 12: IFNλv5 with an N-terminal Met, fused to an $(ED)_5$ linker, fused to SABA1.4 | MKPTTTGKGCHIGRFKSLSPQELASFKK ARDALEESLKLKNWSCSSPVFPGNWDLR LLQVRERPVALEAELALTLKVLEAAAGP ALEDVLDQPLHTLHHILSQLQACIQPQP TAGPRPRGRLHHWLHRLQEAPKKESAGC LEASVTFNLFRLLTRDLKYVADANLSLR TSTHPESTEDEDEDEDEDGVSDVPRDLE VVAATPTSLLISWHSYYEQNSYYRITYG ETGGNSPVQEFTVPYSQTTATISGLKPG VDYTITVYAVYGSKYYYPISINYRTE |
| 270 | IFNλ-SABA1 v13 | IFNλ-SABA1 variant 13: IFNλv6 with an N-terminal Met, fused to an $(ED)_5$ linker, fused to SABA1.4 | MGPVPTSKPTTTGKGCHIGRFKSLSPQE LASFKKARDALEESLKLKNWSCSSPVFP GNWDLRLLQVRERPVALEAELALTLKVL EAAAGPALEDVLDQPLHTLHHILSQLQA CIQPQPTAGPRPRGRLHHWLHRLQEAPK KESAGCLEASVTFNLFRLLTRDLKYVAE GNLSLRTSTHPESTEDEDEDEDEDGVSD VPRDLEVVAATPTSLLISWHSYYEQNSY YRITYGETGGNSPVQEFTVPYSQTTATI SGLKPGVDYTITVYAVYGSKYYYPISIN YRTE |
| 271 | IFNλ-SABA1 v14 | IFNλ-SABA1 variant 14: IFNλv7 with an N-terminal Met, fused to an $(ED)_5$ linker, fused to SABA1.4 | MGPVPTSKPTTTGKGCHIGRFKSLSPQE LASFKKARDALEESLKLKNWSCSSPVFP GNWDLRLLQVRERPVALEAELALTLKVL EAAAGPALEDVLDQPLHTLHHILSQLQA CIQPQPTAGPRPRGRLHHWLHRLQEAPK KESAGCLEASVTFNLFRLLTRDLKYVAD ANLSLRTSTHPESTEDEDEDEDEDGVSD VPRDLEVVAATPTSLLISWHSYYEQNSY YRITYGETGGNSPVQEFTVPYSQTTATI SGLKPGVDYTITVYAVYGSKYYYPISIN YRTE |
| 272 | SABA1-IFNλv1 | SABA1-IFNλ variant 1: SABA1.5, fused to a $(GGGGS)_3$ linker, fused to IFNλv1 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSGPVP TSKPTTTGKGCHIGRFKSLSPQELASFK KARDALEESLKLKNWSCSSPVFPGNWDL RLLQVRERPVALEAELALTLKVLEAAAG PALEDVLDQPLHTLHHILSQLQACIQPQ PTAGPRPRGRLHHWLHRLQEAPKKESAG CLEASVTFNLFRLLTRDLKYVADGNLCL RTSTHPEST |

TABLE 2 -continued

Summary of exemplary sequences

| SEQ ID NO: | Sequence Name | Description | Sequence |
|---|---|---|---|
| 273 | SABA1-IFNλv2 | SABA1-IFNλ variant 2: SABA1.5, fused to a $(GGGGS)_3$ linker, fused to IFNλv2 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSGPVP TSKPTTTGKGCHIGRFKSLSPQELASFK KARDALEESLKLKNWSCSSPVFPGNWDL RLLQVRERPVALEAELALTLKVLEAAAG PALEDVLDQPLHTLHHILSQLQACIQPQ PTAGPRPRGRLHHWLHRLQEAPKKESAG CLEASVTFNLFRLLTRDLKYVADGNLSL RTSTHPEST* |
| 274 | SABA1-IFNλv3 | SABA1-IFNλ variant 3: SABA1.5, fused to a $(GGGGS)_3$ linker, fused to IFNλv3 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSKPTT TGKGCHIGRFKSLSPQELASFKKARDAL EESLKLKNWSCSSPVFPGNWDLRLLQVR ERPVALEAELALTLKVLEAAAGPALEDV LDQPLHTLHHILSQLQACIQPQPTAGPR PRGRLHHWLHRLQEAPKKESAGCLEASV TFNLFRLLTRDLKYVADGNLSLRTSTHP EST |
| 275 | SABA1-IFNλv4 | SABA1-IFNλ variant 4: SABA1.5, fused to a $(GGGGS)_3$ linker, fused to IFNλv4 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSKPTT TGKGCHIGRFKSLSPQELASFKKARDAL EESLKLKNWSCSSPVFPGNWDLRLLQVR ERPVALEAELALTLKVLEAAAGPALEDV LDQPLHTLHHILSQLQACIQPQPTAGPR PRGRLHHWLHRLQEAPKKESAGCLEASV TFNLFRLLTRDLKYVAEGNLSLRTSTHP EST |
| 276 | SABA1-IFNλv5 | SABA1-IFNλ variant 5: SABA1.5, fused to a $(GGGGS)_3$ linker, fused to IFNλv5 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSKPTT TGKGCHIGRFKSLSPQELASFKKARDAL EESLKLKNWSCSSPVFPGNWDLRLLQVR ERPVALEAELALTLKVLEAAAGPALEDV LDQPLHTLHHILSQLQACIQPQPTAGPR PRGRLHHWLHRLQEAPKKESAGCLEASV TFNLFRLLTRDLKYVADANLSLRTSTHP EST |
| 277 | SABA1-IFNλv6 | SABA1-IFNλ variant 6: SABA1.5, fused to a $(GGGGS)_3$ linker, fused to IFNλv6 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSGPVP TSKPTTTGKGCHIGRFKSLSPQELASFK KARDALEESLKLKNWSCSSPVFPGNWDL RLLQVRERPVALEAELALTLKVLEAAAG PALEDVLDQPLHTLHHILSQLQACIQPQ PTAGPRPRGRLHHWLHRLQEAPKKESAG CLEASVTFNLFRLLTRDLKYVAEGNLSL RTSTHPEST |
| 278 | SABA1-IFNλv7 | SABA1-IFNλ variant 7: SABA1.5, fused to a $(GGGGS)_3$ linker, fused to IFNλv7 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSGPVP TSKPTTTGKGCHIGRFKSLSPQELASFK KARDALEESLKLKNWSCSSPVFPGNWDL RLLQVRERPVALEAELALTLKVLEAAAG PALEDVLDQPLHTLHHILSQLQACIQPQ PTAGPRPRGRLHHWLHRLQEAPKKESAG CLEASVTFNLFRLLTRDLKYVADANLSL RTSTHPEST |

TABLE 2 -continued

Summary of exemplary sequences

| SEQ ID NO: | Sequence Name | Description | Sequence |
|---|---|---|---|
| 279 | SABA1-IFNλv8 | SABA1-IFNλ variant 8: SABA1.5, fused to an $(ED)_5$ linker, fused to IFNλv1 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLCLRTSTHPEST |
| 280 | SABA1-IFNλv9 | SABA1-IFNλ variant 9: SABA1.5, fused to an $(ED)_5$ linker, fused to IFNλv2 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLSLRTSTHPEST |
| 281 | SABA1-IFNλv10 | SABA1-IFNλ variant 10: SABA1.5, fused to an $(ED)_5$ linker, fused to IFNλv3 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADGNLSLRTSTHPEST |
| 282 | SABA1-IFNλv11 | SABA1-IFNλ variant 11: SABA1.5, fused to an $(ED)_5$ linker, fused to IFNλv4 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVAEGNLSLRTSTHPEST |
| 283 | SABA1-IFNλv12 | SABA1-IFNλ variant 12: SABA1.5, fused to an $(ED)_5$ linker, fused to IFNλv5 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADANLSLRTSTHPEST |
| 284 | SABA1-IFNλv13 | SABA1-IFNλ variant 13: SABA1.5, fused to an $(ED)_5$ linker, fused to IFNλv6 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVAEGNLSLRTSTHPEST |

TABLE 2 -continued

Summary of exemplary sequences

| SEQ ID NO: | Sequence Name | Description | Sequence |
|---|---|---|---|
| 285 | SABA1-IFNλv14 | SABA1-IFNλ variant 14: SABA1.5, fused to an $(ED)_5$ linker, fused to IFNλv7 | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDGPVPTSKPTTTGKGCHIGRFKSLSPQELASFKKARDALEESLKLKNWSCSSPVFPGNWDLRLLQVRERPVALEAELALTLKVLEAAAGPALEDVLDQPLHTLHHILSQLQACIQPQPTAGPRPRGRLHHWLHRLQEAPKKESAGCLEASVTFNLFRLLTRDLKYVADANLSLRTSTHPEST |
| | | **Exemplary IL-21 Sequences and Fusions** | |
| 286 | IL21v1 | IL-21 variant 1: human IL-21 with the native leader sequence underlined | MDSSPGNMERIVICLMVIFLGTLVHKSSSQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS |
| 287 | IL21v2 | IL-21 variant 2: human IL-21 without a leader sequence | MQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS |
| 288 | IL21na1 | IL21 nucleic acid sequence variant 1: nucleotide sequence encoding the human IL-21 sequence with the native leader, the portion of the sequence encoding the leader is underlined; for expression in mammalian cells | ATGGATTCCAGTCCTGGCAACATGGAGAGGATTGTCATCTGTCTGATGGTCATCTTCTTGGGGACACTGGTCCACAAATCAAGCTCCCAAGGTCAAGATCGCCACATGATTAGAATGCGTCAACTTATAGATATTGTTGATCAGCTGAAAAATTATGTGAATGACTTGGTCCCTGAATTTCTGCCAGCTCCAGAAGATGTAGAGACAAACTGTGAGTGGTCAGCTTTTTCCTGTTTTCAGAAGGCCCAACTAAAGTCAGCAAATACAGGAAACAATGAAAGGATAATCAATGTATCAATTAAAAAGCTGAAGAGGAAACCACCTTCCACAAATGCAGGGAGAAGACAGAAACACAGACTAACATGCCCTTCATGTGATTCTTATGAGAAAAAACCACCCAAAGAATTCCTAGAAAGATTCAAATCACTTCTCCAAAAGATGATTCATCAGCATCTGTCCTCTAGAACACACGGAAGTGAAGATTCCTGA |
| 289 | IL21na2 | IL21 nucleic acid sequence variant 2: nucleotide sequence encoding the human IL-21 sequence without the leader sequence; sequence has been partially codon optimized for expression in *E. coli* | ATGCAAGGTCAAGATCGCCACATGATTAGAATGCGTCAACTTATAGATATTGTTGATCAGCTGAAAAATTATGTGAATGACCTGGTTCCGGAATTCCTGCCGGCTCCGGAAGATGTTGAGACCAACTGTGAGTGGTCCGCTTTCTCCTGTTTCCAGAAAGCCCAGCTGAAATCCGCAAACACCGGTAACAACGAACGTATCATCAACGTTTCCATTAAAAAACTGAAACGTAAACCGCCGTCCACCAACGCAGGTCGTCGTCAGAAACACCGTCTGACCTGCCCGTCCTGTGATTCTTATGAGAAAAAACCGCCGAAAGAATTCCTGGAACGTTTCAAATCCCTGCTGCAGAAAATGATTCACCAGCACCTGTCCTCTCGTACCCACGGTTCCGAAGATTCCTGA |
| 290 | IL21-SABA1v1 | IL21-SABA1 variant 1: IL21 with native leader, fused to a $(GGGS)_3$ linker, fused to SABA1.4 | MDSSPGNMERIVICLMVIFLGTLVHKSSSQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDSGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |

TABLE 2 -continued

| SEQ ID NO: | Sequence Name | Description | Sequence |
|---|---|---|---|
| | | Summary of exemplary sequences | |
| 291 | IL21-SABA1v2 | IL21-SABA1 variant 2: IL21 without a leader, fused to a $(GGGS)_3$ linker, fused to SABA1.4 | MQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDSGGGGSGGGGSGGGGSGVSDVPRDLEVVAATPTSLLISWHSYYEQNSYYRITYGETGGNSPVQEFTVPYSQTTATISGLKPGVDYTITVYAVYGSKYYYPISINYRTE |
| 292 | IL21-SABA1v3 | IL21-SABA1 variant 3: IL21 with native leader, fused to a $(ED)_5$ linker, fused to SABA1.4 | MDSSPGNMERIVICLMVIFLGTLVHKSSSQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDSEDEDEDEDEDGVSDVPRDLEVVAATPTSLLISWHSYYEQNSYYRITYGETGGNSPVQEFTVPYSQTTATISGLKPGVDYTITVYAVYGSKYYYPISINYRTE |
| 293 | IL21-SABA1v4 | IL21-SABA1 variant 4: IL21 without a leader, fused to a $(ED)_5$ linker, fused to SABA1.4 | MQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDSEDEDEDEDEDGVSDVPRDLEVVAATPTSLLISWHSYYEQNSYYRITYGETGGNSPVQEFTVPYSQTTATISGLKPGVDYTITVYAVYGSKYYYPISINYRTE |
| 294 | SABA1-IL21v1 | SABA1-IL21 variant 1: SABA1.5, fused to a $(GGGS)_3$ linker, fused to IL-21 without a leader) | MGVSDVPRDLEVVAATPTSLLISWHSYYEQNSYYRITYGETGGNSPVQEFTVPYSQTTATISGLKPGVDYTITVYAVYGSKYYYPISINYRTEGGGGSGGGGSGGGGSMQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS |
| 295 | SABA1-IL21v2 | SABA1-IL21 variant 2: SABA1.5, fused to a $(ED)_5$ linker, fused to IL-21 without a leader) | MGVSDVPRDLEVVAATPTSLLISWHSYYEQNSYYRITYGETGGNSPVQEFTVPYSQTTATISGLKPGVDYTITVYAVYGSKYYYPISINYRTEEDEDEDEDEDMQGQDRHMIRMRQLIDIVDQLKNYVNDLVPEFLPAPEDVETNCEWSAFSCFQKAQLKSANTGNNERIINVSIKKLKRKPPSTNAGRRQKHRLTCPSCDSYEKKPPKEFLERFKSLLQKMIHQHLSSRTHGSEDS |
| | | Exemplary Amylin Sequences and Fusions | |
| 296 | AMYv1 | Amylin (AMY) variant 1: Human Amylin (with a Cys 2-7 disulfide bond and a C-terminal amidation) | KCNTATCATQRLANFLVHSSNNFGAILSSTNVGSNTY |
| 297 | AMYv2 | AMY variant 2: Pramlintide (with a Cys 2-7 disulfide bond and a C-terminal amidation) | KCNTATCATQRLANFLVHSSNNFGPILPPTNVGSNTY |
| 298 | AMYv3 | AMY varient 3: Davalintide (with a Cys 2-7 disulfide bond and a C-terminal amidation) | KCNTATCVLGRLSQELHRLQTYPRTNTGSNTY |
| 299 | AMYv4 | AMY variant 4: UPG-281 (with a Cys 1-7 disulfide bond and a C-terminal amidation) | CSNLSTCVLGKLSNELHKLNTYPRTDVGANTY |

TABLE 2 -continued

Summary of exemplary sequences

| SEQ ID NO: | Sequence Name | Description | Sequence |
| --- | --- | --- | --- |
| 300 | AMYv5 | AMY variant 5: Rat Amylin (with a Cys 2-7 disulfide bond and a C-terminal amidation) | KCNTATCATQRLANFLVRSSNNLGPVLPPTNVGSNTY |
| 301 | AMYv6 | AMY variant 6: Porcine Amylin (with a Cys 2-7 disulfide bond and a C-terminal amidation) | KCNMATCATQHLANFLDRSRNNLGTIFSPTKVGSNTY |
| 302 | AMYv7 | AMY variant 7: Feline Amylin (with a Cys 2-7 disulfide bond and a C-terminal amidation) | KCNTATCATQRLANFLIRSSNNLGAILSPTNVGSNTY |
| 303 | AMYv8 | AMY variant 8: Salmon Calcitonin (with a Cys 1-7 disulfide bond and a C-Terminal amidation) | CSNLSTCVLGKLSNELHKLNTYPRTNTGSGTP |
| 304 | SABA1-AMYv1 | SABA-Amylin fusion variant 1: SABA1.6, fused to an $(ED)_5$ linker, fused to AMYv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQEDEDEDEDEDKCNTATCATQRLANFLVHSSNNFGAILSSTNVGSNTY |
| 305 | SABA1-AMYv2 | SABA-Amylin fusion variant 1: SABA1.7, fused to an $(ED)_5$ linker, fused to AMYv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDKCNTATCATQRLANFLVHSSNNFGAILSSTNVGSNTY |
| 306 | SABA1-AMYv3 | SABA-Amylin fusion variant 3: SABA1.6, fused to a $G(GS)_4$ linker, fused to AMYv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGGSGSGSGSKCNTATCATQRLANFLVHSSNNFGAILSSTNVGSNTY |
| 307 | SABA1-AMYv4 | SABA-Amylin fusion variant 4: SABA1.7, fused to a $G(GS)_4$ linker, fused to AMYv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIGGSGSGSGSKCNTATCATQRLANFLVHSSNNFGAILSSTNVGSNTY |
| 308 | SABA1-AMYv5 | SABA-Amylin fusion variant 5: SABA1.6, fused to an $(ED)_5$ linker, fused to AMYv2, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQEDEDEDEDEDKCNTATCATQRLANFLVHSSNNFGPILPPTNVGSNTY |
| 309 | SABA1-AMYv6 | SABA-Amylin fusion variant 6: SABA1.7, fused to an $(ED)_5$ linker, fused to AMYv2, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDKCNTATCATQRLANFLVHSSNNFGPILPPTNVGSNTY |
| 310 | SABA1-AMYv7 | SABA-Amylin fusion variant 7: SABA1.6, fused to a $G(GS)_4$ linker, fused to AMYv2, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGGSGSGSGSKCNTATCATQRLANFLVHSSNNFGPILPPTNVGSNTY |

TABLE 2 -continued

Summary of exemplary sequences

| SEQ ID NO: | Sequence Name | Description | Sequence |
|---|---|---|---|
| 311 | SABA1-AMYv8 | SABA-Amylin fusion variant 8: SABA1.7, fused to a G(GS)$_4$ linker, fused to AMYv2, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIGGSGSGSGSKCNTATCATQRLANFLVHSSNNFGPILPPTNVGSNTY |
| 312 | SABA1-AMYv9 | SABA-Amylin fusion variant 9: SABA1.6, fused to an (ED)$_5$ linker, fused to AMYv3, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQEDEDEDEDEDKCNTATCVLGRLSQELHRLQTYPRTNTGSNTY |
| 313 | SABA1-AMYv10 | SABA-Amylin fusion variant 10: SABA1.7, fused to an (ED)$_5$ linker, fused to AMYv3, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDKCNTATCVLGRLSQELHRLQTYPRTNTGSNTY |
| 314 | SABA1-AMYv11 | SABA-Amylin fusion variant 11: SABA1.6, fused to a G(GS)$_4$ linker, fused to AMYv3, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGGSGSGSGSKCNTATCVLGRLSQELHRLQTYPRTNTGSNTY |
| 315 | SABA1-AMYv12 | SABA-Amylin fusion variant 12: SABA1.7, fused to a G(GS)$_4$ linker, fused to AMYv3, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIGGSGSGSGSKCNTATCVLGRLSQELHRLQTYPRTNTGSNTY |
| 316 | SABA1-AMYv13 | SABA-Amylin fusion variant 13: SABA1.6, fused to an (ED)$_5$ linker, fused to AMYv4, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQEDEDEDEDEDCSNLSTCVLGKLSNELHKLNTYPRTDVGANTY |
| 317 | SABA1-AMYv14 | SABA-Amylin fusion variant 14: SABA1.7, fused to an (ED)$_5$ linker, fused to AMYv4, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDCSNLSTCVLGKLSNELHKLNTYPRTDVGANTY |
| 318 | SABA1-AMYv15 | SABA-Amylin fusion variant 15: SABA1.6, fused to a G(GS)$_4$ linker, fused to AMYv4, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGGSGSGSGSCSNLSTCVLGKLSNELHKLNTYPRTDVGANTY |
| 319 | SABA1-AMYv16 | SABA-Amylin fusion variant 16: SABA1.7, fused to a G(GS)$_4$ linker, fused to AMYv4, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIGGSGSGSGSCSNLSTCVLGKLSNELHKLNTYPRTDVGANTY |
| 320 | SABA1-AMYv17 | SABA-Amylin fusion variant 17: SABA1.6-Cys-$X_1$-AMYv1, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQC-$X_1$-KCNTATCATQRLANFLVHSSNNFGAILSSTNVGSNTY |

TABLE 2 -continued

Summary of exemplary sequences

| SEQ ID NO: | Sequence Name | Description | Sequence |
|---|---|---|---|
| 321 | SABA1-AMYv18 | SABA-Amylin fusion variant 18: SABA1.7-(ED)$_5$G-Cys-$X_1$-AMYv1, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGC-$X_1$-KCNTATCATQRLANFLVHSSNNFGAILSSTNVGSNTY |
| 322 | SABA1-AMYv19 | SABA-Amylin fusion variant 19: SABA1.6-Cys-$X_1$-AMYv2, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQC-$X_1$-KCNTATCATQRLANFLVHSSNNFGPILPPTNVGSNTY |
| 323 | SABA1-AMYv20 | SABA-Amylin fusion variant 20: SABA1.7-(ED)$_5$G-Cys-$X_1$-AMYv2, with C-terminal amidation, wherein $X_1$ is Maleimide-PEG20 | MGVSDVPRDLEVVAATPTSLLISWHSYYEQNSYYRITYGETGGNSPVQEFTVPYSQTTATISCLKPGVDYTITVYAVYGSKYYYPISINYRTEIEDEDEDEDEDGC-$X_1$-KCNTATCATQRLANFLVHSSNNFGPILPPTNVGSNTY |
| 324 | SABA1-AMYv21 | SABA-Amylin fusion variant 21: SABA1.6-Cys-$X_1$-AMYv3, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQC-$X_1$-KCNTATCVLGRLSQELHRLQTYPRTNTGSNTY |
| 325 | SABA1-AMYv22 | SABA-Amylin fusion variant 22: SABA1.7-(ED)$_5$G-Cys-$X_1$-AMYv3, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGC-$X_1$-KCNTATCVLGRLSQELHRLQTYPRTNTGSNTY |
| 326 | SABA1-AMYv23 | SABA-Amylin fusion variant 23: SABA1.6-Cys-$X_1$-AMYv4, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQC-$X_1$-CSNLSTCVLGKLSNELHKLNTYPRTDVGANTY |
| 327 | SABA1-AMYv24 | SABA-Amylin fusion variant 24: SABA1.7-(ED)$_5$G-Cys-$X_1$-AMYv4, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGC-$X_1$-CSNLSTCVLGKLSNELHKLNTYPRTDVGANTY |
| 328 | SABA1-AMYv25 | SABA-Amylin fusion variant 24: SABA1.7-(ED)$_5$G-Cys-$X_1$-AMYv5, with C-terminal amidation and a disulfide bridge between the two shaded Cys residues, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGC-$X_1$-KCNTATCATQRLANFLVRSSNNLGPVLPPTNVGSNTY |
| | | Exemplary PYY Sequences and Fusions | |
| 329 | PYYv1 | Peptide YY (PYY) variant 1: Human PYY (with a C-terminal amidation) | YPIKPEAPGEDASPEELNRYYASLRHYLNLVTRQRY |

TABLE 2 -continued

Summary of exemplary sequences

| SEQ ID NO: | Sequence Name | Description | Sequence |
|---|---|---|---|
| 408 | PYYv2 | Peptide YY (PYY) variant 2: Human $PYY_{3-36}$ (with a C-terminal amidation) | IKPEAPGEDASPEELNRYYASLRHYLNLVTRQRY |
| 409 | PYYv3 | Peptide YY (PYY) variant 3: Human $PYY_{13-36}$ (with a C-terminal amidation) | SPEELNRYYASLRHYLNLVTRQRY |
| 410 | PYYv4 | Peptide YY (PYY) variant 4: Human $PYY_{21-36}$ (with a C-terminal amidation) | YASLRHYLNLVTRQRY |
| 411 | PYYv5 | Peptide YY (PYY) variant 5: Human $PYY_{22-36}$ (with a C-terminal amidation) | ASLRHYLNLVTRQRY |
| 412 | PYYv6 | Peptide YY (PYY) variant 6: Human $PYY_{24-36}$ (with a C-terminal amidation) | LRHYLNLVTRQRY |
| 413 | PYYv7 | Peptide YY (PYY) variant 7: Human $PYY_{25-36}$ (with a C- | RHYLNLVTRQRY |
| 414 | PYYv8 | Peptide YY (PYY) variant 8: Human $PYY_{13-36(L31)}$ (with a C-terminal amidation) | SPEELNRYYASLRHYLNLLTRQRY |
| 415 | PYYv9 | Peptide YY (PYY) variant 9: Human $PYY_{21-36(L31)}$ (with a C-terminal amidation) | YASLRHYLNLLTRQRY |
| 416 | PYYv10 | Peptide YY (PYY) variant 10: Human $PYY_{22-36(L31)}$ (with a C-terminal amidation) | ASLRHYLNLLTRQRY |
| 417 | PYYv11 | Peptide YY (PYY) variant 11: Human $PYY_{24-36(L31)}$ (with a C-terminal amidation) | LRHYLNLLTRQRY |
| 418 | PYYv12 | Peptide YY (PYY) variant 12: Human $PYY_{25-36(L31)}$ (with a C-terminal amidation) | RHYLNLLTRQRY |
| 330 | PYYv13 | PYY variant 13: Baboon PYY (with a C-terminal amidation) | YPIKPEAPGEDASPEELSRYYASLRHYLNLVTRQRY |
| 331 | PYYv14 | PYY variant 14: Dog PYY (with a C-terminal amidation) | YPAKPEAPGEDASPEELSRYYASLRHYLNLVTRQRY |
| 332 | PYYv15 | PYY variant 15: Rabbit PYY (with a C-terminal amidation) | YPSKPEAPGEDASPEELNRYYASLRHYLNLVTRQRY |
| 333 | PYYv16 | PYY variant 16: mouse PYY (with a C-terminal amidation) | YPAKPEAPGEDASPEELSRYYASLRHYLNLVTRQRY |

TABLE 2 -continued

Summary of exemplary sequences

| SEQ ID NO: | Sequence Name | Description | Sequence |
|---|---|---|---|
| 334 | PYYv17 | PYY variant 17: mouse $PYY_{3-36}$ (with a C-terminal amidation) | AKPEAPGEDASPEELSRYYASLRHYLNL VTRQRY |
| 335 | PYYv18 | PYY variant 18: Pig/Dog/Rat PYY (with a C-terminal amidation) | YPAKPEAPGEDASPEELSRYYASLRHYL NLVTRQRY |
| 336 | PYYv19 | PYY variant 19: Cow PYY (with a C-terminal amidation) | YPKPQAPGEHASPDELNRYYTSLRHYL NLVTRQRF |
| 337 | PYYv20 | PYY variant 20: Chicken PYY (with a C-terminal amidation) | AYPPKPESPGDAASPEEIAQYFSALRHY INLVTRQRY |
| 338 | SABA1-PYYv1 | SABA1-PYY fusion variant 1: SABA1.6, fused to an $(ED)_5$ linker, fused to PYYv2 with C-terminal amidation | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQEDEDEDEDEDIKP EAPGEDASPEELNRYYASLRHYLNLVTR QRY |
| 339 | SABA1-PYYv2 | SABA1-PYY fusion variant 2: SABA1.7, fused to an $(ED)_5$ linker, fused to PYYv2 with C-terminal amidation | MGVSDVPRDLEVVAATPTSLLISWHSYY EQNSYYRITYGETGGNSPVQEFTVPYSQ TTATISGLKPGVDYTITVYAVYGSKYYY PISINYRTEIEDEDEDEDEDIKPEAPGE DASPEELNRYYASLRHYLNLVTRQRY |
| 340 | SABA1-PYYv3 | SABA1-PYY fusion variant 3: SABA1.6, fused to a $G(GS)_4$ linker, fused to PYYv2 with C-terminal amidation | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQGGSGSGSGSIKPE APGEDASPEELNRYYASLRHYLNLVTRQ RY |
| 341 | SABA1-PYYv4 | SABA1-PYY fusion variant 4: SABA1.7, fused to a $G(GS)_4$ linker, fused to PYYv2 with C-terminal amidation | MGVSDVPRDLEVVAATPTSLLISWHSYY EQNSYYRITYGETGGNSPVQEFTVPYSQ TTATISGLKPGVDYTITVYAVYGSKYYY PISINYRTEIGGSGSGSGSIKPEAPGED ASPEELNRYYASLRHYLNLVTRQRY |
| 342 | SABA1-PYYv5 | SABA1-PYY fusion variant 5: SABA1.6-Cys-$X_1$-PYYv2, with C-terminal amidation, wherein $X_1$ is Maleimide-PEG20 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQC-$X_1$-IKPEAPGE DASPEELNRYYASLRHYLNLVTRQRY |
| 343 | SABA1-PYYv6 | SABA1-PYY fusion variant 6: SABA1.7-$(ED)_5$G-Cys-$X_1$-PYYv2, with C-terminal amidation, wherein $X_1$ is Maleimide-PEG20 | MGVSDVPRDLEVVAATPTSLLISWHSYY EQNSYYRITYGETGGNSPVQEFTVPYSQ TTATISGLKPGVDYTITVYAVYGSKYYY PISINYRTEIEDEDEDEDEDGC-$X_1$-IK PEAPGEDASPEELNRYYASLRHYLNLVT RQRY |
| 344 | SABA1-PYYv7 | SABA1-PYY fusion variant 7: SABA1.7-$(ED)_5$G-Cys-$X_1$-PYYv17, with C-terminal amidation, wherein $X_1$ is Maleimide-PEG20 | MGVSDVPRDLEVVAATPTSLLISWHSYY EQNSYYRITYGETGGNSPVQEFTVPYSQ TTATISGLKPGVDYTITVYAVYGSKYYY PISINYRTEIEDEDEDEDEDGC-$X_1$-AK PEAPGEDASPEELSRYYASLRHYLNLVT RQRY |

TABLE 2 -continued

Summary of exemplary sequences

| SEQ ID NO: | Sequence Name | Description | Sequence |
|---|---|---|---|
| Exemplary PP Sequences and Fusions | | | |
| 345 | PPv1 | Pancreatic Polypeptide (PP) variant 1: Human/Monkey PP (with a C-terminal amidation) | APLEPVYPGDNATPEQMAQYAADLRRYINMLTRPRY |
| 346 | PPv2 | PP variant 2: Ox PP (with a C-terminal amidation) | APLEPEYPGDNATPEQMAQYAAELRRYINMLTRPRY |
| 347 | PPv3 | PP variant 3: Pig/Dog PP (with a C-terminal amidation) | APLEPVYPGDDATPEQMAQYAAELRRYINMLTRPRY |
| 348 | PPv4 | PP variant 4: Sheep PP (with a C-terminal amidation) | ASLEPEYPGDNATPEQMAQYAAELRRYINMLTRPRY |
| 349 | PPv5 | PP variant 5: Horse/Zebra PP (with a C-terminal amidation) | APMEPVYPGDNATPEQMAQYAAELRRYINMLTRPRY |
| 350 | PPv6 | PP variant 6: Cat/Lion/Tiger/Leopard/Cheetah/Tapir PP (with a C-terminal amidation) | APLEPVYPGDNATPEQMAQYAAELRRYINMLTRPRY |
| 351 | PPv7 | PP variant 7: Rhinoceros PP (with a C-terminal amidation) | SPLEPVYPGDNATPEQMAQYAAELRRYINMLTRPRY |
| 352 | PPv8 | PP variant 8: Guinea pig PP (with a C-terminal amidation) | APLEPVYPGDDATPQQMAQYAAEMRRYINMLTRPRY |
| 353 | PPv9 | PP variant 9: Mouse PP (with a C-terminal amidation) | APLEPMYPGDYATPEQMAQYETQLRRYINTLTRPRY |
| 354 | PPv10 | PP variant 10: Rat PP (with a C-terminal amidation) | APLEPMYPGDYATHEQRAQYETQLRRYINTLTRPRY |
| 355 | PPv11 | PP variant 11: Chinchilla PP (with a C-terminal amidation) | APLEPVYPGDNATPEQMAQYAAELRRYINMLTRPRY |
| 356 | PPv12 | PP variant 12: Rabbit PP (with a C-terminal amidation) | APPEPVYPGDDATPEQMAEYVADLRRYINMLTRPRY |
| 357 | PPv13 | PP variant 13: Hedgehog PP (with a C-terminal amidation) | VPLEPVYPGDNATPEQMAQYAAELRRYINMLTRPRY |
| 358 | SABA1-PPv1 | SABA1-PP fusion variant 1: SABA1.6, fused to an $(ED)_5$ linker, fused to PPv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQEDEDEDEDEDAPLEPVYPGDNATPEQMAQYAADLRRYINMLTRPRY |
| 359 | SABA1-PPv2 | SABA1-PP fusion variant 2: SABA1.7, fused to an $(ED)_5$ linker, fused to PPv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDAPLEPVYPGDNATPEQMAQYAADLRRYINMLTRPRY |

TABLE 2 -continued

Summary of exemplary sequences

| SEQ ID NO: | Sequence Name | Description | Sequence |
|---|---|---|---|
| 360 | SABA1-PPv3 | SABA1-PP fusion variant 3: SABA1.6, fused to a $G(GS)_4$ linker, fused to PPv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQGGSGSGSGSAPLEPVYPGDNATPEQMAQYAADLRRYINMLTRPRY |
| 361 | SABA1-PPv4 | SABA1-PP fusion variant 4: SABA1.7, fused to a $G(GS)_4$ linker, fused to PPv1, with C-terminal amidation | MGVSDVPRDLEVVAATPTSLLISWHSYYEQNSYYRITYGETGGNSPVQEFTVPYSQTTATISGLKPGVDYTITVYAVYGSKYYYPISINYRTEIGGSGSGSGSAPLEPVYPGDNATPEQMAQYAADLRRYINMLTRPRY |
| 362 | SABA1-PPv5 | SABA1-PP fusion variant 5: SABA1.6-Cys-$X_1$-PPv1, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEKPSQC-$X_1$-APLEPVYPGDNATPEQMAQYAADLRRYINMLTRPRY |
| 363 | SABA1-PPv6 | SABA1-PP fusion variant 6: SABA1.7-$(ED)_5$G-Cys-$X_1$-PPv1, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGC-$X_1$-APLEPVYPGDNATPEQMAQYAADLRRYINMLTRPRY |
| 364 | SABA1-PPv7 | SABA1-PP fusion variant 7: SABA1.7-$(ED)_5$G-Cys-$X_1$-PPv9, with C-terminal amidation, wherein $X_1$ is Maleimide-PEG20 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDGC-$X_1$-APLEPMYPGDYATPEQMAQYETQLRRYINTLTRPRY |

Exemplary Osteocalcin Sequences and Fusions

| SEQ ID NO: | Sequence Name | Description | Sequence |
|---|---|---|---|
| 365 | OCNv1 | Osteocalcin (OCN) variant 1: Human OCN | YLYQWLGAPVPYPDPLEPRREVCELNPDCDELADHIGFQEAYRRFYGPV |
| 366 | OCNv2 | OCN variant 2: hum_G316A | YLYQWLGAPVPYPDPLEPRREVCELNPDCDKLADHIGFQEAYRRFYGPV |
| 367 | OCNv3 | OCN variant 3: hum_G353A | YLYQWLGAPVPYPDPLEPRREVCELNPDCDELADHIGFQEAYQRFYGPV |
| 368 | OCNv4 | OCN variant 4: chimp | YLYQWLGAPVPYPDTLEPRREVCELNPDCDELADHIGFQEAYRRFYGPV |
| 369 | OCNv5 | OCN variant 5: rhesus monkey | YLYQWLGAPAPYPDPLEPKREVCELNPDCDELADHIGFQEAYRRFYGPV |
| 370 | OCNv6 | OCN variant 6: cattle | YLDHWLGAPAPYPDPLEPKREVCELNPDCDELADHIGFQEAYRRFYGPV |
| 371 | OCNv7 | OCN variant 7: dog | YLDSGLGAPVPYPDPLEPKREVCELNPNCDELADHIGFQEAYQRFYGPV |
| 372 | OCNv8 | OCN variant 8: pig | YLDHGLGAPAPYPDPLEPRREVCELNPDCDELADHIGFQEAYRRFYGIA |
| 373 | OCNv9 | OCN variant 9: sheep | YLDPGLGAPAPYPDPLEPRREVCELNPDCDELADHIGFQEAYRRFYGPV |
| 374 | OCNv10 | OCN variant 10: rabbit | QLIDGQGAPAPYPDPLEPKREVCELNPDCDELADQVGLQDAYQRFYGPV |
| 375 | OCNv11 | OCN variant 11: mouse | YLGASVPSPDPLEPTREQCELNPACDELSDQYGLKTAYKRIYGITI |

TABLE 2 -continued

| Summary of exemplary sequences | | | |
|---|---|---|---|
| SEQ ID NO: | Sequence Name | Description | Sequence |
| 376 | OCNv12 | OCN variant 12: rat | YLNNGLGAPAPYPDPLEPHREVCELNPN CDELADHIGFQDAYKRIYGTTV |
| 377 | OCNv13 | OCN variant 13: chicken | HYAQDSGVAGAPPNPLEAQREVCELSPD CDELADQIGFQEAYRRFYGPV |
| 378 | OCNv14 | OCN variant 14: *xenopus laevis* | SYGNNVGQGAAVGSPLESQREVCELNPD CDELADHIGFQEAYRRFYGPV |
| 379 | SABA1-OCNv1 | SABA1-OCN fusion vaiant 1: SABA1.5, fused to an $(ED)_5$ linker, fused to OCNv1 | MGVSDVPRDLEVVAATPTSLLISWHSYY EQNSYYRITYGETGGNSPVQEFTVPYSQ TTATISGLKPGVDYTITVYAVYGSKYYY PISINYRTEEDEDEDEDEDYLYQWLGAP VPYPDPLEPRREVCELNPDCDELADHIG FQEAYRRFYGPV |
| 380 | SABA1-OCNv2 | SABA1-OCN fusion variant 2: SABA1.5, fused to an $(GGGGS)_3$ linker, fused to OCNv1 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSYLYQ WLGAPVPYPDPLEPRREVCELNPDCDEL ADHIGFQEAYRRFYGPV |
| 381 | SABA1-OCNv3 | SABA1-OCN fusion variant 3: SABA1.6-Cys-$X_1$-OCNv1, wherein $X_1$ is Maleimide-PEG20 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQC-$X_1$-YLYQWLGA PVPYPDPLEPRREVCELNPDCDELADHI GFQEAYRRFYGPV |
| 382 | SABA1-OCNv4 | SABA1-OCN fusion variant 4: SABA1.5, fused to an $(ED)_5$ linker, fused to OCNv2 | MGVSDVPRDLEVVAATPTSLLISWHSYY EQNSYYRITYGETGGNSPVQEFTVPYSQ TTATISGLKPGVDYTITVYAVYGSKYYY PISINYRTEEDEDEDEDEDYLYQWLGAP VPYPDPLEPRREVCELNPDCDKLADHIG FQEAYRRFYGPV |
| 383 | SABA1-OCNv5 | SABA1-OCN fusion variant 5: SABA1.5, fused to an $(GGGGS)_3$ linker, fused to OCNv2 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSYLYQ WLGAPVPYPDPLEPRREVCELNPDCDKL ADHIGFQEAYRRFYGPV |
| 384 | SABA1-OCNv6 | SABA1-OCN fusion variant 6: SABA1.6-Cys-$X_1$-OCNv2, wherein $X_1$ is Maleimide-PEG20 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQC-$X_1$-YLYQWLGA PVPYPDPLEPRREVCELNPDCDKLADHI GFQEAYRRFYGPV |
| 385 | SABA1-OCNv7 | SABA1-OCN fusion variant 7: SABA1.5, fused to an $(ED)_5$ linker, fused to OCNv3 | MGVSDVPRDLEVVAATPTSLLISWHSYY EQNSYYRITYGETGGNSPVQEFTVPYSQ TTATISGLKPGVDYTITVYAVYGSKYYY PISINYRTEEDEDEDEDEDYLYQWLGAP VPYPDPLEPRREVCELNPDCDELADHIG FQEAYQRFYGPV |
| 386 | SABA1-OCNv8 | SABA1-OCN fusion variant 8: SABA1.5, fused to an $(GGGGS)_3$ linker, fused to OCNv3 | MGVSDVPRDLEVVAATPTSLLISWHSYY EQNSYYRITYGETGGNSPVQEFTVPYSQ TTATISGLKPGVDYTITVYAVYGSKYYY PISINYRTEGGGGSGGGGSGGGGSYLYQ WLGAPVPYPDPLEPRREVCELNPDCDEL ADHIGFQEAYQRFYGPV |

TABLE 2 -continued

| SEQ ID NO: | Sequence Name | Description | Sequence |
|---|---|---|---|
| Summary of exemplary sequences | | | |
| 387 | SABA1-OCNv9 | SABA1-OCN fusion variant 9: SABA1.6-Cys-$X_1$-OCNv3, wherein $X_1$ is Maleimide-PEG20 | MGVSDVPRDLEVVAATPTSLLISWHSYY EQNSYYRITYGETGGNSPVQEFTVPYSQ TTATISGLKPGVDYTITVYAVYGSKYYY PISINYRTEIEKPSQC-$X_1$-YLYQWLGA PVPYPDPLEPRREVCELNPDCDELADHI GFQEAYQRFYGPV |
| 388 | OCN-SABA1v1 | OCN-SABA1 fusion varint 1: OCNv1, fused to an $(ED)_5$ linker, fused to SABA1.4, may have an optional N-terminal methionine | YLYQWLGAPVPYPDPLEPRREVCELNPD CDELADHIGFQEAYRRFYGPVEDEDEDE DEDGVSDVPRDLEVVAATPTSLLISWHS YYEQNSYYRITYGETGGNSPVQEFTVPY SQTTATISGLKPGVDYTITVYAVYGSKY YYPISINYRTE |
| 389 | OCN-SABA1v2 | OCN-SABA1 fusion variant 2: OCNv1, fused to an $(GGGGs)_3$ linker, fused to SABA1.4, may have an optional N-terminal methionine | YLYQWLGAPVPYPDPLEPRREVCELNPD CDELADHIGFQEAYRRFYGPVGGGGSGG GGSGGGGSGVSDVPRDLEVVAATPTSLL ISWHSYYEQNSYYRITYGETGGNSPVQE FTVPYSQTTATISGLKPGVDYTITVYAV YGSKYYYPISINYRTE |
| 390 | OCN-SABA1v3 | OCN-SABA1 fusion variant 3: OCNv1-$(ED)_5$G-Cys-$X_1$-SABA1.4, wherein $X_1$ is Maleimide-PEG20, may have an optional N-terminal methionine | YLYQWLGAPVPYPDPLEPRREVCELNPD CDELADHIGFQEAYRRFYGPVEDEDEDE DEDGC-$X_1$-GVSDVPRDLEVVAATPTSL LISWHSYYEQNSYYRITYGETGGNSPVQ EFTVPYSQTTATISGLKPGVDYTITVYA VYGSKYYYPISINYRTE |
| 391 | OCN-SABA1v4 | OCN-SABA1 fusion variant 4: OCNv2, fused to an $(ED)_5$ linker, fused to SABA1.4, may have an optional N-terminal methionine | YLYQWLGAPVPYPDPLEPRREVCELNPD CDKLADHIGFQEAYRRFYGPVEDEDEDE DEDGVSDVPRDLEVVAATPTSLLISWHS YYEQNSYYRITYGETGGNSPVQEFTVPY SQTTATISGLKPGVDYTITVYAVYGSKY YYPISINYRTE |
| 392 | OCN-SABA1v5 | OCN-SABA1 fusion variant 5: OCNv2, fused to an $(GGGGs)_3$ linker, fused to SABA1.4, may have an optional N-terminal methionine | YLYQWLGAPVPYPDPLEPRREVCELNPD CDKLADHIGFQEAYRRFYGPVGGGGSGG GGSGGGGSGVSDVPRDLEVVAATPTSLL ISWHSYYEQNSYYRITYGETGGNSPVQE FTVPYSQTTATISGLKPGVDYTITVYAV YGSKYYYPISINYRTE |
| 393 | OCN-SABA1v6 | OCN-SABA1 fusion variant 6: OCNv2-$(ED)_5$G-Cys-$X_1$-SABA1.4, wherein $X_1$ is Maleimide-PEG20, may have an optional N-terminal methionine | YLYQWLGAPVPYPDPLEPRREVCELNPD CDKLADHIGFQEAYRRFYGPVEDEDEDE DEDGC-$X_1$-GVSDVPRDLEVVAATPTSL LISWHSYYEQNSYYRITYGETGGNSPVQ EFTVPYSQTTATISGLKPGVDYTITVYA VYGSKYYYPISINYRTE |
| 394 | OCN-SABA1v7 | OCN-SABA1 fusion variant 7: OCNv3, fused to an $(ED)_5$ linker, fused to SABA1.4, may have an optional N-terminal methionine | YLYQWLGAPVPYPDPLEPRREVCELNPD CDELADHIGFQEAYQRFYGPVEDEDEDE DEDGVSDVPRDLEVVAATPTSLLISWHS YYEQNSYYRITYGETGGNSPVQEFTVPY SQTTATISGLKPGVDYTITVYAVYGSKY YYPISINYRTE |
| 395 | OCN-SABA1v8 | OCN-SABA1 fusion variant 8: OCNv3, fused to an $(GGGGs)_3$ linker, fused to SABA1.4, may have an optional N-terminal methionine | YLYQWLGAPVPYPDPLEPRREVCELNPD CDELADHIGFQEAYQRFYGPVGGGGSGG GGSGGGGSGVSDVPRDLEVVAATPTSLL ISWHSYYEQNSYYRITYGETGGNSPVQE FTVPYSQTTATISGLKPGVDYTITVYAV YGSKYYYPISINYRTE |

TABLE 2 -continued

Summary of exemplary sequences

| SEQ ID NO: | Sequence Name | Description | Sequence |
|---|---|---|---|
| 396 | OCN-SABA1v9 | OCN-SABA1 fusion variant 9: OCNv3-(ED)$_5$G-Cys-X$_1$-SABA1.4, wherein X$_1$ is Maleimide-PEG20, may have an optional N-terminal methionine | YLYQWLGAPVPYPDPLEPRREVCELNPDCDKLADHIGFQEAYRRFYGPVEDEDEDEDEDGC-X$_1$-GVSDVPRDLEVVAATPTSLLISWHSYYEQNSYYRITYGETGGNSPVQEFTVPYSQTTATISGLKPGVDYTITVYAVYGSKYYYPISINYRTE |
| | | Exemplary Apelin Sequences and Fusions | |
| 419 | APLVv1 | Apelin (APLN) variant 1 | MNLRLCVQALLLLWLSLTAVCGGSLMPLPDGNGLEDGNVRHLVQPRGSRNGPGPWQGGRRKFRRQRPRLSHKGPMPF |
| 420 | APLNv2 | APLN variant 2: corresponds to residues 42-77 of APLNv1 | LVQPRGSRNGPGPWQGGRRKFRRQRPRLSHKGPMPF |
| 421 | APLNv3 | APLN variant 3: corresponds to residues 61-77 of APLNv1 | KFRRQRPRLSHKGPMPF |
| 422 | APLNv4 | APLN variant 4: corresponds to residues 65-77 of APLNv1 | QRPRLSHKGPMPF |
| 423 | APLNv5 | APLN variant 5: corresponds to residues 66-77 of APLNv1 | RPRLSHKGPMPF |
| 424 | SABA1-APLNv1 | SABA1-APLN fusion variant 1: SABA1.7, fused to an (ED)$_5$ linker, fused to APLNv4 | MGVSDVPRDLEVVAATPTSLLISWHSYYEQNSYYRITYGETGGNSPVQEFTVPYSQTTATISGLKPGVDYTITVYAVYGSKYYYPISINYRTEIEDEDEDEDEDQRPRLSHKGPMPF |
| 425 | SABA1-APLNv2 | SABA1-APLN fusion variant 2: SABA1.6, fused to a 6XHis and (GS)$_7$ linker, fused to APLNv4 | MGVSDVPRDLEVVAATPTSLLISWHSYYEQNSYYRITYGETGGNSPVQEFTVPYSQTTATISGLKPGVDYTITVYAVYGSKYYYPISINYRTEIDKPSQHHHHHHGSGSGSGSGSGSGSQRPRLSHKGPMPF |
| 426 | SABA1-APLNv3 | SABA1-APLN fusion variant 3: SABA1.6, fused to a (GS)$_7$ linker, fused to APLNv4 | MGVSDVPRDLEVVAATPTSLLISWHSYYEQNSYYRITYGETGGNSPVQEFTVPYSQTTATISGLKPGVDYTITVYAVYGSKYYYPISINYRTEIDKPSQGSGSGSGSGSGSGSQRPRLSHKGPMPF |
| 427 | SABA1-APLNv4 | SABA1-APLN fusion variant 4: SABA1.6, fused to a 6XHis and (GS)$_7$ linker, fused to APLNv2 | MGVSDVPRDLEVVAATPTSLLISWHSYYEQNSYYRITYGETGGNSPVQEFTVPYSQTTATISGLKPGVDYTITVYAVYGSKYYYPISINYRTEIDKPSQHHHHHHGSGSGSGSGSGSGSLVQPRGSRNGPGPWQGGRRKFRRQRPRLSHKGPMPF |
| 428 | SABA1-APLNv5 | SABA1-APLN fusion variant 5: SABA1.6, fused to a (GS)$_7$ linker, fused to APLNv2 | MGVSDVPRDLEVVAATPTSLLISWHSYYEQNSYYRITYGETGGNSPVQEFTVPYSQTTATISGLKPGVDYTITVYAVYGSKYYYPISINYRTEIDKPSQGSGSGSGSGSGSGSLVOPRGSRNGPGPWQGGRRKFRRQRPRLSHKGPMPF |
| 429 | APLN-SABA1v1 | APLN-SABA1 fusion variant 1: APLNv4, fused to (GS)$_7$ linker, fused to SABA1.4, may have an optional N-terminal methionine | QRPRLSHKGPMPFGSGSGSGSGSGSGSGVSDVPRDLEVVAATPTSLLISWHSYYEQNSYYRITYGETGGNSPVQEFTVPYSQTTATISGLKPGVDYTITVYAVYGSKYYYPISINYRTE |

TABLE 2 -continued

| Summary of exemplary sequences | | | |
|---|---|---|---|
| SEQ ID NO: | Sequence Name | Description | Sequence |
| 430 | APLN-SABA1v2 | APLN-SABA1 fusion variant 2: APLNv2, fused to (GS)$_7$ linker, fused to SABA1.4, may have an optional N-terminal methionine | LVQPRGSRNGPGPWQGGRRKFRRQRPRL SHKGPMPFGSGSGSGSGSGSGSGVSDVP RDLEVVAATPTSLLISWHSYYEQNSYYR ITYGETGGNSPVQEFTVPYSQTTATISG LKPGVDYTITVYAVYGSKYYYPISINYR TE |

TABLE 3

| Certain exemplary nucleic acid sequences (SEQ ID NOs: 176-214 and 397-407). | | | |
|---|---|---|---|
| SEQ ID NO: | aa length | Sequence name | DNA sequence |
| 176 | 299 | SABA1-FGF21v2 | atgggtgtttctgatgttccgcgtgatctggaagttgttgcagcaaccccgacc agcctgctgattagctggcatagctattatgaacagaatagctattatcgcatt acctatggtgaaaccggtggtaattctccggttcaggaatttaccgttccgtat agccagaccaccgcaaccattagcggtctgaaaccgggtgttgattataccatt accgtgtatgcagtgtatggcagcaaatattattatccgattagcattaattat cgcaccgaaattgataaaccgagccagcatcatcatcaccatcatggtagcggt agcggttcaggtagcggttctggttctggtagccatccgattccggatagctct ccgctgctgcagtttggtggtcaggttcgtcagcgttatctgtataccgatgat gcacagcagaccgaagcacatctggaaattcgtgaagatggcaccgttggtggt gcagcagatcagtctccggaaagcctgctgcagctgaaagcactgaagccaggt gttattcagattctgggtgttaaaaccagccgttttctgtgtcagcgtccggat ggtgcactgtatggtagcctgcattttgatccggaagcatgcagctttcgtgaa ctgctgctggaagatggctataatgtgtatcagagcgaagcacatggtctgccg ctgcatttacctggtaataaatctccgcatcgtgatccggcaccgcgtggtccg gcacgtttcctgcctctgcctggtctgcctccggcactgccagaacctccgggt attctggcaccgcagcctccggatgttggtagcagcgatccgctgtctatggtt ggtccgagccagggtcgtagcccgagctatgca |
| 177 | 299 | SABA1-FGF21v3 | atgggtgtttctgatgttccgcgtgatctggaagttgttgcagcaaccccgacc agcctgctgattagctggcatagctattatgaacagaatagctattatcgcatt acctatggtgaaaccggtggtaattctccggttcaggaatttaccgttccgtat agccagaccaccgcaaccattagcggtctgaaaccgggtgttgattataccatt accgtgtatgcagtgtatggcagcaaatattattatccgattagcattaattat cgcaccgaaattgataaaccgagccagcatcatcatcaccatcatggtagcggt agcggttcaggtagcggttctggttctggtagcccgattccggatagctctccg ctgctgcagtttggtggtcaggttcgtcagcgttatctgtataccgatgatgca cagcagaccgaagcacatctggaaattcgtgaagatggcaccgttggtggtgca gcagatcagtctccggaaagcctgctgcagctgaaagcactgaagccaggtgtt attcagattctgggtgttaaaaccagccgttttctgtgtcagcgtccggatggt gcactgtatggtagcctgcattttgatccggaagcatgcagctttcgtgaactg ctgctggaagatggctataatgtgtatcagagcgaagcacatggtctgccgctg catttacctggtaataaatctccgcatcgtgatccggcaccgcgtggtccggca cgtttcctgcctctgcctggtctgcctccggcactgccagaacctccgggtatt ctggcaccgcagcctccggatgttggtagcagcgatccgctgtctatggttggt ccgagccagggtcgtagcccgagctatgcaagc |
| 178 | 299 | SABA1-FGF21v4 | atgggtgtttctgatgttccgcgtgatctggaagttgttgcagcaaccccgacc agcctgctgattagctggcatagctattatgaacagaatagctattatcgcatt acctatggtgaaaccggtggtaattctccggttcaggaatttaccgttccgtat agccagaccaccgcaaccattagcggtctgaaaccgggtgttgattataccatt accgtgtatgcagtgtatggcagcaaatattattatccgattagcattaattat cgcaccgaaattgataaaccgagcggtggtagcggtagcggttcaggtagcggt tctggttctggtagcccgattccggatagctctccgctgctgcagtttggtggt caggttcgtcagcgttatctgtataccgatgatgcacagcagaccgaagcacat ctggaaattcgtgaagatggcaccgttggtggtgcagcagatcagtctccggaa agcctgctgcagctgaaagcactgaagccaggtgttattcagattctgggtgtt aaaaccagccgttttctgtgtcagcgtccggatggtgcactgtatggtagcctg cattttgatccggaagcatgcagctttcgtgaactgctgctggaagatggctat aatgtgtatcagagcgaagcacatggtctgccgctgcatttacctggtaataaa tctccgcatcgtgatccggcaccgcgtggtccggcacgtttcctgcctctgcct ggtctgcctccggcactgccagaacctccgggtattctggcaccgcagcctccg gatgttggtagcagcgatccgctgtctatggttggtccgagccagggtcgtagc ccgagctatgcaagccatcatcatcaccatcat |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| 179 | 299 | SABA1-FGF21v5 | atgggtgtttctgatgttccgcgtgatctggaagttgttgcagcaaccccgacc<br>agcctgctgattagctggcatagctattatgaacagaatagctattatcgcatt<br>acctatggtgaaaccggtggtaattctccggttcaggaatttaccgttccgtat<br>agccagaccaccgcaaccattagcggtctgaaaccgggtgttgattataccatt<br>accgtgtatgcagtgtatggcagcaaatattattatccgattagcattaattat<br>cgcaccgaaattgataaaccgagcggtggtagcggtagcggttcaggtagcggt<br>tctggttctggtagccatccgattccggatagctctccgctgctgcagtttggt<br>ggtcaggttcgtcagcgttatctgtataccgatgatgcacagcagaccgaagca<br>catctggaaattcgtgaagatggcaccgttggtggtgcagcagatcagtctccg<br>gaaagcctgctgcagctgaaagcactgaagccaggtgttattcagattctgggt<br>gttaaaaccagccgttttctgtgtcagcgtccggatggtgcactgtatggtagc<br>ctgcattttgatccggaagcatgcagctttcgtgaactgctgctggaagatggc<br>tataatgtgtatcagagcgaagcacatggtctgccgctgcatttacctggtaat<br>aaatctccgcatcgtgatccggcaccgcgtggtccggcacgtttcctgcctctg<br>cctggtctgcctccggcactgccagaacctccgggtattctggcaccgcagcct<br>ccggatgttggtagcagcgatccgctgtctatggttggtccgagccagggtcgt<br>agcccgagctatgcacatcatcatcaccatcat |
| 180 | 300 | FGF21-SABA1v1 | atgccgattccggatagctctccgctgctgcagtttggtggtcaggttcgtcag<br>cgttatctgtataccgatgatgcacagcagaccgaagcacatctggaaattcgt<br>gaagatggcaccgttggtggtgcagcagatcagtctccggaaagcctgctgcag<br>ctgaaagcactgaaaccgggtgttattcagattctgggtgttaaaaccagccgt<br>tttctgtgtcagcgtccggatggtgcactgtatggtagcctgcattttgatccg<br>gaagcatgcagctttcgtgaactgctgctggaagatggctataatgtgtatcag<br>agcgaagcacatggtctgccgctgcatctgcctggtaataaatctccgcatcgt<br>gatccggcaccgcgtggtccggcacgtttcctgccgctgcctggtctgcctccg<br>gcactgccagaacctccgggtattctggcaccgcagcctccggatgttggtagc<br>agcgatccgctgtctatggttggtccgagccagggtcgtagcccgagctatgca<br>agcggtggtagcggtagcggttctggtagcggttcaggttctggttctggtgtt<br>tctgatgttccgcgtgatctggaagttgttgcagcaaccccgaccagcctgctg<br>attagctggcatagctattatgaacagaatagctattatcgcattacctatggt<br>gaaaccggtggtaattctccggttcaggaatttaccgttccgtatagccagacc<br>accgcaaccattagcggtctgaagcctggtgtggattataccattaccgtgtat<br>gcagtttatggcagcaaatattattatccgattagcattaattatcgcaccgaa<br>attgataaaccgagccagcatcatcatcaccatcat |
| 181 | 303 | SABA5-FGF21 | atgggtgtttctgatgttccgcgtgatctggaagttgttgcagcaaccccgacc<br>agcctgctgattagctgggaagatgatagctattatagccgctattatcgcatt<br>acctatggtgaaaccggtggtaattctccggttcaggaatttaccgttccgagc<br>gatctgtataccgcaaccattagcggtctgaaaccgggtgttgactataccatt<br>accgtttatgccgttacctatgacgttaccgatctgattatgcatgaaccgatc<br>agcattaattatcgcaccgagattgataaaccgagcggtggtagcggtagcggt<br>tctggtagcggttcaggttcaggtagcccgattccggatagctctccgctgctg<br>cagtttggtggtcaggttcgtcagcgttatctgtatactgatgatgcacagcag<br>accgaagcacatctggaaattcgtgaagatggcaccgttggtggtgcagcagat<br>cagtctccggaaagcctgctgcagctgaaagcactgaaacctggtgttattcag<br>attctgggtgttaaaaccagccgttttctgtgtcagcgtccggatggtgcactg<br>tatggtagcctgcattttgatccggaagcatgcagctttcgtgaactgctgctg<br>gaagatggctataatgtgtatcagagcgaagcacatggtctgccgctgcatctg<br>cctggtaataaatctccgcatcgtgatccggcaccgcgtggtccggcacgtttt<br>ctgccgctgcctggtctgcctccggcactgcctgaaccgcctggtattctggca<br>ccgcagcctccggatgttggtagcagcgatccgctgtctatggttggtccgagc<br>cagggtcgtagcccgagctatgcaagccatcatcatcatcaccattga |
| 182 | 184 | FGF21v5 | atgcatcatcatcatcaccatgatagctctccgctgctgcagtttggtggtcag<br>gttcgtcagcgttatctgtataccgatgatgcacagcagaccgaagcacatctg<br>gaaattcgtgaagatggcaccgttggtggtgcagcagatcagtctccggaaagc<br>ctgctgcagctgaaagcactgaaaccgggtgttattcagattctgggtgttaaa<br>accagccgttttctgtgtcagcgtccggatggtgcactgtatggtagcctgcat<br>tttgatccggaagcatgcagctttcgtgaactgctgctggaagatggctataat<br>gtgtatcagagcgaagcacatggcctgccgctgcatctgcctggtaataaatct<br>ccgcatcgtgatccggcaccgcgtggtccggcacgttttctgccgctgcctggt<br>ctgcctccggcactgcctgaaccgcctggtattctggcaccgcagcctccggat<br>gttggtagcagcgatccgctgtctatggttggtccgagccagggtcgtagcccg<br>agctatgcaagctga |
| 183 | 489 | FGF21-SABA1-FGF21v1 | atgcatcaccaccatcatcatattccggatagcagtccgctgctgcagtttggt<br>ggtcaggttcgtcagcgttatctgtataccgatgatgcacagcagaccgaagcc<br>catctggaaattcgtgaagatggcaccgttggtggtgcagcagatcagagtccg<br>gaaagcctgctgcagctgaaagcactgaaaccgggtgttattcagattctgggt<br>gttaaaaccagccgttttctgtgtcagcgtccggatggtgcactgtatggtagc<br>ctgcattttgatccggaagcatgtagctttcgtgaactgctgctggaagatggt<br>tataatgtttatcagagcgaagcacatggtctgccgctgcatctgcctggtaat |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | aaaagtccgcatcgtgatccggcaccgcgtggtccggcacgttttctgccgctg<br>cctggtctgcctccggcactgcctgaaccgcctggtattctggcaccgcagcct<br>ccggatgttggtagcagcgatccgctgagcatggttggtccgagccagggtcgt<br>agcccgagctatgcaagcggtagcggttcaggtagcggtagtggtagcggcagc<br>ggtagcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaacctggtgttgattataccatt<br>accgtgtatgcagtgtatggcagcaaatattattatccgattagcatcaattat<br>cgcaccgaaattgataaaccgagcggtggtagcggttctggttcaggttcaggt<br>agtggttctggtagtccggatagctcacctctgctgcagtttggtggccaggtg<br>cgccagcgctatctgtacacagatgatgcccagcagacagaagcccatctggaa<br>atccgcgaagatggtacagtgggtggcgctgccgatcagtcaccggaatcactg<br>ctgcagctgaaagccctgaaacctggcgtgatccagatcctgggcgtgaaaacc<br>tcacgctttctgtgccagcgtcctgatggcgctctgtatggctcactgcatttt<br>gatcctgaagcctgctcatttcgcgaactgctgctggaagatggctataacgtg<br>tatcagtctgaagcccatggcttacctctgcatctgccaggcaacaaatcacct<br>catcgtgatcctgcccctcgcggtcctgctcgctttctgccactgccaggcctg<br>cctccagccctgccagaacctccaggcatcctggcacctcagccacctgatgtg<br>ggttcaagtgatccgctgtcaatggtgggtccgtcacagggtcgtagtccgtct<br>tatgccagctga |
| 184 | 293 | SABA1-<br>FGF21v1 | atgggtgtttctgatgttccgcgtgatctggaagttgttgcagcaaccccgacc<br>agcctgctgattagctggcatagctattatgaacagaatagctattatcgcatt<br>acctatggtgaaaccggtggtaattctccggttcaggaatttaccgttccgtat<br>agccagaccaccgcaaccattagcggtctgaaaccgggtgttgattataccatt<br>accgtgtatgcagtgtatggcagcaaatattattatccgattagcattaattat<br>cgcaccgaaattgaaaaaccgagccagggtagcggtagcggttcaggtagcggt<br>tctggttctggtagcccgattccggatagctctccgctgctgcagtttggtggt<br>caggttcgtcagcgttatctgtataccgatgatgcacagcagaccgaagcacat<br>ctggaaattcgtgaagatggcaccgttggtggtgcagcagatcagtctccggaa<br>agcctgctgcagctgaaagcactgaagccaggtgttattcagattctgggtgtt<br>aaaaccagccgttttctgtgtcagcgtccggatggtgcactgtatggtagcctg<br>cattttgatccggaagcatgcagctttcgtgaactgctgctggaagatggctat<br>aatgtgtatcagagcgaagcacatggtctgccgctgcatttacctggtaataaa<br>tctccgcatcgtgatccggcaccgcgtggtccggcacgtttcctgcctctgcct<br>ggtctgcctccggcactgccagaacctccgggtattctggcaccgcagcctccg<br>gatgttggtagcagcgatccgctgtctatggttggtccgagccagggtcgtagc<br>ccgagctatgcaagctga |
| 185 | 283 | SABA1-<br>FGF21v9 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtggtagcggtagcggttcaggtagcccgattccggatagc<br>agtccgctgctgcagtttggtggtcaggttcgtcagcgttatctgtataccgat<br>gatgcacagcagaccgaagcacatctggaaattcgtgaagatggcaccgttggt<br>ggtgcagcagatcagagtccggaaagcctgctgcagctgaaagcactgaaacct<br>ggtgttattcagattctgggtgttaaaaccagccgttttctgtgtcagcgtccg<br>gatggtgcactgtatggtagcctgcattttgatccggaagcatgtagctttcgt<br>gaactgctgctggaagatggttataatgtttatcagagcgaagctcatggtctg<br>ccgctgcatctgcctggtaataaaagtccgcatcgtgatccggcaccgcgtggt<br>ccggcacgttttctgcctctgcctggtttacctccggcactgcctgaaccgcct<br>ggtattctggcaccgcagcctccggatgttggtagcagcgatccgctgagcatg<br>gttggtccgagccagggtcgtagcccgagctatgcaagctga |
| 186 | 279 | SABA1-<br>FGF21v10 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtggtagcggtagcccgattccggatagcagtccgctgctg<br>cagtttggtggtcaggttcgtcagcgttatctgtataccgatgatgcacagcag<br>accgaagcacatctggaaattcgtgaagatggcaccgttggtggtgcagcagat<br>cagagtccggaaagcctgctgcagctgaaagcactgaaacctggcgttattcag<br>attctgggtgttaaaaccagccgttttctgtgtcagcgtccggatggtgcactg<br>tatggtagcctgcattttgatccggaagcatgtagctttcgtgaactgctgctg<br>gaagatggttataatgtttatcagagcgaagctcatggtctgccgctgcatctg<br>cctggtaataaaagtccgcatcgtgatccggcaccgcgtggtccggcacgtttt<br>ctgcctctgcctggtttacctccggcactgcctgaaccgcctggtattctggca<br>ccgcagcctccggatgttggtagcagcgatccgctgagcatggttggtccgagc<br>cagggtcgtagcccgagctatgcaagctga |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| 187 | 274 | SABA1-FGF21v11 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattacaccatt<br>accgtttatgcggtgtatggcagcaaatattattatccgattagcatcaattat<br>cgcaccgaaatcccgattccggatagcagtccgctgctgcagtttggtggtcag<br>gttcgtcagcgttatctgtataccgatgatgcacagcagaccgaagcacatctg<br>gaaattcgtgaagatggcaccgttggtggtgcagcagatcagagtccggaaagc<br>ctgctgcagctgaaagcactgaaacctggtgttattcagattctgggtgttaaa<br>accagccgttttctgtgtcagcgtccggatggtgcactgtatggtagcctgcat<br>tttgatccggaagcatgtagctttcgtgaactgctgctggaagatggttataat<br>gtttatcagagcgaagctcatggtctgccgctgcatctgcctggtaataaaagt<br>ccgcatcgtgatccggcaccgcgtggtccggcacgttttctgcctctgcctggt<br>ttacctccggcactgcctgaaccgcctggtattctggcaccgcagcctccggat<br>gttggtagcagcgatccgctgagcatggttggtccgagccagggtcgtagcccg<br>agctatgcaagctga |
| 188 | 288 | SABA1-FGF21v12 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatccatcaccaccatcatcatggtagcggtagcggttcaggtagc<br>ccgattccggatagcagtccgctgctgcagtttggtggtcaggttcgtcagcgt<br>tatctgtataccgatgatgcacagcagaccgaagcacatctggaaattcgtgaa<br>gatggcaccgttggtggtgcagcagatcagagtccggaaagcctgctgcagctg<br>aaagcactgaaacctggtgttattcagattctgggtgttaaaaccagccgtttt<br>ctgtgtcagcgtccggatggtgcactgtatggtagcctgcattttgatccggaa<br>gcatgtagctttcgtgaactgctgctggaagatggttataatgtttatcagagc<br>gaagctcatggtctgccgctgcatctgcctggtaataaaagtccgcatcgtgat<br>ccggcaccgcgtggtccggcacgttttctgcctctgcctggtttacctccggca<br>ctgcctgaaccgcctggtattctggcaccgcagcctccggatgttggtagcagc<br>gatccgctgagcatggttggtccgagccagggtcgtagcccgagctatgcaagc<br>tga |
| 189 | 284 | SABA1-FGF21v13 | atgggcgttagtgatgttccgcgtgacctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatccatcaccaccatcaccatggtagcggtagcccgattccggat<br>agcagtccgctgctgcagtttggtggtcaggttcgtcagcgttatctgtatacc<br>gatgatgcacagcagaccgaagcacatctggaaattcgtgaagatggcaccgtt<br>ggtggtgcagcagatcagagtccggaaagcctgctgcagctgaaagcactgaaa<br>cctggtgttattcagattctgggtgttaaaaccagccgttttctgtgtcagcgt<br>ccggatggtgcactgtatggtagcctgcattttgatccggaagcatgtagcttt<br>cgtgaactgctgctggaagatggttataatgtttatcagagcgaagctcatggt<br>ctgccgctgcatctgcctggtaataaaagtccgcatcgtgatccggcaccgcgt<br>ggtccggcacgttttctgcctctgcctggtttacctccggcactgcctgaaccg<br>cctggtattctggcaccgcagcctccggatgttggtagcagcgatccgctgagc<br>atggttggtccgagccagggtcgtagcccgagctatgcaagctga |
| 190 | 280 | SABA1-FGF21v14 | atgggcgttagtgatgttccgcgtgatctggaagttgctgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattacaccatt<br>accgtttatgcggtgtatggcagcaaatattattatccgattagcatcaattat<br>cgcaccgaaatccatcaccaccatcatcatccgattccggatagcagtccgctg<br>ctgcagtttggtggtcaggttcgtcagcgttatctgtataccgatgatgcacag<br>cagaccgaagcacatctggaaattcgtgaagatggcaccgttggtggtgcagca<br>gatcagagtccggaaagcctgctgcagctgaaagcactgaaacctggtgttatt<br>cagattctgggtgttaaaaccagccgttttctgtgtcagcgtccggatggtgca<br>ctgtatggtagcctgcattttgatccggaagcatgtagctttcgtgaactgctg<br>ctggaagatggttataatgtttatcagagcgaagctcatggtctgccgctgcat<br>ctgcctggtaataaaagtccgcatcgtgatccggcaccgcgtggtccggcacgt<br>tttctgcctctgcctggtttacctccggcactgcctgaaccgcctggtattctg<br>gcaccgcagcctccggatgttggtagcagcgatccgctgagcatggttggtccg<br>agccagggtcgtagcccgagctatgcaagctga |
| 191 | 284 | SABA1-FGF21v15 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | cgcaccgaaatcgaagatgaagatgaggacgaagatgaggatccgattccggat<br>agcagtccgctgctgcagtttggtggtcaggttcgtcagcgttatctgtatacc<br>gatgatgcacagcagaccgaagcacatctggaaattcgtgaagatggcaccgtt<br>ggtggtgcagcagatcagagtccggaaagcctgctgcagctgaaagcactgaaa<br>cctggtgttattcagattctgggtgttaaaaccagccgttttctgtgtcagcgt<br>ccggatggtgcactgtatggtagcctgcattttgatccggaagcatgtagcttt<br>cgtgaactgctgctggaagatggttataatgtttatcagagcgaagctcatggt<br>ctgccgctgcatctgcctggtaataaaagtccgcatcgtgatccggcaccgcgt<br>ggtccggcacgttttctgcctctgcctggtttacctccggcactgcctgaaccg<br>cctggtattctggcaccgcagcctccggatgtcggtagcagcgatccgctgagc<br>atggttggtccgagccagggtcgtagcccgagctatgcaagctga |
| 192 | 292 | SABA1-FGF21v16 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattacaccact<br>accgtttatgcggtgtatggcagcaaatattattatccgattagcatcaattat<br>cgcaccgaaatcgaagatgaagatgaggacgaagatgaggatggtagcggtagc<br>ggttcaggtagcccgattccggatagcagtccgctgccgcagcttggcggtcag<br>gttcgtcagcgttatctgtataccgatgatgcacagcagaccgaagcacatctg<br>gaaattcgtgaagatggcaccgttggtggtgcagcagatcagagtccggaaagc<br>ctgctgcagctgaaagcactgaaacctggtgttattcagattctgggtgttaaa<br>accagccgttttctgtgtcagcgtccggatggtgcactgtatggtagcctgcat<br>tttgatccggaagcatgtagctttcgtgaactgctgctggaagatggttataat<br>gtttatcagagcgaagctcatggtctgccgctgcatctgcctggtaataaaagt<br>ccgcatcgtgatccggcaccgcgtggtccggcacgttttctgcctctgcctggt<br>ttacctccggcactgcctgaaccgcctggtattctggcaccgcagcctccggat<br>gttggtagcagcgatccgctgagcatggttggtccgagccagggtcgtagcccg<br>agctatgcaagctga |
| 193 | 287 | SABA1-FGF21v17 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtagcgcagcagcagcagccgctgcagcagccggtagcccg<br>attccggatagcagtccgctgctgcagtttggtggtcaggttcgtcagcgttat<br>ctgtataccgatgatgcacagcagaccgaagcacatctggaaattcgtgaagat<br>ggcaccgttggtggtgcagcagatcagagtccggaaagcctgctgcagctgaaa<br>gcactgaaacctggtgttattcagattctgggtgttaaaaccagccgttttctg<br>tgtcagcgtccggatggtgcactgtatggtagcctgcattttgatccggaagca<br>tgtagctttcgtgaactgctgctggaagatggttataatgtttatcagagcgaa<br>gctcatggtctgccgctgcatctgcctggtaataaaagtccgcatcgtgatccg<br>gcaccgcgtggtccggcacgttttctgcctctgcctggtttacctccggcactg<br>cctgaaccgcctggtattctggcaccgcagcctccggatgttggtagcagcgat<br>ccgctgagcatggttggtccgagccagggtcgtagcccgagctatgcaagctga |
| 194 | 289 | SABA1-FGF21v18 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtagtgaaggtagcgaaggttcagaaggttctgaaggcagc<br>gaaccgattccggatagcagtccgctgctgcagtttggtggtcaggttcgtcag<br>cgttatctgtataccgatgatgcacagcagaccgaagcacatctggaaattcgt<br>gaagatggcaccgttggtggtgcagcagatcagagtccggaaagcctgctgcag<br>ctgaaagcactgaaacctggtgttattcagattctgggtgttaaaaccagccgt<br>tttctgtgtcagcgtccggatggtgcactgtatggtagcctgcattttgatccg<br>gaagcatgcagctttcgtgaactgctgctggaagatggttataatgtttatcag<br>agcgaagctcatggtctgccgctgcatctgcctggtaataaaagtccgcatcgt<br>gatccggcaccgcgtggtccggcacgttttctgcctctgcctggtttacctccg<br>gcactgcctgaaccgcctggtattctggcaccgcagcctccggatgttggtagc<br>agcgatccgctgagcatggttggtccgagccagggtcgtagcccgagctatgca<br>agctga |
| 195 | 289 | SABA1-FGF21v19 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatccctgcaagtccggcatcaccggcaagtccggctagtccggca<br>agcccgattccggatagcagtccgctgctgcagtttggtggtcaggttcgtcag<br>cgttatctgtataccgatgatgcacagcagaccgaagcacatctggaaattcgt<br>gaagatggcaccgttggtggtgcagcagatcagagtccggaaagcctgctgcag |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | ctgaaagcactgaaacctggtgttattcagattctgggtgttaaaaccagccgt<br>tttctgtgtcagcgtccggatggtgcactgtatggtagcctgcattttgatccg<br>gaagcatgtagctttcgtgaactgctgctggaagatggttataatgtttatcag<br>agcgaagctcatggtctgccgctgcacctgcctggtaataaaagtccgcatcgt<br>gatccggcaccgcgtggtccggcacgttttctgcctctgcctggtttacctccg<br>gcactgcctgaaccgcctggtattctggcaccgcagcctccggatgttggtagc<br>agcgatccgctgagcatggttggtccgagccagggtcgtagcccgagctatgca<br>agctga |
| 196 | 289 | SABA1-FGF21v20 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtagtccgggttcaccgggtagccctggttctccgggtagt<br>cctccgattccggatagcagtccgctgctgcagtttggtggtcaggttcgtcag<br>cgttatctgtataccgatgatgcacagcagaccgaagcacatctggaaattcgt<br>gaagatggcaccgttggtggtgcagcagatcagagtccggaaagcctgctgcag<br>ctgaaagcactgaaacctggtgttattcagattctgggtgttaaaaccagccgt<br>tttctgtgtcagcgtccggatggtgcactgtatggtagcctgcattttgatccg<br>gaagcatgtagctttcgtgaactgctgctggaagatggttataatgtttatcag<br>agcgaagctcatggtctgccgctgcatctgcctggtaataaaagtccgcatcgt<br>gatccggcaccgcgtggtccggcacgttttctgcctctgcctggtttacctccg<br>gcactgcctgaaccgcctggtattctggcaccgcagcctccggatgttggtagc<br>agcgatccgctgagcatggttggtccgagccagggtcgtagcccgagctatgca<br>agctga |
| 197 | 288 | SABA1-FGF21v21 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtagcaccgttgcagcaccgagcaccgttgccgctccgtca<br>ccgattccggatagcagtccgctgctgcagtttggtggtcaggttcgtcagcgt<br>tatctgtataccgatgatgcacagcagaccgaagcacatctggaaattcgtgaa<br>gatggcaccgttggtggtgcagcagatcagagtccggaaagcctgctgcagctg<br>aaagcactgaaacctggtgttattcagattctgggtgttaaaaccagccgtttt<br>ctgtgtcagcgtccggatggtgcactgtatggtagcctgcattttgatccggaa<br>gcatgtagctttcgtgaactgctgctggaagatggttataatgtttatcagagc<br>gaagctcatggtctgccgctgcatctgcctggtaataaaagtccgcatcgtgat<br>ccggcaccgcgtggtccggcacgttttctgcctctgcctggtttacctccggca<br>ctgcctgaaccgcctggtattctggcaccgcagcctccggatgttggtagcagc<br>gatccgctgagcatggttggtccgagccagggtcgtagcccgagctatgcaagc<br>tga |
| 198 | 282 | SABA1-FGF21v22 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcggtggtagcgaaggtggtagtgaaccgattccggatagcagt<br>ccgctgctgcagtttggtggtcaggttcgtcagcgttatctgtataccgatgat<br>gcacagcagaccgaagcacatctggaaattcgtgaagatggcaccgttggtggt<br>gcagcagatcagagtccggaaagcctgctgcagctgaaagcactgaaacctggt<br>gttattcagattctgggtgttaaaaccagccgttttctgtgtcagcgtccggat<br>ggtgcactgtatggtagcctgcattttgatccggaagcatgtagctttcgtgaa<br>ctgctgctggaagatggttataatgtttatcagagcgaagctcatggtctgccg<br>ctgcatctgcctggtaataaaagtccgcatcgtgatccggcaccgcgtggtccg<br>gcacgttttctgcctctgcctggtttacctccggcactgcctgaaccgcctggt<br>attctggcaccgcagcctccggatgttggtagcagcgatccgctgagcatggtt<br>ggtccgagccagggtcgtagcccgagctatgcaagctga |
| 199 | 281 | SABA1-FGF21v23 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcagcaccagcaccagtaccggtccgattccggatagcagtccg<br>ctgctgcagtttggtggtcaggttcgtcagcgttatctgtataccgatgatgca<br>cagcagaccgaagcacatctggaaattcgtgaagatggcaccgttggtggtgca<br>gcagatcagagtccggaaagcctgctgcagctgaaagcactgaaacctggtgtt<br>attcagattctgggtgttaaaaccagccgttttctgtgtcagcgtccggatggt<br>gcactgtatggtagcctgcattttgatccggaagcatgtagctttcgtgaactg<br>ctgctggaagatggttataatgtttatcagagcgaagctcatggtctgccgctg |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | catctgcctggtaataaaagtccgcatcgtgatccggcaccgcgtggtccggca<br>cgttttctgcctctgcctggtttacctccggcactgcctgaaccgcctggtatt<br>ctggcaccgcagcctccggatgttggtagcagcgatccgctgagcatggttggt<br>ccgagccagggtcgtagcccgagctatgcaagctga |
| 200 | 288 | SABA1-FGF21v24 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggcgtatggcagcaaatattattatccgatcagcatcaattat<br>cgcaccgaaatcgaaaaaccgagccaaggtggtagcggtagcggttcaggtagc<br>ccgattccggatagcagtccgctgctgcagtttggtggtcaggttcgtcagcgt<br>tatctgtataccgatgatgcacagcagaccgaagcacatctggaaattcgtgaa<br>gatggcaccgttggtggtgcagcagatcagagtccggaaagcctgctgcagctg<br>aaagcactgaaacctggtgttattcagattctgggtgttaaaaccagccgtttt<br>ctgtgtcagcgtccggatggtgcactgtatggtagcctgcattttgatccggaa<br>gcatgtagctttcgtgaactgctgctggaagatggttataatgtttatcagagc<br>gaagctcatggtctgccgctgcatctgcctggtaataaaagtccgcatcgtgat<br>ccggcaccgcgtggtccggcacgttttctgcctctgcctggtttacctccggca<br>ctgcctgaaccgcctggtattctggcaccgcagcctccggatgttggtagcagc<br>gatccgctgagcatggttggtccgagccagggtcgtagcccgagctatgcaagc<br>tga |
| 201 | 284 | SABA1-FGF21v25 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcgaaaaaccgagccaaggtggttcaggtagcccgattccggat<br>agcagtccgctgctgcagtttggtggtcaggttcgtcagcgttatctgtatacc<br>gatgatgcacagcagaccgaagcacatctggaaattcgtgaagatggcaccgtt<br>ggtggtgcagcagatcagagtccggaaagcctgctgcagctgaaagcactgaaa<br>cctggtgttattcagattctgggtgttaaaaccagccgttttctgtgtcagcgt<br>ccggatggtgcactgtatggtagcctgcattttgatccggaagcatgtagcttt<br>cgtgaactgctgctggaagatggttataatgtttatcagagcgaagctcatggt<br>ccgccgctgcatctgcctggtaataaaagcccgcatcgtgatccggcaccgcgt<br>ggtccggcacgttttctgcctctgcctggtttacctccggcactgcctgaaccg<br>cctggtattctggcaccgcagcctccggatgttggtagcagcgatccgccgagc<br>atggttggtccgagccagggtcgtagcccgagctatgcaagctga |
| 202 | 279 | SABA1-FGF21v26 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgattagcatcaattat<br>cgcaccgaaatcgaaaaaccgagccaaccgattccggatagcagtccgctgctg<br>cagtttggtggtcaggttcgtcagcgttatctgtataccgatgatgcacagcag<br>accgaagcacacctggaaattcgtgaagacggcaccgttggtggtgcagcagat<br>cagagtccggaaagcctgctgcagctgaaagcactgaaacctggtgttattcag<br>attctgggtgttaaaaccagccgttttctgtgtcagcgtccggatggtgcactg<br>tatggtagcctgcattttgatccggaagcatgtagctttcgtgaactgctgctg<br>gaagatggttataatgtttatcagagcgaagctcatggtctgccgctgcatctg<br>cctggtaataaaagtccgcatcgtgatccggcaccgcgtggtccggcacgtttt<br>ctgcctctgcctggtttacctccggcactgcctgaaccgcctggtattctggca<br>ccgcagcctccggatgttggtagcagcgatccgctgagcatggttggtccgagc<br>cagggtcgtagcccgagctatgcaagctga |
| 203 | 293 | SABA1-FGF21v27 | atgggcgttagtgatgttccgcgtgatctggaagttgttgcagcaaccccgacc<br>agcctgctgattagctggcatagctattatgaacagaatagctattatcgcatt<br>acctatggtgaaaccggtggtaatagtccggttcaggaatttaccgttccgtat<br>agccagaccaccgcaaccattagcggtctgaaaccgggtgttgattataccatt<br>accgtttatgcggtgtatggcagcaaatattattatccgatcagcatcaattat<br>cgcaccgaaatcgaaaaaccgagccaacatcaccaccatcatcatggcagcggt<br>agcggttcaggtagcccgattccggatagcagtccgctgctgcagtttggtggt<br>caggttcgtcagcgttatctgtataccgatgatgcacagcagaccgaagcacat<br>ctggaaattcgtgaagatggcaccgttggtggtgcagcagatcagagtccggaa<br>agcctgctgcagctgaaagcactgaaacctggtgttattcagattctgggtgtt<br>aaaaccagccgttttctgtgtcagcgtccggatggtgcactgtatggtagcctg<br>cattttgatccggaagcatgtagctttcgtgaactgctgctggaagatggttat<br>aatgtttatcagagcgaagctcatggtctgccgctgcatctgcctggtaataaa<br>agtccgcatcgtgatccggcaccgcgtggtccggcacgttttctgcctctgcct<br>ggtttacctccggcactgcctgaaccgcctggtattctggcaccgcagcctccg<br>gatgttggtagcagcgatccgctgagcatggttggtccgagccagggtcgtagc<br>ccgagctatgcaagctga |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| 204 | 289 | SABA1-FGF21v28 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaacatcaccaccatcatcatggttcaggt agcccgattccggatagcagtccgctgctgcagtttggtggtcaggttcgtcag cgttatctgtataccgatgatgcacagcagaccgaagcacatctggaaattcgt gaagatggcaccgttggtggtgcagcagatcagagtccggaaagcctgctgcag ctgaaagcactgaaacctggtgttattcagattctgggtgttaaaaccagccgt tttctgtgtcagcgtccggatggtgcactgtatggtagcctgcattctgatccg gaagcatgtagctttcgtgaactgctgctggaagatggttataatgtttatcag agcgaagctcatggtctgccgctgcatctgcctggtaataaaagtccgcatcgt gatccggcaccgcgtggtccggcacgttttctgcctctgcctggtttacctccg gcactgcctgaaccgcctggtattctggcaccgcagcctccggatgttggtagc agcgatccgctgagcatggttggtccgagccagggtcgtagcccgagctatgca agctga |
| 205 | 285 | SABA1-FGF21v29 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaacatcaccaccatcatcatccgattccg gatagcagtccgctgctgcagtttggtggtcaggttcgtcagcgttatctgtat accgatgatgcacagcagaccgaagcacatctggaaattcgtgaagatggcacc gttggtggtgcagcagatcagagtccggaaagcctgctgcagctgaaagcactg aaacctggtgttattcagattctgggtgttaaaaccagccgttttctgtgtcag cgtccggatggtgcactgtatggtagcctgcattttgatccggaagcatgtagc tttcgtgaactgctgctggaagatggttataatgtttatcagagcgaagctcat ggtctgccgctgcatctgcctggtaataaaagtccgcatcgtgatccggcaccg cgtggtccggcacgttttctgcctctgcctggtttacctccggcactgcctgaa ccgcctggtattctggcaccgcagcctccggatgttggtagcagcgatccgctg agcatggttggtccgagccagggtcgtagcccgagctatgcaagctga |
| 206 | 289 | SABA1-FGF21v30 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggcctgaaaccgggtgttgattataccatt accgtttatgcggtgtatggcagcaaatattattatccgattagcatcaattat cgcaccgaaatcgaaaaaccgagccaagaagatgaggacgaggacgaagatgag gatccgattccggatagcagtccgctgctgcagtttggtggtcaggttcgtcag cgttatctgtataccgatgatgcacagcagaccgaagcacatctggaaattcgt gaagatggcaccgctggtggtgcagcagatcagagtccggaaagcctgccgcag ctgaaagcactgaaacctggtgttattcagattctgggtgttaaaaccagccgt tttctgtgtcagcgtccggatggtgcactgtatggtagcctgcattttgatccg gaagcatgtagctttcgtgaactgctgctggaagatggttataatgtttatcag agcgaagctcatggtctgccgctgcatctgcctggtaataaaagtccgcatcgt gatccggcaccgcgtggtccggcacgttttctgcctctgcctggtttacctccg gcactgcctgaaccgcctggtattctggcaccgcagcctccggatgttggtagc agcgatccgctgagcatggttggtccgagccagggtcgtagcccgagctatgca agctga |
| 207 | 297 | SABA1-FGF21v31 | atgggcgtcagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaagaagatgaggacgaggacgaagatgag gatggtagcggtagcggttcaggtagcccgattccggatagcagtccgctgctg cagtttggtggtcaggttcgtcagcgttatctgtataccgatgatgcacagcag accgaagcacatctggaaattcgtgaagatggcaccgttggtggtgcagcagat cagagtccggaaagcctgctgcagctgaaagcactgaaacctggtgttattcag attctgggtgttaaaaccagccgttttctgtgtcagcgtccggatggtgcactg tatggtagcctgcattttgatccggaagcatgtagctttcgtgaactgctgctg gaagatggttataatgtttatcagagcgaagctcatggtctgccgctgcatctg cctggtaataaaagtccgcatcgtgatccggcaccgcgtggtccggcacgtttt ctgcctctgcctggtttacctccggcactgcctgaaccgcctggtattctggca ccgcagcctccggatgttggtagcagcgatccgctgagcatggttggtccgagc cagggtcgtagcccgagctatgcaagctga |
| 208 | 292 | SABA1-FGF21v32 | atgggcgttagtgatgttccgcgtgatctggaagttgttgcagcaaccccgacc agcctgctgattagctggcatagctattatgaacagaatagctattatcgcatt |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaaggtagcgcagcagcagcagccgctgca gcagccggtagcccgattccggatagcagtccgctgctgcagtttggtggtcag gttcgtcagcgttatctgtataccgatgatgcacagcagaccgaagcacatctg gaaattcgtgaagatggcaccgttggtggtgcagcagatcagagtccggaaagc ctgctgcagctgaaagcactgaaacctggtgttattcagattctgggtgctaaa accagccgttttctgtgtcagcgtccggatggtgcactgtatggtagcctgcat tttgatccggaagcatgtagctttcgtgaactgctgctggaagatggttataat gtttatcagagcgaagctcatggtctgccgctgcatctgcctggtaataaaagt ccgcatcgtgatccggcaccgcgtggtccggcacgttttctgcctctgcctggt ttacctccggcactgcctgaaccgcctggtattctggcaccgcagcctccggat gttggtagcagcgatccgctgagcatggttggtccgagccagggtcgtagcccg agctatgcaagctga |
| 209 | 294 | SABA1-FGF21v33 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaaggtagcgaaggtagtgaaggttcagaa ggttctgaaggtagcgaaccgattccggatagcagtccgctgctgcagtttggt ggtcaggttcgtcagcgttatctgtataccgatgatgcacagcagaccgaagca catctggaaattcgtgaagatggcaccgttggtggtgcagcagatcagagtccg gaaagcctgctgcagctgaaagcactgaaacctggtgttattcagattctgggt gttaaaaccagccgttttctgtgtcagcgtccggatggtgcactgtatggtagc ctgcattttgatccggaagcatgtagctttcgtgaactgctgctggaagatggt tataatgtttatcagagcgaagctcatggtctgccgctgcatctgcctggtaat aaaagtccgcatcgtgatccggcaccgcgtggtccggcacgttttctgcctctg cctggtttacctccggcactgcctgaaccgcctggtattctggcaccgcagcct ccggatgttggtagcagcgatccgctgagcatggttggtccgagccagggtcgt agcccgagctatgcaagctga |
| 210 | 294 | SABA1-FGF21v34 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaaccggcaagtccggcatcaccggcatct ccggctagtccggcaagcccgattccggatagcagtccgctgctgcagtttggt ggtcaggttcgtcagcgttatctgtataccgatgatgcacagcagaccgaagca catctggaaattcgtgaagatggcaccgttggtggtgcagcagatcagagtccg gaaagcctgctgcagctgaaagcactgaaacctggtgttattcagattctgggt gttaaaaccagccgttttctgtgtcagcgtccggatggtgcactgtatggtagc ctgcattttgatccggaagcatgtagctttcgtgaactgctgctggaagatggt tataatgtttatcagagcgaagctcatggtctgccgctgcatctgcctggtaat aaaagtccgcatcgtgatccggcaccgcgtggtccggcacgttttctgcctctg cctggtttacctccggcactgcctgaaccgcctggtattctggcaccgcagcct ccggatgttggtagcagcgatccgctgagcatggttggtccgagccagggtcgt agcccgagctatgcaagctga |
| 211 | 294 | SABA1-FGF21v35 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaaggtagccctggtagtccgggttcaccg ggttctccgggtagccctccgattccggatagcagtccgctgctgcagtttggt ggtcaggttcgtcagcgttatctgtataccgatgatgcacagcagaccgaagca catctggaaattcgtgaagatggcaccgttggtggtgcagcagatcagagtccg gaaagcctgctgcagctgaaagcactgaaacctggtgttattcagattctgggt gttaaaaccagccgttttctgtgtcagcgtccggatggtgcactgtatggtagc ctgcattttgatccggaagcatgtagctttcgtgaactgctgctggaagatggt tataatgtttatcagagcgaagctcatggtctgccgctgcatctgcctggtaat aaaagtccgcatcgtgatccggcaccgcgtggtccggcacgttttctgcctctg cctggtttacctccggcactgcctgaaccgcctggtattctggcaccgcagcct ccggatgttggtagcagcgatccgctgagcatggttggtccgagccagggtcgt agcccgagctatgcaagctga |
| 212 | 293 | SABA1-FGF21v36 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | accgtttatgcggtgtatggcagcaaatattattatccgattagcatcaattat cgcaccgaaatcgaaaaaccgagccaaggtagcaccgttgcagcaccgagcacc gcggcagcccctagcccgattccggacagcagtccgctgctgcagtttggtggt caggttcgtcagcgttatctgtataccgatgatgcacagcagaccgaagcacat ctggaaattcgtgaagatggcaccgttggtggtgcagcagatcagagtccggaa agcccgctgcagctgaaagcactgaaacctggtgttattcagattctgggtgtt aaaaccagccgttctctgcgtcagcgtccggatggtgcactgtatggtagcctg catcttgatccggaagcatgtagctttcgtgaactgctgctggaagatggttat aatgtttatcagagcgaagctcatggtctgccgctgcatctgcctggtaataaa agtccgcatcgtgatccggcaccgcgtggtccggcacgttttctgcctctgcct ggtctacctccggcactgcctgaaccgcctggtattctggcaccgcagcctccg gatgttggtagcagcgatccgctgagcatggttggtccgagccagggtcgtagc ccgagctatgcaagctga |
| 213 | 287 | SABA1-FGF21v37 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattacaccatt accgtttatgcggtgtatggcagcaaatattattatccgattagcatcaattat cgcaccgaaatcgaaaaaccgagccaaggtggtagcgaaggtggtagtgaaccg attccggatagcagtccgctgctgcagtttggtggtcaggttcgtcagcgttat ctgtataccgatgatgcacagcagaccgaagcacatctggaaattcgtgaagat ggcaccgttggtggtgcagcagatcagagtccggaaagcctgctgcagctgaaa gcactgaaacctggtgttattcagattctgggtgttaaaaccagccgttttctg tgtcagcgtccggatggtgcactgtatggtagcctgcattttgatccggaagca tgtagctttcgtgaactgctgctggaagatggttataatgtttatcagagcgaa gctcatggtctgccgctgcatctgcctggtaataaaagtccgcatcgtgatccg gcaccgcgtggtccggcacgttttctgcctctgcctggtttacctccggcactg cctgaaccgcctggtattctggcaccgcagcctccggatgttggtagcagcgat ccgctgagcatggttggtccgagccagggtcgtagcccgagctatgcaagctga |
| 214 | 286 | SABA1-FGF21v38 | atgggcgttagtgatgttccgcgtgatctggaagttgttgcagcaaccccgacc agcctgctgattagctggcatagctattatgaacagaatagctattatcgcatt acctatggtgaaaccggtggtaatagtccggttcaggaatttaccgttccgtat agccagaccaccgcaaccattagcggtctgaaaccgggtgttgattataccatt accgtttatgcggtgtatggcagcaaatattattatccgattagcatcaattat cgcaccgaaatcgaaaaaccgagccaaagcaccagcaccagtaccggtccgatt ccggatagcagtccgctgctgcagtttggtggtcaggttcgtcagcgttatctg tataccgatgatgcacagcagaccgaagcacatctggaaattcgtgaagatggc accgttggtggtgcagcagatcagagtccggaaagcctgctgcagctgaaagca ctgaaacctggtgttattcagattctgggtgctaaaaccagccgttttccgtgt cagcgtccggatggtgcactgtatggtagcctgcattttgatccggaagcatgt agctttcgtgaactgctgctggaagatggttataatgtttatcagagcgaagct catggtctgccgctgcatctgcctggtaataaaagtccgcatcgtgatccggca ccgcgtggtccggcacgttttctgcctctgcctggtttacctccggcactgcct gaaccgcctggtattctggcaccgcagcctccggatgttggtagcagcgatccg ctgagcatggttggtccgagccagggtcgtagcccgagctatgcaagctga |
| 397 | 187 | FGF21v1 | atgcatcatcatcatcaccatccgattccggatagcagcccgctgctgcagttt ggcggccaggtgcgtcagcgttatctgtataccgatgatgcgcagcagaccgaa gcgcatctggaaattcgtgaagatggcaccgtgggcggtgcggcggatcagagc ccggaaagcctgctgcagctgaaagcgctgaaaccgggcgtgattcagattctg ggcgtgaaaaccagccgttttctgtgccagcgtccggatggcgcgctgtatggc agcctgcattttgatccggaagcgtgcagctttcgtgaactgctgctggaagat ggctataacgtgtatcagagcgaagcgcatggcctgccgctgcatctgccgggc aacaaaagcccgcatcgtgatccggcaccgcgtggtccggcacgttttctgccg ctgccgggtctgccgccagcactgccggaaccgccgggtattctggcaccgcag ccgccggatgttggtagcagcgatccgctgtctatggtgggtccgagccagggt cgtagcccgagctatgcgagctaataa |
| 398 | 187 | FGF21v2 | atgcatccgattccggatagcagcccgctgctgcagtttggcggccaggtgcgt cagcgttatctgtataccgatgatgcgcagcagaccgaagcgcatctggaaatt cgtgaagatggcaccgtgggcggtgcggcggatcagagcccggaaagcctgctg cagctgaaagcgctgaaaccgggcgtgattcagattctgggcgtgaaaaccagc cgttttctgtgccagcgtccggatggcgcgctgtatggcagcctgcattttgat ccggaagcgtgcagctttcgtgaactgctgctggaagatggctataacgtgtat cagagcgaagcgcatggcctgccgctgcatctgccgggcaacaaaagcccgcat cgtgatccggcaccgcgtggtccggcacgttttctgccgctgccgggtctgccg ccagcactgccggaaccgccgggtattctggcaccgcagccgccggatgttggt agcagcgatccgctgtctatggtgggtccgagccagggtcgtagcccgagctat gcgcatcatcatcatcaccattaataa |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| 399 | 188 | FGF21v3 | atgcatccgattccggatagcagcccgctgctgcagtttggcggccaggtgcgt cagcgttatctgtataccgatgatgcgcagcagaccgaagcgcatctggaaatt cgtgaagatggcaccgtgggcggtgcggcggatcagagcccggaaagcccgctg cagctgaaagcgctgaaaccgggcgtgattcagattccgggcgtgaaaaccagc cgttttctgtgccagcgtccggatggcgcgctgtatggcagcctgcattttgat ccggaagcgtgcagctttcgtgaactgctgctggaagatggctataacgtgtat cagagcgaagcgcatggcctgccgctgcatctgccgggcaacaaaagcccgcat cgtgatccggcaccgcgtggtccggcacgttttctgccgctgccgggtctgccg ccagcactgccggaaccgccgggtattctggcaccgcagccgccggatgttggt agcagcgatccgctgtctatggtgggtccgagccagggtcgtagcccgagctat gcgagccatcatcatcatcaccattaataa |
| 400 | 186 | FGF21v4 | atgcatcatcatcatcaccatccgattccggatagcagcccgctgctgcagttt ggcggccaggtgcgtcagcgttatctgtacaccgatgatgcgcagcagaccgaa gcgcatctggaaattcgtgaagatggcaccgtgggcggtgcggcggatcagagc ccggaaagcctgctgcagctgaaagcgctgaaaccgggcgtgattcagattctg ggcgtgaaaaccagccgttttctgtgccagcgtccggatggcgcgctgtatggc agcctgcattttgatccggaagcgtgcagctttcgtgaactgctgctggaagat ggctataacgtgtatcagagcgaagcgcatggcctgccgctgcatctgccgggc aacaaaagcccgcatcgtgatccggcaccgcgtggtccggcacgttttctgccg ctgccgggtctgccgccagcactgccggaaccgccgggtattctggcaccgcag ccgccggatgttggtagcagcgatccgctgtctatggtgggtccgagccagggt cgtagcccgagctatgcgtaataa |
| 401 | 293 | SABA1-FGf21v6 | Atgggtgtttctgatgttccgcgtgatctggaagttgttgcagcaaccccgacc agcctgctgattagctggcatagctattatgaacagaatagctattatcgcatt acctatggtgaaaccggtggtaattctccggttcaggaatttaccgttccgtat agccagaccaccgcaaccattagcggtctgaaaccgggtgttgattataccatt accgtgtatgcagtgtatggcagcaaatattattatccgattagcattaattat cgcaccgaaatcgataaaccgagcggtggtagcggtagcggttcaggtagcggt tctggttctggtagcccgattccggatagctctccgctgctgcagtttggtggt caggttcgtcagcgttatctgtataccgatgatgcacagcagaccgaagcacat ctggaaatccgcgaagatggcaccgttggtggcgcagcagatcagtctccggaa agcctgctgcagctgaaagcactgaagccaggtgttattcagattctgggtgtt aaaaccagccgttttctgtgtcagcgtccggatggtgcactgtatggtagcctg cattttgatccggaagcatgcagctttcgtgaactctgctggaagatggctata atgtgtatcagagcgaagcacatggtctgccgctgcatttacctggtaataaat ctccgcatcgtgatccggcaccgcgtggtccggcacgtttcctgcctctgcctg gtctgcctccggcactgccagaacctccgggtattctggcaccgcagcctccgg atgttggtagcagcgatccgctgtctatggttggtccgagccagggtcgtagcc cgagctatgcaagctga |
| 402 | 293 | SABA1-FGF21v7 | atgggtgtttctgatgttccgcgtgatctggaagttgttgcagcaaccccgacc agcctgctgattagctggcatagctattatgaacagaatagctattatcgcatt acctatggtgaaaccggtggtaattctccggttcaggaatttaccgttccgtat agccagaccaccgcaaccattagcggtctgaaaccgggtgttgattataccatt accgtgtatgcagtgtatggcagcaaatattattatccgattagcattaattat cgcaccgaaattgataaaccgagcggtggtagcggtagcggttcaggtagcggt tctggttctggtagccatccgattccggatagctctccgctgctgcagtttggt ggtcaggttcgtcagcgttatctgtataccgatgatgcacagcagaccgaagca catctggaaattcgtgaagatggcaccgttggtggtgcagcagatcagtctccg gaaagcctgctgcagctgaaagcactgaagccaggtgttattcagattctgggt gttaaaaccagccgttttctgtgtcagcgtccggatggtgcactgtatggtagc ctgcattttgatccggaagcatgcagctttcgtgaactgctgctggaagatggc tataatgtgtatcagagcgaagcacatggtctgccgctgcatttacctggtaat aaatctccgcatcgtgatccggcaccgcgtggtccggcacgtttcctgcctctg cctggtctgcctccggcactgccagaacctccgggtattctggcaccgcagcct ccggatgttggtagcagcgatccgctgtctatggttggtccgagccagggtcgt agcccgagctatgcatga |
| 403 | 299 | SABA1-FGF21v8 | atgggtgtttctgatgttccgcgtgatctggaagttgttgcagcaaccccgacc agcctgctgattagctggcatagctattatgaacagaatagctattatcgcatt acctatggtgaaaccggtggtaattctccggttcaggaatttaccgttccgtat agccagaccaccgcaaccattagcggtctgaaaccgggtgttgattataccatt accgtgtatgcagtgtatggcagcaaatattattatccgattagcattaattat cgcaccgaaattgaaaaaccgagccagcatcatcatcaccatcatggtagcggt agcggttcaggtagcggttctggttctggtagcccgattccggatagctctccg ctgctgcagtttggtggtcaggttcgtcagcgttatctgtataccgatgatgca cagcagaccgaagcacatctggaaattcgtgaagatggcaccgttggtggtgca |

TABLE 3-continued

Certain exemplary nucleic acid sequences (SEQ ID NOs: 176-214 and 397-407).

| SEQ ID NO: | aa length | Sequence name | DNA sequence |
|---|---|---|---|
| | | | gcagatcagtctccggaaagcctgctgcagctgaaagcactgaagccaggtgtt<br>attcagattctgggtgttaaaaccagccgttttctgtgtcagcgtccggatggt<br>gcactgtatggtagcctgcattttgatccggaagcatgcagctttcgtgaactg<br>ctgctggaagatggctataatgtgtatcagagcgaagcacatggtctgccgctg<br>catttacctggtaataaatctccgcatcgtgatccggcaccgcgtggtccggca<br>cgtttcctgcctctgcctggtctgcctccggcactgccagaacctccgggtatt<br>ctggcaccgcagcctccggatgttggtagcagcgatccgctgtctatggttggt<br>ccgagccagggtcgtagcccgagctatgcaagctga |
| 404 | 300 | FGF21-SABA1v2 | atgccgattccggatagctctccgctgctgcagtttggtggtcaggttcgtcag<br>cgttatctgtataccgatgatgcacagcagaccgaagcacatctggaaattcgt<br>gaagatggcaccgttggtggtgcagcagatcagtctccggaaagcctgctgcag<br>ctgaaagcactgaaaccgggtgttattcagattctgggtgttaaaaccagccgt<br>tttctgtgtcagcgtccggatggtgcactgtatggtagcctgcattttgatccg<br>gaagcatgcagctttcgtgaactgctgctggaagatggctataatgtgtatcag<br>agcgaagcacatggtctgccgctgcatctgcctggtaataaatctccgcatcgt<br>gatccggcaccgcgtggtccggcacgtttcctgccgctgcctggtctgcctccg<br>gcactgccagaacctccgggtattctggcaccgcagcctccggatgttggtagc<br>agcgatccgctgtctatggttggtccgagccagggtcgtagcccgagctatgca<br>agcggtggtagcggtagcggttctggtagcggttcaggttctggttctggtgtt<br>tctgatgttccgcgtgatctggaagttgttgcagcaaccccgaccagcctgctg<br>attagctggcatagctattatgaacagaatagctattatcgcattacctatggt<br>gaaaccggtggtaattctccggttcaggaatttaccgttccgtatagccagacc<br>accgcaaccattagcggtctgaagcctggtgtggattataccattaccgtgtat<br>gcagtttatggcagcaaatattattatccgattagcattaattatcgcaccgaa<br>attgaaaaaccgagccagcatcatcatcaccatcattga |
| 405 | 294 | FGF21-SABA1v3 | atgccgattccggatagctctccgctgctgcagtttggtggtcaggttcgtcag<br>cgttatctgtataccgatgatgcacagcagaccgaagcacatctggaaattcgt<br>gaagatggcaccgttggtggtgcagcagatcagtctccggaaagcctgctgcag<br>ctgaaagcactgaaaccgggtgttattcagattctgggtgttaaaaccagccgt<br>tttctgtgtcagcgtccggatggtgcactgtatggtagcctgcattttgatccg<br>gaagcatgcagctttcgtgaactgctgctggaagatggctataatgtgtatcag<br>agcgaagcacatggtctgccgctgcatctgcctggtaataaatctccgcatcgt<br>gatccggcaccgcgtggtccggcacgtttcctgccgctgcctggtctgcctccg<br>gcactgccagaacctccgggtattctggcaccgcagcctccggatgttggtagc<br>agcgatccgctgtctatggttggtccgagccagggtcgtagcccgagctatgca<br>agcggtggtagcggtagcggttctggtagcggttcaggttctggttctggtgtt<br>tctgatgttccgcgtgatctggaagttgttgcagcaaccccgaccagcctgctg<br>attagctggcatagctattatgaacagaatagctattatcgcattacctatggt<br>gaaaccggtggtaattctccggttcaggaatttaccgttccgtatagccagacc<br>accgcaaccattagcggtctgaagcctggtgtggattataccattaccgtgtat<br>gcagtttatggcagcaaatattattatccgattagcattaattatcgcaccgaa<br>attgaaaaaccgagccagtga |
| 406 | 186 | FGF21v6 | atgcatcatcatcaccatcatattccggatagctctccgctgctgcagtttggt<br>ggtcaggttcgtcagcgttatctgtataccgatgatgcacagcagaccgaagca<br>catctggaaattcgtgaagatggcaccgttggtggtgcagcagatcagtctccg<br>gaaagcctgctgcagctgaaagcactgaaaccgggtgttattcagattctgggt<br>gttaaaaccagccgttttctgtgtcagcgtccggatggtgcactgtatggtagc<br>ctgcattttgatccggaagcatgtagctttcgtgaactgctgctggaagatggc<br>tataatgtgtatcagagcgaagcacatggtctgccgctgcatctgcctggtaat<br>aaatctccgcatcgtgatccggcaccgcgtggtccggcacgttttctgccactg<br>cctggtctgcctccggcactgccagaaccgccgggtattctggcaccgcagccg<br>ccggatgttggtagcagcgatccgctgagcatggttggtccgagccagggtcgt<br>agcccgagctatgcaagc |
| 407 | 181 | FGF21v7 | atgcatcatcatcaccatcatccgctgctgcagtttggtggtcaggttcgtcag<br>cgttatctgtataccgatgatgcacagcagaccgaagcacatctggaaattcgt<br>gaagatggcaccgttggtggtgcagcagatcagtctccggaaagcctgctgcag<br>ctgaaagcactgaaaccgggtgttattcagattctgggtgttaaaaccagccgt<br>tttctgtgtcagcgtccggatggtgcactgtatggtagcctgcattttgatccg<br>gaagcatgtagctttcgtgaactgctgctggaagatggctataatgtgtatcag<br>agcgaagcacatggtctgccgctgcatctgcctggtaataaatctccgcatcgt<br>gatccggcaccgcgtggtccggcacgttttctgccactgcctggtctgcctccg<br>gcactgccagaaccgccgggtattctggcaccgcagccgccggatgttggtagc<br>agcgatccgctgagcatggttggtccgagccagggtcgtagcccgagctatgca<br>agc |

A. Serum Albumin-Binding Adnectins™ (SABA)

Example A1

Screening and Selection of Candidate Serum Albumin-Binding Adnectin™

Overview

A selection technique known as PROfusion (see e.g., Roberts and Szostak, Proc Natl Acad Sci USA. 94(23): 12297-302, 1997 and WO 2008/066752) was applied to a DNA library with variable regions designed into the BC, DE and FG loops of $^{10}$Fn3. A random library of greater than $10^{13}$ molecules was created from this design, and selection pressure was applied against a biotinylated form of HSA to isolate candidate serum albumin-binding Adnectin™ (SABA) with desirable binding properties.

High Throughput Protein Production (HTTP) Process

The various HSA binding Adnectins™ were purified using a high throughput protein production process (HTPP). Selected binders were cloned into pET9d vector containing a HIS6 tag and transformed into *E. coli* BL21(DE3)pLysS cells. Transformed cells were inoculated in 5 ml LB medium containing 50 μg/mL Kanamycin in a 24-well format and grown at 37° C. overnight. Fresh 5 ml LB medium (50 μg/mL Kanamycin) cultures were prepared for inducible expression by aspirating 200 μl from the overnight culture and dispensing it into the appropriate well. The cultures were grown at 37° C. until $A_{600}$ 0.6-0.9. After induction with 1 mM isopropyl-β-thiogalactoside (IPTG), the culture was grown for another 4 hours at 30° C. and harvested by centrifugation for 10 minutes at 3220×g at 4° C. Cell Pellets were frozen at −80° C.

Cell pellets (in 24-well format) were lysed by resuspension in 450 μl of Lysis buffer (50 mM $NaH_2PO_4$, 0.5 M NaCl, 1x Complete™ Protease Inhibitor Cocktail-EDTA free (Roche), 1 mM PMSF, 10 mM CHAPS, 40 mM Imidazole, 1 mg/ml lysozyme, 30 ug/ml DNAse, 2 ug/ml aprotonin, pH 8.0) and shaken at room temperature for 1 hour. Lysates were clarified and re-racked into a 96-well format by transfer into a 96-well Whatman GF/D Unifilter fitted with a 96-well, 650 μl catch plate and centrifuged for 5 minutes at 200×g. The clarified lysates were transferred to a 96-well Ni-Chelating Plate that had been equilibrated with equilibration buffer (50 mM $NaH_2PO_4$, 0.5 M NaCl, 10 mM CHAPS, 40 mM Imidazole, pH 8.0) and incubated for 5 min. Unbound material was removed. The resin was washed 2×0.3 ml/well with Wash buffer #1 (50 mM $NaH_2PO_4$, 0.5 M NaCl, 5 mM CHAPS, 40 mM Imidazole, pH 8.0). Next the resin was washed with 3×0.3 ml/well with PBS. Prior to elution each well was washed with 50 μl Elution buffer (PBS+20 mM EDTA), incubated for 5 min and this wash discarded by vacuum. Protein was eluted by applying an additional 100 ul of Elution buffer to each well. After 30 minute incubation at room temperature the plate(s) were centrifuged for 5 minutes at 200×g and eluted protein collected in 96-well catch plates containing 5 μl of 0.5M $MgCl_2$ affixed to the bottom of the Ni-plates. Eluted protein was quantified using a BCA Protein assay with SGE (control Adnectin™) as the protein standard. The SGE Adnectin is a wild-type $^{10}$Fn3 domain (SEQ ID NO: 1) in which integrin binding domain (amino acids RGD at positions 78-80) have been replaced with SGE.

HSA, RhSA & MuSA Direct Binding ELISA

For assaying direct binders to HSA, MaxiSorp™ plates (Nunc International, Rochester, N.Y.) were coated with 10 ug/mL HSA (Sigma, St. Louis, Mo.) in PBS at 4° C. overnight followed by blocking in casein block buffer (Thermo Scientific, Rockford, Ill.) for 1-3 hours at room temperature. For single-point screening assays, purified HTPP Adnectins™ were diluted 1:20 in casein block buffer and allowed to bind to HSA in each well for 1 hour at room temperature. For dose response assays, concentrations ranging from 0.1 nM up to 1 μM were used. After washing in PBST to remove unbound Adnectins™, anti-His mAb-HRP conjugate (R&D Systems, MN) diluted 1:2500 in casein block buffer was added to the bound His-tagged Adnectins™ for 1 hour at room temperature. Excess conjugate was removed by washing with PBST and bound Adnectins™ detected using TMB detection reagents (BD Biosciences) according to the manufacturer's instructions.

Aggregation Measurement by Analytical Size Exclusion Chromatography

Size exclusion chromatography (SEC) was performed on the SABAs resulting from the HTPP. SEC of HTPP derived material was performed using a Superdex 200 5/150 or Superdex 75 5/150 column (GE Healthcare) on an Agilent 1100 or 1200 HPLC system with UV detection at $A_{214}$ nm and $A_{280}$ nm and with fluorescence detection (excitation=280 nm, emission=350 nm). A buffer of 100 mM sodium sulfate, 100 mM sodium phosphate, 150 mM sodium chloride, pH 6.8 at appropriate flow rate of the SEC column employed. Gel filtration standards (Bio-Rad Laboratories, Hercules, Calif.) were used for molecular weight calibration.

The results of the SEC on the HTPP purified SABAs were shown to be predominantly monomeric and eluted in the approximate range of 10 kDa vs. globular Gel Filtration standards (BioRad).

5. Identification of Candidate Serum Albumin-Binding Adnectin™ (SABA)

As a result of the screening for HSA/RhSA/MuSA binding and biophysical criteria, four unique serum albumin-binding Adnectins™ (SABA) were identified and chosen to have their half-lives evaluated in mice. In order to carry out in vitro and in vivo characterization, midscales were undertaken for the four SABAs. Table 2 provides the sequences of twenty-six unique SABA core sequences identified from PROfusion, designated as SABA1-26. SABA4 had a scaffold mutation that was fixed prior to midscaling. The scaffold-perfect version of SABA4 is SABA5. SABA4 and SABA5 have identical sequences in the BC, DE, and FG loops.

Example A2

Production and Formulation of Candidate SABAs

Midscale Protein Production of SABAs

The selected SABAs described in Example A1, followed by the $His_6$ tag, were cloned into a pET 9d vector and expressed in *E. coli* BL21(DE3)pLysS cells (see Table 2 for each His-tagged SABA sequence designated SABA1.1, SABA2.1, SABA3.1, and SABA5.1). 20 ml of an inoculum culture (generated from a single plated colony) was used to inoculate 1 liter of LB medium containing 50 μg/mL Kanamycin. The culture was grown at 37° C. until $A_{600}$ 0.6-1.0. After induction with 1 mM isopropyl-β-thiogalactoside (IPTG) the culture was grown for another 4 hours at 30° C. and harvested by centrifugation for 30 minutes at ≥10,000×g at 4° C. Cell Pellets were frozen at −80° C. The cell pellet was resuspended in 25 mL of lysis buffer (20 mM $NaH_2PO_4$, 0.5 M NaCl, 1x Complete™ Protease Inhibitor Cocktail-EDTA free (Roche), pH 7.4) using an Ultra-turrax homgenizer (IKA works) on ice. Cell lysis was achieved by high pressure homogenization (≥18,000 psi) using a Model M-110S Microfluidizer (Microfluidics). The soluble fraction was separated by centrifugation for 30 minutes at 23,300×g at 4° C. The supernatant was clarified via 0.45 μm filter. The clarified lysate was loaded onto a HisTrap column (GE) pre-equilibrated with 20 mM $NaH_2PO_4$, 0.5 M NaCl, pH 7.4. The column was then washed with 25 column volumes of 20 mM $NaH_2PO_4$, 0.5 M NaCl, pH 7.4, followed by 20 column volumes of 20 mM $NaH_2PO_4$, 0.5 M NaCl, 25 mM imidazole pH 7.4, and then 35 column volumes of 20 mM $NaH_2PO_4$, 0.5 M NaCl, 40 mM imidazole pH 7.4. Protein was eluted with 15 column volumes of 20 mM $NaH_2PO_4$, 0.5 M NaCl, 500 mM imidazole pH 7.4, fractions pooled based on absorbance at $A_{280}$ and dialyzed against 1x PBS, 50 mM Tris, 150 mM NaCl pH 8.5 or 50 mM NaOAc; 150 mM NaCl; pH 4.5. Any precipitate was removed by filtering at 0.22 μm.

Midscale expression and purification yielded highly pure and active Adnectins™ that were expressed in a soluble form and purified from the soluble fraction of the bacterial cytosol. SEC analysis on a Superdex 200 or Superdex 75 10/30GL in a mobile phase of 100 mM $NaPO_4$, 100 mM $NaSO_4$, 150 mM NaCl, pH 6.8 (GE Healthcare) demonstrated predominantly monomeric Adnectins™.

Formulation of SABA1.2

One specific SABA, SABA1.2 (SEQ ID NO: 80), was chosen for a preliminary formulation screen. SABA1.2 comprises an $(ED)_5$ extension on the "core 1" sequence of $^{10}$Fn3. For SABA1.2, a stable formulation of 10 mM succinic acid, 8% sorbitol, 5% glycine at pH 6.0 and at a product concentration of 5 mg/mL was identified. In this formulation the protein melting temperature was 75° C. as determined by Differential Scanning calorimetry (DSC) using a protein concentration of 1.25 mg/mL. The formulation provided satisfactory physical and chemical stability at 4° C. and 25° C., with an initial aggregate level at 1.2%. After one month of stability, the level of aggregation was very low (1.6% at 4° C. and 3.8% at 25° C.). The protein was also stable in this formulation after five cycles of freeze-thaw as transitioned from −80° C. and −20° C. to ambient temperature. In addition, in this formulation SABA1.2 was soluble to at least 20 mg/mL protein concentration at 4° C. and ambient temperature with no precipitation or increase in aggregation.

Example A3

Biophysical Characterization of Candidate SABAs

Size Exclusion Chromotography

Standard size exclusion chromatography (SEC) was performed on the candidate SABAs resulting from the midscale process. SEC of midscaled material was performed using a Superdex 200 10/30 or on a Superdex 75 10/30 column (GE Healthcare) on an Agilent 1100 or 1200 HPLC system with UV detection at $A_{214}$ nm and $A_{280}$ nm and with fluorescence detection (excitation=280 nm, emission=350 nm). A buffer of 100 mM sodium sulfate, 100 mM sodium phosphate, 150 mM sodium chloride, pH 6.8 at appropriate flow rate of the SEC column employed. Gel filtration standards (Bio-Rad Laboratories, Hercules, Calif.) were used for molecular weight calibration.

The results of the SEC on the midscaled purified SABAs showed predominantly monomeric Adnectin™ and elution in the approximate range of 10 kDa vs. globular Gel Filtration standards (BioRad) as showed.

Thermostability

Differential Scanning calorimetry (DSC) analyses of the midscaled SABAs were performed to determine their respective $T_m$'s. A 1 mg/ml solution was scanned in a N-DSC II calorimeter (calorimetry Sciences Corp) by ramping the temperature from 5° C. to 95° C. at a rate of 1 degree per minute under 3 atm pressure. The data was analyzed vs. a control run of the appropriate buffer using a best fit using Orgin Software (OrginLab Corp). The results of the SEC and DSC analyses are summarized in Table 4.

TABLE 4

Summary of SEC and DSC analyses on candidate SABAs.

| Clone | SEC Monomer (%) | SEC Dimer (%) | DSC (Tm) |
|---|---|---|---|
| SABA1.1 | 92.3 | 7.7 | 63.9° C. |
| SABA5.1 | 88 | 12 | 70.1° C. |
| SABA2.1 | 91 | 9 | 58.5° C./78.2° C. |
| SABA3.1 | 99 | BLD | 65.2° C. |

Example A4

Characterization of Candidate SABA1 Binding to Serum Albumin

The kinetics of selected SABA clones purified from HTPP and/or midscaled material described in Examples A1 and A2 were determined by immobilizing the respective serum albumin (HSA/RhSA/MuSA) on the surface of a Biasensor CMS chip and flowing a concentration series of SABAs over both the reference flow cell and the immobilized albumins. In addition, binding to albumin was carried out under various pH conditions ranging from pH 5.5 to pH 7.4. HSA-binding Adnectins™ SABA2.1, SABA3.1, SABA4.1 (SABA5.1) & SABA1.1 cross reacted with RhSA but did not cross react with MuSA. SABA2 and SABA4 binding is pH sensitive whereas clone SABA3 demonstrated pH resistant binding to HSA down to pH 6.0. SABA1.1 fits biochemical criteria for pH resistance and affinity/kinetics down to pH 5.5.

Domain mapping was determined by Biacore. Selected SABA clones purified from HTPP and/or midscaled material were determined by immobilizing HSA or a construct consisting of just HSA-domain I & II or HSA-domain III on the surface of a Biasensor CMS chip and flowing a concentration series of the SABAs over both the reference flow cell and the immobilized albumins. Clones SABA2 and SABA1 bound to HSA and the HSA-domain I-II construct but not the HSA-domain III construct. Clones SABA3 and SABA4 bound to HSA but not to either the HSA-domain I-II or HSA-domain III constructs. The results are summarized in Table 5.

TABLE 5

| Binding Affinity and Kinetics of Candidate SABAs (SABA1.1, 2.1, 3.1 and 4.1). | | | | | |
|---|---|---|---|---|---|
| Adnectin ™ | Target | $K_D$ (nM) | $K_{off}$ ($s^{-1}$) | Resistant to pH 7.4→5.5? | Epitope on HSA |
| SABA2 | HSA | 33.8 +/− 20.5 (n = 6) | 1.71E−04 | --- | Domain I-II |
| | RhSA | 63.6 | 4.42E−04 | | |
| SABA3 | HSA | 863 | 6.82E−02 | +++ (down to pH 6.0) | Neither domain I-II nor III (interfacial?) |
| | RhSA | 431 | 3.37E−02 | | |
| SABA4 | HSA | 412 +/− 8 (n = 4) | 7.82E−04 | -- | Neither domain I-II nor III (interfacial?) |
| | RhSA | >1000 | 3.83E−03 | | |
| SABA1 | HSA | 47.2 +/− 18.2 (n = 9) | 4.57E−04 | +++ | Domain I-II |
| | RhSA | 778 +/− 313 (n = 4) | 5.45E−03 | | |

Example A5

Examination of the In Vivo $t_{1/2}$ of Candidate SABAs

The half-life of HSA in mice was determined to allow for evaluation of HSA-binding Adnectins™ in mice as the HSA-binding Adnectins™ do not cross react with MuSA. HSA was injected into the tail vein of approximately 6 week old Ncr nude female mice at a 20 mg/kg (FIG. 1A) and 50 mg/kg dose (FIG. 1B), and the concentration of HSA in blood samples taken at intervals post-injection was determined by ELISA. Using WinNonlin software and non-compartmental modeling, the $t_{1/2}$ of HSA injected into mice at 20 mg/kg and 50 mg/kg were determined to be ~24 hrs and ~20 hrs, respectively.

Half-Life Determination of SABA1-4 in Mice

One liter *E. coli* growth of HSA binding clones SABA1.1, SABA2.1, SABA3.1, and SABA4.1 were prepared, purified and endotoxin removed. Each SABA variant was injected with or without HSA into the tail vein of mice, and the concentration in blood samples taken at intervals post-injection was determined using a quantitative ELISA-based assay that was developed to detect the Adnectin™ in plasma samples. The pharmacokinetic parameters of each Adnectin™ were determined using non-compartmental modeling with WinNonlin software.

Figure 2D:
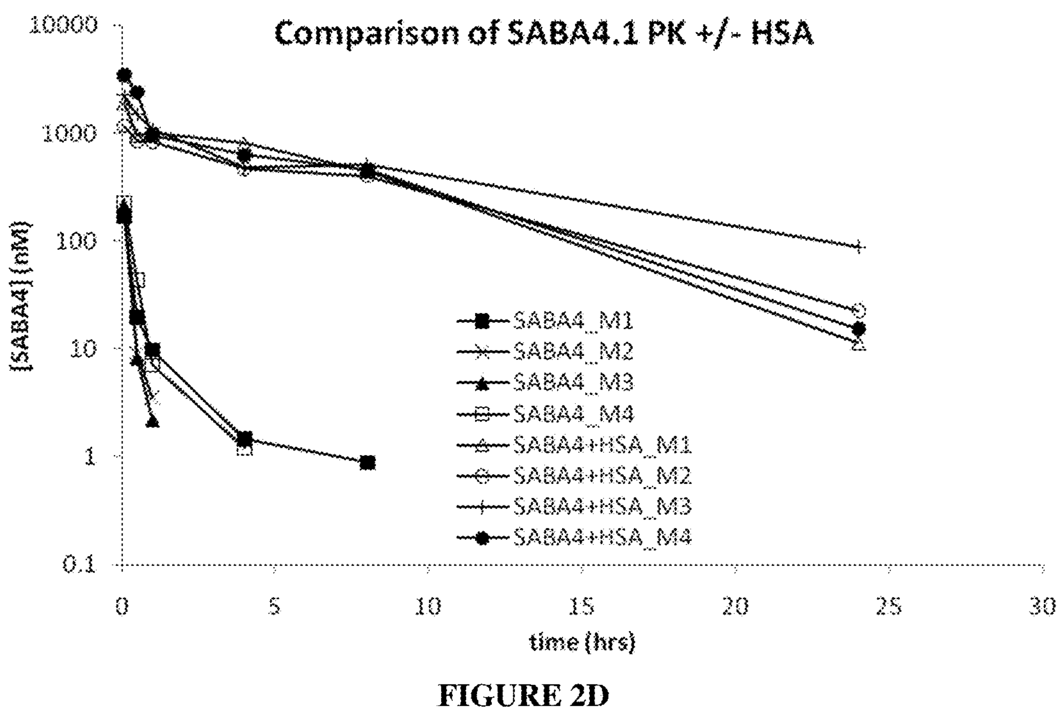

The pharmacokinetic profiles of each SABA were compared in the presence or absence of HSA in approximately 6 week old Ncr nude female mice. The mice that were co-injected with HSA had the HSA premixed with each SABA (HSA in a 3-4 molar excess) because the binding clone was selective for HSA and RhSA and did not bind the mouse serum albumin. The half-life of SABA1.1 in mice plasma was 0.56 hours whereas the half-life of SABA1.1 co-injected with HSA was 5.6 hours, a ~10-fold increase in half life (FIG. 2A). The half-life of SABA2.1 in mice plasma was 0.24 hours whereas the half-life of SABA2.1 co-injected with HSA was 2.8 hours, a ~12-fold increase in half life (FIG. 2B). The half-life of SABA3.1 in mice plasma was 0.28 hours whereas the half-life of SABA3.1 co-injected with HSA was 0.53 hours, a ~2-fold increase in half life (FIG. 2C). The half-life of SABA4.1 in mice plasma was 0.66 hours whereas the half-life of SABA4 co-injected with HSA was 4.6 hours, a ~7-fold increase in half life (FIG. 2D). A summary of the present example is shown in FIG. 3. Table 6 summarizes similar data for SABA1.1, SABA2.1, SABA3.1, SABA4.1 and SABA5.1; comparison is made to half life in cyno, where available.

TABLE 6

| Data for SABA1.1, SABA2.1, SABA3.1, SABA4.1 and SABA5.1 in mice and monkey. | | | |
|---|---|---|---|
| | PK (T½) | | |
| CLONE | Mice | Cyno | Comments |
| SABA1.1 | 5.6 hrs | 96-137 hrs | T½ = 96-137 hrs |
| SABA4.1 | 4.6 hrs | ND | Poor binding affinity for RhSA. >2-fold decrease in $K_D$ observed at pH <6.0 |
| SABA5.1 | 4.6 hrs | 12 hrs | Poor binding affinity for RhSA. >2-fold decrease in $K_D$ observed at pH <6.0 |
| SABA2.1 | 2.8 hrs | NA | Loss of binding at pH ≤6.5 |
| SABA3.1 | 32 min | NA | Poor T½ observed in mice |

Half-Life Determination of SABA1.1 and SABA5.1 in Cynomolgous Monkeys

A three week single dose proof of concept study of SABA1.1 (FIG. 4A) and SABA5.1 (FIG. 4B) was conducted in cynomolgus monkeys to assess pharmacokinetics at a 1 mg per kg (mpk) dose IV in 2 cynomolgus monkeys. The pharmacokinetics were evaluated using a quantitative ELISA-based assay that was developed to detect the Adnectin™ in plasma samples. SABA1.1 has a half-life in the range of 96-137 hours (FIG. 4A and Table 7). SABA5.1 has a half-life of approximately 12 hours and was only measurable in the ELISA up to 120 hours (FIG. 4B and Table 8). Table 7 summarizes data for SABA1.1; Table 8 summarizes data for SABA5.1.

TABLE 7

| Data for SABA1.1. | | | | | |
|---|---|---|---|---|---|
| Monkey | t½ (hrs) | Cmax (μg/mL) | AUCall (hr * μg/mL) | Cl_obs (mL/hr/kg) | Vz_obs (mL/kg) |
| #1 | 95.8 | 9.03 | 673.7 | 1.45 | 200.8 |
| #2 | 136.6 | 7.24 | 625.1 | 1.60 | 315.2 |

TABLE 8

| Data for SABA5.1. | | | | | |
|---|---|---|---|---|---|
| | HL_Lambda_z (hr) | Cmax (μg/mL) | AUCall (hr * μg/mL) | Cl_obs (mL/hr/kg) | Vz_obs (mL/kg) |
| N | 2 | 2 | 2 | 2 | 2 |
| Mean | 12.186 | 17.358 | 246.882 | 4.089 | 72.507 |

TABLE 8-continued

| Data for SABA5.1. | | | | | |
|---|---|---|---|---|---|
| | HL_Lambda_z (hr) | Cmax (μg/mL) | AUCall (hr * μg/mL) | Cl_obs (mL/hr/kg) | Vz_obs (mL/kg) |
| SD | 1.451 | 3.08 | 36.245 | 0.596 | 19.045 |
| Min | 11.16 | 15.18 | 221.25 | 3.67 | 59.04 |
| Max | 13.21 | 19.54 | 272.51 | 4.51 | 85.97 |
| CV % | 11.9 | 17.7 | 14.7 | 14.6 | 26.3 |

Example A6

Characterization of SABA1 Binding to Serum Albumin

SABA1.1 and 1.2 Bind to HSA and RhSA

SABA1.2, a “core 1” $^{10}$Fn3 comprising an $(ED)_5$ extension (SEQ ID NO: 90) bound to human serum albumin (HSA) at neutral pH and 25° C. with an average association rate constant ($k_a$) of 8.21E+03 $M^{-1}$ $s^{-1}$, and an average dissociation rate constant ($k_d$) of 4.43E-04 $s^{-1}$, for a calculated average $K_D$ of 55.3 nM (Table 9). For rhesus serum albumin (RhSA), the measured average association rate constant was 6.6E+03 $M^{-1}s^{-1}$, and the dissociation rate constant was 3.78E-03 $s^{-1}$, giving a calculated average $K_D$ of 580 nM. No measurable interaction between SABA1.2 and mouse or rat serum albumin could be observed up to 1 μM (Table 9 and FIG. 5). At 37° C., the $k_a$ and $k_d$ increased between 2 to 5-fold, leading to a ~2-fold increase in affinity for HSA and ½ the affinity for RhSA (Table 9).

TABLE 9

| Kinetic parameters for SABA1.2 binding to albumins, in HBS-P buffer. | | | | |
|---|---|---|---|---|
| Albumin | Temp (° C.) | $k_a$ (1/Ms) | $k_d$ (1/s) | $K_D$ (nM) |
| Human | 25 | 8.21 ± 1.19E+03 | 4.43 ± 0.65E−04 | 55.3 ± 13.7 |
| Rhesus | | 6.60 ± 1.18E+03 | 3.78 ± 0.45E−03 | 580 ± 62.6 |
| Mouse | | no observable binding | | |
| Human | 37 | 3.38E+04 | 8.15E−04 | 24.1 |
| Rhesus | | 1.89E+04 | 1.85E−02 | 977.4 |
| Mouse | | no observable binding | | |

Additionally, a calorimetric titration was performed to determine the stoichiometry between SABA1 and HSA. For this study, SABA1.1, a “core 1” $^{10}$Fn3 comprising a His6 extension (SEQ ID NO: 89), was used. HSA (10 μl per injection of 115 μM protein solution) was injected into the calorimetric cell containing SABA1.1 at a concentration of 8.1 μM. The experiment was performed at 37° C. in PBS buffer pH 7.4. FIG. 6 shows that SABA1.1 binds to HSA with 1:1 stoichiometry.

SABA1.2 Binds Potently to HSA at Low pH

The long half-life of albumins (e.g., $t_{1/2}$ of HSA is 19 days) is due in large part to the fact that they are recycled from an endocytic pathway by binding to the neonatal Fc receptor, FcRn, under the low pH conditions that exist inside the endosome. As shown in Table 10 SABA1.2 potently bound HSA at the endosomal pH of 5.5, suggesting that the $t_{1/2}$ of SABA1, once bound to HSA, would also benefit from the FcRn recycling mechanism.

TABLE 10

| Comparison of albumin binding kinetics at pH 7.4 and 5.5, in MES buffer. | | | | |
|---|---|---|---|---|
| albumin | pH | $k_a$ (1/Ms) | $k_d$ (1/s) | $K_D$ (nM) |
| Human | 7.4 | 9.26E+03 | 3.88E−04 | 41.9 |
| | 5.5 | 9.44E+03 | 2.70E−04 | 28.6 |
| Rhesus | 7.4 | 6.16E+03 | 2.95E−03 | 479 |
| | 5.5 | 7.57E+03 | 2.72E−03 | 359 |

SABA1.2 Binds to Domains I and II of HSA, but not Domain III

The binding site SABA1.2 on albumin was mapped to the N-terminal domains I or II using recombinant HSA fragments and has no detectable binding to domain III (FIG. 7). Because domain III is the domain of HSA that primarily interacts with FcRn, it is less likely that SABA1.2 would compete for HSA binding to FcRn, again increasing the possibility of fully leveraging the recycling mechanism for enhanced half-life.

Example A7

In Vivo Pharmacology of SABA1.2

A four week single dose pre-toxicology study of SABA1.2 was conducted in cynomolgus monkeys to assess pharmacokinetics at two different dose levels. The pharmacokinetics and bioavailability were also evaluated in a three-week, single-dose pre-toxicology study that included both intravenous and subcutaneous administration arms. In each of these studies, the pharmacokinetics of SABA1.2 was evaluated using a quantitative ELISA-based assay that was developed to detect SABA1.2 in plasma samples in combination with non-compartmental modeling with WinNonlin software.

SABA1.2 was administered to monkeys at 1 mpk and 10 mpk IV. Non-compartmental analyses using WinNonlin software were performed to evaluate pharmacokinetic parameters. As shown in FIG. 20 and the parameters described below, SABA1.2 exhibited dose-dependent pharmacokinetics in this study as determined by area under the concentration-time curve (AUC) evaluation. The clearance (CL) for SABA1.2 at 10 mpk was 0.15 ml/hr/kg, the beta phase half-life ($t_{1/2}$) was 143 hours, the volume of distribution (Vz) was 30 mL/kg, and total drug exposure (AUCall) was 5,609,457 hr*nmol/L (Table 11). The clearance (CL) for SABA1.2 at 1 mpk was 0.4 ml/hr/kg, the half-life ($t_{1/2}$) was 124 hours, the volume of distribution (Vz) was 72 mL/kg, and total drug exposure (AUCall) was 214,636 hr*nmol/L (Table 11).

After SC or IV administration of SABA1.2, the beta-phase pharmacokinetic profiles were similar (FIG. 9). The clearance (CL) for SABA1.2 at 1 mpk IV was 0.22 ml/hr/kg, the beta phase half-life ($t_{1/2}$) was 125 hours, the volume of distribution (Vz) was 40 mL/kg, and total drug exposure (AUCall) was 357,993 hr*nmol/L (Table 11). The clearance (CL) for SABA1.2 at 1 mpk SC was 0.32 ml/hr/kg, the beta phase half-life ($t_{1/2}$) was 134 hours, the volume of distribution (Vz) was 62 mL/kg, and total drug exposure (AUCall) was 251,339 hr*nmol/L (Table 11). The SC relative bioavailability (F) compared to IV was 0.7.

TABLE 11

| Pharmacokinetic Parameters for SABA1.2 in Monkeys. | | | | |
|---|---|---|---|---|
| | Study # | | | |
| | 1 | | 2 | |
| Dose (mg/kg) | 1 | 10 | 1 | 1 |
| Route of administration | i.v. | i.v. | i.v. | s.c. |
| N | 3 | 3 | 1 | 2 |
| CL (mL/hr/kg) | 0.4 | 0.15 | 0.22 | 0.32 |
| Vz (mL/kg) | 72 | 30 | 40 | 62 |
| AUCall (hr * nmol/L) | 214,636 | 5,609,457 | 357,993 | 251,339 |
| beta $T_{1/2}$ (h) | 124 | 143 | 125 | 134 |
| Bioavailability (F) | n/a | n/a | n/a | 0.7 |

Example A8

Structure of Human Serum Albumin in Complex with SABA1.2

The complex of Human Serum Albumin and SABA1.2 was crystallized by Proteros Biostructures GmbH from 100 mM Na-acetate, pH 4.75, 100 mM NaCl, and 28% PEG200. Diffraction from the crystals was optimized using the Free Mounting System (FMS) and flash-cooled under oil.

Data were collected by Proteros Biostructures GmbH at the Swiss Light Source beamline PXI/X06SA with the crystal maintained at 100 K. The wavelength was 1.0015 Å and the detector was a Pilatus 6M (Dectris). Data were processed with XDS and XSCALE (W. Kabsch (2010), XDS. *Acta Crystallogr. Sect. D* 66, 125-132; W. Kabsch (2010), Integration, scaling, space-group assignment and post-refinement, *Acta Crystallogr. Sect. D* 66, 133-144) and yielded the following statistics: Space Group: $P2_12_12_1$; Unit Cell: a=61.6 Å; b=124.1 Å; c=100.0 Å.

TABLE 12

| Summary of structure data. | | | | | | | |
|---|---|---|---|---|---|---|---|
| | Resolution | Measured | Unique | Redun. | % Complete | R-value | $I/\sigma_I$ |
| Overall | 50.00-1.96 | 330257 | 55260 | 6.0 | 99.0 | 0.039 | 23.1 |
| First Shell | 50.00-4.30 | 30746 | 5523 | 5.6 | 99.2 | 0.024 | 56.1 |
| Last Shell | 2.03-1.96 | 32596 | 5527 | 5.9 | 98.6 | 0.681 | 2.7 |

The structure of the Human Serum Albumin was determined using the program MOLREP (Vagin, A., & Teplyakov, A. (1997), MOLREP: an Automated Program for Molecular Replacement. *J. App. Crystallogr.,* 30, 1022-1025) for molecular replacement and PDB entry 1BM0 as the search model. The structure of the Adnectin moiety was determined from a search model based on PDB entry 1FNF residues 1423-1502 using the molecular replacement program PHASER (A. J. McCoy, R. W. Grosse-Kunstleve, P. D. Adams, M. D. Winn, L. C. Storoni & R. J. Read (2007), Phaser Crystallographic Software, *J. Appl. Crystallogr.* 40, 658-674).

Refinement of the model was carried out using BUSTER/TNT (Blanc, E., Roversi, P., Vonrhein, C., Flensburg, C., Lea, S. M. & Bricogne, G. (2004), Refinement of severely incomplete structures with maximum likelihood in BUSTER/TNT, *Acta Crystallogr. Sect. D* 60, 2210-2221) and model building was carried out with COOT (Emsley, P. & Cowtan, K. (2004), Coot: model-building tools for molecular graphics, *Acta Crystallogr Sect. D* 60: 2126-2132; Emsley, P., Lokhamp, B., Scott, W. G. & Cowtan, K. (2010), Features and Development of *Coot, Acta Crystallogr Sect. D* 66: 486-501). Figures for display were prepared with PyMol (DeLano, W. L. (2002), The PyMol Molecular graphics System, DeLano Scientific, San Carlos, Calif., US; available on the world wide web at pymol.org).

The final round of refinement yielded the statistics shown in Table 13.

TABLE 13

| Statistics from the final round of refinement. | | | | | |
|---|---|---|---|---|---|
| | Cycle | R-free | R-work | rms bonds | rms angles |
| Start | 1 | 0.264 | 0.233 | 0.011 | 1.1 |
| End | 5 | 0.248 | 0.211 | 0.010 | 1.1 |

Description of the Structure

The binding site for SABA1.2 is strictly on Domain 1 of human serum albumin (HuSA) (FIGS. 17A and B). The following residues of HuSA were in contact with the Adnectin (numbering based on the mature HuSA sequence, minus the signal and propeptide regions): Pro 35, Phe 36, Glu 37, Pro 113, Arg 114, Leu 115, Arg 117, Pro 118, Glu 119, Val 122, Met 123, Phe 134, Lys 137, Tyr 140, Glu 141, Arg 144, Arg 145, and Tyr 161. (Sheriff, S., Hendrickson, W. A. & Smith, J. L. (1987), Structure of Myohemerythrin in the Azidomet State at 1.7/1.3 A Resolution, *J. Mol. Biol.* 197, 273-296; Sheriff, S. (1993), Some methods for examining the interactions between two molecules, *Immunomethods* 3, 191-196). A broader definition of interacting residues would be those that are at least partially buried, which includes in addition to the residues listed above as being in contact, the following residues: Asp 38, Thr 125, Ala 126, Asp 129, Thr 133, Tyr 138, and Leu 182.

The Adnectin interacts through the BC, DE, and FG loops and has the following residues in contact with HuSA: His 25, Ser 26, Tyr 27, Glu 29, Gln 30, Asn 31, Pro 53, Tyr 54, Ser 55, Thr 57, Tyr 78, Tyr 83, and Tyr 84 (of SABA1.2, e.g., SEQ ID NO:90). In addition to the previously listed residues, the following residues are at least partially buried by the interaction: Trp 24, Ser 32, Tyr 33, Gln 56, Gly 79, and Lys 81 (of SABA1.2, e.g., SEQ ID NO:90).

Example A9

Phase I Design of SABA Safety Study

A Phase 1, partially blinded, placebo-controlled, pharmacokinetic study of intravenously administered SABA1.2 in healthy male volunteers will be conducted. The volunteers will be healthy adult male subjects aged 18 to 60 years not currently receiving treatment with prescription or over-thecounter medications and who meet protocol defined limits for health and organ function. SABA1.2 is a non-therapeutic Adnectin with binding affinity for human serum albumin (HSA). It is intended to serve as an albumin binder to extend the serum half-life (T-HALF) when integrated into a single polypeptide chain with a separate therapeutic Adnectin or other protein that would otherwise be rapidly eliminated. Cohorts of subjects will be treated with 0.1, 0.3, or 1.0 mg/kg SABA1.2 or placebo once every two weeks for a total of two drug administrations.

Study Design.

Volunteer subjects will be randomized to receive either SABA1.2 or placebo, and will receive two doses of their randomized treatment 14 days apart, each time as a 1-hour infusion followed by a 2-week sample collection and observation period; after the second observation period subjects will be followed for an additional 4 weeks for safety. Treatment (SABA1.2 or placebo) will be administered on Days 1 and 15.

Three sequential cohorts will be recruited at escalating dose levels of SABA1.2. Each individual dose cohort will additionally be divided into 3 subgroups sequentially exposed to either SABA1.2 or placebo in a partially blinded (the subject and investigative staff will be blinded to the identity of the infusate; the pharmacist will not be blinded) fashion (see FIG. 18). The first subgroup of each cohort will only contain 1 active drug treated subject in order to minimize risk.

After all the subjects in Cohort 1 have completed their Day 29 visits and the PK findings have been assessed (expected up to 4 weeks), Cohort 2 will begin the study assuming criteria surpassing the defined no observed adverse event level (NOAEL) have not been met in Cohort 1 (see below). Similarly, Cohort 3 will not begin until completion and PK assessment of Cohort 2, assuming the NOAEL has not been surpassed.

The NOAEL will be defined as the dose level 1 level below the lowest dose level in which either a) 2 or more actively treated (non-placebo) subjects experience any grade 2 National Cancer Institute (NCI; US)-Common Terminology Criteria for Adverse Events (CTCAE v4.03) SABA1.2-related toxicity or b) at least 1 actively treated subject experiences any grade ≥3 SABA1.2-related toxicity. The NOAEL will be the highest dose level completed if neither of these criteria is met. In the case that NOAEL criteria are surpassed in Cohorts 2 or 3, the next lower cohort will be declared the NOAEL and all remaining subjects will be treated at the NOAEL, such that a total of 37 subjects (28 receiving SABA1.2 and 9 receiving placebo) are treated in the study. This is in order to maintain the statistical precision sought to support the pharmacokinetic (PK) and immunogenicity evaluation, and to support an adequate number of subjects with safety observations. If the dose level of Cohort 1 is found to exceed the NOAEL, then no additional subjects will be dosed and the study will terminate.

Study Assessments and Primary Endpoint.

The primary endpoints of the study will be PK and will include mean T-HALF across all doses, maximum plasma concentration (Cmax), systemic clearance (CL), area under the concentration-time curve from dosing to the end of the dosing interval ($AUC_{tlast}$), and volume of distribution at steady state ($V_{SS}$). Serial samples for PK analysis will be collected before and at 0.5 (mid-infusion), 1 (end infusion), 1.5, 2, 3, 5, 7, 24, 48, 72, 96 or 120, and 168 hours after the start of each infusion on study Days 1 and 15. In addition, single random samples for SABA1.2 plasma concentration will be collected on Days 29 (336 hour specimen following Day 15 dose), 36, 43, 50, and 57.

Safety assessments will include vital signs, physical examinations, electrocardiograms, clinical laboratory assessments, and adverse events. In addition, immunogenicity will be assessed by measuring antidrug antibodies (ADA), serum indicators of autoimmunity (antinuclear antibodies [ANA], C3, and C4), and clinical observations (e.g., rash, infusion reactions, muscle or joint pain, etc.). HLA typing and T-cell stimulation assays will be performed to try to understand the mechanism of any observed immunogenicity.

Statistical Methods.

With 25 subjects, the lower bound of a single-sided 95% confidence interval (CI) for an observed T-HALF of 133.159 hours or greater will not extend to 120 hours. To obtain 25 actively treated completers, 1 extra subject per dose cohort will be included, for a total of 28 actively treated subjects.

Summary statistics will be tabulated for plasma PK parameters by dose and across doses. PK parameters will be derived from SABA1.2 plasma concentration versus time using non-compartmental methods. A compartmental approach may be used to further understand the disposition if warranted. Mean T-HALF will be estimated by 95% CIs. Geometric means and CV will be reported for Cmax, $AUC_{tlast}$, R, and CL; medians (min, max) for Tmax; and means and standard deviations for other parameters. The dose proportionality of SABA1.2 will be assessed. Log-transformed AUC and Cmax will be fitted to log-transformed dose using linear mixed effects modeling. A symmetrical, asymptotic 95% CI for the slope of the relationship will be constructed. If the 95% CI includes a value of 1.0, dose proportionality will be concluded. Conversely, if the 95% CI does not include a value of 1.0, non-proportionality will be concluded.

Safety results will be summarized descriptively by dose level and overall.

Starting Dose Rationale.

The NOEL (No observed effective level) in cyno monkeys is 30 mg/kg IV when dosed twice weekly for 5 doses. Based on dose expressed in terms of body surface area, the starting dose of SABA1.2 in this human clinical trial (0.1 mg/kg) represents a safety factor of 100-fold less than the NOEL in the monkey; while the highest planned dose in this study (1 mg/kg) represents a safety factor of 10-fold less. Based on projected human Cmax and AUC, the starting dose in this clinical study represents safety factors of approximately 600-fold and 200-fold, respectively, against the Day 15 monkey Cmax and AUC at the monkey NOEL; while based on the highest planned dose in this study, the projected human Cmax and AUC represent safety factors of approximately 50-fold and 20-fold, respectively, against the Day 15 monkey parameters. Thus, ample safety factors have been taken into consideration for the dosing levels in this study."

B. FGF21-SABA Fusion Molecules

Example B1

Preparation of FGF21-SABA Fusion Molecules

Overview

All FGF21-SABA DNA sequences disclosed herein were placed in a commercially available expression vector, pET29b (EMD Biosciences, San Diego, Calif., USA). Sequences were appropriately placed between the NDEI and XHOI restriction endonuclease sites of the plasmid vector just downstream from the ribosome binding site (FIG. 10).

The expression vectors were transformed into the host strain BL21(DE3) (EMD Biosciences) and expressed to various levels as inclusion bodies. Alternatively they can be transformed into oxidizing strains of *E. coli* strains such as "Origami™" (EMD Biosciences). The latter host strain contains mutations in both the thioredoxin reductase (trxB) and glutathione reductase (gor) genes, which greatly enhance disulfide bond formation in the *E. coli* cytoplasm. With proper care, various FGF21-SABA fusions such as those described in Table 2 have been expressed.

The purified plasmid DNA expression vectors were incorporated or "transformed" into the *E. coli* hosts noted above by standard transformation methods known commonly to those skilled in the field. Briefly, commercially prepared competent cells (EMD biosciences) were thawed on ice and mixed gently to ensure that the cells are evenly suspended. 20 μl aliquots of these cells were pipetted into 1.5-ml polypropylene microcentrifuge tubes ice pre-chilled on ice. Approximately 1 μl of or purified plasmid DNA (1-10 ng/μl plasmid) was added directly to the cells and stirred gently to mix. The tubes were kept on ice for 5 min and then heated for exactly 30 seconds in a 42° C. water bath. The heated tubes were placed immediately on ice and allowed to rest for 2 min. 80 μl of room temperature SOC or LB media was added to each tube. Selection for transformants was accomplished by plating on media containing kanamycin for the pET 29b plasmid-encoded drug resistance.

Expression of soluble FGF21-SABA fusion polypeptides in the Origami 2 cell line was initiated by growing an overnight starter culture of the transformed cells. Cells were used to inoculate 2 liter shake flasks containing 1 liter each of LB medium (Luria Broth) and were grown with vigorous shaking at 250-300 RPM at 37° C. until an O.D. 600 nm of 0.6 to 0.8 was reached. At this time, 0.1 mM IPTG (Isopropyl β-D-1-thiogalactopyranoside) was added to initiate T7 RNA polymerase induction and the temperature of the shaking incubator was lowered to 18° C. The fermentation was allowed to continue for 12-16 hours and the cells were harvested by centrifugation and frozen as a packed wet cell paste at −80° C.

Expression of FGF21-SABA fusion polypeptides as inclusion bodies (IB) in the BL21(DE3) cell line were also initiated by growing an overnight starter culture of the transformed cells. Cells were used to inoculate 2 liter shake flasks containing 1 liter each of Overnight Express™ medium (EMD Biosciences, and *Nature Methods* 2, 233-235, 2005). For the purposes of inclusion body formation, there was no need to lower the fermentation temperature and cells were instead grown at 37° C. for 12-16 hours prior to harvest by centrifugation. Harvested cells were frozen as a packed wet cell paste at −80° C.

Purification of the FGF21-SABA variants described varies depending on the exact sequence variant employed and whether or not the protein was expressed as a cytosol soluble form in the Origami cell line or as inclusion bodies in the BL21 cell line. Methods also depend on whether or not the sequence contains a 6×-Histidine tag to aid in purification. In general however, the purification methods share common techniques familiar to those skilled in the field. Below is a detailed description of the purification method.

Cell Lysis and Preparation of Inclusion Body (IB) Pellet

Cells were suspended in lysis buffer at a dilution of 8-10 parts buffer to one part packed cell paste. Cells were mechanically lysed using a Avestin C-5 Homogenizer (Avestin Inc. Ottawa, Ontario, Canada) by employing two passages at 2000PSI. After lysis, the lysate was spun down (4,000 RPM for 20-30 minutes) and the soluble fraction is discarded. The inclusion body pellet was washed with 0.5% Triton X-100 to remove cell debris and the suspension was centrifuged again. This process was repeated (typically 2 or 3 times) until the pellet appeared to be a homogenous white color. The resultant enriched IB preparation body pellet was then washed with PBS buffer to remove excess detergent.

Solubilization of Inclusion Bodies

The washed, detergent depleted IB pellet was then solubilized in 6M Guanidine-HCl buffered with 50 mM Tris-HCl pH 8.0 and 500 mM NaCl. Most of the material prepared in this way freely enters the solution phase, however a small amount of cell debris remains and was removed by centrifugation at 16,000 RPM in an SS-34 rotor for one hour. The supernatant was retained for the refolding and oxidation steps. Protein fusion variants containing a 6×His tag can alternatively be captured and further polished at this stage using a metal chelation chromatography step (IMAC). The chaotrope denatured material can be bound to the column and contaminants washed prior to elution in the presence of the denaturation buffer supplemented with immidazole.

Refolding and Oxidation

The guanidine-HCl solubilized material was diluted to about 1 mg/mL protein (estimated by absorbance at 280 nM) and placed into 3.5 MWCO dialysis tubing. The sample in the dialysis device was then was then floated in 4 L of refold buffer (50 mM Tris, 150 mM NaCl, 1 mM EDTA, pH 9.0) overnight at 4° C. with gentle stirring. The dialysis refold buffer is exchanged with fresh refold buffer the following morning. During this process, the disulfide bridge in the FGF21 domain of the fusion protein is readily air oxidized. This simple dialysis method is convenient and several samples can be processed at once if needed. Alternatively, the protein can be denatured in urea instead of guanidine-HCl. Alternatively, refolding and oxidation can also be carried out using rapid dilution of the molecule from high chaotropic salt concentrations to lower salt concentrations. Instead of air oxidation, the system can alternatively be refolded using a defined redox mixture of reduced and oxidized glutathione (GSH/GSSG).

Alternatively, instead of refolding these proteins in free diffusion phase via dialysis or rapid dilution as described above, they may also be refolded while bound to a chromatographic resin support. This method often has the advantage and improved yields as it minimizes protein interactions during the refolding phase that can lead to bulk aggregation and yield loss.

Removal of Precipitant

At the conclusion of the Refold and Oxidation step under these conditions, not all of the protein remains soluble. A portion of the molecule exists in an aggregated state and falls readily out of solution as a precipitant. This was removed via centrifugation at 16,000 RPM for an hour in an SS-34 rotor and is then typically filtered through a 0.2 μm syringe filter prior to chromatography.

Chromatographic Separation

Refolded FGF21-SABA fusion can be polished to remove DNA and other contaminants though the use of a Resource Q or similar ion exchange media system (GE Healthcare, Piscataway N.J.). A 40 mL Resource Q column is equilibrated in the refold buffer (50 mM Tris pH 9.0 with 150 mM NaCl, 1 mM EDTA) and the clarified, refolded material is passed through the column. Under these conditions, most of FGF21-SABA variants pass through the resin bed without binding. DNA and other cell debris from the washed inclusion bodes are retained on the column resin. Folded protein fusion variants containing a 6×His tag can alternatively be captured at this point using an immobilized metal ion affinity chromatography (IMAC) step and eluted with a gradient of immidazole or histidine.

Concentration

The protein sample enriched in the first chromatographic steps was then concentrated using a Pellicon® XL Device and Labscale™ tangential flow filtration (TFF) system (Millipore Inc., Billerica, Mass.) to approximately 4 mg/mL.

Size Exclusion Chromatography

The ~4 mg/mL sample of FGF21-SABA fusion was then further purified using a 26/60 Sephacryl S100 or 26/60 Superdex 75 size exclusion column (GE Healthcare, Piscataway N.J., USA) pre-equilibrated in PBS buffer pH 7.2. Sample corresponding to the monomeric protein fusion was pooled and the samples diluted to 1-2 mg/ml if necessary prior to freezing at −80° C. Using this method, up to 20 mg of FGF21-SABA fusion can be purified per 100 mL of original auto-induction media produced inclusion bodies.

Example B2

Characterization of FGF21-SABA Fusion Binding to Serum Albumin

The binding competency and thermodynamic characterization of FGF21-SABA fusion variants to human serum albumin were performed using Isothermal Titration calorimetry on a Microcal VP-ITC instrument (Microcal Inc. Amherst Mass., USA). Additionally, the binding competency and kinetic characterization of FGF21-SABA1 fusion variants to human serum albumin (HSA, Sigma #A3782,St. Louis Mo., USA), cynomolgous monkey serum albumin (CySA, Equitech-Bio #CMSA, Kerrville, Tex., USA), and murine serum albumin (MuSA, Sigma#A3559) were performed on a Biacore T100 instrument (GE Healthcare Inc, Piscataway, N.J.). The detailed experimental conditions are described below.

For the calorimetry assay, the FGF21-SABA variant SABA1-FGF21v1 (SEQ ID NO: 132) was used. A representative titration curve at 37° C. is shown in FIG. 11, and the $K_D$ was calculated to be 3.8 nM. For the SPR studies, SABA1-FGF21v1 and SABA1-FGF21v3 (SEQ ID NO: 134) were examined. SPR sensogram data for the binding of 1000, 500, 250, 125, and 62.5 nM fusion to serum albumin from human (HSA), cynomolgous monkey (CySA), and murine (MuSA) are shown in FIG. 12. Table 14 summarizes the kinetic data for the binding of these fusions to HSA, CySA, and MuSA.

TABLE 14

SPR kinetic data for the binding of SABA1-FGF21v1 and SABA1-FGF21v3 to HSA, CySA, and MuSA.

| Analyte | Ligand | Flow rate (µl/min) | Temp (° C.) | $k_a$ (1/Ms) | $k_d$ (1/s) | $K_D$ (nM) |
|---|---|---|---|---|---|---|
| SABA1-FGF21v3 | HSA | 30 | 37 | 6.16E+03 | 1.03E−03 | 170 |
| | | 60 | 37 | 5.87E+03 | 1.07E−03 | 180 |
| | CySA | 30 | 37 | 5.31E+03 | 1.17E−02 | 2200 |
| | | 60 | 37 | 4.38E+03 | 1.36E−02 | 3100 |
| | MuSA | 30 | 37 | no binding observed up to 1 uM analyte | | |
| | | 60 | 37 | no binding observed up to 1 uM analyte | | |
| SABA1-FGF21v1 | HSA | 30 | 25 | 3.38E+03 | 3.33E−04 | 98 |
| | | 30 | 37 | 5.96E+03 | 1.11E−03 | 190 |
| | CySA | 30 | 25 | 3.93E+03 | 4.70E−03 | 1200 |
| | | 30 | 37 | 4.44E+03 | 1.23E−02 | 2800 |
| | MuSA | 30 | 25 | no binding observed up to 1 uM analyte | | |
| | | 30 | 37 | no binding observed up to 1 uM analyte | | |

Detailed Protocol

Isothermal Titration Calorimetry

Purified SABA1-FGF21 fusion protein and commercially prepared human serum albumin (HSA, Sigma #A3782,St. Louis Mo., USA) were dialyzed in separate 3,500 MW dialysis bags against PBS buffer (10 mM sodium phosphate, 130 mM sodium chloride, pH 7.1) to ensure proper solvent matching for the experiment. SABA-FGF21 fusion protein plus buffer was placed in the instrument sample cell at a concentration range of 0.4 to 1.0 mg/mL protein. The matching buffer was placed in the reference cell. Concentrations were determined using extinction coefficients calculated from the protein sequences of the pure proteins. The instrument reaction cell was equilibrated at 37° C. Repeated injections of 10 ul each were made into the reaction cell form the injection syringe and the excess heat per mole of HSA was monitored. Data sets obtained were baseline-subtracted and corrected for the heat of dilution of the HSA injected into the cell. The resultant thermogram data was fitted using Origin™ evaluation software package (Microcal Inc.) version 2.0.2 to estimate the stochiometry, enthalpy, and equilibrium disassociation constant ($K_D$) of the protein-protein binding reaction.

Surface Plasmon Resonance

Serum albumins were dissolved in PBS buffer (10 mM sodium phosphate, 130 mM sodium chloride, pH 7.1) to a concentration of 10 mg/ml, and subsequently diluted to 8-10 µg/ml in 10 mM sodium acetate pH 5.0 for immobilization. Serum albumins were immobilized on a Series S CMS sensor chip using standard ethyl(dimethylaminopropyl) carbodiimide (EDC)/N-hydroxysuccinimide (NHS) chemistry in HBS-EP+ running buffer at 25° C., following general manufacturer guidelines. Flow cell 1 was activated with EDC/NHS and blocked with ethanolamine. Flow cells 2, 3 and 4 were each activated with EDC/NHS, followed by immobilization of 8-10 µg/ml serum albumins, and blocking with ethanolamine to achieve surface densities of 700 RU HSA (flow cell 2), 1100 RU CySA (flow cell 3), and 1050 RU MuSA (flow cell 4). Kinetic experiments were performed in PBS buffer containing 0.05% tween-20 (running buffer) at either 25° C. or 37° C. Stock solutions of SABA1-FGF21v3 (15.3 µM) or SABA1-FGF21v1 (40.6 µM) in PBS pH 7.2, were diluted to 1 µM with PBS running buffer, followed by serial dilutions (2:1) to generate concentration series of 1.0 µM, 0.5 µM, 0.25 µM, 0.125 µM, 0.063 µM for each protein. These samples were injected across flow cells 1-4 for 300 s, with a 420 s dissociation time, at flow rates of 30 µl/min or 60 µl/min to check for mass transfer limitation. All surfaces were regenerated with 2 pulses of 10 mM glycine pH 2.0 at 30 µl/min for 30 s. Raw sensograms were "double-referenced" by subtracting flow cell 1 data from flow cell 2, 3 or 4 data, and then subtracting a separate buffer cycle from each sensogram. The double-referenced sensogram data was fitted to a 1:1 Langmuir model using Biacore T100 Evaluation software version 2.0.2 to determine the association rate constant (ka), the dissociation rate constant ($k_d$), and the equilibrium dissociation constant ($K_D$).

Example B3

In Vitro Activity of SABA1-FGF21 Fusion in HEK-β-Klotho Cells

FGF21 induces ERK phosphorylation in the presence of β-klotho. Accordingly, the present HEK-β-klotho assay system was constructed to examine the functional activity of the FGF21-SABA fusions in vitro. Specifically, in vitro activity, potency ($EC_{50}$) and efficacy (as a percentage of maximal activity observed from an FGF21 molecule that is not fused to a SABA), were determined for the SABA1-FGF21v1 (SEQ ID NO: 132) fusion protein, as measured in the HEK β-Klotho expressing stable cell pERK 1/2 assay using the non-fused His-tagged FGF21 ("FGFv1"; SEQ ID NO: 125) as a comparator.

As shown in FIG. 13, SABA1-FGF21v1 dose dependently stimulates pERK 1/2 levels in HEK cells stably expressing human β-klotho. The potency ($EC_{50}$) is right shifted approximately 15 fold relative to the His-tagged FGF21, and the efficacy is 62% of His-tagged FGF21 (see Table 15 below). Therefore, SABA1-FGF21v1 retains FGF21 activity even when bound to human serum albumin.

TABLE 15

Potency of SABA-FGF21 fusion as compared to control FGF21.

| Protein | $EC_{50}$ (nM) | Efficacy (%) |
|---|---|---|
| His6-tagged FGF21 | 7 ± 4 | 100 |
| SABAl-FGF21v1 | 102 ± 53 | 62 ± 9 |

*Potency ($EC_{50}$) and efficacy (% of His6-tagged FGF21 maximal activity) of compounds as measured in the HEK β-Klotho expressing stable cells pERK ½ assay. Compiled data from multiple experiments given as mean ± std. dev. from N ≥4 independent assays.

In specificity assays in parental HEK cells, which do not express β-klotho endogenously, neither His-tagged FGF21 nor SABA1-FGF21v1 stimulated pERK 1/2 levels, while the positive control, FGF1, did (FIG. 14A). In a parallel experiment using the same dilutions of proteins, but the standard assay HEK β-klotho stable cells, all three proteins showed activity (FIG. 14B). Hence, SABA1-FGF21v1 retains the specificity of FGF21 even when bound to albumin.

For the present cell-based assays, it was necessary to first determine the concentration of drug necessary to activate the pERK phosphorylation pathway. To this end, the fusion protein was titrated into the cells in the presence and in the absence of HSA in the cell media. In the case where HSA was added, it was added at physiological concentrations found in the blood stream (30 to 40 mg/mL-500 uM HSA). This concentration is several thousand fold above the concentration necessary to saturate all the FGF21-SABA fusion protein. The FGF21-SABA-HSA solution binding constant is ~4 nM (see FIG. 11). There was no change in the activity of the protein fusion in the assay regardless of the presence of HSA, indicating that the activity of the FGF21 domain is not altered when the fusion protein is in complex with HSA.

Below is a detailed description of the experimental methods.

HEK-β-Klotho Stable Cell Line Construction

A HEK cell line stably expressing human β-klotho was constructed. The human β-klotho construct encoded the full length protein under the control of a CMV promoter with a C-terminal FLAG tag. HEK 293 cells were transfected with the linearized cDNA using Lipofectamine 2000 (Invitrogen catalog #11668027) following the manufactures protocol using standard techniques. Positive clones were isolated after 14 days of selection in 600 ug/ml (Invitrogen catalog #10131) of geneticin in Dulbecco's Modified Eagle Medium with high glucose containing L-Glutamine, Hepes (Invitrogen catalog #12430054) and 10% FBS (HyClone catalog # SH30071). Positive stable clones were further characterized by Western Blot analysis and p-ERK activation by AlphaScreen (Perkin Elmer catalog # TGRES50K) analysis.

HEK β-Klotho pERK 1/2 Assay

HEK cells stably expressing human β-klotho were plated at 20,000 cells/well in 96 well tissue culture plates in DMEM high glucose media (Gibco) containing 10% (v/v) FBS (Hyclone) and 600 μg/ml G418 (Gibco). The following day, the media was removed and replaced with DMEM high glucose media without serum and the cells were incubated overnight. The morning of the third day the serum free media was removed and the cells were incubated for a total of seven minutes with dilutions of the proteins made in PBS containing 3% (w/v) fatty acid free human serum albumin. Dilutions were tested in triplicate, one well on each of three plates. At the end of the seven minute incubation, the protein dilutions were removed and 100 μl of 1x AlphaScreen lysis buffer (Perkin-Elmer) was added per well and allowed to incubate with shaking for approximately 10-15 minutes. The plates containing the cellular lysates were frozen at −80° C. for at least 30 minutes or until ready to assay. Four μl from each well of thawed cell lysate was analyzed for pERK 1/2 using the Surefire AlphaScreen pERK 1/2 kit (Perkin Elmer) using 384 well white Proxiplates (Perkin Elmer) following the manufacturer's directions. Plates were incubated at room temperature for two hours in the dark and then read on an Envision 2103 Multiplate reader (Perkin Elmer). Data were analyzed using Graph Pad Prism software using a non-linear regression analysis.

Selectivity assays were performed as above using the parental HEK cell line which does not express β-klotho endogenously. FGF1 was used as a positive control in those experiments.

Example B4

In Vitro Activity of SABA1-FGF21v1 in 3T3-L1 Adipocytes

3T3-L1 cells (ATCC # CL-173) are mouse fibroblasts that can be differentiated into mouse adipocytes. Since β-klotho is expressed only in differentiated 3T3-L1 cells, it was necessary to first differentiate them before performing a β-klotho pERK 1/2 assay as described in Example B3. Similar to its activity in the HEK system, SABA1-FGF21v1 retains the ability to phosphorylate ERK in 3T3-L1 adipocytes, and this activity is comparable to His-tagged FGF21. The results are shown in Table 16.

TABLE 16

SABA1-FGF21v1 activity is comparable to His-tagged FGF21 in 3T3-L1 adipocytes.

| Compound | $EC_{50}$ (nM) | Fold Activation |
|---|---|---|
| His-tagged FGF21 | 4 ± 2 | 2.1 ± 0.2 |
| SABA1-FGF21v1 | 11 ± 4 | 1.8 ± 0.2 |

Below is a detailed description of the experimental methods.

Differentiating of 3T3-L1 Adipocytes

The cells were grown in DMEM media (Invitrogen #12430-054) supplemented with 10% characterized fetal bovine serum (Hyclone # SH30071.03) and 1X Antibiotic-Antimycotic (Gibco #15240-096). Cells were cultured in a 37° C. incubator with 5% $CO_2$. The sub-culturing procedure was followed as described in ATCC's product information sheet with the exception that TrypLE Express (Gibco #12605) was used instead of the Trypsin-EDTA solution.

Approximately 68 hours before differentiation, 5500 cells per well (in 150 μl media) were seeded into 96 well plates (Falcon #353072); cell numbers could be adjusted according to the time of the seeding and their doubling time, but cells were 100% confluent at the time the differentiation procedure was started. To start the differentiation, the cell supernatant was carefully aspirated and 200 μl of fresh differentiation media I (Growth media containing IBMX 500 μM, dexamethasone 100 nM, insulin 240 nM, all from Sigma) was added to each cell well. The cells were then incubated for 41 to 48 hours before the cell supernatant was carefully aspirated and 200 μl of differentiation media II (Growth media containing insulin at 240 nM) was added to each cell well. After the cells were incubated for a second 48 hour period, the cell supernatant was carefully aspirated and 200 μl of regular growth media was added to each well. The cells were then incubated for another 48 to 72 hour, at which point they would be well differentiated into adipocytes.

Establishment of pERK Assay in 3T3-L1 Adipocytes

At the ninth to tenth day of differentiation, the growth media was aspirated off the cells and cells were starved with 200 μl of DMEM (Invitrogen #12320-032) with 2% fetal bovine serum overnight. The following day, the starved cells were stimulated with 100 ul DMEM plus 0.1% fatty acid free BSA (Sigma # A6003) containing the test agent (FGF21 or one of its variants) or PBS as control using a Tomtec Quadra to ensure simultaneous addition to all 96 wells in the plate. The plate was then incubated for 7 minutes in a 37° C. incubator with 95% air/5% $CO_2$. After 7 minutes, the treatment medium was removed from the cells and 100 ul lysis buffer was added to each well. The lysis buffer stock was PerkinElmer's AlphaScreen SureFire p-ERK1/2 Assay kit (Cat# TGRES10K), supplemented with 0.5 mM DTT (Sigma, D9779), 5 mM Sodium Pyrophosphate (Sigma, S6422), 1 mM Sodium Orthovanadate (Sigma 56508) and Roche's protease inhibitor tablet (#04693159001). The detection protocol was based on the assay kit: The plate with lysis buffer was agitated on a plate shaker for approximately 15 minutes and frozen in −80° C. for 30 minutes. The plate was thawed at room temperature (approximately 40 minutes) and lysate was agitated (by pipeting up and down 20 times) to ensure complete lysis. Then 4 μl lysate from each well was transferred into a 384 well plate and 7 μl of reaction mix (activation buffer and IgG detection donor and acceptor beads [PerkinElmer #6760617M] mixed according to the kit protocol) was added into each well. The plate was sealed and agitated for 1-2 minutes followed by incubation at 22° C. for 2 hours in light-proof area. The plate was finally read on a PerkinElmer Envision 2103 Multilabel Reader, using standard Alpha Screening settings.

Example B5

In Vivo Efficacy of SABA1-FGF21v1 in Diabetic Ob/Ob Mice

FGF21 has been shown to increase glucose uptake in 3T3-L1 adipocytes and primary human adipocyte cultures. Thus, monitoring plasma glucose levels in diabetic ob/ob mice represents one way that the functional activity of the FGF21-SABA fusion proteins can be assessed. Beginning at 8 weeks of age, diabetic ob/ob mice received daily subcutaneous doses for 7 days (n=8 per group). All protocols were approved by the BMS ACUC committee. Fed glucose levels were examined both 24 hr and 3 hr post-dose on day 7 beginning at 8:00 AM. His-tagged FGF21 and SABA1-FGF21v1 were formulated in PBS and dosed at 0.3 mg/kg, and 1.0 mg/kg. respectively.

To evaluate the efficacy of SABA1-FGF21v1 bound to human albumin, the fusion protein (1 mg/kg) was incubated with a molar excess of human serum albumin (6 mg/kg) and the mixture was injected in an additional group (q.d. s.c. for 7 days). Human serum albumin (6 mg/kg) was used as an additional control group.

The results shown in FIG. 15 indicate that SABA1-FGF21v1 lowers glucose by 29% compared to the PBS vehicle control at 3 hours post dose and this lowering is comparable to that by His-tagged FGF21 on day 7 (FIG. 15A). In contrast, the combination of SABA1-FGF21v1 and human albumin lowers plasma glucose levels by 46% compared to the HSA control.

At 24 hours post dose, the magnitude of glucose lowering by SABA1-FGF21v1 is 7% while the combination of SABA1-FGF21v1 and HSA was 41%, and therefore sustained 24 hr after the last dose, on day 7 (FIG. 15B). Hence, SABA1-FGF21v1 was very effective at lowering plasma glucose levels in ob/ob mice even when bound to human serum albumin. The exposures of SABA1-FGF21v1 with and without human albumin are shown in Tables 17 and 18. The exposure of SABA1-FGF21v1 is greater in the presence of human serum albumin than in its absence.

TABLE 17

Plasma concentrations of His-tagged FGF21 and SABA1-FGF21v1 at 3 hours post dose.

| | His6-tagged FGF21 (0.3 mg/kg) | SABA1-FGF21v1 (1 mg/kg) | HSA + SABA1-FGF21v1 (1 mg/kg) |
|---|---|---|---|
| Concentration (ng/ml) | 99 | 1370 | 8757 |
| S.D. | 39 | 326 | 895 |

S.D.: standard deviation

TABLE 18

| Plasma concentrations of His-tagged FGF21 and SABA1-FGF21v1 at 24 hours post dose. | His6-tagged FGF21 (0.3 mg/kg) | SABA1-FGF21v1 (1 mg/kg) | HSA + SABA1-FGF21v1 (1 mg/kg) |
|---|---|---|---|
| Concentration (ng/ml) | <LLOQ | <LLOQ | 5095 |
| S.D. | | | 2166 |

<LLOQ is less than lower limit of quantitation.

Example B6

Measurement of SABA1-FGF21v1 Plasma $t_{1/2}$ in Mice and Monkeys

Various in vivo studies were conducted in mice and monkeys to characterize the pharmacokinetics of His-tagged FGF21 and SABA1-FGF21v1. An ELISA-based ligand binding assay was used to measure the His-tagged FGF21 and SABA1-FGF21v1 in all mouse and monkey plasma samples.

Pharmacokinetics of his-Tagged FGF21 and SABA1-FGF21v1 in Mice Following Intravenous and Subcutaneous Administration His-Tagged FGF21

After intravenous administration (1 mg/kg) in CD-1 mice, the steady-state volume of distribution (Vss) for His-tagged FGF21 was 0.27 L/kg. The total body plasma clearance (CLTp) value was 12 mL/min/kg. The terminal half-life ($T_{1/2}$) was 0.5 h. Following subcutaneous administration, His-tagged FGF21 was well absorbed. The absolute subcutaneous bioavailability was ~100%. The apparent subcutaneous terminal half-life ($T_{1/2}$) was 0.6 h.

SABA1-FGF21v1

After intravenous administration (1.6 mg/kg) in CD-1 mice, the steady-state volume of distribution (Vss) for SABA1-FGF21v1 was 0.12 L/kg. The total body plasma clearance (CLTp) value was 2.9 mL/min/kg. The terminal half-life ($T_{1/2}$) was 1.9 h, longer than His-tagged FGF21 (0.5 h). Following subcutaneous administration, SABA1-FGF21v1 was well absorbed. The apparent subcutaneous terminal half-life ($T_{1/2}$) was 1.9 h.

SABA1-FGF21v1 was also administered to ob/ob mice at 1 mg/kg subcutaneously after pre-mix with human serum albumin (6 mg/kg). The apparent subcutaneous terminal half-life ($T_{1/2}$) was further increased to 9 h.

Pharmacokinetics of his-Tagged FGF21 and SABA1-FGF21v1 in Monkeys Following Intravenous and Subcutaneous Administration His-Tagged FGF21

After intravenous administration (0.5 mg/kg), the steady-state volume of distribution (Vss) for His-tagged FGF21 was 1 L/kg. The total body plasma clearance (CLTp) value was 6.4 mL/min/kg. The terminal half-life ($T_{1/2}$) was 1.9 h. Following subcutaneous administration, His-tagged FGF21 was well absorbed. The absolute subcutaneous bioavailability was 65%. The apparent subcutaneous terminal half-life ($T_{1/2}$) was 4.3 h.

SABA1-FGF21v1

After intravenous administration (0.08 mg/kg), the steady-state volume of distribution (Vss) for SABA1-FGF21v1 was 0.08 L/kg. The total body plasma clearance (CLTp) value was 0.012 mL/min/kg. The terminal half-life ($T_{1/2}$) was 97 h. Following subcutaneous administration, SABA1-FGF21v1 was well absorbed. The absolute subcutaneous bioavailability was 68%. The apparent subcutaneous terminal half-life ($T_{1/2}$) was 67 h.

FIG. 16 shows $t_{1/2}$ of exemplary fusions, SABA1-FGF21v3 (SEQ ID NO:134) and FGF21-SABA1v1 in which the SABA moiety is at the C-terminus of FGF21 (SEQ ID NO: 171), in monkeys as compared to His-tagged FGF21. The results indicate that the fusions increased $t_{1/2}$~27-fold compared to FGF21 alone. The data is summarized in Table 19 below.

TABLE 19

| Pharmacokinetic data for SABA-FGF21 fusions. | CL mL/min/Kg | Vdss L/kg | T½ h |
|---|---|---|---|
| His-tagged FGF21 | 6.4 | 1.0 | 1.9 |
| SABA1-FGF21v3 | 0.04 | 0.11 | 52.7 |
| FGF21-SABA1v1 | 0.02 | 0.06 | 50.3 |

Example B7

SABA1-FGF21v1 Lowers HbA1c in Ob/Ob Mice

Additional acute and chronic effects of SABA1-FGF21v1 were examined in the diabetic ob/ob mice. At study termination after 3 weeks of daily treatment, reductions in plasma glucose, insulin and total cholesterol were observed. Plasma alanine aminotransferase was reduced and β-hydroxybutyrate levels were elevated. In an oral glucose tolerance test, SABA1-FGF21v1 treated animals demonstrated an increased capacity to handle a glucose load.

Another experiment was performed in diabetic ob/ob mice (n=8 per group) receiving one of three different doses of SABA1-FGF21v1 (0.01, or 0.1 or 1 mg/kg) premixed with human serum albumin (HSA at 6 mg/kg) and injected (s.c. q.d.) for 14 days. The control group received HSA (6 mg/kg in PBS) only. HbA1c was measured in plasma samples 24 hours after the last dose (see FIG. 19). The control group (receiving HSA only) showed no decrease in HbA1c levels compared to baseline values. The lowest dose (0.01 mg/kg) showed no decrease, the intermediate dose (0.1 mg/kg) showed a decrease of 0.39%, which was not statistically significant. The highest dose of 1 mg/kg (or mpk) showed a decrease of 0.9% with respect to baseline, and a 0.94% vehicle subtracted decrease in HbA1c, which was statistically significant. Hence, SABA1-FGF21v1 co-injected with human albumin was effective in lowering HbA1c levels in diabetic mice.

SABA1-FGF21v1 plasma levels at the 0.01, 0.1 and 1 mg/kg doses were 3.85, 2.28 and 28.73 ng/ml respectively, 24 hours after the last dose.

Example B8

Pharmacokinetics of SABA1-FGF21v1 in Cynomolgus Monkeys

Following intravenous (IV) administration, the steady-state volume of distribution (Vss) of SABA1-FGF21v1 was 0.076 L/kg. This value was greater than plasma volume, but less than the volume of extracellular fluid, indicating that SABA1-FGF21v1 largely resides in the extracellular space. Total body plasma clearance of SABA1-FGF21v1 was low (0.71 mL/h/kg) consistent with high affinity binding to monkey serum albumin. The terminal half-life (T½) was 97 h (see FIG. 20 and Table 20). Furthermore, SABA1-FGF21v1 demonstrated good subcutaneous (SC) bioavailability in monkeys (see FIG. 20 and Table 20). The absolute SC bioavailability was 68%.

TABLE 20

Single-dose Pharmacokinetic Parameters (mean ± SD) of SABA1-FGF21v1 in Monkeys.

| Species | Route | Strain | Dose (mg/kg) | Cmax (nM) | Tmax (h) | AUCtot (nM · h) | T½ (h) | CLTp (mL/h/kg) | Vss (L/kg) | F (%) |
|---|---|---|---|---|---|---|---|---|---|---|
| Monkey | IV | cyno | 0.08 | — | — | 3621 | 97 | 0.71 | 0.076 | — |
| | SC | cyno | 0.08 | 22.4 ± 10.8* | 13 ± 9* | 2454 ± 779 | — | — | — | 68 |

*Plasma sample at 24 h post dose in one of three animals was not collected;
Monkey: N = 2 (IV) and 3 (SC).

C. SABA-Synthetic Peptide Fusion Molecules

Example C1

Preparation of SABA Polypeptides for Use in SABA-Synthetic Peptide Fusion Molecules Linked by a Chemically Derived Spacer The method described below was used to produce SABA1.7-$(ED)_5$G-Cys polypeptides for conjugation to a synthetically derived peptide to form a SABA fusion protein. This process may also be used to produce SABA-peptide fusions covalently attached via a polypeptide linker.

DNA sequences encoding SABA1.7 (SEQ ID NO: 225) with an $(ED)_5$G C-terminal tail (SEQ ID NO: 397) and a C-terminal His residue (SABA1.7-$(ED)_5$G-Cys) were placed in a commercially available expression vector, pET29b (EMD Biosciences, San Diego, Calif., USA). Sequences were appropriately placed between the NDEI and XHOI restriction endonuclease sites of the plasmid vector just downstream from the ribosome binding site (FIG. 10). The expression vector was transformed into the host strain BL21(DE3) (EMD Biosciences) and expressed as inclusion bodies.

The purified plasmid DNA expression vector was incorporated or "transformed" into the *E. coli* host noted above by standard transformation methods known commonly to those skilled in the field. Briefly, commercially prepared competent cells (EMD biosciences) were thawed on ice and mixed gently to ensure that the cells are evenly suspended. 20 µl aliquots of these cells were pipetted into 1.5-ml polypropylene microcentrifuge tubes ice pre-chilled on ice. Approximately 1 of purified plasmid DNA (1-10 ng/µl plasmid) was added directly to the cells and stirred gently to mix. The tubes were kept on ice for 5 min and then heated for exactly 30 seconds in a 42° C. water bath. The heated tubes were placed immediately on ice and allowed to rest for 2 min. 80 µl of room temperature SOC or LB media was added to each tube. Selection for transformants was accomplished by plating on media containing kanamycin for the pET 29b plasmid-encoded drug resistance.

Expression of soluble SABA1.7-$(ED)_5$G-Cys in *E. coli* was initiated by growing an overnight starter culture of the transformed cells. Cells were used to inoculate 2 liter shake flasks containing 1 liter each of Overnight Express™ medium (EMD Biosciences, and Nature Methods 2: 233-235 (2005)). Reduction of the temperature of the shaking incubator can be lowered to 18° C. to improve soluble yield. The fermentation was allowed to continue for 12-16 hours and the cells were harvested by centrifugation and frozen as a packed wet cell paste at −80° C. Formation of protein inclusion bodies (IB) was found to be favorable as it helps to protect and minimize host cell protease cleavage.

Cell Lysis and Preparation of Inclusion Body (IB) Pellet

Cells were thawed and suspended in lysis buffer at a dilution of 8-10 parts buffer to one part packed cell paste. Cells were mechanically lysed using a Avestin C-5 Homogenizer (Avestin Inc. Ottawa, Ontario, Canada) by employing two passages at 2000PSI. After lysis, the lysate was spun down (4,000 RPM for 20-30 minutes) and the soluble fraction is discarded. The inclusion body pellet was washed with 0.5% Triton X-100 to remove cell debris and the suspension was centrifuged again. This process was repeated (typically 2 or 3 times) after which the pellet appears a homogenous white color. The resultant enriched IB preparation body pellet was then washed with PBS buffer to remove excess detergent.

Solubilization of Inclusion Bodies

The washed, detergent depleted IB pellet was then solubilized in 6M Guanidine-HCl buffered with 50 mM Tris-HCl pH 8.0 and 500 mM NaCl. Most of the material prepared in this way freely enters the solution phase, however a small amount of cell debris remains and was removed by centrifugation at 16,000 RPM in an SS-34 rotor for one hour. The supernatant was retained for the refolding and oxidation steps. Proteins containing a 6×His tag can alternatively be captured and further polished at this stage using a metal chelation chromatography step (IMAC). The chaotrope denatured material can be bound to the column and contaminants washed prior to elution in the presence of the denaturation buffer supplemented with immidazole.

Refolding (and Control of Oxidation)

The guanidine-HCl solubilized material was diluted to about 1 mg/mL protein (estimated by absorbance at 280 nM) and placed into 3.5 MWCO dialysis tubing. The sample in the dialysis device was then floated in 4 L of refold buffer (50 mM Tris, 150 mM NaCl, 1 mM EDTA, pH 9.0) overnight at 4° C. with gentle stirring. The dialysis refold buffer is exchanged with fresh refold buffer the following morning.

During this process, modulation of the disulfide oxidation and/or bridge formation of a fusion protein may be accomplished depending on need. For Peptides such as Amylin, which require a disulfide bridged to be formed between two Cysteine residues in its polypeptide sequence to attain proper final form, the system is allowed to air oxidize during the dialysis process. For SABA1.7-$(ED)_5$G-Cys, which contains a single Cysteine residue that must be reduced so that it can be Maleimide conjugated to a peptide of interest later, oxidation can be minimized by addition of reducing agents (e.g. TCEP tris[2-carboxyethyl]phosphine (TCEP) or dithiothreitol (DTT)) at the end of the refold process. Refolding with minimal oxidation can also be accomplished by refolding at pH 4.5 where the thiolate anion of the Cys amino acid does not readily populate and initiate disulfide bridge formation.

These simple dialysis methods are convenient and several samples can be processed at once if needed. Alternatively, the protein can be denatured in urea instead of guanidine-HCl. Alternatively, refolding and oxidation can also be carried out using rapid dilution of the molecule from high chaotropic salt concentrations to lower salt concentrations. Instead of air oxidation, the system can alternatively be refolded using a defined redox mixture of reduced and oxidized glutathione (GSH/GSSG). Alternatively, instead of refolding these proteins in free diffusion phase via dialysis or rapid dilution as described above, they may also be refolded while bound to a chromatographic resin support. This method often has improved yields as it minimizes protein interactions during the refolding phase that can lead to bulk aggregation and yield loss.

Removal of Precipitant

At the conclusion of the Refold step (and oxidation step if needed), not all of the protein remains soluble. A portion of the protein exists in an aggregated state and falls readily out of solution as a precipitant. This material was removed via centrifugation at 16,000 RPM for an hour in an SS-34 rotor and is then typically filtered through a 0.2 μm syringe filter prior to chromatography.

Chromatographic Separation

Refolded SABA1.7-$(ED)_5$G-Cys can be polished to remove DNA and other contaminants though the use of a Resource Q or similar ion exchange media system (GE Healthcare, Piscataway N.J.). A 40 mL Resource Q column is equilibrated in the refold buffer (50 mM Tris pH 9.0 with 150 mM NaCl, 1 mM EDTA) and the clarified, refolded material is passed through the column. Under these conditions, most of polypeptides pass through the resin bed without binding. DNA and other cell debris from the washed inclusion bodes are retained on the column resin. Folded polypeptides containing a 6×His tag can alternatively be captured at this point using an immobilized metal ion affinity chromatography (IMAC) step and eluted with a gradient of immidazole or histidine.

Size Exclusion Chromatography

SABA1.7-$(ED)_5$G-Cys can then be further purified using a 26/60 Sephacryl S100 or 26/60 Superdex 75 size exclusion column (GE Healthcare, Piscataway N.J., USA) pre-equilibrated in PBS buffer pH 7.2. Sample corresponding to the monomeric protein was pooled and the samples diluted to 1-2 mg/ml if necessary prior to freezing at −80° C. Expression and purification yields of the proteins expressed and purified herein vary. Using these methods, purified yields from 0.5 to 10 mg or more of purified protein can be produced per L of original auto-induction media produced inclusion bodies.

Example C2

Chemical Synthesis of Neuropeptides for Use in SABA-Neuropeptide Fusion Molecules Linked by a Chemically Derived Spacer

Example C2-1

Synthesis of 3-Maleimidopropionyl-$PEG_{20}$-Rat Amylin: Mal-$(PEG)_{20}$-KCNTATCATQRLANFLVRSSNNLGPVLPPTNVGSNTY-$NH_2$ The peptide was prepared by solid phase synthesis using a Liberty microwave peptide synthesizer (CEM Corp., Matthews, N.C.). The Fmoc deprotection and the coupling steps were performed at 75° C. using microwave heating provided by power pulsing sequences of 20 W. The reaction temperatures were monitored with a fiberoptic probe inserted into the reaction vessel. The synthesis was started from 0.25 mmol of Fmoc-protected PAL-PEG resin (0.34 mmol/g) placed into a 50 mL polypropylene vessel. The amino acids were coupled using the 0.25 mmol scale method provided by the manufacturer. At the beginning of each coupling step, the Fmoc group was removed by two 5 min. treatment with 5% piperazine in DMF containing 0.1 M HOBt. After 5 20 mL DMF washes, the required Fmoc-amino acids were successively coupled by activation with 0.5 M HCTU (4 eq.) in DMF and 2 M DIEA (8 eq.) in NMP for 5 minutes. At the end of each coupling, the resin was washed with 5 20 mL DMF washes. Prior to coupling of the Fmoc-$PEG_{20}$, half of the peptidyl-resin (0.125 mmol) was removed, and Fmoc-$PEG_{20}$ was coupled on the synthesizer as described above. The Fmoc-deprotected peptidyl-resin was transferred into a fritted polypropylene reactor and 3-maleimido propionic acid was manually coupled by activation with HOAt/DIC (5 eq.) for 16 hrs. The peptidyl-resin was washed with DMF (4×5 mL) and DCM (4×5 mL) and DMF again (4×5 mL). A solution of $I_2$ (20 eq.) in 10 mL of DMF was added and the mixture was stirred for 1 hr. The resin was washed with DMF (5×5 mL) and DCM (3×5 mL), yielding the desired rat Amylin peptide derivative Mal-$(PEG)_{20}$-KCNTATCATQRLANFLVRSSNNLGPVLPPTNVGSNTY-$NH_2$ (amide) as a cyclic disulfide product.

The peptide was deprotected and released from the resin by treatment with TFA/water/phenol (90:5:5; v:v:w) (15 mL) for 90 minutes at RT. The spent resin was filtered off and rinsed with additional cleavage solution (2×2.5 mL). The combined filtrates were evaporated to ~4 mL and the product was precipitated by addition of $Et_2O$ (35 mL). The precipitated product was collected by centrifugation, washed with additional $Et_2O$ and dried to yield an off-white solid (50% of theory).

The crude peptide was purified by preparative RP-HPLC on a Shimadzu Model LC-8A liquid chromatograph as follows. The peptide was dissolved into water/AcCN/TFA (60:40:0.1), filtered through a 0.45 micron filter, and 30 mg at a time were injected onto a Phenomenex Luna C18 column (21.2×100 mm; 5μ). A gradient of 25-45% B in A over 45 min was used to elute the product at 15 mL/min with UV detection at 220 nm. Solvent A: 0.1% TFA in water; Solvent B: 0.1% TFA in AcCN. The fractions containing a clean product as determined by analytical HPLC were combined and lyophilized to yield an at least 95% pure product as a white lyophilate. The identity of the peptide was confirmed by LC/MS analysis in electrospray mode. The experimentally observed m/z ions $(M+3H)^{3+}/3=1464.0$ and $(M+4H)^{4+}/4=1097.9$ are consistent with the calculated molecular weight, 4389.9 D.

Example C2-2

Synthesis of 3-Maleimidopropionyl-$(GS)_5$—Rat Amylin: Mal-GSGSGSGSGS-KCNTATCATQRLANFLVRSSNNLGPVLPPTNVGSNTY-$NH_2$ The peptide was prepared using the same solid phase coupling and disulfide cyclization method described in Example C2-1, yielding the desired rat Amylin peptide derivative Mal-GSGSGSGSGS-KCNTATCATQRLANFLVRSSNNLGPVLPPTNVGSNTY-$NH_2$ (amide) as a cyclic disulfide product. After deprotection and release from the resin, the crude peptide was purified by preparative RP-HPLC as described in Example C2-1, except that a gradient of 10-55% B in A over 40 min was used to elute the peptide, yielding an at least 98% pure product. The identity of the peptide was confirmed by LC/MS analysis in electrospray mode. The 4792.2 D molecular weight derived from the experimentally observed m/z ions $(M+3H)^{3+}/3=1598.3$ and $(M+4H)^{4+}/4=1199.3$ is within 1 Dalton of the calculated molecular weight, 4791.2 D.

Example C2-3

Synthesis of 3-Maleimidopropionyl-Ahx-Mouse PYY(3-36): Mal-Ahx-AKPEAPGE-DASPEELSRYYASLRHYLNLVTRQRY-$NH_2$ This peptide was prepared using the same solid phase procedures described in Example C2-1, yielding the desired mouse PYY(3-36) peptide derivative Mal-Ahx-AKPEAPGEDASPEELSRYYASLRHYLNLVTRQRY-$NH_2$. The $Ala^{12}$-$Ser^{13}$ and $Ala^{22}$-$Ser^{23}$ residue pairs were coupled as the Fmoc-Ala-Ser($\psi^{Me,Me}$pro)-OH pseudoproline dipeptide (EMD Chemicals, Inc., San Diego, Calif.). After deprotection and release from the resin, the crude peptide was purified by preparative RP-HPLC as described in Example C2-1, except that a gradient of 5-50% B in A over 45 min was used to elute the peptide, yielding an at least 97% pure product. The identity of the peptide was confirmed by LC/MS analysis in electrospray mode. The experimentally observed m/z ions $(M+3H)^{3+}/3=1415.8$ and $(M+4H)^{4+}/4=1062.2$ are consistent with the calculated molecular weight, 4244.7 D.

Example C2-4

Synthesis of 3-Maleimidopropionyl-$PEG_{20}$-Mouse PYY(3-36): Mal-$PEG_{20}$-AKPEAPGE-DASPEELSRYYASLRHYLNLVTRQRY-$NH_2$ This peptide was prepared using the same solid phase coupling procedures described in Example C2-3, except that Fmoc-$PEG_{20}$-OH was coupled in place of Fmoc-6-Ahx-OH, thus yielding the desired mouse PYY(3-36) peptide derivative Mal-$PEG_{20}$-AKPEAPGEDASPEELSRYYASLRHYLNLVTRQRY-$NH_2$. After de-protection and release from the resin, the crude peptide was purified by preparative RP-HPLC as described in Example C2-3, yielding an at least 86% pure product. The identity of the peptide was confirmed by LC/MS analysis in electrospray mode. The experimentally observed m/z ions $(M+3H)^{3+}/3=1484.8$ and $(M+4H)^{4+}/4=1113.5$ are consistent with the calculated molecular weight, 4449.9 D.

Example C2-5

Synthesis of 3-Maleimidopropionyl-$(GS)_5$-Mouse PYY(3-36): Mal-GSGSGSGSGS-AKPEAPGE-DASPEELSRYYASLRHYLNLVTRQRY-$NH_2$ This peptide was custom synthesized by GenScript USA, Inc., Piscataway, N.J., using solid phase procedures similar to those described in Example C2-3, yielding the desired mouse PYY(3-36) peptide derivative Mal-GSGSGSGSGS-AKPEAPGEDASPEELSRYYASLRHYLNLVTRQ RY-$NH_2$ in 95% purity. The identity of the peptide was confirmed by LC/MS analysis in electrospray mode. The experimentally observed m/z ions $(M+3H)^{3+}/3=1618.5$ and $(M+4H)^{4+}/4=1214.1$ are consistent with the calculated molecular weight, 4852.2 D.

Example C2-6

Synthesis of 3-Maleimidopropionyl-Ahx-Mouse PP: Mal-Ahx-APLEPMYPGDYATPEQMAQYETQLR-RYINTLTRPRY-$NH_2$ This peptide was prepared using the same solid phase procedures described in Example C2-3, yielding the desired mouse PP peptide derivative Mal-Ahx-APLEPMYPGDYATPEQMAQYETQLRRYINTLTRPRY-$NH_2$ (amide). The $Ala^{12}$-$Thr^{13}$ residue pair was coupled as the Fmoc-Ala-Thr($\psi^{Me,Me}$pro)-OH pseudoproline dipeptide (EMD Chemicals, Inc., San Diego, Calif.). After de-protection and release from the resin, the crude peptide was purified by preparative RP-HPLC as described in Example C2-3, yielding an at least 99% pure product. The identity of the peptide was confirmed by LC/MS analysis in electrospray mode. The 4597.5 D molecular weight derived from the experimentally observed m/z ions $(M+3H)^{3+}/3=1533.5$ and $(M+4H)^{4+}/4=1150.4$ is within 1 Dalton of the calculated molecular weight, 4598.2 D.

Example C2-7

Synthesis of 3-Maleimidopropionyl-$PEG_{20}$-Mouse PP: Mal-$PEG_{20}$-APLEPMYPGDYATPEQMAQY-ETQLRRYINTLTRPRY-$NH_2$ This peptide was prepared using the same solid phase procedures described in Example C2-6, except that Fmoc-$PEG_{20}$-OH was coupled in place of Fmoc-6-Ahx-OH, yielding the desired mouse PP peptide derivative Mal-$PEG_{20}$-APLEPMYPGDYATPEQMAQYETQLR RYINTLTRPRY-$NH_2$ (amide). After deprotection and release from the resin, the crude peptide was purified by preparative RP-HPLC as described in Example C2-3, yielding an at least 91% pure product. The identity of the peptide was confirmed by LC/MS analysis in electrospray mode. The 4803.0 D molecular weight derived from the experimentally observed m/z ions $(M+3H)^{3+}/3=1601.9$ and $(M+4H)^{4+}/4=1201.7$ is within 1 Dalton of the calculated molecular weight, 4803.4 D.

Example C2-8

Synthesis of 3-Maleimidopropionyl-$(GS)_5$-Mouse PP: Mal-GSGSGSGSGS-APLEPMYPGDYATPEQ-MAQYETQLRRYINTLTRPRY-$NH_2$ This peptide was custom synthesized by GenScript USA, Inc., Piscataway, N.J., using solid phase procedures similar to those described in Example C2-6, yielding the desired mouse PP peptide derivative Mal-GSGSGSGSGS-APLEPMYPGDYATPEQMAQYETQLRRYINTLTR PRY-$NH_2$ (amide) in 90% purity. The identity of the peptide was confirmed by LC/MS analysis in electrospray mode. The experimentally observed m/z ions $(M+4H)^{4+}/4=1302.5$ and $(M+5H)^{5+}/5=1042.1$ are consistent with the calculated molecular weight, 5205.7 D.

Example C2-9

Synthesis of Human Osteocalcin: YLYQWLGAPVPYPDPLEPRRE VCELNPDCDELADHIGFQEAYRRFYGPV, Cyclized via $Cys^{23}$-$Cys^{29}$ Disulfide The linear peptide was custom synthesized by GenScript USA, Inc., Piscataway, N.J., using solid phase procedures similar to those described in Example C2-6, yielding the desired linear precursor of human OCN in 87% purity. The oxidative disulfide cyclization of the peptide was effected by stirring a solution of the linear peptide (0.5 mg/mL; 20 mL) in 50 mM TRIS buffer (pH 8.1), 5 mM reduced glutathione and 0.5 mM oxidized glutathione for 4 days at rt. The solution was concentrated to 10 mL by rotary evaporation and the peptide was purified by preparative HPLC as described in Example C2-1, except that a gradient of 20-50% B in A over 40 min. was used for elution. This yielded the desired cyclic human OCN peptide in 99% purity. The identity of the peptide was confirmed by LC/MS analysis in electrospray mode. The experimentally observed m/z ions $(M+3H)^{3+}/3=1933.3$ and $(M+4H)^{4+}/4=1449.8$ are consistent with the calculated molecular weight, 5797.4 D.

Example C2-10

Synthesis of Mouse Osteocalcin: YLGASVPSPDPLEPT REQCELNPACDELSDQYGLKTAYKRIYGITI, Cyclized via $Cys^{19}$-$Cys^{25}$ Disulfide The linear peptide was custom synthesized by GenScript USA, Inc., Piscataway, N.J., using solid phase procedures similar to those described in Example C2-9, yielding the desired linear precursor of mouse OCN in 90% purity. The peptide was cyclized and purified by preparative HPLC as described in Example C2-9, yielding the cyclic mouse OCN peptide in 98% purity. The identity of the peptide was confirmed by LC/MS analysis in electrospray mode. The experimentally observed m/z ions $(M+3H)^{3+}/3=1705.3$ and $(M+4H)^{4+}/4=1279.5$ are consistent with the calculated molecular weight, 5114.7 D.

Example C2-11

Synthesis of Rat Osteocalcin: YLNNGLGAPAPYPDPLEPH REVCELNPNCDELADHIGFQDAYKRIYGTTV, Cyclized via $Cys^{23}$-$Cys^{29}$ Disulfide The disulfide cyclic peptide was custom synthesized by GenScript USA, Inc., Piscataway, N.J., using solid phase and oxidative cyclization procedures similar to those described in Example C2-9, yielding the desired cyclic rat OCN in 96% purity. The identity of the peptide was confirmed by LC/MS analysis in electrospray mode. The experimentally observed m/z ions $(M+3H)^{3+}/3=1862.5$ and $(M+4H)^{4+}/4=1397.5$ are consistent with the calculated molecular weight, 5586.1 D.

Example C3

Formation of SABA-Amylin, SABA-PYY and SABA-PP Fusion Molecules Linked by a Chemically Derived Spacer Using a Maleimide Conjugation Reaction SABA1.7-$(ED)_5$G-Cys protein, purified as outlined above on a Q Sepharose column (GE Healthcare, Piscataway N.J.), was reduced with 0.5 mM TCEP. TCEP was removed and the protein further polished via a size exclusion chromatography on a Superdex75 column (GE Healthcare) equilibrated in 50 mM sodium acetate, 150 mM sodium chloride, pH 5.2. The SABA1.7-$(ED)_5$G-Cys protein eluted was combined in this buffer with a 1:1 molar ratio of Maleimide-PEG20-Amylin-$CONH_2$, Maleimide-PEG20-PYY-$CONH_2$ or Maleimide-PEG20-PP-$CONH_2$ synthetic peptide and incubated overnight at 4° C. with gentle shaking. Following incubation, the reaction mixture was 0.2 μm filtered and the modified proteins, SABA1.7-$(ED)_5$G-Cys-PEG20-Amylin-$CONH_2$ (SEQ ID NO: 328), SABA1.7-$(ED)_5$G-Cys-PEG20-PYY-$CONH_2$ (SEQ ID NO: 344) or SABA1.7-$(ED)_5$G-Cys-PEG20-PP-$CONH_2$ (SEQ ID NO: 364), were isolated form free reactants using a Superdex75 SEC column in PBS pH 7.4.

Example C4

Binding Efficacy of SABA-Neuropeptide (Amylin, PYY and PP) Fusions to Human Serum Albumin Surface Plasmon Resonance (SPR) is a direct binding technique by which molecular interactions can be observed in real time. For these experiments, SPR binding studies were performed using a ProteOn XPR36 instrument (Bio-Rad Laboratories). The running buffer, phosphate buffered saline 0.05% Tween 20 pH 7.4, was purchased from Teknova (cat #P1192) and all experiments were run at 25° C. Human serum albumin was directly immobilized on a Bio-Rad GLC chip via amine coupling as per manufacturer's guidelines using amine coupling reagents purchased from BioRad Laboratories. Human serum albumin was purchased from Novozymes (Recombumin™). About 5000 resonance units (RU) of human serum albumin were immobilized onto 4 separate lanes of the GLC chip surface. For each analyte, five concentrations ranging from 15.6 nM to 250 nM were injected over the surface at 30 μl/min for 240 seconds. The dissociation was monitored for 600 seconds. The surface was regenerated with 100 mM HCl. The resultant data were fitted to a Langumuir 1:1 binding model using the ProteOn Manager Software. The experiment was repeated with a different concentration range. In this second experiment, 5 concentrations ranging from 500 nM to 32 nM were injected over the surfaces, and the data analyzed as above. The results of these experiments were averaged and are shown in Table 21. The $K_D$ is the disassociation constant. Smaller numbers indicate tighter binding to serum albumin. Molecules covalently attached to SABA that bind to serum albumin display longer in vivo pharmokinetic half-lives, as described earlier with respect to SABA-FGF-21 fusions.

TABLE 21

$K_{on}$, $K_{off}$ and $K_D$ values of SABA-neuropeptide fusions for binding to Human Serum Albumin.

| Protein Species Analyte | $K_{on}$ (1/Ms) | $K_{off}$ (1/s) | $K_D$ (M) |
|---|---|---|---|
| SABA-Amylin-CONH2 conjugate (SABA1-AMYv25; SEQ ID NO: 328) | 9.34 $10^3$ | 2.41 $10^{-4}$ | 25.8 $10^{-9}$ |
| SABA-$PYY_{3-36}$-CONH2 conjugate (SABA1-PYYv7; SEQ ID NO: 344) | 9.29 $10^3$ | 2.08 $10^{-4}$ | 22.5 $10^{-9}$ |
| SABA-PP-CONH2 conjugate (SABA1-APPv7; SEQ ID NO: 364) | 7.88 $10^3$ | 1.42 $10^{-4}$ | 18.8 $10^{-9}$ |

Example C5

In Vitro Activity of SABA-Synthetic Peptide Fusions

Example C5-1

In Vitro Activity of SABA-Amylin Fusions

Amylin induces cellular cyclic Adenosine Monophosphate (cAMP) production by activating the amylin receptor, which is a $G_s$-coupled GPCR. Therefore, cellular cAMP production is used as a read out of the in vitro functional activity for Amylin agonists. Specifically, in vitro activity including the potency ($EC_{50}$) and efficacy (as a percentage of maximal activity observed from Amylin peptide) was determined for the SABA1-AMYv25 (SEQ ID NO: 328) protein.

As shown below in Table 22, SABA1-AMYv25 stimulates cAMP production in HEK cells stably expressing Amylin receptor. The potency (EC50) of SABA1-AMYv25 is 12.2 nM and the efficacy is about 119% of the Amylin peptide. Therefore, SABA1-AMYv25 retains full Amylin functional activity in an in vitro assay even when it is linked to a SABA. In additional experiments, both rat Amylin and SABA1-AMYv25 had no significant effect on cAMP levels in the HEK parental cells, demonstrating their specificity for the Amylin receptor.

Amylin Receptor Stable Cell Line Construction

The Amylin receptor is a heterodimer of calcitonin receptor (CT) and one of the Receptor Activity Modifying Proteins (RAMPs). The recombinant Amylin receptor cell lines were generated by stably transfecting both chimpanzee CT(a) and human Receptor Activity Modifying Protein 3 (RAMP3) in HEK-293 cells. These recombinant receptor cell lines were selected and characterized using several Amylin agonist peptides, including rat Amylin, salmon calcitonin, human calcitonin and human CGRP. The stable cell lines were cultured in complete DMEM with 10% FBS, 300 μg/ml Neomycin and 250 μg/ml Hygromycin at 37° C. and 5% $CO_2$.

In Vitro Cyclic AMP (cAMP) Functional Assay for Assessment of SABA1-AMYv25 Activity The cAMP assays were conducted by using a HTRF® cAMP assay kit from Cisbio (Bedford, Mass.). Amylin receptor stable cells were grown in medium (DMEM with 10% FBS, 300 μg/ml Neomycin and 250 μg/ml Hygromycin) in a BD Falcon™ 75 $cm^2$ Flask (BD Biosciences, Bedford, Mass.) at 37° C. and 5% $CO_2$. Cells were harvested from the flasks using a Cell Dissociation Buffer (Enzyme-free) from Invitrogen. After washing once with PBS buffer, cells were re-suspended in the assay buffer (HBSS buffer, 2.5 mM HEPES, pH 7.5, 100 μM IBMX) and loaded into a 96-well assay plates (~2,000 cells/well). The cells were then incubated with either Amylin peptide or SABA-Amylin for 30 minutes at 37° C. The cAMP amounts in cells were determined according to manufacturer's protocol (Cisbio).

Example C5-2

In Vitro Activity of SABA-$PYY_{3-36}$ and SABA-PP Fusions

Peptide YY (PYY) and pancreatic polypeptide (PP) are native satiety factors secreted from intestine and pancreas, respectively, in response to food ingestion, and are reduced upon fasting. PYY and PP may both be isolated in their full-length form which are 36-residue peptide amides. PYY can also be further cleaved by the enzyme DPPIV into a shorter biologically active form PYY(3-36). Peripheral injection of PYY(3-36) or PP causes reduction in food intake and body weight in animal models and in humans. Patients with morbid obesity have both reduced basal and meal-stimulated PYY(3-36) and/or PP levels. In contrast, patients with anorexia, or weight loss after bypass surgery, have higher than normal plasma PYY(3-36) and/or PP. Agonism of PYY(3-36) and PP are of great therapeutic value in treating obesity and metabolic diseases. NPY Y2 and Y4 are receptors with the highest affinity to PYY(3-36) and PP, respectively. NPY receptors belong to the G-protein coupled receptor family. Upon agonist stimulation, the NPY receptor may stimulate the down-streamed G-protein, exchanging its bound GDP for a GTP. Competition binding assays were used to measure the binding affinity of SABA1-PYYv7 (SEQ ID NO:344) and SABA1-PPv7 (SEQ ID NO: 364) toward their respective receptors, and GTPγS binding assays were used to measure a functional consequence of receptor occupancy at one of the earliest receptor-mediated events.

As shown in Table 22, the measured potency (EC50) in the described assay o is 0.6 nM for $PYY_{3-36}$ and 52 nM for the SABA1-PYYv7 fusion. The measured potency (EC50) in the described assay is 1.7 nM for PP and >1 uM for the SABA1-PPv7 fusion. The decrease in potency for the SABA1-PPv7 fusion may be due to the PEG20 linker used to conjugate the SABA and PP polypeptides. The PEG20 linker may be sub-optimum in this construct and constructs with alternative linkers will be used to improve the potency of the SABA-PP fusion.

Receptor Membrane Preparation:

One T150 flask of recombinant CHO cells over-expressing human NPY Y2 or Y4 receptors were grown in F-12 medium (HAM, with L-glutamine) with G418 at 0.5 mg/ml until confluent. Before harvest, cells were washed once with PBS (without $Ca^{2+}$ and $Mg^{2+}$), and then detached using Cell Dissociation Solution. After centrifugation, the cell pellets were resuspended in 1 ml of lysis buffer (20 mM Tris-Cl pH7.5, 1 mM EDTA and proteinase inhibitors) and homogenized using a Polytron homogenizer, (set 5, 10 sec×2). The homogenized cells were centrifuged for 10 min at 1,000 g. The supernatant was collected and the pellets were re-suspended into 1 ml of lysis buffer, homogenized, and centrifuged again at 1,000 g for 10 min. The supernatants from both spins were pooled and centrifuged at 100,000 g for 60 min. The resultant membrane pellets were re-suspended in 250 μl assay buffer (TBS pH 7.4, 1 mM $MgCl_2$, 2.5 mM $CaCl_2$). Protein concentration was measured and aliquots were stored at −80° C. until use.

Competition Binding Assays:

The assay was carried out in a total volume of 250 μl assay buffer (TBS pH 7.4, 1 mM $MgCl_2$, 2.5 mM $CaCl_2$,) in 96 well-plate. The reaction mixture consisted of assay sample (SABA1-PYYv7/SABA1-PPv7, control PP/PYY(3-36), control medium), membranes, and 0.025 nM of $^{125}$1-hPYY or $^{125}$1-hPP (2200 Ci/mmol, PerkinElmer). The order of reagent addition was: 150 μl of assay sample, 50 μl of $^{125}$1-PYY or $^{125}$1-hPP, followed by 50 μl of membranes (1-3 μg/well in assay buffer). The binding mixture is incubated for 120 minutes at room temperature. The binding reaction was terminated by transferring the reaction onto GF/C plates (pre-soaked with 0.5% polyethylenimine and 0.1% BSA) using Packard Cell Harvester. The filter plates were then washed 4×200 ml with ice cold 50 mM Tris buffer (pH7.4). After wash, 40 μl of MicroScint20 were added into each well and the plates were counted on a Packard Top-Count Scintillation counter.

GTP γS Binding Assay:

The assay was carried out in a total volume of 100 μl on a 96-well plate. First 10 μl of universal buffer (20 mM HEPES pH 7.4, 100 mM NaCl, 1 mM $MgCl_2$, 10 μM GDP, 0.1% BSA) was added to each well. Then 10 μl of testing sample, followed by 40 μl of membranes (1-3 μg/well in assay buffer), were added and mixed well. The reaction was incubated at 25° C. for 30 minutes with shacking. Then 40 μl of SPA beads (0.5 mg/well) with $^{35}$S-GTP (0.25 μCi/ml) was added and incubated at 25° C. for another 60 minutes with shaking. The reaction was terminated by spinning at 1000 rpm for 5 minutes.

TABLE 22

Functional Activities of SABA-Amylin, SABA-$PYY_{3-36}$ and SABA-PP Fusions.

| | Cell based Potency | Efficacy | Method | Affinity for hSA [by SPR] (nM) |
|---|---|---|---|---|
| Amylin Control Peptide (SEQ ID NO: 300) | 5.1 ± 1.08 ($EC_{50}$, nM) | 100%* | Cellular cAMP assay | — |
| SABA1-AMYv25 (SEQ ID NO: 328) | 12.2 ± 1.07 ($EC_{50}$, nM) | 119% ± 3.1* | Cellular cAMP assay | 25.8 |
| $PYY_{3-36}$ Control Peptide (SEQ ID NO: 334) | 0.6 ($EC_{50}$, nM) | 100 | GTPγS binding functional assay | — |
| SABA1-PYYv7 (SEQ ID NO: 344) | 52 ($EC_{50}$, nM) | — | GTPγS binding functional assay | 22.5 |
| PP Control Peptide (SEQ ID NO: 353) | 1.7 ($EC_{50}$, nM) | 100 | GTPγS binding functional assay | — |
| SABA-PP MAL conjugate (SEQ ID NO: 364) | >1 uM | — | GTPγS binding functional assay | 18.8 |

*Presented as % of native peptide ligand maximal activity of test compounds. Results are expressed as the mean ± SEM of triplicate measurements from an experiment.

D. Other SABA Fusion Molecules

Example D1

In Vitro Activity of SABA-Osteocalcin Fusions

Osteocalcin (OCN) stimulates insulin secretion in pancreatic β cells, hence insulin production from rodent islets is used as a readout to assess the biological function of osteocalcin (OCN) in vitro. Rodent islets are treated with native human OCN (hOCN) and adnectin SABA-fused human OCN (SABA-hOCN) and the degree of enhancement of insulin secretion associated with each construct is determined.

Example D2

SABA-Apelin Fusion

SABA-APLNv2 is a fusion of SABA1.6 fused to APLNv4 via a 6×His tag and a $(GS)_7$ linker. In anesthetized rats, APLNv4 exhibited a robust hypotensive effect at 60 μg/kg delivered intravenously. SABA-APLNv2 exhibits a molecular weight of 15,000, with APLNv4 representing 10% of the mass of the fusion protein. SABA-APLNv2 was delivered intravenously to anesthetized rats at a dose of 600 μg/kg, without affecting blood pressure. Potential explanations for the absence of activity with the SABA-APLNv2 construct can include lessened potency due to poorer productive collision frequency, steric hindrance, or peptide-PKE annealing. SABA-APLNv2 was not tested to determine if it bound to HSA.

We claim:

1. A nucleic acid encoding a polypeptide comprising a fibronectin type III tenth ($^{10}$Fn3) domain, wherein the $^{10}$Fn3 domain binds to domain 1 or 2 of human serum albumin with a $K_D$ of 1 μM or less, and wherein the $^{10}$Fn3 domain comprises a modified amino acid sequence in one or more of the BC, DE and FG loops relative to the wild-type human $^{10}$Fn3 domain (SEQ ID NO: 1), and wherein the polypeptide comprises an amino acid sequence at least 75% identical to an amino acid sequence selected from SEQ ID NOs: 4, 8, 12, 16, 20, and 24-44.

2. A vector comprising a nucleic acid of claim 1.

3. The vector of claim 2, wherein the vector is an expression vector.

4. A host cell comprising the vector of claim 2.

5. The host cell of claim 4, wherein the cell is a bacterial cell.

6. The host cell of claim 4, wherein the cell is a mammalian cell.

7. The nucleic acid of claim 1, which encodes a polypeptide comprising an amino acid sequence at least 80% identical to an amino acid sequence selected from the group consisting of: SEQ ID NOs: 4, 8, 12, 16, 20, and 24-44.

8. The nucleic acid of claim 7, which encodes a polypeptide comprising an amino acid sequence at least 85% identical to an amino acid sequence selected from the group consisting of: SEQ ID NOs: 4, 8, 12, 16, 20, and 24-44.

9. The nucleic acid of claim 8, which encodes a polypeptide comprising an amino acid sequence at least 90% identical to an amino acid sequence selected from the group consisting of: SEQ ID NOs: 4, 8, 12, 16, 20, and 24-44.

10. The nucleic acid of claim 9, which encodes a polypeptide comprising an amino acid sequence selected from the group consisting of SEQ ID NOs: 4, 8, 12, 16, 20, and 24-44.

11. The nucleic acid of claim 1, which encodes a polypeptide comprising an amino acid sequence at least 75% identical to the amino acid sequence of SEQ ID NO: 4.

12. The nucleic acid of claim 7, which encodes a polypeptide comprising an amino acid sequence at least 80% identical to the amino acid sequence of SEQ ID NO: 4.

13. The nucleic acid of claim 8, which encodes a polypeptide comprising an amino acid sequence at least 85% identical to the amino acid sequence of SEQ ID NO: 4.

14. The nucleic acid of claim 9, which encodes a polypeptide comprising an amino acid sequence at least 90% identical to the amino acid sequence of SEQ ID NO: 4.

15. The nucleic acid of claim 10, which encodes a polypeptide comprising the amino acid sequence of SEQ ID NO: 4.

16. A nucleic acid encoding a fusion polypeptide comprising a fibronectin type III tenth ($^{10}$Fn3) domain and a heterologous protein, wherein the $^{10}$Fn3 domain binds to human serum albumin with a $K_D$ of 1 μM or less and comprises an amino acid sequence at least 75% identical to an amino acid sequence selected from the group consisting of SEQ ID NOs: 4, 8, 12, 16, 20, and 24-44.

17. The nucleic acid of claim 16, wherein the nucleic acid comprises a sequence selected from the group consisting of SEQ ID NOs: 176-214 and 401-405.

18. The nucleic acid of claim 16, wherein the $^{10}$Fn3 domain comprises an amino acid sequence at least 85% identical to an amino acid sequence selected from the group consisting of SEQ ID NOs: 4, 8, 12, 16, 20, and 24-44.

19. The nucleic acid of claim 18, wherein the $^{10}$Fn3 domain comprises an amino acid sequence selected from SEQ ID NOs: 4, 8, 12, 16, 20, and 24-44.

* * * * *

SEQUENCE LISTING

```
<160> NUMBER OF SEQ ID NOS: 444

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
```

```
                85                  90


<210> SEQ ID NO 2
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid and this region may encompass
      1-15, 2-15, 1-10, 2-10, 1-8, 2-8, 1-5, 2-5, 1-4, 2-4, 1-3, 2-3,
      or 1-2 residues
<220> FEATURE:
<221> NAME/KEY: MOD_RES
<222> LOCATION: (26)..(45)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (54)..(73)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (79)..(98)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (102)..(121)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (131)..(150)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<223> OTHER INFORMATION: see specification as filed for detailed
      description of substitutions and preferred embodiments

<400> SEQUENCE: 2

Glu Val Val Ala Ala Thr Xaa Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Tyr Tyr Arg
        35                  40                  45

Ile Thr Tyr Gly Glu Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Gln Glu Phe Thr Val Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Ala Thr Ile Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Asp Tyr Thr Ile Thr Val Tyr
        115                 120                 125

Ala Val Xaa Xaa Xaa Xaa Xaa Xaa Xaa Xaa Xaa Xaa Xaa Xaa Xaa Xaa
    130                 135                 140
```

```
Xaa Xaa Xaa Xaa Xaa Xaa Ile Ser Ile Asn Tyr Arg Thr
145                 150                 155


<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(32)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (53)..(72)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<221> NAME/KEY: MOD_RES
<222> LOCATION: (92)..(111)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues
<220> FEATURE:
<223> OTHER INFORMATION: see specification as filed for detailed
      description of substitutions and preferred embodiments

<400> SEQUENCE: 3

Glu Val Val Ala Ala Thr Pro Thr Ser Leu Leu Ile Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Tyr Tyr Arg Ile Thr Tyr Gly Glu Thr Gly Gly Asn Ser Pro Val Gln
        35                  40                  45

Glu Phe Thr Val Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Ala Thr Ile Ser Gly Leu Lys Pro
65                  70                  75                  80

Gly Val Asp Tyr Thr Ile Thr Val Tyr Ala Val Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Ile
            100                 105                 110

Ser Ile Asn Tyr Arg Thr
        115


<210> SEQ ID NO 4
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Val Ala Ala Thr Pro Thr Ser Leu Leu Ile Ser Trp His Ser
1               5                   10                  15

Tyr Tyr Glu Gln Asn Ser Tyr Tyr Arg Ile Thr Tyr Gly Glu Thr Gly
            20                  25                  30

Gly Asn Ser Pro Val Gln Glu Phe Thr Val Pro Tyr Ser Gln Thr Thr
        35                  40                  45
```

```
Ala Thr Ile Ser Gly Leu Lys Pro Gly Val Asp Tyr Thr Ile Thr Val
    50                  55                  60

Tyr Ala Val Tyr Gly Ser Lys Tyr Tyr Tyr Pro Ile Ser Ile Asn Tyr
65                  70                  75                  80

Arg Thr


<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Ser Tyr Tyr Glu Gln Asn Ser
1               5


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ser Gln Thr
1


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Gly Ser Lys Tyr Tyr Tyr
1               5


<210> SEQ ID NO 8
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Val Ala Ala Thr Pro Thr Ser Leu Leu Ile Ser Trp Pro Lys
1               5                   10                  15

Tyr Asp Lys Thr Gly His Tyr Tyr Arg Ile Thr Tyr Gly Glu Thr Gly
            20                  25                  30

Gly Asn Ser Pro Val Gln Glu Phe Thr Val Pro Thr Arg Gln Thr Thr
        35                  40                  45

Ala Thr Ile Ser Gly Leu Lys Pro Gly Val Asp Tyr Thr Ile Thr Val
    50                  55                  60

Tyr Ala Val Ser Lys Asp Asp Tyr Tyr Pro His Glu His Arg Pro Ile
65                  70                  75                  80

Ser Ile Asn Tyr Arg Thr
                85
```

```
<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Lys Tyr Asp Lys Thr Gly His
1               5


<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Arg Gln Thr
1


<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Lys Asp Asp Tyr Tyr Pro His Glu His Arg
1               5                   10


<210> SEQ ID NO 12
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Val Ala Ala Thr Pro Thr Ser Leu Leu Ile Ser Trp Ser Asn
1               5                   10                  15

Asp Gly Pro Gly Leu Ser Tyr Tyr Arg Ile Thr Tyr Gly Glu Thr Gly
            20                  25                  30

Gly Asn Ser Pro Val Gln Glu Phe Thr Val Pro Ser Ser Gln Thr Thr
        35                  40                  45

Ala Thr Ile Ser Gly Leu Lys Pro Gly Val Asp Tyr Thr Ile Thr Val
    50                  55                  60

Tyr Ala Val Ser Tyr Tyr Thr Lys Lys Ala Tyr Ser Ala Gly Pro Ile
65                  70                  75                  80

Ser Ile Asn Tyr Arg Thr
                85


<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 13

Ser Asn Asp Gly Pro Gly Leu Ser
1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ser Gln Thr
1

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Tyr Tyr Thr Lys Lys Ala Tyr Ser Ala Gly
1               5                   10

<210> SEQ ID NO 16
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Met Val Ala Ala Thr Pro Thr Ser Leu Leu Ile Ser Trp Glu Asp
1               5                   10                  15

Asp Ser Tyr Tyr Ser Arg Tyr Tyr Arg Ile Thr Tyr Gly Glu Thr Gly
            20                  25                  30

Gly Asn Ser Pro Val Gln Glu Phe Thr Val Pro Ser Asp Leu Tyr Thr
        35                  40                  45

Ala Thr Ile Ser Gly Leu Lys Pro Gly Val Asp Tyr Thr Ile Thr Val
    50                  55                  60

Tyr Ala Val Thr Tyr Asp Val Thr Asp Leu Ile Met His Glu Pro Ile
65                  70                  75                  80

Ser Ile Asn Tyr Arg Thr
                85

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Asp Asp Ser Tyr Tyr Ser Arg
1               5

<210> SEQ ID NO 18

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Asp Leu Tyr
1


<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Asp Val Thr Asp Leu Ile Met His Glu
1               5                   10


<210> SEQ ID NO 20
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Val Ala Ala Thr Pro Thr Ser Leu Leu Ile Ser Trp Glu Asp
1               5                   10                  15

Asp Ser Tyr Tyr Ser Arg Tyr Tyr Arg Ile Thr Tyr Gly Glu Thr Gly
            20                  25                  30

Gly Asn Ser Pro Val Gln Glu Phe Thr Val Pro Ser Asp Leu Tyr Thr
        35                  40                  45

Ala Thr Ile Ser Gly Leu Lys Pro Gly Val Asp Tyr Thr Ile Thr Val
    50                  55                  60

Tyr Ala Val Thr Tyr Asp Val Thr Asp Leu Ile Met His Glu Pro Ile
65                  70                  75                  80

Ser Ile Asn Tyr Arg Thr
                85


<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Asp Asp Ser Tyr Tyr Ser Arg
1               5


<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

```
Ser Asp Leu Tyr
1


<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Asp Val Thr Asp Leu Ile Met His Glu
1               5                   10


<210> SEQ ID NO 24
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Val Ala Ala Thr Pro Thr Ser Leu Leu Ile Ser Trp Tyr Met
1               5                   10                  15

Asp Glu Tyr Asp Val Arg Tyr Tyr Arg Ile Thr Tyr Gly Glu Thr Gly
            20                  25                  30

Gly Asn Ser Pro Val Gln Glu Phe Thr Val Pro Asn Tyr Tyr Asn Thr
        35                  40                  45

Ala Thr Ile Ser Gly Leu Lys Pro Gly Val Asp Tyr Thr Ile Thr Val
    50                  55                  60

Tyr Ala Val Thr Arg Ile Lys Ala Asn Asn Tyr Met Tyr Gly Pro Ile
65                  70                  75                  80

Ser Ile Asn Tyr Arg Thr
                85


<210> SEQ ID NO 25
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Val Ala Ala Thr Pro Thr Ser Leu Leu Ile Ser Trp Asn His
1               5                   10                  15

Leu Glu His Val Ala Arg Tyr Tyr Arg Ile Thr Tyr Gly Glu Thr Gly
            20                  25                  30

Gly Asn Ser Pro Val Gln Glu Phe Thr Val Pro Glu Tyr Pro Thr Thr
        35                  40                  45

Ala Thr Ile Ser Gly Leu Lys Pro Gly Val Asp Tyr Thr Ile Thr Val
    50                  55                  60

Tyr Ala Val Thr Ile Thr Met Leu Lys Tyr Pro Thr Gln Ser Pro Ile
65                  70                  75                  80

Ser Ile Asn Tyr Arg Thr
                85


<210> SEQ ID NO 26
<211> LENGTH: 86
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Glu Val Val Ala Ala Thr Pro Thr Ser Leu Leu Ile Ser Trp Gly His
1               5                   10                  15

Tyr Arg Arg Ser Gly His Tyr Tyr Arg Ile Thr Tyr Gly Glu Thr Gly
            20                  25                  30

Gly Asn Ser Pro Val Gln Glu Phe Thr Val Asp Pro Ser Ser Tyr Thr
        35                  40                  45

Ala Thr Ile Ser Gly Leu Lys Pro Gly Val Asp Tyr Thr Ile Thr Val
    50                  55                  60

Tyr Ala Val Ser Lys Asp Asp Tyr Tyr Pro His Glu His Arg Pro Ile
65                  70                  75                  80

Ser Ile Asn Tyr Arg Thr
                85
```

<210> SEQ ID NO 27
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Glu Val Val Ala Ala Thr Pro Thr Ser Leu Leu Ile Ser Trp Asp Ala
1               5                   10                  15

Ser His Tyr Glu Arg Arg Tyr Tyr Arg Ile Thr Tyr Gly Glu Thr Gly
            20                  25                  30

Gly Asn Ser Pro Val Gln Glu Phe Thr Val Pro Arg Tyr His His Thr
        35                  40                  45

Ala Thr Ile Ser Gly Leu Lys Pro Gly Val Asp Tyr Thr Ile Thr Val
    50                  55                  60

Tyr Ala Val Thr Gln Ala Gln Glu His Tyr Gln Pro Pro Ile Ser Ile
65                  70                  75                  80

Asn Tyr Arg Thr
```

<210> SEQ ID NO 28
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Glu Val Val Ala Ala Thr Pro Thr Ser Leu Leu Ile Ser Trp Asn Ser
1               5                   10                  15

Tyr Tyr His Ser Ala Asp Tyr Tyr Arg Ile Thr Tyr Gly Glu Thr Gly
            20                  25                  30

Gly Asn Ser Pro Val Gln Glu Phe Thr Val Pro Tyr Pro Pro Thr Thr
        35                  40                  45

Ala Thr Ile Ser Gly Leu Lys Pro Gly Val Asp Tyr Thr Ile Thr Val
    50                  55                  60

Tyr Ala Val Tyr Ser Ala Lys Ser Tyr Tyr Pro Ile Ser Ile Asn Tyr
65                  70                  75                  80
```

Arg Thr

<210> SEQ ID NO 29
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
            20                  25                  30

Gly Asn Ser Pro Val Gln Glu Phe Thr Val Pro Ser Gly Asn Ala Thr
        35                  40                  45

Ala Thr Ile Ser Gly Leu Lys Pro Gly Val Asp Tyr Thr Ile Thr Val
    50                  55                  60

Tyr Ala Val Glu Asp Thr Asn Asp Tyr Pro His Thr His Arg Pro Ile
65                  70                  75                  80

Ser Ile Asn Tyr Arg Thr
                85
```

<210> SEQ ID NO 30
<211> LENGTH: 84
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Glu Val Val Ala Ala Thr Pro Thr Ser Leu Leu Ile Ser Trp His Gly
1               5                   10                  15

Glu Pro Asp Gln Thr Arg Tyr Tyr Arg Ile Thr Tyr Gly Glu Thr Gly
            20                  25                  30

Gly Asn Ser Pro Val Gln Glu Phe Thr Val Pro Pro Tyr Arg Arg Thr
        35                  40                  45

Ala Thr Ile Ser Gly Leu Lys Pro Gly Val Asp Tyr Thr Ile Thr Val
    50                  55                  60

Tyr Ala Val Thr Ser Gly Tyr Thr Gly His Tyr Gln Pro Ile Ser Ile
65                  70                  75                  80

Asn Tyr Arg Thr
```

<210> SEQ ID NO 31
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
            20                  25                  30

Gly Asn Ser Pro Val Gln Glu Phe Thr Val Asp Pro Ser Ser Tyr Thr
        35                  40                  45
```

```
Ala Thr Ile Ser Gly Leu Lys Pro Gly Val Asp Tyr Thr Ile Thr Val
    50                  55                  60

Tyr Ala Val Ser Lys Asp Asp Tyr Tyr Pro His Glu His Arg Pro Ile
65                  70                  75                  80

Ser Ile Asn Tyr Arg Thr
                85
```

<210> SEQ ID NO 32
<211> LENGTH: 82
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Glu Val Val Ala Ala Thr Pro Thr Ser Leu Leu Ile Ser Trp Tyr Glu
1               5                   10                  15

Pro Tyr Thr Pro Ile His Tyr Tyr Arg Ile Thr Tyr Gly Glu Thr Gly
            20                  25                  30

Gly Asn Ser Pro Val Gln Glu Phe Thr Val Pro Gly Tyr Tyr Gly Thr
        35                  40                  45

Ala Thr Ile Ser Gly Leu Lys Pro Gly Val Asp Tyr Thr Ile Thr Val
    50                  55                  60

Tyr Ala Val Tyr Gly Tyr Tyr Gln Tyr Thr Pro Ile Ser Ile Asn Tyr
65                  70                  75                  80

Arg Thr
```

<210> SEQ ID NO 33
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
            20                  25                  30

Gly Asn Ser Pro Val Gln Glu Phe Thr Val Pro Ser Gly Asn Ala Thr
        35                  40                  45

Ala Thr Ile Ser Gly Leu Lys Pro Gly Val Asp Tyr Thr Ile Thr Val
    50                  55                  60

Tyr Ala Val Ser Asp Asp Asn Lys Tyr Tyr His Gln His Arg Pro Ile
65                  70                  75                  80

Ser Ile Asn Tyr Arg Thr
                85
```

<210> SEQ ID NO 34
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Glu Val Val Ala Ala Thr Pro Thr Ser Leu Leu Ile Ser Trp Gly His
```

-continued

```
1               5                   10                  15

Tyr Arg Arg Ser Gly His Tyr Tyr Arg Ile Thr Tyr Gly Glu Thr Gly
            20                  25                  30

Gly Asn Ser Pro Val Gln Glu Phe Thr Val Asp Pro Ser Ser Tyr Thr
        35                  40                  45

Ala Thr Ile Ser Gly Leu Lys Pro Gly Val Asp Tyr Thr Ile Thr Val
    50                  55                  60

Tyr Ala Val Ser Lys Asp Asp Tyr Tyr Pro His Glu His Arg Pro Ile
65                  70                  75                  80

Ser Ile Asn Tyr Arg Thr
                85


<210> SEQ ID NO 35
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Val Ala Ala Thr Pro Thr Ser Leu Leu Ile Ser Trp Ser Lys
1               5                   10                  15

Tyr Ser Lys His Gly His Tyr Tyr Arg Ile Thr Tyr Gly Glu Thr Gly
            20                  25                  30

Gly Asn Ser Pro Val Gln Glu Phe Thr Val Pro Ser Gly Asn Ala Thr
        35                  40                  45

Ala Thr Ile Ser Gly Leu Lys Pro Gly Val Asp Tyr Thr Ile Thr Val
    50                  55                  60

Tyr Ala Val Glu Asp Thr Asn Asp Tyr Pro His Thr His Arg Pro Ile
65                  70                  75                  80

Ser Ile Asn Tyr Arg Thr
                85


<210> SEQ ID NO 36
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Val Ala Ala Thr Pro Thr Ser Leu Leu Ile Ser Trp Tyr Glu
1               5                   10                  15

Pro Gly Ala Ser Val Tyr Tyr Tyr Arg Ile Thr Tyr Gly Glu Thr Gly
            20                  25                  30

Gly Asn Ser Pro Val Gln Glu Phe Thr Val Pro Ser Tyr Tyr His Thr
        35                  40                  45

Ala Thr Ile Ser Gly Leu Lys Pro Gly Val Asp Tyr Thr Ile Thr Val
    50                  55                  60

Tyr Ala Val Tyr Gly Tyr Tyr Glu Tyr Glu Pro Ile Ser Ile Asn Tyr
65                  70                  75                  80

Arg Thr


<210> SEQ ID NO 37
<211> LENGTH: 82
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 37

Glu Val Val Ala Ala Thr Pro Thr Ser Leu Leu Ile Ser Trp Gln Ser
1               5                   10                  15

Tyr Tyr Ala His Ser Asp Tyr Tyr Arg Ile Thr Tyr Gly Glu Thr Gly
            20                  25                  30

Gly Asn Ser Pro Val Gln Glu Phe Thr Val Pro Tyr Pro Pro Gln Thr
        35                  40                  45

Ala Thr Ile Ser Gly Leu Lys Pro Gly Val Asp Tyr Thr Ile Thr Val
    50                  55                  60

Tyr Ala Val Tyr Ala Gly Ser Ser Tyr Tyr Pro Ile Ser Ile Asn Tyr
65                  70                  75                  80

Arg Thr


<210> SEQ ID NO 38
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Val Ala Ala Thr Pro Thr Ser Leu Leu Ile Ser Trp Gly His
1               5                   10                  15

Tyr Arg Arg Ser Gly His Tyr Tyr Arg Ile Thr Tyr Gly Glu Thr Gly
            20                  25                  30

Gly Asn Ser Pro Val Gln Glu Phe Thr Val Asp Pro Ser Ser Tyr Thr
        35                  40                  45

Ala Thr Ile Ser Gly Leu Lys Pro Gly Val Asp Tyr Thr Ile Thr Val
    50                  55                  60

Tyr Ala Val Ser Lys Asp Asp Tyr Tyr Pro His Glu His Arg Pro Ile
65                  70                  75                  80

Ser Ile Asn Tyr Arg Thr
                85


<210> SEQ ID NO 39
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Val Ala Ala Thr Pro Thr Ser Leu Leu Ile Ser Trp Pro Glu
1               5                   10                  15

Pro Gly Thr Pro Val Tyr Tyr Tyr Arg Ile Thr Tyr Gly Glu Thr Gly
            20                  25                  30

Gly Asn Ser Pro Val Gln Glu Phe Thr Val Pro Ala Tyr Tyr Gly Thr
        35                  40                  45

Ala Thr Ile Ser Gly Leu Lys Pro Gly Val Asp Tyr Thr Ile Thr Val
    50                  55                  60

Tyr Ala Val Tyr Gly Tyr Tyr Asp Tyr Ser Pro Ile Ser Ile Asn Tyr
65                  70                  75                  80

Arg Thr
```

<210> SEQ ID NO 40
<211> LENGTH: 86
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Glu Val Val Ala Ala Thr Pro Thr Ser Leu Leu Ile Ser Trp Tyr Arg
1               5                   10                  15

Tyr Glu Lys Thr Gln His Tyr Tyr Arg Ile Thr Tyr Gly Glu Thr Gly
            20                  25                  30

Gly Asn Ser Pro Val Gln Glu Phe Thr Val Pro Pro Glu Ser Gly Thr
        35                  40                  45

Ala Thr Ile Ser Gly Leu Lys Pro Gly Val Asp Tyr Thr Ile Thr Val
    50                  55                  60

Tyr Ala Val Tyr Ala Gly Tyr Glu Tyr Pro His Thr His Arg Pro Ile
65                  70                  75                  80

Ser Ile Asn Tyr Arg Thr
                85
```

<210> SEQ ID NO 41
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

```
Glu Val Val Ala Ala Thr Pro Thr Ser Leu Leu Ile Ser Trp Val Lys
1               5                   10                  15

Ser Glu Glu Tyr Tyr Arg Tyr Tyr Arg Ile Thr Tyr Gly Glu Thr Gly
            20                  25                  30

Gly Asn Ser Pro Val Gln Glu Phe Thr Val Pro Tyr Tyr Val His Thr
        35                  40                  45

Ala Thr Ile Ser Gly Leu Lys Pro Gly Val Asp Tyr Thr Ile Thr Val
    50                  55                  60

Tyr Ala Val Thr Glu Tyr Tyr Tyr Ala Gly Ala Val Val Ser Val Pro
65                  70                  75                  80

Ile Ser Ile Asn Tyr Arg Thr
                85
```

<210> SEQ ID NO 42
<211> LENGTH: 82
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Glu Val Val Ala Ala Thr Pro Thr Ser Leu Leu Ile Ser Trp Tyr Asp
1               5                   10                  15

Pro Tyr Thr Tyr Gly Ser Tyr Tyr Arg Ile Thr Tyr Gly Glu Thr Gly
            20                  25                  30

Gly Asn Ser Pro Val Gln Glu Phe Thr Val Gly Pro Tyr Thr Thr Thr
        35                  40                  45
```

```
Ala Thr Ile Ser Gly Leu Lys Pro Gly Val Asp Tyr Thr Ile Thr Val
    50                  55                  60

Tyr Ala Val Ser Tyr Tyr Tyr Ser Thr Gln Pro Ile Ser Ile Asn Tyr
65                  70                  75                  80

Arg Thr


<210> SEQ ID NO 43
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Val Ala Ala Thr Pro Thr Ser Leu Leu Ile Ser Trp Ser Asn
1               5                   10                  15

Asp Gly Pro Gly Leu Ser Tyr Tyr Arg Ile Thr Tyr Gly Glu Thr Gly
            20                  25                  30

Gly Asn Ser Pro Val Gln Glu Phe Thr Val Pro Ser Ser Gln Thr Thr
        35                  40                  45

Ala Thr Ile Ser Gly Leu Lys Pro Gly Val Asp Tyr Thr Ile Thr Val
    50                  55                  60

Tyr Ala Val Ser Tyr Tyr Thr Lys Lys Ala Tyr Ser Ala Gly Pro Ile
65                  70                  75                  80

Ser Ile Asn Tyr Arg Thr
                85


<210> SEQ ID NO 44
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Val Ala Ala Thr Pro Thr Ser Leu Leu Ile Ser Trp Pro Asp
1               5                   10                  15

Pro Tyr Tyr Lys Pro Asp Tyr Tyr Arg Ile Thr Tyr Gly Glu Thr Gly
            20                  25                  30

Gly Asn Ser Pro Val Gln Glu Phe Thr Val Pro Arg Asp Tyr Thr Thr
        35                  40                  45

Ala Thr Ile Ser Gly Leu Lys Pro Gly Val Asp Tyr Thr Ile Thr Val
    50                  55                  60

Tyr Ala Val Tyr Ser Tyr Tyr Gly Tyr Tyr Pro Ile Ser Ile Asn Tyr
65                  70                  75                  80

Arg Thr


<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Met Gly Val Ser Asp Val Pro Arg Asp Leu
1               5                   10
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Gly Val Ser Asp Val Pro Arg Asp Leu
1 5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Val Ser Asp Val Pro Arg Asp Leu
1 5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Ser Asp Val Pro Arg Asp Leu
1 5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Asp Val Pro Arg Asp Leu
1 5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Val Pro Arg Asp Leu
1 5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Pro Arg Asp Leu
1

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Arg Asp Leu
1

<210> SEQ ID NO 53
<211> LENGTH: 2
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Asp Leu
1

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Glu Ile Asp Lys Pro Ser Gln
1 5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Glu Ile Asp Lys Pro Ser
1 5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Glu Ile Asp Lys Pro Cys
1 5

<210> SEQ ID NO 57
<211> LENGTH: 5
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 57

Glu Ile Asp Lys Pro
1 5

<210> SEQ ID NO 58
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Glu Ile Asp Lys
1

<210> SEQ ID NO 59
<211> LENGTH: 2
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Glu Ile
1

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Glu Ile Glu Lys Pro Ser Gln
1 5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Glu Ile Asp Lys Pro Ser Gln Leu Glu
1 5

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Glu Ile Glu Asp Glu Asp Glu Asp Glu Asp Glu Asp
1 5 10

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Glu Ile Glu Lys Pro Ser Gln Glu Asp Glu Asp Glu Asp Glu Asp Glu
1 5 10 15

Asp

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Glu Gly Ser Gly Ser
1 5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Gly Gly Ser Gly Ser
1 5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Gly Gly Ser Gly Ser Gly Ser Gly Ser
1 5

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Gly Gly Ser Gly Ser Gly Ser Gly Ser Gly Ser Gly Ser
1 5 10

<210> SEQ ID NO 68
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 68

Gly Gly Ser Gly Ser Gly Ser Gly Ser Gly Ser Gly Ser Gly Ser
1               5                   10                  15


<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Ser Gly Ser Gly Ser Gly Ser Gly Ser Gly Ser Gly Ser Gly
1               5                   10                  15


<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Ser Gly Ser
1


<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Gly Ser Gly Ser Gly Ser
1               5


<210> SEQ ID NO 72
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Gly Ser Gly Ser Gly Ser Gly Ser Gly Ser Gly Ser
1               5                   10


<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ser Ala Ala Ala Ala Ala Ala Ala Ala Ala Gly Ser
1               5                   10
```

```
<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Ser Glu Gly Ser Glu Gly Ser Glu Gly Ser Glu Gly Ser Glu
1               5                   10                  15


<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Ala Ser Pro Ala Ser Pro Ala Ser Pro Ala Ser Pro Ala Ser
1               5                   10                  15


<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Pro Gly Ser Pro Gly Ser Pro Gly Ser Pro Gly Ser Pro
1               5                   10                  15


<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ser Thr Val Ala Ala Pro Ser Thr Val Ala Ala Pro Ser
1               5                   10


<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Ser Glu Gly Gly Ser Glu
1               5


<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79
```

Ser Thr Ser Thr Ser Thr Gly
1 5

<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser
35

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Gly Gly Gly Gly Ser Gly Gly Gly Gly Ser Gly Gly Gly Gly Ser Gly
1 5 10 15

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Gly Pro Gly Pro Gly Pro Gly
1 5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

-continued

```
Gly Pro Gly Pro Gly Pro Gly Pro Gly Pro Gly
1               5                   10


<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Pro Ser Thr Ser Thr Ser Thr
1               5


<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Pro Ala Pro Ala Pro Ala
1               5


<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Ala Pro Ala Pro Ala Pro Ala Pro Ala Pro Ala
1               5                   10


<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Pro Ala Pro Ala Pro Ala Pro Ala Pro Ala Pro Ala Pro Ala Pro Ala
1               5                   10                  15

Pro Ala


<210> SEQ ID NO 89
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30
```

```
Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln His His His His His His
            100                 105


<210> SEQ ID NO 90
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp
            100


<210> SEQ ID NO 91
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp His His His His His His
            100                 105                 110
```

<210> SEQ ID NO 92
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Met Gly Val Ser Asp Val Pro Arg Asp Leu Glu Val Val Ala Ala Thr
1               5                   10                  15

Pro Thr Ser Leu Leu Ile Ser Trp Pro Lys Tyr Asp Lys Thr Gly His
            20                  25                  30

Tyr Tyr Arg Ile Thr Tyr Gly Glu Thr Gly Gly Asn Ser Pro Val Gln
        35                  40                  45

Glu Phe Thr Val Pro Thr Arg Gln Thr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His
            100                 105
```

<210> SEQ ID NO 93
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Met Gly Val Ser Asp Val Pro Arg Asp Leu Glu Val Val Ala Ala Thr
1               5                   10                  15

Pro Thr Ser Leu Leu Ile Ser Trp Ser Asn Asp Gly Pro Gly Leu Ser
            20                  25                  30

Tyr Tyr Arg Ile Thr Tyr Gly Glu Thr Gly Gly Asn Ser Pro Val Gln
        35                  40                  45

Glu Phe Thr Val Pro Ser Ser Gln Thr Thr Ala Thr Ile Ser Gly Leu
    50                  55                  60

Lys Pro Gly Val Asp Tyr Thr Ile Thr Val Tyr Ala Val Ser Tyr Tyr
65                  70                  75                  80

Thr Lys Lys Ala Tyr Ser Ala Gly Pro Ile Ser Ile Asn Tyr Arg Thr
                85                  90                  95

Glu Ile Asp Lys Pro Ser Gln His His His His His His
            100                 105
```

<210> SEQ ID NO 94
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Met Gly Val Ser Asp Val Pro Arg Asp Leu Glu Met Val Ala Ala Thr
1               5                   10                  15

Pro Thr Ser Leu Leu Ile Ser Trp Glu Asp Asp Ser Tyr Tyr Ser Arg
```

```
            20                  25                  30

Tyr Tyr Arg Ile Thr Tyr Gly Glu Thr Gly Gly Asn Ser Pro Val Gln
        35                  40                  45

Glu Phe Thr Val Pro Ser Asp Leu Tyr Thr Ala Thr Ile Ser Gly Leu
    50                  55                  60

Lys Pro Gly Val Asp Tyr Thr Ile Thr Val Tyr Ala Val Thr Tyr Asp
65                  70                  75                  80

Val Thr Asp Leu Ile Met His Glu Pro Ile Ser Ile Asn Tyr Arg Thr
                85                  90                  95

Glu Ile Asp Lys Pro Ser Gln His His His His His His
            100                 105


<210> SEQ ID NO 95
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Gly Val Ser Asp Val Pro Arg Asp Leu Glu Val Val Ala Ala Thr
1               5                   10                  15

Pro Thr Ser Leu Leu Ile Ser Trp Glu Asp Asp Ser Tyr Tyr Ser Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Asp Leu Tyr Thr Ala Thr Ile Ser Gly Leu
    50                  55                  60

Lys Pro Gly Val Asp Tyr Thr Ile Thr Val Tyr Ala Val Thr Tyr Asp
65                  70                  75                  80

Val Thr Asp Leu Ile Met His Glu Pro Ile Ser Ile Asn Tyr Arg Thr
                85                  90                  95

Glu Ile Asp Lys Pro Ser Gln His His His His His His
            100                 105


<210> SEQ ID NO 96
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Gly Val Ser Asp Val Pro Arg Asp Leu Glu Val Val Ala Ala Thr
1               5                   10                  15

Pro Thr Ser Leu Leu Ile Ser Trp Tyr Met Asp Glu Tyr Asp Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Asn Tyr Tyr Asn Thr Ala Thr Ile Ser Gly Leu
    50                  55                  60

Lys Pro Gly Val Asp Tyr Thr Ile Thr Val Tyr Ala Val Thr Arg Ile
65                  70                  75                  80

Lys Ala Asn Asn Tyr Met Tyr Gly Pro Ile Ser Ile Asn Tyr Arg Thr
                85                  90                  95

Glu Ile Asp Lys Pro Ser Gln His His His His His His
```

```
        100                 105


<210> SEQ ID NO 97
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Gly Val Ser Asp Val Pro Arg Asp Leu Glu Val Val Ala Ala Thr
1               5                   10                  15

Pro Thr Ser Leu Leu Ile Ser Trp Asn His Leu Glu His Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Glu Tyr Pro Thr Thr Ala Thr Ile Ser Gly Leu
    50                  55                  60

Lys Pro Gly Val Asp Tyr Thr Ile Thr Val Tyr Ala Val Thr Ile Thr
65                  70                  75                  80

Met Leu Lys Tyr Pro Thr Gln Ser Pro Ile Ser Ile Asn Tyr Arg Thr
                85                  90                  95

Glu Ile Asp Lys Pro Ser Gln His His His His His His
            100                 105


<210> SEQ ID NO 98
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Gly Val Ser Asp Val Pro Arg Asp Leu Glu Val Val Ala Ala Thr
1               5                   10                  15

Pro Thr Ser Leu Leu Ile Ser Trp Gly His Tyr Arg Arg Ser Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His
            100                 105


<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Gly Val Ser Asp Val Pro Arg Asp Leu Glu Val Val Ala Ala Thr
1               5                   10                  15
```

```
Pro Thr Ser Leu Leu Ile Ser Trp Asp Ala Ser His Tyr Glu Arg Arg
            20                  25                  30

Tyr Tyr Arg Ile Thr Tyr Gly Glu Thr Gly Gly Asn Ser Pro Val Gln
        35                  40                  45

Glu Phe Thr Val Pro Arg Tyr His His Thr Ala Thr Ile Ser Gly Leu
    50                  55                  60

Lys Pro Gly Val Asp Tyr Thr Ile Thr Val Tyr Ala Val Thr Gln Ala
65                  70                  75                  80

Gln Glu His Tyr Gln Pro Pro Ile Ser Ile Asn Tyr Arg Thr Glu Ile
                85                  90                  95

Asp Lys Pro Ser Gln His His His His His His
            100                 105


<210> SEQ ID NO 100
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Gly Val Ser Asp Val Pro Arg Asp Leu Glu Val Val Ala Ala Thr
1               5                   10                  15

Pro Thr Ser Leu Leu Ile Ser Trp Asn Ser Tyr Tyr His Ser Ala Asp
            20                  25                  30

Tyr Tyr Arg Ile Thr Tyr Gly Glu Thr Gly Gly Asn Ser Pro Val Gln
        35                  40                  45

Glu Phe Thr Val Pro Tyr Pro Pro Thr Thr Ala Thr Ile Ser Gly Leu
    50                  55                  60

Lys Pro Gly Val Asp Tyr Thr Ile Thr Val Tyr Ala Val Tyr Ser Ala
65                  70                  75                  80

Lys Ser Tyr Tyr Pro Ile Ser Ile Asn Tyr Arg Thr Glu Ile Asp Lys
                85                  90                  95

Pro Ser Gln His His His His His His
            100                 105


<210> SEQ ID NO 101
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Gly Val Ser Asp Val Pro Arg Asp Leu Glu Val Val Ala Ala Thr
1               5                   10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Pro Ser Gly Asn Ala Thr Ala Thr Ile Ser Gly Leu
    50                  55                  60

Lys Pro Gly Val Asp Tyr Thr Ile Thr Val Tyr Ala Val Glu Asp Thr
65                  70                  75                  80

Asn Asp Tyr Pro His Thr His Arg Pro Ile Ser Ile Asn Tyr Arg Thr
                85                  90                  95
```

```
Glu Ile Asp Lys Pro Ser Gln His His His His His His
            100                 105


<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Met Gly Val Ser Asp Val Pro Arg Asp Leu Glu Val Val Ala Ala Thr
1               5                   10                  15

Pro Thr Ser Leu Leu Ile Ser Trp His Gly Glu Pro Asp Gln Thr Arg
            20                  25                  30

Tyr Tyr Arg Ile Thr Tyr Gly Glu Thr Gly Gly Asn Ser Pro Val Gln
        35                  40                  45

Glu Phe Thr Val Pro Pro Tyr Arg Arg Thr Ala Thr Ile Ser Gly Leu
    50                  55                  60

Lys Pro Gly Val Asp Tyr Thr Ile Thr Val Tyr Ala Val Thr Ser Gly
65                  70                  75                  80

Tyr Thr Gly His Tyr Gln Pro Ile Ser Ile Asn Tyr Arg Thr Glu Ile
                85                  90                  95

Asp Lys Pro Ser Gln His His His His His His
            100                 105


<210> SEQ ID NO 103
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Gly Val Ser Asp Val Pro Arg Asp Leu Glu Val Val Ala Ala Thr
1               5                   10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His
            100                 105


<210> SEQ ID NO 104
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104
```

-continued

```
Met Gly Val Ser Asp Val Pro Arg Asp Leu Glu Val Val Ala Ala Thr
1               5                   10                  15

Pro Thr Ser Leu Leu Ile Ser Trp Tyr Glu Pro Tyr Thr Pro Ile His
            20                  25                  30

Tyr Tyr Arg Ile Thr Tyr Gly Glu Thr Gly Gly Asn Ser Pro Val Gln
        35                  40                  45

Glu Phe Thr Val Pro Gly Tyr Tyr Gly Thr Ala Thr Ile Ser Gly Leu
    50                  55                  60

Lys Pro Gly Val Asp Tyr Thr Ile Thr Val Tyr Ala Val Tyr Gly Tyr
65                  70                  75                  80

Tyr Gln Tyr Thr Pro Ile Ser Ile Asn Tyr Arg Thr Glu Ile Asp Lys
                85                  90                  95

Pro Ser Gln His His His His His His
            100                 105
```

<210> SEQ ID NO 105
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Met Gly Val Ser Asp Val Pro Arg Asp Leu Glu Val Val Ala Ala Thr
1               5                   10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Pro Ser Gly Asn Ala Thr Ala Thr Ile Ser Gly Leu
    50                  55                  60

Lys Pro Gly Val Asp Tyr Thr Ile Thr Val Tyr Ala Val Ser Asp Asp
65                  70                  75                  80

Asn Lys Tyr Tyr His Gln His Arg Pro Ile Ser Ile Asn Tyr Arg Thr
                85                  90                  95

Glu Ile Asp Lys Pro Ser Gln His His His His His His
            100                 105
```

<210> SEQ ID NO 106
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Arg Arg Ser Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80
```

```
Asp Tyr Tyr Pro His Glu His Arg Pro Ile Ser Ile Asn Tyr Arg Thr
                85                  90                  95

Glu Ile Asp Lys Pro Ser Gln His His His His His His
            100                 105


<210> SEQ ID NO 107
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Met Gly Val Ser Asp Val Pro Arg Asp Leu Glu Val Val Ala Ala Thr
1               5                   10                  15

Pro Thr Ser Leu Leu Ile Ser Trp Ser Lys Tyr Ser Lys His Gly His
            20                  25                  30

Tyr Tyr Arg Ile Thr Tyr Gly Glu Thr Gly Gly Asn Ser Pro Val Gln
        35                  40                  45

Glu Phe Thr Val Pro Ser Gly Asn Ala Thr Ala Thr Ile Ser Gly Leu
    50                  55                  60

Lys Pro Gly Val Asp Tyr Thr Ile Thr Val Tyr Ala Val Glu Asp Thr
65                  70                  75                  80

Asn Asp Tyr Pro His Thr His Arg Pro Ile Ser Ile Asn Tyr Arg Thr
                85                  90                  95

Glu Ile Asp Lys Pro Ser Gln His His His His His His
            100                 105


<210> SEQ ID NO 108
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Met Gly Val Ser Asp Val Pro Arg Asp Leu Glu Val Val Ala Ala Thr
1               5                   10                  15

Pro Thr Ser Leu Leu Ile Ser Trp Tyr Glu Pro Gly Ala Ser Val Tyr
            20                  25                  30

Tyr Tyr Arg Ile Thr Tyr Gly Glu Thr Gly Gly Asn Ser Pro Val Gln
        35                  40                  45

Glu Phe Thr Val Pro Ser Tyr Tyr His Thr Ala Thr Ile Ser Gly Leu
    50                  55                  60

Lys Pro Gly Val Asp Tyr Thr Ile Thr Val Tyr Ala Val Tyr Gly Tyr
65                  70                  75                  80

Tyr Glu Tyr Glu Pro Ile Ser Ile Asn Tyr Arg Thr Glu Ile Asp Lys
                85                  90                  95

Pro Ser Gln His His His His His His
            100                 105


<210> SEQ ID NO 109
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 109

```
Met Gly Val Ser Asp Val Pro Arg Asp Leu Glu Val Val Ala Ala Thr
1               5                   10                  15

Pro Thr Ser Leu Leu Ile Ser Trp Gln Ser Tyr Tyr Ala His Ser Asp
            20                  25                  30

Tyr Tyr Arg Ile Thr Tyr Gly Glu Thr Gly Gly Asn Ser Pro Val Gln
        35                  40                  45

Glu Phe Thr Val Pro Tyr Pro Pro Gln Thr Ala Thr Ile Ser Gly Leu
    50                  55                  60

Lys Pro Gly Val Asp Tyr Thr Ile Thr Val Tyr Ala Val Tyr Ala Gly
65                  70                  75                  80

Ser Ser Tyr Tyr Pro Ile Ser Ile Asn Tyr Arg Thr Glu Ile Asp Lys
                85                  90                  95

Pro Ser Gln His His His His His His
            100                 105
```

<210> SEQ ID NO 110
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Gly Val Ser Asp Val Pro Arg Asp Leu Glu Val Val Ala Ala Thr
1               5                   10                  15

Pro Thr Ser Leu Leu Ile Ser Trp Gly His Tyr Arg Arg Ser Gly His
            20                  25                  30

Tyr Tyr Arg Ile Thr Tyr Gly Glu Thr Gly Gly Asn Ser Pro Val Gln
        35                  40                  45

Glu Phe Thr Val Asp Pro Ser Ser Tyr Thr Ala Thr Ile Ser Gly Leu
    50                  55                  60

Lys Pro Gly Val Asp Tyr Thr Ile Thr Val Tyr Ala Val Ser Lys Asp
65                  70                  75                  80

Asp Tyr Tyr Pro His Glu His Arg Pro Ile Ser Ile Asn Tyr Arg Thr
                85                  90                  95

Glu Ile Asp Lys Pro Ser Gln His His His His His His
            100                 105
```

<210> SEQ ID NO 111
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Met Gly Val Ser Asp Val Pro Arg Asp Leu Glu Val Val Ala Ala Thr
1               5                   10                  15

Pro Thr Ser Leu Leu Ile Ser Trp Pro Glu Pro Gly Thr Pro Val Tyr
            20                  25                  30

Tyr Tyr Arg Ile Thr Tyr Gly Glu Thr Gly Gly Asn Ser Pro Val Gln
        35                  40                  45

Glu Phe Thr Val Pro Ala Tyr Tyr Gly Thr Ala Thr Ile Ser Gly Leu
    50                  55                  60

Lys Pro Gly Val Asp Tyr Thr Ile Thr Val Tyr Ala Val Tyr Gly Tyr
```

```
65                  70                  75                  80

Tyr Asp Tyr Ser Pro Ile Ser Ile Asn Tyr Arg Thr Glu Ile Asp Lys
                85                  90                  95

Pro Ser Gln His His His His His His
            100                 105


<210> SEQ ID NO 112
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Gly Val Ser Asp Val Pro Arg Asp Leu Glu Val Val Ala Ala Thr
1               5                   10                  15

Pro Thr Ser Leu Leu Ile Ser Trp Tyr Arg Tyr Glu Lys Thr Gln His
            20                  25                  30

Tyr Tyr Arg Ile Thr Tyr Gly Glu Thr Gly Gly Asn Ser Pro Val Gln
        35                  40                  45

Glu Phe Thr Val Pro Pro Glu Ser Gly Thr Ala Thr Ile Ser Gly Leu
    50                  55                  60

Lys Pro Gly Val Asp Tyr Thr Ile Thr Val Tyr Ala Val Tyr Ala Gly
65                  70                  75                  80

Tyr Glu Tyr Pro His Thr His Arg Pro Ile Ser Ile Asn Tyr Arg Thr
                85                  90                  95

Glu Ile Asp Lys Pro Ser Gln His His His His His His
            100                 105


<210> SEQ ID NO 113
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Met Gly Val Ser Asp Val Pro Arg Asp Leu Glu Val Val Ala Ala Thr
1               5                   10                  15

Pro Thr Ser Leu Leu Ile Ser Trp Val Lys Ser Glu Glu Tyr Tyr Arg
            20                  25                  30

Tyr Tyr Arg Ile Thr Tyr Gly Glu Thr Gly Gly Asn Ser Pro Val Gln
        35                  40                  45

Glu Phe Thr Val Pro Tyr Tyr Val His Thr Ala Thr Ile Ser Gly Leu
    50                  55                  60

Lys Pro Gly Val Asp Tyr Thr Ile Thr Val Tyr Ala Val Thr Glu Tyr
65                  70                  75                  80

Tyr Tyr Ala Gly Ala Val Val Ser Val Pro Ile Ser Ile Asn Tyr Arg
                85                  90                  95

Thr Glu Ile Asp Lys Pro Ser Gln His His His His His His
            100                 105                 110


<210> SEQ ID NO 114
<211> LENGTH: 105
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 114

Met Gly Val Ser Asp Val Pro Arg Asp Leu Glu Val Val Ala Ala Thr
1               5                   10                  15

Pro Thr Ser Leu Leu Ile Ser Trp Tyr Asp Pro Tyr Thr Tyr Gly Ser
            20                  25                  30

Tyr Tyr Arg Ile Thr Tyr Gly Glu Thr Gly Gly Asn Ser Pro Val Gln
        35                  40                  45

Glu Phe Thr Val Gly Pro Tyr Thr Thr Thr Ala Thr Ile Ser Gly Leu
    50                  55                  60

Lys Pro Gly Val Asp Tyr Thr Ile Thr Val Tyr Ala Val Ser Tyr Tyr
65                  70                  75                  80

Tyr Ser Thr Gln Pro Ile Ser Ile Asn Tyr Arg Thr Glu Ile Asp Lys
                85                  90                  95

Pro Ser Gln His His His His His His
            100                 105

<210> SEQ ID NO 115
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Gly Val Ser Asp Val Pro Arg Asp Leu Glu Val Val Ala Ala Thr
1               5                   10                  15

Pro Thr Ser Leu Leu Ile Ser Trp Ser Asn Asp Gly Pro Gly Leu Ser
            20                  25                  30

Tyr Tyr Arg Ile Thr Tyr Gly Glu Thr Gly Gly Asn Ser Pro Val Gln
        35                  40                  45

Glu Phe Thr Val Pro Ser Ser Gln Thr Thr Ala Thr Ile Ser Gly Leu
    50                  55                  60

Lys Pro Gly Val Asp Tyr Thr Ile Thr Val Tyr Ala Val Ser Tyr Tyr
65                  70                  75                  80

Thr Lys Lys Ala Tyr Ser Ala Gly Pro Ile Ser Ile Asn Tyr Arg Thr
                85                  90                  95

Glu Ile Asp Lys Pro Ser Gln His His His His His His
            100                 105

<210> SEQ ID NO 116
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Met Gly Val Ser Asp Val Pro Arg Asp Leu Glu Val Val Ala Ala Thr
1               5                   10                  15

Pro Thr Ser Leu Leu Ile Ser Trp Pro Asp Pro Tyr Tyr Lys Pro Asp
            20                  25                  30

Tyr Tyr Arg Ile Thr Tyr Gly Glu Thr Gly Gly Asn Ser Pro Val Gln
        35                  40                  45

Glu Phe Thr Val Pro Arg Asp Tyr Thr Thr Ala Thr Ile Ser Gly Leu
    50                  55                  60

```
Lys Pro Gly Val Asp Tyr Thr Ile Thr Val Tyr Ala Val Tyr Ser Tyr
65                  70                  75                  80

Tyr Gly Tyr Tyr Pro Ile Ser Ile Asn Tyr Arg Thr Glu Ile Asp Lys
                85                  90                  95

Pro Ser Gln His His His His His His
            100                 105


<210> SEQ ID NO 117
<211> LENGTH: 208
<212> TYPE: PRT
<213> ORGANISM: Homo sapiens

<400> SEQUENCE: 117

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro Asp
            20                  25                  30

Ser Ser Pro Leu Leu Gln Phe Gly Gly Gln Val Arg Gln Arg Tyr Leu
        35                  40                  45

Tyr Thr Asp Asp Ala Gln Gln Thr Glu Ala His Leu Glu Ile Arg Glu
    50                  55                  60

Asp Gly Thr Val Gly Gly Ala Ala Asp Gln Ser Pro Glu Ser Leu Leu
65                  70                  75                  80

Gln Leu Lys Ala Leu Lys Pro Gly Val Ile Gln Ile Leu Gly Val Lys
                85                  90                  95

Thr Ser Arg Phe Leu Cys Gln Arg Pro Asp Gly Ala Leu Tyr Gly Ser
            100                 105                 110

Leu His Phe Asp Pro Glu Ala Cys Ser Phe Arg Glu Leu Leu Leu Glu
        115                 120                 125

Asp Gly Tyr Asn Val Tyr Gln Ser Glu Ala His Gly Leu Pro Leu His
    130                 135                 140

Leu Pro Gly Asn Lys Ser Pro His Arg Asp Pro Ala Pro Arg Gly Pro
145                 150                 155                 160

Ala Arg Phe Leu Pro Leu Pro Gly Leu Pro Pro Ala Leu Pro Glu Pro
                165                 170                 175

Pro Gly Ile Leu Ala Pro Gln Pro Pro Asp Val Gly Ser Ser Asp Pro
            180                 185                 190

Leu Ser Met Val Gly Pro Ser Gln Gly Arg Ser Pro Ser Tyr Ala Ser
        195                 200                 205


<210> SEQ ID NO 118
<211> LENGTH: 173
<212> TYPE: PRT
<213> ORGANISM: Homo sapiens

<400> SEQUENCE: 118

Pro Leu Leu Gln Phe Gly Gly Gln Val Arg Gln Arg Tyr Leu Tyr Thr
1               5                   10                  15

Asp Asp Ala Gln Gln Thr Glu Ala His Leu Glu Ile Arg Glu Asp Gly
            20                  25                  30

Thr Val Gly Gly Ala Ala Asp Gln Ser Pro Glu Ser Leu Leu Gln Leu
        35                  40                  45

Lys Ala Leu Lys Pro Gly Val Ile Gln Ile Leu Gly Val Lys Thr Ser
    50                  55                  60

Arg Phe Leu Cys Gln Arg Pro Asp Gly Ala Leu Tyr Gly Ser Leu His
65                  70                  75                  80
```

```
Phe Asp Pro Glu Ala Cys Ser Phe Arg Glu Leu Leu Leu Glu Asp Gly
                85                  90                  95

Tyr Asn Val Tyr Gln Ser Glu Ala His Gly Leu Pro Leu His Leu Pro
            100                 105                 110

Gly Asn Lys Ser Pro His Arg Asp Pro Ala Pro Arg Gly Pro Ala Arg
        115                 120                 125

Phe Leu Pro Leu Pro Gly Leu Pro Pro Ala Leu Pro Glu Pro Pro Gly
    130                 135                 140

Ile Leu Ala Pro Gln Pro Pro Asp Val Gly Ser Ser Asp Pro Leu Ser
145                 150                 155                 160

Met Val Gly Pro Ser Gln Gly Arg Ser Pro Ser Tyr Ala
                165                 170


<210> SEQ ID NO 119
<211> LENGTH: 34
<212> TYPE: PRT
<213> ORGANISM: Homo sapiens

<400> SEQUENCE: 119

Met Asp Ser Asp Glu Thr Gly Phe Glu His Ser Gly Leu Trp Val Ser
1               5                   10                  15

Val Leu Ala Gly Leu Leu Gly Ala Cys Gln Ala His Pro Ile Pro Asp
            20                  25                  30

Ser Ser


<210> SEQ ID NO 120
<211> LENGTH: 7
<212> TYPE: PRT
<213> ORGANISM: Homo sapiens

<400> SEQUENCE: 120

His Pro Ile Pro Asp Ser Ser
1               5


<210> SEQ ID NO 121
<211> LENGTH: 6
<212> TYPE: PRT
<213> ORGANISM: Homo sapiens

<400> SEQUENCE: 121

Pro Ile Pro Asp Ser Ser
1               5


<210> SEQ ID NO 122
<211> LENGTH: 3
<212> TYPE: PRT
<213> ORGANISM: Homo sapiens

<400> SEQUENCE: 122

Asp Ser Ser
1


<210> SEQ ID NO 123
<211> LENGTH: 5
<212> TYPE: PRT
<213> ORGANISM: Homo sapiens

<400> SEQUENCE: 123

Ile Pro Asp Ser Ser
1               5
```

<210> SEQ ID NO 124
<211> LENGTH: 4
<212> TYPE: PRT
<213> ORGANISM: Homo sapiens

<400> SEQUENCE: 124

Pro Asp Ser Ser
1

<210> SEQ ID NO 125
<211> LENGTH: 187
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 125

```
Met His His His His His His Pro Ile Pro Asp Ser Ser Pro Leu Leu
1               5                   10                  15

Gln Phe Gly Gly Gln Val Arg Gln Arg Tyr Leu Tyr Thr Asp Asp Ala
            20                  25                  30

Gln Gln Thr Glu Ala His Leu Glu Ile Arg Glu Asp Gly Thr Val Gly
        35                  40                  45

Gly Ala Ala Asp Gln Ser Pro Glu Ser Leu Leu Gln Leu Lys Ala Leu
    50                  55                  60

Lys Pro Gly Val Ile Gln Ile Leu Gly Val Lys Thr Ser Arg Phe Leu
65                  70                  75                  80

Cys Gln Arg Pro Asp Gly Ala Leu Tyr Gly Ser Leu His Phe Asp Pro
                85                  90                  95

Glu Ala Cys Ser Phe Arg Glu Leu Leu Leu Glu Asp Gly Tyr Asn Val
            100                 105                 110

Tyr Gln Ser Glu Ala His Gly Leu Pro Leu His Leu Pro Gly Asn Lys
        115                 120                 125

Ser Pro His Arg Asp Pro Ala Pro Arg Gly Pro Ala Arg Phe Leu Pro
    130                 135                 140

Leu Pro Gly Leu Pro Pro Ala Leu Pro Glu Pro Pro Gly Ile Leu Ala
145                 150                 155                 160

Pro Gln Pro Pro Asp Val Gly Ser Ser Asp Pro Leu Ser Met Val Gly
                165                 170                 175

Pro Ser Gln Gly Arg Ser Pro Ser Tyr Ala Ser
            180                 185
```

<210> SEQ ID NO 126
<211> LENGTH: 187
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 126

```
Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
```

```
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala His His His His His His
            180                 185


<210> SEQ ID NO 127
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met His Pro Ile Pro Asp Ser Ser Pro Leu Leu Gln Phe Gly Gly Gln
1               5                   10                  15

Val Arg Gln Arg Tyr Leu Tyr Thr Asp Asp Ala Gln Gln Thr Glu Ala
            20                  25                  30

His Leu Glu Ile Arg Glu Asp Gly Thr Val Gly Gly Ala Ala Asp Gln
        35                  40                  45

Ser Pro Glu Ser Leu Leu Gln Leu Lys Ala Leu Lys Pro Gly Val Ile
    50                  55                  60

Gln Ile Leu Gly Val Lys Thr Ser Arg Phe Leu Cys Gln Arg Pro Asp
65                  70                  75                  80

Gly Ala Leu Tyr Gly Ser Leu His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu His Leu Pro Gly Asn Lys Ser Pro His Arg Asp
        115                 120                 125

Pro Ala Pro Arg Gly Pro Ala Arg Phe Leu Pro Leu Pro Gly Leu Pro
    130                 135                 140

Pro Ala Leu Pro Glu Pro Pro Gly Ile Leu Ala Pro Gln Pro Pro Asp
145                 150                 155                 160

Val Gly Ser Ser Asp Pro Leu Ser Met Val Gly Pro Ser Gln Gly Arg
                165                 170                 175

Ser Pro Ser Tyr Ala Ser His His His His His His
            180                 185


<210> SEQ ID NO 128
<211> LENGTH: 186
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 128

Met His His His His His His Pro Ile Pro Asp Ser Ser Pro Leu Leu
1               5                   10                  15

Gln Phe Gly Gly Gln Val Arg Gln Arg Tyr Leu Tyr Thr Asp Asp Ala
            20                  25                  30

Gln Gln Thr Glu Ala His Leu Glu Ile Arg Glu Asp Gly Thr Val Gly
        35                  40                  45

Gly Ala Ala Asp Gln Ser Pro Glu Ser Leu Leu Gln Leu Lys Ala Leu
    50                  55                  60

Lys Pro Gly Val Ile Gln Ile Leu Gly Val Lys Thr Ser Arg Phe Leu
65                  70                  75                  80

Cys Gln Arg Pro Asp Gly Ala Leu Tyr Gly Ser Leu His Phe Asp Pro
                85                  90                  95

Glu Ala Cys Ser Phe Arg Glu Leu Leu Leu Glu Asp Gly Tyr Asn Val
            100                 105                 110

Tyr Gln Ser Glu Ala His Gly Leu Pro Leu His Leu Pro Gly Asn Lys
        115                 120                 125

Ser Pro His Arg Asp Pro Ala Pro Arg Gly Pro Ala Arg Phe Leu Pro
    130                 135                 140

Leu Pro Gly Leu Pro Pro Ala Leu Pro Glu Pro Pro Gly Ile Leu Ala
145                 150                 155                 160

Pro Gln Pro Pro Asp Val Gly Ser Ser Asp Pro Leu Ser Met Val Gly
                165                 170                 175

Pro Ser Gln Gly Arg Ser Pro Ser Tyr Ala
            180                 185

<210> SEQ ID NO 129
<211> LENGTH: 184
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Met His His His His His His Asp Ser Ser Pro Leu Leu Gln Phe Gly
1               5                   10                  15

Gly Gln Val Arg Gln Arg Tyr Leu Tyr Thr Asp Asp Ala Gln Gln Thr
            20                  25                  30

Glu Ala His Leu Glu Ile Arg Glu Asp Gly Thr Val Gly Gly Ala Ala
        35                  40                  45

Asp Gln Ser Pro Glu Ser Leu Leu Gln Leu Lys Ala Leu Lys Pro Gly
    50                  55                  60

Val Ile Gln Ile Leu Gly Val Lys Thr Ser Arg Phe Leu Cys Gln Arg
65                  70                  75                  80

Pro Asp Gly Ala Leu Tyr Gly Ser Leu His Phe Asp Pro Glu Ala Cys
                85                  90                  95

Ser Phe Arg Glu Leu Leu Leu Glu Asp Gly Tyr Asn Val Tyr Gln Ser
            100                 105                 110

Glu Ala His Gly Leu Pro Leu His Leu Pro Gly Asn Lys Ser Pro His
        115                 120                 125

Arg Asp Pro Ala Pro Arg Gly Pro Ala Arg Phe Leu Pro Leu Pro Gly
    130                 135                 140

```
Leu Pro Pro Ala Leu Pro Glu Pro Pro Gly Ile Leu Ala Pro Gln Pro
145                 150                 155                 160

Pro Asp Val Gly Ser Ser Asp Pro Leu Ser Met Val Gly Pro Ser Gln
                165                 170                 175

Gly Arg Ser Pro Ser Tyr Ala Ser
            180
```

<210> SEQ ID NO 130
<211> LENGTH: 186
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Met His His His His His His Ile Pro Asp Ser Ser Pro Leu Leu Gln
1               5                   10                  15

Phe Gly Gly Gln Val Arg Gln Arg Tyr Leu Tyr Thr Asp Asp Ala Gln
            20                  25                  30

Gln Thr Glu Ala His Leu Glu Ile Arg Glu Asp Gly Thr Val Gly Gly
        35                  40                  45

Ala Ala Asp Gln Ser Pro Glu Ser Leu Leu Gln Leu Lys Ala Leu Lys
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser
            180                 185
```

<210> SEQ ID NO 131
<211> LENGTH: 181
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

```
Met His His His His His His Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60
```

```
Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180


<210> SEQ ID NO 132
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Ser Gly Ser Gly Ser Gly Ser Gly Ser Gly Ser Gly
            100                 105                 110

Ser Pro Ile Pro Asp Ser Ser Pro Leu Leu Gln Phe Gly Gly Gln Val
        115                 120                 125

Arg Gln Arg Tyr Leu Tyr Thr Asp Asp Ala Gln Gln Thr Glu Ala His
    130                 135                 140

Leu Glu Ile Arg Glu Asp Gly Thr Val Gly Gly Ala Ala Asp Gln Ser
145                 150                 155                 160

Pro Glu Ser Leu Leu Gln Leu Lys Ala Leu Lys Pro Gly Val Ile Gln
                165                 170                 175

Ile Leu Gly Val Lys Thr Ser Arg Phe Leu Cys Gln Arg Pro Asp Gly
            180                 185                 190

Ala Leu Tyr Gly Ser Leu His Phe Asp Pro Glu Ala Cys Ser Phe Arg
        195                 200                 205

Glu Leu Leu Leu Glu Asp Gly Tyr Asn Val Tyr Gln Ser Glu Ala His
    210                 215                 220

Gly Leu Pro Leu His Leu Pro Gly Asn Lys Ser Pro His Arg Asp Pro
225                 230                 235                 240
```

```
Ala Pro Arg Gly Pro Ala Arg Phe Leu Pro Leu Pro Gly Leu Pro Pro
                245                 250                 255

Ala Leu Pro Glu Pro Pro Gly Ile Leu Ala Pro Gln Pro Pro Asp Val
            260                 265                 270

Gly Ser Ser Asp Pro Leu Ser Met Val Gly Pro Ser Gln Gly Arg Ser
        275                 280                 285

Pro Ser Tyr Ala Ser
    290


<210> SEQ ID NO 133
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln His His His His His His Gly Ser Gly Ser Gly Ser Gly
            100                 105                 110

Ser Gly Ser Gly Ser Gly Ser His Pro Ile Pro Asp Ser Ser Pro Leu
        115                 120                 125

Leu Gln Phe Gly Gly Gln Val Arg Gln Arg Tyr Leu Tyr Thr Asp Asp
    130                 135                 140

Ala Gln Gln Thr Glu Ala His Leu Glu Ile Arg Glu Asp Gly Thr Val
145                 150                 155                 160

Gly Gly Ala Ala Asp Gln Ser Pro Glu Ser Leu Leu Gln Leu Lys Ala
                165                 170                 175

Leu Lys Pro Gly Val Ile Gln Ile Leu Gly Val Lys Thr Ser Arg Phe
            180                 185                 190

Leu Cys Gln Arg Pro Asp Gly Ala Leu Tyr Gly Ser Leu His Phe Asp
        195                 200                 205

Pro Glu Ala Cys Ser Phe Arg Glu Leu Leu Leu Glu Asp Gly Tyr Asn
    210                 215                 220

Val Tyr Gln Ser Glu Ala His Gly Leu Pro Leu His Leu Pro Gly Asn
225                 230                 235                 240

Lys Ser Pro His Arg Asp Pro Ala Pro Arg Gly Pro Ala Arg Phe Leu
                245                 250                 255

Pro Leu Pro Gly Leu Pro Pro Ala Leu Pro Glu Pro Pro Gly Ile Leu
            260                 265                 270

Ala Pro Gln Pro Pro Asp Val Gly Ser Ser Asp Pro Leu Ser Met Val
        275                 280                 285

Gly Pro Ser Gln Gly Arg Ser Pro Ser Tyr Ala
```

290 295

<210> SEQ ID NO 134
<211> LENGTH: 299
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 134

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln His His His His His His Gly Ser Gly Ser Gly Ser Gly
            100                 105                 110

Ser Gly Ser Gly Ser Gly Ser Pro Ile Pro Asp Ser Ser Pro Leu Leu
        115                 120                 125

Gln Phe Gly Gly Gln Val Arg Gln Arg Tyr Leu Tyr Thr Asp Asp Ala
    130                 135                 140

Gln Gln Thr Glu Ala His Leu Glu Ile Arg Glu Asp Gly Thr Val Gly
145                 150                 155                 160

Gly Ala Ala Asp Gln Ser Pro Glu Ser Leu Leu Gln Leu Lys Ala Leu
                165                 170                 175

Lys Pro Gly Val Ile Gln Ile Leu Gly Val Lys Thr Ser Arg Phe Leu
            180                 185                 190

Cys Gln Arg Pro Asp Gly Ala Leu Tyr Gly Ser Leu His Phe Asp Pro
        195                 200                 205

Glu Ala Cys Ser Phe Arg Glu Leu Leu Leu Glu Asp Gly Tyr Asn Val
    210                 215                 220

Tyr Gln Ser Glu Ala His Gly Leu Pro Leu His Leu Pro Gly Asn Lys
225                 230                 235                 240

Ser Pro His Arg Asp Pro Ala Pro Arg Gly Pro Ala Arg Phe Leu Pro
                245                 250                 255

Leu Pro Gly Leu Pro Pro Ala Leu Pro Glu Pro Pro Gly Ile Leu Ala
            260                 265                 270

Pro Gln Pro Pro Asp Val Gly Ser Ser Asp Pro Leu Ser Met Val Gly
        275                 280                 285

Pro Ser Gln Gly Arg Ser Pro Ser Tyr Ala Ser
    290                 295
```

<210> SEQ ID NO 135
<211> LENGTH: 299
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 135

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Asp Lys
85 90 95

Pro Ser Gly Gly Ser Gly Ser Gly Ser Gly Ser Gly Ser Gly Ser Gly
100 105 110

Ser Pro Ile Pro Asp Ser Ser Pro Leu Leu Gln Phe Gly Gly Gln Val
115 120 125

Arg Gln Arg Tyr Leu Tyr Thr Asp Asp Ala Gln Gln Thr Glu Ala His
130 135 140

Leu Glu Ile Arg Glu Asp Gly Thr Val Gly Gly Ala Ala Asp Gln Ser
145 150 155 160

Pro Glu Ser Leu Leu Gln Leu Lys Ala Leu Lys Pro Gly Val Ile Gln
165 170 175

Ile Leu Gly Val Lys Thr Ser Arg Phe Leu Cys Gln Arg Pro Asp Gly
180 185 190

Ala Leu Tyr Gly Ser Leu His Phe Asp Pro Glu Ala Cys Ser Phe Arg
195 200 205

Glu Leu Leu Leu Glu Asp Gly Tyr Asn Val Tyr Gln Ser Glu Ala His
210 215 220

Gly Leu Pro Leu His Leu Pro Gly Asn Lys Ser Pro His Arg Asp Pro
225 230 235 240

Ala Pro Arg Gly Pro Ala Arg Phe Leu Pro Leu Pro Gly Leu Pro Pro
245 250 255

Ala Leu Pro Glu Pro Pro Gly Ile Leu Ala Pro Gln Pro Pro Asp Val
260 265 270

Gly Ser Ser Asp Pro Leu Ser Met Val Gly Pro Ser Gln Gly Arg Ser
275 280 285

Pro Ser Tyr Ala Ser His His His His His His
290 295

<210> SEQ ID NO 136
<211> LENGTH: 299
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Asp Lys
85 90 95

Pro Ser Gly Gly Ser Gly Ser Gly Ser Gly Ser Gly Ser Gly Ser Gly
100 105 110

Ser His Pro Ile Pro Asp Ser Ser Pro Leu Leu Gln Phe Gly Gly Gln
115 120 125

Val Arg Gln Arg Tyr Leu Tyr Thr Asp Asp Ala Gln Gln Thr Glu Ala
130 135 140

His Leu Glu Ile Arg Glu Asp Gly Thr Val Gly Gly Ala Ala Asp Gln
145 150 155 160

Ser Pro Glu Ser Leu Leu Gln Leu Lys Ala Leu Lys Pro Gly Val Ile
165 170 175

Gln Ile Leu Gly Val Lys Thr Ser Arg Phe Leu Cys Gln Arg Pro Asp
180 185 190

Gly Ala Leu Tyr Gly Ser Leu His Phe Asp Pro Glu Ala Cys Ser Phe
195 200 205

Arg Glu Leu Leu Leu Glu Asp Gly Tyr Asn Val Tyr Gln Ser Glu Ala
210 215 220

His Gly Leu Pro Leu His Leu Pro Gly Asn Lys Ser Pro His Arg Asp
225 230 235 240

Pro Ala Pro Arg Gly Pro Ala Arg Phe Leu Pro Leu Pro Gly Leu Pro
245 250 255

Pro Ala Leu Pro Glu Pro Pro Gly Ile Leu Ala Pro Gln Pro Pro Asp
260 265 270

Val Gly Ser Ser Asp Pro Leu Ser Met Val Gly Pro Ser Gln Gly Arg
275 280 285

Ser Pro Ser Tyr Ala His His His His His His
290 295

<210> SEQ ID NO 137
<211> LENGTH: 293
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 137

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Asp Lys
85 90 95

Pro Ser Gly Gly Ser Gly Ser Gly Ser Gly Ser Gly Ser Gly Ser Gly
100 105 110

Ser Pro Ile Pro Asp Ser Ser Pro Leu Leu Gln Phe Gly Gly Gln Val
115 120 125

Arg Gln Arg Tyr Leu Tyr Thr Asp Asp Ala Gln Gln Thr Glu Ala His
130 135 140

Leu Glu Ile Arg Glu Asp Gly Thr Val Gly Gly Ala Ala Asp Gln Ser
145 150 155 160

Pro Glu Ser Leu Leu Gln Leu Lys Ala Leu Lys Pro Gly Val Ile Gln
165 170 175

Ile Leu Gly Val Lys Thr Ser Arg Phe Leu Cys Gln Arg Pro Asp Gly
180 185 190

Ala Leu Tyr Gly Ser Leu His Phe Asp Pro Glu Ala Cys Ser Phe Arg
195 200 205

Glu Leu Leu Leu Glu Asp Gly Tyr Asn Val Tyr Gln Ser Glu Ala His
210 215 220

Gly Leu Pro Leu His Leu Pro Gly Asn Lys Ser Pro His Arg Asp Pro
225 230 235 240

Ala Pro Arg Gly Pro Ala Arg Phe Leu Pro Leu Pro Gly Leu Pro Pro
245 250 255

Ala Leu Pro Glu Pro Pro Gly Ile Leu Ala Pro Gln Pro Pro Asp Val
260 265 270

Gly Ser Ser Asp Pro Leu Ser Met Val Gly Pro Ser Gln Gly Arg Ser
275 280 285

Pro Ser Tyr Ala Ser
290

<210> SEQ ID NO 138
<211> LENGTH: 293
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Asp Lys
85 90 95

Pro Ser Gly Gly Ser Gly Ser Gly Ser Gly Ser Gly Ser Gly Ser Gly
100 105 110

Ser His Pro Ile Pro Asp Ser Ser Pro Leu Leu Gln Phe Gly Gly Gln
115 120 125

Val Arg Gln Arg Tyr Leu Tyr Thr Asp Asp Ala Gln Gln Thr Glu Ala
130 135 140

His Leu Glu Ile Arg Glu Asp Gly Thr Val Gly Gly Ala Ala Asp Gln
145 150 155 160

Ser Pro Glu Ser Leu Leu Gln Leu Lys Ala Leu Lys Pro Gly Val Ile

```
                165                 170                 175

Gln Ile Leu Gly Val Lys Thr Ser Arg Phe Leu Cys Gln Arg Pro Asp
            180                 185                 190

Gly Ala Leu Tyr Gly Ser Leu His Phe Asp Pro Glu Ala Cys Ser Phe
        195                 200                 205

Arg Glu Leu Leu Leu Glu Asp Gly Tyr Asn Val Tyr Gln Ser Glu Ala
    210                 215                 220

His Gly Leu Pro Leu His Leu Pro Gly Asn Lys Ser Pro His Arg Asp
225                 230                 235                 240

Pro Ala Pro Arg Gly Pro Ala Arg Phe Leu Pro Leu Pro Gly Leu Pro
                245                 250                 255

Pro Ala Leu Pro Glu Pro Pro Gly Ile Leu Ala Pro Gln Pro Pro Asp
            260                 265                 270

Val Gly Ser Ser Asp Pro Leu Ser Met Val Gly Pro Ser Gln Gly Arg
        275                 280                 285

Ser Pro Ser Tyr Ala
    290


<210> SEQ ID NO 139
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln His His His His His His Gly Ser Gly Ser Gly Ser Gly
            100                 105                 110

Ser Gly Ser Gly Ser Gly Ser Pro Ile Pro Asp Ser Ser Pro Leu Leu
        115                 120                 125

Gln Phe Gly Gly Gln Val Arg Gln Arg Tyr Leu Tyr Thr Asp Asp Ala
    130                 135                 140

Gln Gln Thr Glu Ala His Leu Glu Ile Arg Glu Asp Gly Thr Val Gly
145                 150                 155                 160

Gly Ala Ala Asp Gln Ser Pro Glu Ser Leu Leu Gln Leu Lys Ala Leu
                165                 170                 175

Lys Pro Gly Val Ile Gln Ile Leu Gly Val Lys Thr Ser Arg Phe Leu
            180                 185                 190

Cys Gln Arg Pro Asp Gly Ala Leu Tyr Gly Ser Leu His Phe Asp Pro
        195                 200                 205

Glu Ala Cys Ser Phe Arg Glu Leu Leu Leu Glu Asp Gly Tyr Asn Val
    210                 215                 220
```

```
Tyr Gln Ser Glu Ala His Gly Leu Pro Leu His Leu Pro Gly Asn Lys
225                 230                 235                 240

Ser Pro His Arg Asp Pro Ala Pro Arg Gly Pro Ala Arg Phe Leu Pro
                245                 250                 255

Leu Pro Gly Leu Pro Pro Ala Leu Pro Glu Pro Pro Gly Ile Leu Ala
            260                 265                 270

Pro Gln Pro Pro Asp Val Gly Ser Ser Asp Pro Leu Ser Met Val Gly
        275                 280                 285

Pro Ser Gln Gly Arg Ser Pro Ser Tyr Ala Ser
    290                 295


<210> SEQ ID NO 140
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
                85                  90                  95

Ser Gly Ser Gly Ser Gly Ser Pro Ile Pro Asp Ser Ser Pro Leu Leu
            100                 105                 110

Gln Phe Gly Gly Gln Val Arg Gln Arg Tyr Leu Tyr Thr Asp Asp Ala
        115                 120                 125

Gln Gln Thr Glu Ala His Leu Glu Ile Arg Glu Asp Gly Thr Val Gly
    130                 135                 140

Gly Ala Ala Asp Gln Ser Pro Glu Ser Leu Leu Gln Leu Lys Ala Leu
145                 150                 155                 160

Lys Pro Gly Val Ile Gln Ile Leu Gly Val Lys Thr Ser Arg Phe Leu
                165                 170                 175

Cys Gln Arg Pro Asp Gly Ala Leu Tyr Gly Ser Leu His Phe Asp Pro
            180                 185                 190

Glu Ala Cys Ser Phe Arg Glu Leu Leu Leu Glu Asp Gly Tyr Asn Val
        195                 200                 205

Tyr Gln Ser Glu Ala His Gly Leu Pro Leu His Leu Pro Gly Asn Lys
    210                 215                 220

Ser Pro His Arg Asp Pro Ala Pro Arg Gly Pro Ala Arg Phe Leu Pro
225                 230                 235                 240

Leu Pro Gly Leu Pro Pro Ala Leu Pro Glu Pro Pro Gly Ile Leu Ala
                245                 250                 255

Pro Gln Pro Pro Asp Val Gly Ser Ser Asp Pro Leu Ser Met Val Gly
            260                 265                 270

Pro Ser Gln Gly Arg Ser Pro Ser Tyr Ala Ser
        275                 280
```

<210> SEQ ID NO 141
<211> LENGTH: 279
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 141

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
                85                  90                  95

Ser Gly Ser Pro Ile Pro Asp Ser Ser Pro Leu Leu Gln Phe Gly Gly
            100                 105                 110

Gln Val Arg Gln Arg Tyr Leu Tyr Thr Asp Asp Ala Gln Gln Thr Glu
        115                 120                 125

Ala His Leu Glu Ile Arg Glu Asp Gly Thr Val Gly Gly Ala Ala Asp
    130                 135                 140

Gln Ser Pro Glu Ser Leu Leu Gln Leu Lys Ala Leu Lys Pro Gly Val
145                 150                 155                 160

Ile Gln Ile Leu Gly Val Lys Thr Ser Arg Phe Leu Cys Gln Arg Pro
                165                 170                 175

Asp Gly Ala Leu Tyr Gly Ser Leu His Phe Asp Pro Glu Ala Cys Ser
            180                 185                 190

Phe Arg Glu Leu Leu Leu Glu Asp Gly Tyr Asn Val Tyr Gln Ser Glu
        195                 200                 205

Ala His Gly Leu Pro Leu His Leu Pro Gly Asn Lys Ser Pro His Arg
    210                 215                 220

Asp Pro Ala Pro Arg Gly Pro Ala Arg Phe Leu Pro Leu Pro Gly Leu
225                 230                 235                 240

Pro Pro Ala Leu Pro Glu Pro Pro Gly Ile Leu Ala Pro Gln Pro Pro
                245                 250                 255

Asp Val Gly Ser Ser Asp Pro Leu Ser Met Val Gly Pro Ser Gln Gly
            260                 265                 270

Arg Ser Pro Ser Tyr Ala Ser
        275
```

<210> SEQ ID NO 142
<211> LENGTH: 274
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 142

```
Met Gly Val Ser Asp Val Pro Arg Asp Leu Glu Val Val Ala Ala Thr
1               5                   10                  15
```

```
Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Pro Ile
                85                  90                  95

Pro Asp Ser Ser Pro Leu Leu Gln Phe Gly Gly Gln Val Arg Gln Arg
            100                 105                 110

Tyr Leu Tyr Thr Asp Asp Ala Gln Gln Thr Glu Ala His Leu Glu Ile
        115                 120                 125

Arg Glu Asp Gly Thr Val Gly Gly Ala Ala Asp Gln Ser Pro Glu Ser
    130                 135                 140

Leu Leu Gln Leu Lys Ala Leu Lys Pro Gly Val Ile Gln Ile Leu Gly
145                 150                 155                 160

Val Lys Thr Ser Arg Phe Leu Cys Gln Arg Pro Asp Gly Ala Leu Tyr
                165                 170                 175

Gly Ser Leu His Phe Asp Pro Glu Ala Cys Ser Phe Arg Glu Leu Leu
            180                 185                 190

Leu Glu Asp Gly Tyr Asn Val Tyr Gln Ser Glu Ala His Gly Leu Pro
        195                 200                 205

Leu His Leu Pro Gly Asn Lys Ser Pro His Arg Asp Pro Ala Pro Arg
    210                 215                 220

Gly Pro Ala Arg Phe Leu Pro Leu Pro Gly Leu Pro Pro Ala Leu Pro
225                 230                 235                 240

Glu Pro Pro Gly Ile Leu Ala Pro Gln Pro Pro Asp Val Gly Ser Ser
                245                 250                 255

Asp Pro Leu Ser Met Val Gly Pro Ser Gln Gly Arg Ser Pro Ser Tyr
            260                 265                 270

Ala Ser


<210> SEQ ID NO 143
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile His His
                85                  90                  95
```

```
His His His His Gly Ser Gly Ser Gly Ser Gly Ser Pro Ile Pro Asp
            100                 105                 110

Ser Ser Pro Leu Leu Gln Phe Gly Gly Gln Val Arg Gln Arg Tyr Leu
        115                 120                 125

Tyr Thr Asp Asp Ala Gln Gln Thr Glu Ala His Leu Glu Ile Arg Glu
    130                 135                 140

Asp Gly Thr Val Gly Gly Ala Ala Asp Gln Ser Pro Glu Ser Leu Leu
145                 150                 155                 160

Gln Leu Lys Ala Leu Lys Pro Gly Val Ile Gln Ile Leu Gly Val Lys
                165                 170                 175

Thr Ser Arg Phe Leu Cys Gln Arg Pro Asp Gly Ala Leu Tyr Gly Ser
            180                 185                 190

Leu His Phe Asp Pro Glu Ala Cys Ser Phe Arg Glu Leu Leu Leu Glu
        195                 200                 205

Asp Gly Tyr Asn Val Tyr Gln Ser Glu Ala His Gly Leu Pro Leu His
    210                 215                 220

Leu Pro Gly Asn Lys Ser Pro His Arg Asp Pro Ala Pro Arg Gly Pro
225                 230                 235                 240

Ala Arg Phe Leu Pro Leu Pro Gly Leu Pro Pro Ala Leu Pro Glu Pro
                245                 250                 255

Pro Gly Ile Leu Ala Pro Gln Pro Pro Asp Val Gly Ser Ser Asp Pro
            260                 265                 270

Leu Ser Met Val Gly Pro Ser Gln Gly Arg Ser Pro Ser Tyr Ala Ser
        275                 280                 285


<210> SEQ ID NO 144
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile His His
                85                  90                  95

His His His His Gly Ser Gly Ser Pro Ile Pro Asp Ser Ser Pro Leu
            100                 105                 110

Leu Gln Phe Gly Gly Gln Val Arg Gln Arg Tyr Leu Tyr Thr Asp Asp
        115                 120                 125

Ala Gln Gln Thr Glu Ala His Leu Glu Ile Arg Glu Asp Gly Thr Val
    130                 135                 140

Gly Gly Ala Ala Asp Gln Ser Pro Glu Ser Leu Leu Gln Leu Lys Ala
145                 150                 155                 160

Leu Lys Pro Gly Val Ile Gln Ile Leu Gly Val Lys Thr Ser Arg Phe
```

```
                165                 170                 175

Leu Cys Gln Arg Pro Asp Gly Ala Leu Tyr Gly Ser Leu His Phe Asp
            180                 185                 190

Pro Glu Ala Cys Ser Phe Arg Glu Leu Leu Leu Glu Asp Gly Tyr Asn
        195                 200                 205

Val Tyr Gln Ser Glu Ala His Gly Leu Pro Leu His Leu Pro Gly Asn
    210                 215                 220

Lys Ser Pro His Arg Asp Pro Ala Pro Arg Gly Pro Ala Arg Phe Leu
225                 230                 235                 240

Pro Leu Pro Gly Leu Pro Pro Ala Leu Pro Glu Pro Pro Gly Ile Leu
                245                 250                 255

Ala Pro Gln Pro Pro Asp Val Gly Ser Ser Asp Pro Leu Ser Met Val
            260                 265                 270

Gly Pro Ser Gln Gly Arg Ser Pro Ser Tyr Ala Ser
        275                 280


<210> SEQ ID NO 145
<211> LENGTH: 280
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile His His
                85                  90                  95

His His His His Pro Ile Pro Asp Ser Ser Pro Leu Leu Gln Phe Gly
            100                 105                 110

Gly Gln Val Arg Gln Arg Tyr Leu Tyr Thr Asp Asp Ala Gln Gln Thr
        115                 120                 125

Glu Ala His Leu Glu Ile Arg Glu Asp Gly Thr Val Gly Gly Ala Ala
    130                 135                 140

Asp Gln Ser Pro Glu Ser Leu Leu Gln Leu Lys Ala Leu Lys Pro Gly
145                 150                 155                 160

Val Ile Gln Ile Leu Gly Val Lys Thr Ser Arg Phe Leu Cys Gln Arg
                165                 170                 175

Pro Asp Gly Ala Leu Tyr Gly Ser Leu His Phe Asp Pro Glu Ala Cys
            180                 185                 190

Ser Phe Arg Glu Leu Leu Leu Glu Asp Gly Tyr Asn Val Tyr Gln Ser
        195                 200                 205

Glu Ala His Gly Leu Pro Leu His Leu Pro Gly Asn Lys Ser Pro His
    210                 215                 220

Arg Asp Pro Ala Pro Arg Gly Pro Ala Arg Phe Leu Pro Leu Pro Gly
225                 230                 235                 240
```

-continued

```
Leu Pro Pro Ala Leu Pro Glu Pro Pro Gly Ile Leu Ala Pro Gln Pro
                245                 250                 255

Pro Asp Val Gly Ser Ser Asp Pro Leu Ser Met Val Gly Pro Ser Gln
            260                 265                 270

Gly Arg Ser Pro Ser Tyr Ala Ser
        275                 280
```

<210> SEQ ID NO 146
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Pro Ile Pro Asp Ser Ser Pro Leu
            100                 105                 110

Leu Gln Phe Gly Gly Gln Val Arg Gln Arg Tyr Leu Tyr Thr Asp Asp
        115                 120                 125

Ala Gln Gln Thr Glu Ala His Leu Glu Ile Arg Glu Asp Gly Thr Val
    130                 135                 140

Gly Gly Ala Ala Asp Gln Ser Pro Glu Ser Leu Leu Gln Leu Lys Ala
145                 150                 155                 160

Leu Lys Pro Gly Val Ile Gln Ile Leu Gly Val Lys Thr Ser Arg Phe
                165                 170                 175

Leu Cys Gln Arg Pro Asp Gly Ala Leu Tyr Gly Ser Leu His Phe Asp
            180                 185                 190

Pro Glu Ala Cys Ser Phe Arg Glu Leu Leu Leu Glu Asp Gly Tyr Asn
        195                 200                 205

Val Tyr Gln Ser Glu Ala His Gly Leu Pro Leu His Leu Pro Gly Asn
    210                 215                 220

Lys Ser Pro His Arg Asp Pro Ala Pro Arg Gly Pro Ala Arg Phe Leu
225                 230                 235                 240

Pro Leu Pro Gly Leu Pro Pro Ala Leu Pro Glu Pro Pro Gly Ile Leu
                245                 250                 255

Ala Pro Gln Pro Pro Asp Val Gly Ser Ser Asp Pro Leu Ser Met Val
            260                 265                 270

Gly Pro Ser Gln Gly Arg Ser Pro Ser Tyr Ala Ser
        275                 280
```

<210> SEQ ID NO 147
<211> LENGTH: 292
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Ser Gly Ser Gly Ser Gly Ser
            100                 105                 110

Pro Ile Pro Asp Ser Ser Pro Leu Leu Gln Phe Gly Gly Gln Val Arg
        115                 120                 125

Gln Arg Tyr Leu Tyr Thr Asp Asp Ala Gln Gln Thr Glu Ala His Leu
    130                 135                 140

Glu Ile Arg Glu Asp Gly Thr Val Gly Gly Ala Ala Asp Gln Ser Pro
145                 150                 155                 160

Glu Ser Leu Leu Gln Leu Lys Ala Leu Lys Pro Gly Val Ile Gln Ile
                165                 170                 175

Leu Gly Val Lys Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
        195                 200                 205

Leu Leu Leu Glu Asp Gly Tyr Asn Val Tyr Gln Ser Glu Ala His Gly
    210                 215                 220

Leu Pro Leu His Leu Pro Gly Asn Lys Ser Pro His Arg Asp Pro Ala
225                 230                 235                 240

Pro Arg Gly Pro Ala Arg Phe Leu Pro Leu Pro Gly Leu Pro Pro Ala
                245                 250                 255

Leu Pro Glu Pro Pro Gly Ile Leu Ala Pro Gln Pro Pro Asp Val Gly
            260                 265                 270

Ser Ser Asp Pro Leu Ser Met Val Gly Pro Ser Gln Gly Arg Ser Pro
        275                 280                 285

Ser Tyr Ala Ser
    290
```

<210> SEQ ID NO 148
<211> LENGTH: 287
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30
```

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Gly Ser
85 90 95

Ala Ala Ala Ala Ala Ala Ala Ala Ala Gly Ser Pro Ile Pro Asp Ser
100 105 110

Ser Pro Leu Leu Gln Phe Gly Gly Gln Val Arg Gln Arg Tyr Leu Tyr
115 120 125

Thr Asp Asp Ala Gln Gln Thr Glu Ala His Leu Glu Ile Arg Glu Asp
130 135 140

Gly Thr Val Gly Gly Ala Ala Asp Gln Ser Pro Glu Ser Leu Leu Gln
145 150 155 160

Leu Lys Ala Leu Lys Pro Gly Val Ile Gln Ile Leu Gly Val Lys Thr
165 170 175

Ser Arg Phe Leu Cys Gln Arg Pro Asp Gly Ala Leu Tyr Gly Ser Leu
180 185 190

His Phe Asp Pro Glu Ala Cys Ser Phe Arg Glu Leu Leu Leu Glu Asp
195 200 205

Gly Tyr Asn Val Tyr Gln Ser Glu Ala His Gly Leu Pro Leu His Leu
210 215 220

Pro Gly Asn Lys Ser Pro His Arg Asp Pro Ala Pro Arg Gly Pro Ala
225 230 235 240

Arg Phe Leu Pro Leu Pro Gly Leu Pro Pro Ala Leu Pro Glu Pro Pro
245 250 255

Gly Ile Leu Ala Pro Gln Pro Pro Asp Val Gly Ser Ser Asp Pro Leu
260 265 270

Ser Met Val Gly Pro Ser Gln Gly Arg Ser Pro Ser Tyr Ala Ser
275 280 285

<210> SEQ ID NO 149
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Gly Ser
85 90 95

Glu Gly Ser Glu Gly Ser Glu Gly Ser Glu Gly Ser Glu Pro Ile Pro

```
            100                 105                 110

Asp Ser Ser Pro Leu Leu Gln Phe Gly Gly Gln Val Arg Gln Arg Tyr
        115                 120                 125

Leu Tyr Thr Asp Asp Ala Gln Gln Thr Glu Ala His Leu Glu Ile Arg
    130                 135                 140

Glu Asp Gly Thr Val Gly Gly Ala Ala Asp Gln Ser Pro Glu Ser Leu
145                 150                 155                 160

Leu Gln Leu Lys Ala Leu Lys Pro Gly Val Ile Gln Ile Leu Gly Val
                165                 170                 175

Lys Thr Ser Arg Phe Leu Cys Gln Arg Pro Asp Gly Ala Leu Tyr Gly
            180                 185                 190

Ser Leu His Phe Asp Pro Glu Ala Cys Ser Phe Arg Glu Leu Leu Leu
        195                 200                 205

Glu Asp Gly Tyr Asn Val Tyr Gln Ser Glu Ala His Gly Leu Pro Leu
    210                 215                 220

His Leu Pro Gly Asn Lys Ser Pro His Arg Asp Pro Ala Pro Arg Gly
225                 230                 235                 240

Pro Ala Arg Phe Leu Pro Leu Pro Gly Leu Pro Pro Ala Leu Pro Glu
                245                 250                 255

Pro Pro Gly Ile Leu Ala Pro Gln Pro Pro Asp Val Gly Ser Ser Asp
            260                 265                 270

Pro Leu Ser Met Val Gly Pro Ser Gln Gly Arg Ser Pro Ser Tyr Ala
        275                 280                 285

Ser


<210> SEQ ID NO 150
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Pro Ala
                85                  90                  95

Ser Pro Ala Ser Pro Ala Ser Pro Ala Ser Pro Ala Ser Pro Ile Pro
            100                 105                 110

Asp Ser Ser Pro Leu Leu Gln Phe Gly Gly Gln Val Arg Gln Arg Tyr
        115                 120                 125

Leu Tyr Thr Asp Asp Ala Gln Gln Thr Glu Ala His Leu Glu Ile Arg
    130                 135                 140

Glu Asp Gly Thr Val Gly Gly Ala Ala Asp Gln Ser Pro Glu Ser Leu
145                 150                 155                 160

Leu Gln Leu Lys Ala Leu Lys Pro Gly Val Ile Gln Ile Leu Gly Val
```

```
                165                 170                 175

Lys Thr Ser Arg Phe Leu Cys Gln Arg Pro Asp Gly Ala Leu Tyr Gly
            180                 185                 190

Ser Leu His Phe Asp Pro Glu Ala Cys Ser Phe Arg Glu Leu Leu Leu
        195                 200                 205

Glu Asp Gly Tyr Asn Val Tyr Gln Ser Glu Ala His Gly Leu Pro Leu
    210                 215                 220

His Leu Pro Gly Asn Lys Ser Pro His Arg Asp Pro Ala Pro Arg Gly
225                 230                 235                 240

Pro Ala Arg Phe Leu Pro Leu Pro Gly Leu Pro Pro Ala Leu Pro Glu
                245                 250                 255

Pro Pro Gly Ile Leu Ala Pro Gln Pro Pro Asp Val Gly Ser Ser Asp
            260                 265                 270

Pro Leu Ser Met Val Gly Pro Ser Gln Gly Arg Ser Pro Ser Tyr Ala
        275                 280                 285

Ser


<210> SEQ ID NO 151
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Ser
                85                  90                  95

Pro Gly Ser Pro Gly Ser Pro Gly Ser Pro Gly Ser Pro Pro Ile Pro
            100                 105                 110

Asp Ser Ser Pro Leu Leu Gln Phe Gly Gly Gln Val Arg Gln Arg Tyr
        115                 120                 125

Leu Tyr Thr Asp Asp Ala Gln Gln Thr Glu Ala His Leu Glu Ile Arg
    130                 135                 140

Glu Asp Gly Thr Val Gly Gly Ala Ala Asp Gln Ser Pro Glu Ser Leu
145                 150                 155                 160

Leu Gln Leu Lys Ala Leu Lys Pro Gly Val Ile Gln Ile Leu Gly Val
                165                 170                 175

Lys Thr Ser Arg Phe Leu Cys Gln Arg Pro Asp Gly Ala Leu Tyr Gly
            180                 185                 190

Ser Leu His Phe Asp Pro Glu Ala Cys Ser Phe Arg Glu Leu Leu Leu
        195                 200                 205

Glu Asp Gly Tyr Asn Val Tyr Gln Ser Glu Ala His Gly Leu Pro Leu
    210                 215                 220

His Leu Pro Gly Asn Lys Ser Pro His Arg Asp Pro Ala Pro Arg Gly
```

```
225                 230                 235                 240

Pro Ala Arg Phe Leu Pro Leu Pro Gly Leu Pro Pro Ala Leu Pro Glu
                245                 250                 255

Pro Pro Gly Ile Leu Ala Pro Gln Pro Pro Asp Val Gly Ser Ser Asp
            260                 265                 270

Pro Leu Ser Met Val Gly Pro Ser Gln Gly Arg Ser Pro Ser Tyr Ala
        275                 280                 285

Ser


<210> SEQ ID NO 152
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Ser
                85                  90                  95

Thr Val Ala Ala Pro Ser Thr Val Ala Ala Pro Ser Pro Ile Pro Asp
            100                 105                 110

Ser Ser Pro Leu Leu Gln Phe Gly Gly Gln Val Arg Gln Arg Tyr Leu
        115                 120                 125

Tyr Thr Asp Asp Ala Gln Gln Thr Glu Ala His Leu Glu Ile Arg Glu
    130                 135                 140

Asp Gly Thr Val Gly Gly Ala Ala Asp Gln Ser Pro Glu Ser Leu Leu
145                 150                 155                 160

Gln Leu Lys Ala Leu Lys Pro Gly Val Ile Gln Ile Leu Gly Val Lys
                165                 170                 175

Thr Ser Arg Phe Leu Cys Gln Arg Pro Asp Gly Ala Leu Tyr Gly Ser
            180                 185                 190

Leu His Phe Asp Pro Glu Ala Cys Ser Phe Arg Glu Leu Leu Leu Glu
        195                 200                 205

Asp Gly Tyr Asn Val Tyr Gln Ser Glu Ala His Gly Leu Pro Leu His
    210                 215                 220

Leu Pro Gly Asn Lys Ser Pro His Arg Asp Pro Ala Pro Arg Gly Pro
225                 230                 235                 240

Ala Arg Phe Leu Pro Leu Pro Gly Leu Pro Pro Ala Leu Pro Glu Pro
                245                 250                 255

Pro Gly Ile Leu Ala Pro Gln Pro Pro Asp Val Gly Ser Ser Asp Pro
            260                 265                 270

Leu Ser Met Val Gly Pro Ser Gln Gly Arg Ser Pro Ser Tyr Ala Ser
        275                 280                 285
```

<210> SEQ ID NO 153
<211> LENGTH: 282
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
                85                  90                  95

Ser Glu Gly Gly Ser Glu Pro Ile Pro Asp Ser Ser Pro Leu Leu Gln
            100                 105                 110

Phe Gly Gly Gln Val Arg Gln Arg Tyr Leu Tyr Thr Asp Asp Ala Gln
        115                 120                 125

Gln Thr Glu Ala His Leu Glu Ile Arg Glu Asp Gly Thr Val Gly Gly
    130                 135                 140

Ala Ala Asp Gln Ser Pro Glu Ser Leu Leu Gln Leu Lys Ala Leu Lys
145                 150                 155                 160

Pro Gly Val Ile Gln Ile Leu Gly Val Lys Thr Ser Arg Phe Leu Cys
                165                 170                 175

Gln Arg Pro Asp Gly Ala Leu Tyr Gly Ser Leu His Phe Asp Pro Glu
            180                 185                 190

Ala Cys Ser Phe Arg Glu Leu Leu Leu Glu Asp Gly Tyr Asn Val Tyr
        195                 200                 205

Gln Ser Glu Ala His Gly Leu Pro Leu His Leu Pro Gly Asn Lys Ser
    210                 215                 220

Pro His Arg Asp Pro Ala Pro Arg Gly Pro Ala Arg Phe Leu Pro Leu
225                 230                 235                 240

Pro Gly Leu Pro Pro Ala Leu Pro Glu Pro Pro Gly Ile Leu Ala Pro
                245                 250                 255

Gln Pro Pro Asp Val Gly Ser Ser Asp Pro Leu Ser Met Val Gly Pro
            260                 265                 270

Ser Gln Gly Arg Ser Pro Ser Tyr Ala Ser
        275                 280
```

<210> SEQ ID NO 154
<211> LENGTH: 281
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
```

```
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Ser Thr
                85                  90                  95

Ser Thr Ser Thr Gly Pro Ile Pro Asp Ser Ser Pro Leu Leu Gln Phe
            100                 105                 110

Gly Gly Gln Val Arg Gln Arg Tyr Leu Tyr Thr Asp Asp Ala Gln Gln
        115                 120                 125

Thr Glu Ala His Leu Glu Ile Arg Glu Asp Gly Thr Val Gly Gly Ala
    130                 135                 140

Ala Asp Gln Ser Pro Glu Ser Leu Leu Gln Leu Lys Ala Leu Lys Pro
145                 150                 155                 160

Gly Val Ile Gln Ile Leu Gly Val Lys Thr Ser Arg Phe Leu Cys Gln
                165                 170                 175

Arg Pro Asp Gly Ala Leu Tyr Gly Ser Leu His Phe Asp Pro Glu Ala
            180                 185                 190

Cys Ser Phe Arg Glu Leu Leu Leu Glu Asp Gly Tyr Asn Val Tyr Gln
        195                 200                 205

Ser Glu Ala His Gly Leu Pro Leu His Leu Pro Gly Asn Lys Ser Pro
    210                 215                 220

His Arg Asp Pro Ala Pro Arg Gly Pro Ala Arg Phe Leu Pro Leu Pro
225                 230                 235                 240

Gly Leu Pro Pro Ala Leu Pro Glu Pro Pro Gly Ile Leu Ala Pro Gln
                245                 250                 255

Pro Pro Asp Val Gly Ser Ser Asp Pro Leu Ser Met Val Gly Pro Ser
            260                 265                 270

Gln Gly Arg Ser Pro Ser Tyr Ala Ser
        275                 280


<210> SEQ ID NO 155
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95
```

-continued

```
Pro Ser Gln Gly Gly Ser Gly Ser Gly Ser Gly Ser Pro Ile Pro Asp
            100                 105                 110

Ser Ser Pro Leu Leu Gln Phe Gly Gly Gln Val Arg Gln Arg Tyr Leu
        115                 120                 125

Tyr Thr Asp Asp Ala Gln Gln Thr Glu Ala His Leu Glu Ile Arg Glu
    130                 135                 140

Asp Gly Thr Val Gly Gly Ala Ala Asp Gln Ser Pro Glu Ser Leu Leu
145                 150                 155                 160

Gln Leu Lys Ala Leu Lys Pro Gly Val Ile Gln Ile Leu Gly Val Lys
                165                 170                 175

Thr Ser Arg Phe Leu Cys Gln Arg Pro Asp Gly Ala Leu Tyr Gly Ser
            180                 185                 190

Leu His Phe Asp Pro Glu Ala Cys Ser Phe Arg Glu Leu Leu Leu Glu
        195                 200                 205

Asp Gly Tyr Asn Val Tyr Gln Ser Glu Ala His Gly Leu Pro Leu His
    210                 215                 220

Leu Pro Gly Asn Lys Ser Pro His Arg Asp Pro Ala Pro Arg Gly Pro
225                 230                 235                 240

Ala Arg Phe Leu Pro Leu Pro Gly Leu Pro Pro Ala Leu Pro Glu Pro
                245                 250                 255

Pro Gly Ile Leu Ala Pro Gln Pro Pro Asp Val Gly Ser Ser Asp Pro
            260                 265                 270

Leu Ser Met Val Gly Pro Ser Gln Gly Arg Ser Pro Ser Tyr Ala Ser
        275                 280                 285


<210> SEQ ID NO 156
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Gly Ser Gly Ser Pro Ile Pro Asp Ser Ser Pro Leu
            100                 105                 110

Leu Gln Phe Gly Gly Gln Val Arg Gln Arg Tyr Leu Tyr Thr Asp Asp
        115                 120                 125

Ala Gln Gln Thr Glu Ala His Leu Glu Ile Arg Glu Asp Gly Thr Val
    130                 135                 140

Gly Gly Ala Ala Asp Gln Ser Pro Glu Ser Leu Leu Gln Leu Lys Ala
145                 150                 155                 160

Leu Lys Pro Gly Val Ile Gln Ile Leu Gly Val Lys Thr Ser Arg Phe
                165                 170                 175
```

```
Leu Cys Gln Arg Pro Asp Gly Ala Leu Tyr Gly Ser Leu His Phe Asp
            180                 185                 190

Pro Glu Ala Cys Ser Phe Arg Glu Leu Leu Leu Glu Asp Gly Tyr Asn
        195                 200                 205

Val Tyr Gln Ser Glu Ala His Gly Leu Pro Leu His Leu Pro Gly Asn
    210                 215                 220

Lys Ser Pro His Arg Asp Pro Ala Pro Arg Gly Pro Ala Arg Phe Leu
225                 230                 235                 240

Pro Leu Pro Gly Leu Pro Pro Ala Leu Pro Glu Pro Pro Gly Ile Leu
                245                 250                 255

Ala Pro Gln Pro Pro Asp Val Gly Ser Ser Asp Pro Leu Ser Met Val
            260                 265                 270

Gly Pro Ser Gln Gly Arg Ser Pro Ser Tyr Ala Ser
        275                 280


<210> SEQ ID NO 157
<211> LENGTH: 279
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Pro Ile Pro Asp Ser Ser Pro Leu Leu Gln Phe Gly Gly
            100                 105                 110

Gln Val Arg Gln Arg Tyr Leu Tyr Thr Asp Asp Ala Gln Gln Thr Glu
        115                 120                 125

Ala His Leu Glu Ile Arg Glu Asp Gly Thr Val Gly Gly Ala Ala Asp
    130                 135                 140

Gln Ser Pro Glu Ser Leu Leu Gln Leu Lys Ala Leu Lys Pro Gly Val
145                 150                 155                 160

Ile Gln Ile Leu Gly Val Lys Thr Ser Arg Phe Leu Cys Gln Arg Pro
                165                 170                 175

Asp Gly Ala Leu Tyr Gly Ser Leu His Phe Asp Pro Glu Ala Cys Ser
            180                 185                 190

Phe Arg Glu Leu Leu Leu Glu Asp Gly Tyr Asn Val Tyr Gln Ser Glu
        195                 200                 205

Ala His Gly Leu Pro Leu His Leu Pro Gly Asn Lys Ser Pro His Arg
    210                 215                 220

Asp Pro Ala Pro Arg Gly Pro Ala Arg Phe Leu Pro Leu Pro Gly Leu
225                 230                 235                 240

Pro Pro Ala Leu Pro Glu Pro Pro Gly Ile Leu Ala Pro Gln Pro Pro
```

```
                245                 250                 255

Asp Val Gly Ser Ser Asp Pro Leu Ser Met Val Gly Pro Ser Gln Gly
            260                 265                 270

Arg Ser Pro Ser Tyr Ala Ser
        275


<210> SEQ ID NO 158
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln His His His His His His Gly Ser Gly Ser Gly Ser Gly
            100                 105                 110

Ser Pro Ile Pro Asp Ser Ser Pro Leu Leu Gln Phe Gly Gly Gln Val
        115                 120                 125

Arg Gln Arg Tyr Leu Tyr Thr Asp Asp Ala Gln Gln Thr Glu Ala His
    130                 135                 140

Leu Glu Ile Arg Glu Asp Gly Thr Val Gly Gly Ala Ala Asp Gln Ser
145                 150                 155                 160

Pro Glu Ser Leu Leu Gln Leu Lys Ala Leu Lys Pro Gly Val Ile Gln
                165                 170                 175

Ile Leu Gly Val Lys Thr Ser Arg Phe Leu Cys Gln Arg Pro Asp Gly
            180                 185                 190

Ala Leu Tyr Gly Ser Leu His Phe Asp Pro Glu Ala Cys Ser Phe Arg
        195                 200                 205

Glu Leu Leu Leu Glu Asp Gly Tyr Asn Val Tyr Gln Ser Glu Ala His
    210                 215                 220

Gly Leu Pro Leu His Leu Pro Gly Asn Lys Ser Pro His Arg Asp Pro
225                 230                 235                 240

Ala Pro Arg Gly Pro Ala Arg Phe Leu Pro Leu Pro Gly Leu Pro Pro
                245                 250                 255

Ala Leu Pro Glu Pro Pro Gly Ile Leu Ala Pro Gln Pro Pro Asp Val
            260                 265                 270

Gly Ser Ser Asp Pro Leu Ser Met Val Gly Pro Ser Gln Gly Arg Ser
        275                 280                 285

Pro Ser Tyr Ala Ser
    290


<210> SEQ ID NO 159
<211> LENGTH: 289
```

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 159

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln His His His His His His Gly Ser Gly Ser Pro Ile Pro
            100                 105                 110

Asp Ser Ser Pro Leu Leu Gln Phe Gly Gly Gln Val Arg Gln Arg Tyr
        115                 120                 125

Leu Tyr Thr Asp Asp Ala Gln Gln Thr Glu Ala His Leu Glu Ile Arg
    130                 135                 140

Glu Asp Gly Thr Val Gly Gly Ala Ala Asp Gln Ser Pro Glu Ser Leu
145                 150                 155                 160

Leu Gln Leu Lys Ala Leu Lys Pro Gly Val Ile Gln Ile Leu Gly Val
                165                 170                 175

Lys Thr Ser Arg Phe Leu Cys Gln Arg Pro Asp Gly Ala Leu Tyr Gly
            180                 185                 190

Ser Leu His Phe Asp Pro Glu Ala Cys Ser Phe Arg Glu Leu Leu Leu
        195                 200                 205

Glu Asp Gly Tyr Asn Val Tyr Gln Ser Glu Ala His Gly Leu Pro Leu
    210                 215                 220

His Leu Pro Gly Asn Lys Ser Pro His Arg Asp Pro Ala Pro Arg Gly
225                 230                 235                 240

Pro Ala Arg Phe Leu Pro Leu Pro Gly Leu Pro Pro Ala Leu Pro Glu
                245                 250                 255

Pro Pro Gly Ile Leu Ala Pro Gln Pro Pro Asp Val Gly Ser Ser Asp
            260                 265                 270

Pro Leu Ser Met Val Gly Pro Ser Gln Gly Arg Ser Pro Ser Tyr Ala
        275                 280                 285

Ser
```

<210> SEQ ID NO 160
<211> LENGTH: 285
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 160

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
```

```
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln His His His His His His Pro Ile Pro Asp Ser Ser Pro
            100                 105                 110

Leu Leu Gln Phe Gly Gly Gln Val Arg Gln Arg Tyr Leu Tyr Thr Asp
        115                 120                 125

Asp Ala Gln Gln Thr Glu Ala His Leu Glu Ile Arg Glu Asp Gly Thr
    130                 135                 140

Val Gly Gly Ala Ala Asp Gln Ser Pro Glu Ser Leu Leu Gln Leu Lys
145                 150                 155                 160

Ala Leu Lys Pro Gly Val Ile Gln Ile Leu Gly Val Lys Thr Ser Arg
                165                 170                 175

Phe Leu Cys Gln Arg Pro Asp Gly Ala Leu Tyr Gly Ser Leu His Phe
            180                 185                 190

Asp Pro Glu Ala Cys Ser Phe Arg Glu Leu Leu Leu Glu Asp Gly Tyr
        195                 200                 205

Asn Val Tyr Gln Ser Glu Ala His Gly Leu Pro Leu His Leu Pro Gly
    210                 215                 220

Asn Lys Ser Pro His Arg Asp Pro Ala Pro Arg Gly Pro Ala Arg Phe
225                 230                 235                 240

Leu Pro Leu Pro Gly Leu Pro Pro Ala Leu Pro Glu Pro Pro Gly Ile
                245                 250                 255

Leu Ala Pro Gln Pro Pro Asp Val Gly Ser Ser Asp Pro Leu Ser Met
            260                 265                 270

Val Gly Pro Ser Gln Gly Arg Ser Pro Ser Tyr Ala Ser
        275                 280                 285


<210> SEQ ID NO 161
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95
```

```
Pro Ser Gln Glu Asp Glu Asp Glu Asp Glu Asp Glu Asp Pro Ile Pro
            100                 105                 110

Asp Ser Ser Pro Leu Leu Gln Phe Gly Gly Gln Val Arg Gln Arg Tyr
        115                 120                 125

Leu Tyr Thr Asp Asp Ala Gln Gln Thr Glu Ala His Leu Glu Ile Arg
    130                 135                 140

Glu Asp Gly Thr Val Gly Gly Ala Ala Asp Gln Ser Pro Glu Ser Leu
145                 150                 155                 160

Leu Gln Leu Lys Ala Leu Lys Pro Gly Val Ile Gln Ile Leu Gly Val
                165                 170                 175

Lys Thr Ser Arg Phe Leu Cys Gln Arg Pro Asp Gly Ala Leu Tyr Gly
            180                 185                 190

Ser Leu His Phe Asp Pro Glu Ala Cys Ser Phe Arg Glu Leu Leu Leu
        195                 200                 205

Glu Asp Gly Tyr Asn Val Tyr Gln Ser Glu Ala His Gly Leu Pro Leu
    210                 215                 220

His Leu Pro Gly Asn Lys Ser Pro His Arg Asp Pro Ala Pro Arg Gly
225                 230                 235                 240

Pro Ala Arg Phe Leu Pro Leu Pro Gly Leu Pro Pro Ala Leu Pro Glu
                245                 250                 255

Pro Pro Gly Ile Leu Ala Pro Gln Pro Pro Asp Val Gly Ser Ser Asp
            260                 265                 270

Pro Leu Ser Met Val Gly Pro Ser Gln Gly Arg Ser Pro Ser Tyr Ala
        275                 280                 285

Ser


<210> SEQ ID NO 162
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Glu Asp Glu Asp Glu Asp Glu Asp Glu Asp Gly Ser Gly
            100                 105                 110

Ser Gly Ser Gly Ser Pro Ile Pro Asp Ser Ser Pro Leu Leu Gln Phe
        115                 120                 125

Gly Gly Gln Val Arg Gln Arg Tyr Leu Tyr Thr Asp Asp Ala Gln Gln
    130                 135                 140

Thr Glu Ala His Leu Glu Ile Arg Glu Asp Gly Thr Val Gly Gly Ala
145                 150                 155                 160
```

-continued

```
Ala Asp Gln Ser Pro Glu Ser Leu Leu Gln Leu Lys Ala Leu Lys Pro
                165                 170                 175

Gly Val Ile Gln Ile Leu Gly Val Lys Thr Ser Arg Phe Leu Cys Gln
            180                 185                 190

Arg Pro Asp Gly Ala Leu Tyr Gly Ser Leu His Phe Asp Pro Glu Ala
        195                 200                 205

Cys Ser Phe Arg Glu Leu Leu Leu Glu Asp Gly Tyr Asn Val Tyr Gln
    210                 215                 220

Ser Glu Ala His Gly Leu Pro Leu His Leu Pro Gly Asn Lys Ser Pro
225                 230                 235                 240

His Arg Asp Pro Ala Pro Arg Gly Pro Ala Arg Phe Leu Pro Leu Pro
                245                 250                 255

Gly Leu Pro Pro Ala Leu Pro Glu Pro Pro Gly Ile Leu Ala Pro Gln
            260                 265                 270

Pro Pro Asp Val Gly Ser Ser Asp Pro Leu Ser Met Val Gly Pro Ser
        275                 280                 285

Gln Gly Arg Ser Pro Ser Tyr Ala Ser
    290                 295


<210> SEQ ID NO 163
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Ser Ala Ala Ala Ala Ala Ala Ala Ala Ala Gly Ser
            100                 105                 110

Pro Ile Pro Asp Ser Ser Pro Leu Leu Gln Phe Gly Gly Gln Val Arg
        115                 120                 125

Gln Arg Tyr Leu Tyr Thr Asp Asp Ala Gln Gln Thr Glu Ala His Leu
    130                 135                 140

Glu Ile Arg Glu Asp Gly Thr Val Gly Gly Ala Ala Asp Gln Ser Pro
145                 150                 155                 160

Glu Ser Leu Leu Gln Leu Lys Ala Leu Lys Pro Gly Val Ile Gln Ile
                165                 170                 175

Leu Gly Val Lys Thr Ser Arg Phe Leu Cys Gln Arg Pro Asp Gly Ala
            180                 185                 190

Leu Tyr Gly Ser Leu His Phe Asp Pro Glu Ala Cys Ser Phe Arg Glu
        195                 200                 205

Leu Leu Leu Glu Asp Gly Tyr Asn Val Tyr Gln Ser Glu Ala His Gly
    210                 215                 220
```

```
Leu Pro Leu His Leu Pro Gly Asn Lys Ser Pro His Arg Asp Pro Ala
225                 230                 235                 240

Pro Arg Gly Pro Ala Arg Phe Leu Pro Leu Pro Gly Leu Pro Pro Ala
                245                 250                 255

Leu Pro Glu Pro Pro Gly Ile Leu Ala Pro Gln Pro Pro Asp Val Gly
            260                 265                 270

Ser Ser Asp Pro Leu Ser Met Val Gly Pro Ser Gln Gly Arg Ser Pro
        275                 280                 285

Ser Tyr Ala Ser
    290


<210> SEQ ID NO 164
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Ser Glu Gly Ser Glu Gly Ser Glu Gly Ser Glu Gly
            100                 105                 110

Ser Glu Pro Ile Pro Asp Ser Ser Pro Leu Leu Gln Phe Gly Gly Gln
        115                 120                 125

Val Arg Gln Arg Tyr Leu Tyr Thr Asp Asp Ala Gln Gln Thr Glu Ala
    130                 135                 140

His Leu Glu Ile Arg Glu Asp Gly Thr Val Gly Gly Ala Ala Asp Gln
145                 150                 155                 160

Ser Pro Glu Ser Leu Leu Gln Leu Lys Ala Leu Lys Pro Gly Val Ile
                165                 170                 175

Gln Ile Leu Gly Val Lys Thr Ser Arg Phe Leu Cys Gln Arg Pro Asp
            180                 185                 190

Gly Ala Leu Tyr Gly Ser Leu His Phe Asp Pro Glu Ala Cys Ser Phe
        195                 200                 205

Arg Glu Leu Leu Leu Glu Asp Gly Tyr Asn Val Tyr Gln Ser Glu Ala
    210                 215                 220

His Gly Leu Pro Leu His Leu Pro Gly Asn Lys Ser Pro His Arg Asp
225                 230                 235                 240

Pro Ala Pro Arg Gly Pro Ala Arg Phe Leu Pro Leu Pro Gly Leu Pro
                245                 250                 255

Pro Ala Leu Pro Glu Pro Pro Gly Ile Leu Ala Pro Gln Pro Pro Asp
            260                 265                 270

Val Gly Ser Ser Asp Pro Leu Ser Met Val Gly Pro Ser Gln Gly Arg
```

275 280 285

Ser Pro Ser Tyr Ala Ser
290

<210> SEQ ID NO 165
<211> LENGTH: 294
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Lys
85 90 95

Pro Ser Gln Pro Ala Ser Pro Ala Ser Pro Ala Ser Pro Ala Ser Pro
100 105 110

Ala Ser Pro Ile Pro Asp Ser Ser Pro Leu Leu Gln Phe Gly Gly Gln
115 120 125

Val Arg Gln Arg Tyr Leu Tyr Thr Asp Asp Ala Gln Gln Thr Glu Ala
130 135 140

His Leu Glu Ile Arg Glu Asp Gly Thr Val Gly Gly Ala Ala Asp Gln
145 150 155 160

Ser Pro Glu Ser Leu Leu Gln Leu Lys Ala Leu Lys Pro Gly Val Ile
165 170 175

Gln Ile Leu Gly Val Lys Thr Ser Arg Phe Leu Cys Gln Arg Pro Asp
180 185 190

Gly Ala Leu Tyr Gly Ser Leu His Phe Asp Pro Glu Ala Cys Ser Phe
195 200 205

Arg Glu Leu Leu Leu Glu Asp Gly Tyr Asn Val Tyr Gln Ser Glu Ala
210 215 220

His Gly Leu Pro Leu His Leu Pro Gly Asn Lys Ser Pro His Arg Asp
225 230 235 240

Pro Ala Pro Arg Gly Pro Ala Arg Phe Leu Pro Leu Pro Gly Leu Pro
245 250 255

Pro Ala Leu Pro Glu Pro Pro Gly Ile Leu Ala Pro Gln Pro Pro Asp
260 265 270

Val Gly Ser Ser Asp Pro Leu Ser Met Val Gly Pro Ser Gln Gly Arg
275 280 285

Ser Pro Ser Tyr Ala Ser
290

<210> SEQ ID NO 166
<211> LENGTH: 294
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 166

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Ser Pro Gly Ser Pro Gly Ser Pro Gly Ser Pro Gly
            100                 105                 110

Ser Pro Pro Ile Pro Asp Ser Ser Pro Leu Leu Gln Phe Gly Gly Gln
        115                 120                 125

Val Arg Gln Arg Tyr Leu Tyr Thr Asp Asp Ala Gln Gln Thr Glu Ala
    130                 135                 140

His Leu Glu Ile Arg Glu Asp Gly Thr Val Gly Gly Ala Ala Asp Gln
145                 150                 155                 160

Ser Pro Glu Ser Leu Leu Gln Leu Lys Ala Leu Lys Pro Gly Val Ile
                165                 170                 175

Gln Ile Leu Gly Val Lys Thr Ser Arg Phe Leu Cys Gln Arg Pro Asp
            180                 185                 190

Gly Ala Leu Tyr Gly Ser Leu His Phe Asp Pro Glu Ala Cys Ser Phe
        195                 200                 205

Arg Glu Leu Leu Leu Glu Asp Gly Tyr Asn Val Tyr Gln Ser Glu Ala
    210                 215                 220

His Gly Leu Pro Leu His Leu Pro Gly Asn Lys Ser Pro His Arg Asp
225                 230                 235                 240

Pro Ala Pro Arg Gly Pro Ala Arg Phe Leu Pro Leu Pro Gly Leu Pro
                245                 250                 255

Pro Ala Leu Pro Glu Pro Pro Gly Ile Leu Ala Pro Gln Pro Pro Asp
            260                 265                 270

Val Gly Ser Ser Asp Pro Leu Ser Met Val Gly Pro Ser Gln Gly Arg
        275                 280                 285

Ser Pro Ser Tyr Ala Ser
    290
```

<210> SEQ ID NO 167
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30
```

```
Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Ser Thr Val Ala Ala Pro Ser Thr Val Ala Ala Pro
            100                 105                 110

Ser Pro Ile Pro Asp Ser Ser Pro Leu Leu Gln Phe Gly Gly Gln Val
        115                 120                 125

Arg Gln Arg Tyr Leu Tyr Thr Asp Asp Ala Gln Gln Thr Glu Ala His
    130                 135                 140

Leu Glu Ile Arg Glu Asp Gly Thr Val Gly Gly Ala Ala Asp Gln Ser
145                 150                 155                 160

Pro Glu Ser Leu Leu Gln Leu Lys Ala Leu Lys Pro Gly Val Ile Gln
                165                 170                 175

Ile Leu Gly Val Lys Thr Ser Arg Phe Leu Cys Gln Arg Pro Asp Gly
            180                 185                 190

Ala Leu Tyr Gly Ser Leu His Phe Asp Pro Glu Ala Cys Ser Phe Arg
        195                 200                 205

Glu Leu Leu Leu Glu Asp Gly Tyr Asn Val Tyr Gln Ser Glu Ala His
    210                 215                 220

Gly Leu Pro Leu His Leu Pro Gly Asn Lys Ser Pro His Arg Asp Pro
225                 230                 235                 240

Ala Pro Arg Gly Pro Ala Arg Phe Leu Pro Leu Pro Gly Leu Pro Pro
                245                 250                 255

Ala Leu Pro Glu Pro Pro Gly Ile Leu Ala Pro Gln Pro Pro Asp Val
            260                 265                 270

Gly Ser Ser Asp Pro Leu Ser Met Val Gly Pro Ser Gln Gly Arg Ser
        275                 280                 285

Pro Ser Tyr Ala Ser
    290


<210> SEQ ID NO 168
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95
```

Pro Ser Gln Gly Gly Ser Glu Gly Gly Ser Glu Pro Ile Pro Asp Ser
100 105 110

Ser Pro Leu Leu Gln Phe Gly Gly Gln Val Arg Gln Arg Tyr Leu Tyr
115 120 125

Thr Asp Asp Ala Gln Gln Thr Glu Ala His Leu Glu Ile Arg Glu Asp
130 135 140

Gly Thr Val Gly Gly Ala Ala Asp Gln Ser Pro Glu Ser Leu Leu Gln
145 150 155 160

Leu Lys Ala Leu Lys Pro Gly Val Ile Gln Ile Leu Gly Val Lys Thr
165 170 175

Ser Arg Phe Leu Cys Gln Arg Pro Asp Gly Ala Leu Tyr Gly Ser Leu
180 185 190

His Phe Asp Pro Glu Ala Cys Ser Phe Arg Glu Leu Leu Leu Glu Asp
195 200 205

Gly Tyr Asn Val Tyr Gln Ser Glu Ala His Gly Leu Pro Leu His Leu
210 215 220

Pro Gly Asn Lys Ser Pro His Arg Asp Pro Ala Pro Arg Gly Pro Ala
225 230 235 240

Arg Phe Leu Pro Leu Pro Gly Leu Pro Pro Ala Leu Pro Glu Pro Pro
245 250 255

Gly Ile Leu Ala Pro Gln Pro Pro Asp Val Gly Ser Ser Asp Pro Leu
260 265 270

Ser Met Val Gly Pro Ser Gln Gly Arg Ser Pro Ser Tyr Ala Ser
275 280 285

<210> SEQ ID NO 169
<211> LENGTH: 286
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 169

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Lys
85 90 95

Pro Ser Gln Ser Thr Ser Thr Ser Thr Gly Pro Ile Pro Asp Ser Ser
100 105 110

Pro Leu Leu Gln Phe Gly Gly Gln Val Arg Gln Arg Tyr Leu Tyr Thr
115 120 125

Asp Asp Ala Gln Gln Thr Glu Ala His Leu Glu Ile Arg Glu Asp Gly
130 135 140

Thr Val Gly Gly Ala Ala Asp Gln Ser Pro Glu Ser Leu Leu Gln Leu
145 150 155 160

Lys Ala Leu Lys Pro Gly Val Ile Gln Ile Leu Gly Val Lys Thr Ser

```
                165                 170                 175

Arg Phe Leu Cys Gln Arg Pro Asp Gly Ala Leu Tyr Gly Ser Leu His
            180                 185                 190

Phe Asp Pro Glu Ala Cys Ser Phe Arg Glu Leu Leu Leu Glu Asp Gly
        195                 200                 205

Tyr Asn Val Tyr Gln Ser Glu Ala His Gly Leu Pro Leu His Leu Pro
    210                 215                 220

Gly Asn Lys Ser Pro His Arg Asp Pro Ala Pro Arg Gly Pro Ala Arg
225                 230                 235                 240

Phe Leu Pro Leu Pro Gly Leu Pro Pro Ala Leu Pro Glu Pro Pro Gly
                245                 250                 255

Ile Leu Ala Pro Gln Pro Pro Asp Val Gly Ser Ser Asp Pro Leu Ser
            260                 265                 270

Met Val Gly Pro Ser Gln Gly Arg Ser Pro Ser Tyr Ala Ser
        275                 280                 285


<210> SEQ ID NO 170
<211> LENGTH: 303
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Met Gly Val Ser Asp Val Pro Arg Asp Leu Glu Val Val Ala Ala Thr
1               5                   10                  15

Pro Thr Ser Leu Leu Ile Ser Trp Glu Asp Asp Ser Tyr Tyr Ser Arg
            20                  25                  30

Tyr Tyr Arg Ile Thr Tyr Gly Glu Thr Gly Gly Asn Ser Pro Val Gln
        35                  40                  45

Glu Phe Thr Val Pro Ser Asp Leu Tyr Thr Ala Thr Ile Ser Gly Leu
    50                  55                  60

Lys Pro Gly Val Asp Tyr Thr Ile Thr Val Tyr Ala Val Thr Tyr Asp
65                  70                  75                  80

Val Thr Asp Leu Ile Met His Glu Pro Ile Ser Ile Asn Tyr Arg Thr
                85                  90                  95

Glu Ile Glu Lys Pro Ser Gly Gly Ser Gly Ser Gly Ser Gly Ser Gly
            100                 105                 110

Ser Gly Ser Gly Ser Pro Ile Pro Asp Ser Ser Pro Leu Leu Gln Phe
        115                 120                 125

Gly Gly Gln Val Arg Gln Arg Tyr Leu Tyr Thr Asp Asp Ala Gln Gln
    130                 135                 140

Thr Glu Ala His Leu Glu Ile Arg Glu Asp Gly Thr Val Gly Gly Ala
145                 150                 155                 160

Ala Asp Gln Ser Pro Glu Ser Leu Leu Gln Leu Lys Ala Leu Lys Pro
                165                 170                 175

Gly Val Ile Gln Ile Leu Gly Val Lys Thr Ser Arg Phe Leu Cys Gln
            180                 185                 190

Arg Pro Asp Gly Ala Leu Tyr Gly Ser Leu His Phe Asp Pro Glu Ala
        195                 200                 205

Cys Ser Phe Arg Glu Leu Leu Leu Glu Asp Gly Tyr Asn Val Tyr Gln
    210                 215                 220

Ser Glu Ala His Gly Leu Pro Leu His Leu Pro Gly Asn Lys Ser Pro
225                 230                 235                 240
```

```
His Arg Asp Pro Ala Pro Arg Gly Pro Ala Arg Phe Leu Pro Leu Pro
                245                 250                 255

Gly Leu Pro Pro Ala Leu Pro Glu Pro Pro Gly Ile Leu Ala Pro Gln
            260                 265                 270

Pro Pro Asp Val Gly Ser Ser Asp Pro Leu Ser Met Val Gly Pro Ser
        275                 280                 285

Gln Gly Arg Ser Pro Ser Tyr Ala Ser His His His His His His
    290                 295                 300


<210> SEQ ID NO 171
<211> LENGTH: 300
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Met Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser Gly Gly Ser Gly Ser Gly Ser Gly Ser Gly Ser
            180                 185                 190

Gly Ser Gly Ser Gly Val Ser Asp Val Pro Arg Asp Leu Glu Val Val
        195                 200                 205

Ala Ala Thr Pro Thr Ser Leu Leu Ile Ser Trp His Ser Tyr Tyr Glu
    210                 215                 220

Gln Asn Ser Tyr Tyr Arg Ile Thr Tyr Gly Glu Thr Gly Gly Asn Ser
225                 230                 235                 240

Pro Val Gln Glu Phe Thr Val Pro Tyr Ser Gln Thr Thr Ala Thr Ile
                245                 250                 255

Ser Gly Leu Lys Pro Gly Val Asp Tyr Thr Ile Thr Val Tyr Ala Val
            260                 265                 270

Tyr Gly Ser Lys Tyr Tyr Tyr Pro Ile Ser Ile Asn Tyr Arg Thr Glu
        275                 280                 285

Ile Asp Lys Pro Ser Gln His His His His His His
    290                 295                 300
```

<210> SEQ ID NO 172
<211> LENGTH: 300
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

```
Met Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser Gly Gly Ser Gly Ser Gly Ser Gly Ser Gly Ser
            180                 185                 190

Gly Ser Gly Ser Gly Val Ser Asp Val Pro Arg Asp Leu Glu Val Val
        195                 200                 205

Ala Ala Thr Pro Thr Ser Leu Leu Ile Ser Trp His Ser Tyr Tyr Glu
    210                 215                 220

Gln Asn Ser Tyr Tyr Arg Ile Thr Tyr Gly Glu Thr Gly Gly Asn Ser
225                 230                 235                 240

Pro Val Gln Glu Phe Thr Val Pro Tyr Ser Gln Thr Thr Ala Thr Ile
                245                 250                 255

Ser Gly Leu Lys Pro Gly Val Asp Tyr Thr Ile Thr Val Tyr Ala Val
            260                 265                 270

Tyr Gly Ser Lys Tyr Tyr Tyr Pro Ile Ser Ile Asn Tyr Arg Thr Glu
        275                 280                 285

Ile Glu Lys Pro Ser Gln His His His His His His
    290                 295                 300
```

<210> SEQ ID NO 173
<211> LENGTH: 294
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

```
Met Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser Gly Gly Ser Gly Ser Gly Ser Gly Ser Gly Ser
            180                 185                 190

Gly Ser Gly Ser Gly Val Ser Asp Val Pro Arg Asp Leu Glu Val Val
        195                 200                 205

Ala Ala Thr Pro Thr Ser Leu Leu Ile Ser Trp His Ser Tyr Tyr Glu
    210                 215                 220

Gln Asn Ser Tyr Tyr Arg Ile Thr Tyr Gly Glu Thr Gly Gly Asn Ser
225                 230                 235                 240

Pro Val Gln Glu Phe Thr Val Pro Tyr Ser Gln Thr Thr Ala Thr Ile
                245                 250                 255

Ser Gly Leu Lys Pro Gly Val Asp Tyr Thr Ile Thr Val Tyr Ala Val
            260                 265                 270

Tyr Gly Ser Lys Tyr Tyr Tyr Pro Ile Ser Ile Asn Tyr Arg Thr Glu
        275                 280                 285

Ile Glu Lys Pro Ser Gln
    290
```

<210> SEQ ID NO 174
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 174

```
Met His His His His His His Ile Pro Asp Ser Ser Pro Leu Leu Gln
1               5                   10                  15

Phe Gly Gly Gln Val Arg Gln Arg Tyr Leu Tyr Thr Asp Asp Ala Gln
            20                  25                  30

Gln Thr Glu Ala His Leu Glu Ile Arg Glu Asp Gly Thr Val Gly Gly
        35                  40                  45

Ala Ala Asp Gln Ser Pro Glu Ser Leu Leu Gln Leu Lys Ala Leu Lys
```

```
    50                  55                  60

Pro Gly Val Ile Gln Ile Leu Gly Val Lys Thr Ser Arg Phe Leu Cys
65                  70                  75                  80

Gln Arg Pro Asp Gly Ala Leu Tyr Gly Ser Leu His Phe Asp Pro Glu
                85                  90                  95

Ala Cys Ser Phe Arg Glu Leu Leu Leu Glu Asp Gly Tyr Asn Val Tyr
            100                 105                 110

Gln Ser Glu Ala His Gly Leu Pro Leu His Leu Pro Gly Asn Lys Ser
        115                 120                 125

Pro His Arg Asp Pro Ala Pro Arg Gly Pro Ala Arg Phe Leu Pro Leu
    130                 135                 140

Pro Gly Leu Pro Pro Ala Leu Pro Glu Pro Pro Gly Ile Leu Ala Pro
145                 150                 155                 160

Gln Pro Pro Asp Val Gly Ser Ser Asp Pro Leu Ser Met Val Gly Pro
                165                 170                 175

Ser Gln Gly Arg Ser Pro Ser Tyr Ala Ser Gly Ser Gly Ser Gly Ser
            180                 185                 190

Gly Ser Gly Ser Gly Ser Gly Ser Val Ser Asp Val Pro Arg Asp Leu
        195                 200                 205

Glu Val Val Ala Ala Thr Pro Thr Ser Leu Leu Ile Ser Trp His Ser
    210                 215                 220

Tyr Tyr Glu Gln Asn Ser Tyr Tyr Arg Ile Thr Tyr Gly Glu Thr Gly
225                 230                 235                 240

Gly Asn Ser Pro Val Gln Glu Phe Thr Val Pro Tyr Ser Gln Thr Thr
                245                 250                 255

Ala Thr Ile Ser Gly Leu Lys Pro Gly Val Asp Tyr Thr Ile Thr Val
            260                 265                 270

Tyr Ala Val Tyr Gly Ser Lys Tyr Tyr Tyr Pro Ile Ser Ile Asn Tyr
        275                 280                 285

Arg Thr Glu Ile Asp Lys Pro Ser Gly Gly Ser Gly Ser Gly Ser Gly
    290                 295                 300

Ser Gly Ser Gly Ser Gly Ser Pro Asp Ser Ser Pro Leu Leu Gln Phe
305                 310                 315                 320

Gly Gly Gln Val Arg Gln Arg Tyr Leu Tyr Thr Asp Asp Ala Gln Gln
                325                 330                 335

Thr Glu Ala His Leu Glu Ile Arg Glu Asp Gly Thr Val Gly Gly Ala
            340                 345                 350

Ala Asp Gln Ser Pro Glu Ser Leu Leu Gln Leu Lys Ala Leu Lys Pro
        355                 360                 365

Gly Val Ile Gln Ile Leu Gly Val Lys Thr Ser Arg Phe Leu Cys Gln
    370                 375                 380

Arg Pro Asp Gly Ala Leu Tyr Gly Ser Leu His Phe Asp Pro Glu Ala
385                 390                 395                 400

Cys Ser Phe Arg Glu Leu Leu Leu Glu Asp Gly Tyr Asn Val Tyr Gln
                405                 410                 415

Ser Glu Ala His Gly Leu Pro Leu His Leu Pro Gly Asn Lys Ser Pro
            420                 425                 430

His Arg Asp Pro Ala Pro Arg Gly Pro Ala Arg Phe Leu Pro Leu Pro
        435                 440                 445

Gly Leu Pro Pro Ala Leu Pro Glu Pro Pro Gly Ile Leu Ala Pro Gln
    450                 455                 460

Pro Pro Asp Val Gly Ser Ser Asp Pro Leu Ser Met Val Gly Pro Ser
465                 470                 475                 480
```

Gln Gly Arg Ser Pro Ser Tyr Ala Ser
485

<210> SEQ ID NO 175
<211> LENGTH: 24
<212> TYPE: PRT
<213> ORGANISM: Unknown
<220> FEATURE:
<223> OTHER INFORMATION: Description of Unknown: Insulin receptor peptide

<400> SEQUENCE: 175

Lys Thr Asp Ser Gln Ile Leu Lys Glu Leu Glu Glu Ser Ser Phe Arg
1 5 10 15

Lys Thr Phe Glu Asp Tyr Leu His
20

<210> SEQ ID NO 176
<211> LENGTH: 897
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 176
atgggtgttt ctgatgttcc gcgtgatctg gaagttgttg cagcaacccc gaccagcctg 60
ctgattagct ggcatagcta ttatgaacag aatagctatt atcgcattac ctatggtgaa 120
accggtggta attctccggt tcaggaattt accgttccgt atagccagac caccgcaacc 180
attagcggtc tgaaaccggg tgttgattat accattaccg tgtatgcagt gtatggcagc 240
aaatattatt atccgattag cattaattat cgcaccgaaa ttgataaacc gagccagcat 300
catcatcacc atcatggtag cggtagcggt tcaggtagcg gttctggttc tggtagccat 360
ccgattccgg atagctctcc gctgctgcag tttggtggtc aggttcgtca gcgttatctg 420
tataccgatg atgcacagca gaccgaagca catctggaaa ttcgtgaaga tggcaccgtt 480
ggtggtgcag cagatcagtc tccggaaagc ctgctgcagc tgaaagcact gaagccaggt 540
gttattcaga ttctgggtgt taaaaccagc cgttttctgt gtcagcgtcc ggatggtgca 600
ctgtatggta gcctgcattt tgatccggaa gcatgcagct ttcgtgaact gctgctggaa 660
gatggctata atgtgtatca gagcgaagca catggtctgc cgctgcattt acctggtaat 720
aaatctccgc atcgtgatcc ggcaccgcgt ggtccggcac gtttcctgcc tctgcctggt 780
ctgcctccgg cactgccaga acctccgggt attctggcac cgcagcctcc ggatgttggt 840
agcagcgatc cgctgtctat ggttggtccg agccagggtc gtagcccgag ctatgca 897

<210> SEQ ID NO 177
<211> LENGTH: 897
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 177
atgggtgttt ctgatgttcc gcgtgatctg gaagttgttg cagcaacccc gaccagcctg 60
ctgattagct ggcatagcta ttatgaacag aatagctatt atcgcattac ctatggtgaa 120
accggtggta attctccggt tcaggaattt accgttccgt atagccagac caccgcaacc 180

```
attagcggtc tgaaaccggg tgttgattat accattaccg tgtatgcagt gtatggcagc    240

aaatattatt atccgattag cattaattat cgcaccgaaa ttgataaacc gagccagcat    300

catcatcacc atcatggtag cggtagcggt tcaggtagcg gttctggttc tggtagcccg    360

attccggata gctctccgct gctgcagttt ggtggtcagg ttcgtcagcg ttatctgtat    420

accgatgatg cacagcagac cgaagcacat ctggaaattc gtgaagatgg caccgttggt    480

ggtgcagcag atcagtctcc ggaaagcctg ctgcagctga aagcactgaa gccaggtgtt    540

attcagattc tgggtgttaa aaccagccgt tttctgtgtc agcgtccgga tggtgcactg    600

tatggtagcc tgcattttga tccggaagca tgcagctttc gtgaactgct gctggaagat    660

ggctataatg tgtatcagag cgaagcacat ggtctgccgc tgcatttacc tggtaataaa    720

tctccgcatc gtgatccggc accgcgtggt ccggcacgtt tcctgcctct gcctggtctg    780

cctccggcac tgccagaacc tccgggtatt ctggcaccgc agcctccgga tgttggtagc    840

agcgatccgc tgtctatggt tggtccgagc cagggtcgta gcccgagcta tgcaagc       897
```

<210> SEQ ID NO 178
<211> LENGTH: 897
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 178

```
atgggtgttt ctgatgttcc gcgtgatctg gaagttgttg cagcaacccc gaccagcctg     60

ctgattagct ggcatagcta ttatgaacag aatagctatt atcgcattac ctatggtgaa    120

accggtggta attctccggt tcaggaattt accgttccgt atagccagac caccgcaacc    180

attagcggtc tgaaaccggg tgttgattat accattaccg tgtatgcagt gtatggcagc    240

aaatattatt atccgattag cattaattat cgcaccgaaa ttgataaacc gagcggtggt    300

agcggtagcg gttcaggtag cggttctggt tctggtagcc cgattccgga tagctctccg    360

ctgctgcagt ttggtggtca ggttcgtcag cgttatctgt ataccgatga tgcacagcag    420

accgaagcac atctggaaat tcgtgaagat ggcaccgttg gtggtgcagc agatcagtct    480

ccggaaagcc tgctgcagct gaaagcactg aagccaggtg ttattcagat tctgggtgtt    540

aaaaccagcc gttttctgtg tcagcgtccg gatggtgcac tgtatggtag cctgcatttt    600

gatccggaag catgcagctt tcgtgaactg ctgctggaag atggctataa tgtgtatcag    660

agcgaagcac atggtctgcc gctgcattta cctggtaata aatctccgca tcgtgatccg    720

gcaccgcgtg gtccggcacg tttcctgcct ctgcctggtc tgcctccggc actgccagaa    780

cctccgggta ttctggcacc gcagcctccg gatgttggta gcagcgatcc gctgtctatg    840

gttggtccga gccagggtcg tagcccgagc tatgcaagcc atcatcatca ccatcat       897
```

<210> SEQ ID NO 179
<211> LENGTH: 897
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179

```
atgggtgttt ctgatgttcc gcgtgatctg gaagttgttg cagcaacccc gaccagcctg     60

ctgattagct ggcatagcta ttatgaacag aatagctatt atcgcattac ctatggtgaa    120
```

```
accggtggta attctccggt tcaggaattt accgttccgt atagccagac caccgcaacc    180

attagcggtc tgaaaccggg tgttgattat accattaccg tgtatgcagt gtatggcagc    240

aaatattatt atccgattag cattaattat cgcaccgaaa ttgataaacc gagcggtggt    300

agcggtagcg gttcaggtag cggttctggt tctggtagcc atccgattcc ggatagctct    360

ccgctgctgc agtttggtgg tcaggttcgt cagcgttatc tgtataccga tgatgcacag    420

cagaccgaag cacatctgga aattcgtgaa gatggcaccg ttggtggtgc agcagatcag    480

tctccggaaa gcctgctgca gctgaaagca ctgaagccag gtgttattca gattctgggt    540

gttaaaacca gccgttttct gtgtcagcgt ccggatggtg cactgtatgg tagcctgcat    600

tttgatccgg aagcatgcag ctttcgtgaa ctgctgctgg aagatggcta taatgtgtat    660

cagagcgaag cacatggtct gccgctgcat ttacctggta ataaatctcc gcatcgtgat    720

ccggcaccgc gtggtccggc acgtttcctg cctctgcctg gtctgcctcc ggcactgcca    780

gaacctccgg gtattctggc accgcagcct ccggatgttg gtagcagcga tccgctgtct    840

atggttggtc cgagccaggg tcgtagcccg agctatgcac atcatcatca ccatcat       897
```

<210> SEQ ID NO 180
<211> LENGTH: 900
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 180

```
atgccgattc cggatagctc tccgctgctg cagtttggtg gtcaggttcg tcagcgttat     60

ctgtataccg atgatgcaca gcagaccgaa gcacatctgg aaattcgtga agatggcacc    120

gttggtggtg cagcagatca gtctccggaa agcctgctgc agctgaaagc actgaaaccg    180

ggtgttattc agattctggg tgttaaaacc agccgttttc tgtgtcagcg tccggatggt    240

gcactgtatg gtagcctgca ttttgatccg gaagcatgca gctttcgtga actgctgctg    300

gaagatggct ataatgtgta tcagagcgaa gcacatggtc tgccgctgca tctgcctggt    360

aataaatctc cgcatcgtga tccggcaccg cgtggtccgg cacgtttcct gccgctgcct    420

ggtctgcctc cggcactgcc agaacctccg ggtattctgg caccgcagcc tccggatgtt    480

ggtagcagcg atccgctgtc tatggttggt ccgagccagg gtcgtagccc gagctatgca    540

agcggtggta gcggtagcgg ttctggtagc ggttcaggtt ctggttctgg tgtttctgat    600

gttccgcgtg atctggaagt tgttgcagca accccgacca gcctgctgat tagctggcat    660

agctattatg aacagaatag ctattatcgc attacctatg gtgaaaccgg tggtaattct    720

ccggttcagg aatttaccgt tccgtatagc cagaccaccg caaccattag cggtctgaag    780

cctggtgtgg attataccat taccgtgtat gcagtttatg gcagcaaata ttattatccg    840

attagcatta attatcgcac cgaaattgat aaaccgagcc agcatcatca tcaccatcat    900
```

<210> SEQ ID NO 181
<211> LENGTH: 912
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 181
atgggtgttt ctgatgttcc gcgtgatctg gaagttgttg cagcaacccc gaccagcctg 60
ctgattagct gggaagatga tagctattat agccgctatt atcgcattac ctatggtgaa 120
accggtggta attctccggt tcaggaattt accgttccga gcgatctgta taccgcaacc 180
attagcggtc tgaaaccggg tgttgactat accattaccg tttatgccgt tacctatgac 240
gttaccgatc tgattatgca tgaaccgatc agcattaatt atcgcaccga gattgataaa 300
ccgagcggtg gtagcggtag cggttctggt agcggttcag gttcaggtag cccgattccg 360
gatagctctc cgctgctgca gtttggtggt caggttcgtc agcgttatct gtatactgat 420
gatgcacagc agaccgaagc acatctggaa attcgtgaag atggcaccgt tggtggtgca 480
gcagatcagt ctccggaaag cctgctgcag ctgaaagcac tgaaacctgg tgttattcag 540
attctgggtg ttaaaaccag ccgttttctg tgtcagcgtc cggatggtgc actgtatggt 600
agcctgcatt ttgatccgga agcatgcagc tttcgtgaac tgctgctgga agatggctat 660
aatgtgtatc agagcgaagc acatggtctg ccgctgcatc tgcctggtaa taaatctccg 720
catcgtgatc cggcaccgcg tggtccggca cgttttctgc cgctgcctgg tctgcctccg 780
gcactgcctg aaccgcctgg tattctggca ccgcagcctc cggatgttgg tagcagcgat 840
ccgctgtcta tggttggtcc gagccagggt cgtagcccga gctatgcaag ccatcatcat 900
catcaccatt ga 912

<210> SEQ ID NO 182
<211> LENGTH: 555
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182
atgcatcatc atcatcacca tgatagctct ccgctgctgc agtttggtgg tcaggttcgt 60
cagcgttatc tgtataccga tgatgcacag cagaccgaag cacatctgga aattcgtgaa 120
gatggcaccg ttggtggtgc agcagatcag tctccggaaa gcctgctgca gctgaaagca 180
ctgaaaccgg gtgttattca gattctgggt gttaaaacca gccgttttct gtgtcagcgt 240
ccggatggtg cactgtatgg tagcctgcat tttgatccgg aagcatgcag ctttcgtgaa 300
ctgctgctgg aagatggcta taatgtgtat cagagcgaag cacatggcct gccgctgcat 360
ctgcctggta ataaatctcc gcatcgtgat ccggcaccgc gtggtccggc acgttttctg 420
ccgctgcctg gtctgcctcc ggcactgcct gaaccgcctg gtattctggc accgcagcct 480
ccggatgttg gtagcagcga tccgctgtct atggttggtc cgagccaggg tcgtagcccg 540
agctatgcaa gctga 555

<210> SEQ ID NO 183
<211> LENGTH: 1470
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183
atgcatcacc accatcatca tattccggat agcagtccgc tgctgcagtt tggtggtcag 60
gttcgtcagc gttatctgta taccgatgat gcacagcaga ccgaagccca tctggaaatt 120
cgtgaagatg gcaccgttgg tggtgcagca gatcagagtc cggaaagcct gctgcagctg 180

```
aaagcactga aaccgggtgt tattcagatt ctgggtgtta aaaccagccg ttttctgtgt    240
cagcgtccgg atggtgcact gtatggtagc ctgcattttg atccggaagc atgtagcttt    300
cgtgaactgc tgctggaaga tggttataat gtttatcaga gcgaagcaca tggtctgccg    360
ctgcatctgc ctggtaataa aagtccgcat cgtgatccgg caccgcgtgg tccggcacgt    420
tttctgccgc tgcctggtct gcctccggca ctgcctgaac cgcctggtat tctggcaccg    480
cagcctccgg atgttggtag cagcgatccg ctgagcatgg ttggtccgag ccagggtcgt    540
agcccgagct atgcaagcgg tagcggttca ggtagcggta gtggtagcgg cagcggtagc    600
gttagtgatg ttccgcgtga tctggaagtt gttgcagcaa ccccgaccag cctgctgatt    660
agctggcata gctattatga acagaatagc tattatcgca ttacctatgg tgaaaccggt    720
ggtaatagtc cggttcagga atttaccgtt ccgtatagcc agaccaccgc aaccattagc    780
ggtctgaaac ctggtgttga ttataccatt accgtgtatg cagtgtatgg cagcaaatat    840
tattatccga ttagcatcaa ttatcgcacc gaaattgata aaccgagcgg tggtagcggt    900
tctggttcag gttcaggtag tggttctggt agtccggata gctcacctct gctgcagttt    960
ggtggccagg tgcgccagcg ctatctgtac acagatgatg cccagcagac agaagcccat   1020
ctggaaatcc gcgaagatgg tacagtgggt ggcgctgccg atcagtcacc ggaatcactg   1080
ctgcagctga aagccctgaa acctggcgtg atccagatcc tgggcgtgaa aacctcacgc   1140
tttctgtgcc agcgtcctga tggcgctctg tatggctcac tgcattttga tcctgaagcc   1200
tgctcatttc gcgaactgct gctggaagat ggctataacg tgtatcagtc tgaagcccat   1260
ggcttacctc tgcatctgcc aggcaacaaa tcacctcatc gtgatcctgc ccctcgcggt   1320
cctgctcgct ttctgccact gccaggcctg cctccagccc tgccagaacc tccaggcatc   1380
ctggcacctc agccacctga tgtgggttca agtgatccgc tgtcaatggt gggtccgtca   1440
cagggtcgta gtccgtctta tgccagctga                                   1470
```

<210> SEQ ID NO 184
<211> LENGTH: 882
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184

```
atgggtgttt ctgatgttcc gcgtgatctg gaagttgttg cagcaacccc gaccagcctg     60
ctgattagct ggcatagcta ttatgaacag aatagctatt atcgcattac ctatggtgaa    120
accggtggta attctccggt tcaggaattt accgttccgt atagccagac caccgcaacc    180
attagcggtc tgaaaccggg tgttgattat accattaccg tgtatgcagt gtatggcagc    240
aaatattatt atccgattag cattaattat cgcaccgaaa ttgaaaaacc gagccagggt    300
agcggtagcg gttcaggtag cggttctggt tctggtagcc cgattccgga tagctctccg    360
ctgctgcagt ttggtggtca ggttcgtcag cgttatctgt ataccgatga tgcacagcag    420
accgaagcac atctggaaat tcgtgaagat ggcaccgttg gtggtgcagc agatcagtct    480
ccggaaagcc tgctgcagct gaaagcactg aagccaggtg ttattcagat tctgggtgtt    540
aaaaccagcc gttttctgtg tcagcgtccg gatggtgcac tgtatggtag cctgcatttt    600
gatccggaag catgcagctt tcgtgaactg ctgctggaag atggctataa tgtgtatcag    660
agcgaagcac atggtctgcc gctgcattta cctggtaata aatctccgca tcgtgatccg    720
```

```
gcaccgcgtg gtccggcacg tttcctgcct ctgcctggtc tgcctccggc actgccagaa    780

cctccgggta ttctggcacc gcagcctccg gatgttggta gcagcgatcc gctgtctatg    840

gttggtccga gccagggtcg tagcccgagc tatgcaagct ga                       882
```

<210> SEQ ID NO 185
<211> LENGTH: 852
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 185

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcggtggtag cggtagcggt    300

tcaggtagcc cgattccgga tagcagtccg ctgctgcagt ttggtggtca ggttcgtcag    360

cgttatctgt ataccgatga tgcacagcag accgaagcac atctggaaat tcgtgaagat    420

ggcaccgttg gtggtgcagc agatcagagt ccggaaagcc tgctgcagct gaaagcactg    480

aaacctggtg ttattcagat tctgggtgtt aaaaccagcc gttttctgtg tcagcgtccg    540

gatggtgcac tgtatggtag cctgcatttt gatccggaag catgtagctt tcgtgaactg    600

ctgctggaag atggttataa tgtttatcag agcgaagctc atggtctgcc gctgcatctg    660

cctggtaata aaagtccgca tcgtgatccg gcaccgcgtg gtccggcacg ttttctgcct    720

ctgcctggtt tacctccggc actgcctgaa ccgcctggta ttctggcacc gcagcctccg    780

gatgttggta gcagcgatcc gctgagcatg gttggtccga gccagggtcg tagcccgagc    840

tatgcaagct ga                                                        852
```

<210> SEQ ID NO 186
<211> LENGTH: 840
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcggtggtag cggtagcccg    300

attccggata gcagtccgct gctgcagttt ggtggtcagg ttcgtcagcg ttatctgtat    360

accgatgatg cacagcagac cgaagcacat ctggaaattc gtgaagatgg caccgttggt    420

ggtgcagcag atcagagtcc ggaaagcctg ctgcagctga aagcactgaa acctggtgtt    480

attcagattc tgggtgttaa aaccagccgt tttctgtgtc agcgtccgga tggtgcactg    540

tatggtagcc tgcattttga tccggaagca tgtagctttc gtgaactgct gctggaagat    600
```

-continued

```
ggttataatg tttatcagag cgaagctcat ggtctgccgc tgcatctgcc tggtaataaa    660

agtccgcatc gtgatccggc accgcgtggt ccggcacgtt ttctgcctct gcctggttta    720

cctccggcac tgcctgaacc gcctggtatt ctggcaccgc agcctccgga tgttggtagc    780

agcgatccgc tgagcatggt tggtccgagc cagggtcgta gcccgagcta tgcaagctga    840
```

<210> SEQ ID NO 187
<211> LENGTH: 825
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 187

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcccgattcc ggatagcagt    300

ccgctgctgc agtttggtgg tcaggttcgt cagcgttatc tgtataccga tgatgcacag    360

cagaccgaag cacatctgga aattcgtgaa gatggcaccg ttggtggtgc agcagatcag    420

agtccggaaa gcctgctgca gctgaaagca ctgaaacctg gtgttattca gattctgggt    480

gttaaaacca gccgttttct gtgtcagcgt ccggatggtg cactgtatgg tagcctgcat    540

tttgatccgg aagcatgtag ctttcgtgaa ctgctgctgg aagatggtta taatgtttat    600

cagagcgaag ctcatggtct gccgctgcat ctgcctggta ataaaagtcc gcatcgtgat    660

ccggcaccgc gtggtccggc acgttttctg cctctgcctg gtttacctcc ggcactgcct    720

gaaccgcctg gtattctggc accgcagcct ccggatgttg gtagcagcga tccgctgagc    780

atggttggtc cgagccaggg tcgtagcccg agctatgcaa gctga                    825
```

<210> SEQ ID NO 188
<211> LENGTH: 867
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 188

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tccatcacca ccatcatcat    300

ggtagcggta gcggttcagg tagcccgatt ccggatagca gtccgctgct gcagtttggt    360

ggtcaggttc gtcagcgtta tctgtatacc gatgatgcac agcagaccga agcacatctg    420

gaaattcgtg aagatggcac cgttggtggt gcagcagatc agagtccgga aagcctgctg    480

cagctgaaag cactgaaacc tggtgttatt cagattctgg gtgttaaaac cagccgtttt    540

ctgtgtcagc gtccggatgg tgcactgtat ggtagcctgc attttgatcc ggaagcatgt    600

agctttcgtg aactgctgct ggaagatggt tataatgttt atcagagcga agctcatggt    660
```

ctgccgctgc atctgcctgg taataaaagt ccgcatcgtg atccggcacc gcgtggtccg 720
gcacgttttc tgcctctgcc tggtttacct ccggcactgc ctgaaccgcc tggtattctg 780
gcaccgcagc ctccggatgt tggtagcagc gatccgctga gcatggttgg tccgagccag 840
ggtcgtagcc cgagctatgc aagctga 867

<210> SEQ ID NO 189
<211> LENGTH: 855
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 189
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tccatcacca ccatcatcat 300
ggtagcggta gcccgattcc ggatagcagt ccgctgctgc agtttggtgg tcaggttcgt 360
cagcgttatc tgtataccga tgatgcacag cagaccgaag cacatctgga aattcgtgaa 420
gatggcaccg ttggtggtgc agcagatcag agtccggaaa gcctgctgca gctgaaagca 480
ctgaaacctg gtgttattca gattctgggt gttaaaacca gccgttttct gtgtcagcgt 540
ccggatggtg cactgtatgg tagcctgcat tttgatccgg aagcatgtag ctttcgtgaa 600
ctgctgctgg aagatggtta taatgtttat cagagcgaag ctcatggtct gccgctgcat 660
ctgcctggta ataaaagtcc gcatcgtgat ccggcaccgc gtggtccggc acgttttctg 720
cctctgcctg gtttacctcc ggcactgcct gaaccgcctg gtattctggc accgcagcct 780
ccggatgttg gtagcagcga tccgctgagc atggttggtc cgagccaggg tcgtagcccg 840
agctatgcaa gctga 855

<210> SEQ ID NO 190
<211> LENGTH: 843
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 190
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tccatcacca ccatcatcat 300
ccgattccgg atagcagtcc gctgctgcag tttggtggtc aggttcgtca gcgttatctg 360
tataccgatg atgcacagca gaccgaagca catctggaaa ttcgtgaaga tggcaccgtt 420
ggtggtgcag cagatcagag tccggaaagc ctgctgcagc tgaaagcact gaaacctggt 480
gttattcaga ttctgggtgt taaaaccagc cgttttctgt gtcagcgtcc ggatggtgca 540
ctgtatggta gcctgcattt tgatccggaa gcatgtagct ttcgtgaact gctgctggaa 600
gatggttata atgtttatca gagcgaagct catggtctgc cgctgcatct gcctggtaat 660
aaaagtccgc atcgtgatcc ggcaccgcgt ggtccggcac gttttctgcc tctgcctggt 720
ttacctccgg cactgcctga accgcctggt attctggcac cgcagcctcc ggatgttggt 780
agcagcgatc cgctgagcat ggttggtccg agccagggtc gtagcccgag ctatgcaagc 840
tga 843

<210> SEQ ID NO 191
<211> LENGTH: 855
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 191
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaagatga agatgaggac 300
gaagatgagg atccgattcc ggatagcagt ccgctgctgc agtttggtgg tcaggttcgt 360
cagcgttatc tgtataccga tgatgcacag cagaccgaag cacatctgga aattcgtgaa 420
gatggcaccg ttggtggtgc agcagatcag agtccggaaa gcctgctgca gctgaaagca 480
ctgaaacctg gtgttattca gattctgggt gttaaaacca gccgttttct gtgtcagcgt 540
ccggatggtg cactgtatgg tagcctgcat tttgatccgg aagcatgtag ctttcgtgaa 600
ctgctgctgg aagatggtta taatgtttat cagagcgaag ctcatggtct gccgctgcat 660
ctgcctggta ataaaagtcc gcatcgtgat ccggcaccgc gtggtccggc acgttttctg 720
cctctgcctg gtttacctcc ggcactgcct gaaccgcctg gtattctggc accgcagcct 780
ccggatgttg gtagcagcga tccgctgagc atggttggtc cgagccaggg tcgtagcccg 840
agctatgcaa gctga 855

<210> SEQ ID NO 192
<211> LENGTH: 879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 192
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaagatga agatgaggac 300
gaagatgagg atggtagcgg tagcggttca ggtagcccga ttccggatag cagtccgctg 360
ctgcagtttg gtggtcaggt tcgtcagcgt tatctgtata ccgatgatgc acagcagacc 420
gaagcacatc tggaaattcg tgaagatggc accgttggtg gtgcagcaga tcagagtccg 480
gaaagcctgc tgcagctgaa agcactgaaa cctggtgtta ttcagattct gggtgttaaa 540
accagccgtt ttctgtgtca gcgtccggat ggtgcactgt atggtagcct gcattttgat 600
ccggaagcat gtagctttcg tgaactgctg ctggaagatg gttataatgt ttatcagagc 660
gaagctcatg gtctgccgct gcatctgcct ggtaataaaa gtccgcatcg tgatccggca 720
ccgcgtggtc cggcacgttt tctgcctctg cctggtttac ctccggcact gcctgaaccg 780
cctggtattc tggcaccgca gcctccggat gttggtagca gcgatccgct gagcatggtt 840
ggtccgagcc agggtcgtag cccgagctat gcaagctga 879

<210> SEQ ID NO 193
<211> LENGTH: 864
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 193
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcggtagcgc agcagcagca 300
gccgctgcag cagccggtag cccgattccg gatagcagtc cgctgctgca gtttggtggt 360
caggttcgtc agcgttatct gtataccgat gatgcacagc agaccgaagc acatctggaa 420
attcgtgaag atggcaccgt tggtggtgca gcagatcaga gtccggaaag cctgctgcag 480
ctgaaagcac tgaaacctgg tgttattcag attctgggtg ttaaaaccag ccgttttctg 540
tgtcagcgtc cggatggtgc actgtatggt agcctgcatt ttgatccgga agcatgtagc 600
tttcgtgaac tgctgctgga agatggttat aatgtttatc agagcgaagc tcatggtctg 660
ccgctgcatc tgcctggtaa taaaagtccg catcgtgatc cggcaccgcg tggtccggca 720
cgttttctgc ctctgcctgg tttacctccg gcactgcctg aaccgcctgg tattctggca 780
ccgcagcctc cggatgttgg tagcagcgat ccgctgagca tggttggtcc gagccagggt 840
cgtagcccga gctatgcaag ctga 864

<210> SEQ ID NO 194
<211> LENGTH: 870
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 194
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcggtagtga aggtagcgaa 300
ggttcagaag gttctgaagg cagcgaaccg attccggata gcagtccgct gctgcagttt 360

-continued

```
ggtggtcagg ttcgtcagcg ttatctgtat accgatgatg cacagcagac cgaagcacat    420

ctggaaattc gtgaagatgg caccgttggt ggtgcagcag atcagagtcc ggaaagcctg    480

ctgcagctga aagcactgaa acctggtgtt attcagattc tgggtgttaa aaccagccgt    540

tttctgtgtc agcgtccgga tggtgcactg tatggtagcc tgcattttga tccggaagca    600

tgtagctttc gtgaactgct gctggaagat ggttataatg tttatcagag cgaagctcat    660

ggtctgccgc tgcatctgcc tggtaataaa agtccgcatc gtgatccggc accgcgtggt    720

ccggcacgtt ttctgcctct gcctggttta cctccggcac tgcctgaacc gcctggtatt    780

ctggcaccgc agcctccgga tgttggtagc agcgatccgc tgagcatggt tggtccgagc    840

cagggtcgta gcccgagcta tgcaagctga                                     870
```

```
<210> SEQ ID NO 195
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 195

atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tccctgcaag tccggcatca    300

ccggcaagtc cggctagtcc ggcaagcccg attccggata gcagtccgct gctgcagttt    360

ggtggtcagg ttcgtcagcg ttatctgtat accgatgatg cacagcagac cgaagcacat    420

ctggaaattc gtgaagatgg caccgttggt ggtgcagcag atcagagtcc ggaaagcctg    480

ctgcagctga aagcactgaa acctggtgtt attcagattc tgggtgttaa aaccagccgt    540

tttctgtgtc agcgtccgga tggtgcactg tatggtagcc tgcattttga tccggaagca    600

tgtagctttc gtgaactgct gctggaagat ggttataatg tttatcagag cgaagctcat    660

ggtctgccgc tgcatctgcc tggtaataaa agtccgcatc gtgatccggc accgcgtggt    720

ccggcacgtt ttctgcctct gcctggttta cctccggcac tgcctgaacc gcctggtatt    780

ctggcaccgc agcctccgga tgttggtagc agcgatccgc tgagcatggt tggtccgagc    840

cagggtcgta gcccgagcta tgcaagctga                                     870
```

```
<210> SEQ ID NO 196
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 196

atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcggtagtcc gggttcaccg    300
```

```
ggtagccctg gttctccggg tagtcctccg attccggata gcagtccgct gctgcagttt    360

ggtggtcagg ttcgtcagcg ttatctgtat accgatgatg cacagcagac cgaagcacat    420

ctggaaattc gtgaagatgg caccgttggt ggtgcagcag atcagagtcc ggaaagcctg    480

ctgcagctga aagcactgaa acctggtgtt attcagattc tgggtgttaa aaccagccgt    540

tttctgtgtc agcgtccgga tggtgcactg tatggtagcc tgcattttga tccggaagca    600

tgtagctttc gtgaactgct gctggaagat ggttataatg tttatcagag cgaagctcat    660

ggtctgccgc tgcatctgcc tggtaataaa agtccgcatc gtgatccggc accgcgtggt    720

ccggcacgtt ttctgcctct gcctggttta cctccggcac tgcctgaacc gcctggtatt    780

ctggcaccgc agcctccgga tgttggtagc agcgatccgc tgagcatggt tggtccgagc    840

cagggtcgta gcccgagcta tgcaagctga                                     870
```

<210> SEQ ID NO 197
<211> LENGTH: 867
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcggtagcac cgttgcagca    300

ccgagcaccg ttgccgctcc gtcaccgatt ccggatagca gtccgctgct gcagtttggt    360

ggtcaggttc gtcagcgtta tctgtatacc gatgatgcac agcagaccga agcacatctg    420

gaaattcgtg aagatggcac cgttggtggt gcagcagatc agagtccgga aagcctgctg    480

cagctgaaag cactgaaacc tggtgttatt cagattctgg gtgttaaaac cagccgtttt    540

ctgtgtcagc gtccggatgg tgcactgtat ggtagcctgc attttgatcc ggaagcatgt    600

agctttcgtg aactgctgct ggaagatggt tataatgttt atcagagcga agctcatggt    660

ctgccgctgc atctgcctgg taataaaagt ccgcatcgtg atccggcacc gcgtggtccg    720

gcacgttttc tgcctctgcc tggtttacct ccggcactgc ctgaaccgcc tggtattctg    780

gcaccgcagc ctccggatgt tggtagcagc gatccgctga gcatggttgg tccgagccag    840

ggtcgtagcc cgagctatgc aagctga                                        867
```

<210> SEQ ID NO 198
<211> LENGTH: 849
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180
```

-continued

```
attagcggtc tgaaaccggg tgttgattat accattaccg tttatgcggt gtatggcagc    240

aaatattatt atccgattag catcaattat cgcaccgaaa tcggtggtag cgaaggtggt    300

agtgaaccga ttccggatag cagtccgctg ctgcagtttg gtggtcaggt tcgtcagcgt    360

tatctgtata ccgatgatgc acagcagacc gaagcacatc tggaaattcg tgaagatggc    420

accgttggtg gtgcagcaga tcagagtccg gaaagcctgc tgcagctgaa agcactgaaa    480

cctggtgtta ttcagattct gggtgttaaa accagccgtt ttctgtgtca gcgtccggat    540

ggtgcactgt atggtagcct gcattttgat ccggaagcat gtagctttcg tgaactgctg    600

ctggaagatg gttataatgt ttatcagagc gaagctcatg gtctgccgct gcatctgcct    660

ggtaataaaa gtccgcatcg tgatccggca ccgcgtggtc cggcacgttt tctgcctctg    720

cctggtttac ctccggcact gcctgaaccg cctggtattc tggcaccgca gcctccggat    780

gttggtagca gcgatccgct gagcatggtt ggtccgagcc agggtcgtag cccgagctat    840

gcaagctga                                                             849
```

<210> SEQ ID NO 199
<211> LENGTH: 846
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcagcaccag caccagtacc    300

ggtccgattc cggatagcag tccgctgctg cagtttggtg gtcaggttcg tcagcgttat    360

ctgtataccg atgatgcaca gcagaccgaa gcacatctgg aaattcgtga agatggcacc    420

gttggtggtg cagcagatca gagtccggaa agcctgctgc agctgaaagc actgaaacct    480

ggtgttattc agattctggg tgttaaaacc agccgttttc tgtgtcagcg tccggatggt    540

gcactgtatg gtagcctgca ttttgatccg gaagcatgta gctttcgtga actgctgctg    600

gaagatggtt ataatgttta tcagagcgaa gctcatggtc tgccgctgca tctgcctggt    660

aataaaagtc cgcatcgtga tccggcaccg cgtggtccgg cacgttttct gcctctgcct    720

ggtttacctc cggcactgcc tgaaccgcct ggtattctgg caccgcagcc tccggatgtt    780

ggtagcagcg atccgctgag catggttggt ccgagccagg gtcgtagccc gagctatgca    840

agctga                                                                846
```

<210> SEQ ID NO 200
<211> LENGTH: 867
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120
```

-continued

```
accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcgaaaaacc gagccaaggt    300

ggtagcggta gcggttcagg tagcccgatt ccggatagca gtccgctgct gcagtttggt    360

ggtcaggttc gtcagcgtta tctgtatacc gatgatgcac agcagaccga agcacatctg    420

gaaattcgtg aagatggcac cgttggtggt gcagcagatc agagtccgga aagcctgctg    480

cagctgaaag cactgaaacc tggtgttatt cagattctgg gtgttaaaac cagccgtttt    540

ctgtgtcagc gtccggatgg tgcactgtat ggtagcctgc attttgatcc ggaagcatgt    600

agctttcgtg aactgctgct ggaagatggt tataatgttt atcagagcga agctcatggt    660

ctgccgctgc atctgcctgg taataaaagt ccgcatcgtg atccggcacc gcgtggtccg    720

gcacgttttc tgcctctgcc tggtttacct ccggcactgc ctgaaccgcc tggtattctg    780

gcaccgcagc ctccggatgt tggtagcagc gatccgctga gcatggttgg tccgagccag    840

ggtcgtagcc cgagctatgc aagctga                                        867
```

<210> SEQ ID NO 201
<211> LENGTH: 855
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcgaaaaacc gagccaaggt    300

ggttcaggta gcccgattcc ggatagcagt ccgctgctgc agtttggtgg tcaggttcgt    360

cagcgttatc tgtataccga tgatgcacag cagaccgaag cacatctgga aattcgtgaa    420

gatggcaccg ttggtggtgc agcagatcag agtccggaaa gcctgctgca gctgaaagca    480

ctgaaacctg gtgttattca gattctgggt gttaaaacca gccgttttct gtgtcagcgt    540

ccggatggtg cactgtatgg tagcctgcat tttgatccgg aagcatgtag ctttcgtgaa    600

ctgctgctgg aagatggtta taatgtttat cagagcgaag ctcatggtct gccgctgcat    660

ctgcctggta ataaaagtcc gcatcgtgat ccggcaccgc gtggtccggc acgttttctg    720

cctctgcctg gtttacctcc ggcactgcct gaaccgcctg gtattctggc accgcagcct    780

ccggatgttg gtagcagcga tccgctgagc atggttggtc cgagccaggg tcgtagcccg    840

agctatgcaa gctga                                                     855
```

<210> SEQ ID NO 202
<211> LENGTH: 840
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202

-continued

```
atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcgaaaaacc gagccaaccg    300

attccggata gcagtccgct gctgcagttt ggtggtcagg ttcgtcagcg ttatctgtat    360

accgatgatg cacagcagac cgaagcacat ctggaaattc gtgaagatgg caccgttggt    420

ggtgcagcag atcagagtcc ggaaagcctg ctgcagctga aagcactgaa acctggtgtt    480

attcagattc tgggtgttaa aaccagccgt tttctgtgtc agcgtccgga tggtgcactg    540

tatggtagcc tgcattttga tccggaagca tgtagctttc gtgaactgct gctggaagat    600

ggttataatg tttatcagag cgaagctcat ggtctgccgc tgcatctgcc tggtaataaa    660

agtccgcatc gtgatccggc accgcgtggt ccggcacgtt ttctgcctct gcctggttta    720

cctccggcac tgcctgaacc gcctggtatt ctggcaccgc agcctccgga tgttggtagc    780

agcgatccgc tgagcatggt tggtccgagc cagggtcgta gcccgagcta tgcaagctga    840
```

```
<210> SEQ ID NO 203
<211> LENGTH: 882
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 203

atgggcgtta gtgatgttcc gcgtgatctg gaagttgttg cagcaacccc gaccagcctg     60

ctgattagct ggcatagcta ttatgaacag aatagctatt atcgcattac ctatggtgaa    120

accggtggta atagtccggt tcaggaattt accgttccgt atagccagac caccgcaacc    180

attagcggtc tgaaaccggg tgttgattat accattaccg tttatgcggt gtatggcagc    240

aaatattatt atccgattag catcaattat cgcaccgaaa tcgaaaaacc gagccaacat    300

caccaccatc atcatggtag cggtagcggt tcaggtagcc cgattccgga tagcagtccg    360

ctgctgcagt ttggtggtca ggttcgtcag cgttatctgt ataccgatga tgcacagcag    420

accgaagcac atctggaaat tcgtgaagat ggcaccgttg gtggtgcagc agatcagagt    480

ccggaaagcc tgctgcagct gaaagcactg aaacctggtg ttattcagat tctgggtgtt    540

aaaaccagcc gttttctgtg tcagcgtccg gatggtgcac tgtatggtag cctgcatttt    600

gatccggaag catgtagctt tcgtgaactg ctgctggaag atggttataa tgtttatcag    660

agcgaagctc atggtctgcc gctgcatctg cctggtaata aaagtccgca tcgtgatccg    720

gcaccgcgtg gtccggcacg ttttctgcct ctgcctggtt tacctccggc actgcctgaa    780

ccgcctggta ttctggcacc gcagcctccg gatgttggta gcagcgatcc gctgagcatg    840

gttggtccga gccagggtcg tagcccgagc tatgcaagct ga                        882
```

```
<210> SEQ ID NO 204
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
```

atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaacat 300
caccaccatc atcatggttc aggtagcccg attccggata gcagtccgct gctgcagttt 360
ggtggtcagg ttcgtcagcg ttatctgtat accgatgatg cacagcagac cgaagcacat 420
ctggaaattc gtgaagatgg caccgttggt ggtgcagcag atcagagtcc ggaaagcctg 480
ctgcagctga aagcactgaa acctggtgtt attcagattc tgggtgttaa aaccagccgt 540
tttctgtgtc agcgtccgga tggtgcactg tatggtagcc tgcattttga tccggaagca 600
tgtagctttc gtgaactgct gctggaagat ggttataatg tttatcagag cgaagctcat 660
ggtctgccgc tgcatctgcc tggtaataaa agtccgcatc gtgatccggc accgcgtggt 720
ccggcacgtt ttctgcctct gcctggttta cctccggcac tgcctgaacc gcctggtatt 780
ctggcaccgc agcctccgga tgttggtagc agcgatccgc tgagcatggt tggtccgagc 840
cagggtcgta gcccgagcta tgcaagctga 870

<210> SEQ ID NO 205
<211> LENGTH: 858
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaacat 300
caccaccatc atcatccgat tccggatagc agtccgctgc tgcagtttgg tggtcaggtt 360
cgtcagcgtt atctgtatac cgatgatgca cagcagaccg aagcacatct ggaaattcgt 420
gaagatggca ccgttggtgg tgcagcagat cagagtccgg aaagcctgct gcagctgaaa 480
gcactgaaac ctggtgttat tcagattctg ggtgttaaaa ccagccgttt tctgtgtcag 540
cgtccggatg gtgcactgta tggtagcctg cattttgatc cggaagcatg tagctttcgt 600
gaactgctgc tggaagatgg ttataatgtt tatcagagcg aagctcatgg tctgccgctg 660
catctgcctg gtaataaaag tccgcatcgt gatccggcac cgcgtggtcc ggcacgtttt 720
ctgcctctgc ctggtttacc tccggcactg cctgaaccgc ctggtattct ggcaccgcag 780
cctccggatg ttggtagcag cgatccgctg agcatggttg gtccgagcca gggtcgtagc 840
ccgagctatg caagctga 858

<210> SEQ ID NO 206
<211> LENGTH: 870
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 206
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaagaa 300
gatgaggacg aggacgaaga tgaggatccg attccggata gcagtccgct gctgcagttt 360
ggtggtcagg ttcgtcagcg ttatctgtat accgatgatg cacagcagac cgaagcacat 420
ctggaaattc gtgaagatgg caccgttggt ggtgcagcag atcagagtcc ggaaagcctg 480
ctgcagctga aagcactgaa acctggtgtt attcagattc tgggtgttaa aaccagccgt 540
tttctgtgtc agcgtccgga tggtgcactg tatggtagcc tgcattttga tccggaagca 600
tgtagctttc gtgaactgct gctggaagat ggttataatg tttatcagag cgaagctcat 660
ggtctgccgc tgcatctgcc tggtaataaa agtccgcatc gtgatccggc accgcgtggt 720
ccggcacgtt ttctgcctct gcctggttta cctccggcac tgcctgaacc gcctggtatt 780
ctggcaccgc agcctccgga tgttggtagc agcgatccgc tgagcatggt tggtccgagc 840
cagggtcgta gcccgagcta tgcaagctga 870

<210> SEQ ID NO 207
<211> LENGTH: 894
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaagaa 300
gatgaggacg aggacgaaga tgaggatggt agcggtagcg gttcaggtag cccgattccg 360
gatagcagtc cgctgctgca gtttggtggt caggttcgtc agcgttatct gtataccgat 420
gatgcacagc agaccgaagc acatctggaa attcgtgaag atggcaccgt tggtggtgca 480
gcagatcaga gtccggaaag cctgctgcag ctgaaagcac tgaaacctgg tgttattcag 540
attctgggtg ttaaaaccag ccgttttctg tgtcagcgtc cggatggtgc actgtatggt 600
agcctgcatt ttgatccgga agcatgtagc tttcgtgaac tgctgctgga agatggttat 660
aatgtttatc agagcgaagc tcatggtctg ccgctgcatc tgcctggtaa taaaagtccg 720
catcgtgatc cggcaccgcg tggtccggca cgttttctgc ctctgcctgg tttacctccg 780
gcactgcctg aaccgcctgg tattctggca ccgcagcctc cggatgttgg tagcagcgat 840
ccgctgagca tggttggtcc gagccagggt cgtagcccga gctatgcaag ctga 894

<210> SEQ ID NO 208
<211> LENGTH: 879
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 208
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaggt 300
agcgcagcag cagcagccgc tgcagcagcc ggtagcccga ttccggatag cagtccgctg 360
ctgcagtttg gtggtcaggt tcgtcagcgt tatctgtata ccgatgatgc acagcagacc 420
gaagcacatc tggaaattcg tgaagatggc accgttggtg gtgcagcaga tcagagtccg 480
gaaagcctgc tgcagctgaa agcactgaaa cctggtgtta ttcagattct gggtgttaaa 540
accagccgtt ttctgtgtca gcgtccggat ggtgcactgt atggtagcct gcattttgat 600
ccggaagcat gtagctttcg tgaactgctg ctggaagatg gttataatgt ttatcagagc 660
gaagctcatg gtctgccgct gcatctgcct ggtaataaaa gtccgcatcg tgatccggca 720
ccgcgtggtc cggcacgttt tctgcctctg cctggtttac ctccggcact gcctgaaccg 780
cctggtattc tggcaccgca gcctccggat gttggtagca gcgatccgct gagcatggtt 840
ggtccgagcc agggtcgtag cccgagctat gcaagctga 879

<210> SEQ ID NO 209
<211> LENGTH: 885
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 209
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaggt 300
agcgaaggta gtgaaggttc agaaggttct gaaggtagcg aaccgattcc ggatagcagt 360
ccgctgctgc agtttggtgg tcaggttcgt cagcgttatc tgtataccga tgatgcacag 420
cagaccgaag cacatctgga aattcgtgaa gatggcaccg ttggtggtgc agcagatcag 480
agtccggaaa gcctgctgca gctgaaagca ctgaaacctg gtgttattca gattctgggt 540
gttaaaacca gccgttttct gtgtcagcgt ccggatggtg cactgtatgg tagcctgcat 600
tttgatccgg aagcatgtag ctttcgtgaa ctgctgctgg aagatggtta taatgtttat 660
cagagcgaag ctcatggtct gccgctgcat ctgcctggta ataaaagtcc gcatcgtgat 720
ccggcaccgc gtggtccggc acgttttctg cctctgcctg gtttacctcc ggcactgcct 780
gaaccgcctg gtattctggc accgcagcct ccggatgttg gtagcagcga tccgctgagc 840
atggttggtc cgagccaggg tcgtagcccg agctatgcaa gctga 885

<210> SEQ ID NO 210
<211> LENGTH: 885
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 210
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaccg 300
gcaagtccgg catcaccggc atctccggct agtccggcaa gcccgattcc ggatagcagt 360
ccgctgctgc agtttggtgg tcaggttcgt cagcgttatc tgtataccga tgatgcacag 420
cagaccgaag cacatctgga aattcgtgaa gatggcaccg ttggtggtgc agcagatcag 480
agtccggaaa gcctgctgca gctgaaagca ctgaaacctg gtgttattca gattctgggt 540
gttaaaacca gccgttttct gtgtcagcgt ccggatggtg cactgtatgg tagcctgcat 600
tttgatccgg aagcatgtag ctttcgtgaa ctgctgctgg aagatggtta taatgtttat 660
cagagcgaag ctcatggtct gccgctgcat ctgcctggta ataaaagtcc gcatcgtgat 720
ccggcaccgc gtggtccggc acgttttctg cctctgcctg gtttacctcc ggcactgcct 780
gaaccgcctg gtattctggc accgcagcct ccggatgttg gtagcagcga tccgctgagc 840
atggttggtc cgagccaggg tcgtagcccg agctatgcaa gctga 885

<210> SEQ ID NO 211
<211> LENGTH: 885
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 211
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaggt 300
agccctggta gtccgggttc accgggttct ccgggtagcc ctccgattcc ggatagcagt 360
ccgctgctgc agtttggtgg tcaggttcgt cagcgttatc tgtataccga tgatgcacag 420
cagaccgaag cacatctgga aattcgtgaa gatggcaccg ttggtggtgc agcagatcag 480
agtccggaaa gcctgctgca gctgaaagca ctgaaacctg gtgttattca gattctgggt 540
gttaaaacca gccgttttct gtgtcagcgt ccggatggtg cactgtatgg tagcctgcat 600
tttgatccgg aagcatgtag ctttcgtgaa ctgctgctgg aagatggtta taatgtttat 660
cagagcgaag ctcatggtct gccgctgcat ctgcctggta ataaaagtcc gcatcgtgat 720
ccggcaccgc gtggtccggc acgttttctg cctctgcctg gtttacctcc ggcactgcct 780
gaaccgcctg gtattctggc accgcagcct ccggatgttg gtagcagcga tccgctgagc 840
atggttggtc cgagccaggg tcgtagcccg agctatgcaa gctga 885

<210> SEQ ID NO 212
<211> LENGTH: 882
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaggt 300
agcaccgttg cagcaccgag caccgtggca gcccctagcc cgattccgga tagcagtccg 360
ctgctgcagt ttggtggtca ggttcgtcag cgttatctgt ataccgatga tgcacagcag 420
accgaagcac atctggaaat tcgtgaagat ggcaccgttg gtggtgcagc agatcagagt 480
ccggaaagcc tgctgcagct gaaagcactg aaacctggtg ttattcagat tctgggtgtt 540
aaaaccagcc gttttctgtg tcagcgtccg gatggtgcac tgtatggtag cctgcatttt 600
gatccggaag catgtagctt tcgtgaactg ctgctggaag atggttataa tgtttatcag 660
agcgaagctc atggtctgcc gctgcatctg cctggtaata aaagtccgca tcgtgatccg 720
gcaccgcgtg gtccggcacg ttttctgcct ctgcctggtt tacctccggc actgcctgaa 780
ccgcctggta ttctggcacc gcagcctccg gatgttggta gcagcgatcc gctgagcatg 840
gttggtccga gccagggtcg tagcccgagc tatgcaagct ga 882

<210> SEQ ID NO 213
<211> LENGTH: 864
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaggt 300
ggtagcgaag gtggtagtga accgattccg gatagcagtc cgctgctgca gtttggtggt 360
caggttcgtc agcgttatct gtataccgat gatgcacagc agaccgaagc acatctggaa 420
attcgtgaag atggcaccgt tggtggtgca gcagatcaga gtccggaaag cctgctgcag 480
ctgaaagcac tgaaacctgg tgttattcag attctgggtg ttaaaaccag ccgttttctg 540
tgtcagcgtc cggatggtgc actgtatggt agcctgcatt ttgatccgga agcatgtagc 600
tttcgtgaac tgctgctgga agatggttat aatgtttatc agagcgaagc tcatggtctg 660
ccgctgcatc tgcctggtaa taaaagtccg catcgtgatc cggcaccgcg tggtccggca 720
cgttttctgc ctctgcctgg tttacctccg gcactgcctg aaccgcctgg tattctggca 780
ccgcagcctc cggatgttgg tagcagcgat ccgctgagca tggttggtcc gagccagggt 840
cgtagcccga gctatgcaag ctga 864

<210> SEQ ID NO 214
<211> LENGTH: 861
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 214
atgggcgtta gtgatgttcc gcgtgatctg gaagttgttg cagcaacccc gaccagcctg 60
ctgattagct ggcatagcta ttatgaacag aatagctatt atcgcattac ctatggtgaa 120
accggtggta atagtccggt tcaggaattt accgttccgt atagccagac caccgcaacc 180
attagcggtc tgaaaccggg tgttgattat accattaccg tttatgcggt gtatggcagc 240
aaatattatt atccgattag catcaattat cgcaccgaaa tcgaaaaacc gagccaaagc 300
accagcacca gtaccggtcc gattccggat agcagtccgc tgctgcagtt tggtggtcag 360
gttcgtcagc gttatctgta taccgatgat gcacagcaga ccgaagcaca tctggaaatt 420
cgtgaagatg gcaccgttgg tggtgcagca gatcagagtc cggaaagcct gctgcagctg 480
aaagcactga aacctggtgt tattcagatt ctgggtgtta aaaccagccg ttttctgtgt 540
cagcgtccgg atggtgcact gtatggtagc ctgcattttg atccggaagc atgtagcttt 600
cgtgaactgc tgctggaaga tggttataat gtttatcaga gcgaagctca tggtctgccg 660
ctgcatctgc ctggtaataa aagtccgcat cgtgatccgg caccgcgtgg tccggcacgt 720
tttctgcctc tgcctggttt acctccggca ctgcctgaac cgcctggtat tctggcaccg 780
cagcctccgg atgttggtag cagcgatccg ctgagcatgg ttggtccgag ccagggtcgt 840
agcccgagct atgcaagctg a 861

<210> SEQ ID NO 215
<211> LENGTH: 1
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 215

Glu
1

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 216

Gly Gly Gly Gly Ser Gly Gly Gly Gly Ser Gly Gly Gly Gly Ser
1 5 10 15

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 217

Glu Asp Glu Asp Glu Asp Glu Asp Glu Asp
1 5 10

<210> SEQ ID NO 218
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 218

Glu Asp Glu Asp Glu Asp
1 5

<210> SEQ ID NO 219
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 219

Glu Asp Glu Asp Glu Asp Glu Asp
1 5

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 220

Glu Asp Glu Asp Glu Asp Glu Asp Glu Asp Glu Asp
1 5 10

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Gly Ser Pro Gly Ser Pro Gly Ser Pro Gly Ser Pro Gly Ser
1 5 10

<210> SEQ ID NO 222
<211> LENGTH: 92
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 222

Gly Val Ser Asp Val Pro Arg Asp Leu Glu Val Val Ala Ala Thr Pro
1 5 10 15

Thr Ser Leu Leu Ile Ser Trp His Ser Tyr Tyr Glu Gln Asn Ser Tyr
20 25 30

Tyr Arg Ile Thr Tyr Gly Glu Thr Gly Gly Asn Ser Pro Val Gln Glu
35 40 45

Phe Thr Val Pro Tyr Ser Gln Thr Thr Ala Thr Ile Ser Gly Leu Lys
50 55 60

Pro Gly Val Asp Tyr Thr Ile Thr Val Tyr Ala Val Tyr Gly Ser Lys
65 70 75 80

Tyr Tyr Tyr Pro Ile Ser Ile Asn Tyr Arg Thr Glu
85 90

<210> SEQ ID NO 223
<211> LENGTH: 93
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 223

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu
85 90

<210> SEQ ID NO 224
<211> LENGTH: 99
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Lys
85 90 95

Pro Ser Gln

<210> SEQ ID NO 225
<211> LENGTH: 94
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 225

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile
                85                  90


<210> SEQ ID NO 226
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30


<210> SEQ ID NO 227
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30


<210> SEQ ID NO 228
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 229
<211> LENGTH: 139
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

```
Met His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

Gly Gly Gly Gly Ser Gly Gly Gly Gly Ser Gly Gly Gly Gly Ser Gly
        35                  40                  45

Val Ser Asp Val Pro Arg Asp Leu Glu Val Val Ala Ala Thr Pro Thr
    50                  55                  60

Ser Leu Leu Ile Ser Trp His Ser Tyr Tyr Glu Gln Asn Ser Tyr Tyr
65                  70                  75                  80

Arg Ile Thr Tyr Gly Glu Thr Gly Gly Asn Ser Pro Val Gln Glu Phe
                85                  90                  95

Thr Val Pro Tyr Ser Gln Thr Thr Ala Thr Ile Ser Gly Leu Lys Pro
            100                 105                 110

Gly Val Asp Tyr Thr Ile Thr Val Tyr Ala Val Tyr Gly Ser Lys Tyr
        115                 120                 125

Tyr Tyr Pro Ile Ser Ile Asn Tyr Arg Thr Glu
    130                 135
```

<210> SEQ ID NO 230
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 230

```
Met His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

Glu Asp Glu Asp Glu Asp Glu Asp Glu Asp Gly Val Ser Asp Val Pro
        35                  40                  45

Arg Asp Leu Glu Val Val Ala Ala Thr Pro Thr Ser Leu Leu Ile Ser
    50                  55                  60

Trp His Ser Tyr Tyr Glu Gln Asn Ser Tyr Tyr Arg Ile Thr Tyr Gly
65                  70                  75                  80

Glu Thr Gly Gly Asn Ser Pro Val Gln Glu Phe Thr Val Pro Tyr Ser
                85                  90                  95

Gln Thr Thr Ala Thr Ile Ser Gly Leu Lys Pro Gly Val Asp Tyr Thr
            100                 105                 110

Ile Thr Val Tyr Ala Val Tyr Gly Ser Lys Tyr Tyr Tyr Pro Ile Ser
        115                 120                 125

Ile Asn Tyr Arg Thr Glu
    130
```

<210> SEQ ID NO 231
<211> LENGTH: 139

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 231

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Gly Gly Gly
85 90 95

Gly Ser Gly Gly Gly Gly Ser Gly Gly Gly Gly Ser His Ala Glu Gly
100 105 110

Thr Phe Thr Ser Asp Val Ser Ser Tyr Leu Glu Gly Gln Ala Ala Lys
115 120 125

Glu Phe Ile Ala Trp Leu Val Lys Gly Arg Gly
130 135

<210> SEQ ID NO 232
<211> LENGTH: 134
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 232

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Glu Asp Glu
85 90 95

Asp Glu Asp Glu Asp Glu Asp His Ala Glu Gly Thr Phe Thr Ser Asp
100 105 110

Val Ser Ser Tyr Leu Glu Gly Gln Ala Ala Lys Glu Phe Ile Ala Trp
115 120 125

Leu Val Lys Gly Arg Gly
130

<210> SEQ ID NO 233
<211> LENGTH: 147
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 233

Met His Gly Glu Gly Thr Phe Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser Gly Gly Gly Gly Ser Gly Gly Gly
        35                  40                  45

Gly Ser Gly Gly Gly Gly Ser Gly Val Ser Asp Val Pro Arg Asp Leu
    50                  55                  60

Glu Val Val Ala Ala Thr Pro Thr Ser Leu Leu Ile Ser Trp His Ser
65                  70                  75                  80

Tyr Tyr Glu Gln Asn Ser Tyr Tyr Arg Ile Thr Tyr Gly Glu Thr Gly
                85                  90                  95

Gly Asn Ser Pro Val Gln Glu Phe Thr Val Pro Tyr Ser Gln Thr Thr
            100                 105                 110

Ala Thr Ile Ser Gly Leu Lys Pro Gly Val Asp Tyr Thr Ile Thr Val
        115                 120                 125

Tyr Ala Val Tyr Gly Ser Lys Tyr Tyr Tyr Pro Ile Ser Ile Asn Tyr
    130                 135                 140

Arg Thr Glu
145

<210> SEQ ID NO 234
<211> LENGTH: 134
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 234

Met His Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Gly
            20                  25                  30

Glu Asp Glu Asp Glu Asp Glu Asp Glu Asp Gly Val Ser Asp Val Pro
        35                  40                  45

Arg Asp Leu Glu Val Val Ala Ala Thr Pro Thr Ser Leu Leu Ile Ser
    50                  55                  60

Trp His Ser Tyr Tyr Glu Gln Asn Ser Tyr Tyr Arg Ile Thr Tyr Gly
65                  70                  75                  80

Glu Thr Gly Gly Asn Ser Pro Val Gln Glu Phe Thr Val Pro Tyr Ser
                85                  90                  95

Gln Thr Thr Ala Thr Ile Ser Gly Leu Lys Pro Gly Val Asp Tyr Thr
            100                 105                 110

Ile Thr Val Tyr Ala Val Tyr Gly Ser Lys Tyr Tyr Tyr Pro Ile Ser
        115                 120                 125

Ile Asn Tyr Arg Thr Glu
    130

<210> SEQ ID NO 235
<211> LENGTH: 147
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 235

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser His Gly Glu Gly
            100                 105                 110

Thr Phe Thr Ser Asp Leu Ser Lys Gln Met Glu Glu Glu Ala Val Arg
        115                 120                 125

Leu Phe Ile Glu Trp Leu Lys Asn Gly Gly Pro Ser Ser Gly Ala Pro
    130                 135                 140

Pro Pro Ser
145
```

<210> SEQ ID NO 236
<211> LENGTH: 142
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 236

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp His Gly Glu Gly Thr Phe Thr Ser Asp
            100                 105                 110

Leu Ser Lys Gln Met Glu Glu Glu Ala Val Arg Leu Phe Ile Glu Trp
        115                 120                 125

Leu Lys Asn Gly Gly Pro Ser Ser Gly Ala Pro Pro Pro Ser
    130                 135                 140
```

<210> SEQ ID NO 237
<211> LENGTH: 41
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 237

```
Met Gly Phe Gly Cys Asn Gly Pro Trp Asp Glu Asp Asp Met Gln Cys
1               5                   10                  15

His Asn His Cys Lys Ser Ile Lys Gly Tyr Lys Gly Gly Tyr Cys Ala
            20                  25                  30

Lys Gly Gly Phe Val Cys Lys Cys Tyr
        35                  40
```

<210> SEQ ID NO 238
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Asp Glu Asp
                85                  90                  95

Glu Asp Glu Asp Glu Asp Met Gly Phe Gly Cys Asn Gly Pro Trp Asp
            100                 105                 110

Glu Asp Asp Met Gln Cys His Asn His Cys Lys Ser Ile Lys Gly Tyr
        115                 120                 125

Lys Gly Gly Tyr Cys Ala Lys Gly Gly Phe Val Cys Lys Cys Tyr
    130                 135                 140
```

<210> SEQ ID NO 239
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

```
Met Gly Phe Gly Cys Asn Gly Pro Trp Asp Glu Asp Asp Met Gln Cys
1               5                   10                  15

His Asn His Cys Lys Ser Ile Lys Gly Tyr Lys Gly Gly Tyr Cys Ala
            20                  25                  30

Lys Gly Gly Phe Val Cys Lys Cys Tyr Val Ser Asp Val Pro Arg Asp
        35                  40                  45

Leu Glu Val Val Ala Ala Thr Pro Thr Ser Leu Leu Ile Ser Trp His
    50                  55                  60

Ser Tyr Tyr Glu Gln Asn Ser Tyr Tyr Arg Ile Thr Tyr Gly Glu Thr
65                  70                  75                  80

Gly Gly Asn Ser Pro Val Gln Glu Phe Thr Val Pro Tyr Ser Gln Thr
```

```
                85                  90                  95

Thr Ala Thr Ile Ser Gly Leu Lys Pro Gly Val Asp Tyr Thr Ile Thr
            100                 105                 110

Val Tyr Ala Val Tyr Gly Ser Lys Tyr Tyr Tyr Pro Ile Ser Ile Asn
        115                 120                 125

Tyr Arg Thr Glu Asp Glu Asp Glu Asp Glu Asp Glu Asp
    130                 135                 140


<210> SEQ ID NO 240
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Met Trp Thr Leu Val Ser Trp Val Ala Leu Thr Ala Gly Leu Val Ala
1               5                   10                  15

Gly Thr Arg Cys Pro Asp Gly Gln Phe Cys Pro Val Ala Cys Cys Leu
            20                  25                  30

Asp Pro Gly Gly Ala Ser Tyr Ser Cys Cys Arg Pro Leu Leu Asp Lys
        35                  40                  45

Trp Pro Thr Thr Leu Ser Arg His Leu Gly Gly Pro Cys Gln Val Asp
    50                  55                  60

Ala His Cys Ser Ala Gly His Ser Cys Ile Phe Thr Val Ser Gly Thr
65                  70                  75                  80

Ser Ser Cys Cys Pro Phe Pro Glu Ala Val Ala Cys Gly Asp Gly His
                85                  90                  95

His Cys Cys Pro Arg Gly Phe His Cys Ser Ala Asp Gly Arg Ser Cys
            100                 105                 110

Phe Gln Arg Ser Gly Asn Asn Ser Val Gly Ala Ile Gln Cys Pro Asp
        115                 120                 125

Ser Gln Phe Glu Cys Pro Asp Phe Ser Thr Cys Cys Val Met Val Asp
    130                 135                 140

Gly Ser Trp Gly Cys Cys Pro Met Pro Gln Ala Ser Cys Cys Glu Asp
145                 150                 155                 160

Arg Val His Cys Cys Pro His Gly Ala Phe Cys Asp Leu Val His Thr
                165                 170                 175

Arg Cys Ile Thr Pro Thr Gly Thr His Pro Leu Ala Lys Lys Leu Pro
            180                 185                 190

Ala Gln Arg Thr Asn Arg Ala Val Ala Leu Ser Ser Ser Val Met Cys
        195                 200                 205

Pro Asp Ala Arg Ser Arg Cys Pro Asp Gly Ser Thr Cys Cys Glu Leu
    210                 215                 220

Pro Ser Gly Lys Tyr Gly Cys Cys Pro Met Pro Asn Ala Thr Cys Cys
225                 230                 235                 240

Ser Asp His Leu His Cys Cys Pro Gln Asp Thr Val Cys Asp Leu Ile
                245                 250                 255

Gln Ser Lys Cys Leu Ser Lys Glu Asn Ala Thr Thr Asp Leu Leu Thr
            260                 265                 270

Lys Leu Pro Ala His Thr Val Gly Asp Val Lys Cys Asp Met Glu Val
        275                 280                 285

Ser Cys Pro Asp Gly Tyr Thr Cys Cys Arg Leu Gln Ser Gly Ala Trp
    290                 295                 300
```

Gly Cys Cys Pro Phe Thr Gln Ala Val Cys Cys Glu Asp His Ile His
305 310 315 320

Cys Cys Pro Ala Gly Phe Thr Cys Asp Thr Gln Lys Gly Thr Cys Glu
325 330 335

Gln Gly Pro His Gln Val Pro Trp Met Glu Lys Ala Pro Ala His Leu
340 345 350

Ser Leu Pro Asp Pro Gln Ala Leu Lys Arg Asp Val Pro Cys Asp Asn
355 360 365

Val Ser Ser Cys Pro Ser Ser Asp Thr Cys Cys Gln Leu Thr Ser Gly
370 375 380

Glu Trp Gly Cys Cys Pro Ile Pro Glu Ala Val Cys Cys Ser Asp His
385 390 395 400

Gln His Cys Cys Pro Gln Gly Tyr Thr Cys Val Ala Glu Gly Gln Cys
405 410 415

Gln Arg Gly Ser Glu Ile Val Ala Gly Leu Glu Lys Met Pro Ala Arg
420 425 430

Arg Ala Ser Leu Ser His Pro Arg Asp Ile Gly Cys Asp Gln His Thr
435 440 445

Ser Cys Pro Val Gly Gln Thr Cys Cys Pro Ser Leu Gly Gly Ser Trp
450 455 460

Ala Cys Cys Gln Leu Pro His Ala Val Cys Cys Glu Asp Arg Gln His
465 470 475 480

Cys Cys Pro Ala Gly Tyr Thr Cys Asn Val Lys Ala Arg Ser Cys Glu
485 490 495

Lys Glu Val Val Ser Ala Gln Pro Ala Thr Phe Leu Ala Arg Ser Pro
500 505 510

His Val Gly Val Lys Asp Val Glu Cys Gly Glu Gly His Phe Cys His
515 520 525

Asp Asn Gln Thr Cys Cys Arg Asp Asn Arg Gln Gly Trp Ala Cys Cys
530 535 540

Pro Tyr Arg Gln Gly Val Cys Cys Ala Asp Arg Arg His Cys Cys Pro
545 550 555 560

Ala Gly Phe Arg Cys Ala Ala Arg Gly Thr Lys Cys Leu Arg Arg Glu
565 570 575

Ala Pro Arg Trp Asp Ala Pro Leu Arg Asp Pro Ala Leu Arg Gln Leu
580 585 590

Leu

<210> SEQ ID NO 241
<211> LENGTH: 576
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 241

Thr Arg Cys Pro Asp Gly Gln Phe Cys Pro Val Ala Cys Cys Leu Asp
1 5 10 15

Pro Gly Gly Ala Ser Tyr Ser Cys Cys Arg Pro Leu Leu Asp Lys Trp
20 25 30

Pro Thr Thr Leu Ser Arg His Leu Gly Gly Pro Cys Gln Val Asp Ala
35 40 45

His Cys Ser Ala Gly His Ser Cys Ile Phe Thr Val Ser Gly Thr Ser
50 55 60

-continued

```
Ser Cys Cys Pro Phe Pro Glu Ala Val Ala Cys Gly Asp Gly His His
65                  70                  75                  80

Cys Cys Pro Arg Gly Phe His Cys Ser Ala Asp Gly Arg Ser Cys Phe
                85                  90                  95

Gln Arg Ser Gly Asn Asn Ser Val Gly Ala Ile Gln Cys Pro Asp Ser
            100                 105                 110

Gln Phe Glu Cys Pro Asp Phe Ser Thr Cys Cys Val Met Val Asp Gly
        115                 120                 125

Ser Trp Gly Cys Cys Pro Met Pro Gln Ala Ser Cys Cys Glu Asp Arg
    130                 135                 140

Val His Cys Cys Pro His Gly Ala Phe Cys Asp Leu Val His Thr Arg
145                 150                 155                 160

Cys Ile Thr Pro Thr Gly Thr His Pro Leu Ala Lys Lys Leu Pro Ala
                165                 170                 175

Gln Arg Thr Asn Arg Ala Val Ala Leu Ser Ser Ser Val Met Cys Pro
            180                 185                 190

Asp Ala Arg Ser Arg Cys Pro Asp Gly Ser Thr Cys Cys Glu Leu Pro
        195                 200                 205

Ser Gly Lys Tyr Gly Cys Cys Pro Met Pro Asn Ala Thr Cys Cys Ser
    210                 215                 220

Asp His Leu His Cys Cys Pro Gln Asp Thr Val Cys Asp Leu Ile Gln
225                 230                 235                 240

Ser Lys Cys Leu Ser Lys Glu Asn Ala Thr Thr Asp Leu Leu Thr Lys
                245                 250                 255

Leu Pro Ala His Thr Val Gly Asp Val Lys Cys Asp Met Glu Val Ser
            260                 265                 270

Cys Pro Asp Gly Tyr Thr Cys Cys Arg Leu Gln Ser Gly Ala Trp Gly
        275                 280                 285

Cys Cys Pro Phe Thr Gln Ala Val Cys Cys Glu Asp His Ile His Cys
    290                 295                 300

Cys Pro Ala Gly Phe Thr Cys Asp Thr Gln Lys Gly Thr Cys Glu Gln
305                 310                 315                 320

Gly Pro His Gln Val Pro Trp Met Glu Lys Ala Pro Ala His Leu Ser
                325                 330                 335

Leu Pro Asp Pro Gln Ala Leu Lys Arg Asp Val Pro Cys Asp Asn Val
            340                 345                 350

Ser Ser Cys Pro Ser Ser Asp Thr Cys Cys Gln Leu Thr Ser Gly Glu
        355                 360                 365

Trp Gly Cys Cys Pro Ile Pro Glu Ala Val Cys Cys Ser Asp His Gln
    370                 375                 380

His Cys Cys Pro Gln Gly Tyr Thr Cys Val Ala Glu Gly Gln Cys Gln
385                 390                 395                 400

Arg Gly Ser Glu Ile Val Ala Gly Leu Glu Lys Met Pro Ala Arg Arg
                405                 410                 415

Ala Ser Leu Ser His Pro Arg Asp Ile Gly Cys Asp Gln His Thr Ser
            420                 425                 430

Cys Pro Val Gly Gln Thr Cys Cys Pro Ser Leu Gly Gly Ser Trp Ala
        435                 440                 445

Cys Cys Gln Leu Pro His Ala Val Cys Cys Glu Asp Arg Gln His Cys
    450                 455                 460

Cys Pro Ala Gly Tyr Thr Cys Asn Val Lys Ala Arg Ser Cys Glu Lys
465                 470                 475                 480

Glu Val Val Ser Ala Gln Pro Ala Thr Phe Leu Ala Arg Ser Pro His
```

```
                485                 490                 495

Val Gly Val Lys Asp Val Glu Cys Gly Glu Gly His Phe Cys His Asp
            500                 505                 510

Asn Gln Thr Cys Cys Arg Asp Asn Arg Gln Gly Trp Ala Cys Cys Pro
        515                 520                 525

Tyr Arg Gln Gly Val Cys Cys Ala Asp Arg Arg His Cys Cys Pro Ala
    530                 535                 540

Gly Phe Arg Cys Ala Ala Arg Gly Thr Lys Cys Leu Arg Arg Glu Ala
545                 550                 555                 560

Pro Arg Trp Asp Ala Pro Leu Arg Asp Pro Ala Leu Arg Gln Leu Leu
                565                 570                 575


<210> SEQ ID NO 242
<211> LENGTH: 154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Pro Gln Ala Ser Cys Cys Glu Asp Arg Val His Cys Cys Pro His Gly
1               5                   10                  15

Ala Phe Cys Asp Leu Val His Thr Arg Cys Ile Thr Pro Thr Gly Thr
            20                  25                  30

His Pro Leu Ala Lys Lys Leu Pro Ala Gln Arg Thr Asn Arg Ala Val
        35                  40                  45

Ala Leu Ser Ser Ser Ser Lys Glu Asp Ala Thr Thr Asp Leu Leu Thr
    50                  55                  60

Lys Leu Pro Ala His Thr Val Gly Asp Val Lys Cys Asp Met Glu Val
65                  70                  75                  80

Ser Cys Pro Asp Gly Tyr Thr Cys Cys Arg Leu Gln Ser Gly Ala Trp
                85                  90                  95

Cys Glu Gln Gly Pro His Gln Val Pro Trp Met Glu Lys Ala Pro Ala
            100                 105                 110

His Leu Ser Leu Pro Asp Pro Gln Ala Leu Lys Arg Asp Val Pro Cys
        115                 120                 125

Asp Asn Val Ser Ser Cys Pro Ser Ser Asp Thr Cys Cys Gln Leu Thr
    130                 135                 140

Ser Gly Glu Trp Gly Cys Cys Pro Ile Pro
145                 150


<210> SEQ ID NO 243
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Met Thr Arg Cys Pro Asp Gly Gln Phe Cys Pro Val Ala Cys Cys Leu
1               5                   10                  15

Asp Pro Gly Gly Ala Ser Tyr Ser Cys Cys Arg Pro Leu Leu Asp Lys
            20                  25                  30

Trp Pro Thr Thr Leu Ser Arg His Leu Gly Gly Pro Cys Gln Val Asp
        35                  40                  45

Ala His Cys Ser Ala Gly His Ser Cys Ile Phe Thr Val Ser Gly Thr
```

```
    50                  55                  60

Ser Ser Cys Cys Pro Phe Pro Glu Ala Val Ala Cys Gly Asp Gly His
65                  70                  75                  80

His Cys Cys Pro Arg Gly Phe His Cys Ser Ala Asp Gly Arg Ser Cys
                85                  90                  95

Phe Gln Arg Ser Gly Asn Asn Ser Val Gly Ala Ile Gln Cys Pro Asp
            100                 105                 110

Ser Gln Phe Glu Cys Pro Asp Phe Ser Thr Cys Cys Val Met Val Asp
        115                 120                 125

Gly Ser Trp Gly Cys Cys Pro Met Pro Gln Ala Ser Cys Cys Glu Asp
    130                 135                 140

Arg Val His Cys Cys Pro His Gly Ala Phe Cys Asp Leu Val His Thr
145                 150                 155                 160

Arg Cys Ile Thr Pro Thr Gly Thr His Pro Leu Ala Lys Lys Leu Pro
                165                 170                 175

Ala Gln Arg Thr Asn Arg Ala Val Ala Leu Ser Ser Ser Val Met Cys
            180                 185                 190

Pro Asp Ala Arg Ser Arg Cys Pro Asp Gly Ser Thr Cys Cys Glu Leu
        195                 200                 205

Pro Ser Gly Lys Tyr Gly Cys Cys Pro Met Pro Asn Ala Thr Cys Cys
    210                 215                 220

Ser Asp His Leu His Cys Cys Pro Gln Asp Thr Val Cys Asp Leu Ile
225                 230                 235                 240

Gln Ser Lys Cys Leu Ser Lys Glu Asn Ala Thr Thr Asp Leu Leu Thr
                245                 250                 255

Lys Leu Pro Ala His Thr Val Gly Asp Val Lys Cys Asp Met Glu Val
            260                 265                 270

Ser Cys Pro Asp Gly Tyr Thr Cys Cys Arg Leu Gln Ser Gly Ala Trp
        275                 280                 285

Gly Cys Cys Pro Phe Thr Gln Ala Val Cys Cys Glu Asp His Ile His
    290                 295                 300

Cys Cys Pro Ala Gly Phe Thr Cys Asp Thr Gln Lys Gly Thr Cys Glu
305                 310                 315                 320

Gln Gly Pro His Gln Val Pro Trp Met Glu Lys Ala Pro Ala His Leu
                325                 330                 335

Ser Leu Pro Asp Pro Gln Ala Leu Lys Arg Asp Val Pro Cys Asp Asn
            340                 345                 350

Val Ser Ser Cys Pro Ser Ser Asp Thr Cys Cys Gln Leu Thr Ser Gly
        355                 360                 365

Glu Trp Gly Cys Cys Pro Ile Pro Glu Ala Val Cys Cys Ser Asp His
    370                 375                 380

Gln His Cys Cys Pro Gln Gly Tyr Thr Cys Val Ala Glu Gly Gln Cys
385                 390                 395                 400

Gln Arg Gly Ser Glu Ile Val Ala Gly Leu Glu Lys Met Pro Ala Arg
                405                 410                 415

Arg Ala Ser Leu Ser His Pro Arg Asp Ile Gly Cys Asp Gln His Thr
            420                 425                 430

Ser Cys Pro Val Gly Gln Thr Cys Cys Pro Ser Leu Gly Gly Ser Trp
        435                 440                 445

Ala Cys Cys Gln Leu Pro His Ala Val Cys Cys Glu Asp Arg Gln His
    450                 455                 460

Cys Cys Pro Ala Gly Tyr Thr Cys Asn Val Lys Ala Arg Ser Cys Glu
465                 470                 475                 480
```

```
Lys Glu Val Val Ser Ala Gln Pro Ala Thr Phe Leu Ala Arg Ser Pro
                485                 490                 495

His Val Gly Val Lys Asp Val Glu Cys Gly Glu Gly His Phe Cys His
            500                 505                 510

Asp Asn Gln Thr Cys Cys Arg Asp Asn Arg Gln Gly Trp Ala Cys Cys
        515                 520                 525

Pro Tyr Arg Gln Gly Val Cys Cys Ala Asp Arg Arg His Cys Cys Pro
    530                 535                 540

Ala Gly Phe Arg Cys Ala Ala Arg Gly Thr Lys Cys Leu Arg Arg Glu
545                 550                 555                 560

Ala Pro Arg Trp Asp Ala Pro Leu Arg Asp Pro Ala Leu Arg Gln Leu
                565                 570                 575

Leu Gly Gly Gly Gly Ser Gly Gly Gly Gly Ser Gly Gly Gly Gly Ser
            580                 585                 590

Gly Val Ser Asp Val Pro Arg Asp Leu Glu Val Val Ala Ala Thr Pro
        595                 600                 605

Thr Ser Leu Leu Ile Ser Trp His Ser Tyr Tyr Glu Gln Asn Ser Tyr
    610                 615                 620

Tyr Arg Ile Thr Tyr Gly Glu Thr Gly Gly Asn Ser Pro Val Gln Glu
625                 630                 635                 640

Phe Thr Val Pro Tyr Ser Gln Thr Thr Ala Thr Ile Ser Gly Leu Lys
                645                 650                 655

Pro Gly Val Asp Tyr Thr Ile Thr Val Tyr Ala Val Tyr Gly Ser Lys
            660                 665                 670

Tyr Tyr Tyr Pro Ile Ser Ile Asn Tyr Arg Thr Glu
        675                 680
```

<210> SEQ ID NO 244
<211> LENGTH: 679
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

```
Met Thr Arg Cys Pro Asp Gly Gln Phe Cys Pro Val Ala Cys Cys Leu
1               5                   10                  15

Asp Pro Gly Gly Ala Ser Tyr Ser Cys Cys Arg Pro Leu Leu Asp Lys
            20                  25                  30

Trp Pro Thr Thr Leu Ser Arg His Leu Gly Gly Pro Cys Gln Val Asp
        35                  40                  45

Ala His Cys Ser Ala Gly His Ser Cys Ile Phe Thr Val Ser Gly Thr
    50                  55                  60

Ser Ser Cys Cys Pro Phe Pro Glu Ala Val Ala Cys Gly Asp Gly His
65                  70                  75                  80

His Cys Cys Pro Arg Gly Phe His Cys Ser Ala Asp Gly Arg Ser Cys
                85                  90                  95

Phe Gln Arg Ser Gly Asn Asn Ser Val Gly Ala Ile Gln Cys Pro Asp
            100                 105                 110

Ser Gln Phe Glu Cys Pro Asp Phe Ser Thr Cys Cys Val Met Val Asp
        115                 120                 125

Gly Ser Trp Gly Cys Cys Pro Met Pro Gln Ala Ser Cys Cys Glu Asp
    130                 135                 140

Arg Val His Cys Cys Pro His Gly Ala Phe Cys Asp Leu Val His Thr
```

-continued

```
145                 150                 155                 160

Arg Cys Ile Thr Pro Thr Gly Thr His Pro Leu Ala Lys Lys Leu Pro
                165                 170                 175

Ala Gln Arg Thr Asn Arg Ala Val Ala Leu Ser Ser Ser Val Met Cys
            180                 185                 190

Pro Asp Ala Arg Ser Arg Cys Pro Asp Gly Ser Thr Cys Cys Glu Leu
        195                 200                 205

Pro Ser Gly Lys Tyr Gly Cys Cys Pro Met Pro Asn Ala Thr Cys Cys
    210                 215                 220

Ser Asp His Leu His Cys Cys Pro Gln Asp Thr Val Cys Asp Leu Ile
225                 230                 235                 240

Gln Ser Lys Cys Leu Ser Lys Glu Asn Ala Thr Thr Asp Leu Leu Thr
                245                 250                 255

Lys Leu Pro Ala His Thr Val Gly Asp Val Lys Cys Asp Met Glu Val
            260                 265                 270

Ser Cys Pro Asp Gly Tyr Thr Cys Cys Arg Leu Gln Ser Gly Ala Trp
        275                 280                 285

Gly Cys Cys Pro Phe Thr Gln Ala Val Cys Cys Glu Asp His Ile His
    290                 295                 300

Cys Cys Pro Ala Gly Phe Thr Cys Asp Thr Gln Lys Gly Thr Cys Glu
305                 310                 315                 320

Gln Gly Pro His Gln Val Pro Trp Met Glu Lys Ala Pro Ala His Leu
                325                 330                 335

Ser Leu Pro Asp Pro Gln Ala Leu Lys Arg Asp Val Pro Cys Asp Asn
            340                 345                 350

Val Ser Ser Cys Pro Ser Ser Asp Thr Cys Cys Gln Leu Thr Ser Gly
        355                 360                 365

Glu Trp Gly Cys Cys Pro Ile Pro Glu Ala Val Cys Cys Ser Asp His
    370                 375                 380

Gln His Cys Cys Pro Gln Gly Tyr Thr Cys Val Ala Glu Gly Gln Cys
385                 390                 395                 400

Gln Arg Gly Ser Glu Ile Val Ala Gly Leu Glu Lys Met Pro Ala Arg
                405                 410                 415

Arg Ala Ser Leu Ser His Pro Arg Asp Ile Gly Cys Asp Gln His Thr
            420                 425                 430

Ser Cys Pro Val Gly Gln Thr Cys Cys Pro Ser Leu Gly Gly Ser Trp
        435                 440                 445

Ala Cys Cys Gln Leu Pro His Ala Val Cys Cys Glu Asp Arg Gln His
    450                 455                 460

Cys Cys Pro Ala Gly Tyr Thr Cys Asn Val Lys Ala Arg Ser Cys Glu
465                 470                 475                 480

Lys Glu Val Val Ser Ala Gln Pro Ala Thr Phe Leu Ala Arg Ser Pro
                485                 490                 495

His Val Gly Val Lys Asp Val Glu Cys Gly Glu Gly His Phe Cys His
            500                 505                 510

Asp Asn Gln Thr Cys Cys Arg Asp Asn Arg Gln Gly Trp Ala Cys Cys
        515                 520                 525

Pro Tyr Arg Gln Gly Val Cys Cys Ala Asp Arg Arg His Cys Cys Pro
    530                 535                 540

Ala Gly Phe Arg Cys Ala Ala Arg Gly Thr Lys Cys Leu Arg Arg Glu
545                 550                 555                 560

Ala Pro Arg Trp Asp Ala Pro Leu Arg Asp Pro Ala Leu Arg Gln Leu
                565                 570                 575
```

```
Leu Glu Asp Glu Asp Glu Asp Glu Asp Glu Asp Gly Val Ser Asp Val
            580                 585                 590

Pro Arg Asp Leu Glu Val Val Ala Ala Thr Pro Thr Ser Leu Leu Ile
        595                 600                 605

Ser Trp His Ser Tyr Tyr Glu Gln Asn Ser Tyr Tyr Arg Ile Thr Tyr
    610                 615                 620

Gly Glu Thr Gly Gly Asn Ser Pro Val Gln Glu Phe Thr Val Pro Tyr
625                 630                 635                 640

Ser Gln Thr Thr Ala Thr Ile Ser Gly Leu Lys Pro Gly Val Asp Tyr
                645                 650                 655

Thr Ile Thr Val Tyr Ala Val Tyr Gly Ser Lys Tyr Tyr Tyr Pro Ile
            660                 665                 670

Ser Ile Asn Tyr Arg Thr Glu
        675


<210> SEQ ID NO 245
<211> LENGTH: 684
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Thr Arg Cys Pro
            100                 105                 110

Asp Gly Gln Phe Cys Pro Val Ala Cys Cys Leu Asp Pro Gly Gly Ala
        115                 120                 125

Ser Tyr Ser Cys Cys Arg Pro Leu Leu Asp Lys Trp Pro Thr Thr Leu
    130                 135                 140

Ser Arg His Leu Gly Gly Pro Cys Gln Val Asp Ala His Cys Ser Ala
145                 150                 155                 160

Gly His Ser Cys Ile Phe Thr Val Ser Gly Thr Ser Ser Cys Cys Pro
                165                 170                 175

Phe Pro Glu Ala Val Ala Cys Gly Asp Gly His His Cys Cys Pro Arg
            180                 185                 190

Gly Phe His Cys Ser Ala Asp Gly Arg Ser Cys Phe Gln Arg Ser Gly
        195                 200                 205

Asn Asn Ser Val Gly Ala Ile Gln Cys Pro Asp Ser Gln Phe Glu Cys
    210                 215                 220

Pro Asp Phe Ser Thr Cys Cys Val Met Val Asp Gly Ser Trp Gly Cys
225                 230                 235                 240

Cys Pro Met Pro Gln Ala Ser Cys Cys Glu Asp Arg Val His Cys Cys
```

-continued

```
                245                 250                 255

Pro His Gly Ala Phe Cys Asp Leu Val His Thr Arg Cys Ile Thr Pro
            260                 265                 270

Thr Gly Thr His Pro Leu Ala Lys Lys Leu Pro Ala Gln Arg Thr Asn
        275                 280                 285

Arg Ala Val Ala Leu Ser Ser Ser Val Met Cys Pro Asp Ala Arg Ser
    290                 295                 300

Arg Cys Pro Asp Gly Ser Thr Cys Cys Glu Leu Pro Ser Gly Lys Tyr
305                 310                 315                 320

Gly Cys Cys Pro Met Pro Asn Ala Thr Cys Cys Ser Asp His Leu His
                325                 330                 335

Cys Cys Pro Gln Asp Thr Val Cys Asp Leu Ile Gln Ser Lys Cys Leu
            340                 345                 350

Ser Lys Glu Asn Ala Thr Thr Asp Leu Leu Thr Lys Leu Pro Ala His
        355                 360                 365

Thr Val Gly Asp Val Lys Cys Asp Met Glu Val Ser Cys Pro Asp Gly
    370                 375                 380

Tyr Thr Cys Cys Arg Leu Gln Ser Gly Ala Trp Gly Cys Cys Pro Phe
385                 390                 395                 400

Thr Gln Ala Val Cys Cys Glu Asp His Ile His Cys Cys Pro Ala Gly
                405                 410                 415

Phe Thr Cys Asp Thr Gln Lys Gly Thr Cys Glu Gln Gly Pro His Gln
            420                 425                 430

Val Pro Trp Met Glu Lys Ala Pro Ala His Leu Ser Leu Pro Asp Pro
        435                 440                 445

Gln Ala Leu Lys Arg Asp Val Pro Cys Asp Asn Val Ser Ser Cys Pro
    450                 455                 460

Ser Ser Asp Thr Cys Cys Gln Leu Thr Ser Gly Glu Trp Gly Cys Cys
465                 470                 475                 480

Pro Ile Pro Glu Ala Val Cys Cys Ser Asp His Gln His Cys Cys Pro
                485                 490                 495

Gln Gly Tyr Thr Cys Val Ala Glu Gly Gln Cys Gln Arg Gly Ser Glu
            500                 505                 510

Ile Val Ala Gly Leu Glu Lys Met Pro Ala Arg Arg Ala Ser Leu Ser
        515                 520                 525

His Pro Arg Asp Ile Gly Cys Asp Gln His Thr Ser Cys Pro Val Gly
    530                 535                 540

Gln Thr Cys Cys Pro Ser Leu Gly Gly Ser Trp Ala Cys Cys Gln Leu
545                 550                 555                 560

Pro His Ala Val Cys Cys Glu Asp Arg Gln His Cys Cys Pro Ala Gly
                565                 570                 575

Tyr Thr Cys Asn Val Lys Ala Arg Ser Cys Glu Lys Glu Val Val Ser
            580                 585                 590

Ala Gln Pro Ala Thr Phe Leu Ala Arg Ser Pro His Val Gly Val Lys
        595                 600                 605

Asp Val Glu Cys Gly Glu Gly His Phe Cys His Asp Asn Gln Thr Cys
    610                 615                 620

Cys Arg Asp Asn Arg Gln Gly Trp Ala Cys Cys Pro Tyr Arg Gln Gly
625                 630                 635                 640

Val Cys Cys Ala Asp Arg Arg His Cys Cys Pro Ala Gly Phe Arg Cys
                645                 650                 655

Ala Ala Arg Gly Thr Lys Cys Leu Arg Arg Glu Ala Pro Arg Trp Asp
            660                 665                 670
```

```
Ala Pro Leu Arg Asp Pro Ala Leu Arg Gln Leu Leu
        675                 680


<210> SEQ ID NO 246
<211> LENGTH: 679
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Thr Arg Cys Pro Asp Gly Gln Phe Cys
            100                 105                 110

Pro Val Ala Cys Cys Leu Asp Pro Gly Gly Ala Ser Tyr Ser Cys Cys
        115                 120                 125

Arg Pro Leu Leu Asp Lys Trp Pro Thr Thr Leu Ser Arg His Leu Gly
    130                 135                 140

Gly Pro Cys Gln Val Asp Ala His Cys Ser Ala Gly His Ser Cys Ile
145                 150                 155                 160

Phe Thr Val Ser Gly Thr Ser Ser Cys Cys Pro Phe Pro Glu Ala Val
                165                 170                 175

Ala Cys Gly Asp Gly His His Cys Cys Pro Arg Gly Phe His Cys Ser
            180                 185                 190

Ala Asp Gly Arg Ser Cys Phe Gln Arg Ser Gly Asn Asn Ser Val Gly
        195                 200                 205

Ala Ile Gln Cys Pro Asp Ser Gln Phe Glu Cys Pro Asp Phe Ser Thr
    210                 215                 220

Cys Cys Val Met Val Asp Gly Ser Trp Gly Cys Cys Pro Met Pro Gln
225                 230                 235                 240

Ala Ser Cys Cys Glu Asp Arg Val His Cys Cys Pro His Gly Ala Phe
                245                 250                 255

Cys Asp Leu Val His Thr Arg Cys Ile Thr Pro Thr Gly Thr His Pro
            260                 265                 270

Leu Ala Lys Lys Leu Pro Ala Gln Arg Thr Asn Arg Ala Val Ala Leu
        275                 280                 285

Ser Ser Ser Val Met Cys Pro Asp Ala Arg Ser Arg Cys Pro Asp Gly
    290                 295                 300

Ser Thr Cys Cys Glu Leu Pro Ser Gly Lys Tyr Gly Cys Cys Pro Met
305                 310                 315                 320

Pro Asn Ala Thr Cys Cys Ser Asp His Leu His Cys Cys Pro Gln Asp
                325                 330                 335

Thr Val Cys Asp Leu Ile Gln Ser Lys Cys Leu Ser Lys Glu Asn Ala
```

```
            340                 345                 350

Thr Thr Asp Leu Leu Thr Lys Leu Pro Ala His Thr Val Gly Asp Val
        355                 360                 365

Lys Cys Asp Met Glu Val Ser Cys Pro Asp Gly Tyr Thr Cys Cys Arg
    370                 375                 380

Leu Gln Ser Gly Ala Trp Gly Cys Cys Pro Phe Thr Gln Ala Val Cys
385                 390                 395                 400

Cys Glu Asp His Ile His Cys Cys Pro Ala Gly Phe Thr Cys Asp Thr
                405                 410                 415

Gln Lys Gly Thr Cys Glu Gln Gly Pro His Gln Val Pro Trp Met Glu
            420                 425                 430

Lys Ala Pro Ala His Leu Ser Leu Pro Asp Pro Gln Ala Leu Lys Arg
        435                 440                 445

Asp Val Pro Cys Asp Asn Val Ser Ser Cys Pro Ser Ser Asp Thr Cys
    450                 455                 460

Cys Gln Leu Thr Ser Gly Glu Trp Gly Cys Cys Pro Ile Pro Glu Ala
465                 470                 475                 480

Val Cys Cys Ser Asp His Gln His Cys Cys Pro Gln Gly Tyr Thr Cys
                485                 490                 495

Val Ala Glu Gly Gln Cys Gln Arg Gly Ser Glu Ile Val Ala Gly Leu
            500                 505                 510

Glu Lys Met Pro Ala Arg Arg Ala Ser Leu Ser His Pro Arg Asp Ile
        515                 520                 525

Gly Cys Asp Gln His Thr Ser Cys Pro Val Gly Gln Thr Cys Cys Pro
    530                 535                 540

Ser Leu Gly Gly Ser Trp Ala Cys Cys Gln Leu Pro His Ala Val Cys
545                 550                 555                 560

Cys Glu Asp Arg Gln His Cys Cys Pro Ala Gly Tyr Thr Cys Asn Val
                565                 570                 575

Lys Ala Arg Ser Cys Glu Lys Glu Val Val Ser Ala Gln Pro Ala Thr
            580                 585                 590

Phe Leu Ala Arg Ser Pro His Val Gly Val Lys Asp Val Glu Cys Gly
        595                 600                 605

Glu Gly His Phe Cys His Asp Asn Gln Thr Cys Cys Arg Asp Asn Arg
    610                 615                 620

Gln Gly Trp Ala Cys Cys Pro Tyr Arg Gln Gly Val Cys Cys Ala Asp
625                 630                 635                 640

Arg Arg His Cys Cys Pro Ala Gly Phe Arg Cys Ala Ala Arg Gly Thr
                645                 650                 655

Lys Cys Leu Arg Arg Glu Ala Pro Arg Trp Asp Ala Pro Leu Arg Asp
            660                 665                 670

Pro Ala Leu Arg Gln Leu Leu
        675
```

<210> SEQ ID NO 247
<211> LENGTH: 262
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 247

```
Met Pro Gln Ala Ser Cys Cys Glu Asp Arg Val His Cys Cys Pro His
1               5                   10                  15
```

```
Gly Ala Phe Cys Asp Leu Val His Thr Arg Cys Ile Thr Pro Thr Gly
            20                  25                  30

Thr His Pro Leu Ala Lys Lys Leu Pro Ala Gln Arg Thr Asn Arg Ala
        35                  40                  45

Val Ala Leu Ser Ser Ser Ser Lys Glu Asp Ala Thr Thr Asp Leu Leu
    50                  55                  60

Thr Lys Leu Pro Ala His Thr Val Gly Asp Val Lys Cys Asp Met Glu
65                  70                  75                  80

Val Ser Cys Pro Asp Gly Tyr Thr Cys Cys Arg Leu Gln Ser Gly Ala
                85                  90                  95

Trp Cys Glu Gln Gly Pro His Gln Val Pro Trp Met Glu Lys Ala Pro
            100                 105                 110

Ala His Leu Ser Leu Pro Asp Pro Gln Ala Leu Lys Arg Asp Val Pro
        115                 120                 125

Cys Asp Asn Val Ser Ser Cys Pro Ser Ser Asp Thr Cys Cys Gln Leu
    130                 135                 140

Thr Ser Gly Glu Trp Gly Cys Cys Pro Ile Pro Gly Gly Gly Gly Ser
145                 150                 155                 160

Gly Gly Gly Gly Ser Gly Gly Gly Gly Ser Gly Val Ser Asp Val Pro
                165                 170                 175

Arg Asp Leu Glu Val Val Ala Ala Thr Pro Thr Ser Leu Leu Ile Ser
            180                 185                 190

Trp His Ser Tyr Tyr Glu Gln Asn Ser Tyr Tyr Arg Ile Thr Tyr Gly
        195                 200                 205

Glu Thr Gly Gly Asn Ser Pro Val Gln Glu Phe Thr Val Pro Tyr Ser
    210                 215                 220

Gln Thr Thr Ala Thr Ile Ser Gly Leu Lys Pro Gly Val Asp Tyr Thr
225                 230                 235                 240

Ile Thr Val Tyr Ala Val Tyr Gly Ser Lys Tyr Tyr Tyr Pro Ile Ser
                245                 250                 255

Ile Asn Tyr Arg Thr Glu
            260
```

<210> SEQ ID NO 248
<211> LENGTH: 257
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 248

```
Met Pro Gln Ala Ser Cys Cys Glu Asp Arg Val His Cys Cys Pro His
1               5                   10                  15

Gly Ala Phe Cys Asp Leu Val His Thr Arg Cys Ile Thr Pro Thr Gly
            20                  25                  30

Thr His Pro Leu Ala Lys Lys Leu Pro Ala Gln Arg Thr Asn Arg Ala
        35                  40                  45

Val Ala Leu Ser Ser Ser Ser Lys Glu Asp Ala Thr Thr Asp Leu Leu
    50                  55                  60

Thr Lys Leu Pro Ala His Thr Val Gly Asp Val Lys Cys Asp Met Glu
65                  70                  75                  80

Val Ser Cys Pro Asp Gly Tyr Thr Cys Cys Arg Leu Gln Ser Gly Ala
                85                  90                  95

Trp Cys Glu Gln Gly Pro His Gln Val Pro Trp Met Glu Lys Ala Pro
            100                 105                 110
```

```
Ala His Leu Ser Leu Pro Asp Pro Gln Ala Leu Lys Arg Asp Val Pro
        115                 120                 125

Cys Asp Asn Val Ser Ser Cys Pro Ser Ser Asp Thr Cys Cys Gln Leu
    130                 135                 140

Thr Ser Gly Glu Trp Gly Cys Cys Pro Ile Pro Glu Asp Glu Asp Glu
145                 150                 155                 160

Asp Glu Asp Glu Asp Gly Val Ser Asp Val Pro Arg Asp Leu Glu Val
                165                 170                 175

Val Ala Ala Thr Pro Thr Ser Leu Leu Ile Ser Trp His Ser Tyr Tyr
            180                 185                 190

Glu Gln Asn Ser Tyr Tyr Arg Ile Thr Tyr Gly Glu Thr Gly Gly Asn
        195                 200                 205

Ser Pro Val Gln Glu Phe Thr Val Pro Tyr Ser Gln Thr Thr Ala Thr
    210                 215                 220

Ile Ser Gly Leu Lys Pro Gly Val Asp Tyr Thr Ile Thr Val Tyr Ala
225                 230                 235                 240

Val Tyr Gly Ser Lys Tyr Tyr Tyr Pro Ile Ser Ile Asn Tyr Arg Thr
                245                 250                 255

Glu


<210> SEQ ID NO 249
<211> LENGTH: 262
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Pro Gln Ala Ser
            100                 105                 110

Cys Cys Glu Asp Arg Val His Cys Cys Pro His Gly Ala Phe Cys Asp
        115                 120                 125

Leu Val His Thr Arg Cys Ile Thr Pro Thr Gly Thr His Pro Leu Ala
    130                 135                 140

Lys Lys Leu Pro Ala Gln Arg Thr Asn Arg Ala Val Ala Leu Ser Ser
145                 150                 155                 160

Ser Ser Lys Glu Asp Ala Thr Thr Asp Leu Leu Thr Lys Leu Pro Ala
                165                 170                 175

His Thr Val Gly Asp Val Lys Cys Asp Met Glu Val Ser Cys Pro Asp
            180                 185                 190

Gly Tyr Thr Cys Cys Arg Leu Gln Ser Gly Ala Trp Cys Glu Gln Gly
        195                 200                 205
```

```
Pro His Gln Val Pro Trp Met Glu Lys Ala Pro Ala His Leu Ser Leu
    210                 215                 220

Pro Asp Pro Gln Ala Leu Lys Arg Asp Val Pro Cys Asp Asn Val Ser
225                 230                 235                 240

Ser Cys Pro Ser Ser Asp Thr Cys Cys Gln Leu Thr Ser Gly Glu Trp
                245                 250                 255

Gly Cys Cys Pro Ile Pro
            260


<210> SEQ ID NO 250
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Pro Gln Ala Ser Cys Cys Glu Asp Arg
            100                 105                 110

Val His Cys Cys Pro His Gly Ala Phe Cys Asp Leu Val His Thr Arg
        115                 120                 125

Cys Ile Thr Pro Thr Gly Thr His Pro Leu Ala Lys Lys Leu Pro Ala
    130                 135                 140

Gln Arg Thr Asn Arg Ala Val Ala Leu Ser Ser Ser Ser Lys Glu Asp
145                 150                 155                 160

Ala Thr Thr Asp Leu Leu Thr Lys Leu Pro Ala His Thr Val Gly Asp
                165                 170                 175

Val Lys Cys Asp Met Glu Val Ser Cys Pro Asp Gly Tyr Thr Cys Cys
            180                 185                 190

Arg Leu Gln Ser Gly Ala Trp Cys Glu Gln Gly Pro His Gln Val Pro
        195                 200                 205

Trp Met Glu Lys Ala Pro Ala His Leu Ser Leu Pro Asp Pro Gln Ala
    210                 215                 220

Leu Lys Arg Asp Val Pro Cys Asp Asn Val Ser Ser Cys Pro Ser Ser
225                 230                 235                 240

Asp Thr Cys Cys Gln Leu Thr Ser Gly Glu Trp Gly Cys Cys Pro Ile
                245                 250                 255

Pro


<210> SEQ ID NO 251
<211> LENGTH: 181
<212> TYPE: PRT
<213> ORGANISM: Homo sapiens
```

<400> SEQUENCE: 251

```
Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Gly Asn Leu Cys Leu Arg Thr Ser Thr
                165                 170                 175

His Pro Glu Ser Thr
            180
```

<210> SEQ ID NO 252
<211> LENGTH: 181
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 252

```
Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160
```

```
Asp Leu Lys Tyr Val Ala Asp Gly Asn Leu Ser Leu Arg Thr Ser Thr
                165                 170                 175

His Pro Glu Ser Thr
            180


<210> SEQ ID NO 253
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Lys Pro Thr Thr Thr Gly Lys Gly Cys His Ile Gly Arg Phe Lys Ser
1               5                   10                  15

Leu Ser Pro Gln Glu Leu Ala Ser Phe Lys Lys Ala Arg Asp Ala Leu
            20                  25                  30

Glu Glu Ser Leu Lys Leu Lys Asn Trp Ser Cys Ser Ser Pro Val Phe
        35                  40                  45

Pro Gly Asn Trp Asp Leu Arg Leu Leu Gln Val Arg Glu Arg Pro Val
    50                  55                  60

Ala Leu Glu Ala Glu Leu Ala Leu Thr Leu Lys Val Leu Glu Ala Ala
65                  70                  75                  80

Ala Gly Pro Ala Leu Glu Asp Val Leu Asp Gln Pro Leu His Thr Leu
                85                  90                  95

His His Ile Leu Ser Gln Leu Gln Ala Cys Ile Gln Pro Gln Pro Thr
            100                 105                 110

Ala Gly Pro Arg Pro Arg Gly Arg Leu His His Trp Leu His Arg Leu
        115                 120                 125

Gln Glu Ala Pro Lys Lys Glu Ser Ala Gly Cys Leu Glu Ala Ser Val
    130                 135                 140

Thr Phe Asn Leu Phe Arg Leu Leu Thr Arg Asp Leu Lys Tyr Val Ala
145                 150                 155                 160

Asp Gly Asn Leu Ser Leu Arg Thr Ser Thr His Pro Glu Ser Thr
                165                 170                 175


<210> SEQ ID NO 254
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Lys Pro Thr Thr Thr Gly Lys Gly Cys His Ile Gly Arg Phe Lys Ser
1               5                   10                  15

Leu Ser Pro Gln Glu Leu Ala Ser Phe Lys Lys Ala Arg Asp Ala Leu
            20                  25                  30

Glu Glu Ser Leu Lys Leu Lys Asn Trp Ser Cys Ser Ser Pro Val Phe
        35                  40                  45

Pro Gly Asn Trp Asp Leu Arg Leu Leu Gln Val Arg Glu Arg Pro Val
    50                  55                  60

Ala Leu Glu Ala Glu Leu Ala Leu Thr Leu Lys Val Leu Glu Ala Ala
65                  70                  75                  80

Ala Gly Pro Ala Leu Glu Asp Val Leu Asp Gln Pro Leu His Thr Leu
                85                  90                  95
```

```
His His Ile Leu Ser Gln Leu Gln Ala Cys Ile Gln Pro Gln Pro Thr
            100                 105                 110

Ala Gly Pro Arg Pro Arg Gly Arg Leu His His Trp Leu His Arg Leu
        115                 120                 125

Gln Glu Ala Pro Lys Lys Glu Ser Ala Gly Cys Leu Glu Ala Ser Val
    130                 135                 140

Thr Phe Asn Leu Phe Arg Leu Leu Thr Arg Asp Leu Lys Tyr Val Ala
145                 150                 155                 160

Glu Gly Asn Leu Ser Leu Arg Thr Ser Thr His Pro Glu Ser Thr
                165                 170                 175


<210> SEQ ID NO 255
<211> LENGTH: 175
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Lys Pro Thr Thr Thr Gly Lys Gly Cys His Ile Gly Arg Phe Lys Ser
1               5                   10                  15

Leu Ser Pro Gln Glu Leu Ala Ser Phe Lys Lys Ala Arg Asp Ala Leu
            20                  25                  30

Glu Glu Ser Leu Lys Leu Lys Asn Trp Ser Cys Ser Ser Pro Val Phe
        35                  40                  45

Pro Gly Asn Trp Asp Leu Arg Leu Leu Gln Val Arg Glu Arg Pro Val
    50                  55                  60

Ala Leu Glu Ala Glu Leu Ala Leu Thr Leu Lys Val Leu Glu Ala Ala
65                  70                  75                  80

Ala Gly Pro Ala Leu Glu Asp Val Leu Asp Gln Pro Leu His Thr Leu
                85                  90                  95

His His Ile Leu Ser Gln Leu Gln Ala Cys Ile Gln Pro Gln Pro Thr
            100                 105                 110

Ala Gly Pro Arg Pro Arg Gly Arg Leu His His Trp Leu His Arg Leu
        115                 120                 125

Gln Glu Ala Pro Lys Lys Glu Ser Ala Gly Cys Leu Glu Ala Ser Val
    130                 135                 140

Thr Phe Asn Leu Phe Arg Leu Leu Thr Arg Asp Leu Lys Tyr Val Ala
145                 150                 155                 160

Asp Ala Asn Leu Ser Leu Arg Thr Ser Thr His Pro Glu Ser Thr
                165                 170                 175


<210> SEQ ID NO 256
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45
```

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Glu Gly Asn Leu Ser Leu Arg Thr Ser Thr
                165                 170                 175

His Pro Glu Ser Thr
            180

<210> SEQ ID NO 257
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gly Pro Val Pro Thr Ser Lys Pro Thr Thr Thr Gly Lys Gly Cys His
1               5                   10                  15

Ile Gly Arg Phe Lys Ser Leu Ser Pro Gln Glu Leu Ala Ser Phe Lys
            20                  25                  30

Lys Ala Arg Asp Ala Leu Glu Glu Ser Leu Lys Leu Lys Asn Trp Ser
        35                  40                  45

Cys Ser Ser Pro Val Phe Pro Gly Asn Trp Asp Leu Arg Leu Leu Gln
    50                  55                  60

Val Arg Glu Arg Pro Val Ala Leu Glu Ala Glu Leu Ala Leu Thr Leu
65                  70                  75                  80

Lys Val Leu Glu Ala Ala Ala Gly Pro Ala Leu Glu Asp Val Leu Asp
                85                  90                  95

Gln Pro Leu His Thr Leu His His Ile Leu Ser Gln Leu Gln Ala Cys
            100                 105                 110

Ile Gln Pro Gln Pro Thr Ala Gly Pro Arg Pro Arg Gly Arg Leu His
        115                 120                 125

His Trp Leu His Arg Leu Gln Glu Ala Pro Lys Lys Glu Ser Ala Gly
    130                 135                 140

Cys Leu Glu Ala Ser Val Thr Phe Asn Leu Phe Arg Leu Leu Thr Arg
145                 150                 155                 160

Asp Leu Lys Tyr Val Ala Asp Ala Asn Leu Ser Leu Arg Thr Ser Thr
                165                 170                 175

His Pro Glu Ser Thr
            180

<210> SEQ ID NO 258
<211> LENGTH: 289
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 258

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr Gly Gly Gly Gly Ser Gly Gly Gly Gly Ser
            180                 185                 190

Gly Gly Gly Gly Ser Gly Val Ser Asp Val Pro Arg Asp Leu Glu Val
        195                 200                 205

Val Ala Ala Thr Pro Thr Ser Leu Leu Ile Ser Trp His Ser Tyr Tyr
    210                 215                 220

Glu Gln Asn Ser Tyr Tyr Arg Ile Thr Tyr Gly Glu Thr Gly Gly Asn
225                 230                 235                 240

Ser Pro Val Gln Glu Phe Thr Val Pro Tyr Ser Gln Thr Thr Ala Thr
                245                 250                 255

Ile Ser Gly Leu Lys Pro Gly Val Asp Tyr Thr Ile Thr Val Tyr Ala
            260                 265                 270

Val Tyr Gly Ser Lys Tyr Tyr Tyr Pro Ile Ser Ile Asn Tyr Arg Thr
        275                 280                 285

Glu


<210> SEQ ID NO 259
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30
```

```
Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Ser Leu Arg Thr Ser
                165                 170                 175

Thr His Pro Glu Ser Thr Gly Gly Gly Gly Ser Gly Gly Gly Gly Ser
            180                 185                 190

Gly Gly Gly Gly Ser Gly Val Ser Asp Val Pro Arg Asp Leu Glu Val
        195                 200                 205

Val Ala Ala Thr Pro Thr Ser Leu Leu Ile Ser Trp His Ser Tyr Tyr
    210                 215                 220

Glu Gln Asn Ser Tyr Tyr Arg Ile Thr Tyr Gly Glu Thr Gly Gly Asn
225                 230                 235                 240

Ser Pro Val Gln Glu Phe Thr Val Pro Tyr Ser Gln Thr Thr Ala Thr
                245                 250                 255

Ile Ser Gly Leu Lys Pro Gly Val Asp Tyr Thr Ile Thr Val Tyr Ala
            260                 265                 270

Val Tyr Gly Ser Lys Tyr Tyr Tyr Pro Ile Ser Ile Asn Tyr Arg Thr
        275                 280                 285

Glu
```

<210> SEQ ID NO 260
<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 260

```
Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95
```

Leu His His Ile Leu Ser Gln Leu Gln Ala Cys Ile Gln Pro Gln Pro
100 105 110

Thr Ala Gly Pro Arg Pro Arg Gly Arg Leu His His Trp Leu His Arg
115 120 125

Leu Gln Glu Ala Pro Lys Lys Glu Ser Ala Gly Cys Leu Glu Ala Ser
130 135 140

Val Thr Phe Asn Leu Phe Arg Leu Leu Thr Arg Asp Leu Lys Tyr Val
145 150 155 160

Ala Asp Gly Asn Leu Ser Leu Arg Thr Ser Thr His Pro Glu Ser Thr
165 170 175

Gly Gly Gly Gly Ser Gly Gly Gly Gly Ser Gly Gly Gly Gly Ser Gly
180 185 190

Val Ser Asp Val Pro Arg Asp Leu Glu Val Val Ala Ala Thr Pro Thr
195 200 205

Ser Leu Leu Ile Ser Trp His Ser Tyr Tyr Glu Gln Asn Ser Tyr Tyr
210 215 220

Arg Ile Thr Tyr Gly Glu Thr Gly Gly Asn Ser Pro Val Gln Glu Phe
225 230 235 240

Thr Val Pro Tyr Ser Gln Thr Thr Ala Thr Ile Ser Gly Leu Lys Pro
245 250 255

Gly Val Asp Tyr Thr Ile Thr Val Tyr Ala Val Tyr Gly Ser Lys Tyr
260 265 270

Tyr Tyr Pro Ile Ser Ile Asn Tyr Arg Thr Glu
275 280

<210> SEQ ID NO 261
<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 261

Met Lys Pro Thr Thr Thr Gly Lys Gly Cys His Ile Gly Arg Phe Lys
1 5 10 15

Ser Leu Ser Pro Gln Glu Leu Ala Ser Phe Lys Lys Ala Arg Asp Ala
20 25 30

Leu Glu Glu Ser Leu Lys Leu Lys Asn Trp Ser Cys Ser Ser Pro Val
35 40 45

Phe Pro Gly Asn Trp Asp Leu Arg Leu Leu Gln Val Arg Glu Arg Pro
50 55 60

Val Ala Leu Glu Ala Glu Leu Ala Leu Thr Leu Lys Val Leu Glu Ala
65 70 75 80

Ala Ala Gly Pro Ala Leu Glu Asp Val Leu Asp Gln Pro Leu His Thr
85 90 95

Leu His His Ile Leu Ser Gln Leu Gln Ala Cys Ile Gln Pro Gln Pro
100 105 110

Thr Ala Gly Pro Arg Pro Arg Gly Arg Leu His His Trp Leu His Arg
115 120 125

Leu Gln Glu Ala Pro Lys Lys Glu Ser Ala Gly Cys Leu Glu Ala Ser
130 135 140

Val Thr Phe Asn Leu Phe Arg Leu Leu Thr Arg Asp Leu Lys Tyr Val
145 150 155 160

Ala Glu Gly Asn Leu Ser Leu Arg Thr Ser Thr His Pro Glu Ser Thr

```
                165                 170                 175

Gly Gly Gly Gly Ser Gly Gly Gly Gly Ser Gly Gly Gly Gly Ser Gly
            180                 185                 190

Val Ser Asp Val Pro Arg Asp Leu Glu Val Val Ala Ala Thr Pro Thr
        195                 200                 205

Ser Leu Leu Ile Ser Trp His Ser Tyr Tyr Glu Gln Asn Ser Tyr Tyr
    210                 215                 220

Arg Ile Thr Tyr Gly Glu Thr Gly Gly Asn Ser Pro Val Gln Glu Phe
225                 230                 235                 240

Thr Val Pro Tyr Ser Gln Thr Thr Ala Thr Ile Ser Gly Leu Lys Pro
                245                 250                 255

Gly Val Asp Tyr Thr Ile Thr Val Tyr Ala Val Tyr Gly Ser Lys Tyr
            260                 265                 270

Tyr Tyr Pro Ile Ser Ile Asn Tyr Arg Thr Glu
        275                 280


<210> SEQ ID NO 262
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Ala Asn Leu Ser Leu Arg Thr Ser Thr His Pro Glu Ser Thr
                165                 170                 175

Gly Gly Gly Gly Ser Gly Gly Gly Gly Ser Gly Gly Gly Gly Ser Gly
            180                 185                 190

Val Ser Asp Val Pro Arg Asp Leu Glu Val Val Ala Ala Thr Pro Thr
        195                 200                 205

Ser Leu Leu Ile Ser Trp His Ser Tyr Tyr Glu Gln Asn Ser Tyr Tyr
    210                 215                 220

Arg Ile Thr Tyr Gly Glu Thr Gly Gly Asn Ser Pro Val Gln Glu Phe
225                 230                 235                 240
```

```
Thr Val Pro Tyr Ser Gln Thr Thr Ala Thr Ile Ser Gly Leu Lys Pro
                245                 250                 255

Gly Val Asp Tyr Thr Ile Thr Val Tyr Ala Val Tyr Gly Ser Lys Tyr
            260                 265                 270

Tyr Tyr Pro Ile Ser Ile Asn Tyr Arg Thr Glu
        275                 280


<210> SEQ ID NO 263
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Glu Gly Asn Leu Ser Leu Arg Thr Ser
                165                 170                 175

Thr His Pro Glu Ser Thr Gly Gly Gly Gly Ser Gly Gly Gly Gly Ser
            180                 185                 190

Gly Gly Gly Gly Ser Gly Val Ser Asp Val Pro Arg Asp Leu Glu Val
        195                 200                 205

Val Ala Ala Thr Pro Thr Ser Leu Leu Ile Ser Trp His Ser Tyr Tyr
    210                 215                 220

Glu Gln Asn Ser Tyr Tyr Arg Ile Thr Tyr Gly Glu Thr Gly Gly Asn
225                 230                 235                 240

Ser Pro Val Gln Glu Phe Thr Val Pro Tyr Ser Gln Thr Thr Ala Thr
                245                 250                 255

Ile Ser Gly Leu Lys Pro Gly Val Asp Tyr Thr Ile Thr Val Tyr Ala
            260                 265                 270

Val Tyr Gly Ser Lys Tyr Tyr Tyr Pro Ile Ser Ile Asn Tyr Arg Thr
        275                 280                 285

Glu


<210> SEQ ID NO 264
<211> LENGTH: 289
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Ala Asn Leu Ser Leu Arg Thr Ser
                165                 170                 175

Thr His Pro Glu Ser Thr Gly Gly Gly Gly Ser Gly Gly Gly Gly Ser
            180                 185                 190

Gly Gly Gly Gly Ser Gly Val Ser Asp Val Pro Arg Asp Leu Glu Val
        195                 200                 205

Val Ala Ala Thr Pro Thr Ser Leu Leu Ile Ser Trp His Ser Tyr Tyr
    210                 215                 220

Glu Gln Asn Ser Tyr Tyr Arg Ile Thr Tyr Gly Glu Thr Gly Gly Asn
225                 230                 235                 240

Ser Pro Val Gln Glu Phe Thr Val Pro Tyr Ser Gln Thr Thr Ala Thr
                245                 250                 255

Ile Ser Gly Leu Lys Pro Gly Val Asp Tyr Thr Ile Thr Val Tyr Ala
            260                 265                 270

Val Tyr Gly Ser Lys Tyr Tyr Tyr Pro Ile Ser Ile Asn Tyr Arg Thr
        275                 280                 285

Glu


<210> SEQ ID NO 265
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
```

```
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Cys Leu Arg Thr Ser
                165                 170                 175

Thr His Pro Glu Ser Thr Glu Asp Glu Asp Glu Asp Glu Asp Glu Asp
            180                 185                 190

Gly Val Ser Asp Val Pro Arg Asp Leu Glu Val Val Ala Ala Thr Pro
        195                 200                 205

Thr Ser Leu Leu Ile Ser Trp His Ser Tyr Tyr Glu Gln Asn Ser Tyr
    210                 215                 220

Tyr Arg Ile Thr Tyr Gly Glu Thr Gly Gly Asn Ser Pro Val Gln Glu
225                 230                 235                 240

Phe Thr Val Pro Tyr Ser Gln Thr Thr Ala Thr Ile Ser Gly Leu Lys
                245                 250                 255

Pro Gly Val Asp Tyr Thr Ile Thr Val Tyr Ala Val Tyr Gly Ser Lys
            260                 265                 270

Tyr Tyr Tyr Pro Ile Ser Ile Asn Tyr Arg Thr Glu
        275                 280


<210> SEQ ID NO 266
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95
```

```
Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Gly Asn Leu Ser Leu Arg Thr Ser
                165                 170                 175

Thr His Pro Glu Ser Thr Glu Asp Glu Asp Glu Asp Glu Asp Glu Asp
            180                 185                 190

Gly Val Ser Asp Val Pro Arg Asp Leu Glu Val Val Ala Ala Thr Pro
        195                 200                 205

Thr Ser Leu Leu Ile Ser Trp His Ser Tyr Tyr Glu Gln Asn Ser Tyr
    210                 215                 220

Tyr Arg Ile Thr Tyr Gly Glu Thr Gly Gly Asn Ser Pro Val Gln Glu
225                 230                 235                 240

Phe Thr Val Pro Tyr Ser Gln Thr Thr Ala Thr Ile Ser Gly Leu Lys
                245                 250                 255

Pro Gly Val Asp Tyr Thr Ile Thr Val Tyr Ala Val Tyr Gly Ser Lys
            260                 265                 270

Tyr Tyr Tyr Pro Ile Ser Ile Asn Tyr Arg Thr Glu
        275                 280
```

<210> SEQ ID NO 267
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 267

```
Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Gly Asn Leu Ser Leu Arg Thr Ser Thr His Pro Glu Ser Thr
                165                 170                 175
```

```
Glu Asp Glu Asp Glu Asp Glu Asp Glu Asp Gly Val Ser Asp Val Pro
            180                 185                 190

Arg Asp Leu Glu Val Val Ala Ala Thr Pro Thr Ser Leu Leu Ile Ser
        195                 200                 205

Trp His Ser Tyr Tyr Glu Gln Asn Ser Tyr Tyr Arg Ile Thr Tyr Gly
    210                 215                 220

Glu Thr Gly Gly Asn Ser Pro Val Gln Glu Phe Thr Val Pro Tyr Ser
225                 230                 235                 240

Gln Thr Thr Ala Thr Ile Ser Gly Leu Lys Pro Gly Val Asp Tyr Thr
                245                 250                 255

Ile Thr Val Tyr Ala Val Tyr Gly Ser Lys Tyr Tyr Tyr Pro Ile Ser
            260                 265                 270

Ile Asn Tyr Arg Thr Glu
        275


<210> SEQ ID NO 268
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Glu Gly Asn Leu Ser Leu Arg Thr Ser Thr His Pro Glu Ser Thr
                165                 170                 175

Glu Asp Glu Asp Glu Asp Glu Asp Glu Asp Gly Val Ser Asp Val Pro
            180                 185                 190

Arg Asp Leu Glu Val Val Ala Ala Thr Pro Thr Ser Leu Leu Ile Ser
        195                 200                 205

Trp His Ser Tyr Tyr Glu Gln Asn Ser Tyr Tyr Arg Ile Thr Tyr Gly
    210                 215                 220

Glu Thr Gly Gly Asn Ser Pro Val Gln Glu Phe Thr Val Pro Tyr Ser
225                 230                 235                 240

Gln Thr Thr Ala Thr Ile Ser Gly Leu Lys Pro Gly Val Asp Tyr Thr
```

```
                245                 250                 255

Ile Thr Val Tyr Ala Val Tyr Gly Ser Lys Tyr Tyr Tyr Pro Ile Ser
            260                 265                 270

Ile Asn Tyr Arg Thr Glu
        275


<210> SEQ ID NO 269
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Met Lys Pro Thr Thr Thr Gly Lys Gly Cys His Ile Gly Arg Phe Lys
1               5                   10                  15

Ser Leu Ser Pro Gln Glu Leu Ala Ser Phe Lys Lys Ala Arg Asp Ala
            20                  25                  30

Leu Glu Glu Ser Leu Lys Leu Lys Asn Trp Ser Cys Ser Ser Pro Val
        35                  40                  45

Phe Pro Gly Asn Trp Asp Leu Arg Leu Leu Gln Val Arg Glu Arg Pro
    50                  55                  60

Val Ala Leu Glu Ala Glu Leu Ala Leu Thr Leu Lys Val Leu Glu Ala
65                  70                  75                  80

Ala Ala Gly Pro Ala Leu Glu Asp Val Leu Asp Gln Pro Leu His Thr
                85                  90                  95

Leu His His Ile Leu Ser Gln Leu Gln Ala Cys Ile Gln Pro Gln Pro
            100                 105                 110

Thr Ala Gly Pro Arg Pro Arg Gly Arg Leu His His Trp Leu His Arg
        115                 120                 125

Leu Gln Glu Ala Pro Lys Lys Glu Ser Ala Gly Cys Leu Glu Ala Ser
    130                 135                 140

Val Thr Phe Asn Leu Phe Arg Leu Leu Thr Arg Asp Leu Lys Tyr Val
145                 150                 155                 160

Ala Asp Ala Asn Leu Ser Leu Arg Thr Ser Thr His Pro Glu Ser Thr
                165                 170                 175

Glu Asp Glu Asp Glu Asp Glu Asp Glu Asp Gly Val Ser Asp Val Pro
            180                 185                 190

Arg Asp Leu Glu Val Val Ala Ala Thr Pro Thr Ser Leu Leu Ile Ser
        195                 200                 205

Trp His Ser Tyr Tyr Glu Gln Asn Ser Tyr Tyr Arg Ile Thr Tyr Gly
    210                 215                 220

Glu Thr Gly Gly Asn Ser Pro Val Gln Glu Phe Thr Val Pro Tyr Ser
225                 230                 235                 240

Gln Thr Thr Ala Thr Ile Ser Gly Leu Lys Pro Gly Val Asp Tyr Thr
                245                 250                 255

Ile Thr Val Tyr Ala Val Tyr Gly Ser Lys Tyr Tyr Tyr Pro Ile Ser
            260                 265                 270

Ile Asn Tyr Arg Thr Glu
        275


<210> SEQ ID NO 270
<211> LENGTH: 284
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 270

```
Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Glu Gly Asn Leu Ser Leu Arg Thr Ser
                165                 170                 175

Thr His Pro Glu Ser Thr Glu Asp Glu Asp Glu Asp Glu Asp Glu Asp
            180                 185                 190

Gly Val Ser Asp Val Pro Arg Asp Leu Glu Val Val Ala Ala Thr Pro
        195                 200                 205

Thr Ser Leu Leu Ile Ser Trp His Ser Tyr Tyr Glu Gln Asn Ser Tyr
    210                 215                 220

Tyr Arg Ile Thr Tyr Gly Glu Thr Gly Gly Asn Ser Pro Val Gln Glu
225                 230                 235                 240

Phe Thr Val Pro Tyr Ser Gln Thr Thr Ala Thr Ile Ser Gly Leu Lys
                245                 250                 255

Pro Gly Val Asp Tyr Thr Ile Thr Val Tyr Ala Val Tyr Gly Ser Lys
            260                 265                 270

Tyr Tyr Tyr Pro Ile Ser Ile Asn Tyr Arg Thr Glu
        275                 280
```

<210> SEQ ID NO 271
<211> LENGTH: 284
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 271

```
Met Gly Pro Val Pro Thr Ser Lys Pro Thr Thr Thr Gly Lys Gly Cys
1               5                   10                  15

His Ile Gly Arg Phe Lys Ser Leu Ser Pro Gln Glu Leu Ala Ser Phe
            20                  25                  30

Lys Lys Ala Arg Asp Ala Leu Glu Glu Ser Leu Lys Leu Lys Asn Trp
        35                  40                  45
```

Ser Cys Ser Ser Pro Val Phe Pro Gly Asn Trp Asp Leu Arg Leu Leu
    50                  55                  60

Gln Val Arg Glu Arg Pro Val Ala Leu Glu Ala Glu Leu Ala Leu Thr
65                  70                  75                  80

Leu Lys Val Leu Glu Ala Ala Ala Gly Pro Ala Leu Glu Asp Val Leu
                85                  90                  95

Asp Gln Pro Leu His Thr Leu His His Ile Leu Ser Gln Leu Gln Ala
            100                 105                 110

Cys Ile Gln Pro Gln Pro Thr Ala Gly Pro Arg Pro Arg Gly Arg Leu
        115                 120                 125

His His Trp Leu His Arg Leu Gln Glu Ala Pro Lys Lys Glu Ser Ala
    130                 135                 140

Gly Cys Leu Glu Ala Ser Val Thr Phe Asn Leu Phe Arg Leu Leu Thr
145                 150                 155                 160

Arg Asp Leu Lys Tyr Val Ala Asp Ala Asn Leu Ser Leu Arg Thr Ser
                165                 170                 175

Thr His Pro Glu Ser Thr Glu Asp Glu Asp Glu Asp Glu Asp Glu Asp
            180                 185                 190

Gly Val Ser Asp Val Pro Arg Asp Leu Glu Val Val Ala Ala Thr Pro
        195                 200                 205

Thr Ser Leu Leu Ile Ser Trp His Ser Tyr Tyr Glu Gln Asn Ser Tyr
    210                 215                 220

Tyr Arg Ile Thr Tyr Gly Glu Thr Gly Gly Asn Ser Pro Val Gln Glu
225                 230                 235                 240

Phe Thr Val Pro Tyr Ser Gln Thr Thr Ala Thr Ile Ser Gly Leu Lys
                245                 250                 255

Pro Gly Val Asp Tyr Thr Ile Thr Val Tyr Ala Val Tyr Gly Ser Lys
            260                 265                 270

Tyr Tyr Tyr Pro Ile Ser Ile Asn Tyr Arg Thr Glu
        275                 280

<210> SEQ ID NO 272
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Gly Pro Val Pro
            100                 105                 110

Thr Ser Lys Pro Thr Thr Thr Gly Lys Gly Cys His Ile Gly Arg Phe
        115                 120                 125

Lys Ser Leu Ser Pro Gln Glu Leu Ala Ser Phe Lys Lys Ala Arg Asp
130 135 140

Ala Leu Glu Glu Ser Leu Lys Leu Lys Asn Trp Ser Cys Ser Ser Pro
145 150 155 160

Val Phe Pro Gly Asn Trp Asp Leu Arg Leu Leu Gln Val Arg Glu Arg
165 170 175

Pro Val Ala Leu Glu Ala Glu Leu Ala Leu Thr Leu Lys Val Leu Glu
180 185 190

Ala Ala Ala Gly Pro Ala Leu Glu Asp Val Leu Asp Gln Pro Leu His
195 200 205

Thr Leu His His Ile Leu Ser Gln Leu Gln Ala Cys Ile Gln Pro Gln
210 215 220

Pro Thr Ala Gly Pro Arg Pro Arg Gly Arg Leu His His Trp Leu His
225 230 235 240

Arg Leu Gln Glu Ala Pro Lys Lys Glu Ser Ala Gly Cys Leu Glu Ala
245 250 255

Ser Val Thr Phe Asn Leu Phe Arg Leu Leu Thr Arg Asp Leu Lys Tyr
260 265 270

Val Ala Asp Gly Asn Leu Cys Leu Arg Thr Ser Thr His Pro Glu Ser
275 280 285

Thr

<210> SEQ ID NO 273
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 273

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Gly Gly Gly
85 90 95

Gly Ser Gly Gly Gly Gly Ser Gly Gly Gly Gly Ser Gly Pro Val Pro
100 105 110

Thr Ser Lys Pro Thr Thr Thr Gly Lys Gly Cys His Ile Gly Arg Phe
115 120 125

Lys Ser Leu Ser Pro Gln Glu Leu Ala Ser Phe Lys Lys Ala Arg Asp
130 135 140

Ala Leu Glu Glu Ser Leu Lys Leu Lys Asn Trp Ser Cys Ser Ser Pro
145 150 155 160

Val Phe Pro Gly Asn Trp Asp Leu Arg Leu Leu Gln Val Arg Glu Arg
165 170 175

Pro Val Ala Leu Glu Ala Glu Leu Ala Leu Thr Leu Lys Val Leu Glu
180 185 190

```
Ala Ala Ala Gly Pro Ala Leu Glu Asp Val Leu Asp Gln Pro Leu His
        195                 200                 205

Thr Leu His His Ile Leu Ser Gln Leu Gln Ala Cys Ile Gln Pro Gln
    210                 215                 220

Pro Thr Ala Gly Pro Arg Pro Arg Gly Arg Leu His His Trp Leu His
225                 230                 235                 240

Arg Leu Gln Glu Ala Pro Lys Lys Glu Ser Ala Gly Cys Leu Glu Ala
                245                 250                 255

Ser Val Thr Phe Asn Leu Phe Arg Leu Leu Thr Arg Asp Leu Lys Tyr
            260                 265                 270

Val Ala Asp Gly Asn Leu Ser Leu Arg Thr Ser Thr His Pro Glu Ser
        275                 280                 285

Thr


<210> SEQ ID NO 274
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Lys Pro Thr Thr
            100                 105                 110

Thr Gly Lys Gly Cys His Ile Gly Arg Phe Lys Ser Leu Ser Pro Gln
        115                 120                 125

Glu Leu Ala Ser Phe Lys Lys Ala Arg Asp Ala Leu Glu Glu Ser Leu
    130                 135                 140

Lys Leu Lys Asn Trp Ser Cys Ser Ser Pro Val Phe Pro Gly Asn Trp
145                 150                 155                 160

Asp Leu Arg Leu Leu Gln Val Arg Glu Arg Pro Val Ala Leu Glu Ala
                165                 170                 175

Glu Leu Ala Leu Thr Leu Lys Val Leu Glu Ala Ala Ala Gly Pro Ala
            180                 185                 190

Leu Glu Asp Val Leu Asp Gln Pro Leu His Thr Leu His His Ile Leu
        195                 200                 205

Ser Gln Leu Gln Ala Cys Ile Gln Pro Gln Pro Thr Ala Gly Pro Arg
    210                 215                 220

Pro Arg Gly Arg Leu His His Trp Leu His Arg Leu Gln Glu Ala Pro
225                 230                 235                 240

Lys Lys Glu Ser Ala Gly Cys Leu Glu Ala Ser Val Thr Phe Asn Leu
                245                 250                 255
```

Phe Arg Leu Leu Thr Arg Asp Leu Lys Tyr Val Ala Asp Gly Asn Leu
260 265 270

Ser Leu Arg Thr Ser Thr His Pro Glu Ser Thr
275 280

<210> SEQ ID NO 275
<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 275

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Gly Gly Gly
85 90 95

Gly Ser Gly Gly Gly Gly Ser Gly Gly Gly Gly Ser Lys Pro Thr Thr
100 105 110

Thr Gly Lys Gly Cys His Ile Gly Arg Phe Lys Ser Leu Ser Pro Gln
115 120 125

Glu Leu Ala Ser Phe Lys Lys Ala Arg Asp Ala Leu Glu Glu Ser Leu
130 135 140

Lys Leu Lys Asn Trp Ser Cys Ser Ser Pro Val Phe Pro Gly Asn Trp
145 150 155 160

Asp Leu Arg Leu Leu Gln Val Arg Glu Arg Pro Val Ala Leu Glu Ala
165 170 175

Glu Leu Ala Leu Thr Leu Lys Val Leu Glu Ala Ala Ala Gly Pro Ala
180 185 190

Leu Glu Asp Val Leu Asp Gln Pro Leu His Thr Leu His His Ile Leu
195 200 205

Ser Gln Leu Gln Ala Cys Ile Gln Pro Gln Pro Thr Ala Gly Pro Arg
210 215 220

Pro Arg Gly Arg Leu His His Trp Leu His Arg Leu Gln Glu Ala Pro
225 230 235 240

Lys Lys Glu Ser Ala Gly Cys Leu Glu Ala Ser Val Thr Phe Asn Leu
245 250 255

Phe Arg Leu Leu Thr Arg Asp Leu Lys Tyr Val Ala Glu Gly Asn Leu
260 265 270

Ser Leu Arg Thr Ser Thr His Pro Glu Ser Thr
275 280

<210> SEQ ID NO 276
<211> LENGTH: 283
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 276

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Gly Gly Gly
85 90 95

Gly Ser Gly Gly Gly Gly Ser Gly Gly Gly Gly Ser Lys Pro Thr Thr
100 105 110

Thr Gly Lys Gly Cys His Ile Gly Arg Phe Lys Ser Leu Ser Pro Gln
115 120 125

Glu Leu Ala Ser Phe Lys Lys Ala Arg Asp Ala Leu Glu Glu Ser Leu
130 135 140

Lys Leu Lys Asn Trp Ser Cys Ser Ser Pro Val Phe Pro Gly Asn Trp
145 150 155 160

Asp Leu Arg Leu Leu Gln Val Arg Glu Arg Pro Val Ala Leu Glu Ala
165 170 175

Glu Leu Ala Leu Thr Leu Lys Val Leu Glu Ala Ala Ala Gly Pro Ala
180 185 190

Leu Glu Asp Val Leu Asp Gln Pro Leu His Thr Leu His His Ile Leu
195 200 205

Ser Gln Leu Gln Ala Cys Ile Gln Pro Gln Pro Thr Ala Gly Pro Arg
210 215 220

Pro Arg Gly Arg Leu His His Trp Leu His Arg Leu Gln Glu Ala Pro
225 230 235 240

Lys Lys Glu Ser Ala Gly Cys Leu Glu Ala Ser Val Thr Phe Asn Leu
245 250 255

Phe Arg Leu Leu Thr Arg Asp Leu Lys Tyr Val Ala Asp Ala Asn Leu
260 265 270

Ser Leu Arg Thr Ser Thr His Pro Glu Ser Thr
275 280

<210> SEQ ID NO 277
<211> LENGTH: 289
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 277

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu 50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Gly Gly Gly
85 90 95

Gly Ser Gly Gly Gly Gly Ser Gly Gly Gly Gly Ser Gly Pro Val Pro
100 105 110

Thr Ser Lys Pro Thr Thr Thr Gly Lys Gly Cys His Ile Gly Arg Phe
115 120 125

Lys Ser Leu Ser Pro Gln Glu Leu Ala Ser Phe Lys Lys Ala Arg Asp
130 135 140

Ala Leu Glu Glu Ser Leu Lys Leu Lys Asn Trp Ser Cys Ser Ser Pro
145 150 155 160

Val Phe Pro Gly Asn Trp Asp Leu Arg Leu Leu Gln Val Arg Glu Arg
165 170 175

Pro Val Ala Leu Glu Ala Glu Leu Ala Leu Thr Leu Lys Val Leu Glu
180 185 190

Ala Ala Ala Gly Pro Ala Leu Glu Asp Val Leu Asp Gln Pro Leu His
195 200 205

Thr Leu His His Ile Leu Ser Gln Leu Gln Ala Cys Ile Gln Pro Gln
210 215 220

Pro Thr Ala Gly Pro Arg Pro Arg Gly Arg Leu His His Trp Leu His
225 230 235 240

Arg Leu Gln Glu Ala Pro Lys Lys Glu Ser Ala Gly Cys Leu Glu Ala
245 250 255

Ser Val Thr Phe Asn Leu Phe Arg Leu Leu Thr Arg Asp Leu Lys Tyr
260 265 270

Val Ala Glu Gly Asn Leu Ser Leu Arg Thr Ser Thr His Pro Glu Ser
275 280 285

Thr

<210> SEQ ID NO 278
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 278

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Gly Gly Gly
85 90 95

Gly Ser Gly Gly Gly Gly Ser Gly Gly Gly Gly Ser Gly Pro Val Pro
100 105 110

Thr Ser Lys Pro Thr Thr Thr Gly Lys Gly Cys His Ile Gly Arg Phe
115 120 125

Lys Ser Leu Ser Pro Gln Glu Leu Ala Ser Phe Lys Lys Ala Arg Asp
130 135 140

Ala Leu Glu Glu Ser Leu Lys Leu Lys Asn Trp Ser Cys Ser Ser Pro
145 150 155 160

Val Phe Pro Gly Asn Trp Asp Leu Arg Leu Leu Gln Val Arg Glu Arg
165 170 175

Pro Val Ala Leu Glu Ala Glu Leu Ala Leu Thr Leu Lys Val Leu Glu
180 185 190

Ala Ala Ala Gly Pro Ala Leu Glu Asp Val Leu Asp Gln Pro Leu His
195 200 205

Thr Leu His His Ile Leu Ser Gln Leu Gln Ala Cys Ile Gln Pro Gln
210 215 220

Pro Thr Ala Gly Pro Arg Pro Arg Gly Arg Leu His His Trp Leu His
225 230 235 240

Arg Leu Gln Glu Ala Pro Lys Lys Glu Ser Ala Gly Cys Leu Glu Ala
245 250 255

Ser Val Thr Phe Asn Leu Phe Arg Leu Leu Thr Arg Asp Leu Lys Tyr
260 265 270

Val Ala Asp Ala Asn Leu Ser Leu Arg Thr Ser Thr His Pro Glu Ser
275 280 285

Thr

<210> SEQ ID NO 279
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 279

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Glu Asp Glu
85 90 95

Asp Glu Asp Glu Asp Glu Asp Gly Pro Val Pro Thr Ser Lys Pro Thr
100 105 110

Thr Thr Gly Lys Gly Cys His Ile Gly Arg Phe Lys Ser Leu Ser Pro
115 120 125

Gln Glu Leu Ala Ser Phe Lys Lys Ala Arg Asp Ala Leu Glu Glu Ser
130 135 140

Leu Lys Leu Lys Asn Trp Ser Cys Ser Ser Pro Val Phe Pro Gly Asn
145 150 155 160

Trp Asp Leu Arg Leu Leu Gln Val Arg Glu Arg Pro Val Ala Leu Glu
165 170 175

Ala Glu Leu Ala Leu Thr Leu Lys Val Leu Glu Ala Ala Ala Gly Pro
180 185 190

```
Ala Leu Glu Asp Val Leu Asp Gln Pro Leu His Thr Leu His His Ile
        195                 200                 205

Leu Ser Gln Leu Gln Ala Cys Ile Gln Pro Gln Pro Thr Ala Gly Pro
    210                 215                 220

Arg Pro Arg Gly Arg Leu His His Trp Leu His Arg Leu Gln Glu Ala
225                 230                 235                 240

Pro Lys Lys Glu Ser Ala Gly Cys Leu Glu Ala Ser Val Thr Phe Asn
                245                 250                 255

Leu Phe Arg Leu Leu Thr Arg Asp Leu Lys Tyr Val Ala Asp Gly Asn
            260                 265                 270

Leu Cys Leu Arg Thr Ser Thr His Pro Glu Ser Thr
        275                 280


<210> SEQ ID NO 280
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Gly Pro Val Pro Thr Ser Lys Pro Thr
            100                 105                 110

Thr Thr Gly Lys Gly Cys His Ile Gly Arg Phe Lys Ser Leu Ser Pro
        115                 120                 125

Gln Glu Leu Ala Ser Phe Lys Lys Ala Arg Asp Ala Leu Glu Glu Ser
    130                 135                 140

Leu Lys Leu Lys Asn Trp Ser Cys Ser Ser Pro Val Phe Pro Gly Asn
145                 150                 155                 160

Trp Asp Leu Arg Leu Leu Gln Val Arg Glu Arg Pro Val Ala Leu Glu
                165                 170                 175

Ala Glu Leu Ala Leu Thr Leu Lys Val Leu Glu Ala Ala Ala Gly Pro
            180                 185                 190

Ala Leu Glu Asp Val Leu Asp Gln Pro Leu His Thr Leu His His Ile
        195                 200                 205

Leu Ser Gln Leu Gln Ala Cys Ile Gln Pro Gln Pro Thr Ala Gly Pro
    210                 215                 220

Arg Pro Arg Gly Arg Leu His His Trp Leu His Arg Leu Gln Glu Ala
225                 230                 235                 240

Pro Lys Lys Glu Ser Ala Gly Cys Leu Glu Ala Ser Val Thr Phe Asn
                245                 250                 255

Leu Phe Arg Leu Leu Thr Arg Asp Leu Lys Tyr Val Ala Asp Gly Asn
```

260 265 270

Leu Ser Leu Arg Thr Ser Thr His Pro Glu Ser Thr
275 280

<210> SEQ ID NO 281
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 281

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Glu Asp Glu
85 90 95

Asp Glu Asp Glu Asp Glu Asp Lys Pro Thr Thr Thr Gly Lys Gly Cys
100 105 110

His Ile Gly Arg Phe Lys Ser Leu Ser Pro Gln Glu Leu Ala Ser Phe
115 120 125

Lys Lys Ala Arg Asp Ala Leu Glu Glu Ser Leu Lys Leu Lys Asn Trp
130 135 140

Ser Cys Ser Ser Pro Val Phe Pro Gly Asn Trp Asp Leu Arg Leu Leu
145 150 155 160

Gln Val Arg Glu Arg Pro Val Ala Leu Glu Ala Glu Leu Ala Leu Thr
165 170 175

Leu Lys Val Leu Glu Ala Ala Ala Gly Pro Ala Leu Glu Asp Val Leu
180 185 190

Asp Gln Pro Leu His Thr Leu His His Ile Leu Ser Gln Leu Gln Ala
195 200 205

Cys Ile Gln Pro Gln Pro Thr Ala Gly Pro Arg Pro Arg Gly Arg Leu
210 215 220

His His Trp Leu His Arg Leu Gln Glu Ala Pro Lys Lys Glu Ser Ala
225 230 235 240

Gly Cys Leu Glu Ala Ser Val Thr Phe Asn Leu Phe Arg Leu Leu Thr
245 250 255

Arg Asp Leu Lys Tyr Val Ala Asp Gly Asn Leu Ser Leu Arg Thr Ser
260 265 270

Thr His Pro Glu Ser Thr
275

<210> SEQ ID NO 282
<211> LENGTH: 278
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 282

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Lys Pro Thr Thr Thr Gly Lys Gly Cys
            100                 105                 110

His Ile Gly Arg Phe Lys Ser Leu Ser Pro Gln Glu Leu Ala Ser Phe
        115                 120                 125

Lys Lys Ala Arg Asp Ala Leu Glu Glu Ser Leu Lys Leu Lys Asn Trp
    130                 135                 140

Ser Cys Ser Ser Pro Val Phe Pro Gly Asn Trp Asp Leu Arg Leu Leu
145                 150                 155                 160

Gln Val Arg Glu Arg Pro Val Ala Leu Glu Ala Glu Leu Ala Leu Thr
                165                 170                 175

Leu Lys Val Leu Glu Ala Ala Ala Gly Pro Ala Leu Glu Asp Val Leu
            180                 185                 190

Asp Gln Pro Leu His Thr Leu His His Ile Leu Ser Gln Leu Gln Ala
        195                 200                 205

Cys Ile Gln Pro Gln Pro Thr Ala Gly Pro Arg Pro Arg Gly Arg Leu
    210                 215                 220

His His Trp Leu His Arg Leu Gln Glu Ala Pro Lys Lys Glu Ser Ala
225                 230                 235                 240

Gly Cys Leu Glu Ala Ser Val Thr Phe Asn Leu Phe Arg Leu Leu Thr
                245                 250                 255

Arg Asp Leu Lys Tyr Val Ala Glu Gly Asn Leu Ser Leu Arg Thr Ser
            260                 265                 270

Thr His Pro Glu Ser Thr
        275
```

<210> SEQ ID NO 283
<211> LENGTH: 278
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 283

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60
```

```
Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Lys Pro Thr Thr Thr Gly Lys Gly Cys
            100                 105                 110

His Ile Gly Arg Phe Lys Ser Leu Ser Pro Gln Glu Leu Ala Ser Phe
        115                 120                 125

Lys Lys Ala Arg Asp Ala Leu Glu Glu Ser Leu Lys Leu Lys Asn Trp
    130                 135                 140

Ser Cys Ser Ser Pro Val Phe Pro Gly Asn Trp Asp Leu Arg Leu Leu
145                 150                 155                 160

Gln Val Arg Glu Arg Pro Val Ala Leu Glu Ala Glu Leu Ala Leu Thr
                165                 170                 175

Leu Lys Val Leu Glu Ala Ala Ala Gly Pro Ala Leu Glu Asp Val Leu
            180                 185                 190

Asp Gln Pro Leu His Thr Leu His His Ile Leu Ser Gln Leu Gln Ala
        195                 200                 205

Cys Ile Gln Pro Gln Pro Thr Ala Gly Pro Arg Pro Arg Gly Arg Leu
    210                 215                 220

His His Trp Leu His Arg Leu Gln Glu Ala Pro Lys Lys Glu Ser Ala
225                 230                 235                 240

Gly Cys Leu Glu Ala Ser Val Thr Phe Asn Leu Phe Arg Leu Leu Thr
                245                 250                 255

Arg Asp Leu Lys Tyr Val Ala Asp Ala Asn Leu Ser Leu Arg Thr Ser
            260                 265                 270

Thr His Pro Glu Ser Thr
        275


<210> SEQ ID NO 284
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Gly Pro Val Pro Thr Ser Lys Pro Thr
            100                 105                 110

Thr Thr Gly Lys Gly Cys His Ile Gly Arg Phe Lys Ser Leu Ser Pro
        115                 120                 125

Gln Glu Leu Ala Ser Phe Lys Lys Ala Arg Asp Ala Leu Glu Glu Ser
    130                 135                 140
```

```
Leu Lys Leu Lys Asn Trp Ser Cys Ser Ser Pro Val Phe Pro Gly Asn
145                 150                 155                 160

Trp Asp Leu Arg Leu Leu Gln Val Arg Glu Arg Pro Val Ala Leu Glu
                165                 170                 175

Ala Glu Leu Ala Leu Thr Leu Lys Val Leu Glu Ala Ala Ala Gly Pro
            180                 185                 190

Ala Leu Glu Asp Val Leu Asp Gln Pro Leu His Thr Leu His His Ile
        195                 200                 205

Leu Ser Gln Leu Gln Ala Cys Ile Gln Pro Gln Pro Thr Ala Gly Pro
    210                 215                 220

Arg Pro Arg Gly Arg Leu His His Trp Leu His Arg Leu Gln Glu Ala
225                 230                 235                 240

Pro Lys Lys Glu Ser Ala Gly Cys Leu Glu Ala Ser Val Thr Phe Asn
                245                 250                 255

Leu Phe Arg Leu Leu Thr Arg Asp Leu Lys Tyr Val Ala Glu Gly Asn
            260                 265                 270

Leu Ser Leu Arg Thr Ser Thr His Pro Glu Ser Thr
        275                 280


<210> SEQ ID NO 285
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Gly Pro Val Pro Thr Ser Lys Pro Thr
            100                 105                 110

Thr Thr Gly Lys Gly Cys His Ile Gly Arg Phe Lys Ser Leu Ser Pro
        115                 120                 125

Gln Glu Leu Ala Ser Phe Lys Lys Ala Arg Asp Ala Leu Glu Glu Ser
    130                 135                 140

Leu Lys Leu Lys Asn Trp Ser Cys Ser Ser Pro Val Phe Pro Gly Asn
145                 150                 155                 160

Trp Asp Leu Arg Leu Leu Gln Val Arg Glu Arg Pro Val Ala Leu Glu
                165                 170                 175

Ala Glu Leu Ala Leu Thr Leu Lys Val Leu Glu Ala Ala Ala Gly Pro
            180                 185                 190

Ala Leu Glu Asp Val Leu Asp Gln Pro Leu His Thr Leu His His Ile
        195                 200                 205

Leu Ser Gln Leu Gln Ala Cys Ile Gln Pro Gln Pro Thr Ala Gly Pro
```

```
    210                 215                 220

Arg Pro Arg Gly Arg Leu His His Trp Leu His Arg Leu Gln Glu Ala
225                 230                 235                 240

Pro Lys Lys Glu Ser Ala Gly Cys Leu Glu Ala Ser Val Thr Phe Asn
                245                 250                 255

Leu Phe Arg Leu Leu Thr Arg Asp Leu Lys Tyr Val Ala Asp Ala Asn
            260                 265                 270

Leu Ser Leu Arg Thr Ser Thr His Pro Glu Ser Thr
        275                 280


<210> SEQ ID NO 286
<211> LENGTH: 162
<212> TYPE: PRT
<213> ORGANISM: Homo sapiens

<400> SEQUENCE: 286

Met Asp Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser


<210> SEQ ID NO 287
<211> LENGTH: 134
<212> TYPE: PRT
<213> ORGANISM: Homo sapiens

<400> SEQUENCE: 287

Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95
```

```
Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125

His Gly Ser Glu Asp Ser
    130


<210> SEQ ID NO 288
<211> LENGTH: 489
<212> TYPE: DNA
<213> ORGANISM: Homo sapiens

<400> SEQUENCE: 288

atggattcca gtcctggcaa catggagagg attgtcatct gtctgatggt catcttcttg     60

gggacactgg tccacaaatc aagctcccaa ggtcaagatc gccacatgat tagaatgcgt    120

caacttatag atattgttga tcagctgaaa aattatgtga atgacttggt ccctgaattt    180

ctgccagctc cagaagatgt agagacaaac tgtgagtggt cagctttttc ctgttttcag    240

aaggcccaac taaagtcagc aaatacagga aacaatgaaa ggataatcaa tgtatcaatt    300

aaaaagctga agaggaaacc accttccaca aatgcaggga gaagacagaa acacagacta    360

acatgccctt catgtgattc ttatgagaaa aaaccaccca aagaattcct agaaagattc    420

aaatcacttc tccaaaagat gattcatcag catctgtcct ctagaacaca cggaagtgaa    480

gattcctga                                                            489


<210> SEQ ID NO 289
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289

atgcaaggtc aagatcgcca catgattaga atgcgtcaac ttatagatat tgttgatcag     60

ctgaaaaatt atgtgaatga cctggttccg gaattcctgc cggctccgga agatgttgag    120

accaactgtg agtggtccgc tttctcctgt ttccagaaag cccagctgaa atccgcaaac    180

accggtaaca acgaacgtat catcaacgtt tccattaaaa aactgaaacg taaaccgccg    240

tccaccaacg caggtcgtcg tcagaaacac cgtctgacct gcccgtcctg tgattcttat    300

gagaaaaaac cgccgaaaga attcctggaa cgtttcaaat ccctgctgca gaaaatgatt    360

caccagcacc tgtcctctcg tacccacggt tccgaagatt cctga                    405


<210> SEQ ID NO 290
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Met Asp Ser Ser Pro Gly Asn Met Glu Arg Ile Val Ile Cys Leu Met
1               5                   10                  15

Val Ile Phe Leu Gly Thr Leu Val His Lys Ser Ser Ser Gln Gly Gln
            20                  25                  30

Asp Arg His Met Ile Arg Met Arg Gln Leu Ile Asp Ile Val Asp Gln
```

```
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser Gly Gly Gly Gly Ser Gly Gly Gly Gly Ser Gly Gly Gly Gly
                165                 170                 175

Ser Gly Val Ser Asp Val Pro Arg Asp Leu Glu Val Val Ala Ala Thr
            180                 185                 190

Pro Thr Ser Leu Leu Ile Ser Trp His Ser Tyr Tyr Glu Gln Asn Ser
        195                 200                 205

Tyr Tyr Arg Ile Thr Tyr Gly Glu Thr Gly Gly Asn Ser Pro Val Gln
    210                 215                 220

Glu Phe Thr Val Pro Tyr Ser Gln Thr Thr Ala Thr Ile Ser Gly Leu
225                 230                 235                 240

Lys Pro Gly Val Asp Tyr Thr Ile Thr Val Tyr Ala Val Tyr Gly Ser
                245                 250                 255

Lys Tyr Tyr Tyr Pro Ile Ser Ile Asn Tyr Arg Thr Glu
            260                 265
```

```
<210> SEQ ID NO 291
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125
```

His Gly Ser Glu Asp Ser Gly Gly Gly Gly Ser Gly Gly Gly Gly Ser
130 135 140

Gly Gly Gly Gly Ser Gly Val Ser Asp Val Pro Arg Asp Leu Glu Val
145 150 155 160

Val Ala Ala Thr Pro Thr Ser Leu Leu Ile Ser Trp His Ser Tyr Tyr
165 170 175

Glu Gln Asn Ser Tyr Tyr Arg Ile Thr Tyr Gly Glu Thr Gly Gly Asn
180 185 190

Ser Pro Val Gln Glu Phe Thr Val Pro Tyr Ser Gln Thr Thr Ala Thr
195 200 205

Ile Ser Gly Leu Lys Pro Gly Val Asp Tyr Thr Ile Thr Val Tyr Ala
210 215 220

Val Tyr Gly Ser Lys Tyr Tyr Tyr Pro Ile Ser Ile Asn Tyr Arg Thr
225 230 235 240

Glu

<210> SEQ ID NO 292
<211> LENGTH: 264
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 292

Met Asp Ser Ser Pro Gly Asn Met Glu Arg Ile Val Ile Cys Leu Met
1 5 10 15

Val Ile Phe Leu Gly Thr Leu Val His Lys Ser Ser Ser Gln Gly Gln
20 25 30

Asp Arg His Met Ile Arg Met Arg Gln Leu Ile Asp Ile Val Asp Gln
35 40 45

Leu Lys Asn Tyr Val Asn Asp Leu Val Pro Glu Phe Leu Pro Ala Pro
50 55 60

Glu Asp Val Glu Thr Asn Cys Glu Trp Ser Ala Phe Ser Cys Phe Gln
65 70 75 80

Lys Ala Gln Leu Lys Ser Ala Asn Thr Gly Asn Asn Glu Arg Ile Ile
85 90 95

Asn Val Ser Ile Lys Lys Leu Lys Arg Lys Pro Pro Ser Thr Asn Ala
100 105 110

Gly Arg Arg Gln Lys His Arg Leu Thr Cys Pro Ser Cys Asp Ser Tyr
115 120 125

Glu Lys Lys Pro Pro Lys Glu Phe Leu Glu Arg Phe Lys Ser Leu Leu
130 135 140

Gln Lys Met Ile His Gln His Leu Ser Ser Arg Thr His Gly Ser Glu
145 150 155 160

Asp Ser Glu Asp Glu Asp Glu Asp Glu Asp Glu Asp Gly Val Ser Asp
165 170 175

Val Pro Arg Asp Leu Glu Val Val Ala Ala Thr Pro Thr Ser Leu Leu
180 185 190

Ile Ser Trp His Ser Tyr Tyr Glu Gln Asn Ser Tyr Tyr Arg Ile Thr
195 200 205

Tyr Gly Glu Thr Gly Gly Asn Ser Pro Val Gln Glu Phe Thr Val Pro
210 215 220

Tyr Ser Gln Thr Thr Ala Thr Ile Ser Gly Leu Lys Pro Gly Val Asp
225 230 235 240

```
Tyr Thr Ile Thr Val Tyr Ala Val Tyr Gly Ser Lys Tyr Tyr Tyr Pro
            245                 250                 255

Ile Ser Ile Asn Tyr Arg Thr Glu
            260


<210> SEQ ID NO 293
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Met Gln Gly Gln Asp Arg His Met Ile Arg Met Arg Gln Leu Ile Asp
1               5                   10                  15

Ile Val Asp Gln Leu Lys Asn Tyr Val Asn Asp Leu Val Pro Glu Phe
            20                  25                  30

Leu Pro Ala Pro Glu Asp Val Glu Thr Asn Cys Glu Trp Ser Ala Phe
        35                  40                  45

Ser Cys Phe Gln Lys Ala Gln Leu Lys Ser Ala Asn Thr Gly Asn Asn
    50                  55                  60

Glu Arg Ile Ile Asn Val Ser Ile Lys Lys Leu Lys Arg Lys Pro Pro
65                  70                  75                  80

Ser Thr Asn Ala Gly Arg Arg Gln Lys His Arg Leu Thr Cys Pro Ser
                85                  90                  95

Cys Asp Ser Tyr Glu Lys Lys Pro Pro Lys Glu Phe Leu Glu Arg Phe
            100                 105                 110

Lys Ser Leu Leu Gln Lys Met Ile His Gln His Leu Ser Ser Arg Thr
        115                 120                 125

His Gly Ser Glu Asp Ser Glu Asp Glu Asp Glu Asp Glu Asp Glu Asp
    130                 135                 140

Gly Val Ser Asp Val Pro Arg Asp Leu Glu Val Val Ala Ala Thr Pro
145                 150                 155                 160

Thr Ser Leu Leu Ile Ser Trp His Ser Tyr Tyr Glu Gln Asn Ser Tyr
                165                 170                 175

Tyr Arg Ile Thr Tyr Gly Glu Thr Gly Gly Asn Ser Pro Val Gln Glu
            180                 185                 190

Phe Thr Val Pro Tyr Ser Gln Thr Thr Ala Thr Ile Ser Gly Leu Lys
        195                 200                 205

Pro Gly Val Asp Tyr Thr Ile Thr Val Tyr Ala Val Tyr Gly Ser Lys
    210                 215                 220

Tyr Tyr Tyr Pro Ile Ser Ile Asn Tyr Arg Thr Glu
225                 230                 235


<210> SEQ ID NO 294
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30
```

```
Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Met Gln Gly Gln
            100                 105                 110

Asp Arg His Met Ile Arg Met Arg Gln Leu Ile Asp Ile Val Asp Gln
        115                 120                 125

Leu Lys Asn Tyr Val Asn Asp Leu Val Pro Glu Phe Leu Pro Ala Pro
    130                 135                 140

Glu Asp Val Glu Thr Asn Cys Glu Trp Ser Ala Phe Ser Cys Phe Gln
145                 150                 155                 160

Lys Ala Gln Leu Lys Ser Ala Asn Thr Gly Asn Asn Glu Arg Ile Ile
                165                 170                 175

Asn Val Ser Ile Lys Lys Leu Lys Arg Lys Pro Pro Ser Thr Asn Ala
            180                 185                 190

Gly Arg Arg Gln Lys His Arg Leu Thr Cys Pro Ser Cys Asp Ser Tyr
        195                 200                 205

Glu Lys Lys Pro Pro Lys Glu Phe Leu Glu Arg Phe Lys Ser Leu Leu
    210                 215                 220

Gln Lys Met Ile His Gln His Leu Ser Ser Arg Thr His Gly Ser Glu
225                 230                 235                 240

Asp Ser


<210> SEQ ID NO 295
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Met Gln Gly Gln Asp Arg His Met Ile
            100                 105                 110

Arg Met Arg Gln Leu Ile Asp Ile Val Asp Gln Leu Lys Asn Tyr Val
        115                 120                 125

Asn Asp Leu Val Pro Glu Phe Leu Pro Ala Pro Glu Asp Val Glu Thr
    130                 135                 140
```

```
Asn Cys Glu Trp Ser Ala Phe Ser Cys Phe Gln Lys Ala Gln Leu Lys
145                 150                 155                 160

Ser Ala Asn Thr Gly Asn Asn Glu Arg Ile Ile Asn Val Ser Ile Lys
                165                 170                 175

Lys Leu Lys Arg Lys Pro Pro Ser Thr Asn Ala Gly Arg Arg Gln Lys
            180                 185                 190

His Arg Leu Thr Cys Pro Ser Cys Asp Ser Tyr Glu Lys Lys Pro Pro
        195                 200                 205

Lys Glu Phe Leu Glu Arg Phe Lys Ser Leu Leu Gln Lys Met Ile His
    210                 215                 220

Gln His Leu Ser Ser Arg Thr His Gly Ser Glu Asp Ser
225                 230                 235


<210> SEQ ID NO 296
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35


<210> SEQ ID NO 297
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35


<210> SEQ ID NO 298
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30


<210> SEQ ID NO 299
<211> LENGTH: 32
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 299

Cys Ser Asn Leu Ser Thr Cys Val Leu Gly Lys Leu Ser Asn Glu Leu
1 5 10 15

His Lys Leu Asn Thr Tyr Pro Arg Thr Asp Val Gly Ala Asn Thr Tyr
20 25 30

<210> SEQ ID NO 300
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 300

Lys Cys Asn Thr Ala Thr Cys Ala Thr Gln Arg Leu Ala Asn Phe Leu
1 5 10 15

Val Arg Ser Ser Asn Asn Leu Gly Pro Val Leu Pro Pro Thr Asn Val
20 25 30

Gly Ser Asn Thr Tyr
35

<210> SEQ ID NO 301
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 301

Lys Cys Asn Met Ala Thr Cys Ala Thr Gln His Leu Ala Asn Phe Leu
1 5 10 15

Asp Arg Ser Arg Asn Asn Leu Gly Thr Ile Phe Ser Pro Thr Lys Val
20 25 30

Gly Ser Asn Thr Tyr
35

<210> SEQ ID NO 302
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 302

Lys Cys Asn Thr Ala Thr Cys Ala Thr Gln Arg Leu Ala Asn Phe Leu
1 5 10 15

Ile Arg Ser Ser Asn Asn Leu Gly Ala Ile Leu Ser Pro Thr Asn Val
20 25 30

Gly Ser Asn Thr Tyr
35

<210> SEQ ID NO 303
<211> LENGTH: 32
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 303

```
Cys Ser Asn Leu Ser Thr Cys Val Leu Gly Lys Leu Ser Asn Glu Leu
1               5                   10                  15

His Lys Leu Asn Thr Tyr Pro Arg Thr Asn Thr Gly Ser Gly Thr Pro
            20                  25                  30
```

<210> SEQ ID NO 304
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Glu Asp Glu Asp Glu Asp Glu Asp Glu Asp Lys Cys Asn
            100                 105                 110

Thr Ala Thr Cys Ala Thr Gln Arg Leu Ala Asn Phe Leu Val His Ser
        115                 120                 125

Ser Asn Asn Phe Gly Ala Ile Leu Ser Ser Thr Asn Val Gly Ser Asn
    130                 135                 140

Thr Tyr
145
```

<210> SEQ ID NO 305
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
```

```
                85                  90                  95

Glu Asp Glu Asp Glu Asp Glu Asp Lys Cys Asn Thr Ala Thr Cys Ala
            100                 105                 110

Thr Gln Arg Leu Ala Asn Phe Leu Val His Ser Ser Asn Asn Phe Gly
        115                 120                 125

Ala Ile Leu Ser Ser Thr Asn Val Gly Ser Asn Thr Tyr
    130                 135                 140


<210> SEQ ID NO 306
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Gly Ser Gly Ser Gly Ser Gly Ser Lys Cys Asn Thr
            100                 105                 110

Ala Thr Cys Ala Thr Gln Arg Leu Ala Asn Phe Leu Val His Ser Ser
        115                 120                 125

Asn Asn Phe Gly Ala Ile Leu Ser Ser Thr Asn Val Gly Ser Asn Thr
    130                 135                 140

Tyr
145


<210> SEQ ID NO 307
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
```

```
                85                  90                  95

Ser Gly Ser Gly Ser Gly Ser Lys Cys Asn Thr Ala Thr Cys Ala Thr
            100                 105                 110

Gln Arg Leu Ala Asn Phe Leu Val His Ser Ser Asn Asn Phe Gly Ala
        115                 120                 125

Ile Leu Ser Ser Thr Asn Val Gly Ser Asn Thr Tyr
    130                 135                 140


<210> SEQ ID NO 308
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Glu Asp Glu Asp Glu Asp Glu Asp Glu Asp Lys Cys Asn
            100                 105                 110

Thr Ala Thr Cys Ala Thr Gln Arg Leu Ala Asn Phe Leu Val His Ser
        115                 120                 125

Ser Asn Asn Phe Gly Pro Ile Leu Pro Pro Thr Asn Val Gly Ser Asn
    130                 135                 140

Thr Tyr
145


<210> SEQ ID NO 309
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
```

```
                85                  90                  95

Glu Asp Glu Asp Glu Asp Glu Asp Lys Cys Asn Thr Ala Thr Cys Ala
            100                 105                 110

Thr Gln Arg Leu Ala Asn Phe Leu Val His Ser Ser Asn Asn Phe Gly
        115                 120                 125

Pro Ile Leu Pro Pro Thr Asn Val Gly Ser Asn Thr Tyr
    130                 135                 140


<210> SEQ ID NO 310
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Gly Ser Gly Ser Gly Ser Gly Ser Lys Cys Asn Thr
            100                 105                 110

Ala Thr Cys Ala Thr Gln Arg Leu Ala Asn Phe Leu Val His Ser Ser
        115                 120                 125

Asn Asn Phe Gly Pro Ile Leu Pro Pro Thr Asn Val Gly Ser Asn Thr
    130                 135                 140

Tyr
145


<210> SEQ ID NO 311
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
```

```
                85                  90                  95

Ser Gly Ser Gly Ser Gly Ser Lys Cys Asn Thr Ala Thr Cys Ala Thr
            100                 105                 110

Gln Arg Leu Ala Asn Phe Leu Val His Ser Ser Asn Asn Phe Gly Pro
        115                 120                 125

Ile Leu Pro Pro Thr Asn Val Gly Ser Asn Thr Tyr
    130                 135                 140


<210> SEQ ID NO 312
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Glu Asp Glu Asp Glu Asp Glu Asp Glu Asp Lys Cys Asn
            100                 105                 110

Thr Ala Thr Cys Val Leu Gly Arg Leu Ser Gln Glu Leu His Arg Leu
        115                 120                 125

Gln Thr Tyr Pro Arg Thr Asn Thr Gly Ser Asn Thr Tyr
    130                 135                 140


<210> SEQ ID NO 313
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Lys Cys Asn Thr Ala Thr Cys Val
```

```
            100                 105                 110

Leu Gly Arg Leu Ser Gln Glu Leu His Arg Leu Gln Thr Tyr Pro Arg
        115                 120                 125

Thr Asn Thr Gly Ser Asn Thr Tyr
    130                 135
```

<210> SEQ ID NO 314
<211> LENGTH: 140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 314

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Gly Ser Gly Ser Gly Ser Gly Ser Lys Cys Asn Thr
            100                 105                 110

Ala Thr Cys Val Leu Gly Arg Leu Ser Gln Glu Leu His Arg Leu Gln
        115                 120                 125

Thr Tyr Pro Arg Thr Asn Thr Gly Ser Asn Thr Tyr
    130                 135                 140
```

<210> SEQ ID NO 315
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 315

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
                85                  90                  95

Ser Gly Ser Gly Ser Gly Ser Lys Cys Asn Thr Ala Thr Cys Val Leu
            100                 105                 110

Gly Arg Leu Ser Gln Glu Leu His Arg Leu Gln Thr Tyr Pro Arg Thr
```

115 120 125

Asn Thr Gly Ser Asn Thr Tyr
130 135

<210> SEQ ID NO 316
<211> LENGTH: 141
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 316

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Lys
85 90 95

Pro Ser Gln Glu Asp Glu Asp Glu Asp Glu Asp Glu Asp Cys Ser Asn
100 105 110

Leu Ser Thr Cys Val Leu Gly Lys Leu Ser Asn Glu Leu His Lys Leu
115 120 125

Asn Thr Tyr Pro Arg Thr Asp Val Gly Ala Asn Thr Tyr
130 135 140

<210> SEQ ID NO 317
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 317

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Asp
85 90 95

Glu Asp Glu Asp Glu Asp Glu Asp Cys Ser Asn Leu Ser Thr Cys Val
100 105 110

Leu Gly Lys Leu Ser Asn Glu Leu His Lys Leu Asn Thr Tyr Pro Arg
115 120 125

Thr Asp Val Gly Ala Asn Thr Tyr

```
    130                 135


<210> SEQ ID NO 318
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Gly Ser Gly Ser Gly Ser Gly Ser Cys Ser Asn Leu
            100                 105                 110

Ser Thr Cys Val Leu Gly Lys Leu Ser Asn Glu Leu His Lys Leu Asn
        115                 120                 125

Thr Tyr Pro Arg Thr Asp Val Gly Ala Asn Thr Tyr
    130                 135                 140


<210> SEQ ID NO 319
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
                85                  90                  95

Ser Gly Ser Gly Ser Gly Ser Cys Ser Asn Leu Ser Thr Cys Val Leu
            100                 105                 110

Gly Lys Leu Ser Asn Glu Leu His Lys Leu Asn Thr Tyr Pro Arg Thr
        115                 120                 125

Asp Val Gly Ala Asn Thr Tyr
    130                 135
```

```
<210> SEQ ID NO 320
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100


<210> SEQ ID NO 321
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 322
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30
```

```
Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100


<210> SEQ ID NO 323
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 324
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100
```

```
<210> SEQ ID NO 325
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 326
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100


<210> SEQ ID NO 327
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Met Gly Val Ser Asp Val Pro Arg Asp Leu Glu Val Val Ala Ala Thr
1               5                   10                  15
```

```
Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 328
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 329
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35


<210> SEQ ID NO 330
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 330

Tyr Pro Ile Lys Pro Glu Ala Pro Gly Glu Asp Ala Ser Pro Glu Glu
1 5 10 15

Leu Ser Arg Tyr Tyr Ala Ser Leu Arg His Tyr Leu Asn Leu Val Thr
20 25 30

Arg Gln Arg Tyr
35

<210> SEQ ID NO 331
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 331

Tyr Pro Ala Lys Pro Glu Ala Pro Gly Glu Asp Ala Ser Pro Glu Glu
1 5 10 15

Leu Ser Arg Tyr Tyr Ala Ser Leu Arg His Tyr Leu Asn Leu Val Thr
20 25 30

Arg Gln Arg Tyr
35

<210> SEQ ID NO 332
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 332

Tyr Pro Ser Lys Pro Glu Ala Pro Gly Glu Asp Ala Ser Pro Glu Glu
1 5 10 15

Leu Asn Arg Tyr Tyr Ala Ser Leu Arg His Tyr Leu Asn Leu Val Thr
20 25 30

Arg Gln Arg Tyr
35

<210> SEQ ID NO 333
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 333

Tyr Pro Ala Lys Pro Glu Ala Pro Gly Glu Asp Ala Ser Pro Glu Glu
1 5 10 15

Leu Ser Arg Tyr Tyr Ala Ser Leu Arg His Tyr Leu Asn Leu Val Thr
20 25 30

Arg Gln Arg Tyr
35

<210> SEQ ID NO 334
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 334

Ala Lys Pro Glu Ala Pro Gly Glu Asp Ala Ser Pro Glu Glu Leu Ser
1 5 10 15

Arg Tyr Tyr Ala Ser Leu Arg His Tyr Leu Asn Leu Val Thr Arg Gln
20 25 30

Arg Tyr

<210> SEQ ID NO 335
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 335

Tyr Pro Ala Lys Pro Glu Ala Pro Gly Glu Asp Ala Ser Pro Glu Glu
1 5 10 15

Leu Ser Arg Tyr Tyr Ala Ser Leu Arg His Tyr Leu Asn Leu Val Thr
20 25 30

Arg Gln Arg Tyr
35

<210> SEQ ID NO 336
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 336

Tyr Pro Ala Lys Pro Gln Ala Pro Gly Glu His Ala Ser Pro Asp Glu
1 5 10 15

Leu Asn Arg Tyr Tyr Thr Ser Leu Arg His Tyr Leu Asn Leu Val Thr
20 25 30

Arg Gln Arg Phe
35

<210> SEQ ID NO 337
<211> LENGTH: 37
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 337

Ala Tyr Pro Pro Lys Pro Glu Ser Pro Gly Asp Ala Ala Ser Pro Glu
1 5 10 15

Glu Ile Ala Gln Tyr Phe Ser Ala Leu Arg His Tyr Ile Asn Leu Val
20 25 30

Thr Arg Gln Arg Tyr
35

<210> SEQ ID NO 338
<211> LENGTH: 143
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 338

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Glu Asp Glu Asp Glu Asp Glu Asp Glu Asp Ile Lys Pro
        100                 105                 110

Glu Ala Pro Gly Glu Asp Ala Ser Pro Glu Glu Leu Asn Arg Tyr Tyr
115                 120                 125

Ala Ser Leu Arg His Tyr Leu Asn Leu Val Thr Arg Gln Arg Tyr
130                 135                 140
```

<210> SEQ ID NO 339
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 339

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Ile Lys Pro Glu Ala Pro Gly Glu
            100                 105                 110

Asp Ala Ser Pro Glu Glu Leu Asn Arg Tyr Tyr Ala Ser Leu Arg His
        115                 120                 125

Tyr Leu Asn Leu Val Thr Arg Gln Arg Tyr
    130                 135
```

<210> SEQ ID NO 340
<211> LENGTH: 142
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 340

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Lys
85 90 95

Pro Ser Gln Gly Gly Ser Gly Ser Gly Ser Gly Ser Ile Lys Pro Glu
100 105 110

Ala Pro Gly Glu Asp Ala Ser Pro Glu Glu Leu Asn Arg Tyr Tyr Ala
115 120 125

Ser Leu Arg His Tyr Leu Asn Leu Val Thr Arg Gln Arg Tyr
130 135 140

<210> SEQ ID NO 341
<211> LENGTH: 137
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 341

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Gly Gly
85 90 95

Ser Gly Ser Gly Ser Gly Ser Ile Lys Pro Glu Ala Pro Gly Glu Asp
100 105 110

Ala Ser Pro Glu Glu Leu Asn Arg Tyr Tyr Ala Ser Leu Arg His Tyr
115 120 125

Leu Asn Leu Val Thr Arg Gln Arg Tyr
130 135

<210> SEQ ID NO 342
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 342

Met Gly Val Ser Asp Val Pro Arg Asp Leu Glu Val Val Ala Ala Thr
1 5 10 15

```
Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100


<210> SEQ ID NO 343
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 344
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95
```

Glu Asp Glu Asp Glu Asp Glu Asp Gly Cys
100 105

<210> SEQ ID NO 345
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 345

Ala Pro Leu Glu Pro Val Tyr Pro Gly Asp Asn Ala Thr Pro Glu Gln
1 5 10 15

Met Ala Gln Tyr Ala Ala Asp Leu Arg Arg Tyr Ile Asn Met Leu Thr
20 25 30

Arg Pro Arg Tyr
35

<210> SEQ ID NO 346
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 346

Ala Pro Leu Glu Pro Glu Tyr Pro Gly Asp Asn Ala Thr Pro Glu Gln
1 5 10 15

Met Ala Gln Tyr Ala Ala Glu Leu Arg Arg Tyr Ile Asn Met Leu Thr
20 25 30

Arg Pro Arg Tyr
35

<210> SEQ ID NO 347
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 347

Ala Pro Leu Glu Pro Val Tyr Pro Gly Asp Asp Ala Thr Pro Glu Gln
1 5 10 15

Met Ala Gln Tyr Ala Ala Glu Leu Arg Arg Tyr Ile Asn Met Leu Thr
20 25 30

Arg Pro Arg Tyr
35

<210> SEQ ID NO 348
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 348

Ala Ser Leu Glu Pro Glu Tyr Pro Gly Asp Asn Ala Thr Pro Glu Gln
1 5 10 15

Met Ala Gln Tyr Ala Ala Glu Leu Arg Arg Tyr Ile Asn Met Leu Thr
20 25 30

Arg Pro Arg Tyr
        35

<210> SEQ ID NO 349
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Ala Pro Met Glu Pro Val Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 350
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Ala Pro Leu Glu Pro Val Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 351
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Ser Pro Leu Glu Pro Val Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35

<210> SEQ ID NO 352
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Ala Pro Leu Glu Pro Val Tyr Pro Gly Asp Asp Ala Thr Pro Gln Gln
1               5                   10                  15

Met Ala Gln Tyr Ala Ala Glu Met Arg Arg Tyr Ile Asn Met Leu Thr

```
            20                  25                  30

Arg Pro Arg Tyr
        35


<210> SEQ ID NO 353
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Ala Pro Leu Glu Pro Met Tyr Pro Gly Asp Tyr Ala Thr Pro Glu Gln
1               5                   10                  15

Met Ala Gln Tyr Glu Thr Gln Leu Arg Arg Tyr Ile Asn Thr Leu Thr
            20                  25                  30

Arg Pro Arg Tyr
        35


<210> SEQ ID NO 354
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Ala Pro Leu Glu Pro Met Tyr Pro Gly Asp Tyr Ala Thr His Glu Gln
1               5                   10                  15

Arg Ala Gln Tyr Glu Thr Gln Leu Arg Arg Tyr Ile Asn Thr Leu Thr
            20                  25                  30

Arg Pro Arg Tyr
        35


<210> SEQ ID NO 355
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Ala Pro Leu Glu Pro Val Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35


<210> SEQ ID NO 356
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Ala Pro Pro Glu Pro Val Tyr Pro Gly Asp Asp Ala Thr Pro Glu Gln
1               5                   10                  15
```

```
Met Ala Glu Tyr Val Ala Asp Leu Arg Arg Tyr Ile Asn Met Leu Thr
            20                  25                  30

Arg Pro Arg Tyr
        35


<210> SEQ ID NO 357
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Val Pro Leu Glu Pro Val Tyr Pro Gly Asp Asn Ala Thr Pro Glu Gln
1               5                   10                  15

Met Ala Gln Tyr Ala Ala Glu Leu Arg Arg Tyr Ile Asn Met Leu Thr
            20                  25                  30

Arg Pro Arg Tyr
        35


<210> SEQ ID NO 358
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Glu Asp Glu Asp Glu Asp Glu Asp Glu Asp Ala Pro Leu
            100                 105                 110

Glu Pro Val Tyr Pro Gly Asp Asn Ala Thr Pro Glu Gln Met Ala Gln
        115                 120                 125

Tyr Ala Ala Asp Leu Arg Arg Tyr Ile Asn Met Leu Thr Arg Pro Arg
    130                 135                 140

Tyr
145


<210> SEQ ID NO 359
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Met Gly Val Ser Asp Val Pro Arg Asp Leu Glu Val Val Ala Ala Thr
```

-continued

```
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Ala Pro Leu Glu Pro Val Tyr Pro
            100                 105                 110

Gly Asp Asn Ala Thr Pro Glu Gln Met Ala Gln Tyr Ala Ala Asp Leu
        115                 120                 125

Arg Arg Tyr Ile Asn Met Leu Thr Arg Pro Arg Tyr
    130                 135                 140


<210> SEQ ID NO 360
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Gly Gly Ser Gly Ser Gly Ser Gly Ser Ala Pro Leu Glu
            100                 105                 110

Pro Val Tyr Pro Gly Asp Asn Ala Thr Pro Glu Gln Met Ala Gln Tyr
        115                 120                 125

Ala Ala Asp Leu Arg Arg Tyr Ile Asn Met Leu Thr Arg Pro Arg Tyr
    130                 135                 140


<210> SEQ ID NO 361
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
```

```
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Gly Gly
                85                  90                  95

Ser Gly Ser Gly Ser Gly Ser Ala Pro Leu Glu Pro Val Tyr Pro Gly
            100                 105                 110

Asp Asn Ala Thr Pro Glu Gln Met Ala Gln Tyr Ala Ala Asp Leu Arg
        115                 120                 125

Arg Tyr Ile Asn Met Leu Thr Arg Pro Arg Tyr
    130                 135


<210> SEQ ID NO 362
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100


<210> SEQ ID NO 363
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
```

```
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 364
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gly Cys
            100                 105


<210> SEQ ID NO 365
<211> LENGTH: 49
<212> TYPE: PRT
<213> ORGANISM: Homo sapiens

<400> SEQUENCE: 365

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val


<210> SEQ ID NO 366
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Lys Leu
            20                  25                  30

Ala Asp His Ile Gly Phe Gln Glu Ala Tyr Arg Arg Phe Tyr Gly Pro
        35                  40                  45
```

Val

<210> SEQ ID NO 367
<211> LENGTH: 49
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 367

Tyr Leu Tyr Gln Trp Leu Gly Ala Pro Val Pro Tyr Pro Asp Pro Leu
1 5 10 15

Glu Pro Arg Arg Glu Val Cys Glu Leu Asn Pro Asp Cys Asp Glu Leu
20 25 30

Ala Asp His Ile Gly Phe Gln Glu Ala Tyr Gln Arg Phe Tyr Gly Pro
35 40 45

Val

<210> SEQ ID NO 368
<211> LENGTH: 49
<212> TYPE: PRT
<213> ORGANISM: Pan sp.

<400> SEQUENCE: 368

Tyr Leu Tyr Gln Trp Leu Gly Ala Pro Val Pro Tyr Pro Asp Thr Leu
1 5 10 15

Glu Pro Arg Arg Glu Val Cys Glu Leu Asn Pro Asp Cys Asp Glu Leu
20 25 30

Ala Asp His Ile Gly Phe Gln Glu Ala Tyr Arg Arg Phe Tyr Gly Pro
35 40 45

Val

<210> SEQ ID NO 369
<211> LENGTH: 49
<212> TYPE: PRT
<213> ORGANISM: Macaca sp.

<400> SEQUENCE: 369

Tyr Leu Tyr Gln Trp Leu Gly Ala Pro Ala Pro Tyr Pro Asp Pro Leu
1 5 10 15

Glu Pro Lys Arg Glu Val Cys Glu Leu Asn Pro Asp Cys Asp Glu Leu
20 25 30

Ala Asp His Ile Gly Phe Gln Glu Ala Tyr Arg Arg Phe Tyr Gly Pro
35 40 45

Val

<210> SEQ ID NO 370
<211> LENGTH: 49
<212> TYPE: PRT
<213> ORGANISM: Bos sp.

<400> SEQUENCE: 370

Tyr Leu Asp His Trp Leu Gly Ala Pro Ala Pro Tyr Pro Asp Pro Leu
1 5 10 15

Glu Pro Lys Arg Glu Val Cys Glu Leu Asn Pro Asp Cys Asp Glu Leu
20 25 30

Ala Asp His Ile Gly Phe Gln Glu Ala Tyr Arg Arg Phe Tyr Gly Pro
35 40 45

Val

<210> SEQ ID NO 371
<211> LENGTH: 49
<212> TYPE: PRT
<213> ORGANISM: Canis sp.

<400> SEQUENCE: 371

```
Tyr Leu Asp Ser Gly Leu Gly Ala Pro Val Pro Tyr Pro Asp Pro Leu
1               5                   10                  15

Glu Pro Lys Arg Glu Val Cys Glu Leu Asn Pro Asn Cys Asp Glu Leu
            20                  25                  30

Ala Asp His Ile Gly Phe Gln Glu Ala Tyr Gln Arg Phe Tyr Gly Pro
        35                  40                  45

Val
```

<210> SEQ ID NO 372
<211> LENGTH: 49
<212> TYPE: PRT
<213> ORGANISM: Sus sp.

<400> SEQUENCE: 372

```
Tyr Leu Asp His Gly Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Ile
        35                  40                  45

Ala
```

<210> SEQ ID NO 373
<211> LENGTH: 49
<212> TYPE: PRT
<213> ORGANISM: Ovis sp.

<400> SEQUENCE: 373

```
Tyr Leu Asp Pro Gly Leu Gly Ala Pro Ala Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val
```

<210> SEQ ID NO 374
<211> LENGTH: 49
<212> TYPE: PRT
<213> ORGANISM: Oryctolagus sp.

<400> SEQUENCE: 374

```
Gln Leu Ile Asp Gly Gln Gly Ala Pro Ala Pro Tyr Pro Asp Pro Leu
1               5                   10                  15

Glu Pro Lys Arg Glu Val Cys Glu Leu Asn Pro Asp Cys Asp Glu Leu
            20                  25                  30

Ala Asp Gln Val Gly Leu Gln Asp Ala Tyr Gln Arg Phe Tyr Gly Pro
        35                  40                  45

Val
```

```
<210> SEQ ID NO 375
<211> LENGTH: 46
<212> TYPE: PRT
<213> ORGANISM: Mus sp.

<400> SEQUENCE: 375

Tyr Leu Gly Ala Ser Val Pro Ser Pro Asp Pro Leu Glu Pro Thr Arg
1               5                   10                  15

Glu Gln Cys Glu Leu Asn Pro Ala Cys Asp Glu Leu Ser Asp Gln Tyr
            20                  25                  30

Gly Leu Lys Thr Ala Tyr Lys Arg Ile Tyr Gly Ile Thr Ile
        35                  40                  45


<210> SEQ ID NO 376
<211> LENGTH: 50
<212> TYPE: PRT
<213> ORGANISM: Rattus sp.

<400> SEQUENCE: 376

Tyr Leu Asn Asn Gly Leu Gly Ala Pro Ala Pro Tyr Pro Asp Pro Leu
1               5                   10                  15

Glu Pro His Arg Glu Val Cys Glu Leu Asn Pro Asn Cys Asp Glu Leu
            20                  25                  30

Ala Asp His Ile Gly Phe Gln Asp Ala Tyr Lys Arg Ile Tyr Gly Thr
        35                  40                  45

Thr Val
    50


<210> SEQ ID NO 377
<211> LENGTH: 49
<212> TYPE: PRT
<213> ORGANISM: Gallus sp.

<400> SEQUENCE: 377

His Tyr Ala Gln Asp Ser Gly Val Ala Gly Ala Pro Pro Asn Pro Leu
1               5                   10                  15

Glu Ala Gln Arg Glu Val Cys Glu Leu Ser Pro Asp Cys Asp Glu Leu
            20                  25                  30

Ala Asp Gln Ile Gly Phe Gln Glu Ala Tyr Arg Arg Phe Tyr Gly Pro
        35                  40                  45

Val


<210> SEQ ID NO 378
<211> LENGTH: 49
<212> TYPE: PRT
<213> ORGANISM: Xenopus laevis

<400> SEQUENCE: 378

Ser Tyr Gly Asn Asn Val Gly Gln Gly Ala Ala Val Gly Ser Pro Leu
1               5                   10                  15

Glu Ser Gln Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val


<210> SEQ ID NO 379
<211> LENGTH: 152
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 379

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Tyr Leu Tyr Gln Trp Leu Gly Ala Pro
            100                 105                 110

Val Pro Tyr Pro Asp Pro Leu Glu Pro Arg Arg Glu Val Cys Glu Leu
        115                 120                 125

Asn Pro Asp Cys Asp Glu Leu Ala Asp His Ile Gly Phe Gln Glu Ala
    130                 135                 140

Tyr Arg Arg Phe Tyr Gly Pro Val
145                 150
```

<210> SEQ ID NO 380
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 380

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Tyr Leu Tyr Gln
            100                 105                 110

Trp Leu Gly Ala Pro Val Pro Tyr Pro Asp Pro Leu Glu Pro Arg Arg
        115                 120                 125

Glu Val Cys Glu Leu Asn Pro Asp Cys Asp Glu Leu Ala Asp His Ile
    130                 135                 140

Gly Phe Gln Glu Ala Tyr Arg Arg Phe Tyr Gly Pro Val
145                 150                 155
```

<210> SEQ ID NO 381

<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 381

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100
```

<210> SEQ ID NO 382
<211> LENGTH: 152
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 382

```
Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Tyr Leu Tyr Gln Trp Leu Gly Ala Pro
            100                 105                 110

Val Pro Tyr Pro Asp Pro Leu Glu Pro Arg Arg Glu Val Cys Glu Leu
        115                 120                 125

Asn Pro Asp Cys Asp Lys Leu Ala Asp His Ile Gly Phe Gln Glu Ala
    130                 135                 140

Tyr Arg Arg Phe Tyr Gly Pro Val
145                 150
```

<210> SEQ ID NO 383
<211> LENGTH: 157
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 383

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Tyr Leu Tyr Gln
            100                 105                 110

Trp Leu Gly Ala Pro Val Pro Tyr Pro Asp Pro Leu Glu Pro Arg Arg
        115                 120                 125

Glu Val Cys Glu Leu Asn Pro Asp Cys Asp Lys Leu Ala Asp His Ile
    130                 135                 140

Gly Phe Gln Glu Ala Tyr Arg Arg Phe Tyr Gly Pro Val
145                 150                 155

<210> SEQ ID NO 384
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 384

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Glu Lys
                85                  90                  95

Pro Ser Gln Cys
            100

<210> SEQ ID NO 385
<211> LENGTH: 152
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 385

Met Gly Val Ser Asp Val Pro Arg Asp Leu Glu Val Val Ala Ala Thr
1               5                   10                  15

```
Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Glu Asp Glu
                85                  90                  95

Asp Glu Asp Glu Asp Glu Asp Tyr Leu Tyr Gln Trp Leu Gly Ala Pro
            100                 105                 110

Val Pro Tyr Pro Asp Pro Leu Glu Pro Arg Arg Glu Val Cys Glu Leu
        115                 120                 125

Asn Pro Asp Cys Asp Glu Leu Ala Asp His Ile Gly Phe Gln Glu Ala
    130                 135                 140

Tyr Gln Arg Phe Tyr Gly Pro Val
145                 150


<210> SEQ ID NO 386
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Gly Gly Gly
                85                  90                  95

Gly Ser Gly Gly Gly Gly Ser Gly Gly Gly Gly Ser Tyr Leu Tyr Gln
            100                 105                 110

Trp Leu Gly Ala Pro Val Pro Tyr Pro Asp Pro Leu Glu Pro Arg Arg
        115                 120                 125

Glu Val Cys Glu Leu Asn Pro Asp Cys Asp Glu Leu Ala Asp His Ile
    130                 135                 140

Gly Phe Gln Glu Ala Tyr Gln Arg Phe Tyr Gly Pro Val
145                 150                 155


<210> SEQ ID NO 387
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387
```

-continued

Met Gly Val Ser Asp Val Pro Arg Asp Leu Glu Val Val Ala Ala Thr
1 5 10 15

Pro Thr Ser Leu Leu Ile Ser Trp His Ser Tyr Tyr Glu Gln Asn Ser
20 25 30

Tyr Tyr Arg Ile Thr Tyr Gly Glu Thr Gly Gly Asn Ser Pro Val Gln
35 40 45

Glu Phe Thr Val Pro Tyr Ser Gln Thr Thr Ala Thr Ile Ser Gly Leu
50 55 60

Lys Pro Gly Val Asp Tyr Thr Ile Thr Val Tyr Ala Val Tyr Gly Ser
65 70 75 80

Lys Tyr Tyr Tyr Pro Ile Ser Ile Asn Tyr Arg Thr Glu Ile Glu Lys
85 90 95

Pro Ser Gln Cys
100

<210> SEQ ID NO 388
<211> LENGTH: 152
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: May or may not be present

<400> SEQUENCE: 388

Met Tyr Leu Tyr Gln Trp Leu Gly Ala Pro Val Pro Tyr Pro Asp Pro
1 5 10 15

Leu Glu Pro Arg Arg Glu Val Cys Glu Leu Asn Pro Asp Cys Asp Glu
20 25 30

Leu Ala Asp His Ile Gly Phe Gln Glu Ala Tyr Arg Arg Phe Tyr Gly
35 40 45

Pro Val Glu Asp Glu Asp Glu Asp Glu Asp Glu Asp Gly Val Ser Asp
50 55 60

Val Pro Arg Asp Leu Glu Val Val Ala Ala Thr Pro Thr Ser Leu Leu
65 70 75 80

Ile Ser Trp His Ser Tyr Tyr Glu Gln Asn Ser Tyr Tyr Arg Ile Thr
85 90 95

Tyr Gly Glu Thr Gly Gly Asn Ser Pro Val Gln Glu Phe Thr Val Pro
100 105 110

Tyr Ser Gln Thr Thr Ala Thr Ile Ser Gly Leu Lys Pro Gly Val Asp
115 120 125

Tyr Thr Ile Thr Val Tyr Ala Val Tyr Gly Ser Lys Tyr Tyr Tyr Pro
130 135 140

Ile Ser Ile Asn Tyr Arg Thr Glu
145 150

<210> SEQ ID NO 389
<211> LENGTH: 157
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: May or may not be present

<400> SEQUENCE: 389

Met Tyr Leu Tyr Gln Trp Leu Gly Ala Pro Val Pro Tyr Pro Asp Pro
1 5 10 15

Leu Glu Pro Arg Arg Glu Val Cys Glu Leu Asn Pro Asp Cys Asp Glu
20 25 30

Leu Ala Asp His Ile Gly Phe Gln Glu Ala Tyr Arg Arg Phe Tyr Gly
35 40 45

Pro Val Gly Gly Gly Gly Ser Gly Gly Gly Gly Ser Gly Gly Gly Gly
50 55 60

Ser Gly Val Ser Asp Val Pro Arg Asp Leu Glu Val Val Ala Ala Thr
65 70 75 80

Pro Thr Ser Leu Leu Ile Ser Trp His Ser Tyr Tyr Glu Gln Asn Ser
85 90 95

Tyr Tyr Arg Ile Thr Tyr Gly Glu Thr Gly Gly Asn Ser Pro Val Gln
100 105 110

Glu Phe Thr Val Pro Tyr Ser Gln Thr Thr Ala Thr Ile Ser Gly Leu
115 120 125

Lys Pro Gly Val Asp Tyr Thr Ile Thr Val Tyr Ala Val Tyr Gly Ser
130 135 140

Lys Tyr Tyr Tyr Pro Ile Ser Ile Asn Tyr Arg Thr Glu
145 150 155

<210> SEQ ID NO 390
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: May or may not be present

<400> SEQUENCE: 390

Met Tyr Leu Tyr Gln Trp Leu Gly Ala Pro Val Pro Tyr Pro Asp Pro
1 5 10 15

Leu Glu Pro Arg Arg Glu Val Cys Glu Leu Asn Pro Asp Cys Asp Glu
20 25 30

Leu Ala Asp His Ile Gly Phe Gln Glu Ala Tyr Arg Arg Phe Tyr Gly
35 40 45

Pro Val Glu Asp Glu Asp Glu Asp Glu Asp Glu Asp Gly Cys
50 55 60

<210> SEQ ID NO 391
<211> LENGTH: 152
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: May or may not be present

<400> SEQUENCE: 391

Met Tyr Leu Tyr Gln Trp Leu Gly Ala Pro Val Pro Tyr Pro Asp Pro
1 5 10 15

Leu Glu Pro Arg Arg Glu Val Cys Glu Leu Asn Pro Asp Cys Asp Lys
20 25 30

```
Leu Ala Asp His Ile Gly Phe Gln Glu Ala Tyr Arg Arg Phe Tyr Gly
        35                  40                  45

Pro Val Glu Asp Glu Asp Glu Asp Glu Asp Glu Asp Gly Val Ser Asp
    50                  55                  60

Val Pro Arg Asp Leu Glu Val Val Ala Ala Thr Pro Thr Ser Leu Leu
65                  70                  75                  80

Ile Ser Trp His Ser Tyr Tyr Glu Gln Asn Ser Tyr Tyr Arg Ile Thr
                85                  90                  95

Tyr Gly Glu Thr Gly Gly Asn Ser Pro Val Gln Glu Phe Thr Val Pro
            100                 105                 110

Tyr Ser Gln Thr Thr Ala Thr Ile Ser Gly Leu Lys Pro Gly Val Asp
        115                 120                 125

Tyr Thr Ile Thr Val Tyr Ala Val Tyr Gly Ser Lys Tyr Tyr Tyr Pro
    130                 135                 140

Ile Ser Ile Asn Tyr Arg Thr Glu
145                 150
```

<210> SEQ ID NO 392
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: May or may not be present

<400> SEQUENCE: 392

```
Met Tyr Leu Tyr Gln Trp Leu Gly Ala Pro Val Pro Tyr Pro Asp Pro
1               5                   10                  15

Leu Glu Pro Arg Arg Glu Val Cys Glu Leu Asn Pro Asp Cys Asp Lys
            20                  25                  30

Leu Ala Asp His Ile Gly Phe Gln Glu Ala Tyr Arg Arg Phe Tyr Gly
        35                  40                  45

Pro Val Gly Gly Gly Gly Ser Gly Gly Gly Gly Ser Gly Gly Gly Gly
    50                  55                  60

Ser Gly Val Ser Asp Val Pro Arg Asp Leu Glu Val Val Ala Ala Thr
65                  70                  75                  80

Pro Thr Ser Leu Leu Ile Ser Trp His Ser Tyr Tyr Glu Gln Asn Ser
                85                  90                  95

Tyr Tyr Arg Ile Thr Tyr Gly Glu Thr Gly Gly Asn Ser Pro Val Gln
            100                 105                 110

Glu Phe Thr Val Pro Tyr Ser Gln Thr Thr Ala Thr Ile Ser Gly Leu
        115                 120                 125

Lys Pro Gly Val Asp Tyr Thr Ile Thr Val Tyr Ala Val Tyr Gly Ser
    130                 135                 140

Lys Tyr Tyr Tyr Pro Ile Ser Ile Asn Tyr Arg Thr Glu
145                 150                 155
```

<210> SEQ ID NO 393
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide
<220> FEATURE:

<221> NAME/KEY: MOD_RES
<222> LOCATION: (1)..(1)
<223> OTHER INFORMATION: May or may not be present

<400> SEQUENCE: 393

Met Tyr Leu Tyr Gln Trp Leu Gly Ala Pro Val Pro Tyr Pro Asp Pro
1               5                   10                  15

Leu Glu Pro Arg Arg Glu Val Cys Glu Leu Asn Pro Asp Cys Asp Lys
            20                  25                  30

Leu Ala Asp His Ile Gly Phe Gln Glu Ala Tyr Arg Arg Phe Tyr Gly
        35                  40                  45

Pro Val Glu Asp Glu Asp Glu Asp Glu Asp Glu Asp Gly Cys
    50                  55                  60

<210> SEQ ID NO 394
<211> LENGTH: 152
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present

<400> SEQUENCE: 394

Met Tyr Leu Tyr Gln Trp Leu Gly Ala Pro Val Pro Tyr Pro Asp Pro
1               5                   10                  15

Leu Glu Pro Arg Arg Glu Val Cys Glu Leu Asn Pro Asp Cys Asp Glu
            20                  25                  30

Leu Ala Asp His Ile Gly Phe Gln Glu Ala Tyr Gln Arg Phe Tyr Gly
        35                  40                  45

Pro Val Glu Asp Glu Asp Glu Asp Glu Asp Glu Asp Gly Val Ser Asp
    50                  55                  60

Val Pro Arg Asp Leu Glu Val Val Ala Ala Thr Pro Thr Ser Leu Leu
65                  70                  75                  80

Ile Ser Trp His Ser Tyr Tyr Glu Gln Asn Ser Tyr Tyr Arg Ile Thr
                85                  90                  95

Tyr Gly Glu Thr Gly Gly Asn Ser Pro Val Gln Glu Phe Thr Val Pro
            100                 105                 110

Tyr Ser Gln Thr Thr Ala Thr Ile Ser Gly Leu Lys Pro Gly Val Asp
        115                 120                 125

Tyr Thr Ile Thr Val Tyr Ala Val Tyr Gly Ser Lys Tyr Tyr Tyr Pro
    130                 135                 140

Ile Ser Ile Asn Tyr Arg Thr Glu
145                 150

<210> SEQ ID NO 395
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present

<400> SEQUENCE: 395

Met Tyr Leu Tyr Gln Trp Leu Gly Ala Pro Val Pro Tyr Pro Asp Pro

```
1               5                   10                  15

Leu Glu Pro Arg Arg Glu Val Cys Glu Leu Asn Pro Asp Cys Asp Glu
            20                  25                  30

Leu Ala Asp His Ile Gly Phe Gln Glu Ala Tyr Gln Arg Phe Tyr Gly
        35                  40                  45

Pro Val Gly Gly Gly Gly Ser Gly Gly Gly Gly Ser Gly Gly Gly Gly
    50                  55                  60

Ser Gly Val Ser Asp Val Pro Arg Asp Leu Glu Val Val Ala Ala Thr
65                  70                  75                  80

Pro Thr Ser Leu Leu Ile Ser Trp His Ser Tyr Tyr Glu Gln Asn Ser
                85                  90                  95

Tyr Tyr Arg Ile Thr Tyr Gly Glu Thr Gly Gly Asn Ser Pro Val Gln
            100                 105                 110

Glu Phe Thr Val Pro Tyr Ser Gln Thr Thr Ala Thr Ile Ser Gly Leu
        115                 120                 125

Lys Pro Gly Val Asp Tyr Thr Ile Thr Val Tyr Ala Val Tyr Gly Ser
    130                 135                 140

Lys Tyr Tyr Tyr Pro Ile Ser Ile Asn Tyr Arg Thr Glu
145                 150                 155
```

<210> SEQ ID NO 396
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: May or may not be present

<400> SEQUENCE: 396

```
Met Tyr Leu Tyr Gln Trp Leu Gly Ala Pro Val Pro Tyr Pro Asp Pro
1               5                   10                  15

Leu Glu Pro Arg Arg Glu Val Cys Glu Leu Asn Pro Asp Cys Asp Lys
            20                  25                  30

Leu Ala Asp His Ile Gly Phe Gln Glu Ala Tyr Arg Arg Phe Tyr Gly
        35                  40                  45

Pro Val Glu Asp Glu Asp Glu Asp Glu Asp Glu Asp Gly Cys
    50                  55                  60
```

<210> SEQ ID NO 397
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

```
Glu Asp Glu Asp Glu Asp Glu Asp Glu Asp Gly
1               5                   10
```

<210> SEQ ID NO 398
<211> LENGTH: 567
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 398
atgcatccga ttccggatag cagcccgctg ctgcagtttg gcggccaggt gcgtcagcgt 60
tatctgtata ccgatgatgc gcagcagacc gaagcgcatc tggaaattcg tgaagatggc 120
accgtgggcg gtgcggcgga tcagagcccg gaaagcctgc tgcagctgaa agcgctgaaa 180
ccgggcgtga ttcagattct gggcgtgaaa accagccgtt ttctgtgcca gcgtccggat 240
ggcgcgctgt atggcagcct gcattttgat ccggaagcgt gcagctttcg tgaactgctg 300
ctggaagatg gctataacgt gtatcagagc gaagcgcatg gcctgccgct gcatctgccg 360
ggcaacaaaa gcccgcatcg tgatccggca ccgcgtggtc cggcacgttt tctgccgctg 420
ccgggtctgc cgccagcact gccggaaccg ccgggtattc tggcaccgca gccgccggat 480
gttggtagca gcgatccgct gtctatggtg ggtccgagcc agggtcgtag cccgagctat 540
gcgcatcatc atcatcacca ttaataa 567

<210> SEQ ID NO 399
<211> LENGTH: 570
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 399
atgcatccga ttccggatag cagcccgctg ctgcagtttg gcggccaggt gcgtcagcgt 60
tatctgtata ccgatgatgc gcagcagacc gaagcgcatc tggaaattcg tgaagatggc 120
accgtgggcg gtgcggcgga tcagagcccg gaaagcctgc tgcagctgaa agcgctgaaa 180
ccgggcgtga ttcagattct gggcgtgaaa accagccgtt ttctgtgcca gcgtccggat 240
ggcgcgctgt atggcagcct gcattttgat ccggaagcgt gcagctttcg tgaactgctg 300
ctggaagatg gctataacgt gtatcagagc gaagcgcatg gcctgccgct gcatctgccg 360
ggcaacaaaa gcccgcatcg tgatccggca ccgcgtggtc cggcacgttt tctgccgctg 420
ccgggtctgc cgccagcact gccggaaccg ccgggtattc tggcaccgca gccgccggat 480
gttggtagca gcgatccgct gtctatggtg ggtccgagcc agggtcgtag cccgagctat 540
gcgagccatc atcatcatca ccattaataa 570

<210> SEQ ID NO 400
<211> LENGTH: 564
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 400
atgcatcatc atcatcacca tccgattccg gatagcagcc cgctgctgca gtttggcggc 60
caggtgcgtc agcgttatct gtataccgat gatgcgcagc agaccgaagc gcatctggaa 120
attcgtgaag atggcaccgt gggcggtgcg gcggatcaga gcccggaaag cctgctgcag 180
ctgaaagcgc tgaaaccggg cgtgattcag attctgggcg tgaaaaccag ccgttttctg 240
tgccagcgtc cggatggcgc gctgtatggc agcctgcatt ttgatccgga agcgtgcagc 300
tttcgtgaac tgctgctgga agatggctat aacgtgtatc agagcgaagc gcatggcctg 360
ccgctgcatc tgccgggcaa caaaagcccg catcgtgatc cggcaccgcg tggtccggca 420
cgttttctgc cgctgccggg tctgccgcca gcactgccgg aaccgccggg tattctggca 480
ccgcagccgc cggatgttgg tagcagcgat ccgctgtcta tggtgggtcc gagccagggt 540
cgtagcccga gctatgcgta ataa 564

<210> SEQ ID NO 401
<211> LENGTH: 881
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 401
atgggtgttt ctgatgttcc gcgtgatctg gaagttgttg cagcaacccc gaccagcctg 60
ctgattagct ggcatagcta ttatgaacag aatagctatt atcgcattac ctatggtgaa 120
accggtggta attctccggt tcaggaattt accgttccgt atagccagac caccgcaacc 180
attagcggtc tgaaaccggg tgttgattat accattaccg tgtatgcagt gtatggcagc 240
aaatattatt atccgattag cattaattat cgcaccgaaa ttgataaacc gagcggtggt 300
agcggtagcg gttcaggtag cggttctggt tctggtagcc cgattccgga tagctctccg 360
ctgctgcagt ttggtggtca ggttcgtcag cgttatctgt ataccgatga tgcacagcag 420
accgaagcac atctggaaat tcgtgaagat ggcaccgttg gtggtgcagc agatcagtct 480
ccggaaagcc tgctgcagct gaaagcactg aagccaggtg ttattcagat tctgggtgtt 540
aaaaccagcc gttttctgtg tcagcgtccg gatggtgcac tgtatggtag cctgcatttt 600
gatccggaag catgcagctt tcgtgaactc tgctggaaga tggctataat gtgtatcaga 660
gcgaagcaca tggtctgccg ctgcatttac ctggtaataa atctccgcat cgtgatccgg 720
caccgcgtgg tccggcacgt ttcctgcctc tgcctggtct gcctccggca ctgccagaac 780
ctccgggtat tctggcaccg cagcctccgg atgttggtag cagcgatccg ctgtctatgg 840
ttggtccgag ccagggtcgt agcccgagct atgcaagctg a 881

<210> SEQ ID NO 402
<211> LENGTH: 882
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 402
atgggtgttt ctgatgttcc gcgtgatctg gaagttgttg cagcaacccc gaccagcctg 60
ctgattagct ggcatagcta ttatgaacag aatagctatt atcgcattac ctatggtgaa 120
accggtggta attctccggt tcaggaattt accgttccgt atagccagac caccgcaacc 180
attagcggtc tgaaaccggg tgttgattat accattaccg tgtatgcagt gtatggcagc 240
aaatattatt atccgattag cattaattat cgcaccgaaa ttgataaacc gagcggtggt 300
agcggtagcg gttcaggtag cggttctggt tctggtagcc atccgattcc ggatagctct 360
ccgctgctgc agtttggtgg tcaggttcgt cagcgttatc tgtataccga tgatgcacag 420
cagaccgaag cacatctgga aattcgtgaa gatggcaccg ttggtggtgc agcagatcag 480
tctccggaaa gcctgctgca gctgaaagca ctgaagccag gtgttattca gattctgggt 540
gttaaaacca gccgttttct gtgtcagcgt ccggatggtg cactgtatgg tagcctgcat 600
tttgatccgg aagcatgcag ctttcgtgaa ctgctgctgg aagatggcta taatgtgtat 660
cagagcgaag cacatggtct gccgctgcat ttacctggta ataaatctcc gcatcgtgat 720
ccggcaccgc gtggtccggc acgtttcctg cctctgcctg gtctgcctcc ggcactgcca 780
gaacctccgg gtattctggc accgcagcct ccggatgttg gtagcagcga tccgctgtct 840
atggttggtc cgagccaggg tcgtagcccg agctatgcat ga 882

<210> SEQ ID NO 403
<211> LENGTH: 900
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 403
atgggtgttt ctgatgttcc gcgtgatctg gaagttgttg cagcaacccc gaccagcctg 60
ctgattagct ggcatagcta ttatgaacag aatagctatt atcgcattac ctatggtgaa 120
accggtggta attctccggt tcaggaattt accgttccgt atagccagac caccgcaacc 180
attagcggtc tgaaaccggg tgttgattat accattaccg tgtatgcagt gtatggcagc 240
aaatattatt atccgattag cattaattat cgcaccgaaa ttgaaaaacc gagccagcat 300
catcatcacc atcatggtag cggtagcggt tcaggtagcg gttctggttc tggtagcccg 360
attccggata gctctccgct gctgcagttt ggtggtcagg ttcgtcagcg ttatctgtat 420
accgatgatg cacagcagac cgaagcacat ctggaaattc gtgaagatgg caccgttggt 480
ggtgcagcag atcagtctcc ggaaagcctg ctgcagctga aagcactgaa gccaggtgtt 540
attcagattc tgggtgttaa aaccagccgt tttctgtgtc agcgtccgga tggtgcactg 600
tatggtagcc tgcattttga tccggaagca tgcagctttc gtgaactgct gctggaagat 660
ggctataatg tgtatcagag cgaagcacat ggtctgccgc tgcatttacc tggtaataaa 720
tctccgcatc gtgatccggc accgcgtggt ccggcacgtt tcctgcctct gcctggtctg 780
cctccggcac tgccagaacc tccgggtatt ctggcaccgc agcctccgga tgttggtagc 840
agcgatccgc tgtctatggt tggtccgagc cagggtcgta gcccgagcta tgcaagctga 900

<210> SEQ ID NO 404
<211> LENGTH: 903
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 404
atgccgattc cggatagctc tccgctgctg cagtttggtg gtcaggttcg tcagcgttat 60
ctgtataccg atgatgcaca gcagaccgaa gcacatctgg aaattcgtga agatggcacc 120
gttggtggtg cagcagatca gtctccggaa agcctgctgc agctgaaagc actgaaaccg 180
ggtgttattc agattctggg tgttaaaacc agccgttttc tgtgtcagcg tccggatggt 240
gcactgtatg gtagcctgca ttttgatccg gaagcatgca gctttcgtga actgctgctg 300
gaagatggct ataatgtgta tcagagcgaa gcacatggtc tgccgctgca tctgcctggt 360
aataaatctc cgcatcgtga tccggcaccg cgtggtccgg cacgtttcct gccgctgcct 420
ggtctgcctc cggcactgcc agaacctccg ggtattctgg caccgcagcc tccggatgtt 480
ggtagcagcg atccgctgtc tatggttggt ccgagccagg gtcgtagccc gagctatgca 540
agcggtggta gcggtagcgg ttctggtagc ggttcaggtt ctggttctgg tgtttctgat 600
gttccgcgtg atctggaagt tgttgcagca accccgacca gcctgctgat tagctggcat 660
agctattatg aacagaatag ctattatcgc attacctatg gtgaaaccgg tggtaattct 720
ccggttcagg aatttaccgt tccgtatagc cagaccaccg caaccattag cggtctgaag 780
cctggtgtgg attataccat taccgtgtat gcagtttatg gcagcaaata ttattatccg 840
attagcatta attatcgcac cgaaattgaa aaaccgagcc agcatcatca tcaccatcat 900
tga 903

<210> SEQ ID NO 405
<211> LENGTH: 885
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 405
atgccgattc cggatagctc tccgctgctg cagtttggtg gtcaggttcg tcagcgttat 60
ctgtataccg atgatgcaca gcagaccgaa gcacatctgg aaattcgtga agatggcacc 120
gttggtggtg cagcagatca gtctccggaa agcctgctgc agctgaaagc actgaaaccg 180
ggtgttattc agattctggg tgttaaaacc agccgttttc tgtgtcagcg tccggatggt 240
gcactgtatg gtagcctgca ttttgatccg gaagcatgca gctttcgtga actgctgctg 300
gaagatggct ataatgtgta tcagagcgaa gcacatggtc tgccgctgca tctgcctggt 360
aataaatctc cgcatcgtga tccggcaccg cgtggtccgg cacgtttcct gccgctgcct 420
ggtctgcctc cggcactgcc agaacctccg ggtattctgg caccgcagcc tccggatgtt 480
ggtagcagcg atccgctgtc tatggttggt ccgagccagg gtcgtagccc gagctatgca 540
agcggtggta gcggtagcgg ttctggtagc ggttcaggtt ctggttctgg tgtttctgat 600
gttccgcgtg atctggaagt tgttgcagca accccgacca gcctgctgat tagctggcat 660
agctattatg aacagaatag ctattatcgc attacctatg gtgaaaccgg tggtaattct 720
ccggttcagg aatttaccgt tccgtatagc cagaccaccg caaccattag cggtctgaag 780
cctggtgtgg attataccat taccgtgtat gcagtttatg gcagcaaata ttattatccg 840
attagcatta attatcgcac cgaaattgaa aaaccgagcc agtga 885

<210> SEQ ID NO 406
<211> LENGTH: 558
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 406
atgcatcatc atcaccatca tattccggat agctctccgc tgctgcagtt tggtggtcag 60
gttcgtcagc gttatctgta taccgatgat gcacagcaga ccgaagcaca tctggaaatt 120
cgtgaagatg gcaccgttgg tggtgcagca gatcagtctc cggaaagcct gctgcagctg 180
aaagcactga aaccgggtgt tattcagatt ctgggtgtta aaaccagccg ttttctgtgt 240
cagcgtccgg atggtgcact gtatggtagc ctgcattttg atccggaagc atgtagcttt 300
cgtgaactgc tgctggaaga tggctataat gtgtatcaga gcgaagcaca tggtctgccg 360
ctgcatctgc ctggtaataa atctccgcat cgtgatccgg caccgcgtgg tccggcacgt 420
tttctgccac tgcctggtct gcctccggca ctgccagaac cgccgggtat tctggcaccg 480
cagccgccgg atgttggtag cagcgatccg ctgagcatgg ttggtccgag ccagggtcgt 540
agcccgagct atgcaagc 558

<210> SEQ ID NO 407
<211> LENGTH: 543
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 407
atgcatcatc atcaccatca tccgctgctg cagtttggtg gtcaggttcg tcagcgttat 60
ctgtataccg atgatgcaca gcagaccgaa gcacatctgg aaattcgtga agatggcacc 120
gttggtggtg cagcagatca gtctccggaa agcctgctgc agctgaaagc actgaaaccg 180
ggtgttattc agattctggg tgttaaaacc agccgttttc tgtgtcagcg tccggatggt 240
gcactgtatg gtagcctgca ttttgatccg gaagcatgta gctttcgtga actgctgctg 300
gaagatggct ataatgtgta tcagagcgaa gcacatggtc tgccgctgca tctgcctggt 360
aataaatctc cgcatcgtga tccggcaccg cgtggtccgg cacgttttct gccactgcct 420
ggtctgcctc cggcactgcc agaaccgccg ggtattctgg caccgcagcc gccggatgtt 480
ggtagcagcg atccgctgag catggttggt ccgagccagg gtcgtagccc gagctatgca 540
agc 543

<210> SEQ ID NO 408
<211> LENGTH: 34
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 408

Ile Lys Pro Glu Ala Pro Gly Glu Asp Ala Ser Pro Glu Glu Leu Asn
1 5 10 15

Arg Tyr Tyr Ala Ser Leu Arg His Tyr Leu Asn Leu Val Thr Arg Gln
20 25 30

Arg Tyr

<210> SEQ ID NO 409
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

Ser Pro Glu Glu Leu Asn Arg Tyr Tyr Ala Ser Leu Arg His Tyr Leu
1 5 10 15

Asn Leu Val Thr Arg Gln Arg Tyr
20

<210> SEQ ID NO 410
<211> LENGTH: 16
<212> TYPE: PRT
<213> ORGANISM: Artificial Sequence
<220> FEATURE:

<223> OTHER INFORMATION: Description of Artificial Sequence: Synthetic peptide

<400> SEQUENCE: 410

Tyr Ala Ser Leu Arg His Tyr Leu Asn Leu Val Thr Arg Gln Arg Tyr
1 5 10 15

<210> SEQ ID NO 411
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

Ala Ser Leu Arg His Tyr Leu Asn Leu Val Thr Arg Gln Arg Tyr
1 5 10 15

<210> SEQ ID NO 412
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 412

Leu Arg His Tyr Leu Asn Leu Val Thr Arg Gln Arg Tyr
1 5 10

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

Arg His Tyr Leu Asn Leu Val Thr Arg Gln Arg Tyr
1 5 10

<210> SEQ ID NO 414
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 414

Ser Pro Glu Glu Leu Asn Arg Tyr Tyr Ala Ser Leu Arg His Tyr Leu
1 5 10 15

Asn Leu Leu Thr Arg Gln Arg Tyr
20

<210> SEQ ID NO 415
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 415

Tyr Ala Ser Leu Arg His Tyr Leu Asn Leu Leu Thr Arg Gln Arg Tyr 1 5 10 15

<210> SEQ ID NO 416
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Ala Ser Leu Arg His Tyr Leu Asn Leu Leu Thr Arg Gln Arg Tyr
1 5 10 15

<210> SEQ ID NO 417
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Leu Arg His Tyr Leu Asn Leu Leu Thr Arg Gln Arg Tyr
1 5 10

<210> SEQ ID NO 418
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Arg His Tyr Leu Asn Leu Leu Thr Arg Gln Arg Tyr
1 5 10

<210> SEQ ID NO 419
<211> LENGTH: 77
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 419

Met Asn Leu Arg Leu Cys Val Gln Ala Leu Leu Leu Leu Trp Leu Ser
1 5 10 15

Leu Thr Ala Val Cys Gly Gly Ser Leu Met Pro Leu Pro Asp Gly Asn
20 25 30

Gly Leu Glu Asp Gly Asn Val Arg His Leu Val Gln Pro Arg Gly Ser
35 40 45

Arg Asn Gly Pro Gly Pro Trp Gln Gly Gly Arg Arg Lys Phe Arg Arg
50 55 60

Gln Arg Pro Arg Leu Ser His Lys Gly Pro Met Pro Phe
65 70 75

<210> SEQ ID NO 420
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 420

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35

<210> SEQ ID NO 421
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 421

Lys Phe Arg Arg Gln Arg Pro Arg Leu Ser His Lys Gly Pro Met Pro
1               5                   10                  15

Phe

<210> SEQ ID NO 422
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 422

Gln Arg Pro Arg Leu Ser His Lys Gly Pro Met Pro Phe
1               5                   10

<210> SEQ ID NO 423
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 423

Arg Pro Arg Leu Ser His Lys Gly Pro Met Pro Phe
1               5                   10

<210> SEQ ID NO 424
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 424

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser

```
65                  70                  75                  80

Lys Tyr Tyr Tyr Pro Ile Ser Ile Asn Tyr Arg Thr Glu Ile Glu Asp
                85                  90                  95

Glu Asp Glu Asp Glu Asp Glu Asp Gln Arg Pro Arg Leu Ser His Lys
            100                 105                 110

Gly Pro Met Pro Phe
        115


<210> SEQ ID NO 425
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln His His His His His His Gly Ser Gly Ser Gly Ser Gly
            100                 105                 110

Ser Gly Ser Gly Ser Gly Ser Gln Arg Pro Arg Leu Ser His Lys Gly
        115                 120                 125

Pro Met Pro Phe
    130


<210> SEQ ID NO 426
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln Gly Ser Gly Ser Gly Ser Gly Ser Gly Ser Gly Ser Gly
```

```
            100                 105                 110

Ser Gln Arg Pro Arg Leu Ser His Lys Gly Pro Met Pro Phe
        115                 120                 125


<210> SEQ ID NO 427
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln His His His His His His Gly Ser Gly Ser Gly Ser Gly
            100                 105                 110

Ser Gly Ser Gly Ser Gly Ser Leu Val Gln Pro Arg Gly Ser Arg Asn
        115                 120                 125

Gly Pro Gly Pro Trp Gln Gly Gly Arg Arg Lys Phe Arg Arg Gln Arg
    130                 135                 140

Pro Arg Leu Ser His Lys Gly Pro Met Pro Phe
145                 150                 155


<210> SEQ ID NO 428
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Met Gly Val Ser Asp Val Pro Arg Asp Leu Glu Val Val Ala Ala Thr
1               5                   10                  15

Pro Thr Ser Leu Leu Ile Ser Trp His Ser Tyr Tyr Glu Gln Asn Ser
            20                  25                  30

Tyr Tyr Arg Ile Thr Tyr Gly Glu Thr Gly Gly Asn Ser Pro Val Gln
        35                  40                  45

Glu Phe Thr Val Pro Tyr Ser Gln Thr Thr Ala Thr Ile Ser Gly Leu
    50                  55                  60

Lys Pro Gly Val Asp Tyr Thr Ile Thr Val Tyr Ala Val Tyr Gly Ser
65                  70                  75                  80

Lys Tyr Tyr Tyr Pro Ile Ser Ile Asn Tyr Arg Thr Glu Ile Asp Lys
                85                  90                  95

Pro Ser Gln Gly Ser Gly Ser Gly Ser Gly Ser Gly Ser Gly Ser Gly
            100                 105                 110

Ser Leu Val Gln Pro Arg Gly Ser Arg Asn Gly Pro Gly Pro Trp Gln
```

```
        115                 120                 125

Gly Gly Arg Arg Lys Phe Arg Arg Gln Arg Pro Arg Leu Ser His Lys
    130                 135                 140

Gly Pro Met Pro Phe
145


<210> SEQ ID NO 429
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present

<400> SEQUENCE: 429

Met Gln Arg Pro Arg Leu Ser His Lys Gly Pro Met Pro Phe Gly Ser
1               5                   10                  15

Gly Ser Gly Ser Gly Ser Gly Ser Gly Ser Gly Ser Gly Val Ser Asp
            20                  25                  30

Val Pro Arg Asp Leu Glu Val Val Ala Ala Thr Pro Thr Ser Leu Leu
        35                  40                  45

Ile Ser Trp His Ser Tyr Tyr Glu Gln Asn Ser Tyr Tyr Arg Ile Thr
    50                  55                  60

Tyr Gly Glu Thr Gly Gly Asn Ser Pro Val Gln Glu Phe Thr Val Pro
65                  70                  75                  80

Tyr Ser Gln Thr Thr Ala Thr Ile Ser Gly Leu Lys Pro Gly Val Asp
                85                  90                  95

Tyr Thr Ile Thr Val Tyr Ala Val Tyr Gly Ser Lys Tyr Tyr Tyr Pro
            100                 105                 110

Ile Ser Ile Asn Tyr Arg Thr Glu
        115                 120


<210> SEQ ID NO 430
<211> LENGTH: 143
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: May or may not be present

<400> SEQUENCE: 430

Met Leu Val Gln Pro Arg Gly Ser Arg Asn Gly Pro Gly Pro Trp Gln
1               5                   10                  15

Gly Gly Arg Arg Lys Phe Arg Arg Gln Arg Pro Arg Leu Ser His Lys
            20                  25                  30

Gly Pro Met Pro Phe Gly Ser Gly Ser Gly Ser Gly Ser Gly Ser Gly
        35                  40                  45

Ser Gly Ser Gly Val Ser Asp Val Pro Arg Asp Leu Glu Val Val Ala
    50                  55                  60

Ala Thr Pro Thr Ser Leu Leu Ile Ser Trp His Ser Tyr Tyr Glu Gln
65                  70                  75                  80

Asn Ser Tyr Tyr Arg Ile Thr Tyr Gly Glu Thr Gly Gly Asn Ser Pro
                85                  90                  95
```

```
Val Gln Glu Phe Thr Val Pro Tyr Ser Gln Thr Thr Ala Thr Ile Ser
            100                 105                 110

Gly Leu Lys Pro Gly Val Asp Tyr Thr Ile Thr Val Tyr Ala Val Tyr
        115                 120                 125

Gly Ser Lys Tyr Tyr Tyr Pro Ile Ser Ile Asn Tyr Arg Thr Glu
    130                 135                 140


<210> SEQ ID NO 431
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 431

His His His His His His
1               5


<210> SEQ ID NO 432
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(20)
<223> OTHER INFORMATION: This sequence may encompass 2-10, 2-8, 2-5,
      3-10, 3-8, 3-7, 3-5, 4-7, or 2, 3, 4, 5, 6, 7, 8, 9, or 10
      "Glu-Asp" repeating units

<400> SEQUENCE: 432

Glu Asp Glu Asp Glu Asp Glu Asp Glu Asp Glu Asp Glu Asp Glu Asp
1               5                   10                  15

Glu Asp Glu Asp
            20


<210> SEQ ID NO 433
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(20)
<223> OTHER INFORMATION: This sequence may encompass 2-10, 2-7, 2-5,
      3-10, 3-7, 3-5, 3, 4 or 5 "Glu-Asp" repeating units

<400> SEQUENCE: 433

Glu Asp Glu Asp Glu Asp Glu Asp Glu Asp Glu Asp Glu Asp Glu Asp
1               5                   10                  15

Glu Asp Glu Asp
            20


<210> SEQ ID NO 434
<211> LENGTH: 5
<212> TYPE: PRT
<213> ORGANISM: Unknown
<220> FEATURE:
<223> OTHER INFORMATION: Description of Unknown: Pancreatic peptide

<400> SEQUENCE: 434
```

```
Arg Tyr Tyr Ser Ala
1               5


<210> SEQ ID NO 435
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Gly Ser Gly Ser Gly Ser Gly Ser Gly Ser
1               5                   10


<210> SEQ ID NO 436
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Gly Val Ser Asp Val Pro Arg Asp Leu Glu Val Val Ala Ala Thr Pro
1               5                   10                  15

Thr Ser Leu Leu Ile Ser Trp His Ser Tyr Tyr Glu Gln Asn Ser Tyr
            20                  25                  30

Tyr Arg Ile Thr Tyr Gly Glu Thr Gly Gly Asn Ser Pro Val Gln Glu
        35                  40                  45

Phe Thr Val Pro Tyr Ser Gln Thr Thr Ala Thr Ile Ser Gly Leu Lys
    50                  55                  60

Pro Gly Val Asp Tyr Thr Ile Thr Val Tyr Ala Val Tyr Gly Ser Lys
65                  70                  75                  80

Tyr Tyr Tyr Pro Ile Ser Ile Asn Tyr Arg Thr Glu
                85                  90


<210> SEQ ID NO 437
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 437

atgcatcatc atcatcacca tccgattccg gatagcagcc cgctgctgca gtttggcggc     60

caggtgcgtc agcgttatct gtataccgat gatgcgcagc agaccgaagc gcatctggaa    120

attcgtgaag atggcaccgt gggcggtgcg gcggatcaga gcccggaaag cctgctgcag    180

ctgaaagcgc tgaaaccggg cgtgattcag attctgggcg tgaaaaccag ccgttttctg    240

tgccagcgtc cggatggcgc gctgtatggc agcctgcatt ttgatccgga agcgtgcagc    300

tttcgtgaac tgctgctgga agatggctat aacgtgtatc agagcgaagc gcatggcctg    360

ccgctgcatc tgccgggcaa caaaagcccg catcgtgatc cggcaccgcg tggtccggca    420

cgttttctgc cgctgccggg tctgccgcca gcactgccgg aaccgccggg tattctggca    480

ccgcagccgc cggatgttgg tagcagcgat ccgctgtcta tggtgggtcc gagccagggt    540

cgtagcccga gctatgcgag ctaataa                                        567


<210> SEQ ID NO 438
```

<211> LENGTH: 47
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 438

Gly Ser Gly Ser Gly Ser Gly Ser Gly Ser Lys Cys Asn Thr Ala Thr
1 5 10 15

Cys Ala Thr Gln Arg Leu Ala Asn Phe Leu Val Arg Ser Ser Asn Asn
20 25 30

Leu Gly Pro Val Leu Pro Pro Thr Asn Val Gly Ser Asn Thr Tyr
35 40 45

<210> SEQ ID NO 439
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Ahx

<400> SEQUENCE: 439

Xaa Ala Lys Pro Glu Ala Pro Gly Glu Asp Ala Ser Pro Glu Glu Leu
1 5 10 15

Ser Arg Tyr Tyr Ala Ser Leu Arg His Tyr Leu Asn Leu Val Thr Arg
20 25 30

Gln Arg Tyr
35

<210> SEQ ID NO 440
<211> LENGTH: 44
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 440

Gly Ser Gly Ser Gly Ser Gly Ser Gly Ser Ala Lys Pro Glu Ala Pro
1 5 10 15

Gly Glu Asp Ala Ser Pro Glu Glu Leu Ser Arg Tyr Tyr Ala Ser Leu
20 25 30

Arg His Tyr Leu Asn Leu Val Thr Arg Gln Arg Tyr
35 40

<210> SEQ ID NO 441
<211> LENGTH: 37
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Ahx

<400> SEQUENCE: 441

Xaa Ala Pro Leu Glu Pro Met Tyr Pro Gly Asp Tyr Ala Thr Pro Glu
1 5 10 15

```
Gln Met Ala Gln Tyr Glu Thr Gln Leu Arg Arg Tyr Ile Asn Thr Leu
            20                  25                  30

Thr Arg Pro Arg Tyr
        35


<210> SEQ ID NO 442
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Ala Pro Leu Glu Pro Met Tyr Pro Gly Asp Tyr Ala Thr Pro Glu Gln
1               5                   10                  15

Met Ala Gln Tyr Glu Thr Gln Leu Arg Arg Tyr Ile Asn Thr Leu Thr
            20                  25                  30

Arg Pro Arg Tyr
        35


<210> SEQ ID NO 443
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Gly Ser Gly Ser Gly Ser Gly Ser Gly Ser Ala Pro Leu Glu Pro Met
1               5                   10                  15

Tyr Pro Gly Asp Tyr Ala Thr Pro Glu Gln Met Ala Gln Tyr Glu Thr
            20                  25                  30

Gln Leu Arg Arg Tyr Ile Asn Thr Leu Thr Arg Pro Arg Tyr
        35                  40                  45


<210> SEQ ID NO 444
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(14)
<223> OTHER INFORMATION: This sequence may encompass 3 to 7 "Glu-Asp"
      repeating units

<400> SEQUENCE: 444

Glu Asp Glu Asp Glu Asp Glu Asp Glu Asp Glu Asp Glu Asp
1               5                   10
```